United States Patent
Miyoshi et al.

(10) Patent No.: US 7,582,658 B2
(45) Date of Patent: Sep. 1, 2009

(54) BICYCLIC COMPOUND

(75) Inventors: Shiro Miyoshi, Shizuoka (JP); Toshinori Ishizuya, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 623 days.

(21) Appl. No.: 11/019,632

(22) Filed: Dec. 23, 2004

(65) Prior Publication Data

US 2006/0069098 A1  Mar. 30, 2006

Related U.S. Application Data

(60) Provisional application No. 60/532,636, filed on Dec. 29, 2003, provisional application No. 60/626,926, filed on Nov. 12, 2004.

(30) Foreign Application Priority Data

Dec. 25, 2003 (JP) .............. 2003-429123
Nov. 10, 2004 (JP) .............. 2004-326560

(51) Int. Cl.
  *A61K 31/44* (2006.01)
  *C07D 211/00* (2006.01)
  *A61K 31/40* (2006.01)
  *C07D 307/93* (2006.01)
  *C07D 301/02* (2006.01)

(52) U.S. Cl. ............... 514/339; 514/414; 564/456; 549/465; 549/518

(58) Field of Classification Search .......... 514/415, 514/414, 339; 549/400, 465, 518; 546/339, 546/357; 564/456
See application file for complete search history.

(56) References Cited

U.S. PATENT DOCUMENTS

| 5,648,541 | A | 7/1997 | VanWagenen et al. |
| 6,011,068 | A | 1/2000 | Nemeth et al. |
| 2003/0199497 | A1 | 10/2003 | Ruat et al. |
| 2004/0077619 | A1 | 4/2004 | Kelly et al. |
| 2004/0082625 | A1 | 4/2004 | Kelly et al. |

FOREIGN PATENT DOCUMENTS

| EP | 0 933 354 A1 | 8/1999 |
| WO | WO 93/04373 | 3/1993 |
| WO | WO 94/18959 A1 | 9/1994 |
| WO | WO 95/11221 | 4/1995 |
| WO | WO 97/37967 | 10/1997 |
| WO | WO 97/41090 | 11/1997 |
| WO | WO 00/21910 | 4/2000 |

*Primary Examiner*—Janet L. Andres
*Assistant Examiner*—Binta Robinson
(74) *Attorney, Agent, or Firm*—Young & Thompson

(57) ABSTRACT

A novel compound represented by the following formula (1) or a salt thereof:

[Formula 1]

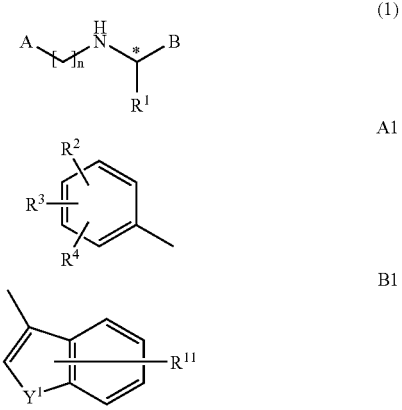

wherein symbol "A" represents a saturated heterocyclic group, a 5-membered heteroaromatic group having two heteroatoms in the ring, a group represented by the formula A1 ($R^2$, $R^3$, and $R^4$ represent hydrogen atom, hydroxyl group, etc.), etc., B represents a group represented by the formula B1 ($R^{11}$ represents hydrogen atom, hydroxyl group, etc.), etc., $R^1$ represents an alkyl group, and symbol "n" represents an integer of 2 to 6, which has a parathyroid hormone depressing action and showing low toxicity, and a medicament containing the compound or salt thereof as an active ingredient.

18 Claims, No Drawings

BICYCLIC COMPOUND

TECHNICAL FIELD

The present invention relates to a novel compound having a parathyroid hormone depressing activity and useful as an active ingredient of a medicament.

BACKGROUND ART

Parathyroid hormone (also abbreviated as "PTH" hereafter in the specification) is a peptide hormone produced by parathyroid chief cells and acts on multiple target organs to play a key role is maintenance of the blood calcium concentration (Furukawa, Y., "Dissection and Physiology of Parathyroid", Saishin Naikagaku Taikei (Latest Internal Medicine System), 14, Endocrinologic Diseases 3 (edited by Inoue, H. et al), pp. 15-33, Nakayama Shoten, Tokyo, 1993).

Therefore, abnormalities in secretion of PTH bring about pathological conditions based on change of the blood calcium concentration and affections of target organs such as kidney and bone. In hyperparathyroidism characterized by unusual rise of PTH secretion, in particular, target organs are exposed to superfluous PTH, and therefore, in bones, for example, the bone metabolic turnover becomes unusual, and pathological changes of bones such as fibrous ostitis occur at the same time. Furthermore, because affections of organs include a wide range of affections such as hypercalcemia, renal calculus, ectopic calcification, pruritus, digestive ulcer, cardiac muscle abnormal contraction, brain wave abnormality and anemia, life prognosis and QOL (Quality of Life) of patients are seriously affected. As the curative medicaments for the diseases in which PTH secretion abnormally rises, activated type vitamin D and the like have already been clinically used. However, development of novel safe medicaments having further superior curative effect and being convenient for patients has been desired.

DISCLOSURE OF THE INVENTION

Object to be Achieved by the Invention

An object of the present invention is to provide a compound having a parathyroid hormone depressing activity and useful as an active ingredient of medicaments for prophylactic and/or therapeutic treatment of diseases such as hyperPTHemia.

Means to Achieve the Object

The inventors of the present invention intensively searched substances having a PTH depressing action to achieve the aforementioned object. As a result, we found that the compounds represented by the following formula (1) had a marked PTH depressing action and were useful as an active ingredient of medicaments for prophylactic and/or therapeutic treatment of diseases such as hyperPTHemia. The present invention was achieved on the basis of the aforementioned finding.

The present invention thus provides:
(1) A compound represented by the following formula (1) or a salt thereof:

[Formula 1]

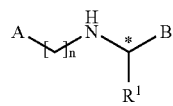

(1)

wherein:
symbol "A" represents a group selected from the group consisting of (1) a saturated heterocyclic group, (2) a 5-membered heteroaromatic group having two heteroatoms in the ring which may be substituted, (3) a group represented by the following formula A1, (4) a group represented by the following formula A2, and (5) a group represented by the following formula A3:

[Formula 2]

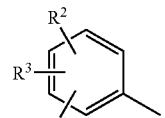

A1

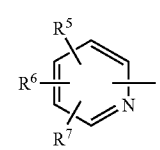

A2

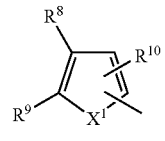

A3 wherein $R^2$, $R^3$, and $R^4$ may be the same or different, and independently represent hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$ wherein $R^{16}$ and $R^{17}$ may be the same or different, and independently represent hydrogen atom, an alkyl group, an acyl group, or $SO_2R^{18}$ wherein $R^{18}$ represents a lower alkyl group, or $R^{16}$ and $R^{17}$ together form a 3- to 7-membered ring to represent a cyclic amine as $N(R^{16})(R^{17})$; $R^5$, $R^6$ and $R^7$ may be the same or different, and independently represent hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$ wherein $R^{16}$ and $R^{17}$ may be the same or different, and independently represent hydrogen atom, an alkyl group, an acyl group, or $SO_2R^{18}$ wherein $R^{18}$ represents a lower alkyl group, or $R^{16}$ and $R^{17}$ together form a 3- to 7-membered ring to represent a cyclic amine as $N(R^{16})(R^{17})$; $R^8$, $R^9$ and $R^{10}$ independently represent hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$ wherein $R^{16}$ and $R^{17}$ may be the same or different, and independently represent hydrogen atom, an alkyl group, an acyl group, or $SO_2R^{18}$ wherein $R^{18}$ represents a lower alkyl group, or $R^{16}$ and $R^{17}$ together form a 3- to 7-membered ring to represent a cyclic amine as $N(R^{16})(R^{17})$, or $R^8$ and $R^9$ may together form a benzene ring to represent a bicyclic heteroaromatic group as the group represented by the formula A3; and $X^1$ represents oxygen atom, sulfur atom, or $N-R^{19}$ wherein $R^{19}$ represents hydrogen atom, an alkyl group, phenyl group, or a substituted phenyl group, B represents a group selected from the group consisting of a group represented by the following formula B1, a group represented by the formula B2, a group represented by the formula B3, a group represented by the formula B4, and a group represented by the formula B5:

[Formula 3]

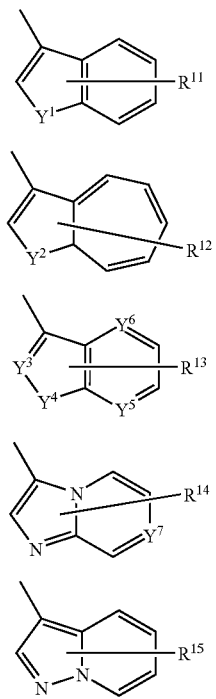

wherein $R^{11}$ represents hydrogen atom, hydroxyl group, a halogen atom, an alkyl group, an alkoxyl group, a thioalkoxyl group, hydroxymethyl group, an alkyl group arbitrarily substituted with one or more halogen atoms, an alkoxyl group arbitrarily substituted with one or more halogen atoms, nitro group, or $N(R^{20})(R^{21})$ wherein $R^{20}$ and $R^{21}$ may be the same or different, and independently represent hydrogen atom, an alkyl group, an acyl group, or $SO_2R^{22}$ wherein $R^{22}$ represents a lower alkyl group, or $R^{20}$ and $R^{21}$ together form a 3- to 7-membered ring to represent a cyclic amine as $N(R^{20})(R^{21})$, $Y^1$ represents sulfur atom or oxygen atom; $R^{12}$ represent hydrogen atom or an alkyl group, $Y^2$ represents CH or nitrogen atom; $R^{13}$ represents hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20})(R^{21})$ wherein $R^{20}$ and $R^{21}$ may be the same or different, and independently represent hydrogen atom, an alkyl group, an acyl group, or $SO_2R^{22}$ wherein $R^{22}$ represents a lower alkyl group, or $R^{20}$ and $R^{21}$ together form a 3- to 7-membered ring to represent a cyclic amine as $N(R^{20})(R^{21})$, $Y^4$ represents sulfur atom or oxygen atom, and one of $Y^3$, $Y^5$, and $Y^6$ represents nitrogen atom, and the remaining groups represent CH; $R^{14}$ represents hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20})(R^{21})$ wherein $R^{20}$ and $R^{21}$ may be the same or different, and independently represent hydrogen atom, an alkyl group, an acyl group, or $SO_2R^{22}$ wherein $R^{22}$ represents a lower alkyl group, or $R^{20}$ and $R^{21}$ together form a 3- to 7-membered ring to represent a cyclic amine as $N(R^{20})(R^{21})$, $Y^7$ represent CH or nitrogen atom; and $R^{15}$ represents hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20})(R^{21})$ wherein $R^{20}$ and $R^{21}$ may be the same or different, and independently represent hydrogen atom, an alkyl group, an acyl group, or $SO_2R^{22}$ wherein $R^{22}$ represents a lower alkyl group, or $R^{16}$ and $R^{17}$ together form a 3- to 7-membered ring to represent a cyclic amine as $N(R^{20})(R^{21})$;

$R^1$ represents an alkyl group, and symbol "n" represents an integer of 2 to 6, (2) The compound or salt thereof according to (1) mentioned above, wherein B is a group represented by the formula B1, B3, B4, or B5, (3) The compound or salt thereof according to (1) mentioned above, wherein B is a group represented by the formula B1, (4) The compound or salt thereof according to (1) mentioned above, wherein B is a group represented by the formula B2, (5) The compound or salt thereof according to (1), wherein A is a group selected from the group consisting of a group represented by the formula A2, a group represented by the formula A3, and a group represented by the following formula A4:

[Formula 4]

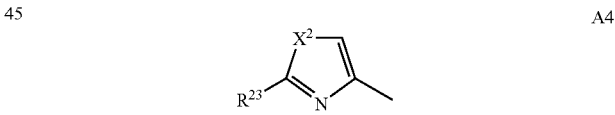

wherein $R^{23}$ represents hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$ wherein $R^{16}$ and $R^{17}$ may be the same or different, and independently represent hydrogen atom, an alkyl group, an acyl group, or $SO_2R^{18}$ wherein $R^{18}$ represents a lower alkyl group, or $R^{16}$ and $R^{17}$ together form a 3- to 7-membered ring to represent a cyclic amine as $N(R^{16})(R^{17})$; and $X^2$ represents oxygen atom, sulfur atom, or $N-R^{19}$ wherein $R^{19}$ represents hydrogen atom, an alkyl group, phenyl group, or a substituted phenyl group, (6) The compound or salt thereof according to any one of (1) to (5), wherein A is a group represented by the formula A2,
(7) The compound or salt thereof according to any one of (1), (4), and (6), wherein A is a group represented by the formula A2 wherein $R^6$ and $R^7$ are hydrogen atoms, $R^5$ is phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, or an alkoxyl group arbitrarily substituted with one or more halogen atoms, and B is a group represented by the formula B2 wherein $R^{12}$ is hydrogen atom, and $Y^2$ is CH,
(8) The compound or salt thereof according to (7), wherein $R^5$ is a substituted phenyl group, a monocyclic heteroaromatic group which may be substituted, or a bicyclic heteroaromatic group which may be substituted,
(9) The compound or salt thereof according to any one of (1) to (5), wherein A is a group represented by the formula A3,
(10) The compound or salt thereof according to any one of (1), (4), and (9), wherein A is a group represented by the formula A3 wherein $R^8$ and $R^{10}$ are hydrogen atoms, and $R^9$ is phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, or an alkoxyl group arbitrarily substituted with one or more halogen atoms, and B is a group represented by the formula B2 wherein $R^{12}$ is hydrogen atom, and $Y^2$ is CH,
(11) The compound or salt thereof according to (10), wherein $R^9$ is a substituted phenyl group, a monocyclic heteroaromatic group which may be substituted, or a bicyclic heteroaromatic group which may be substituted,
(12) The compound or salt thereof according to any one of (1) to (5), wherein A is a group represented by the formula A4,
(13) The compound or salt thereof according to any one of claims (1), (4), and (12), wherein A is a group represented by the formula A4 wherein $R^{23}$ is phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, or an alkoxyl group arbitrarily substituted with one or more halogen atoms, and B is a group represented by the formula B2 wherein $R^{12}$ is hydrogen atom, and $Y^2$ is CH,
(14) The compound or salt thereof according to (13), wherein $R^{23}$ is a substituted phenyl group, a monocyclic heteroaromatic group which may be substituted, or a bicyclic heteroaromatic group which may be substituted, and
(15) The compound or salt thereof according to any one of claims 1 to 4, wherein A is a group represented by the formula A2 or A3, or a 5-membered heteroaromatic group having two hetero atoms in the ring.

Further, from another aspect of the present invention, a medicament containing a compound represented by the aforementioned formula (1) or a physiologically acceptable salt thereof as an active ingredient is provided. The aforementioned medicament can be used as an agent for depressing parathyroid hormone. The medicament of the present invention can be used for hyperPTHemia and hyperparathyroidism (including, for example, primary hyperparathyroidism and secondary hyperparathyroidism), which is a major causative disease of hyperPTHemia. The medicament of the present invention can also be used for complications of hyperparathyroidism (for example, bone diseases accompanied by a bone metabolic disorder and the like). The medicament of the present invention can also be used for various kinds of bone diseases showing a bone metabolic disorder due to a relatively high blood parathyroid hormone concentration, even if the concentration is within a normal range (for example, osteoporosis and the like). Furthermore, the medicament of the present invention can be used for prophylactic and/or therapeutic treatment of hypercalcemia and the like resulting from a malignant tumor and the like on the basis on the action of depressing the blood PTH concentration.

From still further aspects of the present invention, there are provided use of a compound represented by the aforementioned formula (1) or a physiologically acceptable salt thereof for manufacture of the aforementioned medicament; a method for depressing parathyroid hormone, which comprises the step of administrating an effective amount of a compound represented by the aforementioned formula (1) or a physiologically acceptable salt thereof to a mammal including human; a method for prophylactic and/or therapeutic treatment of hyperparathormonemia, which comprises the step of administrating a prophylactically and/or therapeutically effective amount of a compound represented by the aforementioned formula (1) or a physiologically acceptable salt thereof to a mammal including human; a method for prophylactic and/or therapeutic treatment of hyperparathyroidism and/or complications thereof, which comprises the step of administrating a prophylactically and/or therapeutically effective amount of a compound represented by the aforementioned formula (1) or a physiologically acceptable salt thereof to a mammal including human; a method for prophylactic and/or therapeutic treatment of a bone disease accompanying increase in blood parathyroid hormone, which comprises the step of administrating a prophylactically and/or therapeutically effective amount of a compound represented by the aforementioned formula (1) or a physiologically acceptable salt thereof to a mammal including human; and a method for prophylactic and/or therapeutic treatment of hypercalcemia based on an action of depressing blood PTH concentration, which comprises the step of administrating a prophylactically and/or therapeutically effective amount of a compound represented by the aforementioned formula (1) or a physiologically acceptable salt thereof to a mammal including human.

EFFECT OF THE INVENTION

The compounds of the present invention have a potent PTH depressing action, when they are administered to a human or an animal in a free form or in a form of a salt, and they are suitable as active ingredients of medicaments for prophylactic and/or therapeutic treatment of diseases such as hyperPTHemia.

BEST MODE FOR CARRYING OUT THE INVENTION

Hereafter, the present invention will be specifically explained.

In this specification, a halogen atom may be, for example, fluorine atom, chlorine atom, bromine atom, or iodine atom, unless otherwise especially indicated. Further, as the alkyl group, examples include a saturated hydrocarbon group comprising a linear, cyclic, or branched chain or a combination thereof, and the alkyl group is usually preferably a lower alkyl group. The same shall apply to alkyl moieties of other substituents having an alkyl moiety (e.g., an alkoxyl group, an acyl group and the like). As the lower alkyl group, an alkyl group having 1 to 4 carbon atoms is generally preferred.

Specific examples include methyl group, ethyl group, n-propyl group, isopropyl group, cyclopropyl group, n-butyl group, isobutyl group, s-butyl group, t-butyl group, cyclobutyl group, and cyclopropylmethyl group.

As the alkoxyl group, an example includes a saturated alkyl ether group, and the group is generally preferably a lower alkoxyl group. As the lower alkoxyl group, an alkoxyl group having 1 to 4 carbon atoms is generally preferred. Specific examples include methoxy group, ethoxy group, n-propoxy group, isopropoxy group, cyclopropoxy group, n-butoxy group, isobutoxy group, s-butoxy group, t-butoxy group, cyclobutoxy group, and cyclopropylmethoxy group.

As alkyl group arbitrarily substituted with one or more halogen atoms, examples include the aforementioned alkyl group of which one or more hydrogen atoms are replaced with a halogen atom or atoms of an arbitrary type, and the group is generally preferably an alkyl group arbitrarily substituted with one or more halogen atoms and having 1 to 4 carbon atoms. When the group is substituted with two or more halogen atoms, the halogen atom may be the same or different. Specific examples include chloromethyl group, dichloromethyl group, trichloromethyl group, fluoromethyl group, difluoromethyl group, trifluoromethyl group, chloroethyl group, fluoroethyl group, 1,1,1-trichloroethyl group, 1,1,1-trifluoroethyl group, and the like.

As the alkoxyl group arbitrarily substituted with one or more halogen atoms, examples include a saturated alkyl ether group comprising the aforementioned alkyl group of which one or more hydrogen atoms are replaced with a halogen atom or atoms of an arbitrary type, and the group is generally preferably an alkoxyl group arbitrarily substituted with one or more halogen atoms and having 1 to 4 carbon atoms. When the group is substituted with two or more halogen atoms, the halogen atom may be the same or different. Specific examples include trifluoromethoxy group and 1,1,1-trifluoroethoxy group.

As the acyl group, examples include an alkanoyl group (alkylcarbonyl group), an arylcarbonyl group and the like, and a lower alkanoyl group may be preferred. The alkyl moiety of the alkanoyl group may contain one or more unsaturated bonds. As the lower alkanoyl group, an acyl group having 2 to 5 carton atoms is generally preferred. Specifically, examples include acetyl group, propanoyl group, butanoyl group, 2-methylpropanoyl group, cyclopropylcarbonyl group, pentanoyl group, 3-methylbutanoyl group, 2,2-dimethylpropanoyl group, cyclobutylcarbonyl group and the like.

Examples of the substituent in the substituted phenyl group, substituted benzyl group, 5-membered heteroaromatic group having two hetero atoms in the ring which may be substituted, monocyclic heteroaromatic group which may be substituted, and bicyclic heteroaromatic group which may be substituted include hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, cyano group, an acyl group, CON$(R^{24})(R^{25})$ wherein $R^{24}$ and $R^{25}$ may be the same or different, and independently represent hydrogen atom, an alkyl group, or an alkoxy group, or $R^{24}$ and $R^{25}$ together form a 3- to 7-membered ring to represent a cyclic amine as $N(R^{24})(R^{25})$, COOR$^{26}$ wherein $R^{26}$ represents an alkyl group, $S(O)_m R^{27}$ wherein m represents 0 or 1, and $R^{27}$ represents an alkyl group, $SO_2 R^{28}$ wherein $R^{28}$ represents an alkyl group, amino group, aminomethyl group, or dimethylamino group, $CH_2 OR^{29}$ wherein $R^{29}$ represents hydrogen atom, an alkyl group, or an alkyl group arbitrarily substituted with one or more halogens, $CH(OH)CH_3$, $CH_2 N(R^{30})(R^{31})$ wherein $R^{30}$ and $R^{31}$ may be the same or different, and independently represent hydrogen atom, an alkyl group, an acyl group, or $SO_2 R^{34}$ wherein $R^{34}$ represents a lower alkyl group, or $R^{30}$ and $R^{31}$ together form a 3- to 7-membered ring to represent a cyclic amine as $N(R^{30})(R^{31})$, and $N(R^{32})(R^{33})$ wherein $R^{32}$ and $R^{33}$ may be the same or different, and independently represent hydrogen atom, an alkyl group, an acyl group, $SO_2 R^{34}$ wherein $R^{34}$ represents a lower alkyl group, COOR$^{35}$ wherein $R^{35}$ represents hydrogen atom, or a lower alkyl group, CSR$^{36}$ wherein $R^{36}$ represents a lower alkyl group, or an amino group which may be substituted with one or two lower alkyl groups, $CH_2 COR^{37}$ wherein $R^{37}$ represents a lower alkyl group, $CH_2 CH(OR^{38})R^{39}$ wherein $R^{38}$ and $R^{39}$ may be the same or different, and independently represent hydrogen atom, or a lower alkyl group, or $R^{32}$ and $R^{33}$ together form a 3- to 7-membered ring to represent a cyclic amine as $N(R^{32})(R^{33})$, and number of the substituent is 1 to 3. When two or more substituents exist, they may be the same or different.

Examples of the substituted phenyl group include, for example, 2-hydroxyphenyl group, 3-hydroxyphenyl group, 4-hydroxyphenyl group, 3-fluorophenyl group, 4-fluorophenyl group, 3-chlorophenyl group, 3-tolyl group, 4-tolyl group, 2-methoxyphenyl group, 3-methoxyphenyl group, 4-methoxyphenyl group, 4-amino-3-hydroxyphenyl group, 2-trifluoromethylphenyl group, 3-trifluoromethylphenyl group, 4-trifluoromethylphenyl group, 3-aminophenyl group, 4-aminophenyl group, 3-nitrophenyl group, 4-nitrophenyl group, 4-hydroxymethylphenyl group, 4-methoxymethylphenyl group, 3,4-dimethoxyphenyl group, 2-trifluoromethoxyphenyl group, 3-trifluoromethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylphenyl group, 4-(1-hydroxyethyl)phenyl group, 4-methanesulfonylaminophenyl group, and 4-dimethylaminophenyl group.

Examples of the substituted benzyl group include, for example, 3-hydroxybenzyl group, 2-fluorobenzyl group, 3-fluorobenzyl group, 4-fluorobenzyl group, 3-chlorobenzyl group, 4-chlorobenzyl group, 4-methylbenzyl group, 3-methoxybenzyl group, 4-methoxybenzyl group, 2-methoxybenzyl group, 3-trifluoromethylbenzyl group, 4-trifluoromethylbenzyl group, and 4-nitrobenzyl group.

In the 5-membered heteroaromatic group having two heteroatoms in the ring which may be substituted, the heteroatom is preferably nitrogen atom, oxygen atom, or nitrogen atom. Specific examples of the 5-membered heteroaromatic group include a monovalent group formed by eliminating an arbitrary one hydrogen atom from oxazole, thiazole, isoxazole, isothiazole, imidazole, or pyrazole, and examples include, for example, oxazol-2-yl, thiazol-2-yl, imidazol-2-yl, 2-phenylthiazol-4-yl, and 1-phenylpyrazol-3-yl.

Examples of the monocyclic heteroaromatic group which may be substituted include a monocyclic heteroaromatic group having a 5-membered ring or 6-membered ring constituted by ring-constituting carbon atoms and one or two ring-constituting heteroatoms selected from nitrogen atom, oxygen atom, and sulfur atom. Examples include, specifically, a monovalent group formed by eliminating an arbitrary one hydrogen atom from a cyclic compound such as pyrrole, furan, thiophene, oxazole, thiazole, imidazole, pyrazole, pyridine, pyrimidine, or pyrazine, but not limited to these groups. More specifically, examples include 2-pyridyl group, 3-pyridyl group, 4-pyridyl group, 2-methoxypyridin-6-yl, 2-methoxypyridin-5-yl, 2-trifluoromethoxypyridin-5-yl, 2-trifluoromethylpyridin-5-yl, 2-morpholinopyridin-5-yl, 2-fluoropyridin-5-yl, furan-2-yl, furan-3-yl, thiophen-2-yl, thiophen-3-yl, pyrrol-2-yl, N-methylpyrrol-2-yl, 5-chlorothiophen-2-yl, 5-nitrothiophen-2-yl, 5-methylthiophen-2-yl, 5-ethylthiophen-2-yl, 5-acetylthiophen-2-yl, oxazol-2-yl, oxazol-4-yl, 5-phenyloxazol-2-yl, thiazol-2-yl, thiazol-4-yl, thiazol-5-yl, 1-methylpyrazol-4-yl, 2-aminopyrimidin-5-yl, 2-methylaminopyrimidin-5-yl, 2-dimethylaminopyrimidine-5-yl, pyrimidin-2-on-5-yl, 1-methylpyrimidin-2-on-5-yl, and 2-methoxypyrimidin-5-yl.

Examples of the bicyclic heteroaromatic group which may be substituted, include a bicyclic heteroaromatic group having a 5-membered ring or 6-membered ring constituted by ring-constituting carbon atoms and one to three ring-constituting heteroatoms selected from nitrogen atom, oxygen atom, and sulfur atom. Examples include, specifically, a monovalent group formed by eliminating an arbitrary one hydrogen atom from a bicyclic compound such as indole, isoindole, benzofuran, benzothiophene, indazole, benzothiazole, benzimidazole, benzoxazole, quinoline, isoquinoline, cinnoline, phthalazine, quinazoline, or quinoxaline, but not limited to these groups.

Examples include, for example, indol-3-yl, indol-5-yl, indol-6-yl, benzofuran-5-yl, isoindol-5-yl, indazol-5-yl, indazol-6-yl, N-methylindazol-5-yl, N-methylindazol-6-yl, quinolin-6-yl, benzo[b]isoxazol-5-yl, benzo[b]isothiazol-5-yl, isoquinolin-6-yl, benzothiazol-2-yl, benzothiazol-5-yl, benzothiazol-6-yl, benzoxazol-2-yl, benzoxazol-5-yl, and benzoxazol-6-yl.

Examples of the cyclic amine include a cyclic amine having a 3- to 7-membered ring and constituted by ring-constituting carbon atoms and zero to two ring-constituting heteroatoms selected from nitrogen atom, oxygen atom, and sulfur atom, and a substituent may exist on a ring-constituting nitrogen atom and/or ring-constituting carbon atom. Specific examples include cyclopropylamine, cyclobutylamine, pyrrolidine, piperidine, cyclopentylamine, morpholine, piperazine, and thiomorpholine, but not limited to these amines. Examples of the substituent of the cyclic amine include, for example, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, amino group, and cyano group. When a substituent exists, the number of substituent is 1 to 2.

Hereafter, each of various substituents in the compounds represented by the formula (1) will be specifically explained.

$R^2$, $R^3$, and $R^4$ may be the same or different, and independently represent hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$. As $R^2$, $R^3$, and $R^4$, hydrogen atom, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, and an alkoxyl group arbitrarily substituted with one or more halogen atoms are preferred. The halogen atom, alkyl group, alkoxyl group, alkyl group arbitrarily substituted with one or more halogen atoms, and alkoxyl group arbitrarily substituted with one or more halogen atoms have the same meanings as those defined above.

As the halogen atoms represented by $R^2$, $R^3$, and $R^4$, halogen atoms independently selected from the group consisting of fluorine atom, chlorine atom, and bromine atom are preferred, and fluorine atom, and chlorine atom are more preferred. As the alkyl group represented by $R^2$, $R^3$, or $R^4$, an alkyl group having 1 to 4 carbon atoms is preferred, methyl group and ethyl group are more preferred, and methyl group is most preferred. As $R^2$, $R^3$, or $R^4$, phenyl group is also preferred. As the substituted phenyl group represented by $R^2$, $R^3$, or $R^4$, 2-hydroxyphenyl group, 3-hydroxyphenyl group, 4-hydroxyphenyl group, 3-fluorophenyl group, 4-fluorophenyl group, 3-chlorophenyl group, 3-tolyl group, 4-tolyl group, 2-methoxyphenyl group, 3-methoxyphenyl group, 4-methoxyphenyl group, 4-amino-3-hydroxyphenyl group, 2-trifluoromethylphenyl group, 3-trifluoromethylphenyl group, 4-trifluoromethylphenyl group, 3-aminophenyl group, 4-aminophenyl group, 3-nitrophenyl group, 4-nitrophenyl group, 4-hydroxymethylphenyl group, 4-methoxymethylphenyl group, 3,4-dimethoxyphenyl group, 2-trifluoromethoxyphenyl group, 3-trifluoromethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl)phenyl group, methanesulfonylphenyl group, 4-methylsulfinylphenyl group, 4-aminosulfonylphenyl group, 4-methylaminosulfonylphenyl group, 4-dimethylaminosulfonylphenyl group, and 4-dimethylaminophenyl group are preferred, 4-hydroxyphenyl group, 4-fluorophenyl group, 4-methoxyphenyl group, 4-trifluoromethylphenyl group, 4-hydroxymethylphenyl group, 4-methoxymethylphenyl group, 3,4-dimethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-dimethylaminophenyl group are more preferred, and 4-trifluoromethoxyphenyl group, 4-hydroxymethylphenyl group, 4-methoxymethylphenyl group, 4-cyanophenyl group, 4-acetylphenyl group, 4-methoxycarbonylphenyl group, 4-carbamoylphenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-acetamidophenyl group are particularly preferred.

As $R^2$, $R^3$, or $R^4$, benzyl group is also preferred. As the substituted benzyl group represented by $R^2$, $R^3$, or $R^4$, 2-hydroxybenzyl group, 3-hydroxybenzyl group, 4-hydroxybenzyl group, 3-fluorobenzyl group, 4-fluorobenzyl group, 3-chlorobenzyl group, 3-methylbenzyl group, 4-methylbenzyl group, 2-methoxybenzyl group, 3-methoxybenzyl group, 4-methoxybenzyl group, 4-amino-3-hydroxybenzyl group, 2-trifluoromethylbenzyl group, 3-trifluoromethylbenzyl group, 4-trifluoromethylbenzyl group, 3-aminobenzyl group, 4-aminobenzyl group, 3-nitrobenzyl group, 4-nitrobenzyl group, 3,4-dimethoxybenzyl group, 2-trifluoromethoxybenzyl group, 3-trifluoromethoxybenzyl group, 4-trifluoromethoxybenzyl group, 4-cyanobenzyl group, 4-acetylbenzyl group, 4-methoxycarbonylbenzyl group, 4-carbamoylbenzyl group, 4-acetamidobenzyl group, 4-methanesulfonylaminobenzyl group, and 4-dimethylaminobenzyl group are preferred, and 4-trifluoromethoxybenzyl group, 4-cyanobenzyl group, 4-acetylbenzyl group, 4-methoxycarbonylbenzyl group, 4-carbamoylbenzyl group, and 4-acetamidobenzyl group are more preferred.

As the monocyclic heteroaromatic group which may be substituted, represented by $R^2$, $R^3$, or $R^4$, 2-pyridyl group, 3-pyridyl group, 4-pyridyl group, 2-methoxypyridin-6-yl, 2-methoxypyridin-5-yl, 2-trifluoromethoxypyridin-5-yl, 2-trifluoromethylpyridin-5-yl, 2-morpholinopyridin-5-yl, 2-methoxypyrimidin-5-yl, furan-2-yl, furan-3-yl, thiophen-2-yl, thiophen-3-yl, pyrrol-2-yl, N-methylpyrrol-2-yl, 5-chlorothiophen-2-yl, 5-nitrothiophen-2-yl, 5-methylthiophen-2-yl, 5-ethylthiophen-2-yl, oxazol-2-yl, oxazol-4-yl, 5-phenyloxazol-2-yl, 1-methylpyrazol-4-yl, 2-dimethylaminopyridin-5-yl, 5-acetylthiophen-2-yl, 2-cyanopyrimidin-5-yl, 2-methoxypyrimidin-5-yl, 2-dimethylaminopyrimidin-5-yl, 1-(2-oxopropyl)pyrazol-4-yl, 2-methoxythiazol-4-yl, 2-dimethylaminothiazol-4-yl, and thiazol-2-yl are preferred, and 3-pyridyl group, 2-methoxypyridin-5-yl, 2-trifluoromethoxypyridin-5-yl, 2-trifluoromethylpyridin-5-yl, 2-methoxypyrimidin-5-yl, thiophen-2-yl, thiophen-3-yl, N-methylpyrrol-2-yl, 5-chlorothiophen-2-yl, 5-methylthiophen-2-yl, oxazol-2-yl, oxazol-4-yl, 1-methylpyrazol-4-yl, 5-acetylthiophen-2-yl, 2-methoxypyrimidin-5-yl, 2-dimethylaminopyrimidin-5-yl, 2-methoxythiazol-4-yl, and thiazol-2-yl are more preferred. As the bicyclic heteroaromatic group which may be substituted, represented by $R^2$, $R^3$, or $R^4$, indol-3-yl, indol-5-yl, indol-6-yl, benzofuran-5-yl, isoindol-5-yl, indazol-5-yl, indazol-6-yl, N-methylindazol-5-yl, N-methylindazol-6-yl, quinolin-6-yl, benzo[b]isoxazol-5-yl, benzo[b]isothiazol-5-yl, isoquinolin-6-yl, benzothiazol-2-yl, benzothiazol-5-yl, benzothiazol-6-yl, benzoxazol-2-yl, benzoxazol-5-yl, and benzoxazol-6-yl are preferred, and indol-3-yl, indol-5-yl, benzofuran-5-yl, isoindol-5-yl, indazol-5-yl, N-methylindazol-5-yl, quinolin-6-yl, benzo[b]isoxazol-5-yl, benzo[b]isothiazol-5-yl, isoquinolin-6-yl, benzothiazol-2-yl, benzothiazol-5-yl, and benzoxazol-5-yl are more preferred.

As the alkoxyl group represented by $R^2$, $R^3$, or $R^4$, an alkoxyl group having 1 to 4 carbon atoms is preferred, methoxy group and ethoxy group are more preferred, and methoxy group is most preferred. As the alkyl group arbitrarily substituted with one or more halogen atoms represented by $R^2$, $R^3$, or $R^4$, such an alkyl group having 1 to 4 carbon atoms is preferred, monofluoromethyl group, difluoromethyl group, and trifluoromethyl group are more preferred, and trifluoromethyl group is most preferred. As the alkoxyl group arbitrarily substituted with one or more halogen atoms represented by $R^2$, $R^3$, or $R^4$, such an alkoxyl group having 1 to 4 carbon atoms is preferred, and trifluoromethoxy group is preferred.

It is preferred that any one of $R^2$, $R^3$, and $R^4$ is hydrogen atom, and it is more preferred that any two of them are hydrogen atoms. Further, all of $R^2$, $R^3$, and $R^4$ may be hydrogen atoms. When one or more of $R^2$, $R^3$, and $R^4$ are substituents other than hydrogen atom, the substituting positions thereof are not particularly limited, and they may exist on arbitrary positions on the benzene ring. When one or more of $R^2$, $R^3$, and $R^4$ are substituents other than hydrogen atom, the substituting positions thereof are preferably chosen from the para- and meta-positions relative to the aminoalkyl side chain, and the meta-position is particularly preferred. As another embodiment, the para-position is also extremely preferred.

$R^{16}$ and $R^{17}$ may be the same or different, and independently represent hydrogen atom, an alkyl group, an acyl group, or $SO_2R^{18}$ wherein $R^{18}$ is a lower alkyl group, or $R^{16}$ and $R^{17}$ together form a 3- to 7-membered ring to represent a cyclic amine as $N(R^{16})(R^{17})$. The alkyl group and acyl group have the same meanings as those defined above. As $R^{16}$ and $R^{17}$, hydrogen atom is preferred. As the alkyl group represented by $R^{16}$ or $R^{17}$, an alkyl group having 1 to 4 carton atoms is preferred, methyl group and ethyl group are more preferred, and methyl group is particularly preferred. As the acyl group represented by $R^{16}$ or $R^{17}$, an acyl group having 2 to 5 carton atoms is preferred, and acetyl group is particularly preferred. More specifically, examples of $N(R^{16})(R^{17})$ include amino group, a monoalkylamino group, a dialkylamino group, a monoacylamino group, a diacylamino group, and an acylated monoalkylamino group, and preferred examples are amino group, a monoalkylamino group, a dialkylamino group, and monoacylamino group. Among them, amino group is preferred. As the monoalkylamino group represented by $N(R^{16})(R^{17})$, an amino group substituted with an alkyl group having 1 to 4 carton atoms is preferred, and methylamino group and ethylamino group are more preferred. As the dialkylamino group represented by $N(R^{16})(R^{17})$, an amino group substituted with alkyl groups independently having 1 to 4 carton atoms is preferred, and dimethylamino group is more preferred. As the monoacylamino group represented by $N(R^{16})(R^{17})$, an amino group substituted with an acyl group having 2 to 5 carton atoms is preferred, and acetylamino group is more preferred. When $R^{16}$ and $R^{17}$ together form a 3- to 7-membered ring to represent a cyclic amine as $N(R^{16})(R^{17})$, a 3- to 7-membered cyclic amine is preferred, and a 6-membered cyclic amine is more preferred. Specifically, morpholine, piperidine, and piperazine are preferred, and morpholine is more preferred.

$R^5$, $R^6$, and $R^7$ may be the same or different, and independently represent hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$. As $R^5$, $R^6$, and $R^7$, hydrogen atom, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, and an alkoxyl group arbitrarily substituted with one or more halogen atoms are preferred. The halogen atom, alkyl group, alkoxyl group, alkyl group arbitrarily substituted with one or more halogen atoms, and alkoxyl group arbitrarily substituted with one or more halogen atoms have the same meanings as those defined above.

As $R^5$, $R^6$, and $R^7$, hydrogen atom is preferred. As the halogen atom represented by $R^5$, $R^6$, or $R^7$, a halogen atom selected from the group consisting of fluorine atom, chlorine atom, and bromine atom is preferred, and fluorine atom, and chlorine atom are more preferred. As the alkyl group represented by $R^5$, $R^6$, or $R^7$, an alkyl group having 1 to 4 carbon atoms is preferred, methyl group and ethyl group are more preferred, and methyl group is particularly preferred. As $R^5$, $R^6$, and $R^7$, phenyl group is also preferred. As the substituted phenyl group represented by $R^5$, $R^6$, and $R^7$, 2-hydroxyphenyl group, 3-hydroxyphenyl group, 4-hydroxyphenyl group, 3-fluorophenyl group, 4-fluorophenyl group, 3-chlorophenyl group, 3-tolyl group, 4-tolyl group, 2-methoxyphenyl group, 3-methoxyphenyl group, 4-methoxyphenyl group, 4-amino-3-hydroxyphenyl group, 2-trifluoromethylphenyl group, 3-trifluoromethylphenyl group, 4-trifluoromethylphenyl group, 3-aminophenyl group, 4-aminophenyl group, 3-nitrophenyl group, 4-nitrophenyl group, 4-hydroxymethylphenyl group, 4-methoxymethylphenyl group, 3,4-dimethoxyphenyl group, 2-trifluoromethoxyphenyl group, 3-trifluoromethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-dimethylaminophenyl group are preferred, 4-hydroxyphenyl group, 4-fluorophenyl group, 4-methoxyphenyl group, 4-trifluoromethylphenyl group, 4-hydroxymethylphenyl group, 4-methoxymethylphenyl group, 3,4-dimethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl) phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and dimethylaminophenyl group are more preferred, and 4-trifluoromethoxyphenyl group, 4-hydroxymethylphenyl group, 4-methoxymethylphenyl group, 4-cyanophenyl group, 4-acetylphenyl group, 4-methoxycarbonylphenyl group, 4-carbamoylphenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-acetamidophenyl group are particularly preferred.

As $R^5$, $R^6$, and $R^7$, benzyl group is also preferred. As the substituted benzyl group represented by $R^5$, $R^6$, or $R^7$, 2-hydroxybenzyl group, 3-hydroxybenzyl group, 4-hydroxybenzyl group, 3-fluorobenzyl group, 4-fluorobenzyl group, 3-chlorobenzyl group, 3-methylbenzyl group, 4-methylbenzyl group, 2-methoxybenzyl group, 3-methoxybenzyl group, 4-methoxybenzyl group, 4-amino-3-hydroxybenzyl group, 2-trifluoromethylbenzyl group, 3-trifluoromethylbenzyl group, 4-trifluoromethylbenzyl group, 3-aminobenzyl group, 4-aminobenzyl group, 3-nitrobenzyl group, 4-nitrobenzyl group, 3,4-dimethoxybenzyl group, 2-trifluoromethoxybenzyl group, 3-trifluoromethoxybenzyl group, 4-trifluoromethoxybenzyl group, 4-cyanobenzyl group, 4-acetylbenzyl group, 4-methoxycarbonylbenzyl group, 4-carbamoylbenzyl group, 4-acetamidobenzyl group, 4-methanesulfonylaminobenzyl group, and 4-dimethylaminobenzyl group are preferred, and 4-trifluoromethoxybenzyl group, 4-cyanobenzyl group, 4-acetylbenzyl group, 4-methoxycarbonylbenzyl group, 4-carbamoylbenzyl group, and 4-acetamidobenzyl group are more preferred.

As the monocyclic heteroaromatic group which may be substituted, represented by $R^5$, $R^6$, or $R^7$, 2-pyridyl group, 3-pyridyl group, 4-pyridyl group, 2-methoxypyridin-6-yl, 2-methoxypyridin-5-yl, 2-trifluoromethoxypyridin-5-yl, 2-trifluoromethylpyridin-5-yl, 2-morpholinopyridin-5-yl, 2-methoxypyrimidin-5-yl, furan-2-yl, furan-3-yl, thiophen-2-yl, thiophen-3-yl, pyrrol-2-yl, N-methylpyrrol-2-yl, 5-chlorothiophen-2-yl, 5-nitrothiophen-2-yl, 5-methylthiophen-2-yl, 5-ethylthiophen-2-yl, oxazol-2-yl, oxazol-4-yl, 5-phenyloxazol-2-yl, 1-methylpyrazol-4-yl, 2-dimethylaminopyridin-5-yl, 5-acetylthiophen-2-yl, 2-cyanopyrimidin-5-yl, 2-methoxypyrimidin-5-yl, 2-dimethylaminopyrimidin-5-yl, 1-(2-oxopropyl)pyrazol-4-yl, 2-methoxythiazol-4-yl, 2-dimethylaminothiazol-4-yl, and thiazol-2-yl are preferred, and 3-pyridyl group, 2-methoxypyridin-5-yl, 2-trifluoromethoxypyridin-5-yl, 2-trifluoromethylpyridin-5-yl, 2-methoxypyrimidin-5-yl, thiophen-2-yl, thiophen-3-yl, N-methylpyrrol-2-yl, 5-chlorothiophen-2-yl, 5-methylthiophen-2-yl, oxazol-2-yl, oxazol-4-yl, 1-methylpyrazol-4-yl, 5-acetylthiophen-2-yl, 2-methoxypyrimidin-5-yl, 2-dimethylaminopyrimidin-5-yl, 2-methoxythiazol-4-yl, and thiazol-2-yl are more preferred.

As the bicyclic heteroaromatic group which may be substituted, represented by $R^5$, $R^6$, or $R^7$, indol-3-yl, indol-5-yl, indol-6-yl, benzofuran-5-yl, isoindol-5-yl, indazol-5-yl, indazol-6-yl, N-methylindazol-5-yl, N-methylindazol-6-yl, quinolin-6-yl, benzo[b]isoxazol-5-yl, benzo[b]isothiazol-5-yl, isoquinolin-6-yl, benzothiazol-2-yl, benzothiazol-5-yl, benzothiazol-6-yl, benzoxazol-2-yl, benzoxazol-5-yl, and benzoxazol-6-yl are preferred, and indol-3-yl, indol-5-yl, benzofuran-5-yl, isoindol-5-yl, indazol-5-yl, N-methylindazol-5-yl, quinolin-6-yl, benzo[b]isoxazol-5-yl, benzo[b] isothiazol-5-yl, isoquinolin-6-yl, benzothiazol-2-yl, benzothiazol-5-yl, and benzoxazol-5-yl are more preferred. As the alkoxyl group represented by $R^5$, $R^6$, and $R^7$, an alkoxyl group having 1 to 4 carbon atoms is preferred, methoxy group and ethoxy group are more preferred, and methoxy group is particularly preferred. As the the alkyl group arbitrarily substituted with one or more halogen atoms represented by $R^5$, $R^6$, or $R^7$, an alkyl group having 1 to 4 carbon atoms is preferred, monofluoromethyl group, difluoromethyl group, and trifluoromethyl group are more preferred, and trifluoromethyl group is particularly preferred. As the alkoxyl group arbitrarily substituted with one or more halogen atoms represented by $R^5$, $R^6$, or $R^7$, an alkoxyl group having 1 to 4 carbon atoms is preferred, and trifluoromethoxy group is particularly preferred.

It is preferred that any one of $R^5$, $R^6$, and the $R^7$ is hydrogen atom, and it is more preferred that any two of them are hydrogen atoms. Further, all of $R^5$, $R^6$, and $R^7$ may be hydrogen atoms. When one or more of $R^5$, $R^6$, and $R^7$ are substituents other than hydrogen atom, the substituting positions thereof are not particularly limited, and they may exist at arbitrary positions on the benzene ring. When one or more of $R^5$, $R^6$, and $R^7$ are substituents other than hydrogen atom, the substituting positions thereof are preferably selected from the para- and meta-positions relative to the aminoalkyl side chain, and the meta-position is particularly preferred. As another embodiment, the para-position may also be extremely preferred.

$R^8$, $R^9$, and $R^{10}$ may be the same or different, and independently represent hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$, or $R^8$ and $R^9$ may together form a benzene ring to represent a bicyclic heteroaromatic group. As $R^8$, $R^9$, and $R^{10}$, hydrogen atom, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, and an alkoxyl group arbitrarily substituted with one or more halogen atoms are preferred. The halogen atom, alkyl group, alkoxyl group, alkyl group arbitrarily substituted with one or more halogen atoms, and alkoxyl group arbitrarily substituted with one or more halogen atoms have the same meanings as those defined above.

As $R^8$, $R^9$, and $R^{10}$, hydrogen atom is preferred. As the halogen atom represented by $R^8$, $R^9$, or $R^{10}$, halogen atoms independently selected from the group consisting of fluorine atom, chlorine atom, and bromine atom are preferred, and fluorine atom, and chlorine atom are more preferred. As the alkyl group represented by $R^8$, $R^9$, or $R^{10}$, an alkyl group having 1 to 4 carbon atoms is preferred, methyl group, and ethyl group are more preferred, and methyl group is particularly preferred. As $R^8$, $R^9$, and $R^{10}$, phenyl group is also preferred. As the substituted phenyl group represented by $R^8$, $R^9$, or $R^{10}$, 2-hydroxyphenyl group, 3-hydroxyphenyl group, 4-hydroxyphenyl group, 3-fluorophenyl group, 4-fluorophenyl group, 3-chlorophenyl group, 3-tolyl group, 4-tolyl group, 2-methoxyphenyl group, 3-methoxyphenyl group, 4-methoxyphenyl group, 4-amino-3-hydroxyphenyl group, 2-trifluoromethylphenyl group, 3-trifluoromethylphenyl group, 4-trifluoromethylphenyl group, 3-aminophenyl group, 4-aminophenyl group, 3-nitrophenyl group, 4-nitrophenyl group, 4-hydroxymethylphenyl group, 4-methoxymethylphenyl group, 3,4-dimethoxyphenyl group, 2-trifluoromethoxyphenyl group, 3-trifluoromethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl)phenyl group, 4-methanesulfonylphenyl group, 4-methylsulfinylphenyl group, 4-aminosulfonylphenyl group, 4-methylaminosulfonyl phenyl group, 4-dimethylaminosulfonylphenyl group, and 4-dimethylaminophenyl group are preferred, 4-hydroxyphenyl group, 4-fluorophenyl group, 4-methoxyphenyl group, 4-trifluoromethylphenyl group, 4-hydroxymethylphenyl group, 4-methoxymethylphenyl group, 3,4-dimethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and dimethylaminophenyl group are more preferred, and 4-trifluoromethoxyphenyl group, 4-hydroxymethylphenyl group, 4-methoxymethylphenyl group, 4-cyanophenyl group, 4-acetylphenyl group, 4-methoxycarbonylphenyl group, 4-carbamoylphenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-acetamidophenyl group are particularly preferred.

As $R^8$, $R^9$, and $R^{10}$, benzyl group is also preferred. As the substituted benzyl group represented by $R^8$, $R^9$, or $R^{10}$, 2-hydroxybenzyl group, 3-hydroxybenzyl group, 4-hydroxybenzyl group, 3-fluorobenzyl group, 4-fluorobenzyl group, 3-chlorobenzyl group, 3-methylbenzyl group, 4-methylbenzyl group, 2-methoxybenzyl group, 3-methoxybenzyl group, 4-methoxybenzyl group, 4-amino-3-hydroxybenzyl group, 2-trifluoromethylbenzyl group, 3-trifluoromethylbenzyl group, 4-trifluoromethylbenzyl group, 3-aminobenzyl group, 4-aminobenzyl group, 3-nitrobenzyl group, 4-nitrobenzyl group, 3,4-dimethoxybenzyl group, 2-trifluoromethoxybenzyl group, 3-trifluoromethoxybenzyl group, 4-trifluoromethoxybenzyl group, 4-cyanobenzyl group, 4-acetylbenzyl group, 4-methoxycarbonylbenzyl group, 4-carbamoylbenzyl group, 4-acetamidobenzyl group, 4-methanesulfonylaminobenzyl group, and 4-dimethylaminobenzyl group are preferred, and 4-trifluoromethoxybenzyl group, 4-cyanobenzyl group, 4-acetylbenzyl group, 4-methoxycarbonylbenzyl group, 4-carbamoylbenzyl group, and 4-acetamidobenzyl group are more preferred.

As the monocyclic heteroaromatic group which may be substituted, represented by $R^8$, $R^9$, or $R^{10}$, 2-pyridyl group, 3-pyridyl group, 4-pyridyl group, 2-methoxypyridin-6-yl, 2-methoxypyridin-5-yl, 2-trifluoromethoxypyridin-5-yl, 2-trifluoromethylpyridin-5-yl, 2-morpholinopyridin-5-yl, 2-methoxypyrimidin-5-yl, furan-2-yl, furan-3-yl, thiophen-2-yl, thiophen-3-yl, pyrrol-2-yl, N-methylpyrrol-2-yl, 5-chlorothiophen-2-yl, 5-nitrothiophen-2-yl, 5-methylthiophen-2-yl, 5-ethylthiophen-2-yl, oxazol-2-yl, oxazol-4-yl, 5-phenyloxazol-2-yl, 1-methylpyrazol-4-yl, 2-dimethylaminopyridin-5-yl, 5-acetylthiophen-2-yl, 2-cyanopyrimidin-5-yl, 2-methoxypyrimidin-5-yl, 2-dimethylaminopyrimidin-5-yl, 1-(2-oxopropyl)pyrazol-4-yl, 2-methoxythiazol-4-yl, 2-dimethylaminothiazol-4-yl, and thiazol-2-yl are preferred, and 3-pyridyl group, 2-methoxypyridin-5-yl, 2-trifluoromethoxypyridin-5-yl, 2-trifluoromethylpyridin-5-yl, 2-methoxypyrimidin-5-yl, thiophen-2-yl, thiophen-3-yl, N-methylpyrrol-2-yl, 5-chlorothiophen-2-yl, 5-methylthiophen-2-yl, oxazol-2-yl, oxazol-4-yl, 1-methylpyrazol-4-yl, 5-acetylthiophen-2-yl, 2-methoxypyrimidin-5-yl, 2-dimethylaminopyrimidin-5-yl, 2-methoxythiazol-4-yl, and thiazol-2-yl are more preferred.

As the bicyclic heteroaromatic group which may be substituted, represented by $R^8$, $R^9$, or $R^{10}$, indol-3-yl, indol-5-yl, indol-6-yl, benzofuran-5-yl, isoindol-5-yl, indazol-5-yl, indazol-6-yl, N-methylindazol-5-yl, N-methylindazol-6-yl, quinolin-6-yl, benzo[b]isoxazol-5-yl, benzo[b]isothiazol-5-yl, isoquinolin-6-yl, benzothiazol-2-yl, benzothiazol-5-yl, benzothiazol-6-yl, benzoxazol-2-yl, benzoxazol-5-yl, and benzoxazol-6-yl are preferred, and indol-3-yl, indol-5-yl, benzofuran-5-yl, isoindol-5-yl, indazol-5-yl, N-methylindazol-5-yl, quinolin-6-yl, benzo[b]isoxazol-5-yl, benzo[b]isothiazol-5-yl, isoquinolin-6-yl, benzothiazol-2-yl, benzothiazol-5-yl, and benzoxazol-5-yl are more preferred. As the alkoxyl group represented by $R^8$, $R^9$, or $R^{10}$, an alkoxyl group having 1 to 4 carbon atoms is preferred, methoxy group, and ethoxy group are more preferred, and methoxy group is particularly preferred. As the the alkyl group arbitrarily substituted with one or more halogen atoms represented by $R^8$, $R^9$, or $R^{10}$, an alkyl group having 1 to 4 carbon atoms is preferred, monofluoromethyl group, difluoromethyl group, and trifluoromethyl group are more preferred, and trifluoromethyl group is particularly preferred. As the alkoxyl group arbitrarily substituted with one or more halogen atoms represented by $R^8$, $R^9$, or $R^{10}$, an alkoxyl group having 1 to 4 carbon atoms is preferred, and trifluoromethoxy group is particularly preferred.

It is preferred that one of $R^8$ and $R^{10}$ is hydrogen atom, and it is more preferred that $R^8$ and $R^{10}$ are hydrogen atoms. It is preferred that $R^9$ is hydrogen atom, hydroxyl group, a halogen atom, an alkyl group, phenyl group, a substituted phenyl group, a monocyclic heteroaromatic group which may be substituted, a bicyclic heteroaromatic group which may be substituted, or an alkoxyl group, and it is more preferred that $R^9$ is a substituted phenyl group, a monocyclic heteroaromatic group which may be substituted, or a bicyclic heteroaromatic group which may be substituted, and $R^8$ and $R^{10}$ are hydrogen atoms.

Further, $R^8$ and $R^{10}$ may together form a benzene ring and thereby form a bicyclic heteroaromatic group as A3, and as the heteroaromatic group, specifically, a monovalent group formed from benzothiophene, benzofuran, indazole, indole or the like by eliminating one arbitrary hydrogen atom is preferred.

$X^1$ represents oxygen atom, sulfur atom, or $N-R^{19}$ wherein $R^{19}$ represents hydrogen atom, an alkyl group, phenyl group, or a substituted phenyl group. It is preferred that $X^1$ is oxygen atom, and it is also preferred that X is sulfur atom. Further, it is also preferred that $X^1$ is $N-R^{19}$, and a lower alkyl group is preferred as $R^{19}$. As the lower alkyl group, methyl group, and ethyl group are preferred, and methyl group is more preferred.

$R^{23}$ is hydrogen atom, hydroxyl group, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, nitro group, or $N(R^{16})(R^{17})$. As $R^{23}$, hydrogen atom, a halogen atom, an alkyl group, phenyl group, a substituted phenyl group, benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, and an alkoxyl group arbitrarily substituted with one or more halogen atoms are preferred.

As $R^{23}$, hydrogen atom is preferred. As the halogen atom represented by $R^{23}$, a halogen atom selected from the group consisting of fluorine atom, chlorine atom, and bromine atom is preferred, and fluorine atom, and chlorine atom are more preferred. As the alkyl group represented by $R^{23}$, an alkyl group having 1 to 4 carbon atoms is preferred, methyl group, and ethyl group are more preferred, and methyl group is particularly preferred. As $R^{23}$, phenyl group is also preferred. As the substituted phenyl group represented by $R^{23}$, 2-hydroxyphenyl group, 3-hydroxyphenyl group, 4-hydroxyphenyl group, 3-fluorophenyl group, 4-fluorophenyl group, 3-chlorophenyl group, 3-tolyl group, 4-tolyl group, 2-methoxyphenyl group, 3-methoxyphenyl group, 4-methoxyphenyl group, 4-amino-3-hydroxyphenyl group, 2-trifluoromethylphenyl group, 3-trifluoromethylphenyl group, 4-trifluoromethylphenyl group, 3-aminophenyl group, 4-aminophenyl group, 3-nitrophenyl group, 4-nitrophenyl group, 4-hydroxymethylphenyl group, 4-methoxymethylphenyl group, 3,4-dimethoxyphenyl group, 2-trifluoromethoxyphenyl group, 3-trifluoromethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-dimethylaminophenyl group are preferred, 4-hydroxyphenyl group, 4-fluorophenyl group, 4-methoxyphenyl group, 4-trifluoromethylphenyl group, 4-hydroxymethylphenyl group, 4-methoxymethylphenyl group, 3,4-dimethoxyphenyl group, 4-trifluoromethoxyphenyl group, 4-cyanophenyl group, 4-acetylphenyl group, 4-methoxycarbonylphenyl group, 4-carbamoylphenyl group, 4-acetamidophenyl group, 4-methanesulfonylaminophenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-dimethylaminophenyl group are more preferred, and 4-trifluoromethoxyphenyl group, 4-hydroxymethylphenyl group, 4-methoxymethylphenyl group, 4-cyanophenyl group, 4-acetylphenyl group, 4-methoxycarbonylphenyl group, 4-carbamoylphenyl group, 4-(1-hydroxyethyl)phenyl group, 4-methanesulfonylphenyl group, 4-methylsulfinylphenyl group, 4-aminosulfonylphenyl group, 4-methylaminosulfonylphenyl group, 4-dimethylaminosulfonylphenyl group, and 4-acetamidophenyl group are particularly preferred.

As $R^{23}$, benzyl group is also preferred. As the substituted benzyl group represented by $R^{23}$, 2-hydroxybenzyl group, 3-hydroxybenzyl group, 4-hydroxybenzyl group, 3-fluorobenzyl group, 4-fluorobenzyl group, 3-chlorobenzyl group, 3-methylbenzyl group, 4-methylbenzyl group, 2-methoxybenzyl group, 3-methoxybenzyl group, 4-methoxybenzyl group, 4-amino-3-hydroxybenzyl group, 2-trifluoromethylbenzyl group, 3-trifluoromethylbenzyl group, 4-trifluoromethylbenzyl group, 3-aminobenzyl group, 4-aminobenzyl group, 3-nitrobenzyl group, 4-nitrobenzyl group, 3,4-dimethoxybenzyl group, 2-trifluoromethoxybenzyl group, 3-trifluoromethoxybenzyl group, 4-trifluoromethoxybenzyl group, 4-cyanobenzyl group, 4-acetylbenzyl group, 4-methoxycarbonylbenzyl group, 4-carbamoylbenzyl group, 4-acetamidobenzyl group, 4-methanesulfonylaminobenzyl group, and 4-dimethylaminobenzyl group are preferred, and 4-trifluoromethoxybenzyl group, 4-cyanobenzyl group, 4-acetylbenzyl group, 4-methoxycarbonylbenzyl group, 4-carbamoylbenzyl group, and 4-acetamidobenzyl group are more preferred.

As the monocyclic heteroaromatic group which may be substituted, represented by $R^{23}$, 2-pyridyl group, 3-pyridyl group, 4-pyridyl group, 2-methoxypyridin-6-yl, 2-methoxypyridin-5-yl, 2-trifluoromethoxypyridin-5-yl, 2-trifluoromethylpyridin-5-yl, 2-morpholinopyridin-5-yl, 2-methoxypyrimidin-5-yl, furan-2-yl, furan-3-yl, thiophen-2-yl, thiophen-3-yl, pyrrol-2-yl, N-methylpyrrol-2-yl, 5-chlorothiophen-2-yl, 5-nitrothiophen-2-yl, 5-methylthiophen-2-yl, 5-ethylthiophen-2-yl, oxazol-2-yl, oxazol-4-yl, 5-phenyloxazol-2-yl, 1-methylpyrazol-4-yl, 2-dimethylaminopyridin-5-yl, 5-acetylthiophen-2-yl, 2-cyanopyrimidin-5-yl, 2-methoxypyrimidin-5-yl, 2-dimethylaminopyrimidin-5-yl, 1-(2-oxopropyl)pyrazol-4-yl, 2-methoxythiazol-4-yl, 2-dimethylaminothiazol-4-yl, and thiazol-2-yl are preferred, and 3-pyridyl group, 2-methoxypyridin-5-yl, 2-trifluoromethoxypyridin-5-yl, 2-trifluoromethylpyridin-5-yl, 2-methoxypyrimidin-5-yl, thiophen-2-yl, thiophen-3-yl, N-methylpyrrol-2-yl, 5-chlorothiophen-2-yl, 5-methylthiophen-2-yl, oxazol-2-yl, oxazol-4-yl, 1-methylpyrazol-4-yl, 5-acetylthiophen-2-yl, 2-methoxypyrimidin-5-yl, 2-dimethylaminopyrimidin-5-yl, 2-methoxythiazol-4-yl, and thiazol-2-yl are more preferred. As the bicyclic heteroaromatic group which may be substituted, represented by $R^{23}$, indol-3-yl, indol-5-yl, indol-6-yl, benzofuran-5-yl, isoindol-5-yl, indazol-5-yl, indazol-6-yl, N-methylindazol-5-yl, N-methylindazol-6-yl, quinolin-6-yl, benzo[b]isoxazol-5-yl, benzo[b]isothiazol-5-yl, isoquinolin-6-yl, benzothiazol-2-yl, benzothiazol-5-yl, benzothiazol-6-yl, benzoxazol-2-yl, benzoxazol-5-yl, and benzoxazol-6-yl are preferred, and indol-3-yl, indol-5-yl, benzofuran-5-yl, isoindol-5-yl, indazol-5-yl, N-methylindazol-5-yl, quinolin-6-yl, benzo[b]isoxazol-5-yl, benzo[b]isothiazol-5-yl, isoquinolin-6-yl, benzothiazol-2-yl, benzothiazol-5-yl, and benzoxazol-5-yl are more preferred. As the alkoxyl group represented by $R^{23}$, an alkoxyl group having 1 to 4 carbon atoms is preferred, methoxy group, and ethoxy group are more preferred, and methoxy group is particularly preferred. As the alkyl group arbitrarily substituted with one or more halogen atoms represented by $R^{23}$, an alkyl group having 1 to 4 carbon atoms is preferred, monofluoromethyl group, difluoromethyl group, and trifluoromethyl group are more preferred, and trifluoromethyl group is particularly preferred. As the alkoxyl group arbitrarily substituted with one or more halogen atoms represented by $R^{23}$, an alkoxyl group having 1 to 4 carbon atoms is preferred, and trifluoromethoxy group is particularly preferred.

$X^2$ represents oxygen atom, sulfur atom, or N—$R^{19}$ wherein $R^{19}$ represents hydrogen atom, an alkyl group, phenyl group, or a substituted phenyl group. It is preferred that $X^2$ is oxygen atom, and it is also preferred that $X^2$ is sulfur atom. Further, it is also preferred that $X^2$ is N—$R^{19}$, and hydrogen atom, and a lower alkyl group are preferred as $R^{19}$. As the lower alkyl group, methyl group and ethyl group are preferred, and methyl group is more preferred.

$R^{11}$ represents hydrogen atom, hydroxyl group, a halogen atom, an alkyl group, an alkoxyl group, a thioalkoxyl group, hydroxymethyl group, an alkyl group arbitrarily substituted with one or more halogen atoms, an alkoxyl group arbitrarily substituted with one or more halogen atoms, nitro group, or $N(R^{20})(R^{21})$. As the $R^{11}$, hydrogen atom, a halogen atom, an alkyl group, an alkoxyl group, an alkyl group arbitrarily substituted with one or more halogen atoms, or $N(R^{20})(R^{21})$ is preferred, and hydrogen atom, a halogen atom, an alkyl group, or an alkoxyl group is more preferred. The halogen atom, alkyl group, alkoxyl group, alkyl group arbitrarily substituted with one or more halogen atoms, and alkoxyl group arbitrarily substituted with one or more halogen atoms have the same meanings as those defined above. It is preferred that $R^{11}$ is hydrogen atom. As the halogen atom represented by $R^{11}$, fluorine atom, chlorine atom, or bromine atom is preferred, and chlorine atom is more preferred. As the alkyl group represented by $R^{11}$, an alkyl group having 1 to 4 carbon atoms is preferred, and methyl group and ethyl group are more preferred. As the alkoxyl group represented by $R^{11}$, an alkoxyl group having 1 to 4 carbon atoms is preferred, and methoxy group is more preferred. As the alkyl group arbitrarily substituted with one or more halogen atoms represented by $R^{11}$, an alkyl group having 1 to 4 carbon atoms and arbitrarily substituted with one or more halogen atoms is preferred, and trifluoromethyl group is more preferred. As the alkoxyl group arbitrarily substituted with one or more halogen atoms represented by $R^{11}$, an alkoxyl group having 1 to 4 carbon atoms and arbitrarily substituted with one or more halogen atoms is preferred.

$R^{20}$ and $R^{21}$ may be the same or different, and independently represent hydrogen atom, an alkyl group, an acyl group, or $SO_2R^{22}$ wherein $R^{22}$ represents a lower alkyl group, or $R^{20}$ and $R^{21}$ together form a 3- to 7-membered ring to represent a cyclic amine as $N(R^{20})(R^{21})$. The alkyl group and acyl group have the same meanings as those defined above. It is preferred that $R^{20}$ and $R^{21}$ are hydrogen atoms. As the alkyl group represented by $R^{20}$ or $R^{21}$, an alkyl group having 1 to 4 carbon atoms is preferred, and methyl group and ethyl group are more preferred. As the acyl group represented by $R^{20}$ or $R^{21}$, an acyl group having 2 to 5 carbon atoms is preferred, and acetyl group is more preferred. More specifically, examples of $N(R^{20})(R^{21})$ include amino group, a monoalkylamino group, a dialkylamino group, a monoacylamino group, a diacylamino group, and an acylated monoalkylamino group, and preferred examples include amino group, a monoalkylamino group, a dialkylamino group, and a monoacylamino group. As $N(R^{20})(R^{21})$, amino group is preferred. As the monoalkylamino group represented by $N(R^{20})(R^{21})$, an amino group substituted with an alkyl group having 1 to 4 carbon atoms is preferred, and methylamino group and ethylamino group are more preferred. As the dialkylamino group represented by $N(R^{20})(R^{21})$, an amino group substituted with alkyl groups independently having 1 to 4 carbon atoms is preferred, and dimethylamino group is more preferred. As the monoacylamino group represented by $N(R^{20})(R^{21})$, an amino group substituted with an acyl group having 2 to 5 carbon atoms is preferred, and acetylamino group is more preferred. When $R^{20}$ and $R^{21}$ together form a 3- to 7-membered ring and thereby form a cyclic amine as $N(R^{20})(R^{21})$, a 3- to 7-membered cyclic amine is preferred, and a 6-membered cyclic amine is more preferred. Specifically, morpholine, piperidine, and piperazine are preferred, and morpholine is more preferred.

$R^{12}$ represents hydrogen atom or an alkyl group, and it is preferred that $R^{12}$ is hydrogen atom. As the alkyl group represented by $R^{12}$, a lower alkyl group is preferred, an alkyl group having 1 to 4 carbon atoms is more preferred, and methyl group is further preferred. $Y^2$ represents CH or nitrogen atom, and it is preferred that $Y^2$ is CH.

$R^{13}$ represents hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20})(R^{21})$ (in the formula, $R^{20}$ and $R^{21}$ may be the same or different, and independently represents hydrogen atom, an alkyl group, an acyl group, or $SO_2R^{22}$ wherein $R^{22}$ is a lower alkyl group). It is preferred that $R^{13}$ is hydrogen atom. $Y^4$ represents sulfur atom or oxygen atom. Any one of $Y^3$, $Y^5$, and $Y^6$ is nitrogen atom, and the remaining group is CH. It is preferred that $Y^4$ is sulfur atom, $Y^5$ is nitrogen atom, and $Y^3$ and $Y^6$ represent CH.

$R^{14}$ represents hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20})(R^{21})$ (in the formula, $R^{20}$ and $R^{21}$ may be the same or different, and independently represent hydrogen atom, an alkyl group, an acyl group, or $SO_2R^{22}$ wherein $R^{22}$ is a lower alkyl group). It is preferred that $R^{14}$ is hydrogen atom. $Y^7$ represents CH or nitrogen atom, and is preferably CH.

$R^{15}$ represents hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20})(R^{21})$ (in the formula, $R^{20}$ and $R^{21}$ may be the same or different, and independently represent hydrogen atom, an alkyl group, an acyl group, or $SO_2R^{22}$ wherein $R^{22}$ is a lower alkyl group). It is preferred that $R^{15}$ is hydrogen atom.

The substituent(s) in the substituted phenyl group, substituted benzyl group, 5-membered heteroaromatic group having two hetero atoms in the ring which may be substituted, monocyclic heteroaromatic group which may be substituted, and bicyclic heteroaromatic group which may be substituted is (are) selected from hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, nitro group, cyano group, an acyl group, $CON(R^{24})(R^{25})$, $COOR^{26}$, $S(O)_mR^{27}$, $SO_2R^{28}$, $CH_2OR^{29}$, $CH(OH)CH_3$, $CH_2N(R^{30})(R^{31})$, and $N(R^{32})(R^{33})$. Number of the substituent(s) is 1 to 3. The number of the substituent(s) is preferably 1 or 2, more preferably 1. The substituting positions thereof are not particularly limited, and they may exist on arbitrary positions on the phenyl group. However, the substituting positions thereof are preferably chosen from the para- and/or meta-positions relative to the aminoalkyl side chain, and the meta-position is particularly preferred. The para-position is also particularly preferred. As the substituent(s), hydrogen atom, hydroxyl group, a halogen atom, an alkyl group, an alkoxyl group, an alkyl group arbitrarily substituted with one or more halogen atoms, an alkoxyl group arbitrarily substituted with one or more halogen atoms, cyano group, an acyl group, $CON(R^{24})(R^{25})$, $COOR^{26}$, $S(O)_m R^{27}$, $SO_2R^{28}$, $CH_2OR^{29}$, and $CH(OH)CH_3$ are preferred, an alkoxyl group, an alkyl group arbitrarily substituted with one or more halogen atoms, an alkoxyl group arbitrarily substituted with one or more halogen atoms, cyano group, an acyl group, $CON(R^{24})(R^{25})$, $S(O)_m R^{27}$, $SO_2R^{28}$, $CH_2OR^{29}$, and $CH(OH)CH_3$ are more preferred, and cyano group, an acyl group, $CON(R^{24})(R^{25})$, $S(O)_m R^{27}$, $SO_2R^{28}$, $CH_2OR^{29}$, and $CH(OH)CH_3$ are particularly preferred. As the halogen atom as the substituent, fluorine atom, chlorine atom, and bromine atom are preferred, and fluorine atom, and chlorine atom are particularly preferred. As the alkyl group as the substituent, an alkyl group having 1 to 4 carbon atoms is preferred, methyl group, and ethyl group are more preferred, and methyl group is particularly preferred. As the alkoxyl group as the substituent, an alkoxyl group having 1 to 4 carbon atoms is preferred, methoxy group, and ethoxy group are more preferred, and methoxy group is particularly preferred. As the alkyl group arbitrarily substituted with one or more halogen atoms as the substituent, an alkyl group having 1 to 4 carbon atoms and arbitrarily substituted with one or more halogen atoms is preferred, fluoromethyl group, difluoromethyl group, trifluoromethyl group, trichloromethyl group, 1-fluoroethyl group, and 1,1,1-trifluoroethyl group are more preferred, and trifluoromethyl group is particularly preferred. As the alkoxyl group arbitrarily substituted with one or more halogen atoms as the substituent, an alkoxyl group having 1 to 4 carbon atoms and arbitrarily substituted with one or more halogen atoms is preferred, fluoromethoxy group, difluoromethoxy group, trifluoromethoxy group, trichloromethoxy group, 1-fluoroethoxy group, and 1,1,1-trifluoroethoxy group are more preferred, and trifluoromethoxy group is particularly preferred. As the substituent, cyano group is also preferred. As the acyl group as the substituent, an acyl group having 2 to 5 carbon atoms is preferred, acetyl group, and ethylcarbonyl group are more preferred, and acetyl group is particularly preferred. As $CON(R^{24})(R^{25})$ as the substituent, $CONH_2$, $CONH(CH_3)$, $CON(CH_3)_2$, and $CONCH_3(OCH_3)$ are preferred. As $COOR^{26}$ as the substituent, $COOCH_3$ and $COOC_2H_5$ are preferred, and $COOCH_3$ is particularly preferred. As $S(O)_m R^{27}$ as the substituent, $SCH_3$, $SC_2H_5$, $SOCH_3$, and $SOC_2H_5$ are preferred, and $SCH_3$ and $SOCH_3$ are more preferred. As $SO_2R^{28}$ as the substituent, $SO_2CH_3$, $SO_2C_2H_5$, $SO_2NH_2$, $SO_2N(CH_3)_2$, and $SO_2NHCH_3$ are preferred, and $SO_2CH_3$ is particularly preferred. As $CH_2OR^{29}$ as the substituent, $CH_2OH$, and $CH_2OCH_3$ are preferred. As the substituent, $CH(OH)CH_3$ is also preferred. As $CH_2N(R^{30})(R^{31})$ as the substituent, $CH_2NH_2$, $CH_2NHCH_3$, and $CH_2N(CH_3)_2$ are preferred. As $N(R^{32})(R^{33})$ as the substituent, $NH_2$, $NHCH_3$, $N(CH_3)_2$, morpholin-1-yl, piperazin-1-yl, $NHCOCH_3$, $NHCOOCH_3$, $NHCONH_2$, $NHCONH(CH_3)$, $NHCON(CH_3)_2$, and $NHSO_2CH_3$ are preferred. As $CSR^{36}$ as the substituent, $CSCH_3$, $CSC_2H_5$, $CSNH_2$, $CSNHCH_3$, and $CSN(CH_3)_2$ are preferred. As $CH_2COR^{37}$ as the substituent, $CH_2COCH_3$ is preferred. As $CH_2CH(OR^{38})R^{39}$ as the substituent, $CH_2CH(OH)CH_3$ is preferred.

Symbol "A" represents a group represented by the formula A1, A2, or A3, a saturated heterocyclic group, or a 5-membered heteroaromatic group having two heteroatoms in the ring which may be substituted (preferably, a group represented by the formula A4). The saturated heterocyclic group is, specifically, a monovalent group formed by eliminating one arbitrary hydrogen atom form tetrahydrofuran, pyrrolidine, piperidine, morpholine, or the like.

It is preferred that A is a group represented by the formula A1. Further, A may be a group represented by the formula A2, and it is also extremely preferred that A is a group represented by the formula A3. Further, according to another embodiment, it is also preferred that A is a 5-membered heteroaromatic group having two heteroatoms, and it is also extremely preferred that A is a group represented by the formula A4.

Examples of A include a group represented by any of the following formulas (A-1) to (A-590).

[Formula 5]

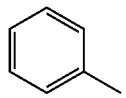
(A-1)

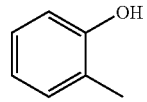
(A-2)

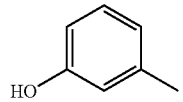
(A-3)

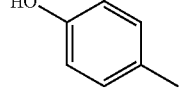
(A-4)

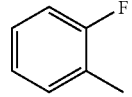
(A-5)

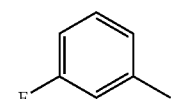
(A-6)

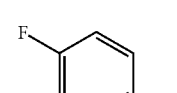
(A-7)

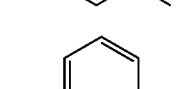
(A-8)

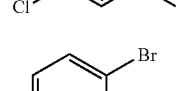
(A-9)

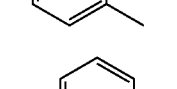
(A-10)

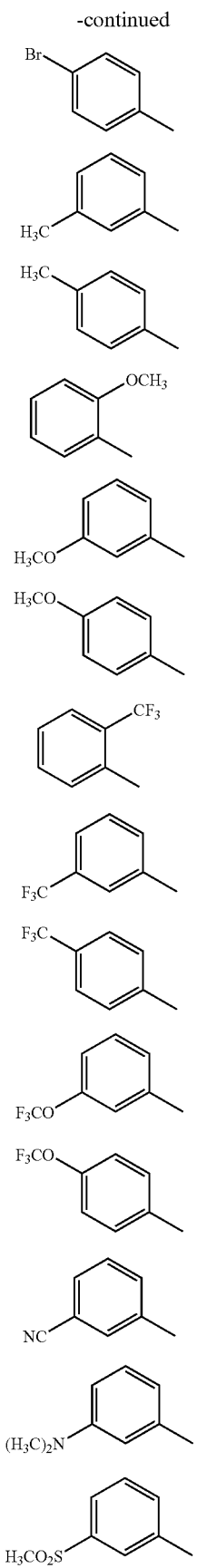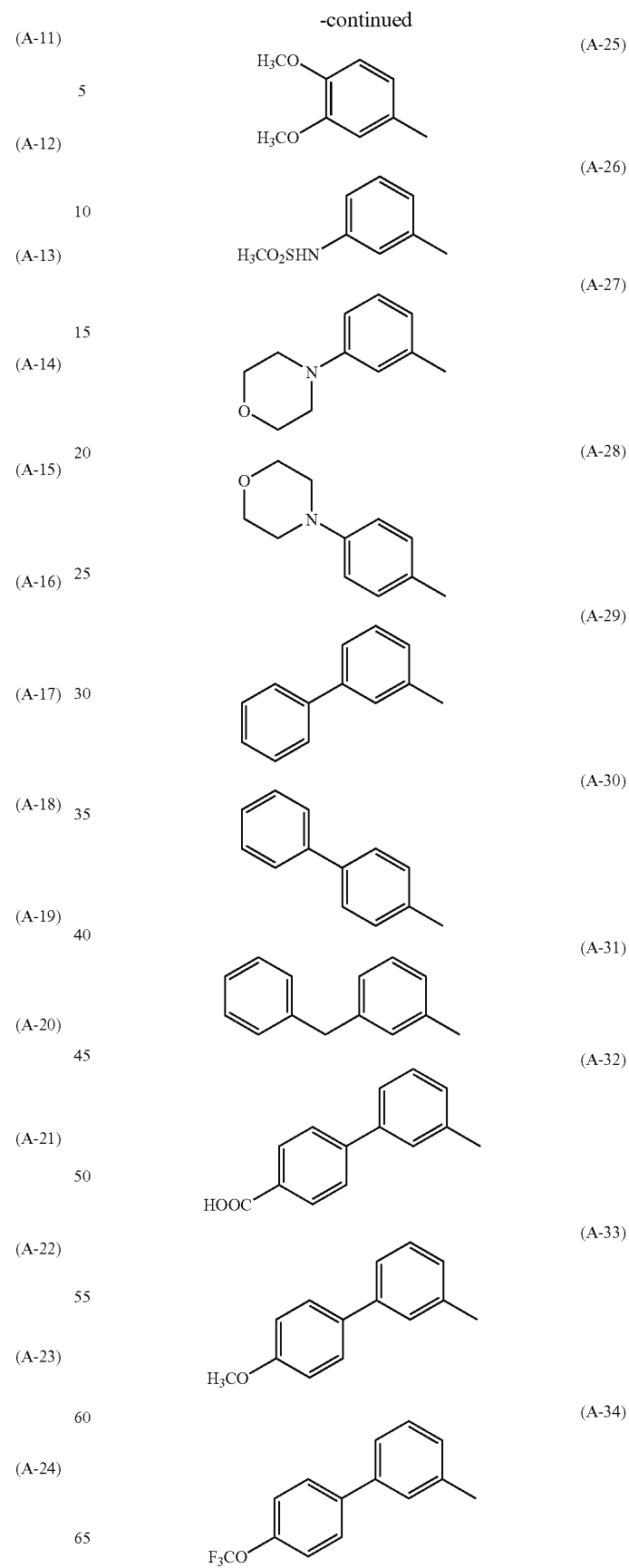

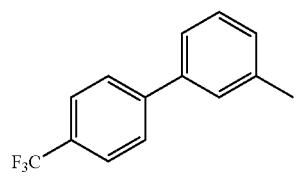
(A-35)
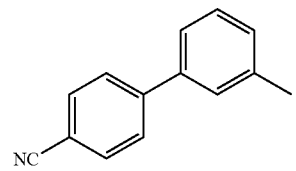
(A-36)
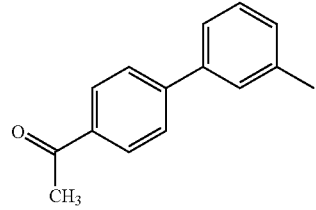
(A-37)
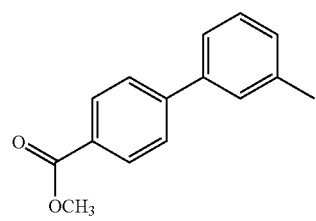
(A-38)
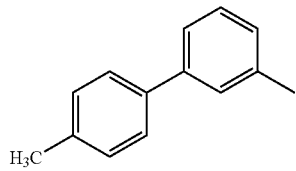
(A-39)
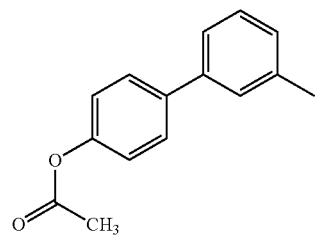
(A-40)
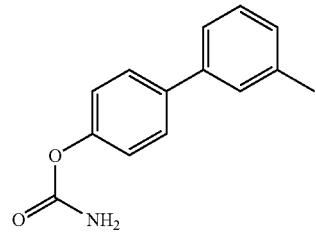
(A-41)
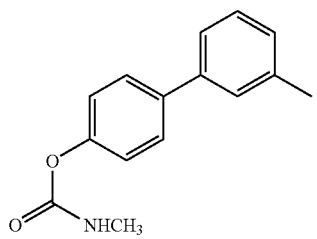
(A-42)
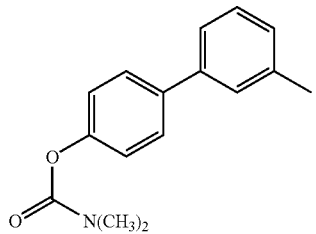
(A-43)
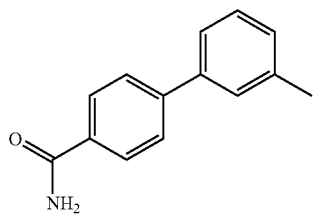
(A-44)
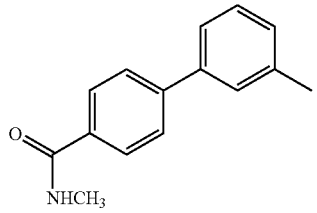
(A-45)
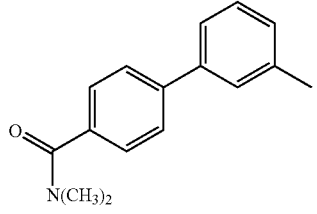
(A-46)
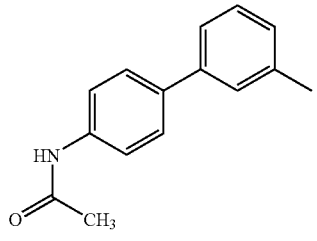
(A-47)
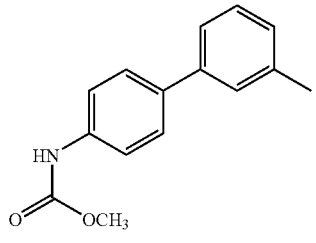
(A-48)

(A-49)
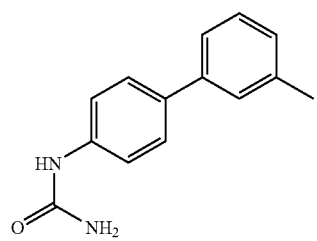
(A-50)
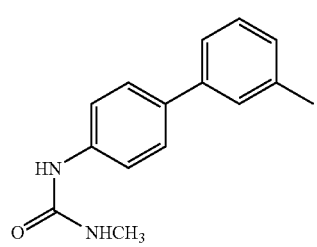
(A-51)
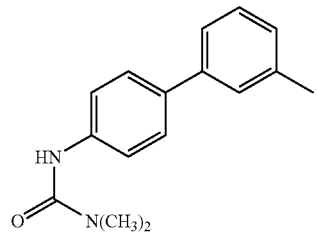
(A-52)
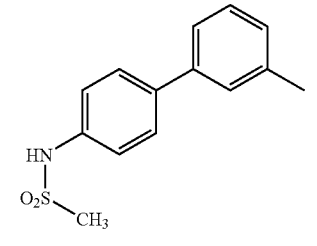
(A-53)
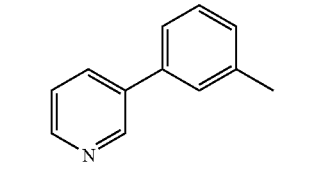
(A-54)
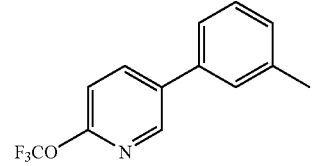
(A-55)
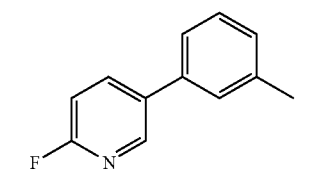
(A-56)
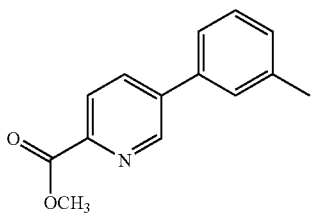
(A-57)
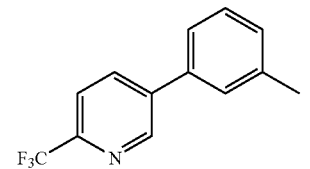
(A-58)
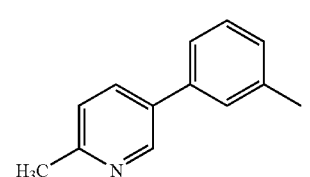
(A-59)
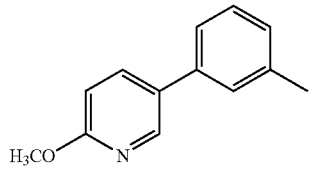
(A-60)
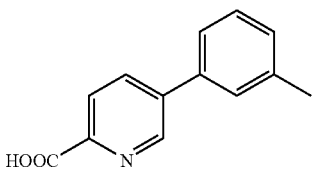
(A-61)
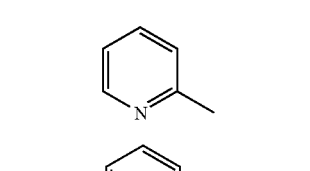
(A-62)
(A-63)
(A-64)
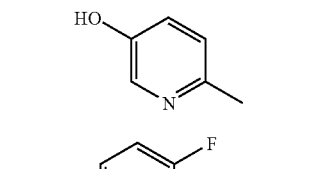
(A-65)
(A-66)
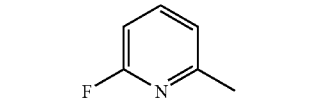

-continued
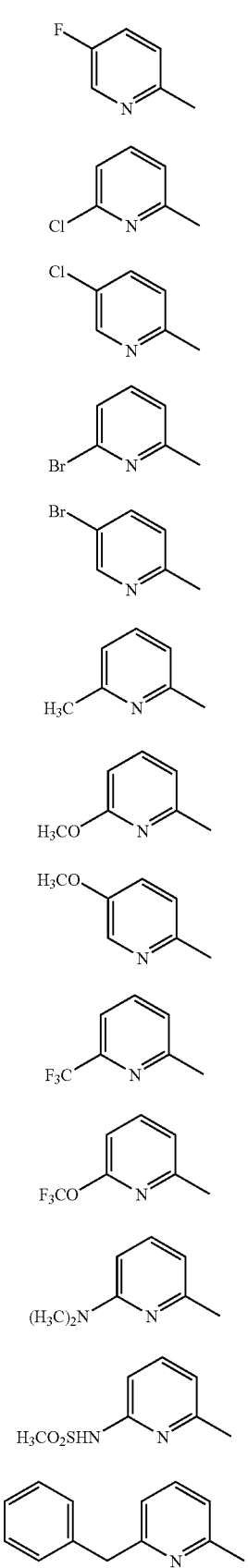
(A-67)
(A-68)
(A-69)
(A-70)
(A-71)
(A-72)
(A-73)
(A-74)
(A-75)
(A-76)
(A-77)
(A-78)
(A-79)
-continued
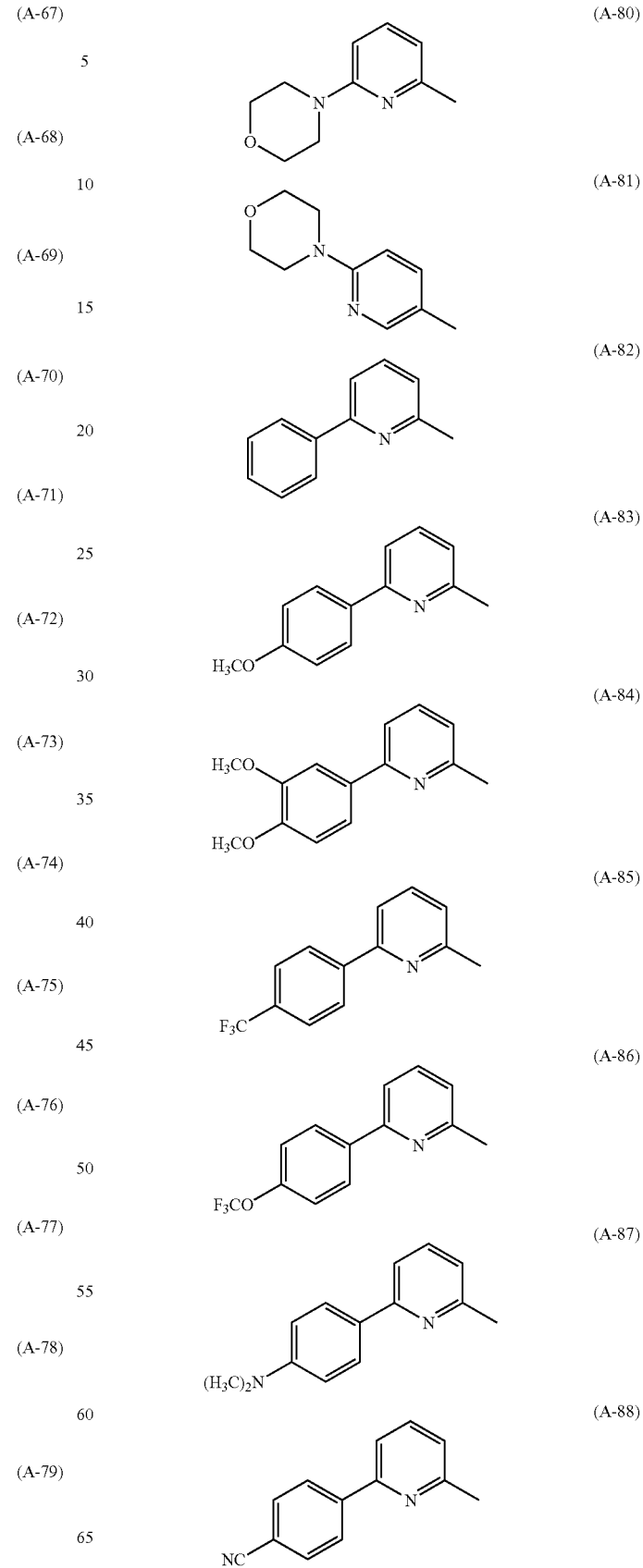
(A-80)
(A-81)
(A-82)
(A-83)
(A-84)
(A-85)
(A-86)
(A-87)
(A-88)

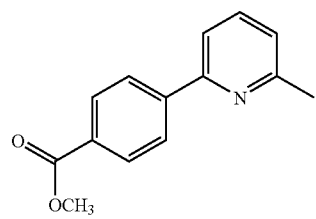
(A-89)
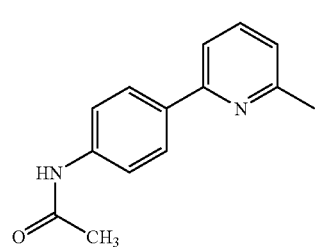
(A-90)
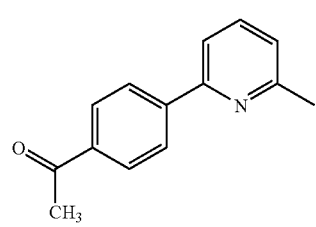
(A-91)
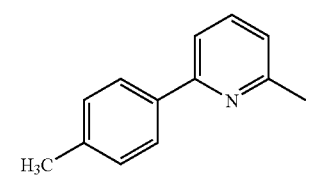
(A-92)
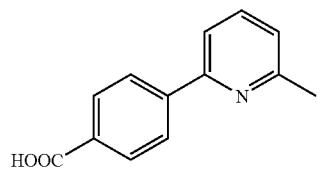
(A-93)
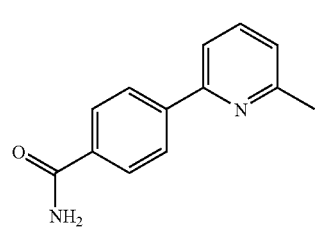
(A-94)
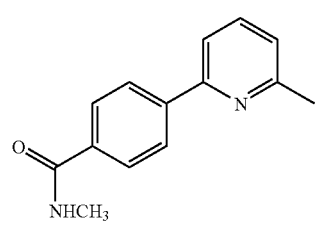
(A-95)
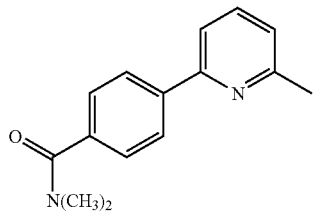
(A-96)
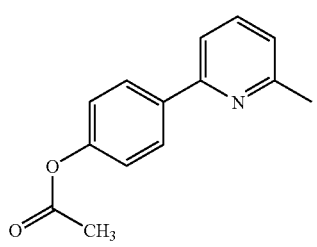
(A-97)
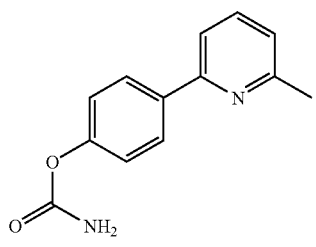
(A-98)
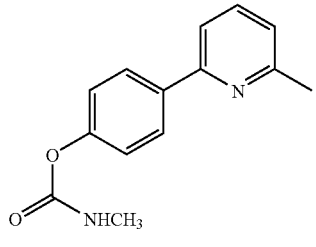
(A-99)
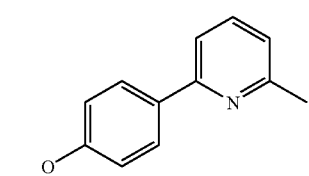
(A-100)
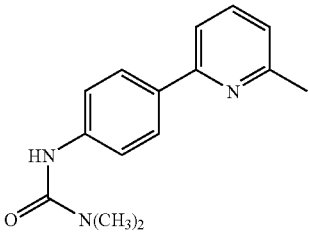
(A-101)

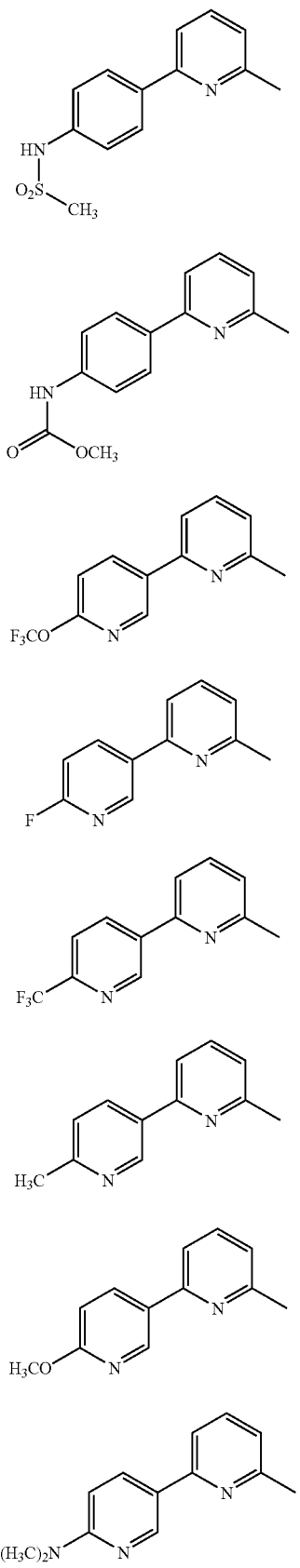
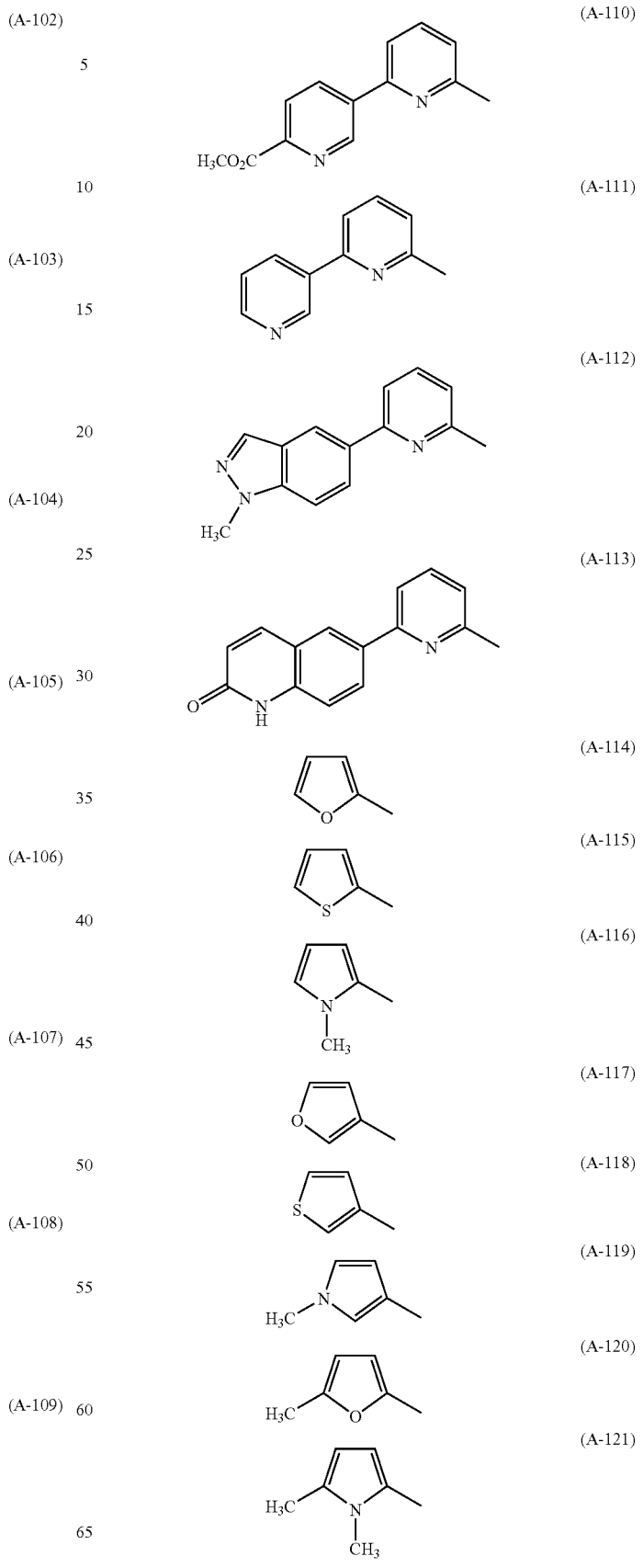

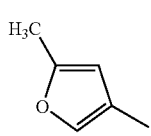 (A-122)
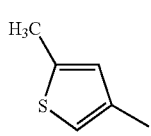 (A-123)
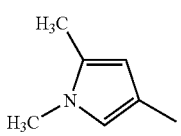 (A-124)
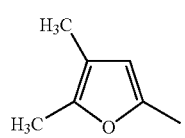 (A-125)
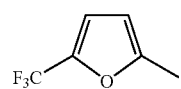 (A-126)
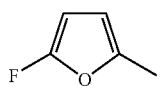 (A-127)
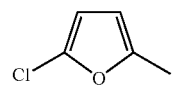 (A-128)
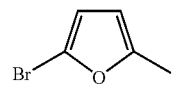 (A-129)
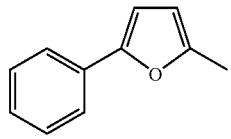 (A-130)
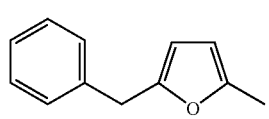 (A-131)
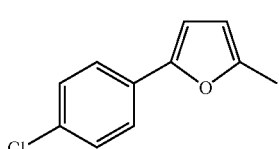 (A-132)
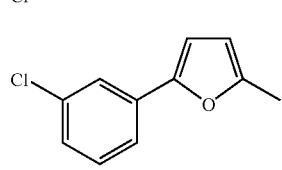 (A-133)
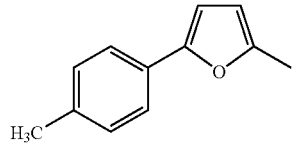 (A-134)
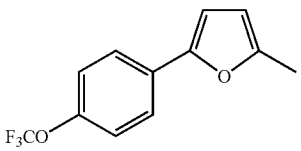 (A-135)
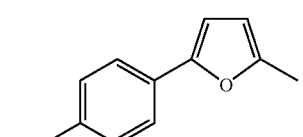 (A-136)
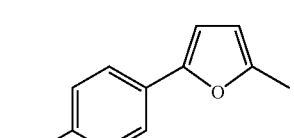 (A-137)
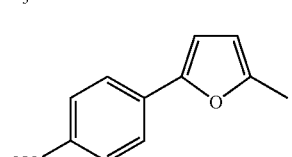 (A-138)
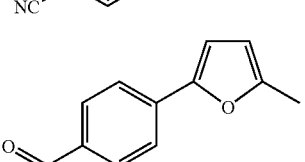 (A-139)
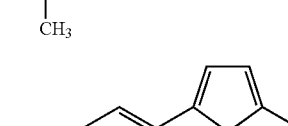 (A-140)
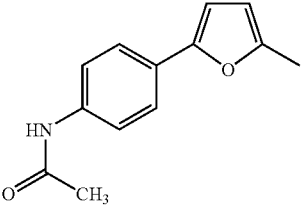 (A-141)
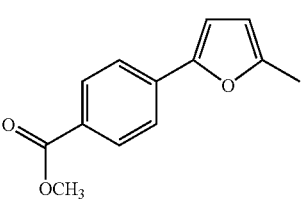 (A-142)

-continued
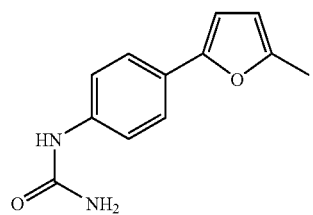 (A-143)
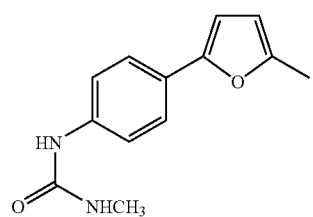 (A-144)
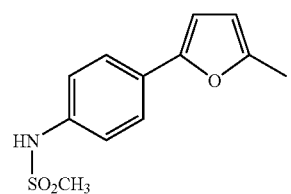 (A-145)
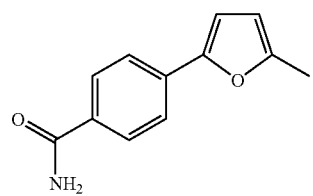 (A-146)
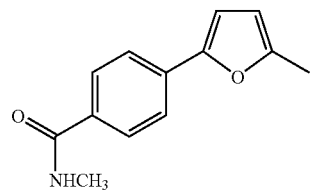 (A-147)
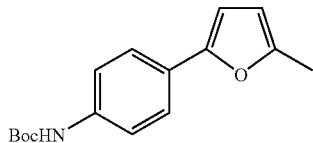 (A-148)
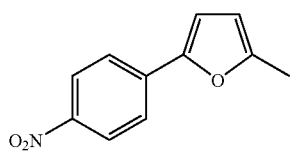 (A-149)
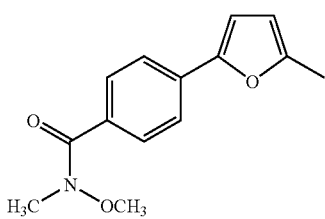 (A-150)
-continued
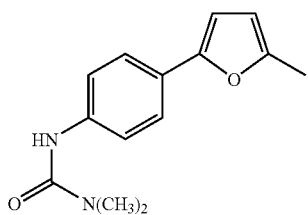 (A-151)
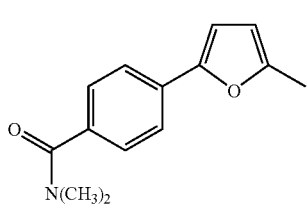 (A-152)
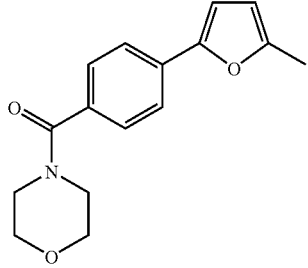 (A-153)
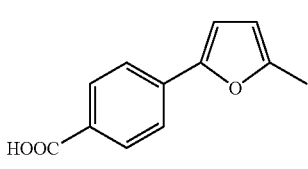 (A-154)
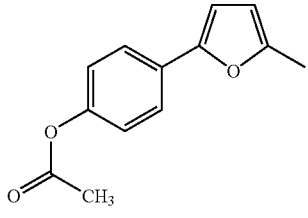 (A-155)
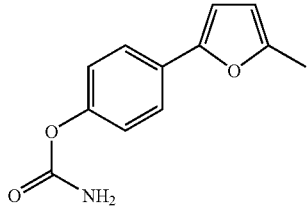 (A-156)
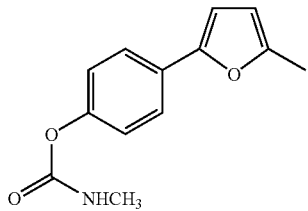 (A-157)

-continued
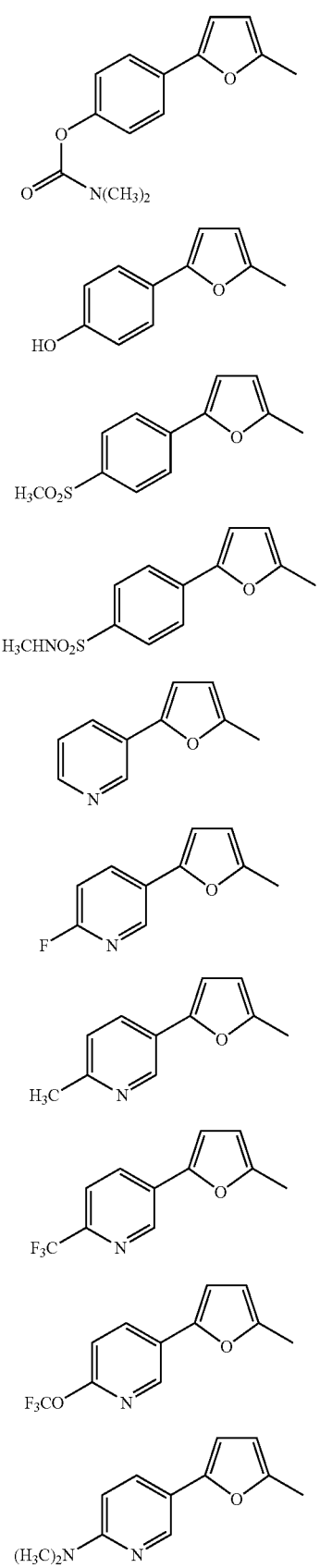
(A-158)
(A-159)
(A-160)
(A-161)
(A-162)
(A-163)
(A-164)
(A-165)
(A-166)
(A-167)
-continued
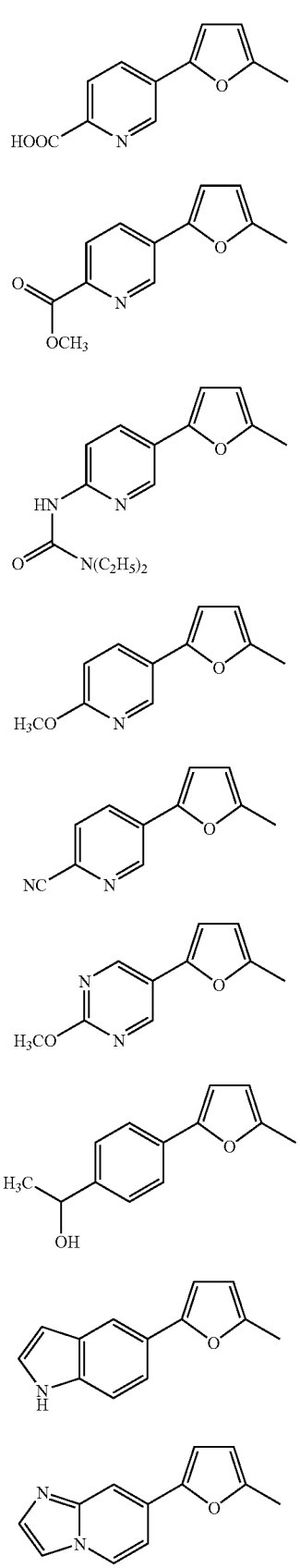
(A-168)
(A-169)
(A-170)
(A-171)
(A-172)
(A-173)
(A-174)
(A-175)
(A-176)

-continued
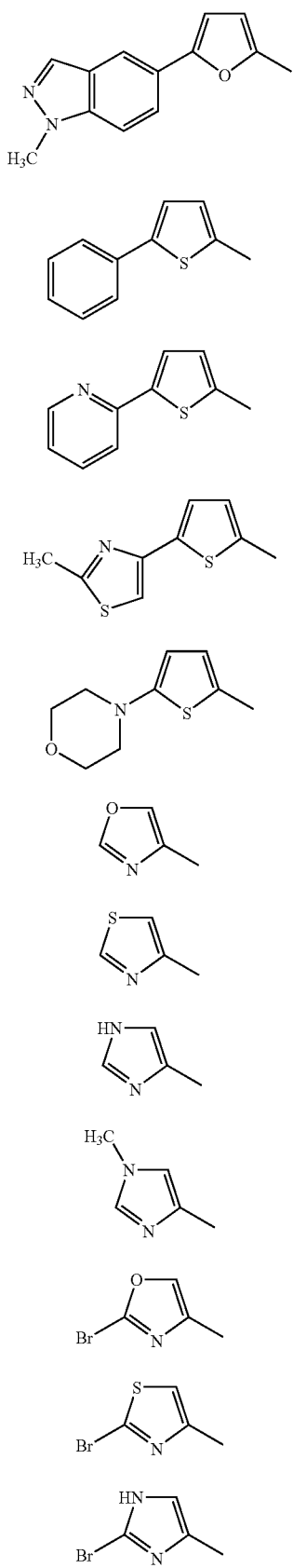
(A-177)
(A-178)
(A-179)
(A-180)
(A-181)
(A-182)
(A-183)
(A-184)
(A-185)
(A-186)
(A-187)
(A-188)
-continued
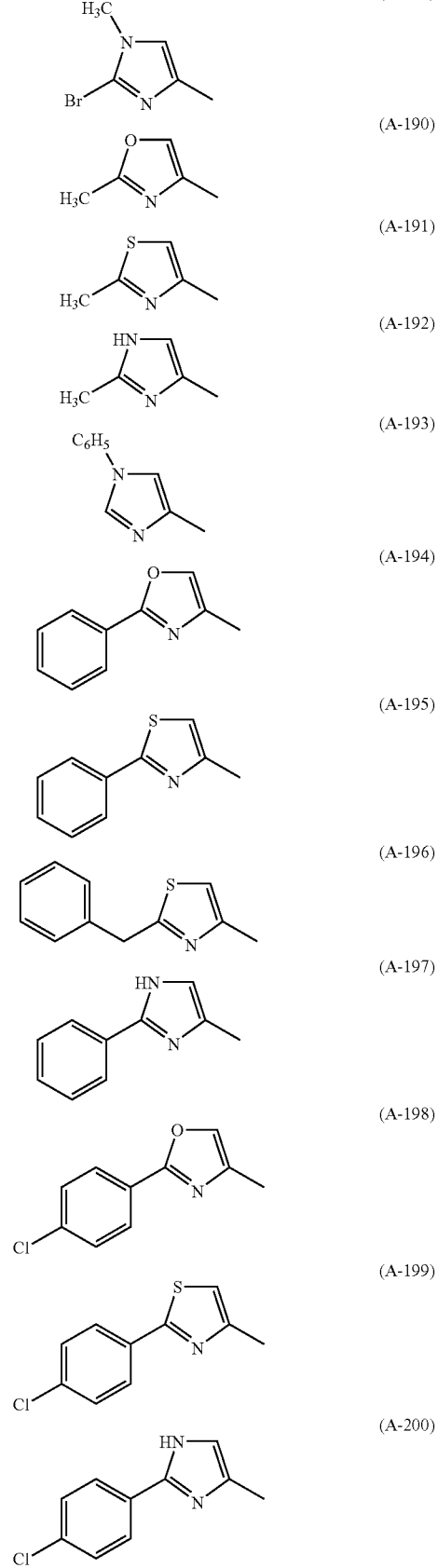
(A-189)
(A-190)
(A-191)
(A-192)
(A-193)
(A-194)
(A-195)
(A-196)
(A-197)
(A-198)
(A-199)
(A-200)

-continued
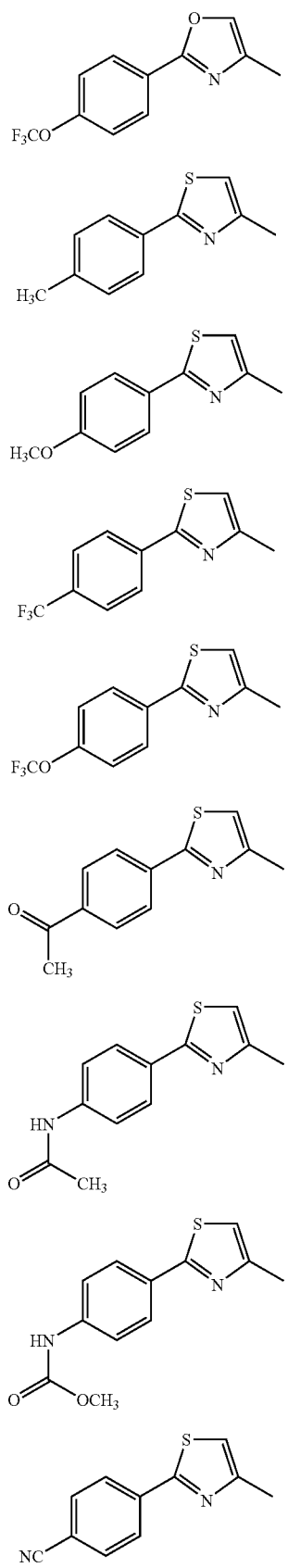
(A-201)
(A-202)
(A-203)
(A-204)
(A-205)
(A-206)
(A-207)
(A-208)
(A-209)
-continued
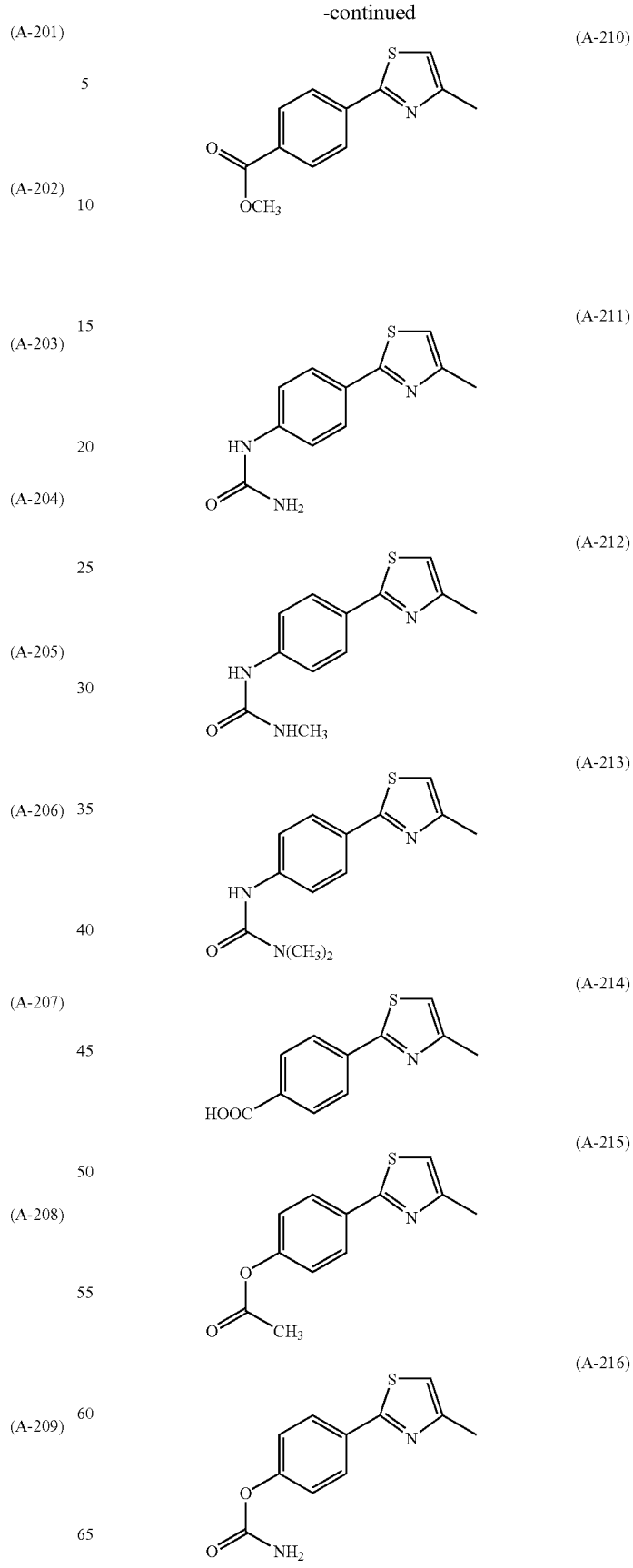
(A-210)
(A-211)
(A-212)
(A-213)
(A-214)
(A-215)
(A-216)

-continued
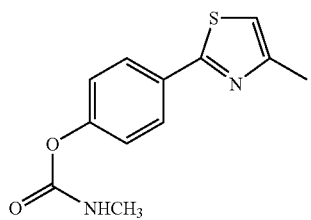 (A-217)
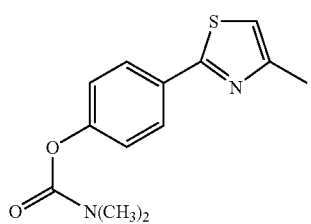 (A-218)
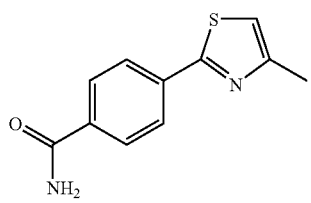 (A-219)
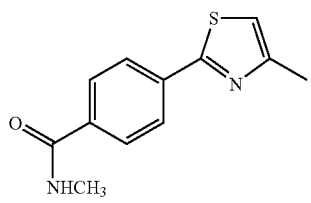 (A-220)
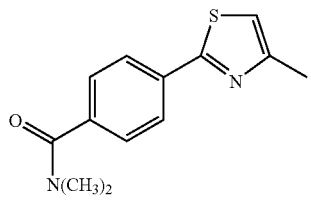 (A-221)
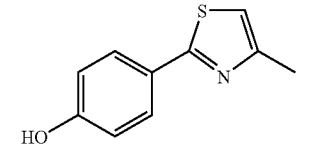 (A-222)
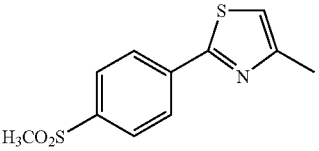 (A-223)
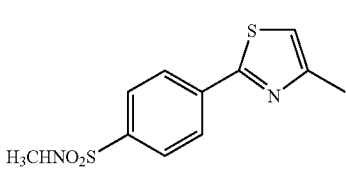 (A-224)
-continued
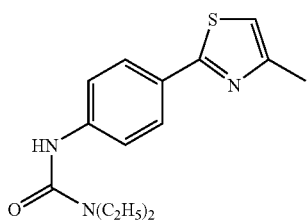 (A-225)
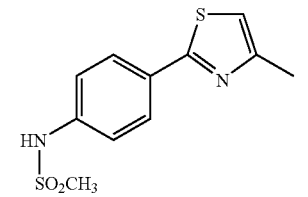 (A-226)
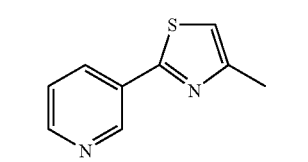 (A-227)
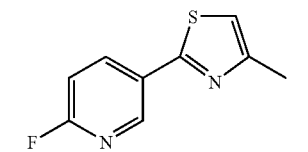 (A-228)
 (A-229)
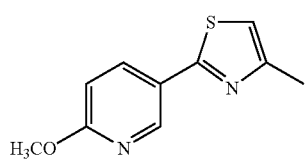 (A-230)
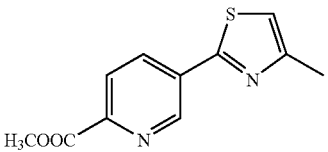 (A-231)
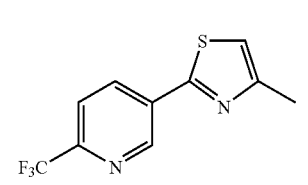 (A-232)
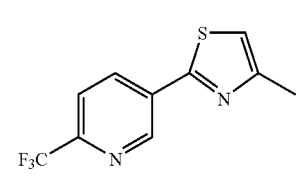 (A-233)

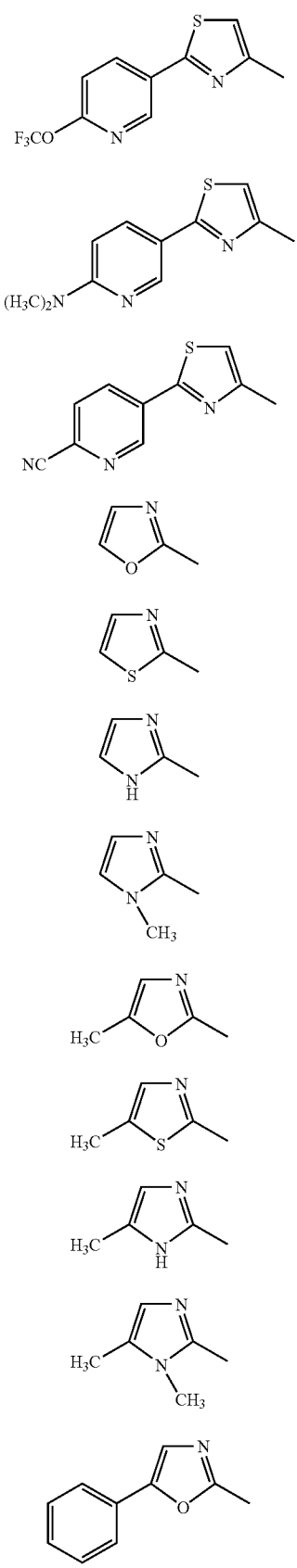
(A-234)
(A-235)
(A-236)
(A-237)
(A-238)
(A-239)
(A-240)
(A-241)
(A-242)
(A-243)
(A-244)
(A-245)
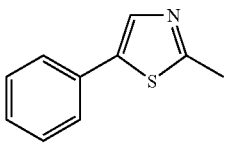
(A-246)
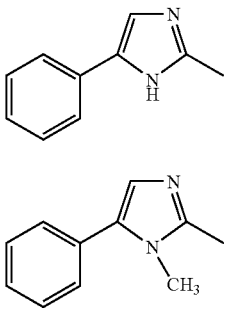
(A-247)
(A-248)
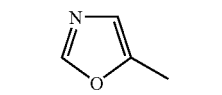
(A-249)
(A-250)
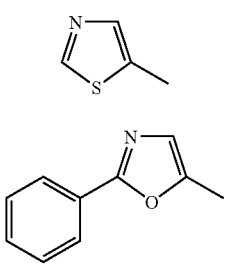
(A-251)
(A-252)
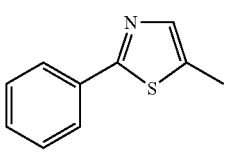
(A-253)
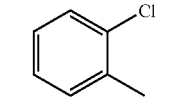
(A-254)
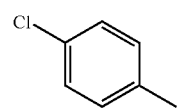
(A-255)
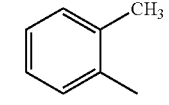
(A-256)
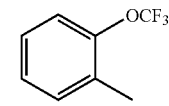
(A-257)
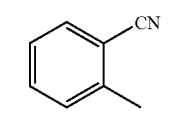

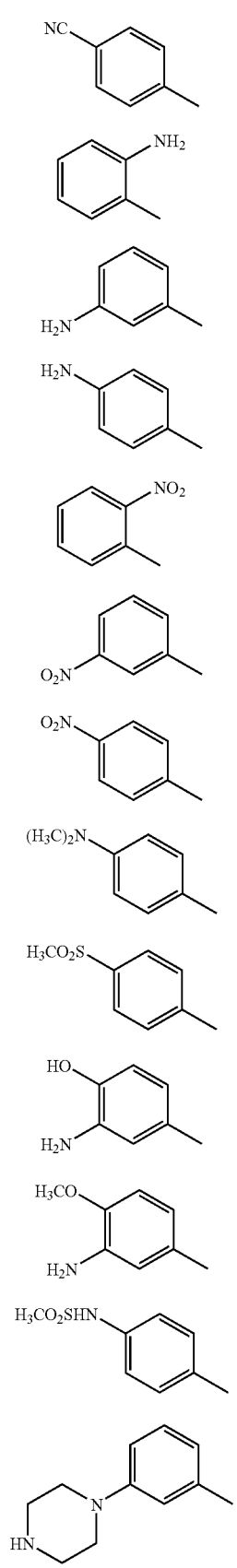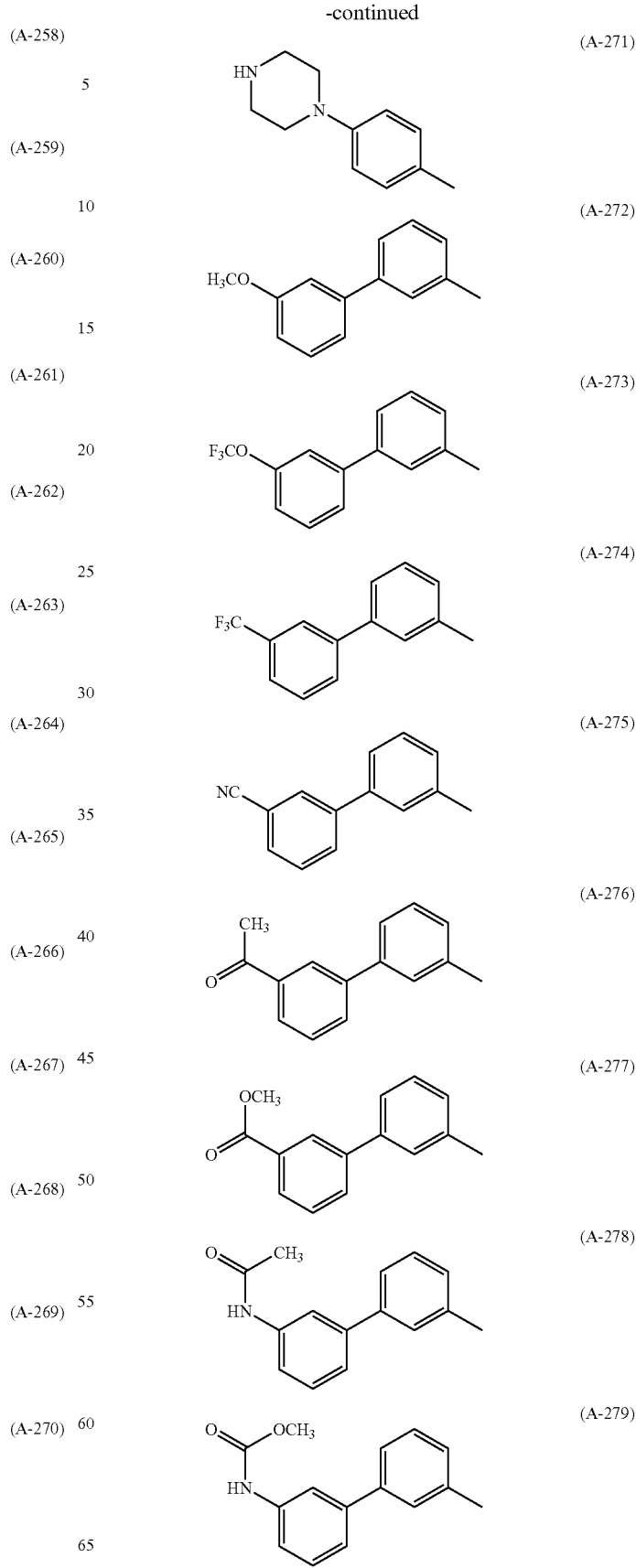

-continued
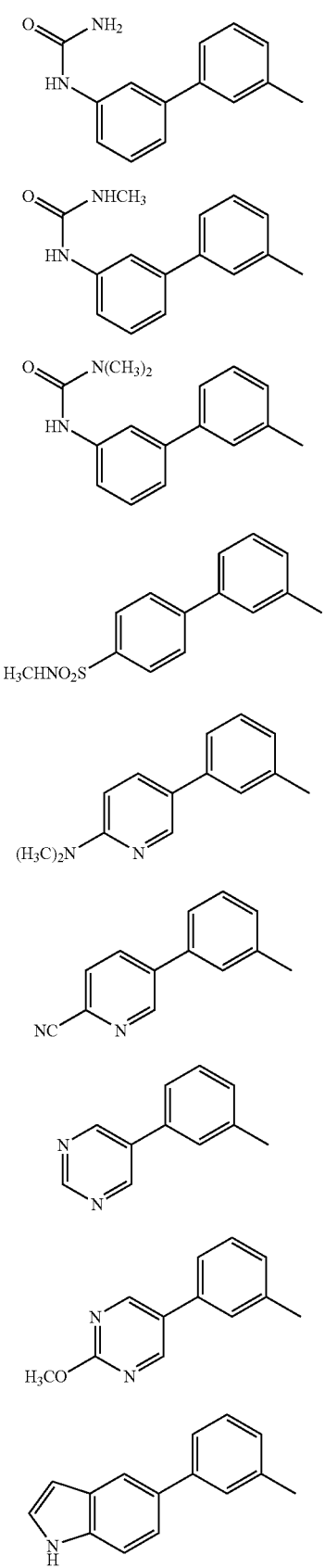
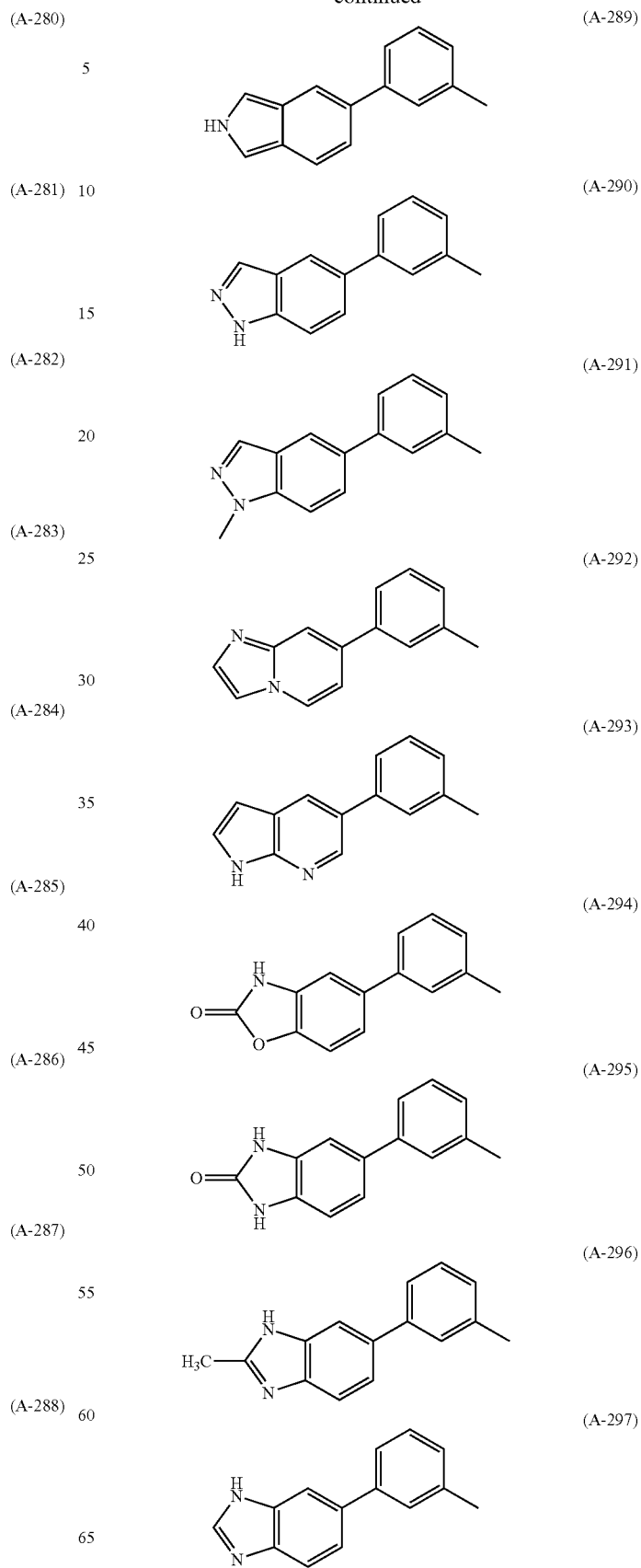

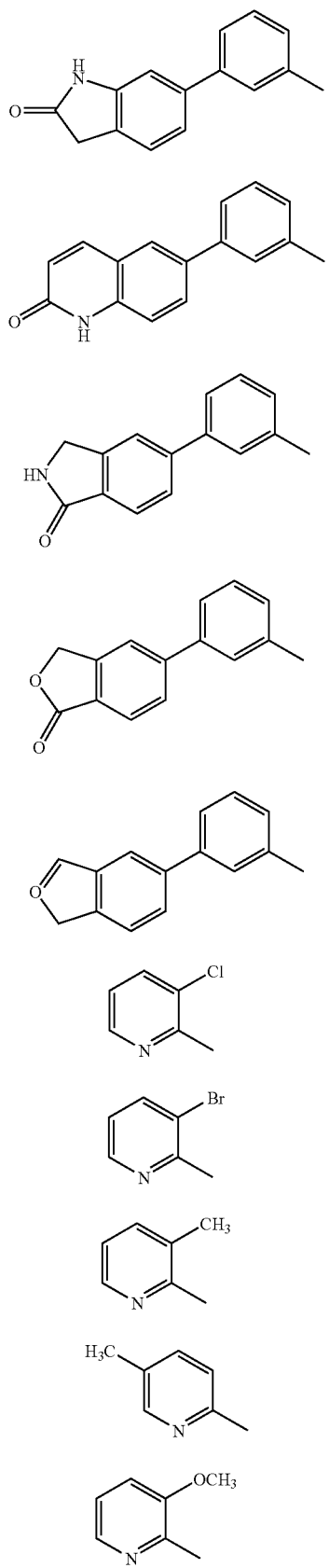
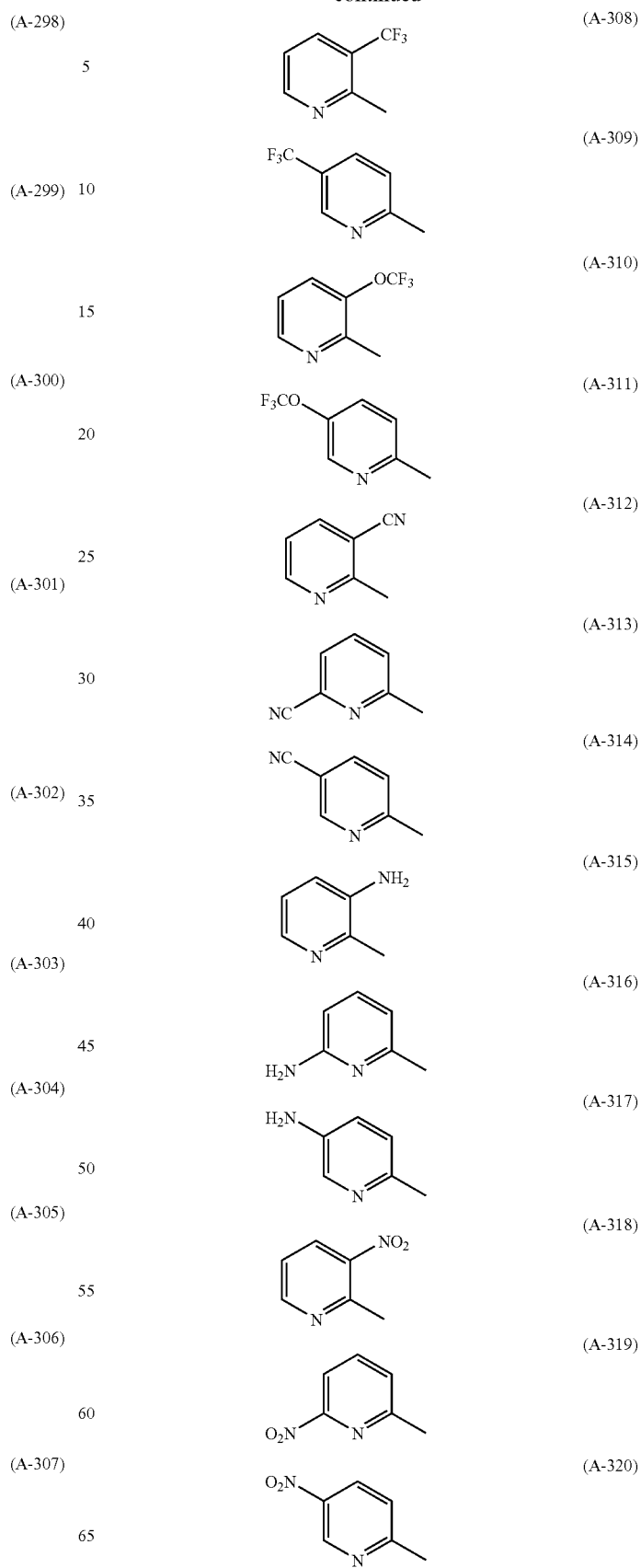

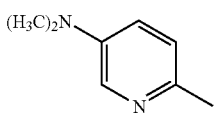 (A-321)
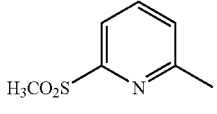 (A-322)
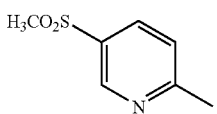 (A-323)
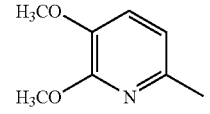 (A-324)
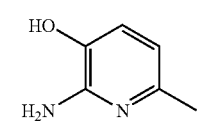 (A-325)
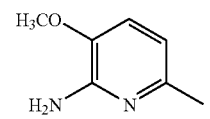 (A-326)
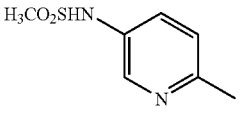 (A-327)
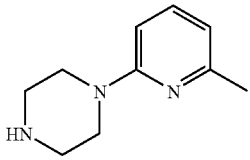 (A-328)
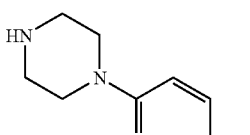 (A-329)
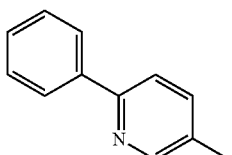 (A-330)
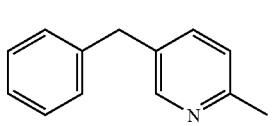 (A-331)
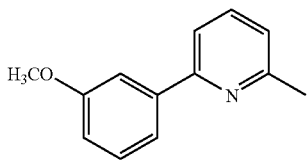 (A-332)
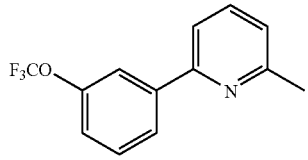 (A-333)
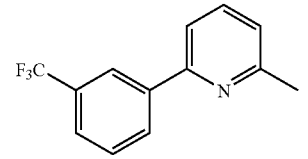 (A-334)
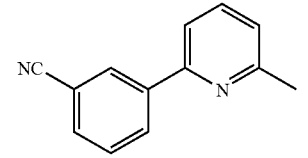 (A-335)
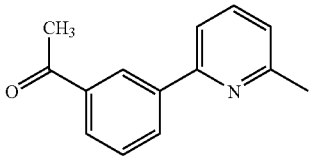 (A-336)
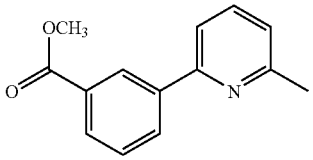 (A-337)
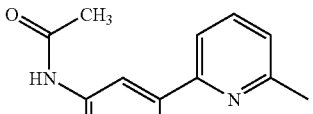 (A-338)
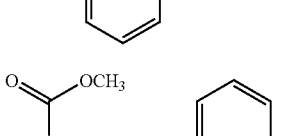 (A-339)
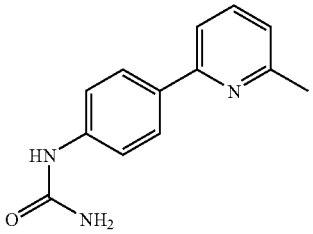 (A-340)

-continued
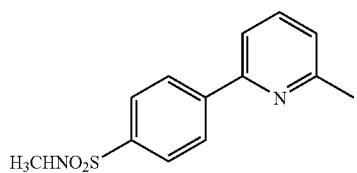 (A-341)
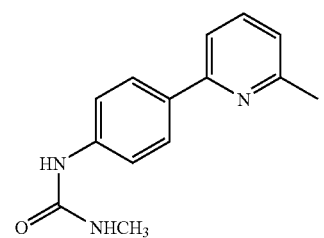 (A-342)
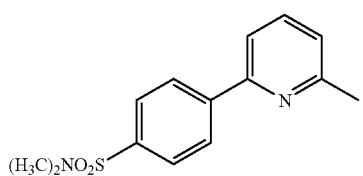 (A-343)
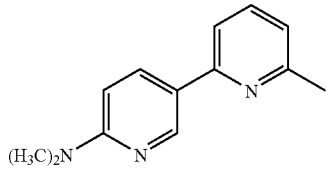 (A-344)
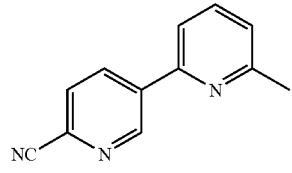 (A-345)
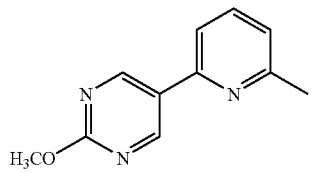 (A-346)
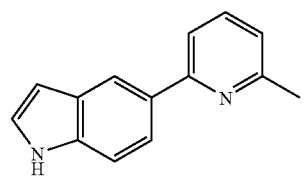 (A-347)
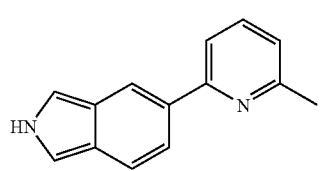 (A-348)
-continued
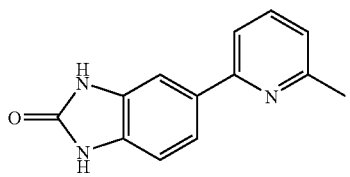 (A-349)
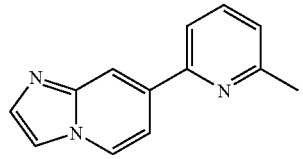 (A-350)
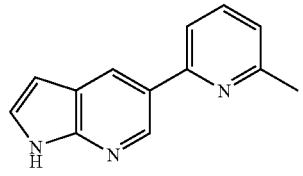 (A-351)
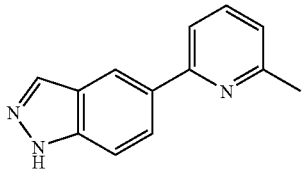 (A-352)
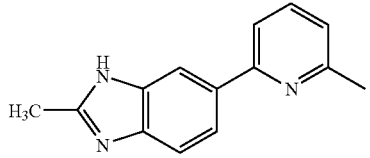 (A-353)
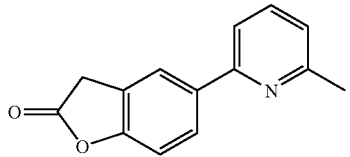 (A-354)
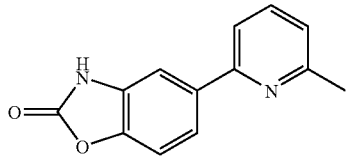 (A-355)
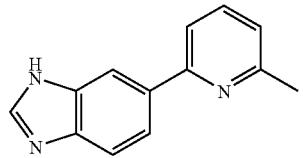 (A-356)
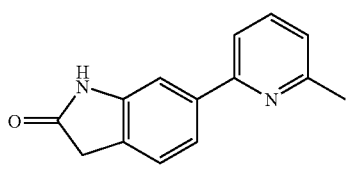 (A-357)

-continued
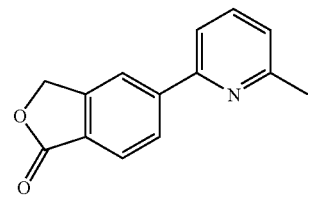
(A-358)
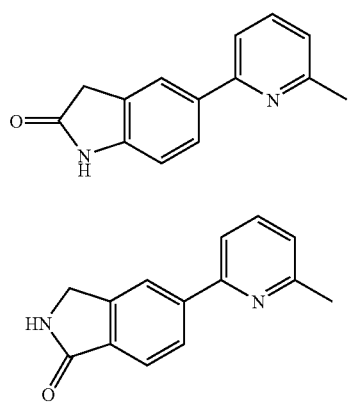
(A-359)
(A-360)
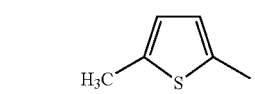
(A-361)
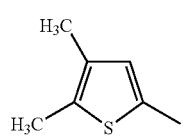
(A-362)
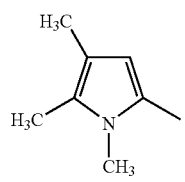
(A-363)
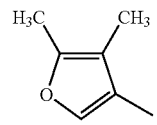
(A-364)
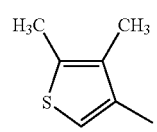
(A-365)
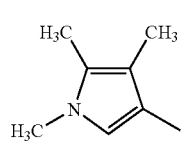
(A-366)
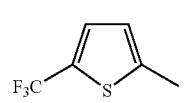
(A-367)
-continued
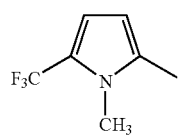
(A-368)
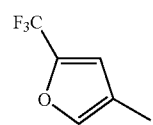
(A-369)
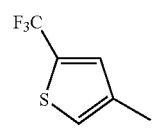
(A-370)
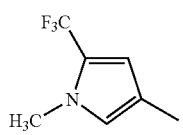
(A-371)
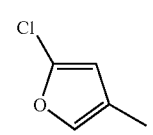
(A-372)
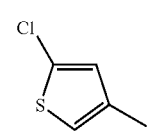
(A-373)
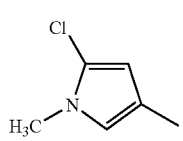
(A-374)
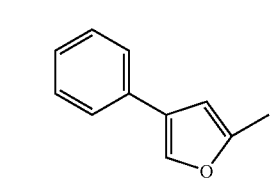
(A-376)
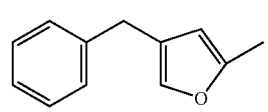
(A-377)
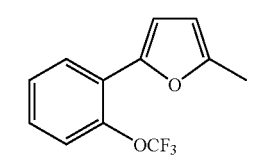
(A-378)
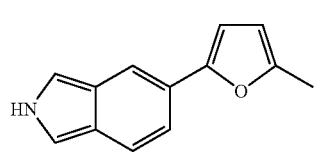
(A-379)

-continued
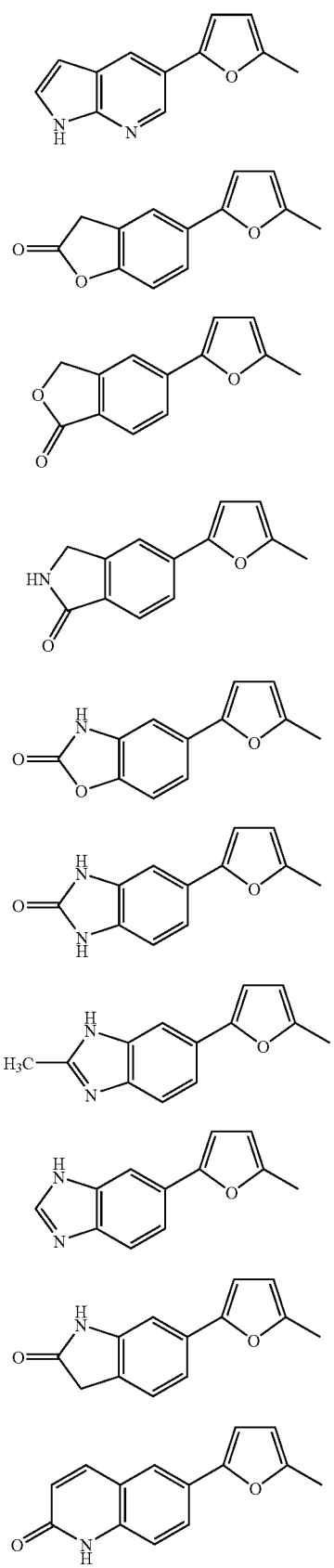
(A-380)
(A-381)
(A-382)
(A-383)
(A-384)
(A-385)
(A-386)
(A-387)
(A-388)
(A-389)
-continued
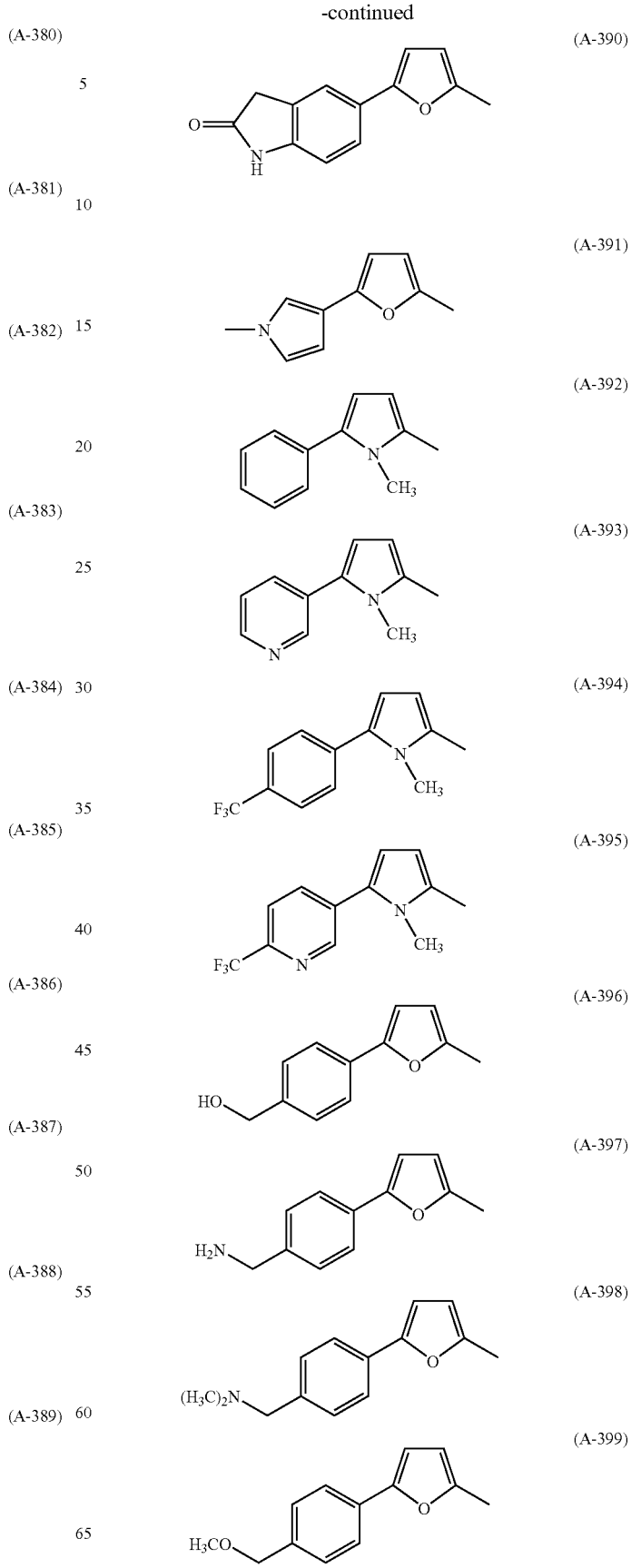
(A-390)
(A-391)
(A-392)
(A-393)
(A-394)
(A-395)
(A-396)
(A-397)
(A-398)
(A-399)

-continued
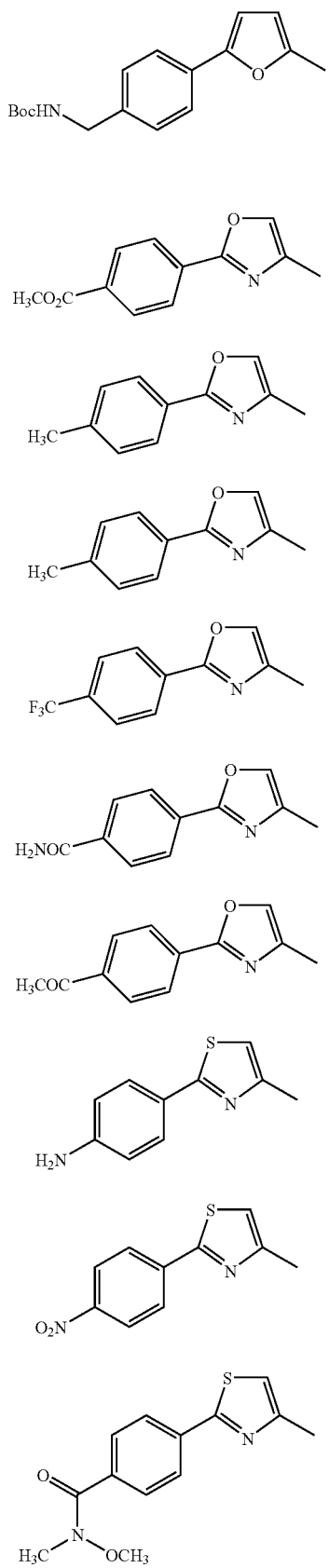
(A-400)
(A-401)
(A-402)
(A-403)
(A-404)
(A-405)
(A-406)
(A-407)
(A-408)
(A-409)
-continued
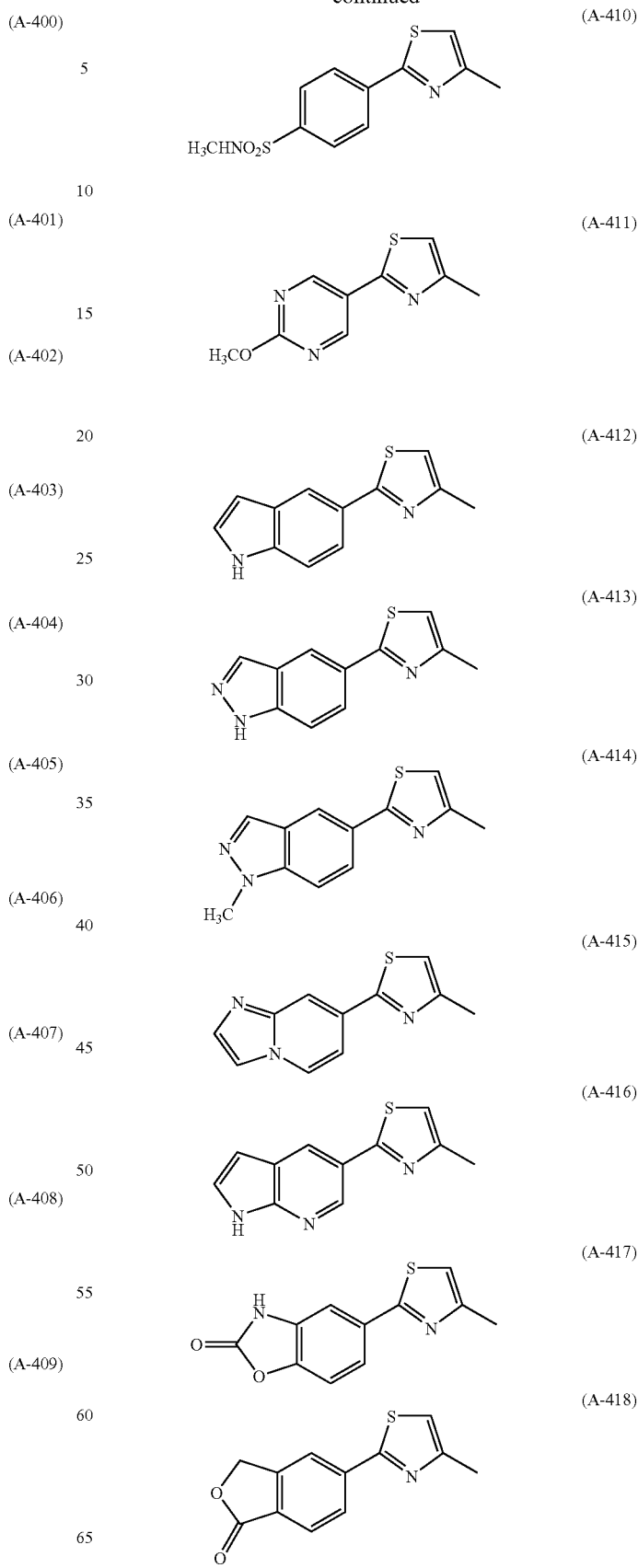
(A-410)
(A-411)
(A-412)
(A-413)
(A-414)
(A-415)
(A-416)
(A-417)
(A-418)

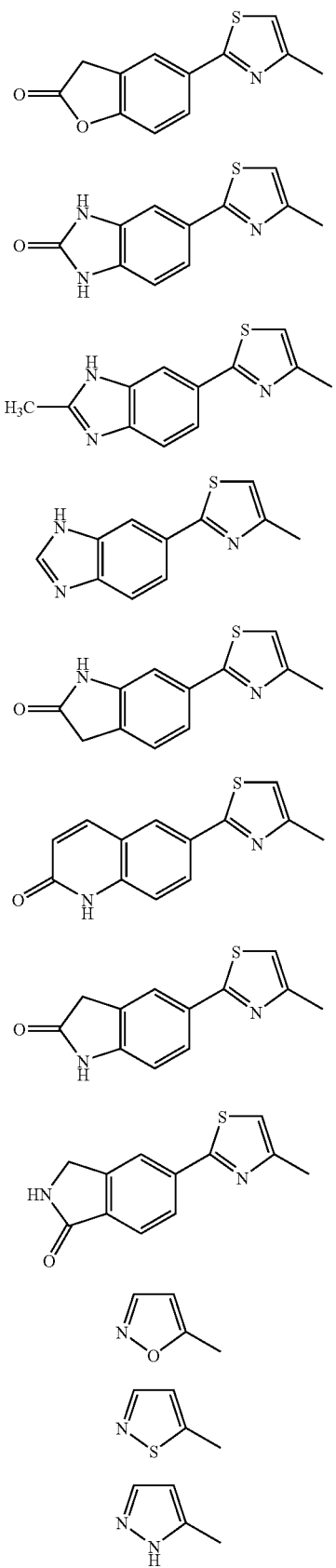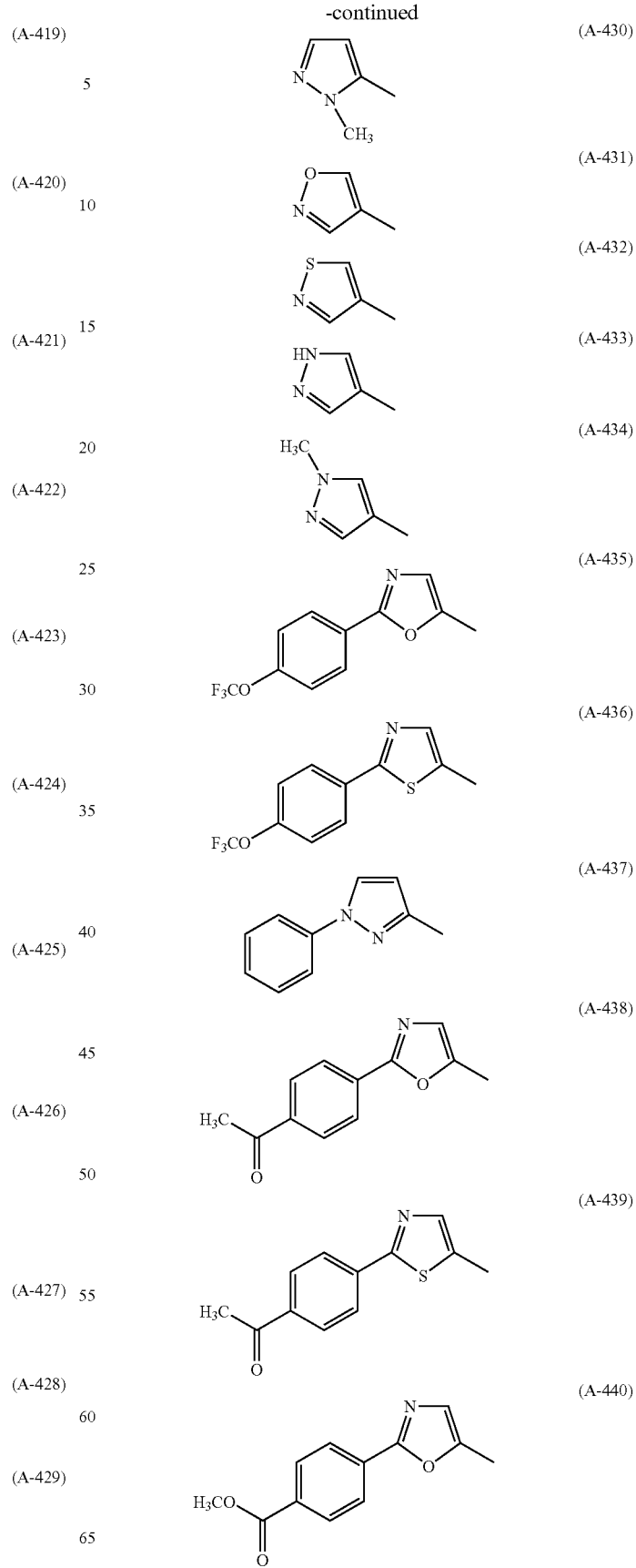

-continued
(A-441)
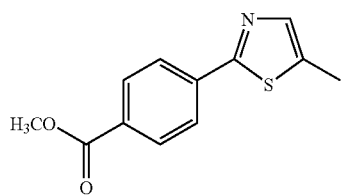
(A-442)
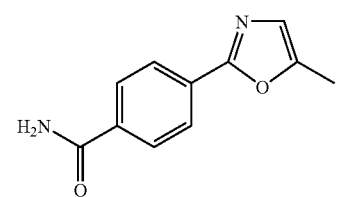
(A-443)
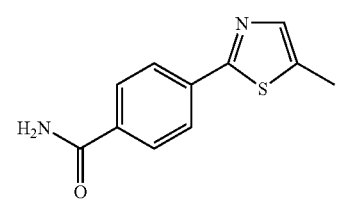
(A-444)
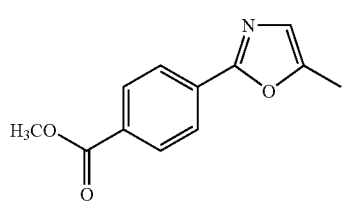
(A-445)
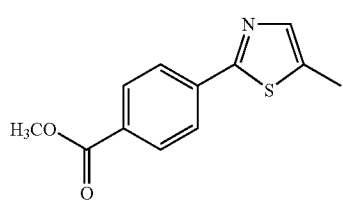
(A-446)
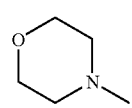
(A-447)
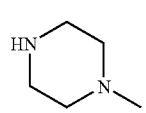
(A-448)
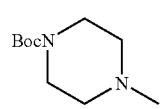
(A-449)
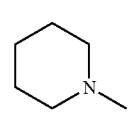
(A-450)
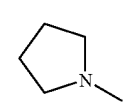
-continued
(A-451)
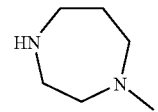
(A-452)
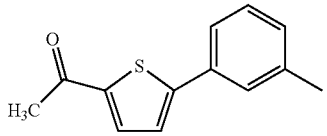
(A-453)
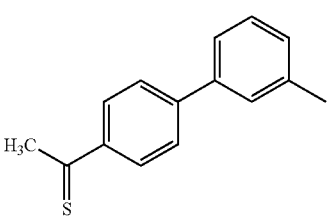
(A-454)
(A-455)
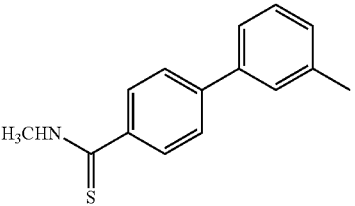
(A-456)
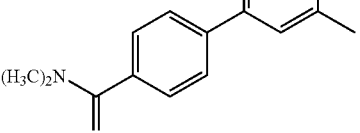
(A-457)
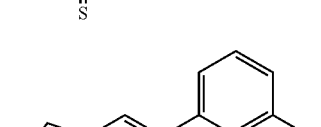
(A-458)
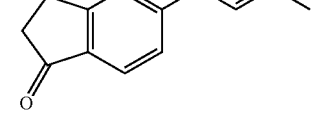

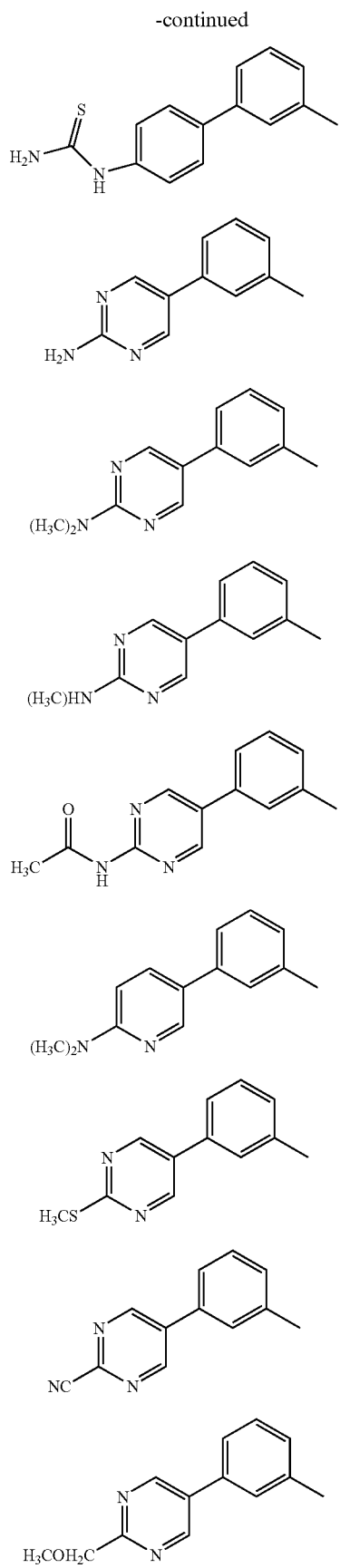

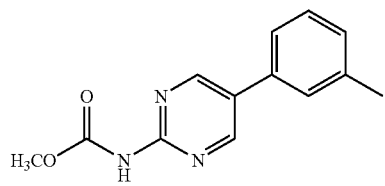
(A-476)
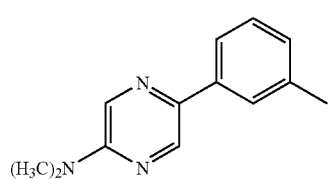
(A-477)
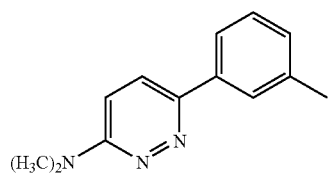
(A-478)
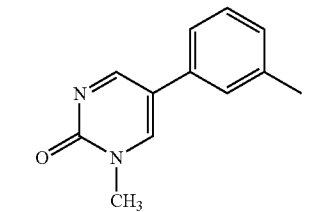
(A-479)
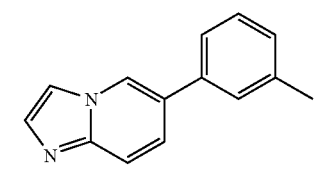
(A-480)
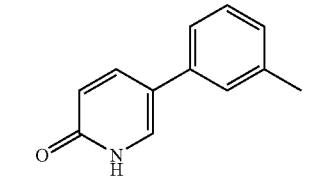
(A-481)
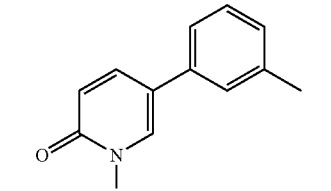
(A-482)
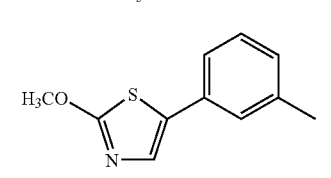
(A-483)
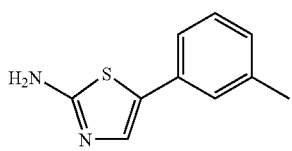
(A-484)
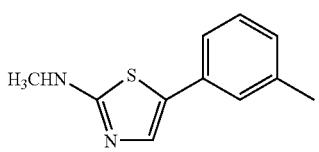
(A-485)
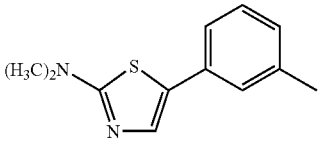
(A-486)
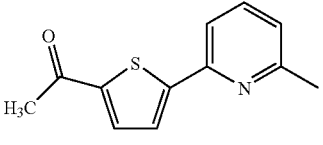
(A-487)
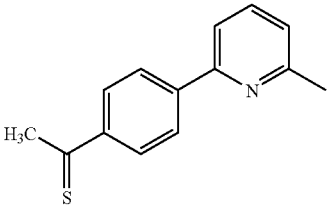
(A-488)
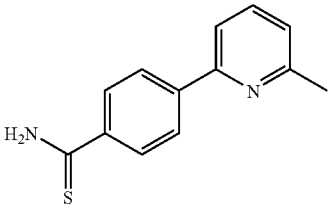
(A-489)
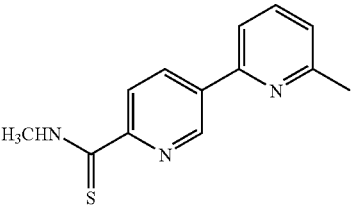
(A-490)
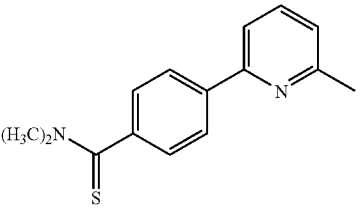
(A-491)

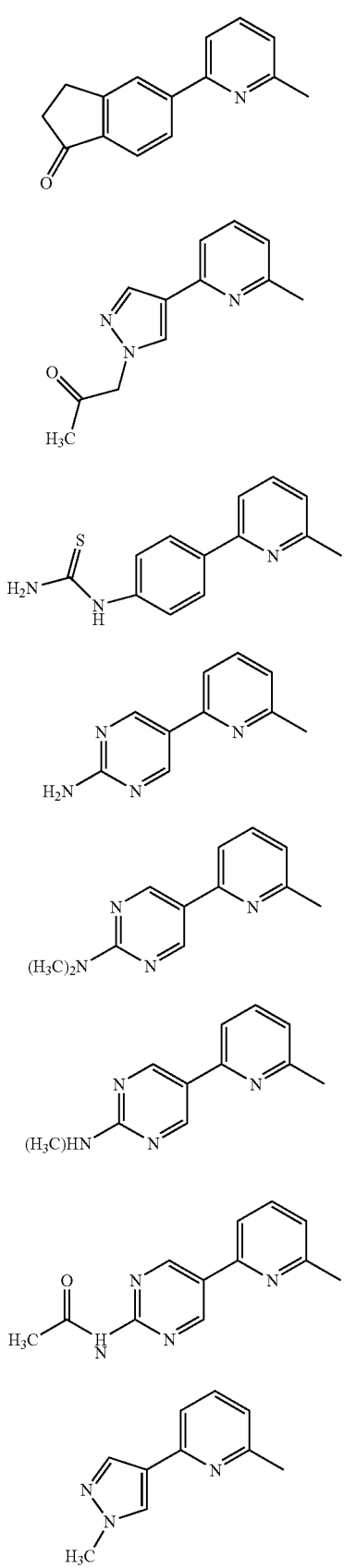

-continued
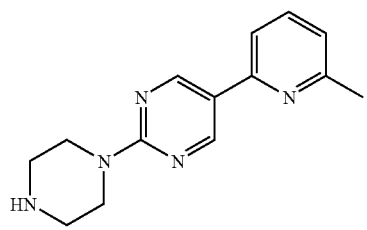 (A-508)
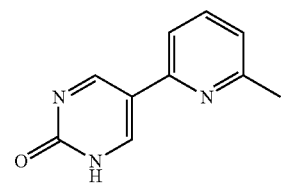 (A-509)
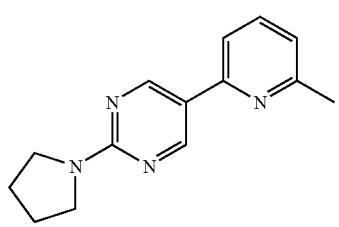 (A-510)
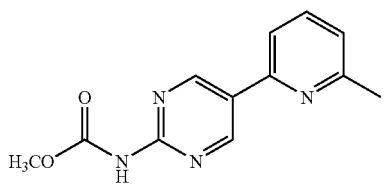 (A-511)
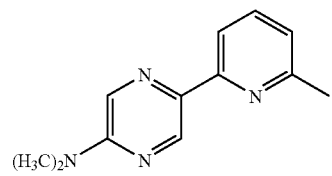 (A-512)
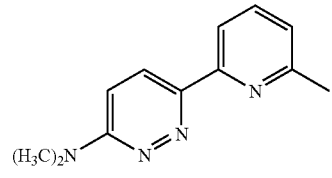 (A-513)
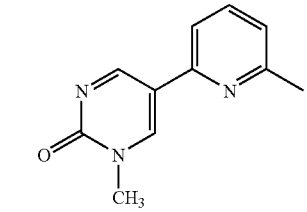 (A-514)
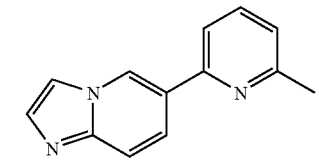 (A-515)
-continued
(A-516)
(A-517)
(A-518)
(A-519)
(A-520)
(A-521)
(A-522)
(A-523)
(A-524)

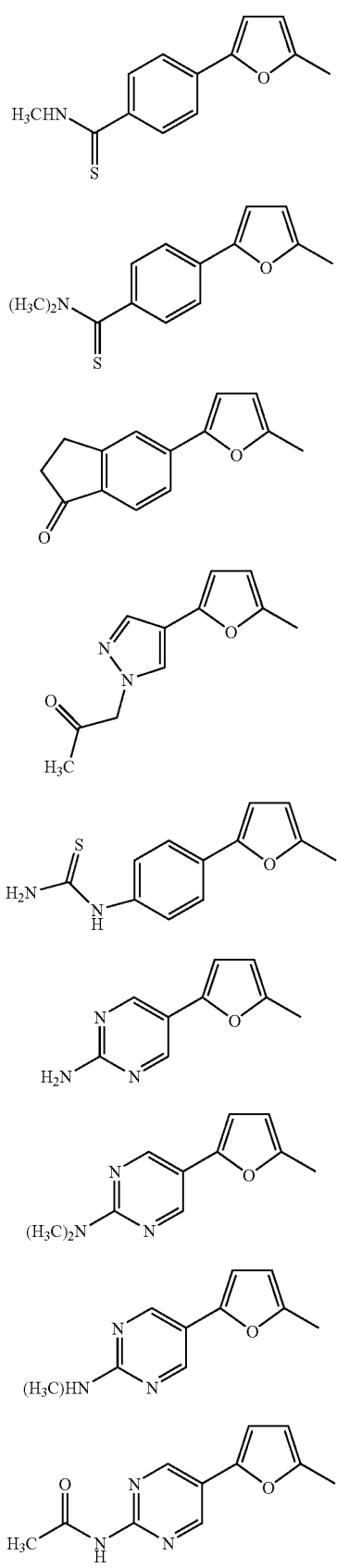
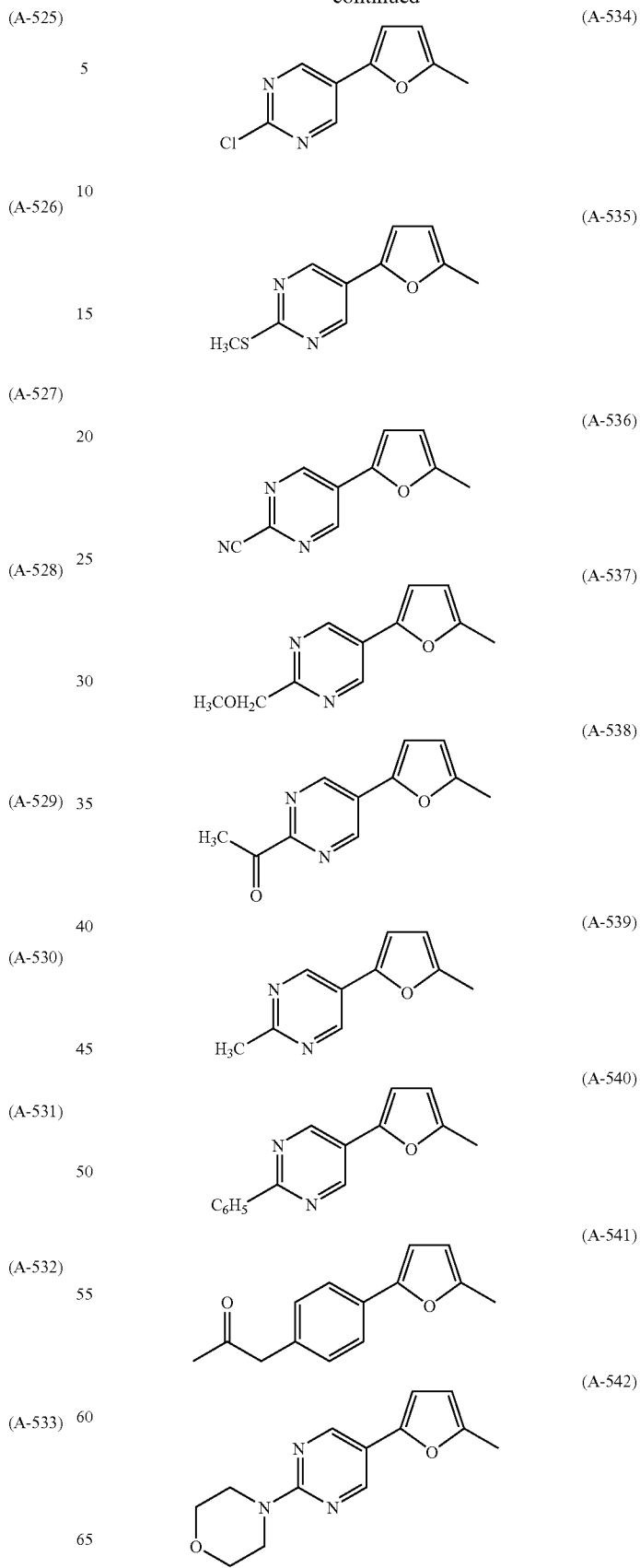

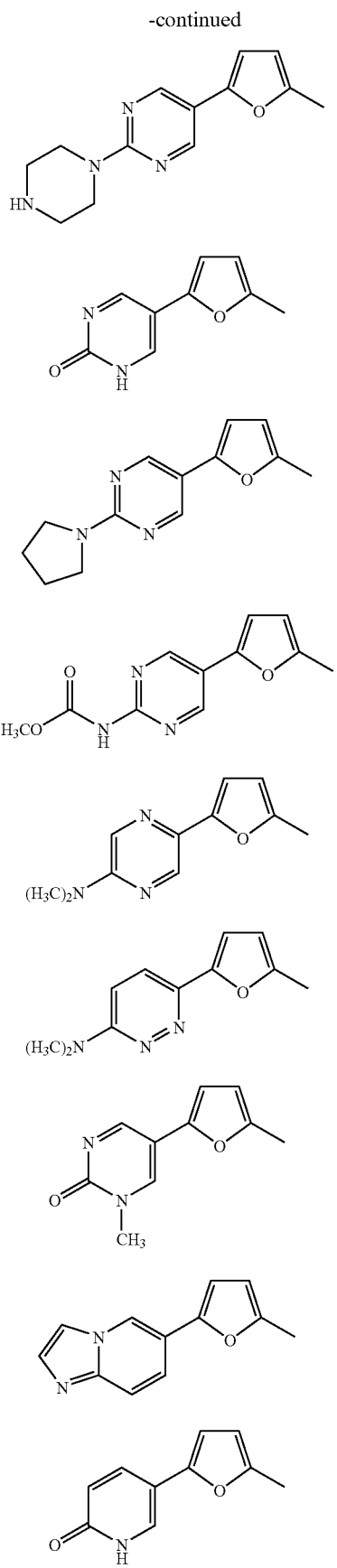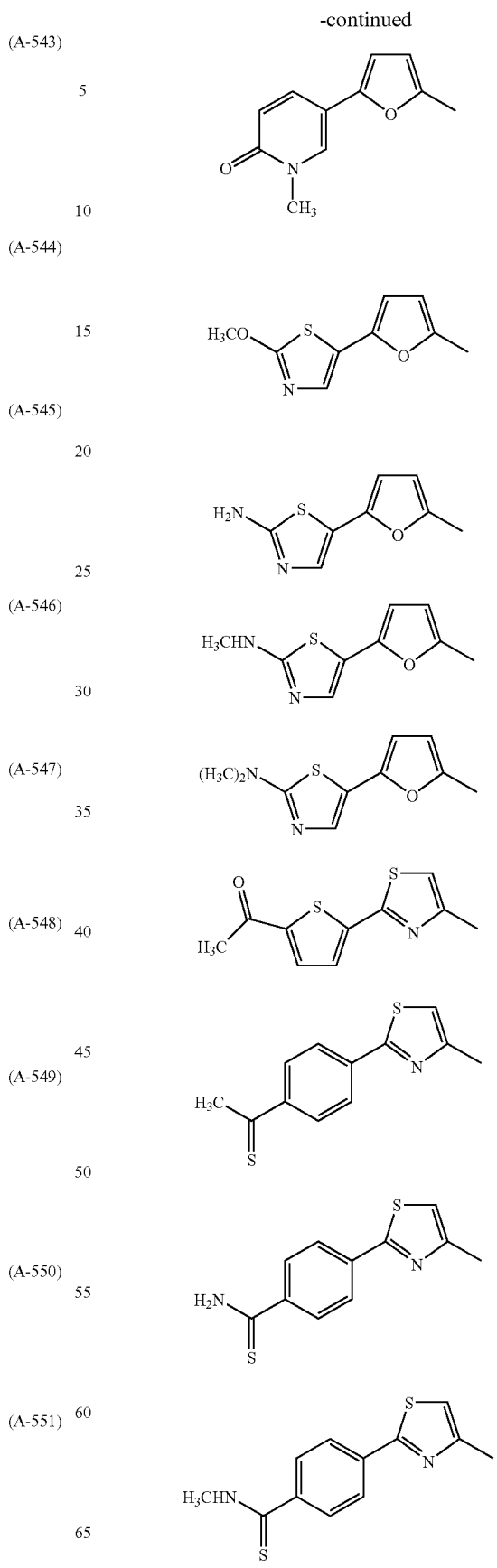

-continued
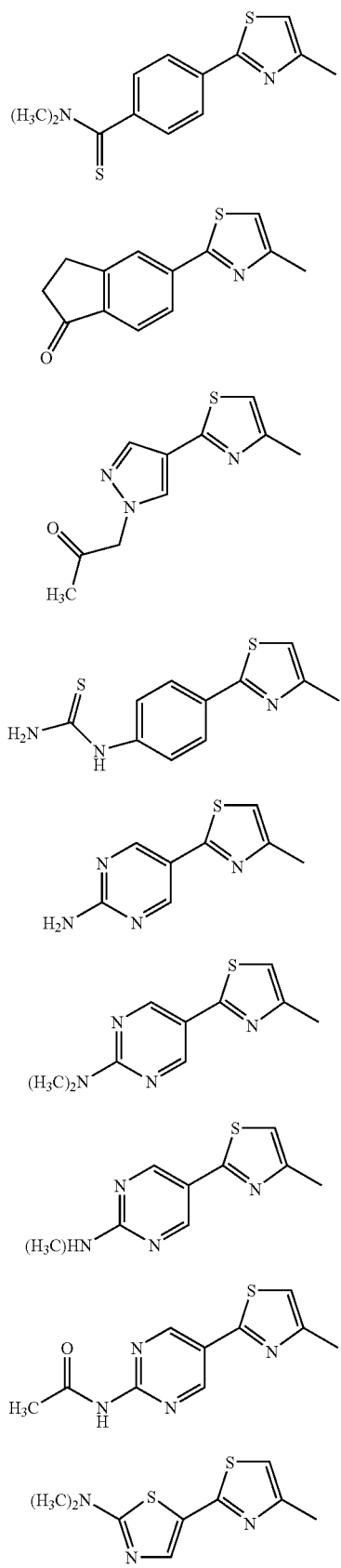
(A-561)
(A-562)
(A-563)
(A-564)
(A-565)
(A-566)
(A-567)
(A-568)
(A-569)
-continued
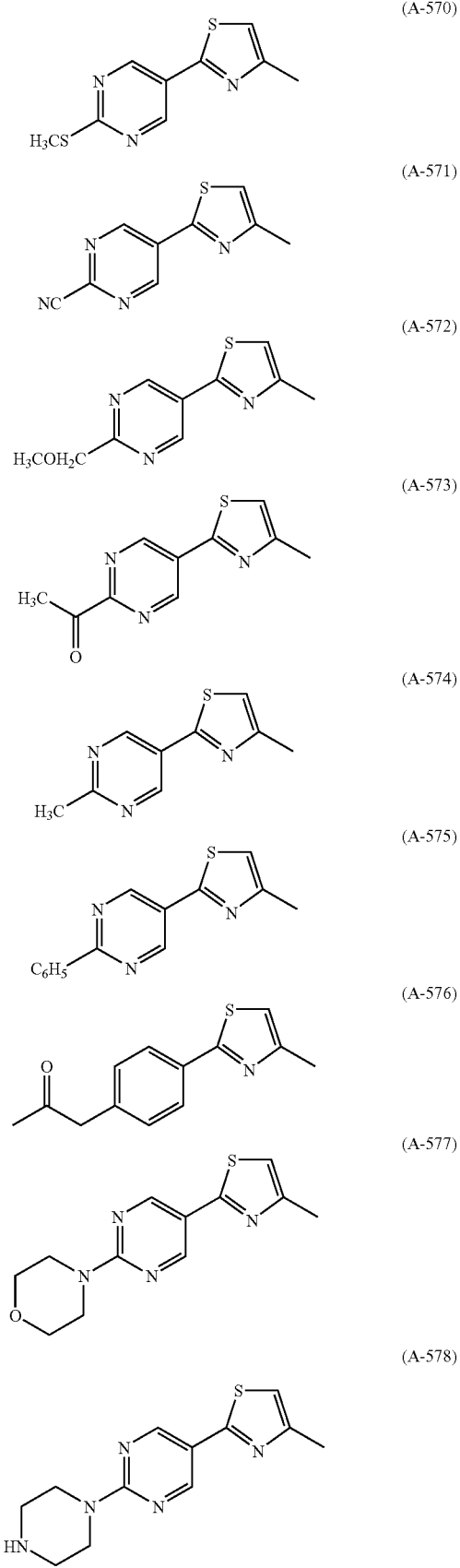
(A-570)
(A-571)
(A-572)
(A-573)
(A-574)
(A-575)
(A-576)
(A-577)
(A-578)

-continued

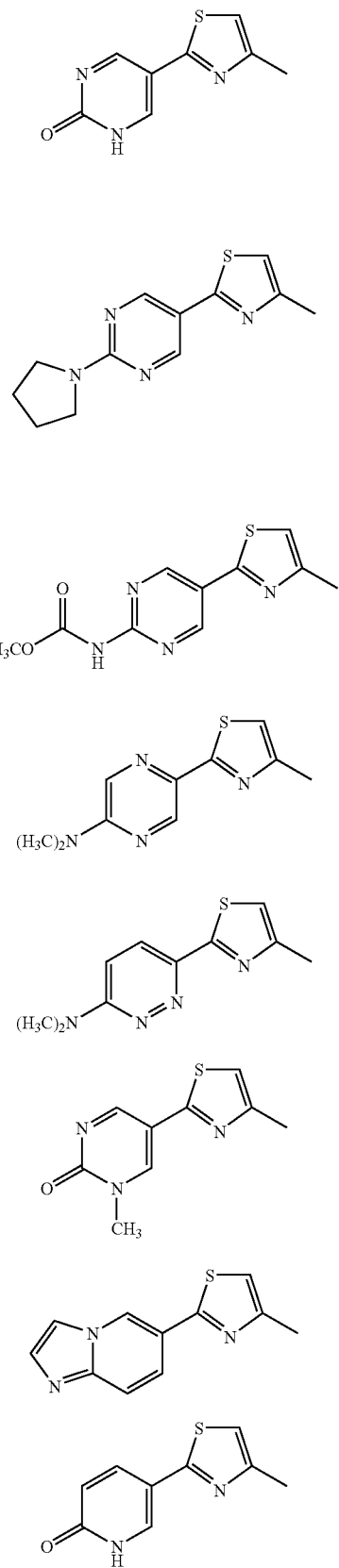

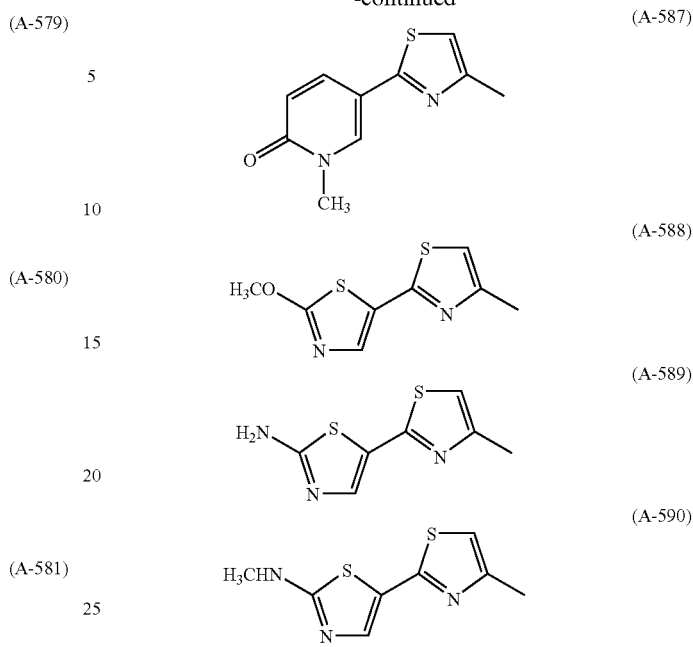

Examples of the group represented by the formula A1 include those represented by the aforementioned formulas (A-1) to (A-60), (A-253) to (A-302), and (A-452) to (A-486), and those represented by the formulas (A-28), (A-34), (A-44), (A-54), (A-56), (A-57), (A-287), (A-452), (A-453), (A-460), (A-461), and (A-486) are preferred.

Examples of the group represented by the formula A2 include those represented by the aforementioned formulas (A-61) to (A-113), (A-303) to (A-360), and (A-487) to (A-521). Those represented by the formulas (A-83), (A-85), (A-86), (A-91), (A-94), (A-104), (A-106), (A-107), (A-108), (A-346), (A-495), (A-496), and (A-521) are preferred, and those represented by the formulas (A-86), (A-104), (A-107), and (A-496) are particularly preferred.

Examples of the group represented by the formula A3 include those represented by the aforementioned formulas (A-114) to (A-181), (A-361) to (A-400), and (A-522) to (A-556). Those represented by the formulas (A-114), (A-118), (A-135) to (A-142), (A-146), (A-153), (A-171), (A-177), (A-396), (A-398), (A-522), (A-523), (A-528), (A-530), (A-531), (A-532), and (A-556) are preferred, and those represented by the formulas (A-135), (A-139), (A-142), (A-153), (A-171), (A-396), (A-398), (A-522), (A-523), (A-531), and (A-556) are particularly preferred.

Examples of the group represented by the formula A4 include those represented by the formulas (A-182) to (A-236), (A-401) to (A-426), and (A-557) to (A-590). Those represented by the formulas (A-201), (A-204), (A-205), (A-206), (A-210), (A-219), (A-222), (A-229), (A-230), (A-233), (A-234), (A-411), (A-563), (A-566), and (A-569) are preferred, and those represented by the formulas (A-204), (A-205), (A-233), and (A-411) are particularly preferred.

Examples of the 5-membered heteroaromatic group having two hetero atoms in the ring include those represented by the formulas (A-237) to (A-252), and (A-427) to (A-445), and those represented by the formulas (A-245), (A-246), (A-251), and (A-252) are preferred.

In the groups represented by the formulas B1, B2, B3, B4, and B5, when each of $R^{11}$, $R^{12}$, $R^{13}$, $R^{14}$, and $R^{15}$ represents a substituent other than hydrogen atom, the substituent can exist at an arbitrary substitutable position on the condensed ring. That is, $R^{11}$ can substitute at any one of the 2-, 4-, 5-, 6-. and 7-positions, and the substituting position of $R^{11}$ is preferably the 5-position. When $Y^2$ is CH, $R^{12}$ can substitute at any of the 2-, 3-, 4-, 5-, 6-, 7-, and 8-position, and the substituting position of $R^{12}$ is preferably the 7-position. When $Y^2$ is nitrogen atom, it can substitute at any one of the 2-, 4-, 5-, 6-, 7-, and 8-positions, and the substituting position of $R^{12}$ is preferably the 5-position. $R^{13}$ can substitute at the 5- or 6-position, and the substituting position of $R^{13}$ is preferably the 5-position. $R^{14}$ can substitute at any one of the 2-, 4-, 6-, and the 7-positions, and the substituting position of $R^{14}$ is preferably the 5-position. $R^{15}$ can substitute at any one of the 2-, 4-, 5-, 6-, and 7-positions, and the substituting position of $R^{15}$ is preferably the 5-position. B is preferably a group represented by the formula B1. Further, it is also preferred that B is a group represented by the formula B2, and B may be a group represented by the formula B3. Further, B may be naphthalene-1-yl group which may be substituted with a substituent (hydroxyl group, halogen atom, alkyl group, alkoxy group). $Y^1$ represents sulfur atom or oxygen atom, and it is preferred that $Y^1$ is sulfur atom.

Examples of the group represented by the formula B1 include the groups represented by following formulas (B-1) to (B-4). The groups represented by the formulas (B-1), and (B-2) are preferred, and the group represented by the formula (B-1) is particularly preferred.

[Formula 6]

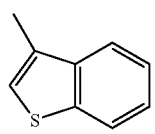
(B-1)

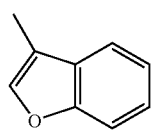
(B-2)

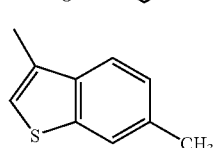
(B-3)

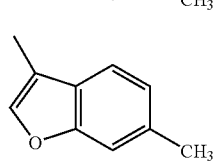
(B-4)

Examples of the group represented by the formula B2 include the groups represented by following formulas (B-5) to (B-8), and the group represented by the formula (B-5) is preferred.

[Formula 7]

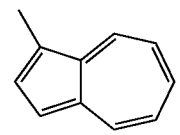
(B-5)

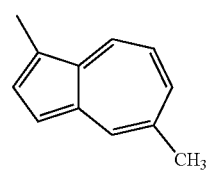
(B-6)

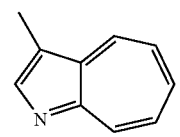
(B-7)

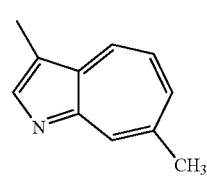
(B-8)

Examples of the group represented by the formula B3 include the groups represented by following formulas (B-9) to (B-14), and the group represented by the formula (B-12) is preferred.

[Formula 8]

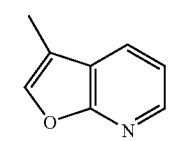
(B-9)

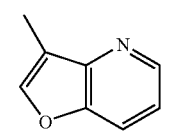
(B-10)

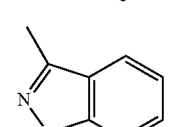
(B-11)

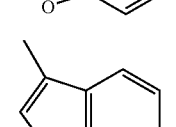
(B-12)

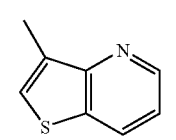
(B-13)

-continued (B-14)
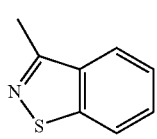

Examples of the group represented by the formula B4 include the groups represented by following formulas (B-15) to (B-17). The groups represented by the formulas (B-15), and (B-16) are preferred, and the group represented by the formula (B-15) is particularly preferred.

[Formula 9]

(B-15)
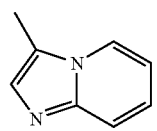

(B-16)
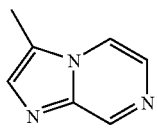

(B-17)
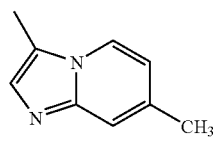

Examples of the group represented by the formula B5 include the groups represented by following formulas (B-18), and (B-19), and the group represented by the formula (B-18) is preferred.

[Formula 10]

(B-18)
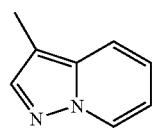

(B-19)
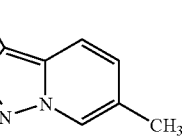

$R^1$ represents an alkyl group. As the alkyl group represented by $R^1$, a lower alkyl group is preferred, an alkyl group having 1 to 4 carton atoms is more preferred, and methyl group and ethyl group are further preferred. Further, methyl group is particularly preferred.

Symbol "n" represents the number of carbon atoms in the alkylene group existing between A and —NH—CH(B)($R^1$). n represents an integer of 2 to 6, preferably 2 to 4, more preferably 2 or 3, most preferably 3.

A combination of the substituents in the formula (1) is not particularly limited. For example, preferred compounds include:

(1) compounds wherein $R^2$ is hydrogen atom, trifluoromethyl group, difluoromethyl group, fluoromethyl group, methyl group, trifluoromethoxy group, hydroxyl group, methoxy group, amino group, phenyl group, benzyl group, pyridyl group, furanyl group, fluorine atom, chlorine atom, or bromine atom, and $R^3$ and $R^4$ are hydrogen atoms;
(2) compounds wherein $R^2$ is 4-hydroxyphenyl group, 4-trifluoromethylphenyl group, 4-cyanophenyl group, 4-acetylphenyl group, 4-methoxycarbonylphenyl group, 4-carbamoylphenyl group, 4-hydroxymethylphenyl group, 4-methoxymethylphenyl group, 2-methoxypyrimidin-5-yl, 2-methoxypyridin-5-yl, 2-trifluoromethylpyridin-5-yl, 4-methanesulfonylphenyl group, 2-dimethylaminopyrimidin-5-yl, or 1-methylindazol-5-yl, and $R^3$ and $R^4$ are hydrogen atoms;
(3) compounds wherein $R^2$, $R^3$, and $R^4$ are hydrogen atoms;
(4) compounds wherein $R^2$ is trifluoromethyl group, and $R^3$ and $R^4$ are hydrogen atoms;
(5) compounds wherein $R^5$ is hydrogen atom, methyl group, methoxy group, amino group, phenyl group, benzyl group, furanyl group, thiofuranyl group, or indolyl group, and $R^6$ and $R^7$ are hydrogen atoms;
(6) compounds wherein $R^5$ is 4-hydroxyphenyl group, 4-trifluoromethylphenyl group, 4-cyanophenyl group, 4-acetylphenyl group, 4-methoxycarbonylphenyl group, 4-carbamoylphenyl group, 4-hydroxymethylphenyl group, 4-methoxymethylphenyl group, 2-methoxypyrimidin-5-yl, 2-methoxypyridin-5-yl, 2-trifluoromethylpyridin-5-yl, 4-methanesulfonylphenyl group, 2-dimethylaminopyrimidin-5-yl, or 1-methylindazol-5-yl, and $R^6$ and $R^7$ are hydrogen atoms;
(7) compounds wherein $R^5$, $R^6$, and $R^7$ are hydrogen atoms;
(8) compounds wherein $R^8$ and $R^{10}$ are hydrogen atoms, and $R^9$ is methyl group, phenyl group, m-chlorophenyl group, p-aminophenyl group, furanyl group, thiofuranyl group, amino group, or nitro group;
(9) compounds wherein $R^8$ and $R^{10}$ are hydrogen atoms, and $R^9$ is 4-hydroxyphenyl group, 4-trifluoromethylphenyl group, 4-cyanophenyl group, 4-acetylphenyl group, 4-methoxycarbonylphenyl group, 4-carbamoylphenyl group, 4-hydroxymethylphenyl group, 4-methoxymethylphenyl group, 2-methoxypyrimidin-5-yl, 2-methoxypyridin-5-yl, 2-trifluoromethylpyridin-5-yl, 4-methanesulfonylphenyl group, 2-dimethylaminopyrimidin-5-yl, or 1-methylindazol-5-yl;
(10) compounds wherein $R^8$ and $R^9$ together form a benzene ring and thereby form benzothiophen-2-yl group, benzothiophen-3-yl group, indol-2-yl group, indol-3-yl group, benzofuran-2-yl group, or benzofuran-3-yl group as a bicyclic heterocyclic group as A3, and $R^{10}$ is hydrogen atom;
(11) compounds wherein $R^8$, $R^9$, and $R^{10}$ are hydrogen atoms;
(12) compounds wherein A is pyrrolidinyl group, piperidinyl group, or morphonyl group as a saturated heterocyclic group;
(13) compounds wherein A is pyrazonyl group, thiazolidinyl group, or isoxazolyl group;
(14) compounds wherein $R^{23}$ is hydrogen atom, trifluoromethyl group, difluoromethyl group, fluoromethyl group, methyl group, trifluoromethoxy group, hydroxyl group, methoxy group, amino group, phenyl group, benzyl group, pyridyl group, furanyl group, fluorine atom, chlorine atom, or bromine atom;
(15) compounds wherein $R^{23}$ is 4-hydroxyphenyl group, 4-trifluoromethylphenyl group, 4-cyanophenyl group, 4-acetylphenyl group, 4-methoxycarbonylphenyl group, 4-carbamoylphenyl group, 4-hydroxymethylphenyl group, 4-methoxymethylphenyl group, 2-methoxypyrimidin-5-yl, 2-methoxypyridin-5-yl, 2-trifluoromethylpyridin-5-yl, 4-methanesulfonylphenyl group, 2-dimethylaminopyrimidin-5-yl, or 1-methylindazol-5-yl;
(16) compounds of (14) or (15) wherein $X^2$ is oxygen atom; and
(17) compounds of (14) or (15) wherein $X^2$ is sulfur atom.
More preferred compounds include:
(18) compounds of (1) to (17) wherein $R^1$ is methyl group or ethyl group; and
(19) compounds of (1) to (18) wherein $R^1$ is methyl group.
Preferred compounds further include:
(20) compounds of (1) to (19) wherein B is a group represented by the formula B1;
(21) compounds of (20) wherein $Y^1$ is sulfur atom;
(22) compounds of (21) wherein $R^{11}$ is hydrogen atom, methyl group, methoxy group, fluorine atom, or chlorine atom;
(23) compounds of (1) to (19) wherein B is a group represented by the formula B2;
(24) compounds of (23) wherein $R^{12}$ is hydrogen atom or methyl group;
(25) compounds of (24) wherein $R^{12}$ is hydrogen atom, and $Y^2$ is CH;
(26) compounds of (1) to (19) wherein B is a group represented by the formula B3;
(27) compounds of (26) wherein $R^{13}$ is hydrogen atom or methyl group;
(28) compounds of (1) to (19) wherein B is a group represented by the formula B4;
(29) compounds of (28) wherein $R^{14}$ is hydrogen atom or methyl group;
(30) compounds of (1) or (19) wherein B is a group represented by the formula B5; and
(31) compounds of (30) wherein $R^{15}$ is hydrogen atom.
Also preferred compounds include:
(32) compounds of (1) to (19) wherein B is naphthalen-1-yl group which may be substituted; and
(33) compounds of (32) wherein B is naphthalen-1-yl group.
Still more preferred compounds include:
(34) compounds wherein A is a group represented by the formula A2, A3, or A4, or a 5-membered heteroaromatic group having two heteroatoms, B is a group represented by the formula B1, $Y^1$ is sulfur atom, and $R^{11}$ is hydrogen atom, methyl group, or methoxy group;
(35) compounds wherein A is a group represented by the formula A2, A3, or A4, or a 5-membered heteroaromatic group having two heteroatoms, B is a group represented by the formula B2, $Y^1$ is CH, and $R^{12}$ is hydrogen atom; and
(36) compounds of (35) wherein A is a group represented by the formula A3, or A4.

In the compounds represented by the aforementioned formula (1), the carbon atoms on which NH, B, and $R^1$ substitute are asymmetric carbons. The steric configuration of these asymmetric carbons are not particularly limited, and the configuration may be S-configuration, or R-configuration. The compounds of the present invention may consist of an arbitrary mixture or racemate of pure optical isomers based on these asymmetric carbons. However, in view of the desired biological action, the steric configuration of the aforementioned asymmetric carbons is preferably R-configuration. Further, the compounds of the present invention may have one or more asymmetric carbons depending on the types of the substituents, and a steric configuration of the atoms other than the asymmetric carbons specified above is not particularly limited and the compounds may be in an arbitrary steric configuration. Pure stereoisomers including optical isomers and diastereoisomers based on one or more asymmetric carbons, any mixtures, racemates and the like of stereoisomers all fall within the scope of the present invention.

Types of salts of the compounds of the formula (1) are not particularly limited, and the salts may be either acid addition salts or base addition salts. The salts may also be in the form of a molecule having an intramolecular counter ion. Examples of the acid addition salts include, for example, hydrochlorides, hydrobromides, sulfates, hydrogensulfates, dihydrogenphosphates, citrates, maleates, tartrates, fumarates, gluconates, methanesulfonates, and addition salts with an optically active acid such as camphorsulfonic acid, mandelic, and a substituted mandelic acid. A base addition salt may be formed when any one or more of $R^2$ to $R^{15}$ are hydroxyl groups, and examples include, for example, metal salts such as sodium salts and potassium salts, ammonium salts and the like. However, the type of the salts is not limited to these examples, and those skilled in the art can appropriately choose a salt. Among them, physiologically acceptable salts are preferred. The compounds of the present invention and salts thereof may exist as hydrates or solvates, and such substances also fall within the scope of the present invention.

Preferred examples of the compounds of the present invention represented by the formula (1) include the following compounds:
[1-(benzothiophen-3-yl)ethyl][3-(3-trifluoromethylphenyl)propyl]amine;
[1-(benzothiophen-3-yl)ethyl][3-(3-methylphenyl)propyl]amine;
[1-(benzothiophen-3-yl)ethyl][3-(3-difluoromethylphenyl)propyl]amine;
[1-(benzothiophen-3-yl)ethyl][3-(3-monofluoromethylphenyl)propyl]amine;
[1-(benzothiophen-3-yl)propyl][3-(3-trifluoromethylphenyl)propyl]amine;
[1-(2-methylbenzothiophen-3-yl)ethyl][3-(3-trifluoromethylphenyl)propyl]amine;
[1-(4-methylbenzothiophen-3-yl)ethyl][3-(3-trifluoromethylphenyl)propyl]amine;
[1-(5-methylbenzothiophen-3-yl)ethyl][3-(3-trifluoromethylphenyl)propyl]amine;
[1-(6-methylbenzothiophen-3-yl)ethyl][3-(3-trifluoromethylphenyl)propyl]amine;
[1-(7-methylbenzothiophen-3-yl)ethyl][3-(3-trifluoromethylphenyl)propyl]amine;
[1-(5-fluorobenzothiophen-3-yl)ethyl][3-(3-trifluoromethylphenyl)propyl]amine;
[1-(5-chlorobenzothiophen-3-yl)ethyl][3-(3-trifluoromethylphenyl)propyl]amine;
[1-(5-bromobenzothiophen-3-yl)ethyl][3-(3-trifluoromethylphenyl)propyl]amine;
[1-(5-methoxybenzothiophen-3-yl)ethyl][3-(3-trifluoromethylphenyl)propyl]amine;
[1-(5-thiomethoxybenzothiophen-3-yl)ethyl][3-(3-trifluoromethylphenyl)propyl]amine;
[1-(5-hydroxybenzothiophen-3-yl)ethyl][3-(3-trifluoromethylphenyl)propyl]amine;
[1-(5-hydroxymethylbenzothiophen-3-yl)ethyl][3-(3-trifluoromethylphenyl)propyl]-amine;
[1-(5-aminobenzothiophen-3-yl)ethyl][3-(3-trifluoromethylphenyl)propyl]amine;
[1-(5-ethylaminobenzothiophen-3-yl)ethyl][3-(3-trifluoromethylphenyl)propyl]amine;
[1-(5-acetylaminobenzothiophen-3-yl)ethyl][3-(3-trifluoromethylphenyl)propyl]amine;
[1-(5-methylsulfonylaminobenzothiophen-3-yl)ethyl][3-(3-trifluoromethylphenyl)propyl]amine;

[1-(benzothiophen-3-yl)ethyl][3-(2-fluorophenyl)propyl]amine;
[1-(benzothiophen-3-yl)ethyl][3-(3-fluorophenyl)propyl]amine;
[1-(benzothiophen-3-yl)ethyl][3-(4-fluorophenyl)propyl]amine;
[1-(benzothiophen-3-yl)ethyl][3-(2-hydroxyphenyl)propyl]amine;
[1-(benzothiophen-3-yl)ethyl][3-(3-hydroxyphenyl)propyl]amine;
[1-(benzothiophen-3-yl)ethyl][3-(4-hydroxyphenyl)propyl]amine;
[1-(benzothiophen-3-yl)ethyl][3-(3-bromophenyl)propyl]amine;
[1-(benzothiophen-3-yl)ethyl][3-(3,5-difluorophenyl)propyl]amine;
[1-(benzothiophen-3-yl)ethyl][3-(2-methoxyphenyl)propyl]amine;
[1-(benzothiophen-3-yl)ethyl][3-(3-methoxyphenyl)propyl]amine;
[1-(benzothiophen-3-yl)ethyl][3-(4-methoxyphenyl)propyl]amine;
[1-(benzothiophen-3-yl)ethyl][3-(3-trifluoromethoxyphenyl)propyl]amine;
[1-(benzothiophen-3-yl)ethyl][3-(2-aminophenyl)propyl]amine;
[1-(benzothiophen-3-yl)ethyl][3-(3-aminophenyl)propyl]amine;
[1-(benzothiophen-3-yl)ethyl][3-(4-aminophenyl)propyl]amine;
[1-(benzothiophen-3-yl)ethyl][3-(4-amino-3-hydroxyphenyl)propyl]amine;
[1-(benzothiophen-3-yl)ethyl][3-(phenyl)propyl]amine;
[1-(benzothiophen-3-yl)ethyl][5-(phenyl)pentyl]amine;
[1-(benzothiophen-3-yl)ethyl][2-(4-fluorophenyl)ethyl]amine;
[1-(2-methylbenzofuran-3-yl)ethyl][3-(3-trifluoromethylphenyl)propyl]amine;
[1-(azulen-1-yl)ethyl][3-(3-trifluoromethylphenyl)propyl]amine;
[1-(azulen-1-yl)ethyl][3-(3-methoxyphenyl)propyl]amine;
[1-(azulen-1-yl)ethyl][3-(3-hydroxyphenyl)propyl]amine;
[1-(azulen-1-yl)ethyl][3-(4-hydroxyphenyl)propyl]amine;
[1-(azulen-1-yl)ethyl][3-(4-aminophenyl)propyl]amine;
[1-(5-isopropylazulen-1-yl)ethyl][3-(3-trifluoromethylphenyl)propyl]amine;
[1-(1-azaazulen-3-yl)ethyl][3-(3-trifluoromethylphenyl)propyl]amine;
[1-(thieno[2,3-b]pyridin-3-yl)ethyl][3-(3-trifluoromethylphenyl)propyl]amine;
[1-(thieno[3,2-b]pyridin-3-yl)ethyl][3-(3-trifluoromethylphenyl)propyl]amine;
[1-(imidazopyidin-3-yl)ethyl][3-(3-methoxyphenyl)propyl]amine;
[1-(imidazopyidin-3-yl)ethyl][3-(3-hydroxyphenyl)propyl]amine;
[1-(imidazopyidin-3-yl)ethyl][3-(4-aminophenyl)propyl]amine;
[1-(imidazopyidin-3-yl)ethyl][3-(4-hydroxyphenyl)propyl]amine;
[1-(pyrazolopyridin-3-yl)ethyl][3-(3-trifluoromethylphenyl)propyl]amine;
[1-(pyrazolopyridin-3-yl)ethyl][3-(3-methoxyphenyl)propyl]amine;
[1-(pyrazolopyridin-3-yl)ethyl][3-(3-hydroxyphenyl)propyl]amine;
[1-(pyrazolopyridin-3-yl)ethyl][3-(4-hydroxyphenyl)propyl]amine;
[1-(benzothiophen-3-yl)ethyl][3-(pyridin-2-yl)propyl]amine;
[1-(benzothiophen-3-yl)ethyl][3-(pyridin-3-yl)propyl]amine;
[1-(benzothiophen-3-yl)ethyl][3-(pyridin-4-yl)propyl]amine;
[1-(azulen-1-yl)ethyl][3-(pyridin-3-yl)propyl]amine;
[1-(imidazopyidin-3-yl)ethyl][3-(pyridin-3-yl)propyl]amine;
[1-(pyrazolopyridin-3-yl)ethyl][3-(pyridin-3-yl)propyl]amine;
[1-(benzothiophen-3-yl)ethyl][3-(furan-2-yl)propyl]amine;
[1-(benzothiophen-3-yl)ethyl][3-(furan-3-yl)propyl]amine;
[1-(benzothiophen-3-yl)ethyl][3-(5-methylfuran-2-yl)propyl]amine;
[1-(benzothiophen-3-yl)ethyl][3-(5-phenylfuran-2-yl)propyl]amine;
[1-(benzothiophen-3-yl)ethyl][3-(5-(3-chlorophenyl)furan-2-yl)propyl]amine;
[1-(benzothiophen-3-yl)ethyl][3-(5-(3-aminophenyl)furan-2-yl)propyl]amine;
[1-(benzothiophen-3-yl)ethyl][3-(5-(2-aminophenyl)furan-2-yl)propyl]amine;
[1-(benzothiophen-3-yl)ethyl][3-(5-(4-aminophenyl)furan-2-yl)propyl]amine;
[1-(benzothiophen-3-yl)ethyl][3-(benzofuran-2-yl)propyl]amine;
[1-(benzothiophen-3-yl)ethyl][3-(thiophen-2-yl)propyl]amine;
[1-(benzothiophen-3-yl)ethyl][3-(thiophen-3-yl)propyl]amine;
[1-(benzothiophen-3-yl)ethyl][2-(thiophen-2-yl)ethyl]amine;
[1-(benzothiophen-3-yl)ethyl][4-(thiophen-2-yl) butyl]amine;
[1-(benzothiophen-3-yl)ethyl][3-(5-nitrothiophen-2-yl)propyl]amine;
[1-(benzothiophen-3-yl)ethyl][3-(5-aminothiophen-2-yl)propyl]amine;
[1-(benzothiophen-3-yl)ethyl][3-(2-nitrothiophen-4-yl)propyl]amine;
[1-(benzothiophen-3-yl)ethyl][3-(2-aminothiophen-4-yl)propyl]amine;
[1-(benzothiophen-3-yl)ethyl][3-(benzothiophen-2-yl)propyl]amine;
[1-(benzothiophen-3-yl)ethyl][3-(pyrrol-1-yl)propyl]amine;
[1-(benzothiophen-3-yl)ethyl][2-(pyrrol-1-yl)ethyl]amine;
[1-(benzothiophen-3-yl)ethyl][3-(1-methylpyrrol-2-yl)propyl]amine;
[1-(benzothiophen-3-yl)ethyl][2-(1-methylpyrrol-2-yl)ethyl]amine;
[1-(benzothiophen-3-yl)ethyl][5-(1-methylpyrrol-2-yl) pentyl]amine;
[1-(benzothiophen-3-yl)ethyl][3-(1-methylpyrrol-3-yl)propyl]amine;
[1-(benzothiophen-3-yl)ethyl][4-(1-methylpyrrol-2-yl)butyl]amine;
[1-(benzothiophen-3-yl)ethyl][3-(indol-3-yl)propyl]amine;
[1-(azulen-1-yl)ethyl][3-(furan-2-yl)propyl]amine;
[1-(azulen-1-yl)ethyl][3-(furan-3-yl)propyl]amine;
[1-(azulen-1-yl)ethyl][3-(5-methylfuran-2-yl)propyl]amine;
[1-(azulen-1-yl)ethyl][3-(5-phenylfuran-2-yl)propyl]amine;
[1-(azulen-1-yl)ethyl][3-(5-(3-chlorophenyl)furan-2-yl)propyl]amine;

[1-(azulen-1-yl)ethyl][3-(5-(3-aminophenyl)furan-2-yl)propyl]amine;
[1-(azulen-1-yl)ethyl][3-(5-(2-aminophenyl)furan-2-yl)propyl]amine;
[1-(azulen-1-yl)ethyl][3-(5-(4-aminophenyl)furan-2-yl)propyl]amine;
[1-(azulen-1-yl)ethyl][3-[5-(pyridin-2-yl)furan-2-yl]propyl]amine;
[1-(azulen-1-yl)ethyl][3-[5-(pyridin-3-yl)furan-2-yl]propyl]amine;
[1-(azulen-1-yl)ethyl][3-[5-(pyridin-4-yl)furan-2-yl]propyl]amine;
[1-(azulen-1-yl)ethyl][3-(benzofuran-2-yl)propyl]amine;
[1-(azulen-1-yl)ethyl][3-(thiophen-2-yl)propyl]amine;
[1-(azulen-1-yl)ethyl][3-(thiophen-3-yl)propyl]amine;
[1-(azulen-1-yl)ethyl][2-(thiophen-2-yl)ethyl]amine;
[1-(azulen-1-yl)ethyl][4-(thiophen-2-yl)butyl]amine;
[1-(azulen-1-yl)ethyl][3-(5-nitrothiophen-2-yl)propyl]amine;
[1-(azulen-1-yl)ethyl][3-(5-aminothiophen-2-yl)propyl]amine;
[1-(azulen-1-yl)ethyl][3-(2-nitrothiophen-4-yl)propyl]amine;
[1-(azulen-1-yl)ethyl][3-(2-aminothiophen-4-yl)propyl]amine;
[1-(azulen-1-yl)ethyl][3-(benzothiophen-2-yl)propyl]amine;
[1-(azulen-1-yl)ethyl][3-(pyrrol-1-yl)propyl]amine;
[1-(azulen-1-yl)ethyl][2-(pyrrol-1-yl)ethyl]amine;
[1-(azulen-1-yl)ethyl][3-(1-methylpyrrol-2-yl)propyl]amine;
[1-(azulen-1-yl)ethyl][2-(1-methylpyrrol-2-yl)ethyl]amine;
[1-(azulen-1-yl)ethyl][5-(1-methylpyrrol-2-yl)pentyl]amine;
[1-(azulen-1-yl)ethyl][3-(1-methylpyrrol-3-yl)propyl]amine;
[1-(azulen-1-yl)ethyl][5-(1-phenylpyrrol-2-yl)pentyl]amine;
[1-(azulen-1-yl)ethyl][3-(1-phenylpyrrol-3-yl)propyl]amine;
[1-(azulen-1-yl)ethyl][3-(indol-3-yl)propyl]amine;
[1-(thieno[2,3-b]pyridin-3-yl)ethyl][3-(furan-2-yl)propyl]amine;
[1-(thieno[3,2-b]pyridin-3-yl)ethyl][3-(furan-3-yl)propyl]amine;
[1-(imidazopyidin-3-yl)ethyl][3-(furan-2-yl)propyl]amine;
[1-(imidazopyidin-3-yl)ethyl][3-(furan-3-yl)propyl]amine;
[1-(pyrazolopyridin-3-yl)ethyl][3-(furan-2-yl)propyl]amine;
[1-(pyrazolopyridin-3-yl)ethyl][3-(furan-3-yl)propyl]amine;
[1-(benzothiophen-3-yl)ethyl][3-(tetrahydrofuran-2-yl)propyl]amine;
[1-(benzothiophen-3-yl)ethyl][3-(tetrahydrofuran-3-yl)propyl]amine;
[1-(benzothiophen-3-yl)ethyl][3-(pyrrolidin-1-yl)propyl]amine;
[1-(benzothiophen-3-yl)ethyl][3-(piperidin-1-yl)propyl]amine;
[1-(benzothiophen-3-yl)ethyl][3-(morpholin-1-yl)propyl]amine;
[1-(benzothiophen-3-yl)ethyl][3-(thiazol-2-yl)propyl]amine;
[1-(azulen-1-yl)ethyl][3-(tetrahydrofuran-2-yl)propyl]amine;
[1-(azulen-1-yl)ethyl][3-(tetrahydrofuran-3-yl)propyl]amine;
[1-(azulen-1-yl)ethyl][3-(pyrrolidin-1-yl)propyl]amine;
[1-(azulen-1-yl)ethyl][3-(piperidin-1-yl)propyl]amine;
[1-(azulen-1-yl)ethyl][3-(morpholin-1-yl)propyl]amine;
[1-(azulen-1-yl)ethyl][3-(thiazol-2-yl)propyl]amine;
[1-(azulen-1-yl)ethyl][3-(2-phenylthiazol-4-yl)propyl]amine;
[1-(azulen-1-yl)ethyl][3-(2,5-dimethyloxazol-4-yl)propyl]amine;
[1-(azulen-1-yl)ethyl][3-(3,5-dimethylisoxazol-4-yl)propyl]amine;
[1-(azulen-1-yl)ethyl][3-(5-(thiophen-2-yl)isoxazol-4-yl)propyl]amine;
[1-(azulen-1-yl)ethyl][3-(3,5-dimethylisoxazol-4-yl)propyl]amine;
[1-(azulen-1-yl)ethyl][3-(1,3-dimethylpyrazol-5-yl)propyl]amine;
[1-(naphthalen-1-yl)ethyl][3-(furan-2-yl)propyl]amine;
[1-(naphthalen-1-yl)ethyl][3-(furan-3-yl)propyl]amine;
[1-(naphthalen-1-yl)ethyl][3-(5-methylfuran-2-yl)propyl]amine;
[1-(naphthalen-1-yl)ethyl][3-(5-phenylfuran-2-yl)propyl]amine;
[1-(naphthalen-1-yl)ethyl][3-(5-(3-chlorophenyl)furan-2-yl)propyl]amine;
[1-(naphthalen-1-yl)ethyl][3-(5-(4-aminophenyl)furan-2-yl)propyl]amine;
[1-(naphthalen-1-yl)ethyl][3-(benzofuran-2-yl)propyl]amine;
[1-(naphthalen-1-yl)ethyl][3-(thiophen-2-yl)propyl]amine;
[1-(naphthalen-1-yl)ethyl][3-(thiophen-3-yl)propyl]amine;
[1-(naphthalen-1-yl)ethyl][4-(thiophen-2-yl)butyl]amine;
[1-(naphthalen-1-yl)ethyl][3-(5-nitrothiophen-2-yl)propyl]amine;
[1-(naphthalen-1-yl)ethyl][3-(5-aminothiophen-2-yl)propyl]amine;
[1-(naphthalen-1-yl)ethyl][3-(2-nitrothiophen-4-yl)propyl]amine;
[1-(naphthalen-1-yl)ethyl][3-(2-aminothiophen-4-yl)propyl]amine;
[1-(naphthalen-1-yl)ethyl][3-(benzothiophen-2-yl)propyl]amine;
[1-(naphthalen-1-yl)ethyl][3-(pyrrol-1-yl)propyl]amine;
[1-(naphthalen-1-yl)ethyl][2-(pyrrol-1-yl)ethyl]amine;
[1-(naphthalen-1-yl)ethyl][3-(1-methylpyrrol-2-yl)propyl]amine;
[1-(naphthalen-1-yl)ethyl][2-(1-methylpyrrol-2-yl)ethyl]amine;
[1-(naphthalen-1-yl)ethyl][5-(1-methylpyrrol-2-yl) pentyl]amine;
[1-(naphthalen-1-yl)ethyl][3-(1-methylpyrrol-3-yl)propyl]amine;
[1-(naphthalen-1-yl)ethyl][3-(indol-3-yl)propyl]amine and the like. However, the compounds of the present invention are not limited to the aforementioned specific compounds. Preferred examples of the compounds of the present invention represented by the formula (1) further include the compounds represented by the formula 24:

[Formula 11]

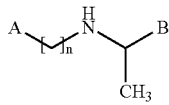

wherein A, B, and n are selected as in any of the combinations shown in Tables 1 and 2. In Tables 1 and 2, example numbers are mentioned in the columns of "epn". Further, the compounds represented by the formula (1) wherein A and B are selected as in any of the combinations shown in Table 1, but n is 2 or 4 instead of 3 are also preferred compounds, and these compounds are also included in the disclosure of Tables 1 and 2 with example numbers n2-1 to n2-12390 and n4-1 to n4-12390. However, the scope of the present invention is not limited to these preferred compounds.

TABLE 1

| | n = 3 | |
|---|---|---|
| epn | A | B |
| n3-1 | A-1 | B-1 |
| n3-2 | A-2 | B-1 |
| n3-3 | A-3 | B-1 |
| n3-4 | A-4 | B-1 |
| n3-5 | A-5 | B-1 |
| n3-6 | A-6 | B-1 |
| n3-7 | A-7 | B-1 |
| n3-8 | A-8 | B-1 |
| n3-9 | A-9 | B-1 |
| n3-10 | A-10 | B-1 |
| n3-11 | A-11 | B-1 |
| n3-12 | A-12 | B-1 |
| n3-13 | A-13 | B-1 |
| n3-14 | A-14 | B-1 |
| n3-15 | A-15 | B-1 |
| n3-16 | A-16 | B-1 |
| n3-17 | A-17 | B-1 |
| n3-18 | A-18 | B-1 |
| n3-19 | A-19 | B-1 |
| n3-20 | A-20 | B-1 |
| n3-21 | A-21 | B-1 |
| n3-22 | A-22 | B-1 |
| n3-23 | A-23 | B-1 |
| n3-24 | A-24 | B-1 |
| n3-25 | A-25 | B-1 |
| n3-26 | A-26 | B-1 |
| n3-27 | A-27 | B-1 |
| n3-28 | A-28 | B-1 |
| n3-29 | A-29 | B-1 |
| n3-30 | A-30 | B-1 |
| n3-31 | A-31 | B-1 |
| n3-32 | A-32 | B-1 |
| n3-33 | A-33 | B-1 |
| n3-34 | A-34 | B-1 |
| n3-35 | A-35 | B-1 |
| n3-36 | A-36 | B-1 |
| n3-37 | A-37 | B-1 |
| n3-38 | A-38 | B-1 |
| n3-39 | A-39 | B-1 |
| n3-40 | A-40 | B-1 |
| n3-41 | A-41 | B-1 |
| n3-42 | A-42 | B-1 |
| n3-43 | A-43 | B-1 |
| n3-44 | A-44 | B-1 |
| n3-45 | A-45 | B-1 |
| n3-46 | A-46 | B-1 |
| n3-47 | A-47 | B-1 |
| n3-48 | A-48 | B-1 |
| n3-49 | A-49 | B-1 |
| n3-50 | A-50 | B-1 |
| n3-51 | A-51 | B-1 |
| n3-52 | A-52 | B-1 |
| n3-53 | A-53 | B-1 |
| n3-54 | A-54 | B-1 |
| n3-55 | A-55 | B-1 |
| n3-56 | A-56 | B-1 |
| n3-57 | A-57 | B-1 |
| n3-58 | A-58 | B-1 |
| n3-59 | A-59 | B-1 |
| n3-60 | A-60 | B-1 |
| n3-61 | A-61 | B-1 |
| n3-62 | A-62 | B-1 |

TABLE 1-continued

| | n = 3 | |
|---|---|---|
| epn | A | B |
| n3-63 | A-63 | B-1 |
| n3-64 | A-64 | B-1 |
| n3-65 | A-65 | B-1 |
| n3-66 | A-66 | B-1 |
| n3-67 | A-67 | B-1 |
| n3-68 | A-68 | B-1 |
| n3-69 | A-69 | B-1 |
| n3-70 | A-70 | B-1 |
| n3-71 | A-71 | B-1 |
| n3-72 | A-72 | B-1 |
| n3-73 | A-73 | B-1 |
| n3-74 | A-74 | B-1 |
| n3-75 | A-75 | B-1 |
| n3-76 | A-76 | B-1 |
| n3-77 | A-77 | B-1 |
| n3-78 | A-78 | B-1 |
| n3-79 | A-79 | B-1 |
| n3-80 | A-80 | B-1 |
| n3-81 | A-81 | B-1 |
| n3-82 | A-82 | B-1 |
| n3-83 | A-83 | B-1 |
| n3-84 | A-84 | B-1 |
| n3-85 | A-85 | B-1 |
| n3-86 | A-86 | B-1 |
| n3-87 | A-87 | B-1 |
| n3-88 | A-88 | B-1 |
| n3-89 | A-89 | B-1 |
| n3-90 | A-90 | B-1 |
| n3-91 | A-91 | B-1 |
| n3-92 | A-92 | B-1 |
| n3-93 | A-93 | B-1 |
| n3-94 | A-94 | B-1 |
| n3-95 | A-95 | B-1 |
| n3-96 | A-96 | B-1 |
| n3-97 | A-97 | B-1 |
| n3-98 | A-98 | B-1 |
| n3-99 | A-99 | B-1 |
| n3-100 | A-100 | B-1 |
| n3-101 | A-101 | B-1 |
| n3-102 | A-102 | B-1 |
| n3-103 | A-103 | B-1 |
| n3-104 | A-104 | B-1 |
| n3-105 | A-105 | B-1 |
| n3-106 | A-106 | B-1 |
| n3-107 | A-107 | B-1 |
| n3-108 | A-108 | B-1 |
| n3-109 | A-109 | B-1 |
| n3-110 | A-110 | B-1 |
| n3-111 | A-111 | B-1 |
| n3-112 | A-112 | B-1 |
| n3-113 | A-113 | B-1 |
| n3-114 | A-114 | B-1 |
| n3-115 | A-115 | B-1 |
| n3-116 | A-116 | B-1 |
| n3-117 | A-117 | B-1 |
| n3-118 | A-118 | B-1 |
| n3-119 | A-119 | B-1 |
| n3-120 | A-120 | B-1 |
| n3-121 | A-121 | B-1 |
| n3-122 | A-122 | B-1 |
| n3-123 | A-123 | B-1 |
| n3-124 | A-124 | B-1 |
| n3-125 | A-125 | B-1 |
| n3-126 | A-126 | B-1 |
| n3-127 | A-127 | B-1 |
| n3-128 | A-128 | B-1 |
| n3-129 | A-129 | B-1 |
| n3-130 | A-130 | B-1 |
| n3-131 | A-131 | B-1 |
| n3-132 | A-132 | B-1 |
| n3-133 | A-133 | B-1 |
| n3-134 | A-134 | B-1 |
| n3-135 | A-135 | B-1 |
| n3-136 | A-136 | B-1 |
| n3-137 | A-137 | B-1 |

TABLE 1-continued

| | n = 3 | |
|---|---|---|
| epn | A | B |
| n3-138 | A-138 | B-1 |
| n3-139 | A-139 | B-1 |
| n3-140 | A-140 | B-1 |
| n3-141 | A-141 | B-1 |
| n3-142 | A-142 | B-1 |
| n3-143 | A-143 | B-1 |
| n3-144 | A-144 | B-1 |
| n3-145 | A-145 | B-1 |
| n3-146 | A-146 | B-1 |
| n3-147 | A-147 | B-1 |
| n3-148 | A-148 | B-1 |
| n3-149 | A-149 | B-1 |
| n3-150 | A-150 | B-1 |
| n3-151 | A-151 | B-1 |
| n3-152 | A-152 | B-1 |
| n3-153 | A-153 | B-1 |
| n3-154 | A-154 | B-1 |
| n3-155 | A-155 | B-1 |
| n3-156 | A-156 | B-1 |
| n3-157 | A-157 | B-1 |
| n3-158 | A-158 | B-1 |
| n3-159 | A-159 | B-1 |
| n3-160 | A-160 | B-1 |
| n3-161 | A-161 | B-1 |
| n3-162 | A-162 | B-1 |
| n3-163 | A-163 | B-1 |
| n3-164 | A-164 | B-1 |
| n3-165 | A-165 | B-1 |
| n3-166 | A-166 | B-1 |
| n3-167 | A-167 | B-1 |
| n3-168 | A-168 | B-1 |
| n3-169 | A-169 | B-1 |
| n3-170 | A-170 | B-1 |
| n3-171 | A-171 | B-1 |
| n3-172 | A-172 | B-1 |
| n3-173 | A-173 | B-1 |
| n3-174 | A-174 | B-1 |
| n3-175 | A-175 | B-1 |
| n3-176 | A-176 | B-1 |
| n3-177 | A-177 | B-1 |
| n3-178 | A-178 | B-1 |
| n3-179 | A-179 | B-1 |
| n3-180 | A-180 | B-1 |
| n3-181 | A-181 | B-1 |
| n3-182 | A-182 | B-1 |
| n3-183 | A-183 | B-1 |
| n3-184 | A-184 | B-1 |
| n3-185 | A-185 | B-1 |
| n3-186 | A-186 | B-1 |
| n3-187 | A-187 | B-1 |
| n3-188 | A-188 | B-1 |
| n3-189 | A-189 | B-1 |
| n3-190 | A-190 | B-1 |
| n3-191 | A-191 | B-1 |
| n3-192 | A-192 | B-1 |
| n3-193 | A-193 | B-1 |
| n3-194 | A-194 | B-1 |
| n3-195 | A-195 | B-1 |
| n3-196 | A-196 | B-1 |
| n3-197 | A-197 | B-1 |
| n3-198 | A-198 | B-1 |
| n3-199 | A-199 | B-1 |
| n3-200 | A-200 | B-1 |
| n3-201 | A-201 | B-1 |
| n3-202 | A-202 | B-1 |
| n3-203 | A-203 | B-1 |
| n3-204 | A-204 | B-1 |
| n3-205 | A-205 | B-1 |
| n3-206 | A-206 | B-1 |
| n3-207 | A-207 | B-1 |
| n3-208 | A-208 | B-1 |
| n3-209 | A-209 | B-1 |
| n3-210 | A-210 | B-1 |
| n3-211 | A-211 | B-1 |
| n3-212 | A-212 | B-1 |
| n3-213 | A-213 | B-1 |
| n3-214 | A-214 | B-1 |
| n3-215 | A-215 | B-1 |
| n3-216 | A-216 | B-1 |
| n3-217 | A-217 | B-1 |
| n3-218 | A-218 | B-1 |
| n3-219 | A-219 | B-1 |
| n3-220 | A-220 | B-1 |
| n3-221 | A-221 | B-1 |
| n3-222 | A-222 | B-1 |
| n3-223 | A-223 | B-1 |
| n3-224 | A-224 | B-1 |
| n3-225 | A-225 | B-1 |
| n3-226 | A-226 | B-1 |
| n3-227 | A-227 | B-1 |
| n3-228 | A-228 | B-1 |
| n3-229 | A-229 | B-1 |
| n3-230 | A-230 | B-1 |
| n3-231 | A-231 | B-1 |
| n3-232 | A-232 | B-1 |
| n3-233 | A-233 | B-1 |
| n3-234 | A-234 | B-1 |
| n3-235 | A-235 | B-1 |
| n3-236 | A-236 | B-1 |
| n3-237 | A-237 | B-1 |
| n3-238 | A-238 | B-1 |
| n3-239 | A-239 | B-1 |
| n3-240 | A-240 | B-1 |
| n3-241 | A-241 | B-1 |
| n3-242 | A-242 | B-1 |
| n3-243 | A-243 | B-1 |
| n3-244 | A-244 | B-1 |
| n3-245 | A-245 | B-1 |
| n3-246 | A-246 | B-1 |
| n3-247 | A-247 | B-1 |
| n3-248 | A-248 | B-1 |
| n3-249 | A-249 | B-1 |
| n3-250 | A-250 | B-1 |
| n3-251 | A-251 | B-1 |
| n3-252 | A-252 | B-1 |
| n3-253 | A-253 | B-1 |
| n3-254 | A-254 | B-1 |
| n3-255 | A-255 | B-1 |
| n3-256 | A-256 | B-1 |
| n3-257 | A-257 | B-1 |
| n3-258 | A-258 | B-1 |
| n3-259 | A-259 | B-1 |
| n3-260 | A-260 | B-1 |
| n3-261 | A-261 | B-1 |
| n3-262 | A-262 | B-1 |
| n3-263 | A-263 | B-1 |
| n3-264 | A-264 | B-1 |
| n3-265 | A-265 | B-1 |
| n3-266 | A-266 | B-1 |
| n3-267 | A-267 | B-1 |
| n3-268 | A-268 | B-1 |
| n3-269 | A-269 | B-1 |
| n3-270 | A-270 | B-1 |
| n3-271 | A-271 | B-1 |
| n3-272 | A-272 | B-1 |
| n3-273 | A-273 | B-1 |
| n3-274 | A-274 | B-1 |
| n3-275 | A-275 | B-1 |
| n3-276 | A-276 | B-1 |
| n3-277 | A-277 | B-1 |
| n3-278 | A-278 | B-1 |
| n3-279 | A-279 | B-1 |
| n3-280 | A-280 | B-1 |
| n3-281 | A-281 | B-1 |
| n3-282 | A-282 | B-1 |
| n3-283 | A-283 | B-1 |
| n3-284 | A-284 | B-1 |
| n3-285 | A-285 | B-1 |
| n3-286 | A-286 | B-1 |
| n3-287 | A-287 | B-1 |

TABLE 1-continued

| epn | n = 3 A | B |
|---|---|---|
| n3-288 | A-288 | B-1 |
| n3-289 | A-289 | B-1 |
| n3-290 | A-290 | B-1 |
| n3-291 | A-291 | B-1 |
| n3-292 | A-292 | B-1 |
| n3-293 | A-293 | B-1 |
| n3-294 | A-294 | B-1 |
| n3-295 | A-295 | B-1 |
| n3-296 | A-296 | B-1 |
| n3-297 | A-297 | B-1 |
| n3-298 | A-298 | B-1 |
| n3-299 | A-299 | B-1 |
| n3-300 | A-300 | B-1 |
| n3-301 | A-301 | B-1 |
| n3-302 | A-302 | B-1 |
| n3-303 | A-303 | B-1 |
| n3-304 | A-304 | B-1 |
| n3-305 | A-305 | B-1 |
| n3-306 | A-306 | B-1 |
| n3-307 | A-307 | B-1 |
| n3-308 | A-308 | B-1 |
| n3-309 | A-309 | B-1 |
| n3-310 | A-310 | B-1 |
| n3-311 | A-311 | B-1 |
| n3-312 | A-312 | B-1 |
| n3-313 | A-313 | B-1 |
| n3-314 | A-314 | B-1 |
| n3-315 | A-315 | B-1 |
| n3-316 | A-316 | B-1 |
| n3-317 | A-317 | B-1 |
| n3-318 | A-318 | B-1 |
| n3-319 | A-319 | B-1 |
| n3-320 | A-320 | B-1 |
| n3-321 | A-321 | B-1 |
| n3-322 | A-322 | B-1 |
| n3-323 | A-323 | B-1 |
| n3-324 | A-324 | B-1 |
| n3-325 | A-325 | B-1 |
| n3-326 | A-326 | B-1 |
| n3-327 | A-327 | B-1 |
| n3-328 | A-328 | B-1 |
| n3-329 | A-329 | B-1 |
| n3-330 | A-330 | B-1 |
| n3-331 | A-331 | B-1 |
| n3-332 | A-332 | B-1 |
| n3-333 | A-333 | B-1 |
| n3-334 | A-334 | B-1 |
| n3-335 | A-335 | B-1 |
| n3-336 | A-336 | B-1 |
| n3-337 | A-337 | B-1 |
| n3-338 | A-338 | B-1 |
| n3-339 | A-339 | B-1 |
| n3-340 | A-340 | B-1 |
| n3-341 | A-341 | B-1 |
| n3-342 | A-342 | B-1 |
| n3-343 | A-343 | B-1 |
| n3-344 | A-344 | B-1 |
| n3-345 | A-345 | B-1 |
| n3-346 | A-346 | B-1 |
| n3-347 | A-347 | B-1 |
| n3-348 | A-348 | B-1 |
| n3-349 | A-349 | B-1 |
| n3-350 | A-350 | B-1 |
| n3-351 | A-351 | B-1 |
| n3-352 | A-352 | B-1 |
| n3-353 | A-353 | B-1 |
| n3-354 | A-354 | B-1 |
| n3-355 | A-355 | B-1 |
| n3-356 | A-356 | B-1 |
| n3-357 | A-357 | B-1 |
| n3-358 | A-358 | B-1 |
| n3-359 | A-359 | B-1 |
| n3-360 | A-360 | B-1 |
| n3-361 | A-361 | B-1 |
| n3-362 | A-362 | B-1 |
| n3-363 | A-363 | B-1 |
| n3-364 | A-364 | B-1 |
| n3-365 | A-365 | B-1 |
| n3-366 | A-366 | B-1 |
| n3-367 | A-367 | B-1 |
| n3-368 | A-368 | B-1 |
| n3-369 | A-369 | B-1 |
| n3-370 | A-370 | B-1 |
| n3-371 | A-371 | B-1 |
| n3-372 | A-372 | B-1 |
| n3-373 | A-373 | B-1 |
| n3-374 | A-374 | B-1 |
| n3-375 | A-375 | B-1 |
| n3-376 | A-376 | B-1 |
| n3-377 | A-377 | B-1 |
| n3-378 | A-378 | B-1 |
| n3-379 | A-379 | B-1 |
| n3-380 | A-380 | B-1 |
| n3-381 | A-381 | B-1 |
| n3-382 | A-382 | B-1 |
| n3-383 | A-383 | B-1 |
| n3-384 | A-384 | B-1 |
| n3-385 | A-385 | B-1 |
| n3-386 | A-386 | B-1 |
| n3-387 | A-387 | B-1 |
| n3-388 | A-388 | B-1 |
| n3-389 | A-389 | B-1 |
| n3-390 | A-390 | B-1 |
| n3-391 | A-391 | B-1 |
| n3-392 | A-392 | B-1 |
| n3-393 | A-393 | B-1 |
| n3-394 | A-394 | B-1 |
| n3-395 | A-395 | B-1 |
| n3-396 | A-396 | B-1 |
| n3-397 | A-397 | B-1 |
| n3-398 | A-398 | B-1 |
| n3-399 | A-399 | B-1 |
| n3-400 | A-400 | B-1 |
| n3-401 | A-401 | B-1 |
| n3-402 | A-402 | B-1 |
| n3-403 | A-403 | B-1 |
| n3-404 | A-404 | B-1 |
| n3-405 | A-405 | B-1 |
| n3-406 | A-406 | B-1 |
| n3-407 | A-407 | B-1 |
| n3-408 | A-408 | B-1 |
| n3-409 | A-409 | B-1 |
| n3-410 | A-410 | B-1 |
| n3-411 | A-411 | B-1 |
| n3-412 | A-412 | B-1 |
| n3-413 | A-413 | B-1 |
| n3-414 | A-414 | B-1 |
| n3-415 | A-415 | B-1 |
| n3-416 | A-416 | B-1 |
| n3-417 | A-417 | B-1 |
| n3-418 | A-418 | B-1 |
| n3-419 | A-419 | B-1 |
| n3-420 | A-420 | B-1 |
| n3-421 | A-421 | B-1 |
| n3-422 | A-422 | B-1 |
| n3-423 | A-423 | B-1 |
| n3-424 | A-424 | B-1 |
| n3-425 | A-425 | B-1 |
| n3-426 | A-426 | B-1 |
| n3-427 | A-427 | B-1 |
| n3-428 | A-428 | B-1 |
| n3-429 | A-429 | B-1 |
| n3-430 | A-430 | B-1 |
| n3-431 | A-431 | B-1 |
| n3-432 | A-432 | B-1 |
| n3-433 | A-433 | B-1 |
| n3-434 | A-434 | B-1 |
| n3-435 | A-435 | B-1 |
| n3-436 | A-436 | B-1 |
| n3-437 | A-437 | B-1 |

TABLE 1-continued

| epn | n = 3 A | B |
|---|---|---|
| n3-438 | A-438 | B-1 |
| n3-439 | A-439 | B-1 |
| n3-440 | A-440 | B-1 |
| n3-441 | A-441 | B-1 |
| n3-442 | A-442 | B-1 |
| n3-443 | A-443 | B-1 |
| n3-444 | A-444 | B-1 |
| n3-445 | A-445 | B-1 |
| n3-446 | A-446 | B-1 |
| n3-447 | A-447 | B-1 |
| n3-448 | A-448 | B-1 |
| n3-449 | A-449 | B-1 |
| n3-450 | A-450 | B-1 |
| n3-451 | A-451 | B-1 |
| n3-452 | A-1 | B-2 |
| n3-453 | A-2 | B-2 |
| n3-454 | A-3 | B-2 |
| n3-455 | A-4 | B-2 |
| n3-456 | A-5 | B-2 |
| n3-457 | A-6 | B-2 |
| n3-458 | A-7 | B-2 |
| n3-459 | A-8 | B-2 |
| n3-460 | A-9 | B-2 |
| n3-461 | A-10 | B-2 |
| n3-462 | A-11 | B-2 |
| n3-463 | A-12 | B-2 |
| n3-464 | A-13 | B-2 |
| n3-465 | A-14 | B-2 |
| n3-466 | A-15 | B-2 |
| n3-467 | A-16 | B-2 |
| n3-468 | A-17 | B-2 |
| n3-469 | A-18 | B-2 |
| n3-470 | A-19 | B-2 |
| n3-471 | A-20 | B-2 |
| n3-472 | A-21 | B-2 |
| n3-473 | A-22 | B-2 |
| n3-474 | A-23 | B-2 |
| n3-475 | A-24 | B-2 |
| n3-476 | A-25 | B-2 |
| n3-477 | A-26 | B-2 |
| n3-478 | A-27 | B-2 |
| n3-479 | A-28 | B-2 |
| n3-480 | A-29 | B-2 |
| n3-481 | A-30 | B-2 |
| n3-482 | A-31 | B-2 |
| n3-483 | A-32 | B-2 |
| n3-484 | A-33 | B-2 |
| n3-485 | A-34 | B-2 |
| n3-486 | A-35 | B-2 |
| n3-487 | A-36 | B-2 |
| n3-488 | A-37 | B-2 |
| n3-489 | A-38 | B-2 |
| n3-490 | A-39 | B-2 |
| n3-491 | A-40 | B-2 |
| n3-492 | A-41 | B-2 |
| n3-493 | A-42 | B-2 |
| n3-494 | A-43 | B-2 |
| n3-495 | A-44 | B-2 |
| n3-496 | A-45 | B-2 |
| n3-497 | A-46 | B-2 |
| n3-498 | A-47 | B-2 |
| n3-499 | A-48 | B-2 |
| n3-500 | A-49 | B-2 |
| n3-501 | A-50 | B-2 |
| n3-502 | A-51 | B-2 |
| n3-503 | A-52 | B-2 |
| n3-504 | A-53 | B-2 |
| n3-505 | A-54 | B-2 |
| n3-506 | A-55 | B-2 |
| n3-507 | A-56 | B-2 |
| n3-508 | A-57 | B-2 |
| n3-509 | A-58 | B-2 |
| n3-510 | A-59 | B-2 |
| n3-511 | A-60 | B-2 |
| n3-512 | A-61 | B-2 |
| n3-513 | A-62 | B-2 |
| n3-514 | A-63 | B-2 |
| n3-515 | A-64 | B-2 |
| n3-516 | A-65 | B-2 |
| n3-517 | A-66 | B-2 |
| n3-518 | A-67 | B-2 |
| n3-519 | A-68 | B-2 |
| n3-520 | A-69 | B-2 |
| n3-521 | A-70 | B-2 |
| n3-522 | A-71 | B-2 |
| n3-523 | A-72 | B-2 |
| n3-524 | A-73 | B-2 |
| n3-525 | A-74 | B-2 |
| n3-526 | A-75 | B-2 |
| n3-527 | A-76 | B-2 |
| n3-528 | A-77 | B-2 |
| n3-529 | A-78 | B-2 |
| n3-530 | A-79 | B-2 |
| n3-531 | A-80 | B-2 |
| n3-532 | A-81 | B-2 |
| n3-533 | A-82 | B-2 |
| n3-534 | A-83 | B-2 |
| n3-535 | A-84 | B-2 |
| n3-536 | A-85 | B-2 |
| n3-537 | A-86 | B-2 |
| n3-538 | A-87 | B-2 |
| n3-539 | A-88 | B-2 |
| n3-540 | A-89 | B-2 |
| n3-541 | A-90 | B-2 |
| n3-542 | A-91 | B-2 |
| n3-543 | A-92 | B-2 |
| n3-544 | A-93 | B-2 |
| n3-545 | A-94 | B-2 |
| n3-546 | A-95 | B-2 |
| n3-547 | A-96 | B-2 |
| n3-548 | A-97 | B-2 |
| n3-549 | A-98 | B-2 |
| n3-550 | A-99 | B-2 |
| n3-551 | A-100 | B-2 |
| n3-552 | A-101 | B-2 |
| n3-553 | A-102 | B-2 |
| n3-554 | A-103 | B-2 |
| n3-555 | A-104 | B-2 |
| n3-556 | A-105 | B-2 |
| n3-557 | A-106 | B-2 |
| n3-558 | A-107 | B-2 |
| n3-559 | A-108 | B-2 |
| n3-560 | A-109 | B-2 |
| n3-561 | A-110 | B-2 |
| n3-562 | A-111 | B-2 |
| n3-563 | A-112 | B-2 |
| n3-564 | A-113 | B-2 |
| n3-565 | A-114 | B-2 |
| n3-566 | A-115 | B-2 |
| n3-567 | A-116 | B-2 |
| n3-568 | A-117 | B-2 |
| n3-569 | A-118 | B-2 |
| n3-570 | A-119 | B-2 |
| n3-571 | A-120 | B-2 |
| n3-572 | A-121 | B-2 |
| n3-573 | A-122 | B-2 |
| n3-574 | A-123 | B-2 |
| n3-575 | A-124 | B-2 |
| n3-576 | A-125 | B-2 |
| n3-577 | A-126 | B-2 |
| n3-578 | A-127 | B-2 |
| n3-579 | A-128 | B-2 |
| n3-580 | A-129 | B-2 |
| n3-581 | A-130 | B-2 |
| n3-582 | A-131 | B-2 |
| n3-583 | A-132 | B-2 |
| n3-584 | A-133 | B-2 |
| n3-585 | A-134 | B-2 |
| n3-586 | A-135 | B-2 |
| n3-587 | A-136 | B-2 |

TABLE 1-continued

| epn | n = 3 A | B |
|---|---|---|
| n3-588 | A-137 | B-2 |
| n3-589 | A-138 | B-2 |
| n3-590 | A-139 | B-2 |
| n3-591 | A-140 | B-2 |
| n3-592 | A-141 | B-2 |
| n3-593 | A-142 | B-2 |
| n3-594 | A-143 | B-2 |
| n3-595 | A-144 | B-2 |
| n3-596 | A-145 | B-2 |
| n3-597 | A-146 | B-2 |
| n3-598 | A-147 | B-2 |
| n3-599 | A-148 | B-2 |
| n3-600 | A-149 | B-2 |
| n3-601 | A-150 | B-2 |
| n3-602 | A-151 | B-2 |
| n3-603 | A-152 | B-2 |
| n3-604 | A-153 | B-2 |
| n3-605 | A-154 | B-2 |
| n3-606 | A-155 | B-2 |
| n3-607 | A-156 | B-2 |
| n3-608 | A-157 | B-2 |
| n3-609 | A-158 | B-2 |
| n3-610 | A-159 | B-2 |
| n3-611 | A-160 | B-2 |
| n3-612 | A-161 | B-2 |
| n3-613 | A-162 | B-2 |
| n3-614 | A-163 | B-2 |
| n3-615 | A-164 | B-2 |
| n3-616 | A-165 | B-2 |
| n3-617 | A-166 | B-2 |
| n3-618 | A-167 | B-2 |
| n3-619 | A-168 | B-2 |
| n3-620 | A-169 | B-2 |
| n3-621 | A-170 | B-2 |
| n3-622 | A-171 | B-2 |
| n3-623 | A-172 | B-2 |
| n3-624 | A-173 | B-2 |
| n3-625 | A-174 | B-2 |
| n3-626 | A-175 | B-2 |
| n3-627 | A-176 | B-2 |
| n3-628 | A-177 | B-2 |
| n3-629 | A-178 | B-2 |
| n3-630 | A-179 | B-2 |
| n3-631 | A-180 | B-2 |
| n3-632 | A-181 | B-2 |
| n3-633 | A-182 | B-2 |
| n3-634 | A-183 | B-2 |
| n3-635 | A-184 | B-2 |
| n3-636 | A-185 | B-2 |
| n3-637 | A-186 | B-2 |
| n3-638 | A-187 | B-2 |
| n3-639 | A-188 | B-2 |
| n3-640 | A-189 | B-2 |
| n3-641 | A-190 | B-2 |
| n3-642 | A-191 | B-2 |
| n3-643 | A-192 | B-2 |
| n3-644 | A-193 | B-2 |
| n3-645 | A-194 | B-2 |
| n3-646 | A-195 | B-2 |
| n3-647 | A-196 | B-2 |
| n3-648 | A-197 | B-2 |
| n3-649 | A-198 | B-2 |
| n3-650 | A-199 | B-2 |
| n3-651 | A-200 | B-2 |
| n3-652 | A-201 | B-2 |
| n3-653 | A-202 | B-2 |
| n3-654 | A-203 | B-2 |
| n3-655 | A-204 | B-2 |
| n3-656 | A-205 | B-2 |
| n3-657 | A-206 | B-2 |
| n3-658 | A-207 | B-2 |
| n3-659 | A-208 | B-2 |
| n3-660 | A-209 | B-2 |
| n3-661 | A-210 | B-2 |
| n3-662 | A-211 | B-2 |
| n3-663 | A-212 | B-2 |
| n3-664 | A-213 | B-2 |
| n3-665 | A-214 | B-2 |
| n3-666 | A-215 | B-2 |
| n3-667 | A-216 | B-2 |
| n3-668 | A-217 | B-2 |
| n3-669 | A-218 | B-2 |
| n3-670 | A-219 | B-2 |
| n3-671 | A-220 | B-2 |
| n3-672 | A-221 | B-2 |
| n3-673 | A-222 | B-2 |
| n3-674 | A-223 | B-2 |
| n3-675 | A-224 | B-2 |
| n3-676 | A-225 | B-2 |
| n3-677 | A-226 | B-2 |
| n3-678 | A-227 | B-2 |
| n3-679 | A-228 | B-2 |
| n3-680 | A-229 | B-2 |
| n3-681 | A-230 | B-2 |
| n3-682 | A-231 | B-2 |
| n3-683 | A-232 | B-2 |
| n3-684 | A-233 | B-2 |
| n3-685 | A-234 | B-2 |
| n3-686 | A-235 | B-2 |
| n3-687 | A-236 | B-2 |
| n3-688 | A-237 | B-2 |
| n3-689 | A-238 | B-2 |
| n3-690 | A-239 | B-2 |
| n3-691 | A-240 | B-2 |
| n3-692 | A-241 | B-2 |
| n3-693 | A-242 | B-2 |
| n3-694 | A-243 | B-2 |
| n3-695 | A-244 | B-2 |
| n3-696 | A-245 | B-2 |
| n3-697 | A-246 | B-2 |
| n3-698 | A-247 | B-2 |
| n3-699 | A-248 | B-2 |
| n3-700 | A-249 | B-2 |
| n3-701 | A-250 | B-2 |
| n3-702 | A-251 | B-2 |
| n3-703 | A-252 | B-2 |
| n3-704 | A-253 | B-2 |
| n3-705 | A-254 | B-2 |
| n3-706 | A-255 | B-2 |
| n3-707 | A-256 | B-2 |
| n3-708 | A-257 | B-2 |
| n3-709 | A-258 | B-2 |
| n3-710 | A-259 | B-2 |
| n3-711 | A-260 | B-2 |
| n3-712 | A-261 | B-2 |
| n3-713 | A-262 | B-2 |
| n3-714 | A-263 | B-2 |
| n3-715 | A-264 | B-2 |
| n3-716 | A-265 | B-2 |
| n3-717 | A-266 | B-2 |
| n3-718 | A-267 | B-2 |
| n3-719 | A-268 | B-2 |
| n3-720 | A-269 | B-2 |
| n3-721 | A-270 | B-2 |
| n3-722 | A-271 | B-2 |
| n3-723 | A-272 | B-2 |
| n3-724 | A-273 | B-2 |
| n3-725 | A-274 | B-2 |
| n3-726 | A-275 | B-2 |
| n3-727 | A-276 | B-2 |
| n3-728 | A-277 | B-2 |
| n3-729 | A-278 | B-2 |
| n3-730 | A-279 | B-2 |
| n3-731 | A-280 | B-2 |
| n3-732 | A-281 | B-2 |
| n3-733 | A-282 | B-2 |
| n3-734 | A-283 | B-2 |
| n3-735 | A-284 | B-2 |
| n3-736 | A-285 | B-2 |
| n3-737 | A-286 | B-2 |

TABLE 1-continued

| epn | n = 3 A | B |
|---|---|---|
| n3-738 | A-287 | B-2 |
| n3-739 | A-288 | B-2 |
| n3-740 | A-289 | B-2 |
| n3-741 | A-290 | B-2 |
| n3-742 | A-291 | B-2 |
| n3-743 | A-292 | B-2 |
| n3-744 | A-293 | B-2 |
| n3-745 | A-294 | B-2 |
| n3-746 | A-295 | B-2 |
| n3-747 | A-296 | B-2 |
| n3-748 | A-297 | B-2 |
| n3-749 | A-298 | B-2 |
| n3-750 | A-299 | B-2 |
| n3-751 | A-300 | B-2 |
| n3-752 | A-301 | B-2 |
| n3-753 | A-302 | B-2 |
| n3-754 | A-303 | B-2 |
| n3-755 | A-304 | B-2 |
| n3-756 | A-305 | B-2 |
| n3-757 | A-306 | B-2 |
| n3-758 | A-307 | B-2 |
| n3-759 | A-308 | B-2 |
| n3-760 | A-309 | B-2 |
| n3-761 | A-310 | B-2 |
| n3-762 | A-311 | B-2 |
| n3-763 | A-312 | B-2 |
| n3-764 | A-313 | B-2 |
| n3-765 | A-314 | B-2 |
| n3-766 | A-315 | B-2 |
| n3-767 | A-316 | B-2 |
| n3-768 | A-317 | B-2 |
| n3-769 | A-318 | B-2 |
| n3-770 | A-319 | B-2 |
| n3-771 | A-320 | B-2 |
| n3-772 | A-321 | B-2 |
| n3-773 | A-322 | B-2 |
| n3-774 | A-323 | B-2 |
| n3-775 | A-324 | B-2 |
| n3-776 | A-325 | B-2 |
| n3-777 | A-326 | B-2 |
| n3-778 | A-327 | B-2 |
| n3-779 | A-328 | B-2 |
| n3-780 | A-329 | B-2 |
| n3-781 | A-330 | B-2 |
| n3-782 | A-331 | B-2 |
| n3-783 | A-332 | B-2 |
| n3-784 | A-333 | B-2 |
| n3-785 | A-334 | B-2 |
| n3-786 | A-335 | B-2 |
| n3-787 | A-336 | B-2 |
| n3-788 | A-337 | B-2 |
| n3-789 | A-338 | B-2 |
| n3-790 | A-339 | B-2 |
| n3-791 | A-340 | B-2 |
| n3-792 | A-341 | B-2 |
| n3-793 | A-342 | B-2 |
| n3-794 | A-343 | B-2 |
| n3-795 | A-344 | B-2 |
| n3-796 | A-345 | B-2 |
| n3-797 | A-346 | B-2 |
| n3-798 | A-347 | B-2 |
| n3-799 | A-348 | B-2 |
| n3-800 | A-349 | B-2 |
| n3-801 | A-350 | B-2 |
| n3-802 | A-351 | B-2 |
| n3-803 | A-352 | B-2 |
| n3-804 | A-353 | B-2 |
| n3-805 | A-354 | B-2 |
| n3-806 | A-355 | B-2 |
| n3-807 | A-356 | B-2 |
| n3-808 | A-357 | B-2 |
| n3-809 | A-358 | B-2 |
| n3-810 | A-359 | B-2 |
| n3-811 | A-360 | B-2 |
| n3-812 | A-361 | B-2 |
| n3-813 | A-362 | B-2 |
| n3-814 | A-363 | B-2 |
| n3-815 | A-364 | B-2 |
| n3-816 | A-365 | B-2 |
| n3-817 | A-366 | B-2 |
| n3-818 | A-367 | B-2 |
| n3-819 | A-368 | B-2 |
| n3-820 | A-369 | B-2 |
| n3-821 | A-370 | B-2 |
| n3-822 | A-371 | B-2 |
| n3-823 | A-372 | B-2 |
| n3-824 | A-373 | B-2 |
| n3-825 | A-374 | B-2 |
| n3-826 | A-375 | B-2 |
| n3-827 | A-376 | B-2 |
| n3-828 | A-377 | B-2 |
| n3-829 | A-378 | B-2 |
| n3-830 | A-379 | B-2 |
| n3-831 | A-380 | B-2 |
| n3-832 | A-381 | B-2 |
| n3-833 | A-382 | B-2 |
| n3-834 | A-383 | B-2 |
| n3-835 | A-384 | B-2 |
| n3-836 | A-385 | B-2 |
| n3-837 | A-386 | B-2 |
| n3-838 | A-387 | B-2 |
| n3-839 | A-388 | B-2 |
| n3-840 | A-389 | B-2 |
| n3-841 | A-390 | B-2 |
| n3-842 | A-391 | B-2 |
| n3-843 | A-392 | B-2 |
| n3-844 | A-393 | B-2 |
| n3-845 | A-394 | B-2 |
| n3-846 | A-395 | B-2 |
| n3-847 | A-396 | B-2 |
| n3-848 | A-397 | B-2 |
| n3-849 | A-398 | B-2 |
| n3-850 | A-399 | B-2 |
| n3-851 | A-400 | B-2 |
| n3-852 | A-401 | B-2 |
| n3-853 | A-402 | B-2 |
| n3-854 | A-403 | B-2 |
| n3-855 | A-404 | B-2 |
| n3-856 | A-405 | B-2 |
| n3-857 | A-406 | B-2 |
| n3-858 | A-407 | B-2 |
| n3-859 | A-408 | B-2 |
| n3-860 | A-409 | B-2 |
| n3-861 | A-410 | B-2 |
| n3-862 | A-411 | B-2 |
| n3-863 | A-412 | B-2 |
| n3-864 | A-413 | B-2 |
| n3-865 | A-414 | B-2 |
| n3-866 | A-415 | B-2 |
| n3-867 | A-416 | B-2 |
| n3-868 | A-417 | B-2 |
| n3-869 | A-418 | B-2 |
| n3-870 | A-419 | B-2 |
| n3-871 | A-420 | B-2 |
| n3-872 | A-421 | B-2 |
| n3-873 | A-422 | B-2 |
| n3-874 | A-423 | B-2 |
| n3-875 | A-424 | B-2 |
| n3-876 | A-425 | B-2 |
| n3-877 | A-426 | B-2 |
| n3-878 | A-427 | B-2 |
| n3-879 | A-428 | B-2 |
| n3-880 | A-429 | B-2 |
| n3-881 | A-430 | B-2 |
| n3-882 | A-431 | B-2 |
| n3-883 | A-432 | B-2 |
| n3-884 | A-433 | B-2 |
| n3-885 | A-434 | B-2 |
| n3-886 | A-435 | B-2 |
| n3-887 | A-436 | B-2 |

TABLE 1-continued

| epn | n = 3 A | B |
|---|---|---|
| n3-888 | A-437 | B-2 |
| n3-889 | A-438 | B-2 |
| n3-890 | A-439 | B-2 |
| n3-891 | A-440 | B-2 |
| n3-892 | A-441 | B-2 |
| n3-893 | A-442 | B-2 |
| n3-894 | A-443 | B-2 |
| n3-895 | A-444 | B-2 |
| n3-896 | A-445 | B-2 |
| n3-897 | A-446 | B-2 |
| n3-898 | A-447 | B-2 |
| n3-899 | A-448 | B-2 |
| n3-900 | A-449 | B-2 |
| n3-901 | A-450 | B-2 |
| n3-902 | A-451 | B-2 |
| n3-903 | A-1 | B-3 |
| n3-904 | A-2 | B-3 |
| n3-905 | A-3 | B-3 |
| n3-906 | A-4 | B-3 |
| n3-907 | A-5 | B-3 |
| n3-908 | A-6 | B-3 |
| n3-909 | A-7 | B-3 |
| n3-910 | A-8 | B-3 |
| n3-911 | A-9 | B-3 |
| n3-912 | A-10 | B-3 |
| n3-913 | A-11 | B-3 |
| n3-914 | A-12 | B-3 |
| n3-915 | A-13 | B-3 |
| n3-916 | A-14 | B-3 |
| n3-917 | A-15 | B-3 |
| n3-918 | A-16 | B-3 |
| n3-919 | A-17 | B-3 |
| n3-920 | A-18 | B-3 |
| n3-921 | A-19 | B-3 |
| n3-922 | A-20 | B-3 |
| n3-923 | A-21 | B-3 |
| n3-924 | A-22 | B-3 |
| n3-925 | A-23 | B-3 |
| n3-926 | A-24 | B-3 |
| n3-927 | A-25 | B-3 |
| n3-928 | A-26 | B-3 |
| n3-929 | A-27 | B-3 |
| n3-930 | A-28 | B-3 |
| n3-931 | A-29 | B-3 |
| n3-932 | A-30 | B-3 |
| n3-933 | A-31 | B-3 |
| n3-934 | A-32 | B-3 |
| n3-935 | A-33 | B-3 |
| n3-936 | A-34 | B-3 |
| n3-937 | A-35 | B-3 |
| n3-938 | A-36 | B-3 |
| n3-939 | A-37 | B-3 |
| n3-940 | A-38 | B-3 |
| n3-941 | A-39 | B-3 |
| n3-942 | A-40 | B-3 |
| n3-943 | A-41 | B-3 |
| n3-944 | A-42 | B-3 |
| n3-945 | A-43 | B-3 |
| n3-946 | A-44 | B-3 |
| n3-947 | A-45 | B-3 |
| n3-948 | A-46 | B-3 |
| n3-949 | A-47 | B-3 |
| n3-950 | A-48 | B-3 |
| n3-951 | A-49 | B-3 |
| n3-952 | A-50 | B-3 |
| n3-953 | A-51 | B-3 |
| n3-954 | A-52 | B-3 |
| n3-955 | A-53 | B-3 |
| n3-956 | A-54 | B-3 |
| n3-957 | A-55 | B-3 |
| n3-958 | A-56 | B-3 |
| n3-959 | A-57 | B-3 |
| n3-960 | A-58 | B-3 |
| n3-961 | A-59 | B-3 |
| n3-962 | A-60 | B-3 |
| n3-963 | A-61 | B-3 |
| n3-964 | A-62 | B-3 |
| n3-965 | A-63 | B-3 |
| n3-966 | A-64 | B-3 |
| n3-967 | A-65 | B-3 |
| n3-968 | A-66 | B-3 |
| n3-969 | A-67 | B-3 |
| n3-970 | A-68 | B-3 |
| n3-971 | A-69 | B-3 |
| n3-972 | A-70 | B-3 |
| n3-973 | A-71 | B-3 |
| n3-974 | A-72 | B-3 |
| n3-975 | A-73 | B-3 |
| n3-976 | A-74 | B-3 |
| n3-977 | A-75 | B-3 |
| n3-978 | A-76 | B-3 |
| n3-979 | A-77 | B-3 |
| n3-980 | A-78 | B-3 |
| n3-981 | A-79 | B-3 |
| n3-982 | A-80 | B-3 |
| n3-983 | A-81 | B-3 |
| n3-984 | A-82 | B-3 |
| n3-985 | A-83 | B-3 |
| n3-986 | A-84 | B-3 |
| n3-987 | A-85 | B-3 |
| n3-988 | A-86 | B-3 |
| n3-989 | A-87 | B-3 |
| n3-990 | A-88 | B-3 |
| n3-991 | A-89 | B-3 |
| n3-992 | A-90 | B-3 |
| n3-993 | A-91 | B-3 |
| n3-994 | A-92 | B-3 |
| n3-995 | A-93 | B-3 |
| n3-996 | A-94 | B-3 |
| n3-997 | A-95 | B-3 |
| n3-998 | A-96 | B-3 |
| n3-999 | A-97 | B-3 |
| n3-1000 | A-98 | B-3 |
| n3-1001 | A-99 | B-3 |
| n3-1002 | A-100 | B-3 |
| n3-1003 | A-101 | B-3 |
| n3-1004 | A-102 | B-3 |
| n3-1005 | A-103 | B-3 |
| n3-1006 | A-104 | B-3 |
| n3-1007 | A-105 | B-3 |
| n3-1008 | A-106 | B-3 |
| n3-1009 | A-107 | B-3 |
| n3-1010 | A-108 | B-3 |
| n3-1011 | A-109 | B-3 |
| n3-1012 | A-110 | B-3 |
| n3-1013 | A-111 | B-3 |
| n3-1014 | A-112 | B-3 |
| n3-1015 | A-113 | B-3 |
| n3-1016 | A-114 | B-3 |
| n3-1017 | A-115 | B-3 |
| n3-1018 | A-116 | B-3 |
| n3-1019 | A-117 | B-3 |
| n3-1020 | A-118 | B-3 |
| n3-1021 | A-119 | B-3 |
| n3-1022 | A-120 | B-3 |
| n3-1023 | A-121 | B-3 |
| n3-1024 | A-122 | B-3 |
| n3-1025 | A-123 | B-3 |
| n3-1026 | A-124 | B-3 |
| n3-1027 | A-125 | B-3 |
| n3-1028 | A-126 | B-3 |
| n3-1029 | A-127 | B-3 |
| n3-1030 | A-128 | B-3 |
| n3-1031 | A-129 | B-3 |
| n3-1032 | A-130 | B-3 |
| n3-1033 | A-131 | B-3 |
| n3-1034 | A-132 | B-3 |
| n3-1035 | A-133 | B-3 |
| n3-1036 | A-134 | B-3 |
| n3-1037 | A-135 | B-3 |

TABLE 1-continued

| | n = 3 | |
|---|---|---|
| epn | A | B |
| n3-1038 | A-136 | B-3 |
| n3-1039 | A-137 | B-3 |
| n3-1040 | A-138 | B-3 |
| n3-1041 | A-139 | B-3 |
| n3-1042 | A-140 | B-3 |
| n3-1043 | A-141 | B-3 |
| n3-1044 | A-142 | B-3 |
| n3-1045 | A-143 | B-3 |
| n3-1046 | A-144 | B-3 |
| n3-1047 | A-145 | B-3 |
| n3-1048 | A-146 | B-3 |
| n3-1049 | A-147 | B-3 |
| n3-1050 | A-148 | B-3 |
| n3-1051 | A-149 | B-3 |
| n3-1052 | A-150 | B-3 |
| n3-1053 | A-151 | B-3 |
| n3-1054 | A-152 | B-3 |
| n3-1055 | A-153 | B-3 |
| n3-1056 | A-154 | B-3 |
| n3-1057 | A-155 | B-3 |
| n3-1058 | A-156 | B-3 |
| n3-1059 | A-157 | B-3 |
| n3-1060 | A-158 | B-3 |
| n3-1061 | A-159 | B-3 |
| n3-1062 | A-160 | B-3 |
| n3-1063 | A-161 | B-3 |
| n3-1064 | A-162 | B-3 |
| n3-1065 | A-163 | B-3 |
| n3-1066 | A-164 | B-3 |
| n3-1067 | A-165 | B-3 |
| n3-1068 | A-166 | B-3 |
| n3-1069 | A-167 | B-3 |
| n3-1070 | A-168 | B-3 |
| n3-1071 | A-169 | B-3 |
| n3-1072 | A-170 | B-3 |
| n3-1073 | A-171 | B-3 |
| n3-1074 | A-172 | B-3 |
| n3-1075 | A-173 | B-3 |
| n3-1076 | A-174 | B-3 |
| n3-1077 | A-175 | B-3 |
| n3-1078 | A-176 | B-3 |
| n3-1079 | A-177 | B-3 |
| n3-1080 | A-178 | B-3 |
| n3-1081 | A-179 | B-3 |
| n3-1082 | A-180 | B-3 |
| n3-1083 | A-181 | B-3 |
| n3-1084 | A-182 | B-3 |
| n3-1085 | A-183 | B-3 |
| n3-1086 | A-184 | B-3 |
| n3-1087 | A-185 | B-3 |
| n3-1088 | A-186 | B-3 |
| n3-1089 | A-187 | B-3 |
| n3-1090 | A-188 | B-3 |
| n3-1091 | A-189 | B-3 |
| n3-1092 | A-190 | B-3 |
| n3-1093 | A-191 | B-3 |
| n3-1094 | A-192 | B-3 |
| n3-1095 | A-193 | B-3 |
| n3-1096 | A-194 | B-3 |
| n3-1097 | A-195 | B-3 |
| n3-1098 | A-196 | B-3 |
| n3-1099 | A-197 | B-3 |
| n3-1100 | A-198 | B-3 |
| n3-1101 | A-199 | B-3 |
| n3-1102 | A-200 | B-3 |
| n3-1103 | A-201 | B-3 |
| n3-1104 | A-202 | B-3 |
| n3-1105 | A-203 | B-3 |
| n3-1106 | A-204 | B-3 |
| n3-1107 | A-205 | B-3 |
| n3-1108 | A-206 | B-3 |
| n3-1109 | A-207 | B-3 |
| n3-1110 | A-208 | B-3 |
| n3-1111 | A-209 | B-3 |
| n3-1112 | A-210 | B-3 |
| n3-1113 | A-211 | B-3 |
| n3-1114 | A-212 | B-3 |
| n3-1115 | A-213 | B-3 |
| n3-1116 | A-214 | B-3 |
| n3-1117 | A-215 | B-3 |
| n3-1118 | A-216 | B-3 |
| n3-1119 | A-217 | B-3 |
| n3-1120 | A-218 | B-3 |
| n3-1121 | A-219 | B-3 |
| n3-1122 | A-220 | B-3 |
| n3-1123 | A-221 | B-3 |
| n3-1124 | A-222 | B-3 |
| n3-1125 | A-223 | B-3 |
| n3-1126 | A-224 | B-3 |
| n3-1127 | A-225 | B-3 |
| n3-1128 | A-226 | B-3 |
| n3-1129 | A-227 | B-3 |
| n3-1130 | A-228 | B-3 |
| n3-1131 | A-229 | B-3 |
| n3-1132 | A-230 | B-3 |
| n3-1133 | A-231 | B-3 |
| n3-1134 | A-232 | B-3 |
| n3-1135 | A-233 | B-3 |
| n3-1136 | A-234 | B-3 |
| n3-1137 | A-235 | B-3 |
| n3-1138 | A-236 | B-3 |
| n3-1139 | A-237 | B-3 |
| n3-1140 | A-238 | B-3 |
| n3-1141 | A-239 | B-3 |
| n3-1142 | A-240 | B-3 |
| n3-1143 | A-241 | B-3 |
| n3-1144 | A-242 | B-3 |
| n3-1145 | A-243 | B-3 |
| n3-1146 | A-244 | B-3 |
| n3-1147 | A-245 | B-3 |
| n3-1148 | A-246 | B-3 |
| n3-1149 | A-247 | B-3 |
| n3-1150 | A-248 | B-3 |
| n3-1151 | A-249 | B-3 |
| n3-1152 | A-250 | B-3 |
| n3-1153 | A-251 | B-3 |
| n3-1154 | A-252 | B-3 |
| n3-1155 | A-253 | B-3 |
| n3-1156 | A-254 | B-3 |
| n3-1157 | A-255 | B-3 |
| n3-1158 | A-256 | B-3 |
| n3-1159 | A-257 | B-3 |
| n3-1160 | A-258 | B-3 |
| n3-1161 | A-259 | B-3 |
| n3-1162 | A-260 | B-3 |
| n3-1163 | A-261 | B-3 |
| n3-1164 | A-262 | B-3 |
| n3-1165 | A-263 | B-3 |
| n3-1166 | A-264 | B-3 |
| n3-1167 | A-265 | B-3 |
| n3-1168 | A-266 | B-3 |
| n3-1169 | A-267 | B-3 |
| n3-1170 | A-268 | B-3 |
| n3-1171 | A-269 | B-3 |
| n3-1172 | A-270 | B-3 |
| n3-1173 | A-271 | B-3 |
| n3-1174 | A-272 | B-3 |
| n3-1175 | A-273 | B-3 |
| n3-1176 | A-274 | B-3 |
| n3-1177 | A-275 | B-3 |
| n3-1178 | A-276 | B-3 |
| n3-1179 | A-277 | B-3 |
| n3-1180 | A-278 | B-3 |
| n3-1181 | A-279 | B-3 |
| n3-1182 | A-280 | B-3 |
| n3-1183 | A-281 | B-3 |
| n3-1184 | A-282 | B-3 |
| n3-1185 | A-283 | B-3 |
| n3-1186 | A-284 | B-3 |
| n3-1187 | A-285 | B-3 |

TABLE 1-continued

| epn | n = 3 A | B |
|---|---|---|
| n3-1188 | A-286 | B-3 |
| n3-1189 | A-287 | B-3 |
| n3-1190 | A-288 | B-3 |
| n3-1191 | A-289 | B-3 |
| n3-1192 | A-290 | B-3 |
| n3-1193 | A-291 | B-3 |
| n3-1194 | A-292 | B-3 |
| n3-1195 | A-293 | B-3 |
| n3-1196 | A-294 | B-3 |
| n3-1197 | A-295 | B-3 |
| n3-1198 | A-296 | B-3 |
| n3-1199 | A-297 | B-3 |
| n3-1200 | A-298 | B-3 |
| n3-1201 | A-299 | B-3 |
| n3-1202 | A-300 | B-3 |
| n3-1203 | A-301 | B-3 |
| n3-1204 | A-302 | B-3 |
| n3-1205 | A-303 | B-3 |
| n3-1206 | A-304 | B-3 |
| n3-1207 | A-305 | B-3 |
| n3-1208 | A-306 | B-3 |
| n3-1209 | A-307 | B-3 |
| n3-1210 | A-308 | B-3 |
| n3-1211 | A-309 | B-3 |
| n3-1212 | A-310 | B-3 |
| n3-1213 | A-311 | B-3 |
| n3-1214 | A-312 | B-3 |
| n3-1215 | A-313 | B-3 |
| n3-1216 | A-314 | B-3 |
| n3-1217 | A-315 | B-3 |
| n3-1218 | A-316 | B-3 |
| n3-1219 | A-317 | B-3 |
| n3-1220 | A-318 | B-3 |
| n3-1221 | A-319 | B-3 |
| n3-1222 | A-320 | B-3 |
| n3-1223 | A-321 | B-3 |
| n3-1224 | A-322 | B-3 |
| n3-1225 | A-323 | B-3 |
| n3-1226 | A-324 | B-3 |
| n3-1227 | A-325 | B-3 |
| n3-1228 | A-326 | B-3 |
| n3-1229 | A-327 | B-3 |
| n3-1230 | A-328 | B-3 |
| n3-1231 | A-329 | B-3 |
| n3-1232 | A-330 | B-3 |
| n3-1233 | A-331 | B-3 |
| n3-1234 | A-332 | B-3 |
| n3-1235 | A-333 | B-3 |
| n3-1236 | A-334 | B-3 |
| n3-1237 | A-335 | B-3 |
| n3-1238 | A-336 | B-3 |
| n3-1239 | A-337 | B-3 |
| n3-1240 | A-338 | B-3 |
| n3-1241 | A-339 | B-3 |
| n3-1242 | A-340 | B-3 |
| n3-1243 | A-341 | B-3 |
| n3-1244 | A-342 | B-3 |
| n3-1245 | A-343 | B-3 |
| n3-1246 | A-344 | B-3 |
| n3-1247 | A-345 | B-3 |
| n3-1248 | A-346 | B-3 |
| n3-1249 | A-347 | B-3 |
| n3-1250 | A-348 | B-3 |
| n3-1251 | A-349 | B-3 |
| n3-1252 | A-350 | B-3 |
| n3-1253 | A-351 | B-3 |
| n3-1254 | A-352 | B-3 |
| n3-1255 | A-353 | B-3 |
| n3-1256 | A-354 | B-3 |
| n3-1257 | A-355 | B-3 |
| n3-1258 | A-356 | B-3 |
| n3-1259 | A-357 | B-3 |
| n3-1260 | A-358 | B-3 |
| n3-1261 | A-359 | B-3 |
| n3-1262 | A-360 | B-3 |
| n3-1263 | A-361 | B-3 |
| n3-1264 | A-362 | B-3 |
| n3-1265 | A-363 | B-3 |
| n3-1266 | A-364 | B-3 |
| n3-1267 | A-365 | B-3 |
| n3-1268 | A-366 | B-3 |
| n3-1269 | A-367 | B-3 |
| n3-1270 | A-368 | B-3 |
| n3-1271 | A-369 | B-3 |
| n3-1272 | A-370 | B-3 |
| n3-1273 | A-371 | B-3 |
| n3-1274 | A-372 | B-3 |
| n3-1275 | A-373 | B-3 |
| n3-1276 | A-374 | B-3 |
| n3-1277 | A-375 | B-3 |
| n3-1278 | A-376 | B-3 |
| n3-1279 | A-377 | B-3 |
| n3-1280 | A-378 | B-3 |
| n3-1281 | A-379 | B-3 |
| n3-1282 | A-380 | B-3 |
| n3-1283 | A-381 | B-3 |
| n3-1284 | A-382 | B-3 |
| n3-1285 | A-383 | B-3 |
| n3-1286 | A-384 | B-3 |
| n3-1287 | A-385 | B-3 |
| n3-1288 | A-386 | B-3 |
| n3-1289 | A-387 | B-3 |
| n3-1290 | A-388 | B-3 |
| n3-1291 | A-389 | B-3 |
| n3-1292 | A-390 | B-3 |
| n3-1293 | A-391 | B-3 |
| n3-1294 | A-392 | B-3 |
| n3-1295 | A-393 | B-3 |
| n3-1296 | A-394 | B-3 |
| n3-1297 | A-395 | B-3 |
| n3-1298 | A-396 | B-3 |
| n3-1299 | A-397 | B-3 |
| n3-1300 | A-398 | B-3 |
| n3-1301 | A-399 | B-3 |
| n3-1302 | A-400 | B-3 |
| n3-1303 | A-401 | B-3 |
| n3-1304 | A-402 | B-3 |
| n3-1305 | A-403 | B-3 |
| n3-1306 | A-404 | B-3 |
| n3-1307 | A-405 | B-3 |
| n3-1308 | A-406 | B-3 |
| n3-1309 | A-407 | B-3 |
| n3-1310 | A-408 | B-3 |
| n3-1311 | A-409 | B-3 |
| n3-1312 | A-410 | B-3 |
| n3-1313 | A-411 | B-3 |
| n3-1314 | A-412 | B-3 |
| n3-1315 | A-413 | B-3 |
| n3-1316 | A-414 | B-3 |
| n3-1317 | A-415 | B-3 |
| n3-1318 | A-416 | B-3 |
| n3-1319 | A-417 | B-3 |
| n3-1320 | A-418 | B-3 |
| n3-1321 | A-419 | B-3 |
| n3-1322 | A-420 | B-3 |
| n3-1323 | A-421 | B-3 |
| n3-1324 | A-422 | B-3 |
| n3-1325 | A-423 | B-3 |
| n3-1326 | A-424 | B-3 |
| n3-1327 | A-425 | B-3 |
| n3-1328 | A-426 | B-3 |
| n3-1329 | A-427 | B-3 |
| n3-1330 | A-428 | B-3 |
| n3-1331 | A-429 | B-3 |
| n3-1332 | A-430 | B-3 |
| n3-1333 | A-431 | B-3 |
| n3-1334 | A-432 | B-3 |
| n3-1335 | A-433 | B-3 |
| n3-1336 | A-434 | B-3 |
| n3-1337 | A-435 | B-3 |

TABLE 1-continued

| epn | n = 3 A | B |
|---|---|---|
| n3-1338 | A-436 | B-3 |
| n3-1339 | A-437 | B-3 |
| n3-1340 | A-438 | B-3 |
| n3-1341 | A-439 | B-3 |
| n3-1342 | A-440 | B-3 |
| n3-1343 | A-441 | B-3 |
| n3-1344 | A-442 | B-3 |
| n3-1345 | A-443 | B-3 |
| n3-1346 | A-444 | B-3 |
| n3-1347 | A-445 | B-3 |
| n3-1348 | A-446 | B-3 |
| n3-1349 | A-447 | B-3 |
| n3-1350 | A-448 | B-3 |
| n3-1351 | A-449 | B-3 |
| n3-1352 | A-450 | B-3 |
| n3-1353 | A-451 | B-3 |
| n3-1354 | A-1 | B-4 |
| n3-1355 | A-2 | B-4 |
| n3-1356 | A-3 | B-4 |
| n3-1357 | A-4 | B-4 |
| n3-1358 | A-5 | B-4 |
| n3-1359 | A-6 | B-4 |
| n3-1360 | A-7 | B-4 |
| n3-1361 | A-8 | B-4 |
| n3-1362 | A-9 | B-4 |
| n3-1363 | A-10 | B-4 |
| n3-1364 | A-11 | B-4 |
| n3-1365 | A-12 | B-4 |
| n3-1366 | A-13 | B-4 |
| n3-1367 | A-14 | B-4 |
| n3-1368 | A-15 | B-4 |
| n3-1369 | A-16 | B-4 |
| n3-1370 | A-17 | B-4 |
| n3-1371 | A-18 | B-4 |
| n3-1372 | A-19 | B-4 |
| n3-1373 | A-20 | B-4 |
| n3-1374 | A-21 | B-4 |
| n3-1375 | A-22 | B-4 |
| n3-1376 | A-23 | B-4 |
| n3-1377 | A-24 | B-4 |
| n3-1378 | A-25 | B-4 |
| n3-1379 | A-26 | B-4 |
| n3-1380 | A-27 | B-4 |
| n3-1381 | A-28 | B-4 |
| n3-1382 | A-29 | B-4 |
| n3-1383 | A-30 | B-4 |
| n3-1384 | A-31 | B-4 |
| n3-1385 | A-32 | B-4 |
| n3-1386 | A-33 | B-4 |
| n3-1387 | A-34 | B-4 |
| n3-1388 | A-35 | B-4 |
| n3-1389 | A-36 | B-4 |
| n3-1390 | A-37 | B-4 |
| n3-1391 | A-38 | B-4 |
| n3-1392 | A-39 | B-4 |
| n3-1393 | A-40 | B-4 |
| n3-1394 | A-41 | B-4 |
| n3-1395 | A-42 | B-4 |
| n3-1396 | A-43 | B-4 |
| n3-1397 | A-44 | B-4 |
| n3-1398 | A-45 | B-4 |
| n3-1399 | A-46 | B-4 |
| n3-1400 | A-47 | B-4 |
| n3-1401 | A-48 | B-4 |
| n3-1402 | A-49 | B-4 |
| n3-1403 | A-50 | B-4 |
| n3-1404 | A-51 | B-4 |
| n3-1405 | A-52 | B-4 |
| n3-1406 | A-53 | B-4 |
| n3-1407 | A-54 | B-4 |
| n3-1408 | A-55 | B-4 |
| n3-1409 | A-56 | B-4 |
| n3-1410 | A-57 | B-4 |
| n3-1411 | A-58 | B-4 |
| n3-1412 | A-59 | B-4 |
| n3-1413 | A-60 | B-4 |
| n3-1414 | A-61 | B-4 |
| n3-1415 | A-62 | B-4 |
| n3-1416 | A-63 | B-4 |
| n3-1417 | A-64 | B-4 |
| n3-1418 | A-65 | B-4 |
| n3-1419 | A-66 | B-4 |
| n3-1420 | A-67 | B-4 |
| n3-1421 | A-68 | B-4 |
| n3-1422 | A-69 | B-4 |
| n3-1423 | A-70 | B-4 |
| n3-1424 | A-71 | B-4 |
| n3-1425 | A-72 | B-4 |
| n3-1426 | A-73 | B-4 |
| n3-1427 | A-74 | B-4 |
| n3-1428 | A-75 | B-4 |
| n3-1429 | A-76 | B-4 |
| n3-1430 | A-77 | B-4 |
| n3-1431 | A-78 | B-4 |
| n3-1432 | A-79 | B-4 |
| n3-1433 | A-80 | B-4 |
| n3-1434 | A-81 | B-4 |
| n3-1435 | A-82 | B-4 |
| n3-1436 | A-83 | B-4 |
| n3-1437 | A-84 | B-4 |
| n3-1438 | A-85 | B-4 |
| n3-1439 | A-86 | B-4 |
| n3-1440 | A-87 | B-4 |
| n3-1441 | A-88 | B-4 |
| n3-1442 | A-89 | B-4 |
| n3-1443 | A-90 | B-4 |
| n3-1444 | A-91 | B-4 |
| n3-1445 | A-92 | B-4 |
| n3-1446 | A-93 | B-4 |
| n3-1447 | A-94 | B-4 |
| n3-1448 | A-95 | B-4 |
| n3-1449 | A-96 | B-4 |
| n3-1450 | A-97 | B-4 |
| n3-1451 | A-98 | B-4 |
| n3-1452 | A-99 | B-4 |
| n3-1453 | A-100 | B-4 |
| n3-1454 | A-101 | B-4 |
| n3-1455 | A-102 | B-4 |
| n3-1456 | A-103 | B-4 |
| n3-1457 | A-104 | B-4 |
| n3-1458 | A-105 | B-4 |
| n3-1459 | A-106 | B-4 |
| n3-1460 | A-107 | B-4 |
| n3-1461 | A-108 | B-4 |
| n3-1462 | A-109 | B-4 |
| n3-1463 | A-110 | B-4 |
| n3-1464 | A-111 | B-4 |
| n3-1465 | A-112 | B-4 |
| n3-1466 | A-113 | B-4 |
| n3-1467 | A-114 | B-4 |
| n3-1468 | A-115 | B-4 |
| n3-1469 | A-116 | B-4 |
| n3-1470 | A-117 | B-4 |
| n3-1471 | A-118 | B-4 |
| n3-1472 | A-119 | B-4 |
| n3-1473 | A-120 | B-4 |
| n3-1474 | A-121 | B-4 |
| n3-1475 | A-122 | B-4 |
| n3-1476 | A-123 | B-4 |
| n3-1477 | A-124 | B-4 |
| n3-1478 | A-125 | B-4 |
| n3-1479 | A-126 | B-4 |
| n3-1480 | A-127 | B-4 |
| n3-1481 | A-128 | B-4 |
| n3-1482 | A-129 | B-4 |
| n3-1483 | A-130 | B-4 |
| n3-1484 | A-131 | B-4 |
| n3-1485 | A-132 | B-4 |
| n3-1486 | A-133 | B-4 |
| n3-1487 | A-134 | B-4 |

TABLE 1-continued

| epn | n = 3 A | B |
|---|---|---|
| n3-1488 | A-135 | B-4 |
| n3-1489 | A-136 | B-4 |
| n3-1490 | A-137 | B-4 |
| n3-1491 | A-138 | B-4 |
| n3-1492 | A-139 | B-4 |
| n3-1493 | A-140 | B-4 |
| n3-1494 | A-141 | B-4 |
| n3-1495 | A-142 | B-4 |
| n3-1496 | A-143 | B-4 |
| n3-1497 | A-144 | B-4 |
| n3-1498 | A-145 | B-4 |
| n3-1499 | A-146 | B-4 |
| n3-1500 | A-147 | B-4 |
| n3-1501 | A-148 | B-4 |
| n3-1502 | A-149 | B-4 |
| n3-1503 | A-150 | B-4 |
| n3-1504 | A-151 | B-4 |
| n3-1505 | A-152 | B-4 |
| n3-1506 | A-153 | B-4 |
| n3-1507 | A-154 | B-4 |
| n3-1508 | A-155 | B-4 |
| n3-1509 | A-156 | B-4 |
| n3-1510 | A-157 | B-4 |
| n3-1511 | A-158 | B-4 |
| n3-1512 | A-159 | B-4 |
| n3-1513 | A-160 | B-4 |
| n3-1514 | A-161 | B-4 |
| n3-1515 | A-162 | B-4 |
| n3-1516 | A-163 | B-4 |
| n3-1517 | A-164 | B-4 |
| n3-1518 | A-165 | B-4 |
| n3-1519 | A-166 | B-4 |
| n3-1520 | A-167 | B-4 |
| n3-1521 | A-168 | B-4 |
| n3-1522 | A-169 | B-4 |
| n3-1523 | A-170 | B-4 |
| n3-1524 | A-171 | B-4 |
| n3-1525 | A-172 | B-4 |
| n3-1526 | A-173 | B-4 |
| n3-1527 | A-174 | B-4 |
| n3-1528 | A-175 | B-4 |
| n3-1529 | A-176 | B-4 |
| n3-1530 | A-177 | B-4 |
| n3-1531 | A-178 | B-4 |
| n3-1532 | A-179 | B-4 |
| n3-1533 | A-180 | B-4 |
| n3-1534 | A-181 | B-4 |
| n3-1535 | A-182 | B-4 |
| n3-1536 | A-183 | B-4 |
| n3-1537 | A-184 | B-4 |
| n3-1538 | A-185 | B-4 |
| n3-1539 | A-186 | B-4 |
| n3-1540 | A-187 | B-4 |
| n3-1541 | A-188 | B-4 |
| n3-1542 | A-189 | B-4 |
| n3-1543 | A-190 | B-4 |
| n3-1544 | A-191 | B-4 |
| n3-1545 | A-192 | B-4 |
| n3-1546 | A-193 | B-4 |
| n3-1547 | A-194 | B-4 |
| n3-1548 | A-195 | B-4 |
| n3-1549 | A-196 | B-4 |
| n3-1550 | A-197 | B-4 |
| n3-1551 | A-198 | B-4 |
| n3-1552 | A-199 | B-4 |
| n3-1553 | A-200 | B-4 |
| n3-1554 | A-201 | B-4 |
| n3-1555 | A-202 | B-4 |
| n3-1556 | A-203 | B-4 |
| n3-1557 | A-204 | B-4 |
| n3-1558 | A-205 | B-4 |
| n3-1559 | A-206 | B-4 |
| n3-1560 | A-207 | B-4 |
| n3-1561 | A-208 | B-4 |
| n3-1562 | A-209 | B-4 |
| n3-1563 | A-210 | B-4 |
| n3-1564 | A-211 | B-4 |
| n3-1565 | A-212 | B-4 |
| n3-1566 | A-213 | B-4 |
| n3-1567 | A-214 | B-4 |
| n3-1568 | A-215 | B-4 |
| n3-1569 | A-216 | B-4 |
| n3-1570 | A-217 | B-4 |
| n3-1571 | A-218 | B-4 |
| n3-1572 | A-219 | B-4 |
| n3-1573 | A-220 | B-4 |
| n3-1574 | A-221 | B-4 |
| n3-1575 | A-222 | B-4 |
| n3-1576 | A-223 | B-4 |
| n3-1577 | A-224 | B-4 |
| n3-1578 | A-225 | B-4 |
| n3-1579 | A-226 | B-4 |
| n3-1580 | A-227 | B-4 |
| n3-1581 | A-228 | B-4 |
| n3-1582 | A-229 | B-4 |
| n3-1583 | A-230 | B-4 |
| n3-1584 | A-231 | B-4 |
| n3-1585 | A-232 | B-4 |
| n3-1586 | A-233 | B-4 |
| n3-1587 | A-234 | B-4 |
| n3-1588 | A-235 | B-4 |
| n3-1589 | A-236 | B-4 |
| n3-1590 | A-237 | B-4 |
| n3-1591 | A-238 | B-4 |
| n3-1592 | A-239 | B-4 |
| n3-1593 | A-240 | B-4 |
| n3-1594 | A-241 | B-4 |
| n3-1595 | A-242 | B-4 |
| n3-1596 | A-243 | B-4 |
| n3-1597 | A-244 | B-4 |
| n3-1598 | A-245 | B-4 |
| n3-1599 | A-246 | B-4 |
| n3-1600 | A-247 | B-4 |
| n3-1601 | A-248 | B-4 |
| n3-1602 | A-249 | B-4 |
| n3-1603 | A-250 | B-4 |
| n3-1604 | A-251 | B-4 |
| n3-1605 | A-252 | B-4 |
| n3-1606 | A-253 | B-4 |
| n3-1607 | A-254 | B-4 |
| n3-1608 | A-255 | B-4 |
| n3-1609 | A-256 | B-4 |
| n3-1610 | A-257 | B-4 |
| n3-1611 | A-258 | B-4 |
| n3-1612 | A-259 | B-4 |
| n3-1613 | A-260 | B-4 |
| n3-1614 | A-261 | B-4 |
| n3-1615 | A-262 | B-4 |
| n3-1616 | A-263 | B-4 |
| n3-1617 | A-264 | B-4 |
| n3-1618 | A-265 | B-4 |
| n3-1619 | A-266 | B-4 |
| n3-1620 | A-267 | B-4 |
| n3-1621 | A-268 | B-4 |
| n3-1622 | A-269 | B-4 |
| n3-1623 | A-270 | B-4 |
| n3-1624 | A-271 | B-4 |
| n3-1625 | A-272 | B-4 |
| n3-1626 | A-273 | B-4 |
| n3-1627 | A-274 | B-4 |
| n3-1628 | A-275 | B-4 |
| n3-1629 | A-276 | B-4 |
| n3-1630 | A-277 | B-4 |
| n3-1631 | A-278 | B-4 |
| n3-1632 | A-279 | B-4 |
| n3-1633 | A-280 | B-4 |
| n3-1634 | A-281 | B-4 |
| n3-1635 | A-282 | B-4 |
| n3-1636 | A-283 | B-4 |
| n3-1637 | A-284 | B-4 |

TABLE 1-continued

| epn | n = 3 A | B |
|---|---|---|
| n3-1638 | A-285 | B-4 |
| n3-1639 | A-286 | B-4 |
| n3-1640 | A-287 | B-4 |
| n3-1641 | A-288 | B-4 |
| n3-1642 | A-289 | B-4 |
| n3-1643 | A-290 | B-4 |
| n3-1644 | A-291 | B-4 |
| n3-1645 | A-292 | B-4 |
| n3-1646 | A-293 | B-4 |
| n3-1647 | A-294 | B-4 |
| n3-1648 | A-295 | B-4 |
| n3-1649 | A-296 | B-4 |
| n3-1650 | A-297 | B-4 |
| n3-1651 | A-298 | B-4 |
| n3-1652 | A-299 | B-4 |
| n3-1653 | A-300 | B-4 |
| n3-1654 | A-301 | B-4 |
| n3-1655 | A-302 | B-4 |
| n3-1656 | A-303 | B-4 |
| n3-1657 | A-304 | B-4 |
| n3-1658 | A-305 | B-4 |
| n3-1659 | A-306 | B-4 |
| n3-1660 | A-307 | B-4 |
| n3-1661 | A-308 | B-4 |
| n3-1662 | A-309 | B-4 |
| n3-1663 | A-310 | B-4 |
| n3-1664 | A-311 | B-4 |
| n3-1665 | A-312 | B-4 |
| n3-1666 | A-313 | B-4 |
| n3-1667 | A-314 | B-4 |
| n3-1668 | A-315 | B-4 |
| n3-1669 | A-316 | B-4 |
| n3-1670 | A-317 | B-4 |
| n3-1671 | A-318 | B-4 |
| n3-1672 | A-319 | B-4 |
| n3-1673 | A-320 | B-4 |
| n3-1674 | A-321 | B-4 |
| n3-1675 | A-322 | B-4 |
| n3-1676 | A-323 | B-4 |
| n3-1677 | A-324 | B-4 |
| n3-1678 | A-325 | B-4 |
| n3-1679 | A-326 | B-4 |
| n3-1680 | A-327 | B-4 |
| n3-1681 | A-328 | B-4 |
| n3-1682 | A-329 | B-4 |
| n3-1683 | A-330 | B-4 |
| n3-1684 | A-331 | B-4 |
| n3-1685 | A-332 | B-4 |
| n3-1686 | A-333 | B-4 |
| n3-1687 | A-334 | B-4 |
| n3-1688 | A-335 | B-4 |
| n3-1689 | A-336 | B-4 |
| n3-1690 | A-337 | B-4 |
| n3-1691 | A-338 | B-4 |
| n3-1692 | A-339 | B-4 |
| n3-1693 | A-340 | B-4 |
| n3-1694 | A-341 | B-4 |
| n3-1695 | A-342 | B-4 |
| n3-1696 | A-343 | B-4 |
| n3-1697 | A-344 | B-4 |
| n3-1698 | A-345 | B-4 |
| n3-1699 | A-346 | B-4 |
| n3-1700 | A-347 | B-4 |
| n3-1701 | A-348 | B-4 |
| n3-1702 | A-349 | B-4 |
| n3-1703 | A-350 | B-4 |
| n3-1704 | A-351 | B-4 |
| n3-1705 | A-352 | B-4 |
| n3-1706 | A-353 | B-4 |
| n3-1707 | A-354 | B-4 |
| n3-1708 | A-355 | B-4 |
| n3-1709 | A-356 | B-4 |
| n3-1710 | A-357 | B-4 |
| n3-1711 | A-358 | B-4 |
| n3-1712 | A-359 | B-4 |
| n3-1713 | A-360 | B-4 |
| n3-1714 | A-361 | B-4 |
| n3-1715 | A-362 | B-4 |
| n3-1716 | A-363 | B-4 |
| n3-1717 | A-364 | B-4 |
| n3-1718 | A-365 | B-4 |
| n3-1719 | A-366 | B-4 |
| n3-1720 | A-367 | B-4 |
| n3-1721 | A-368 | B-4 |
| n3-1722 | A-369 | B-4 |
| n3-1723 | A-370 | B-4 |
| n3-1724 | A-371 | B-4 |
| n3-1725 | A-372 | B-4 |
| n3-1726 | A-373 | B-4 |
| n3-1727 | A-374 | B-4 |
| n3-1728 | A-375 | B-4 |
| n3-1729 | A-376 | B-4 |
| n3-1730 | A-377 | B-4 |
| n3-1731 | A-378 | B-4 |
| n3-1732 | A-379 | B-4 |
| n3-1733 | A-380 | B-4 |
| n3-1734 | A-381 | B-4 |
| n3-1735 | A-382 | B-4 |
| n3-1736 | A-383 | B-4 |
| n3-1737 | A-384 | B-4 |
| n3-1738 | A-385 | B-4 |
| n3-1739 | A-386 | B-4 |
| n3-1740 | A-387 | B-4 |
| n3-1741 | A-388 | B-4 |
| n3-1742 | A-389 | B-4 |
| n3-1743 | A-390 | B-4 |
| n3-1744 | A-391 | B-4 |
| n3-1745 | A-392 | B-4 |
| n3-1746 | A-393 | B-4 |
| n3-1747 | A-394 | B-4 |
| n3-1748 | A-395 | B-4 |
| n3-1749 | A-396 | B-4 |
| n3-1750 | A-397 | B-4 |
| n3-1751 | A-398 | B-4 |
| n3-1752 | A-399 | B-4 |
| n3-1753 | A-400 | B-4 |
| n3-1754 | A-401 | B-4 |
| n3-1755 | A-402 | B-4 |
| n3-1756 | A-403 | B-4 |
| n3-1757 | A-404 | B-4 |
| n3-1758 | A-405 | B-4 |
| n3-1759 | A-406 | B-4 |
| n3-1760 | A-407 | B-4 |
| n3-1761 | A-408 | B-4 |
| n3-1762 | A-409 | B-4 |
| n3-1763 | A-410 | B-4 |
| n3-1764 | A-411 | B-4 |
| n3-1765 | A-412 | B-4 |
| n3-1766 | A-413 | B-4 |
| n3-1767 | A-414 | B-4 |
| n3-1768 | A-415 | B-4 |
| n3-1769 | A-416 | B-4 |
| n3-1770 | A-417 | B-4 |
| n3-1771 | A-418 | B-4 |
| n3-1772 | A-419 | B-4 |
| n3-1773 | A-420 | B-4 |
| n3-1774 | A-421 | B-4 |
| n3-1775 | A-422 | B-4 |
| n3-1776 | A-423 | B-4 |
| n3-1777 | A-424 | B-4 |
| n3-1778 | A-425 | B-4 |
| n3-1779 | A-426 | B-4 |
| n3-1780 | A-427 | B-4 |
| n3-1781 | A-428 | B-4 |
| n3-1782 | A-429 | B-4 |
| n3-1783 | A-430 | B-4 |
| n3-1784 | A-431 | B-4 |
| n3-1785 | A-432 | B-4 |
| n3-1786 | A-433 | B-4 |
| n3-1787 | A-434 | B-4 |

TABLE 1-continued

| epn | n = 3 A | B |
|---|---|---|
| n3-1788 | A-435 | B-4 |
| n3-1789 | A-436 | B-4 |
| n3-1790 | A-437 | B-4 |
| n3-1791 | A-438 | B-4 |
| n3-1792 | A-439 | B-4 |
| n3-1793 | A-440 | B-4 |
| n3-1794 | A-441 | B-4 |
| n3-1795 | A-442 | B-4 |
| n3-1796 | A-443 | B-4 |
| n3-1797 | A-444 | B-4 |
| n3-1798 | A-445 | B-4 |
| n3-1799 | A-446 | B-4 |
| n3-1800 | A-447 | B-4 |
| n3-1801 | A-448 | B-4 |
| n3-1802 | A-449 | B-4 |
| n3-1803 | A-450 | B-4 |
| n3-1804 | A-451 | B-4 |
| n3-1805 | A-1 | B-5 |
| n3-1806 | A-2 | B-5 |
| n3-1807 | A-3 | B-5 |
| n3-1808 | A-4 | B-5 |
| n3-1809 | A-5 | B-5 |
| n3-1810 | A-6 | B-5 |
| n3-1811 | A-7 | B-5 |
| n3-1812 | A-8 | B-5 |
| n3-1813 | A-9 | B-5 |
| n3-1814 | A-10 | B-5 |
| n3-1815 | A-11 | B-5 |
| n3-1816 | A-12 | B-5 |
| n3-1817 | A-13 | B-5 |
| n3-1818 | A-14 | B-5 |
| n3-1819 | A-15 | B-5 |
| n3-1820 | A-16 | B-5 |
| n3-1821 | A-17 | B-5 |
| n3-1822 | A-18 | B-5 |
| n3-1823 | A-19 | B-5 |
| n3-1824 | A-20 | B-5 |
| n3-1825 | A-21 | B-5 |
| n3-1826 | A-22 | B-5 |
| n3-1827 | A-23 | B-5 |
| n3-1828 | A-24 | B-5 |
| n3-1829 | A-25 | B-5 |
| n3-1830 | A-26 | B-5 |
| n3-1831 | A-27 | B-5 |
| n3-1832 | A-28 | B-5 |
| n3-1833 | A-29 | B-5 |
| n3-1834 | A-30 | B-5 |
| n3-1835 | A-31 | B-5 |
| n3-1836 | A-32 | B-5 |
| n3-1837 | A-33 | B-5 |
| n3-1838 | A-34 | B-5 |
| n3-1839 | A-35 | B-5 |
| n3-1840 | A-36 | B-5 |
| n3-1841 | A-37 | B-5 |
| n3-1842 | A-38 | B-5 |
| n3-1843 | A-39 | B-5 |
| n3-1844 | A-40 | B-5 |
| n3-1845 | A-41 | B-5 |
| n3-1846 | A-42 | B-5 |
| n3-1847 | A-43 | B-5 |
| n3-1848 | A-44 | B-5 |
| n3-1849 | A-45 | B-5 |
| n3-1850 | A-46 | B-5 |
| n3-1851 | A-47 | B-5 |
| n3-1852 | A-48 | B-5 |
| n3-1853 | A-49 | B-5 |
| n3-1854 | A-50 | B-5 |
| n3-1855 | A-51 | B-5 |
| n3-1856 | A-52 | B-5 |
| n3-1857 | A-53 | B-5 |
| n3-1858 | A-54 | B-5 |
| n3-1859 | A-55 | B-5 |
| n3-1860 | A-56 | B-5 |
| n3-1861 | A-57 | B-5 |
| n3-1862 | A-58 | B-5 |
| n3-1863 | A-59 | B-5 |
| n3-1864 | A-60 | B-5 |
| n3-1865 | A-61 | B-5 |
| n3-1866 | A-62 | B-5 |
| n3-1867 | A-63 | B-5 |
| n3-1868 | A-64 | B-5 |
| n3-1869 | A-65 | B-5 |
| n3-1870 | A-66 | B-5 |
| n3-1871 | A-67 | B-5 |
| n3-1872 | A-68 | B-5 |
| n3-1873 | A-69 | B-5 |
| n3-1874 | A-70 | B-5 |
| n3-1875 | A-71 | B-5 |
| n3-1876 | A-72 | B-5 |
| n3-1877 | A-73 | B-5 |
| n3-1878 | A-74 | B-5 |
| n3-1879 | A-75 | B-5 |
| n3-1880 | A-76 | B-5 |
| n3-1881 | A-77 | B-5 |
| n3-1882 | A-78 | B-5 |
| n3-1883 | A-79 | B-5 |
| n3-1884 | A-80 | B-5 |
| n3-1885 | A-81 | B-5 |
| n3-1886 | A-82 | B-5 |
| n3-1887 | A-83 | B-5 |
| n3-1888 | A-84 | B-5 |
| n3-1889 | A-85 | B-5 |
| n3-1890 | A-86 | B-5 |
| n3-1891 | A-87 | B-5 |
| n3-1892 | A-88 | B-5 |
| n3-1893 | A-89 | B-5 |
| n3-1894 | A-90 | B-5 |
| n3-1895 | A-91 | B-5 |
| n3-1896 | A-92 | B-5 |
| n3-1897 | A-93 | B-5 |
| n3-1898 | A-94 | B-5 |
| n3-1899 | A-95 | B-5 |
| n3-1900 | A-96 | B-5 |
| n3-1901 | A-97 | B-5 |
| n3-1902 | A-98 | B-5 |
| n3-1903 | A-99 | B-5 |
| n3-1904 | A-100 | B-5 |
| n3-1905 | A-101 | B-5 |
| n3-1906 | A-102 | B-5 |
| n3-1907 | A-103 | B-5 |
| n3-1908 | A-104 | B-5 |
| n3-1909 | A-105 | B-5 |
| n3-1910 | A-106 | B-5 |
| n3-1911 | A-107 | B-5 |
| n3-1912 | A-108 | B-5 |
| n3-1913 | A-109 | B-5 |
| n3-1914 | A-110 | B-5 |
| n3-1915 | A-111 | B-5 |
| n3-1916 | A-112 | B-5 |
| n3-1917 | A-113 | B-5 |
| n3-1918 | A-114 | B-5 |
| n3-1919 | A-115 | B-5 |
| n3-1920 | A-116 | B-5 |
| n3-1921 | A-117 | B-5 |
| n3-1922 | A-118 | B-5 |
| n3-1923 | A-119 | B-5 |
| n3-1924 | A-120 | B-5 |
| n3-1925 | A-121 | B-5 |
| n3-1926 | A-122 | B-5 |
| n3-1927 | A-123 | B-5 |
| n3-1928 | A-124 | B-5 |
| n3-1929 | A-125 | B-5 |
| n3-1930 | A-126 | B-5 |
| n3-1931 | A-127 | B-5 |
| n3-1932 | A-128 | B-5 |
| n3-1933 | A-129 | B-5 |
| n3-1934 | A-130 | B-5 |
| n3-1935 | A-131 | B-5 |
| n3-1936 | A-132 | B-5 |
| n3-1937 | A-133 | B-5 |

TABLE 1-continued

| epn | n = 3 A | B |
|---|---|---|
| n3-1938 | A-134 | B-5 |
| n3-1939 | A-135 | B-5 |
| n3-1940 | A-136 | B-5 |
| n3-1941 | A-137 | B-5 |
| n3-1942 | A-138 | B-5 |
| n3-1943 | A-139 | B-5 |
| n3-1944 | A-140 | B-5 |
| n3-1945 | A-141 | B-5 |
| n3-1946 | A-142 | B-5 |
| n3-1947 | A-143 | B-5 |
| n3-1948 | A-144 | B-5 |
| n3-1949 | A-145 | B-5 |
| n3-1950 | A-146 | B-5 |
| n3-1951 | A-147 | B-5 |
| n3-1952 | A-148 | B-5 |
| n3-1953 | A-149 | B-5 |
| n3-1954 | A-150 | B-5 |
| n3-1955 | A-151 | B-5 |
| n3-1956 | A-152 | B-5 |
| n3-1957 | A-153 | B-5 |
| n3-1958 | A-154 | B-5 |
| n3-1959 | A-155 | B-5 |
| n3-1960 | A-156 | B-5 |
| n3-1961 | A-157 | B-5 |
| n3-1962 | A-158 | B-5 |
| n3-1963 | A-159 | B-5 |
| n3-1964 | A-160 | B-5 |
| n3-1965 | A-161 | B-5 |
| n3-1966 | A-162 | B-5 |
| n3-1967 | A-163 | B-5 |
| n3-1968 | A-164 | B-5 |
| n3-1969 | A-165 | B-5 |
| n3-1970 | A-166 | B-5 |
| n3-1971 | A-167 | B-5 |
| n3-1972 | A-168 | B-5 |
| n3-1973 | A-169 | B-5 |
| n3-1974 | A-170 | B-5 |
| n3-1975 | A-171 | B-5 |
| n3-1976 | A-172 | B-5 |
| n3-1977 | A-173 | B-5 |
| n3-1978 | A-174 | B-5 |
| n3-1979 | A-175 | B-5 |
| n3-1980 | A-176 | B-5 |
| n3-1981 | A-177 | B-5 |
| n3-1982 | A-178 | B-5 |
| n3-1983 | A-179 | B-5 |
| n3-1984 | A-180 | B-5 |
| n3-1985 | A-181 | B-5 |
| n3-1986 | A-182 | B-5 |
| n3-1987 | A-183 | B-5 |
| n3-1988 | A-184 | B-5 |
| n3-1989 | A-185 | B-5 |
| n3-1990 | A-186 | B-5 |
| n3-1991 | A-187 | B-5 |
| n3-1992 | A-188 | B-5 |
| n3-1993 | A-189 | B-5 |
| n3-1994 | A-190 | B-5 |
| n3-1995 | A-191 | B-5 |
| n3-1996 | A-192 | B-5 |
| n3-1997 | A-193 | B-5 |
| n3-1998 | A-194 | B-5 |
| n3-1999 | A-195 | B-5 |
| n3-2000 | A-196 | B-5 |
| n3-2001 | A-197 | B-5 |
| n3-2002 | A-198 | B-5 |
| n3-2003 | A-199 | B-5 |
| n3-2004 | A-200 | B-5 |
| n3-2005 | A-201 | B-5 |
| n3-2006 | A-202 | B-5 |
| n3-2007 | A-203 | B-5 |
| n3-2008 | A-204 | B-5 |
| n3-2009 | A-205 | B-5 |
| n3-2010 | A-206 | B-5 |
| n3-2011 | A-207 | B-5 |
| n3-2012 | A-208 | B-5 |
| n3-2013 | A-209 | B-5 |
| n3-2014 | A-210 | B-5 |
| n3-2015 | A-211 | B-5 |
| n3-2016 | A-212 | B-5 |
| n3-2017 | A-213 | B-5 |
| n3-2018 | A-214 | B-5 |
| n3-2019 | A-215 | B-5 |
| n3-2020 | A-216 | B-5 |
| n3-2021 | A-217 | B-5 |
| n3-2022 | A-218 | B-5 |
| n3-2023 | A-219 | B-5 |
| n3-2024 | A-220 | B-5 |
| n3-2025 | A-221 | B-5 |
| n3-2026 | A-222 | B-5 |
| n3-2027 | A-223 | B-5 |
| n3-2028 | A-224 | B-5 |
| n3-2029 | A-225 | B-5 |
| n3-2030 | A-226 | B-5 |
| n3-2031 | A-227 | B-5 |
| n3-2032 | A-228 | B-5 |
| n3-2033 | A-229 | B-5 |
| n3-2034 | A-230 | B-5 |
| n3-2035 | A-231 | B-5 |
| n3-2036 | A-232 | B-5 |
| n3-2037 | A-233 | B-5 |
| n3-2038 | A-234 | B-5 |
| n3-2039 | A-235 | B-5 |
| n3-2040 | A-236 | B-5 |
| n3-2041 | A-237 | B-5 |
| n3-2042 | A-238 | B-5 |
| n3-2043 | A-239 | B-5 |
| n3-2044 | A-240 | B-5 |
| n3-2045 | A-241 | B-5 |
| n3-2046 | A-242 | B-5 |
| n3-2047 | A-243 | B-5 |
| n3-2048 | A-244 | B-5 |
| n3-2049 | A-245 | B-5 |
| n3-2050 | A-246 | B-5 |
| n3-2051 | A-247 | B-5 |
| n3-2052 | A-248 | B-5 |
| n3-2053 | A-249 | B-5 |
| n3-2054 | A-250 | B-5 |
| n3-2055 | A-251 | B-5 |
| n3-2056 | A-252 | B-5 |
| n3-2057 | A-253 | B-5 |
| n3-2058 | A-254 | B-5 |
| n3-2059 | A-255 | B-5 |
| n3-2060 | A-256 | B-5 |
| n3-2061 | A-257 | B-5 |
| n3-2062 | A-258 | B-5 |
| n3-2063 | A-259 | B-5 |
| n3-2064 | A-260 | B-5 |
| n3-2065 | A-261 | B-5 |
| n3-2066 | A-262 | B-5 |
| n3-2067 | A-263 | B-5 |
| n3-2068 | A-264 | B-5 |
| n3-2069 | A-265 | B-5 |
| n3-2070 | A-266 | B-5 |
| n3-2071 | A-267 | B-5 |
| n3-2072 | A-268 | B-5 |
| n3-2073 | A-269 | B-5 |
| n3-2074 | A-270 | B-5 |
| n3-2075 | A-271 | B-5 |
| n3-2076 | A-272 | B-5 |
| n3-2077 | A-273 | B-5 |
| n3-2078 | A-274 | B-5 |
| n3-2079 | A-275 | B-5 |
| n3-2080 | A-276 | B-5 |
| n3-2081 | A-277 | B-5 |
| n3-2082 | A-278 | B-5 |
| n3-2083 | A-279 | B-5 |
| n3-2084 | A-280 | B-5 |
| n3-2085 | A-281 | B-5 |
| n3-2086 | A-282 | B-5 |
| n3-2087 | A-283 | B-5 |

TABLE 1-continued

| epn | n = 3 A | B |
|---|---|---|
| n3-2088 | A-284 | B-5 |
| n3-2089 | A-285 | B-5 |
| n3-2090 | A-286 | B-5 |
| n3-2091 | A-287 | B-5 |
| n3-2092 | A-288 | B-5 |
| n3-2093 | A-289 | B-5 |
| n3-2094 | A-290 | B-5 |
| n3-2095 | A-291 | B-5 |
| n3-2096 | A-292 | B-5 |
| n3-2097 | A-293 | B-5 |
| n3-2098 | A-294 | B-5 |
| n3-2099 | A-295 | B-5 |
| n3-2100 | A-296 | B-5 |
| n3-2101 | A-297 | B-5 |
| n3-2102 | A-298 | B-5 |
| n3-2103 | A-299 | B-5 |
| n3-2104 | A-300 | B-5 |
| n3-2105 | A-301 | B-5 |
| n3-2106 | A-302 | B-5 |
| n3-2107 | A-303 | B-5 |
| n3-2108 | A-304 | B-5 |
| n3-2109 | A-305 | B-5 |
| n3-2110 | A-306 | B-5 |
| n3-2111 | A-307 | B-5 |
| n3-2112 | A-308 | B-5 |
| n3-2113 | A-309 | B-5 |
| n3-2114 | A-310 | B-5 |
| n3-2115 | A-311 | B-5 |
| n3-2116 | A-312 | B-5 |
| n3-2117 | A-313 | B-5 |
| n3-2118 | A-314 | B-5 |
| n3-2119 | A-315 | B-5 |
| n3-2120 | A-316 | B-5 |
| n3-2121 | A-317 | B-5 |
| n3-2122 | A-318 | B-5 |
| n3-2123 | A-319 | B-5 |
| n3-2124 | A-320 | B-5 |
| n3-2125 | A-321 | B-5 |
| n3-2126 | A-322 | B-5 |
| n3-2127 | A-323 | B-5 |
| n3-2128 | A-324 | B-5 |
| n3-2129 | A-325 | B-5 |
| n3-2130 | A-326 | B-5 |
| n3-2131 | A-327 | B-5 |
| n3-2132 | A-328 | B-5 |
| n3-2133 | A-329 | B-5 |
| n3-2134 | A-330 | B-5 |
| n3-2135 | A-331 | B-5 |
| n3-2136 | A-332 | B-5 |
| n3-2137 | A-333 | B-5 |
| n3-2138 | A-334 | B-5 |
| n3-2139 | A-335 | B-5 |
| n3-2140 | A-336 | B-5 |
| n3-2141 | A-337 | B-5 |
| n3-2142 | A-338 | B-5 |
| n3-2143 | A-339 | B-5 |
| n3-2144 | A-340 | B-5 |
| n3-2145 | A-341 | B-5 |
| n3-2146 | A-342 | B-5 |
| n3-2147 | A-343 | B-5 |
| n3-2148 | A-344 | B-5 |
| n3-2149 | A-345 | B-5 |
| n3-2150 | A-346 | B-5 |
| n3-2151 | A-347 | B-5 |
| n3-2152 | A-348 | B-5 |
| n3-2153 | A-349 | B-5 |
| n3-2154 | A-350 | B-5 |
| n3-2155 | A-351 | B-5 |
| n3-2156 | A-352 | B-5 |
| n3-2157 | A-353 | B-5 |
| n3-2158 | A-354 | B-5 |
| n3-2159 | A-355 | B-5 |
| n3-2160 | A-356 | B-5 |
| n3-2161 | A-357 | B-5 |
| n3-2162 | A-358 | B-5 |
| n3-2163 | A-359 | B-5 |
| n3-2164 | A-360 | B-5 |
| n3-2165 | A-361 | B-5 |
| n3-2166 | A-362 | B-5 |
| n3-2167 | A-363 | B-5 |
| n3-2168 | A-364 | B-5 |
| n3-2169 | A-365 | B-5 |
| n3-2170 | A-366 | B-5 |
| n3-2171 | A-367 | B-5 |
| n3-2172 | A-368 | B-5 |
| n3-2173 | A-369 | B-5 |
| n3-2174 | A-370 | B-5 |
| n3-2175 | A-371 | B-5 |
| n3-2176 | A-372 | B-5 |
| n3-2177 | A-373 | B-5 |
| n3-2178 | A-374 | B-5 |
| n3-2179 | A-375 | B-5 |
| n3-2180 | A-376 | B-5 |
| n3-2181 | A-377 | B-5 |
| n3-2182 | A-378 | B-5 |
| n3-2183 | A-379 | B-5 |
| n3-2184 | A-380 | B-5 |
| n3-2185 | A-381 | B-5 |
| n3-2186 | A-382 | B-5 |
| n3-2187 | A-383 | B-5 |
| n3-2188 | A-384 | B-5 |
| n3-2189 | A-385 | B-5 |
| n3-2190 | A-386 | B-5 |
| n3-2191 | A-387 | B-5 |
| n3-2192 | A-388 | B-5 |
| n3-2193 | A-389 | B-5 |
| n3-2194 | A-390 | B-5 |
| n3-2195 | A-391 | B-5 |
| n3-2196 | A-392 | B-5 |
| n3-2197 | A-393 | B-5 |
| n3-2198 | A-394 | B-5 |
| n3-2199 | A-395 | B-5 |
| n3-2200 | A-396 | B-5 |
| n3-2201 | A-397 | B-5 |
| n3-2202 | A-398 | B-5 |
| n3-2203 | A-399 | B-5 |
| n3-2204 | A-400 | B-5 |
| n3-2205 | A-401 | B-5 |
| n3-2206 | A-402 | B-5 |
| n3-2207 | A-403 | B-5 |
| n3-2208 | A-404 | B-5 |
| n3-2209 | A-405 | B-5 |
| n3-2210 | A-406 | B-5 |
| n3-2211 | A-407 | B-5 |
| n3-2212 | A-408 | B-5 |
| n3-2213 | A-409 | B-5 |
| n3-2214 | A-410 | B-5 |
| n3-2215 | A-411 | B-5 |
| n3-2216 | A-412 | B-5 |
| n3-2217 | A-413 | B-5 |
| n3-2218 | A-414 | B-5 |
| n3-2219 | A-415 | B-5 |
| n3-2220 | A-416 | B-5 |
| n3-2221 | A-417 | B-5 |
| n3-2222 | A-418 | B-5 |
| n3-2223 | A-419 | B-5 |
| n3-2224 | A-420 | B-5 |
| n3-2225 | A-421 | B-5 |
| n3-2226 | A-422 | B-5 |
| n3-2227 | A-423 | B-5 |
| n3-2228 | A-424 | B-5 |
| n3-2229 | A-425 | B-5 |
| n3-2230 | A-426 | B-5 |
| n3-2231 | A-427 | B-5 |
| n3-2232 | A-428 | B-5 |
| n3-2233 | A-429 | B-5 |
| n3-2234 | A-430 | B-5 |
| n3-2235 | A-431 | B-5 |
| n3-2236 | A-432 | B-5 |
| n3-2237 | A-433 | B-5 |

TABLE 1-continued

| epn | n = 3 A | B |
|---|---|---|
| n3-2238 | A-434 | B-5 |
| n3-2239 | A-435 | B-5 |
| n3-2240 | A-436 | B-5 |
| n3-2241 | A-437 | B-5 |
| n3-2242 | A-438 | B-5 |
| n3-2243 | A-439 | B-5 |
| n3-2244 | A-440 | B-5 |
| n3-2245 | A-441 | B-5 |
| n3-2246 | A-442 | B-5 |
| n3-2247 | A-443 | B-5 |
| n3-2248 | A-444 | B-5 |
| n3-2249 | A-445 | B-5 |
| n3-2250 | A-446 | B-5 |
| n3-2251 | A-447 | B-5 |
| n3-2252 | A-448 | B-5 |
| n3-2253 | A-449 | B-5 |
| n3-2254 | A-450 | B-5 |
| n3-2255 | A-451 | B-5 |
| n3-2256 | A-1 | B-6 |
| n3-2257 | A-2 | B-6 |
| n3-2258 | A-3 | B-6 |
| n3-2259 | A-4 | B-6 |
| n3-2260 | A-5 | B-6 |
| n3-2261 | A-6 | B-6 |
| n3-2262 | A-7 | B-6 |
| n3-2263 | A-8 | B-6 |
| n3-2264 | A-9 | B-6 |
| n3-2265 | A-10 | B-6 |
| n3-2266 | A-11 | B-6 |
| n3-2267 | A-12 | B-6 |
| n3-2268 | A-13 | B-6 |
| n3-2269 | A-14 | B-6 |
| n3-2270 | A-15 | B-6 |
| n3-2271 | A-16 | B-6 |
| n3-2272 | A-17 | B-6 |
| n3-2273 | A-18 | B-6 |
| n3-2274 | A-19 | B-6 |
| n3-2275 | A-20 | B-6 |
| n3-2276 | A-21 | B-6 |
| n3-2277 | A-22 | B-6 |
| n3-2278 | A-23 | B-6 |
| n3-2279 | A-24 | B-6 |
| n3-2280 | A-25 | B-6 |
| n3-2281 | A-26 | B-6 |
| n3-2282 | A-27 | B-6 |
| n3-2283 | A-28 | B-6 |
| n3-2284 | A-29 | B-6 |
| n3-2285 | A-30 | B-6 |
| n3-2286 | A-31 | B-6 |
| n3-2287 | A-32 | B-6 |
| n3-2288 | A-33 | B-6 |
| n3-2289 | A-34 | B-6 |
| n3-2290 | A-35 | B-6 |
| n3-2291 | A-36 | B-6 |
| n3-2292 | A-37 | B-6 |
| n3-2293 | A-38 | B-6 |
| n3-2294 | A-39 | B-6 |
| n3-2295 | A-40 | B-6 |
| n3-2296 | A-41 | B-6 |
| n3-2297 | A-42 | B-6 |
| n3-2298 | A-43 | B-6 |
| n3-2299 | A-44 | B-6 |
| n3-2300 | A-45 | B-6 |
| n3-2301 | A-46 | B-6 |
| n3-2302 | A-47 | B-6 |
| n3-2303 | A-48 | B-6 |
| n3-2304 | A-49 | B-6 |
| n3-2305 | A-50 | B-6 |
| n3-2306 | A-51 | B-6 |
| n3-2307 | A-52 | B-6 |
| n3-2308 | A-53 | B-6 |
| n3-2309 | A-54 | B-6 |
| n3-2310 | A-55 | B-6 |
| n3-2311 | A-56 | B-6 |
| n3-2312 | A-57 | B-6 |
| n3-2313 | A-58 | B-6 |
| n3-2314 | A-59 | B-6 |
| n3-2315 | A-60 | B-6 |
| n3-2316 | A-61 | B-6 |
| n3-2317 | A-62 | B-6 |
| n3-2318 | A-63 | B-6 |
| n3-2319 | A-64 | B-6 |
| n3-2320 | A-65 | B-6 |
| n3-2321 | A-66 | B-6 |
| n3-2322 | A-67 | B-6 |
| n3-2323 | A-68 | B-6 |
| n3-2324 | A-69 | B-6 |
| n3-2325 | A-70 | B-6 |
| n3-2326 | A-71 | B-6 |
| n3-2327 | A-72 | B-6 |
| n3-2328 | A-73 | B-6 |
| n3-2329 | A-74 | B-6 |
| n3-2330 | A-75 | B-6 |
| n3-2331 | A-76 | B-6 |
| n3-2332 | A-77 | B-6 |
| n3-2333 | A-78 | B-6 |
| n3-2334 | A-79 | B-6 |
| n3-2335 | A-80 | B-6 |
| n3-2336 | A-81 | B-6 |
| n3-2337 | A-82 | B-6 |
| n3-2338 | A-83 | B-6 |
| n3-2339 | A-84 | B-6 |
| n3-2340 | A-85 | B-6 |
| n3-2341 | A-86 | B-6 |
| n3-2342 | A-87 | B-6 |
| n3-2343 | A-88 | B-6 |
| n3-2344 | A-89 | B-6 |
| n3-2345 | A-90 | B-6 |
| n3-2346 | A-91 | B-6 |
| n3-2347 | A-92 | B-6 |
| n3-2348 | A-93 | B-6 |
| n3-2349 | A-94 | B-6 |
| n3-2350 | A-95 | B-6 |
| n3-2351 | A-96 | B-6 |
| n3-2352 | A-97 | B-6 |
| n3-2353 | A-98 | B-6 |
| n3-2354 | A-99 | B-6 |
| n3-2355 | A-100 | B-6 |
| n3-2356 | A-101 | B-6 |
| n3-2357 | A-102 | B-6 |
| n3-2358 | A-103 | B-6 |
| n3-2359 | A-104 | B-6 |
| n3-2360 | A-105 | B-6 |
| n3-2361 | A-106 | B-6 |
| n3-2362 | A-107 | B-6 |
| n3-2363 | A-108 | B-6 |
| n3-2364 | A-109 | B-6 |
| n3-2365 | A-110 | B-6 |
| n3-2366 | A-111 | B-6 |
| n3-2367 | A-112 | B-6 |
| n3-2368 | A-113 | B-6 |
| n3-2369 | A-114 | B-6 |
| n3-2370 | A-115 | B-6 |
| n3-2371 | A-116 | B-6 |
| n3-2372 | A-117 | B-6 |
| n3-2373 | A-118 | B-6 |
| n3-2374 | A-119 | B-6 |
| n3-2375 | A-120 | B-6 |
| n3-2376 | A-121 | B-6 |
| n3-2377 | A-122 | B-6 |
| n3-2378 | A-123 | B-6 |
| n3-2379 | A-124 | B-6 |
| n3-2380 | A-125 | B-6 |
| n3-2381 | A-126 | B-6 |
| n3-2382 | A-127 | B-6 |
| n3-2383 | A-128 | B-6 |
| n3-2384 | A-129 | B-6 |
| n3-2385 | A-130 | B-6 |
| n3-2386 | A-131 | B-6 |
| n3-2387 | A-132 | B-6 |

TABLE 1-continued

| epn | n = 3 A | B |
|---|---|---|
| n3-2388 | A-133 | B-6 |
| n3-2389 | A-134 | B-6 |
| n3-2390 | A-135 | B-6 |
| n3-2391 | A-136 | B-6 |
| n3-2392 | A-137 | B-6 |
| n3-2393 | A-138 | B-6 |
| n3-2394 | A-139 | B-6 |
| n3-2395 | A-140 | B-6 |
| n3-2396 | A-141 | B-6 |
| n3-2397 | A-142 | B-6 |
| n3-2398 | A-143 | B-6 |
| n3-2399 | A-144 | B-6 |
| n3-2400 | A-145 | B-6 |
| n3-2401 | A-146 | B-6 |
| n3-2402 | A-147 | B-6 |
| n3-2403 | A-148 | B-6 |
| n3-2404 | A-149 | B-6 |
| n3-2405 | A-150 | B-6 |
| n3-2406 | A-151 | B-6 |
| n3-2407 | A-152 | B-6 |
| n3-2408 | A-153 | B-6 |
| n3-2409 | A-154 | B-6 |
| n3-2410 | A-155 | B-6 |
| n3-2411 | A-156 | B-6 |
| n3-2412 | A-157 | B-6 |
| n3-2413 | A-158 | B-6 |
| n3-2414 | A-159 | B-6 |
| n3-2415 | A-160 | B-6 |
| n3-2416 | A-161 | B-6 |
| n3-2417 | A-162 | B-6 |
| n3-2418 | A-163 | B-6 |
| n3-2419 | A-164 | B-6 |
| n3-2420 | A-165 | B-6 |
| n3-2421 | A-166 | B-6 |
| n3-2422 | A-167 | B-6 |
| n3-2423 | A-168 | B-6 |
| n3-2424 | A-169 | B-6 |
| n3-2425 | A-170 | B-6 |
| n3-2426 | A-171 | B-6 |
| n3-2427 | A-172 | B-6 |
| n3-2428 | A-173 | B-6 |
| n3-2429 | A-174 | B-6 |
| n3-2430 | A-175 | B-6 |
| n3-2431 | A-176 | B-6 |
| n3-2432 | A-177 | B-6 |
| n3-2433 | A-178 | B-6 |
| n3-2434 | A-179 | B-6 |
| n3-2435 | A-180 | B-6 |
| n3-2436 | A-181 | B-6 |
| n3-2437 | A-182 | B-6 |
| n3-2438 | A-183 | B-6 |
| n3-2439 | A-184 | B-6 |
| n3-2440 | A-185 | B-6 |
| n3-2441 | A-186 | B-6 |
| n3-2442 | A-187 | B-6 |
| n3-2443 | A-188 | B-6 |
| n3-2444 | A-189 | B-6 |
| n3-2445 | A-190 | B-6 |
| n3-2446 | A-191 | B-6 |
| n3-2447 | A-192 | B-6 |
| n3-2448 | A-193 | B-6 |
| n3-2449 | A-194 | B-6 |
| n3-2450 | A-195 | B-6 |
| n3-2451 | A-196 | B-6 |
| n3-2452 | A-197 | B-6 |
| n3-2453 | A-198 | B-6 |
| n3-2454 | A-199 | B-6 |
| n3-2455 | A-200 | B-6 |
| n3-2456 | A-201 | B-6 |
| n3-2457 | A-202 | B-6 |
| n3-2458 | A-203 | B-6 |
| n3-2459 | A-204 | B-6 |
| n3-2460 | A-205 | B-6 |
| n3-2461 | A-206 | B-6 |
| n3-2462 | A-207 | B-6 |
| n3-2463 | A-208 | B-6 |
| n3-2464 | A-209 | B-6 |
| n3-2465 | A-210 | B-6 |
| n3-2466 | A-211 | B-6 |
| n3-2467 | A-212 | B-6 |
| n3-2468 | A-213 | B-6 |
| n3-2469 | A-214 | B-6 |
| n3-2470 | A-215 | B-6 |
| n3-2471 | A-216 | B-6 |
| n3-2472 | A-217 | B-6 |
| n3-2473 | A-218 | B-6 |
| n3-2474 | A-219 | B-6 |
| n3-2475 | A-220 | B-6 |
| n3-2476 | A-221 | B-6 |
| n3-2477 | A-222 | B-6 |
| n3-2478 | A-223 | B-6 |
| n3-2479 | A-224 | B-6 |
| n3-2480 | A-225 | B-6 |
| n3-2481 | A-226 | B-6 |
| n3-2482 | A-227 | B-6 |
| n3-2483 | A-228 | B-6 |
| n3-2484 | A-229 | B-6 |
| n3-2485 | A-230 | B-6 |
| n3-2486 | A-231 | B-6 |
| n3-2487 | A-232 | B-6 |
| n3-2488 | A-233 | B-6 |
| n3-2489 | A-234 | B-6 |
| n3-2490 | A-235 | B-6 |
| n3-2491 | A-236 | B-6 |
| n3-2492 | A-237 | B-6 |
| n3-2493 | A-238 | B-6 |
| n3-2494 | A-239 | B-6 |
| n3-2495 | A-240 | B-6 |
| n3-2496 | A-241 | B-6 |
| n3-2497 | A-242 | B-6 |
| n3-2498 | A-243 | B-6 |
| n3-2499 | A-244 | B-6 |
| n3-2500 | A-245 | B-6 |
| n3-2501 | A-246 | B-6 |
| n3-2502 | A-247 | B-6 |
| n3-2503 | A-248 | B-6 |
| n3-2504 | A-249 | B-6 |
| n3-2505 | A-250 | B-6 |
| n3-2506 | A-251 | B-6 |
| n3-2507 | A-252 | B-6 |
| n3-2508 | A-253 | B-6 |
| n3-2509 | A-254 | B-6 |
| n3-2510 | A-255 | B-6 |
| n3-2511 | A-256 | B-6 |
| n3-2512 | A-257 | B-6 |
| n3-2513 | A-258 | B-6 |
| n3-2514 | A-259 | B-6 |
| n3-2515 | A-260 | B-6 |
| n3-2516 | A-261 | B-6 |
| n3-2517 | A-262 | B-6 |
| n3-2518 | A-263 | B-6 |
| n3-2519 | A-264 | B-6 |
| n3-2520 | A-265 | B-6 |
| n3-2521 | A-266 | B-6 |
| n3-2522 | A-267 | B-6 |
| n3-2523 | A-268 | B-6 |
| n3-2524 | A-269 | B-6 |
| n3-2525 | A-270 | B-6 |
| n3-2526 | A-271 | B-6 |
| n3-2527 | A-272 | B-6 |
| n3-2528 | A-273 | B-6 |
| n3-2529 | A-274 | B-6 |
| n3-2530 | A-275 | B-6 |
| n3-2531 | A-276 | B-6 |
| n3-2532 | A-277 | B-6 |
| n3-2533 | A-278 | B-6 |
| n3-2534 | A-279 | B-6 |
| n3-2535 | A-280 | B-6 |
| n3-2536 | A-281 | B-6 |
| n3-2537 | A-282 | B-6 |

TABLE 1-continued

| | n = 3 | |
|---|---|---|
| epn | A | B |
| n3-2538 | A-283 | B-6 |
| n3-2539 | A-284 | B-6 |
| n3-2540 | A-285 | B-6 |
| n3-2541 | A-286 | B-6 |
| n3-2542 | A-287 | B-6 |
| n3-2543 | A-288 | B-6 |
| n3-2544 | A-289 | B-6 |
| n3-2545 | A-290 | B-6 |
| n3-2546 | A-291 | B-6 |
| n3-2547 | A-292 | B-6 |
| n3-2548 | A-293 | B-6 |
| n3-2549 | A-294 | B-6 |
| n3-2550 | A-295 | B-6 |
| n3-2551 | A-296 | B-6 |
| n3-2552 | A-297 | B-6 |
| n3-2553 | A-298 | B-6 |
| n3-2554 | A-299 | B-6 |
| n3-2555 | A-300 | B-6 |
| n3-2556 | A-301 | B-6 |
| n3-2557 | A-302 | B-6 |
| n3-2558 | A-303 | B-6 |
| n3-2559 | A-304 | B-6 |
| n3-2560 | A-305 | B-6 |
| n3-2561 | A-306 | B-6 |
| n3-2562 | A-307 | B-6 |
| n3-2563 | A-308 | B-6 |
| n3-2564 | A-309 | B-6 |
| n3-2565 | A-310 | B-6 |
| n3-2566 | A-311 | B-6 |
| n3-2567 | A-312 | B-6 |
| n3-2568 | A-313 | B-6 |
| n3-2569 | A-314 | B-6 |
| n3-2570 | A-315 | B-6 |
| n3-2571 | A-316 | B-6 |
| n3-2572 | A-317 | B-6 |
| n3-2573 | A-318 | B-6 |
| n3-2574 | A-319 | B-6 |
| n3-2575 | A-320 | B-6 |
| n3-2576 | A-321 | B-6 |
| n3-2577 | A-322 | B-6 |
| n3-2578 | A-323 | B-6 |
| n3-2579 | A-324 | B-6 |
| n3-2580 | A-325 | B-6 |
| n3-2581 | A-326 | B-6 |
| n3-2582 | A-327 | B-6 |
| n3-2583 | A-328 | B-6 |
| n3-2584 | A-329 | B-6 |
| n3-2585 | A-330 | B-6 |
| n3-2586 | A-331 | B-6 |
| n3-2587 | A-332 | B-6 |
| n3-2588 | A-333 | B-6 |
| n3-2589 | A-334 | B-6 |
| n3-2590 | A-335 | B-6 |
| n3-2591 | A-336 | B-6 |
| n3-2592 | A-337 | B-6 |
| n3-2593 | A-338 | B-6 |
| n3-2594 | A-339 | B-6 |
| n3-2595 | A-340 | B-6 |
| n3-2596 | A-341 | B-6 |
| n3-2597 | A-342 | B-6 |
| n3-2598 | A-343 | B-6 |
| n3-2599 | A-344 | B-6 |
| n3-2600 | A-345 | B-6 |
| n3-2601 | A-346 | B-6 |
| n3-2602 | A-347 | B-6 |
| n3-2603 | A-348 | B-6 |
| n3-2604 | A-349 | B-6 |
| n3-2605 | A-350 | B-6 |
| n3-2606 | A-351 | B-6 |
| n3-2607 | A-352 | B-6 |
| n3-2608 | A-353 | B-6 |
| n3-2609 | A-354 | B-6 |
| n3-2610 | A-355 | B-6 |
| n3-2611 | A-356 | B-6 |
| n3-2612 | A-357 | B-6 |
| n3-2613 | A-358 | B-6 |
| n3-2614 | A-359 | B-6 |
| n3-2615 | A-360 | B-6 |
| n3-2616 | A-361 | B-6 |
| n3-2617 | A-362 | B-6 |
| n3-2618 | A-363 | B-6 |
| n3-2619 | A-364 | B-6 |
| n3-2620 | A-365 | B-6 |
| n3-2621 | A-366 | B-6 |
| n3-2622 | A-367 | B-6 |
| n3-2623 | A-368 | B-6 |
| n3-2624 | A-369 | B-6 |
| n3-2625 | A-370 | B-6 |
| n3-2626 | A-371 | B-6 |
| n3-2627 | A-372 | B-6 |
| n3-2628 | A-373 | B-6 |
| n3-2629 | A-374 | B-6 |
| n3-2630 | A-375 | B-6 |
| n3-2631 | A-376 | B-6 |
| n3-2632 | A-377 | B-6 |
| n3-2633 | A-378 | B-6 |
| n3-2634 | A-379 | B-6 |
| n3-2635 | A-380 | B-6 |
| n3-2636 | A-381 | B-6 |
| n3-2637 | A-382 | B-6 |
| n3-2638 | A-383 | B-6 |
| n3-2639 | A-384 | B-6 |
| n3-2640 | A-385 | B-6 |
| n3-2641 | A-386 | B-6 |
| n3-2642 | A-387 | B-6 |
| n3-2643 | A-388 | B-6 |
| n3-2644 | A-389 | B-6 |
| n3-2645 | A-390 | B-6 |
| n3-2646 | A-391 | B-6 |
| n3-2647 | A-392 | B-6 |
| n3-2648 | A-393 | B-6 |
| n3-2649 | A-394 | B-6 |
| n3-2650 | A-395 | B-6 |
| n3-2651 | A-396 | B-6 |
| n3-2652 | A-397 | B-6 |
| n3-2653 | A-398 | B-6 |
| n3-2654 | A-399 | B-6 |
| n3-2655 | A-400 | B-6 |
| n3-2656 | A-401 | B-6 |
| n3-2657 | A-402 | B-6 |
| n3-2658 | A-403 | B-6 |
| n3-2659 | A-404 | B-6 |
| n3-2660 | A-405 | B-6 |
| n3-2661 | A-406 | B-6 |
| n3-2662 | A-407 | B-6 |
| n3-2663 | A-408 | B-6 |
| n3-2664 | A-409 | B-6 |
| n3-2665 | A-410 | B-6 |
| n3-2666 | A-411 | B-6 |
| n3-2667 | A-412 | B-6 |
| n3-2668 | A-413 | B-6 |
| n3-2669 | A-414 | B-6 |
| n3-2670 | A-415 | B-6 |
| n3-2671 | A-416 | B-6 |
| n3-2672 | A-417 | B-6 |
| n3-2673 | A-418 | B-6 |
| n3-2674 | A-419 | B-6 |
| n3-2675 | A-420 | B-6 |
| n3-2676 | A-421 | B-6 |
| n3-2677 | A-422 | B-6 |
| n3-2678 | A-423 | B-6 |
| n3-2679 | A-424 | B-6 |
| n3-2680 | A-425 | B-6 |
| n3-2681 | A-426 | B-6 |
| n3-2682 | A-427 | B-6 |
| n3-2683 | A-428 | B-6 |
| n3-2684 | A-429 | B-6 |
| n3-2685 | A-430 | B-6 |
| n3-2686 | A-431 | B-6 |
| n3-2687 | A-432 | B-6 |

TABLE 1-continued

| | n = 3 | |
|---|---|---|
| epn | A | B |
| n3-2688 | A-433 | B-6 |
| n3-2689 | A-434 | B-6 |
| n3-2690 | A-435 | B-6 |
| n3-2691 | A-436 | B-6 |
| n3-2692 | A-437 | B-6 |
| n3-2693 | A-438 | B-6 |
| n3-2694 | A-439 | B-6 |
| n3-2695 | A-440 | B-6 |
| n3-2696 | A-441 | B-6 |
| n3-2697 | A-442 | B-6 |
| n3-2698 | A-443 | B-6 |
| n3-2699 | A-444 | B-6 |
| n3-2700 | A-445 | B-6 |
| n3-2701 | A-446 | B-6 |
| n3-2702 | A-447 | B-6 |
| n3-2703 | A-448 | B-6 |
| n3-2704 | A-449 | B-6 |
| n3-2705 | A-450 | B-6 |
| n3-2706 | A-451 | B-6 |
| n3-2707 | A-1 | B-7 |
| n3-2708 | A-2 | B-7 |
| n3-2709 | A-3 | B-7 |
| n3-2710 | A-4 | B-7 |
| n3-2711 | A-5 | B-7 |
| n3-2712 | A-6 | B-7 |
| n3-2713 | A-7 | B-7 |
| n3-2714 | A-8 | B-7 |
| n3-2715 | A-9 | B-7 |
| n3-2716 | A-10 | B-7 |
| n3-2717 | A-11 | B-7 |
| n3-2718 | A-12 | B-7 |
| n3-2719 | A-13 | B-7 |
| n3-2720 | A-14 | B-7 |
| n3-2721 | A-15 | B-7 |
| n3-2722 | A-16 | B-7 |
| n3-2723 | A-17 | B-7 |
| n3-2724 | A-18 | B-7 |
| n3-2725 | A-19 | B-7 |
| n3-2726 | A-20 | B-7 |
| n3-2727 | A-21 | B-7 |
| n3-2728 | A-22 | B-7 |
| n3-2729 | A-23 | B-7 |
| n3-2730 | A-24 | B-7 |
| n3-2731 | A-25 | B-7 |
| n3-2732 | A-26 | B-7 |
| n3-2733 | A-27 | B-7 |
| n3-2734 | A-28 | B-7 |
| n3-2735 | A-29 | B-7 |
| n3-2736 | A-30 | B-7 |
| n3-2737 | A-31 | B-7 |
| n3-2738 | A-32 | B-7 |
| n3-2739 | A-33 | B-7 |
| n3-2740 | A-34 | B-7 |
| n3-2741 | A-35 | B-7 |
| n3-2742 | A-36 | B-7 |
| n3-2743 | A-37 | B-7 |
| n3-2744 | A-38 | B-7 |
| n3-2745 | A-39 | B-7 |
| n3-2746 | A-40 | B-7 |
| n3-2747 | A-41 | B-7 |
| n3-2748 | A-42 | B-7 |
| n3-2749 | A-43 | B-7 |
| n3-2750 | A-44 | B-7 |
| n3-2751 | A-45 | B-7 |
| n3-2752 | A-46 | B-7 |
| n3-2753 | A-47 | B-7 |
| n3-2754 | A-48 | B-7 |
| n3-2755 | A-49 | B-7 |
| n3-2756 | A-50 | B-7 |
| n3-2757 | A-51 | B-7 |
| n3-2758 | A-52 | B-7 |
| n3-2759 | A-53 | B-7 |
| n3-2760 | A-54 | B-7 |
| n3-2761 | A-55 | B-7 |
| n3-2762 | A-56 | B-7 |
| n3-2763 | A-57 | B-7 |
| n3-2764 | A-58 | B-7 |
| n3-2765 | A-59 | B-7 |
| n3-2766 | A-60 | B-7 |
| n3-2767 | A-61 | B-7 |
| n3-2768 | A-62 | B-7 |
| n3-2769 | A-63 | B-7 |
| n3-2770 | A-64 | B-7 |
| n3-2771 | A-65 | B-7 |
| n3-2772 | A-66 | B-7 |
| n3-2773 | A-67 | B-7 |
| n3-2774 | A-68 | B-7 |
| n3-2775 | A-69 | B-7 |
| n3-2776 | A-70 | B-7 |
| n3-2777 | A-71 | B-7 |
| n3-2778 | A-72 | B-7 |
| n3-2779 | A-73 | B-7 |
| n3-2780 | A-74 | B-7 |
| n3-2781 | A-75 | B-7 |
| n3-2782 | A-76 | B-7 |
| n3-2783 | A-77 | B-7 |
| n3-2784 | A-78 | B-7 |
| n3-2785 | A-79 | B-7 |
| n3-2786 | A-80 | B-7 |
| n3-2787 | A-81 | B-7 |
| n3-2788 | A-82 | B-7 |
| n3-2789 | A-83 | B-7 |
| n3-2790 | A-84 | B-7 |
| n3-2791 | A-85 | B-7 |
| n3-2792 | A-86 | B-7 |
| n3-2793 | A-87 | B-7 |
| n3-2794 | A-88 | B-7 |
| n3-2795 | A-89 | B-7 |
| n3-2796 | A-90 | B-7 |
| n3-2797 | A-91 | B-7 |
| n3-2798 | A-92 | B-7 |
| n3-2799 | A-93 | B-7 |
| n3-2800 | A-94 | B-7 |
| n3-2801 | A-95 | B-7 |
| n3-2802 | A-96 | B-7 |
| n3-2803 | A-97 | B-7 |
| n3-2804 | A-98 | B-7 |
| n3-2805 | A-99 | B-7 |
| n3-2806 | A-100 | B-7 |
| n3-2807 | A-101 | B-7 |
| n3-2808 | A-102 | B-7 |
| n3-2809 | A-103 | B-7 |
| n3-2810 | A-104 | B-7 |
| n3-2811 | A-105 | B-7 |
| n3-2812 | A-106 | B-7 |
| n3-2813 | A-107 | B-7 |
| n3-2814 | A-108 | B-7 |
| n3-2815 | A-109 | B-7 |
| n3-2816 | A-110 | B-7 |
| n3-2817 | A-111 | B-7 |
| n3-2818 | A-112 | B-7 |
| n3-2819 | A-113 | B-7 |
| n3-2820 | A-114 | B-7 |
| n3-2821 | A-115 | B-7 |
| n3-2822 | A-116 | B-7 |
| n3-2823 | A-117 | B-7 |
| n3-2824 | A-118 | B-7 |
| n3-2825 | A-119 | B-7 |
| n3-2826 | A-120 | B-7 |
| n3-2827 | A-121 | B-7 |
| n3-2828 | A-122 | B-7 |
| n3-2829 | A-123 | B-7 |
| n3-2830 | A-124 | B-7 |
| n3-2831 | A-125 | B-7 |
| n3-2832 | A-126 | B-7 |
| n3-2833 | A-127 | B-7 |
| n3-2834 | A-128 | B-7 |
| n3-2835 | A-129 | B-7 |
| n3-2836 | A-130 | B-7 |
| n3-2837 | A-131 | B-7 |

TABLE 1-continued

| epn | n = 3 A | B |
|---|---|---|
| n3-2838 | A-132 | B-7 |
| n3-2839 | A-133 | B-7 |
| n3-2840 | A-134 | B-7 |
| n3-2841 | A-135 | B-7 |
| n3-2842 | A-136 | B-7 |
| n3-2843 | A-137 | B-7 |
| n3-2844 | A-138 | B-7 |
| n3-2845 | A-139 | B-7 |
| n3-2846 | A-140 | B-7 |
| n3-2847 | A-141 | B-7 |
| n3-2848 | A-142 | B-7 |
| n3-2849 | A-143 | B-7 |
| n3-2850 | A-144 | B-7 |
| n3-2851 | A-145 | B-7 |
| n3-2852 | A-146 | B-7 |
| n3-2853 | A-147 | B-7 |
| n3-2854 | A-148 | B-7 |
| n3-2855 | A-149 | B-7 |
| n3-2856 | A-150 | B-7 |
| n3-2857 | A-151 | B-7 |
| n3-2858 | A-152 | B-7 |
| n3-2859 | A-153 | B-7 |
| n3-2860 | A-154 | B-7 |
| n3-2861 | A-155 | B-7 |
| n3-2862 | A-156 | B-7 |
| n3-2863 | A-157 | B-7 |
| n3-2864 | A-158 | B-7 |
| n3-2865 | A-159 | B-7 |
| n3-2866 | A-160 | B-7 |
| n3-2867 | A-161 | B-7 |
| n3-2868 | A-162 | B-7 |
| n3-2869 | A-163 | B-7 |
| n3-2870 | A-164 | B-7 |
| n3-2871 | A-165 | B-7 |
| n3-2872 | A-166 | B-7 |
| n3-2873 | A-167 | B-7 |
| n3-2874 | A-168 | B-7 |
| n3-2875 | A-169 | B-7 |
| n3-2876 | A-170 | B-7 |
| n3-2877 | A-171 | B-7 |
| n3-2878 | A-172 | B-7 |
| n3-2879 | A-173 | B-7 |
| n3-2880 | A-174 | B-7 |
| n3-2881 | A-175 | B-7 |
| n3-2882 | A-176 | B-7 |
| n3-2883 | A-177 | B-7 |
| n3-2884 | A-178 | B-7 |
| n3-2885 | A-179 | B-7 |
| n3-2886 | A-180 | B-7 |
| n3-2887 | A-181 | B-7 |
| n3-2888 | A-182 | B-7 |
| n3-2889 | A-183 | B-7 |
| n3-2890 | A-184 | B-7 |
| n3-2891 | A-185 | B-7 |
| n3-2892 | A-186 | B-7 |
| n3-2893 | A-187 | B-7 |
| n3-2894 | A-188 | B-7 |
| n3-2895 | A-189 | B-7 |
| n3-2896 | A-190 | B-7 |
| n3-2897 | A-191 | B-7 |
| n3-2898 | A-192 | B-7 |
| n3-2899 | A-193 | B-7 |
| n3-2900 | A-194 | B-7 |
| n3-2901 | A-195 | B-7 |
| n3-2902 | A-196 | B-7 |
| n3-2903 | A-197 | B-7 |
| n3-2904 | A-198 | B-7 |
| n3-2905 | A-199 | B-7 |
| n3-2906 | A-200 | B-7 |
| n3-2907 | A-201 | B-7 |
| n3-2908 | A-202 | B-7 |
| n3-2909 | A-203 | B-7 |
| n3-2910 | A-204 | B-7 |
| n3-2911 | A-205 | B-7 |
| n3-2912 | A-206 | B-7 |

TABLE 1-continued

| epn | n = 3 A | B |
|---|---|---|
| n3-2913 | A-207 | B-7 |
| n3-2914 | A-208 | B-7 |
| n3-2915 | A-209 | B-7 |
| n3-2916 | A-210 | B-7 |
| n3-2917 | A-211 | B-7 |
| n3-2918 | A-212 | B-7 |
| n3-2919 | A-213 | B-7 |
| n3-2920 | A-214 | B-7 |
| n3-2921 | A-215 | B-7 |
| n3-2922 | A-216 | B-7 |
| n3-2923 | A-217 | B-7 |
| n3-2924 | A-218 | B-7 |
| n3-2925 | A-219 | B-7 |
| n3-2926 | A-220 | B-7 |
| n3-2927 | A-221 | B-7 |
| n3-2928 | A-222 | B-7 |
| n3-2929 | A-223 | B-7 |
| n3-2930 | A-224 | B-7 |
| n3-2931 | A-225 | B-7 |
| n3-2932 | A-226 | B-7 |
| n3-2933 | A-227 | B-7 |
| n3-2934 | A-228 | B-7 |
| n3-2935 | A-229 | B-7 |
| n3-2936 | A-230 | B-7 |
| n3-2937 | A-231 | B-7 |
| n3-2938 | A-232 | B-7 |
| n3-2939 | A-233 | B-7 |
| n3-2940 | A-234 | B-7 |
| n3-2941 | A-235 | B-7 |
| n3-2942 | A-236 | B-7 |
| n3-2943 | A-237 | B-7 |
| n3-2944 | A-238 | B-7 |
| n3-2945 | A-239 | B-7 |
| n3-2946 | A-240 | B-7 |
| n3-2947 | A-241 | B-7 |
| n3-2948 | A-242 | B-7 |
| n3-2949 | A-243 | B-7 |
| n3-2950 | A-244 | B-7 |
| n3-2951 | A-245 | B-7 |
| n3-2952 | A-246 | B-7 |
| n3-2953 | A-247 | B-7 |
| n3-2954 | A-248 | B-7 |
| n3-2955 | A-249 | B-7 |
| n3-2956 | A-250 | B-7 |
| n3-2957 | A-251 | B-7 |
| n3-2958 | A-252 | B-7 |
| n3-2959 | A-253 | B-7 |
| n3-2960 | A-254 | B-7 |
| n3-2961 | A-255 | B-7 |
| n3-2962 | A-256 | B-7 |
| n3-2963 | A-257 | B-7 |
| n3-2964 | A-258 | B-7 |
| n3-2965 | A-259 | B-7 |
| n3-2966 | A-260 | B-7 |
| n3-2967 | A-261 | B-7 |
| n3-2968 | A-262 | B-7 |
| n3-2969 | A-263 | B-7 |
| n3-2970 | A-264 | B-7 |
| n3-2971 | A-265 | B-7 |
| n3-2972 | A-266 | B-7 |
| n3-2973 | A-267 | B-7 |
| n3-2974 | A-268 | B-7 |
| n3-2975 | A-269 | B-7 |
| n3-2976 | A-270 | B-7 |
| n3-2977 | A-271 | B-7 |
| n3-2978 | A-272 | B-7 |
| n3-2979 | A-273 | B-7 |
| n3-2980 | A-274 | B-7 |
| n3-2981 | A-275 | B-7 |
| n3-2982 | A-276 | B-7 |
| n3-2983 | A-277 | B-7 |
| n3-2984 | A-278 | B-7 |
| n3-2985 | A-279 | B-7 |
| n3-2986 | A-280 | B-7 |
| n3-2987 | A-281 | B-7 |

TABLE 1-continued

| epn | n = 3 A | B |
|---|---|---|
| n3-2988 | A-282 | B-7 |
| n3-2989 | A-283 | B-7 |
| n3-2990 | A-284 | B-7 |
| n3-2991 | A-285 | B-7 |
| n3-2992 | A-286 | B-7 |
| n3-2993 | A-287 | B-7 |
| n3-2994 | A-288 | B-7 |
| n3-2995 | A-289 | B-7 |
| n3-2996 | A-290 | B-7 |
| n3-2997 | A-291 | B-7 |
| n3-2998 | A-292 | B-7 |
| n3-2999 | A-293 | B-7 |
| n3-3000 | A-294 | B-7 |
| n3-3001 | A-295 | B-7 |
| n3-3002 | A-296 | B-7 |
| n3-3003 | A-297 | B-7 |
| n3-3004 | A-298 | B-7 |
| n3-3005 | A-299 | B-7 |
| n3-3006 | A-300 | B-7 |
| n3-3007 | A-301 | B-7 |
| n3-3008 | A-302 | B-7 |
| n3-3009 | A-303 | B-7 |
| n3-3010 | A-304 | B-7 |
| n3-3011 | A-305 | B-7 |
| n3-3012 | A-306 | B-7 |
| n3-3013 | A-307 | B-7 |
| n3-3014 | A-308 | B-7 |
| n3-3015 | A-309 | B-7 |
| n3-3016 | A-310 | B-7 |
| n3-3017 | A-311 | B-7 |
| n3-3018 | A-312 | B-7 |
| n3-3019 | A-313 | B-7 |
| n3-3020 | A-314 | B-7 |
| n3-3021 | A-315 | B-7 |
| n3-3022 | A-316 | B-7 |
| n3-3023 | A-317 | B-7 |
| n3-3024 | A-318 | B-7 |
| n3-3025 | A-319 | B-7 |
| n3-3026 | A-320 | B-7 |
| n3-3027 | A-321 | B-7 |
| n3-3028 | A-322 | B-7 |
| n3-3029 | A-323 | B-7 |
| n3-3030 | A-324 | B-7 |
| n3-3031 | A-325 | B-7 |
| n3-3032 | A-326 | B-7 |
| n3-3033 | A-327 | B-7 |
| n3-3034 | A-328 | B-7 |
| n3-3035 | A-329 | B-7 |
| n3-3036 | A-330 | B-7 |
| n3-3037 | A-331 | B-7 |
| n3-3038 | A-332 | B-7 |
| n3-3039 | A-333 | B-7 |
| n3-3040 | A-334 | B-7 |
| n3-3041 | A-335 | B-7 |
| n3-3042 | A-336 | B-7 |
| n3-3043 | A-337 | B-7 |
| n3-3044 | A-338 | B-7 |
| n3-3045 | A-339 | B-7 |
| n3-3046 | A-340 | B-7 |
| n3-3047 | A-341 | B-7 |
| n3-3048 | A-342 | B-7 |
| n3-3049 | A-343 | B-7 |
| n3-3050 | A-344 | B-7 |
| n3-3051 | A-345 | B-7 |
| n3-3052 | A-346 | B-7 |
| n3-3053 | A-347 | B-7 |
| n3-3054 | A-348 | B-7 |
| n3-3055 | A-349 | B-7 |
| n3-3056 | A-350 | B-7 |
| n3-3057 | A-351 | B-7 |
| n3-3058 | A-352 | B-7 |
| n3-3059 | A-353 | B-7 |
| n3-3060 | A-354 | B-7 |
| n3-3061 | A-355 | B-7 |
| n3-3062 | A-356 | B-7 |
| n3-3063 | A-357 | B-7 |
| n3-3064 | A-358 | B-7 |
| n3-3065 | A-359 | B-7 |
| n3-3066 | A-360 | B-7 |
| n3-3067 | A-361 | B-7 |
| n3-3068 | A-362 | B-7 |
| n3-3069 | A-363 | B-7 |
| n3-3070 | A-364 | B-7 |
| n3-3071 | A-365 | B-7 |
| n3-3072 | A-366 | B-7 |
| n3-3073 | A-367 | B-7 |
| n3-3074 | A-368 | B-7 |
| n3-3075 | A-369 | B-7 |
| n3-3076 | A-370 | B-7 |
| n3-3077 | A-371 | B-7 |
| n3-3078 | A-372 | B-7 |
| n3-3079 | A-373 | B-7 |
| n3-3080 | A-374 | B-7 |
| n3-3081 | A-375 | B-7 |
| n3-3082 | A-376 | B-7 |
| n3-3083 | A-377 | B-7 |
| n3-3084 | A-378 | B-7 |
| n3-3085 | A-379 | B-7 |
| n3-3086 | A-380 | B-7 |
| n3-3087 | A-381 | B-7 |
| n3-3088 | A-382 | B-7 |
| n3-3089 | A-383 | B-7 |
| n3-3090 | A-384 | B-7 |
| n3-3091 | A-385 | B-7 |
| n3-3092 | A-386 | B-7 |
| n3-3093 | A-387 | B-7 |
| n3-3094 | A-388 | B-7 |
| n3-3095 | A-389 | B-7 |
| n3-3096 | A-390 | B-7 |
| n3-3097 | A-391 | B-7 |
| n3-3098 | A-392 | B-7 |
| n3-3099 | A-393 | B-7 |
| n3-3100 | A-394 | B-7 |
| n3-3101 | A-395 | B-7 |
| n3-3102 | A-396 | B-7 |
| n3-3103 | A-397 | B-7 |
| n3-3104 | A-398 | B-7 |
| n3-3105 | A-399 | B-7 |
| n3-3106 | A-400 | B-7 |
| n3-3107 | A-401 | B-7 |
| n3-3108 | A-402 | B-7 |
| n3-3109 | A-403 | B-7 |
| n3-3110 | A-404 | B-7 |
| n3-3111 | A-405 | B-7 |
| n3-3112 | A-406 | B-7 |
| n3-3113 | A-407 | B-7 |
| n3-3114 | A-408 | B-7 |
| n3-3115 | A-409 | B-7 |
| n3-3116 | A-410 | B-7 |
| n3-3117 | A-411 | B-7 |
| n3-3118 | A-412 | B-7 |
| n3-3119 | A-413 | B-7 |
| n3-3120 | A-414 | B-7 |
| n3-3121 | A-415 | B-7 |
| n3-3122 | A-416 | B-7 |
| n3-3123 | A-417 | B-7 |
| n3-3124 | A-418 | B-7 |
| n3-3125 | A-419 | B-7 |
| n3-3126 | A-420 | B-7 |
| n3-3127 | A-421 | B-7 |
| n3-3128 | A-422 | B-7 |
| n3-3129 | A-423 | B-7 |
| n3-3130 | A-424 | B-7 |
| n3-3131 | A-425 | B-7 |
| n3-3132 | A-426 | B-7 |
| n3-3133 | A-427 | B-7 |
| n3-3134 | A-428 | B-7 |
| n3-3135 | A-429 | B-7 |
| n3-3136 | A-430 | B-7 |
| n3-3137 | A-431 | B-7 |

TABLE 1-continued

| epn | n = 3 A | B |
|---|---|---|
| n3-3138 | A-432 | B-7 |
| n3-3139 | A-433 | B-7 |
| n3-3140 | A-434 | B-7 |
| n3-3141 | A-435 | B-7 |
| n3-3142 | A-436 | B-7 |
| n3-3143 | A-437 | B-7 |
| n3-3144 | A-438 | B-7 |
| n3-3145 | A-439 | B-7 |
| n3-3146 | A-440 | B-7 |
| n3-3147 | A-441 | B-7 |
| n3-3148 | A-442 | B-7 |
| n3-3149 | A-443 | B-7 |
| n3-3150 | A-444 | B-7 |
| n3-3151 | A-445 | B-7 |
| n3-3152 | A-446 | B-7 |
| n3-3153 | A-447 | B-7 |
| n3-3154 | A-448 | B-7 |
| n3-3155 | A-449 | B-7 |
| n3-3156 | A-450 | B-7 |
| n3-3157 | A-451 | B-7 |
| n3-3158 | A-1 | B-8 |
| n3-3159 | A-2 | B-8 |
| n3-3160 | A-3 | B-8 |
| n3-3161 | A-4 | B-8 |
| n3-3162 | A-5 | B-8 |
| n3-3163 | A-6 | B-8 |
| n3-3164 | A-7 | B-8 |
| n3-3165 | A-8 | B-8 |
| n3-3166 | A-9 | B-8 |
| n3-3167 | A-10 | B-8 |
| n3-3168 | A-11 | B-8 |
| n3-3169 | A-12 | B-8 |
| n3-3170 | A-13 | B-8 |
| n3-3171 | A-14 | B-8 |
| n3-3172 | A-15 | B-8 |
| n3-3173 | A-16 | B-8 |
| n3-3174 | A-17 | B-8 |
| n3-3175 | A-18 | B-8 |
| n3-3176 | A-19 | B-8 |
| n3-3177 | A-20 | B-8 |
| n3-3178 | A-21 | B-8 |
| n3-3179 | A-22 | B-8 |
| n3-3180 | A-23 | B-8 |
| n3-3181 | A-24 | B-8 |
| n3-3182 | A-25 | B-8 |
| n3-3183 | A-26 | B-8 |
| n3-3184 | A-27 | B-8 |
| n3-3185 | A-28 | B-8 |
| n3-3186 | A-29 | B-8 |
| n3-3187 | A-30 | B-8 |
| n3-3188 | A-31 | B-8 |
| n3-3189 | A-32 | B-8 |
| n3-3190 | A-33 | B-8 |
| n3-3191 | A-34 | B-8 |
| n3-3192 | A-35 | B-8 |
| n3-3193 | A-36 | B-8 |
| n3-3194 | A-37 | B-8 |
| n3-3195 | A-38 | B-8 |
| n3-3196 | A-39 | B-8 |
| n3-3197 | A-40 | B-8 |
| n3-3198 | A-41 | B-8 |
| n3-3199 | A-42 | B-8 |
| n3-3200 | A-43 | B-8 |
| n3-3201 | A-44 | B-8 |
| n3-3202 | A-45 | B-8 |
| n3-3203 | A-46 | B-8 |
| n3-3204 | A-47 | B-8 |
| n3-3205 | A-48 | B-8 |
| n3-3206 | A-49 | B-8 |
| n3-3207 | A-50 | B-8 |
| n3-3208 | A-51 | B-8 |
| n3-3209 | A-52 | B-8 |
| n3-3210 | A-53 | B-8 |
| n3-3211 | A-54 | B-8 |
| n3-3212 | A-55 | B-8 |
| n3-3213 | A-56 | B-8 |
| n3-3214 | A-57 | B-8 |
| n3-3215 | A-58 | B-8 |
| n3-3216 | A-59 | B-8 |
| n3-3217 | A-60 | B-8 |
| n3-3218 | A-61 | B-8 |
| n3-3219 | A-62 | B-8 |
| n3-3220 | A-63 | B-8 |
| n3-3221 | A-64 | B-8 |
| n3-3222 | A-65 | B-8 |
| n3-3223 | A-66 | B-8 |
| n3-3224 | A-67 | B-8 |
| n3-3225 | A-68 | B-8 |
| n3-3226 | A-69 | B-8 |
| n3-3227 | A-70 | B-8 |
| n3-3228 | A-71 | B-8 |
| n3-3229 | A-72 | B-8 |
| n3-3230 | A-73 | B-8 |
| n3-3231 | A-74 | B-8 |
| n3-3232 | A-75 | B-8 |
| n3-3233 | A-76 | B-8 |
| n3-3234 | A-77 | B-8 |
| n3-3235 | A-78 | B-8 |
| n3-3236 | A-79 | B-8 |
| n3-3237 | A-80 | B-8 |
| n3-3238 | A-81 | B-8 |
| n3-3239 | A-82 | B-8 |
| n3-3240 | A-83 | B-8 |
| n3-3241 | A-84 | B-8 |
| n3-3242 | A-85 | B-8 |
| n3-3243 | A-86 | B-8 |
| n3-3244 | A-87 | B-8 |
| n3-3245 | A-88 | B-8 |
| n3-3246 | A-89 | B-8 |
| n3-3247 | A-90 | B-8 |
| n3-3248 | A-91 | B-8 |
| n3-3249 | A-92 | B-8 |
| n3-3250 | A-93 | B-8 |
| n3-3251 | A-94 | B-8 |
| n3-3252 | A-95 | B-8 |
| n3-3253 | A-96 | B-8 |
| n3-3254 | A-97 | B-8 |
| n3-3255 | A-98 | B-8 |
| n3-3256 | A-99 | B-8 |
| n3-3257 | A-100 | B-8 |
| n3-3258 | A-101 | B-8 |
| n3-3259 | A-102 | B-8 |
| n3-3260 | A-103 | B-8 |
| n3-3261 | A-104 | B-8 |
| n3-3262 | A-105 | B-8 |
| n3-3263 | A-106 | B-8 |
| n3-3264 | A-107 | B-8 |
| n3-3265 | A-108 | B-8 |
| n3-3266 | A-109 | B-8 |
| n3-3267 | A-110 | B-8 |
| n3-3268 | A-111 | B-8 |
| n3-3269 | A-112 | B-8 |
| n3-3270 | A-113 | B-8 |
| n3-3271 | A-114 | B-8 |
| n3-3272 | A-115 | B-8 |
| n3-3273 | A-116 | B-8 |
| n3-3274 | A-117 | B-8 |
| n3-3275 | A-118 | B-8 |
| n3-3276 | A-119 | B-8 |
| n3-3277 | A-120 | B-8 |
| n3-3278 | A-121 | B-8 |
| n3-3279 | A-122 | B-8 |
| n3-3280 | A-123 | B-8 |
| n3-3281 | A-124 | B-8 |
| n3-3282 | A-125 | B-8 |
| n3-3283 | A-126 | B-8 |
| n3-3284 | A-127 | B-8 |
| n3-3285 | A-128 | B-8 |
| n3-3286 | A-129 | B-8 |
| n3-3287 | A-130 | B-8 |

TABLE 1-continued

| epn | n = 3 A | B |
|---|---|---|
| n3-3288 | A-131 | B-8 |
| n3-3289 | A-132 | B-8 |
| n3-3290 | A-133 | B-8 |
| n3-3291 | A-134 | B-8 |
| n3-3292 | A-135 | B-8 |
| n3-3293 | A-136 | B-8 |
| n3-3294 | A-137 | B-8 |
| n3-3295 | A-138 | B-8 |
| n3-3296 | A-139 | B-8 |
| n3-3297 | A-140 | B-8 |
| n3-3298 | A-141 | B-8 |
| n3-3299 | A-142 | B-8 |
| n3-3300 | A-143 | B-8 |
| n3-3301 | A-144 | B-8 |
| n3-3302 | A-145 | B-8 |
| n3-3303 | A-146 | B-8 |
| n3-3304 | A-147 | B-8 |
| n3-3305 | A-148 | B-8 |
| n3-3306 | A-149 | B-8 |
| n3-3307 | A-150 | B-8 |
| n3-3308 | A-151 | B-8 |
| n3-3309 | A-152 | B-8 |
| n3-3310 | A-153 | B-8 |
| n3-3311 | A-154 | B-8 |
| n3-3312 | A-155 | B-8 |
| n3-3313 | A-156 | B-8 |
| n3-3314 | A-157 | B-8 |
| n3-3315 | A-158 | B-8 |
| n3-3316 | A-159 | B-8 |
| n3-3317 | A-160 | B-8 |
| n3-3318 | A-161 | B-8 |
| n3-3319 | A-162 | B-8 |
| n3-3320 | A-163 | B-8 |
| n3-3321 | A-164 | B-8 |
| n3-3322 | A-165 | B-8 |
| n3-3323 | A-166 | B-8 |
| n3-3324 | A-167 | B-8 |
| n3-3325 | A-168 | B-8 |
| n3-3326 | A-169 | B-8 |
| n3-3327 | A-170 | B-8 |
| n3-3328 | A-171 | B-8 |
| n3-3329 | A-172 | B-8 |
| n3-3330 | A-173 | B-8 |
| n3-3331 | A-174 | B-8 |
| n3-3332 | A-175 | B-8 |
| n3-3333 | A-176 | B-8 |
| n3-3334 | A-177 | B-8 |
| n3-3335 | A-178 | B-8 |
| n3-3336 | A-179 | B-8 |
| n3-3337 | A-180 | B-8 |
| n3-3338 | A-181 | B-8 |
| n3-3339 | A-182 | B-8 |
| n3-3340 | A-183 | B-8 |
| n3-3341 | A-184 | B-8 |
| n3-3342 | A-185 | B-8 |
| n3-3343 | A-186 | B-8 |
| n3-3344 | A-187 | B-8 |
| n3-3345 | A-188 | B-8 |
| n3-3346 | A-189 | B-8 |
| n3-3347 | A-190 | B-8 |
| n3-3348 | A-191 | B-8 |
| n3-3349 | A-192 | B-8 |
| n3-3350 | A-193 | B-8 |
| n3-3351 | A-194 | B-8 |
| n3-3352 | A-195 | B-8 |
| n3-3353 | A-196 | B-8 |
| n3-3354 | A-197 | B-8 |
| n3-3355 | A-198 | B-8 |
| n3-3356 | A-199 | B-8 |
| n3-3357 | A-200 | B-8 |
| n3-3358 | A-201 | B-8 |
| n3-3359 | A-202 | B-8 |
| n3-3360 | A-203 | B-8 |
| n3-3361 | A-204 | B-8 |
| n3-3362 | A-205 | B-8 |
| n3-3363 | A-206 | B-8 |
| n3-3364 | A-207 | B-8 |
| n3-3365 | A-208 | B-8 |
| n3-3366 | A-209 | B-8 |
| n3-3367 | A-210 | B-8 |
| n3-3368 | A-211 | B-8 |
| n3-3369 | A-212 | B-8 |
| n3-3370 | A-213 | B-8 |
| n3-3371 | A-214 | B-8 |
| n3-3372 | A-215 | B-8 |
| n3-3373 | A-216 | B-8 |
| n3-3374 | A-217 | B-8 |
| n3-3375 | A-218 | B-8 |
| n3-3376 | A-219 | B-8 |
| n3-3377 | A-220 | B-8 |
| n3-3378 | A-221 | B-8 |
| n3-3379 | A-222 | B-8 |
| n3-3380 | A-223 | B-8 |
| n3-3381 | A-224 | B-8 |
| n3-3382 | A-225 | B-8 |
| n3-3383 | A-226 | B-8 |
| n3-3384 | A-227 | B-8 |
| n3-3385 | A-228 | B-8 |
| n3-3386 | A-229 | B-8 |
| n3-3387 | A-230 | B-8 |
| n3-3388 | A-231 | B-8 |
| n3-3389 | A-232 | B-8 |
| n3-3390 | A-233 | B-8 |
| n3-3391 | A-234 | B-8 |
| n3-3392 | A-235 | B-8 |
| n3-3393 | A-236 | B-8 |
| n3-3394 | A-237 | B-8 |
| n3-3395 | A-238 | B-8 |
| n3-3396 | A-239 | B-8 |
| n3-3397 | A-240 | B-8 |
| n3-3398 | A-241 | B-8 |
| n3-3399 | A-242 | B-8 |
| n3-3400 | A-243 | B-8 |
| n3-3401 | A-244 | B-8 |
| n3-3402 | A-245 | B-8 |
| n3-3403 | A-246 | B-8 |
| n3-3404 | A-247 | B-8 |
| n3-3405 | A-248 | B-8 |
| n3-3406 | A-249 | B-8 |
| n3-3407 | A-250 | B-8 |
| n3-3408 | A-251 | B-8 |
| n3-3409 | A-252 | B-8 |
| n3-3410 | A-253 | B-8 |
| n3-3411 | A-254 | B-8 |
| n3-3412 | A-255 | B-8 |
| n3-3413 | A-256 | B-8 |
| n3-3414 | A-257 | B-8 |
| n3-3415 | A-258 | B-8 |
| n3-3416 | A-259 | B-8 |
| n3-3417 | A-260 | B-8 |
| n3-3418 | A-261 | B-8 |
| n3-3419 | A-262 | B-8 |
| n3-3420 | A-263 | B-8 |
| n3-3421 | A-264 | B-8 |
| n3-3422 | A-265 | B-8 |
| n3-3423 | A-266 | B-8 |
| n3-3424 | A-267 | B-8 |
| n3-3425 | A-268 | B-8 |
| n3-3426 | A-269 | B-8 |
| n3-3427 | A-270 | B-8 |
| n3-3428 | A-271 | B-8 |
| n3-3429 | A-272 | B-8 |
| n3-3430 | A-273 | B-8 |
| n3-3431 | A-274 | B-8 |
| n3-3432 | A-275 | B-8 |
| n3-3433 | A-276 | B-8 |
| n3-3434 | A-277 | B-8 |
| n3-3435 | A-278 | B-8 |
| n3-3436 | A-279 | B-8 |
| n3-3437 | A-280 | B-8 |

TABLE 1-continued

| epn | n = 3 A | B |
|---|---|---|
| n3-3438 | A-281 | B-8 |
| n3-3439 | A-282 | B-8 |
| n3-3440 | A-283 | B-8 |
| n3-3441 | A-284 | B-8 |
| n3-3442 | A-285 | B-8 |
| n3-3443 | A-286 | B-8 |
| n3-3444 | A-287 | B-8 |
| n3-3445 | A-288 | B-8 |
| n3-3446 | A-289 | B-8 |
| n3-3447 | A-290 | B-8 |
| n3-3448 | A-291 | B-8 |
| n3-3449 | A-292 | B-8 |
| n3-3450 | A-293 | B-8 |
| n3-3451 | A-294 | B-8 |
| n3-3452 | A-295 | B-8 |
| n3-3453 | A-296 | B-8 |
| n3-3454 | A-297 | B-8 |
| n3-3455 | A-298 | B-8 |
| n3-3456 | A-299 | B-8 |
| n3-3457 | A-300 | B-8 |
| n3-3458 | A-301 | B-8 |
| n3-3459 | A-302 | B-8 |
| n3-3460 | A-303 | B-8 |
| n3-3461 | A-304 | B-8 |
| n3-3462 | A-305 | B-8 |
| n3-3463 | A-306 | B-8 |
| n3-3464 | A-307 | B-8 |
| n3-3465 | A-308 | B-8 |
| n3-3466 | A-309 | B-8 |
| n3-3467 | A-310 | B-8 |
| n3-3468 | A-311 | B-8 |
| n3-3469 | A-312 | B-8 |
| n3-3470 | A-313 | B-8 |
| n3-3471 | A-314 | B-8 |
| n3-3472 | A-315 | B-8 |
| n3-3473 | A-316 | B-8 |
| n3-3474 | A-317 | B-8 |
| n3-3475 | A-318 | B-8 |
| n3-3476 | A-319 | B-8 |
| n3-3477 | A-320 | B-8 |
| n3-3478 | A-321 | B-8 |
| n3-3479 | A-322 | B-8 |
| n3-3480 | A-323 | B-8 |
| n3-3481 | A-324 | B-8 |
| n3-3482 | A-325 | B-8 |
| n3-3483 | A-326 | B-8 |
| n3-3484 | A-327 | B-8 |
| n3-3485 | A-328 | B-8 |
| n3-3486 | A-329 | B-8 |
| n3-3487 | A-330 | B-8 |
| n3-3488 | A-331 | B-8 |
| n3-3489 | A-332 | B-8 |
| n3-3490 | A-333 | B-8 |
| n3-3491 | A-334 | B-8 |
| n3-3492 | A-335 | B-8 |
| n3-3493 | A-336 | B-8 |
| n3-3494 | A-337 | B-8 |
| n3-3495 | A-338 | B-8 |
| n3-3496 | A-339 | B-8 |
| n3-3497 | A-340 | B-8 |
| n3-3498 | A-341 | B-8 |
| n3-3499 | A-342 | B-8 |
| n3-3500 | A-343 | B-8 |
| n3-3501 | A-344 | B-8 |
| n3-3502 | A-345 | B-8 |
| n3-3503 | A-346 | B-8 |
| n3-3504 | A-347 | B-8 |
| n3-3505 | A-348 | B-8 |
| n3-3506 | A-349 | B-8 |
| n3-3507 | A-350 | B-8 |
| n3-3508 | A-351 | B-8 |
| n3-3509 | A-352 | B-8 |
| n3-3510 | A-353 | B-8 |
| n3-3511 | A-354 | B-8 |
| n3-3512 | A-355 | B-8 |
| n3-3513 | A-356 | B-8 |
| n3-3514 | A-357 | B-8 |
| n3-3515 | A-358 | B-8 |
| n3-3516 | A-359 | B-8 |
| n3-3517 | A-360 | B-8 |
| n3-3518 | A-361 | B-8 |
| n3-3519 | A-362 | B-8 |
| n3-3520 | A-363 | B-8 |
| n3-3521 | A-364 | B-8 |
| n3-3522 | A-365 | B-8 |
| n3-3523 | A-366 | B-8 |
| n3-3524 | A-367 | B-8 |
| n3-3525 | A-368 | B-8 |
| n3-3526 | A-369 | B-8 |
| n3-3527 | A-370 | B-8 |
| n3-3528 | A-371 | B-8 |
| n3-3529 | A-372 | B-8 |
| n3-3530 | A-373 | B-8 |
| n3-3531 | A-374 | B-8 |
| n3-3532 | A-375 | B-8 |
| n3-3533 | A-376 | B-8 |
| n3-3534 | A-377 | B-8 |
| n3-3535 | A-378 | B-8 |
| n3-3536 | A-379 | B-8 |
| n3-3537 | A-380 | B-8 |
| n3-3538 | A-381 | B-8 |
| n3-3539 | A-382 | B-8 |
| n3-3540 | A-383 | B-8 |
| n3-3541 | A-384 | B-8 |
| n3-3542 | A-385 | B-8 |
| n3-3543 | A-386 | B-8 |
| n3-3544 | A-387 | B-8 |
| n3-3545 | A-388 | B-8 |
| n3-3546 | A-389 | B-8 |
| n3-3547 | A-390 | B-8 |
| n3-3548 | A-391 | B-8 |
| n3-3549 | A-392 | B-8 |
| n3-3550 | A-393 | B-8 |
| n3-3551 | A-394 | B-8 |
| n3-3552 | A-395 | B-8 |
| n3-3553 | A-396 | B-8 |
| n3-3554 | A-397 | B-8 |
| n3-3555 | A-398 | B-8 |
| n3-3556 | A-399 | B-8 |
| n3-3557 | A-400 | B-8 |
| n3-3558 | A-401 | B-8 |
| n3-3559 | A-402 | B-8 |
| n3-3560 | A-403 | B-8 |
| n3-3561 | A-404 | B-8 |
| n3-3562 | A-405 | B-8 |
| n3-3563 | A-406 | B-8 |
| n3-3564 | A-407 | B-8 |
| n3-3565 | A-408 | B-8 |
| n3-3566 | A-409 | B-8 |
| n3-3567 | A-410 | B-8 |
| n3-3568 | A-411 | B-8 |
| n3-3569 | A-412 | B-8 |
| n3-3570 | A-413 | B-8 |
| n3-3571 | A-414 | B-8 |
| n3-3572 | A-415 | B-8 |
| n3-3573 | A-416 | B-8 |
| n3-3574 | A-417 | B-8 |
| n3-3575 | A-418 | B-8 |
| n3-3576 | A-419 | B-8 |
| n3-3577 | A-420 | B-8 |
| n3-3578 | A-421 | B-8 |
| n3-3579 | A-422 | B-8 |
| n3-3580 | A-423 | B-8 |
| n3-3581 | A-424 | B-8 |
| n3-3582 | A-425 | B-8 |
| n3-3583 | A-426 | B-8 |
| n3-3584 | A-427 | B-8 |
| n3-3585 | A-428 | B-8 |
| n3-3586 | A-429 | B-8 |
| n3-3587 | A-430 | B-8 |

TABLE 1-continued

| epn | n = 3 A | B |
|---|---|---|
| n3-3588 | A-431 | B-8 |
| n3-3589 | A-432 | B-8 |
| n3-3590 | A-433 | B-8 |
| n3-3591 | A-434 | B-8 |
| n3-3592 | A-435 | B-8 |
| n3-3593 | A-436 | B-8 |
| n3-3594 | A-437 | B-8 |
| n3-3595 | A-438 | B-8 |
| n3-3596 | A-439 | B-8 |
| n3-3597 | A-440 | B-8 |
| n3-3598 | A-441 | B-8 |
| n3-3599 | A-442 | B-8 |
| n3-3600 | A-443 | B-8 |
| n3-3601 | A-444 | B-8 |
| n3-3602 | A-445 | B-8 |
| n3-3603 | A-446 | B-8 |
| n3-3604 | A-447 | B-8 |
| n3-3605 | A-448 | B-8 |
| n3-3606 | A-449 | B-8 |
| n3-3607 | A-450 | B-8 |
| n3-3608 | A-451 | B-8 |
| n3-3609 | A-1 | B-9 |
| n3-3610 | A-2 | B-9 |
| n3-3611 | A-3 | B-9 |
| n3-3612 | A-4 | B-9 |
| n3-3613 | A-5 | B-9 |
| n3-3614 | A-6 | B-9 |
| n3-3615 | A-7 | B-9 |
| n3-3616 | A-8 | B-9 |
| n3-3617 | A-9 | B-9 |
| n3-3618 | A-10 | B-9 |
| n3-3619 | A-11 | B-9 |
| n3-3620 | A-12 | B-9 |
| n3-3621 | A-13 | B-9 |
| n3-3622 | A-14 | B-9 |
| n3-3623 | A-15 | B-9 |
| n3-3624 | A-16 | B-9 |
| n3-3625 | A-17 | B-9 |
| n3-3626 | A-18 | B-9 |
| n3-3627 | A-19 | B-9 |
| n3-3628 | A-20 | B-9 |
| n3-3629 | A-21 | B-9 |
| n3-3630 | A-22 | B-9 |
| n3-3631 | A-23 | B-9 |
| n3-3632 | A-24 | B-9 |
| n3-3633 | A-25 | B-9 |
| n3-3634 | A-26 | B-9 |
| n3-3635 | A-27 | B-9 |
| n3-3636 | A-28 | B-9 |
| n3-3637 | A-29 | B-9 |
| n3-3638 | A-30 | B-9 |
| n3-3639 | A-31 | B-9 |
| n3-3640 | A-32 | B-9 |
| n3-3641 | A-33 | B-9 |
| n3-3642 | A-34 | B-9 |
| n3-3643 | A-35 | B-9 |
| n3-3644 | A-36 | B-9 |
| n3-3645 | A-37 | B-9 |
| n3-3646 | A-38 | B-9 |
| n3-3647 | A-39 | B-9 |
| n3-3648 | A-40 | B-9 |
| n3-3649 | A-41 | B-9 |
| n3-3650 | A-42 | B-9 |
| n3-3651 | A-43 | B-9 |
| n3-3652 | A-44 | B-9 |
| n3-3653 | A-45 | B-9 |
| n3-3654 | A-46 | B-9 |
| n3-3655 | A-47 | B-9 |
| n3-3656 | A-48 | B-9 |
| n3-3657 | A-49 | B-9 |
| n3-3658 | A-50 | B-9 |
| n3-3659 | A-51 | B-9 |
| n3-3660 | A-52 | B-9 |
| n3-3661 | A-53 | B-9 |
| n3-3662 | A-54 | B-9 |
| n3-3663 | A-55 | B-9 |
| n3-3664 | A-56 | B-9 |
| n3-3665 | A-57 | B-9 |
| n3-3666 | A-58 | B-9 |
| n3-3667 | A-59 | B-9 |
| n3-3668 | A-60 | B-9 |
| n3-3669 | A-61 | B-9 |
| n3-3670 | A-62 | B-9 |
| n3-3671 | A-63 | B-9 |
| n3-3672 | A-64 | B-9 |
| n3-3673 | A-65 | B-9 |
| n3-3674 | A-66 | B-9 |
| n3-3675 | A-67 | B-9 |
| n3-3676 | A-68 | B-9 |
| n3-3677 | A-69 | B-9 |
| n3-3678 | A-70 | B-9 |
| n3-3679 | A-71 | B-9 |
| n3-3680 | A-72 | B-9 |
| n3-3681 | A-73 | B-9 |
| n3-3682 | A-74 | B-9 |
| n3-3683 | A-75 | B-9 |
| n3-3684 | A-76 | B-9 |
| n3-3685 | A-77 | B-9 |
| n3-3686 | A-78 | B-9 |
| n3-3687 | A-79 | B-9 |
| n3-3688 | A-80 | B-9 |
| n3-3689 | A-81 | B-9 |
| n3-3690 | A-82 | B-9 |
| n3-3691 | A-83 | B-9 |
| n3-3692 | A-84 | B-9 |
| n3-3693 | A-85 | B-9 |
| n3-3694 | A-86 | B-9 |
| n3-3695 | A-87 | B-9 |
| n3-3696 | A-88 | B-9 |
| n3-3697 | A-89 | B-9 |
| n3-3698 | A-90 | B-9 |
| n3-3699 | A-91 | B-9 |
| n3-3700 | A-92 | B-9 |
| n3-3701 | A-93 | B-9 |
| n3-3702 | A-94 | B-9 |
| n3-3703 | A-95 | B-9 |
| n3-3704 | A-96 | B-9 |
| n3-3705 | A-97 | B-9 |
| n3-3706 | A-98 | B-9 |
| n3-3707 | A-99 | B-9 |
| n3-3708 | A-100 | B-9 |
| n3-3709 | A-101 | B-9 |
| n3-3710 | A-102 | B-9 |
| n3-3711 | A-103 | B-9 |
| n3-3712 | A-104 | B-9 |
| n3-3713 | A-105 | B-9 |
| n3-3714 | A-106 | B-9 |
| n3-3715 | A-107 | B-9 |
| n3-3716 | A-108 | B-9 |
| n3-3717 | A-109 | B-9 |
| n3-3718 | A-110 | B-9 |
| n3-3719 | A-111 | B-9 |
| n3-3720 | A-112 | B-9 |
| n3-3721 | A-113 | B-9 |
| n3-3722 | A-114 | B-9 |
| n3-3723 | A-115 | B-9 |
| n3-3724 | A-116 | B-9 |
| n3-3725 | A-117 | B-9 |
| n3-3726 | A-118 | B-9 |
| n3-3727 | A-119 | B-9 |
| n3-3728 | A-120 | B-9 |
| n3-3729 | A-121 | B-9 |
| n3-3730 | A-122 | B-9 |
| n3-3731 | A-123 | B-9 |
| n3-3732 | A-124 | B-9 |
| n3-3733 | A-125 | B-9 |
| n3-3734 | A-126 | B-9 |
| n3-3735 | A-127 | B-9 |
| n3-3736 | A-128 | B-9 |
| n3-3737 | A-129 | B-9 |

TABLE 1-continued

| epn | n = 3 A | B |
|---|---|---|
| n3-3738 | A-130 | B-9 |
| n3-3739 | A-131 | B-9 |
| n3-3740 | A-132 | B-9 |
| n3-3741 | A-133 | B-9 |
| n3-3742 | A-134 | B-9 |
| n3-3743 | A-135 | B-9 |
| n3-3744 | A-136 | B-9 |
| n3-3745 | A-137 | B-9 |
| n3-3746 | A-138 | B-9 |
| n3-3747 | A-139 | B-9 |
| n3-3748 | A-140 | B-9 |
| n3-3749 | A-141 | B-9 |
| n3-3750 | A-142 | B-9 |
| n3-3751 | A-143 | B-9 |
| n3-3752 | A-144 | B-9 |
| n3-3753 | A-145 | B-9 |
| n3-3754 | A-146 | B-9 |
| n3-3755 | A-147 | B-9 |
| n3-3756 | A-148 | B-9 |
| n3-3757 | A-149 | B-9 |
| n3-3758 | A-150 | B-9 |
| n3-3759 | A-151 | B-9 |
| n3-3760 | A-152 | B-9 |
| n3-3761 | A-153 | B-9 |
| n3-3762 | A-154 | B-9 |
| n3-3763 | A-155 | B-9 |
| n3-3764 | A-156 | B-9 |
| n3-3765 | A-157 | B-9 |
| n3-3766 | A-158 | B-9 |
| n3-3767 | A-159 | B-9 |
| n3-3768 | A-160 | B-9 |
| n3-3769 | A-161 | B-9 |
| n3-3770 | A-162 | B-9 |
| n3-3771 | A-163 | B-9 |
| n3-3772 | A-164 | B-9 |
| n3-3773 | A-165 | B-9 |
| n3-3774 | A-166 | B-9 |
| n3-3775 | A-167 | B-9 |
| n3-3776 | A-168 | B-9 |
| n3-3777 | A-169 | B-9 |
| n3-3778 | A-170 | B-9 |
| n3-3779 | A-171 | B-9 |
| n3-3780 | A-172 | B-9 |
| n3-3781 | A-173 | B-9 |
| n3-3782 | A-174 | B-9 |
| n3-3783 | A-175 | B-9 |
| n3-3784 | A-176 | B-9 |
| n3-3785 | A-177 | B-9 |
| n3-3786 | A-178 | B-9 |
| n3-3787 | A-179 | B-9 |
| n3-3788 | A-180 | B-9 |
| n3-3789 | A-181 | B-9 |
| n3-3790 | A-182 | B-9 |
| n3-3791 | A-183 | B-9 |
| n3-3792 | A-184 | B-9 |
| n3-3793 | A-185 | B-9 |
| n3-3794 | A-186 | B-9 |
| n3-3795 | A-187 | B-9 |
| n3-3796 | A-188 | B-9 |
| n3-3797 | A-189 | B-9 |
| n3-3798 | A-190 | B-9 |
| n3-3799 | A-191 | B-9 |
| n3-3800 | A-192 | B-9 |
| n3-3801 | A-193 | B-9 |
| n3-3802 | A-194 | B-9 |
| n3-3803 | A-195 | B-9 |
| n3-3804 | A-196 | B-9 |
| n3-3805 | A-197 | B-9 |
| n3-3806 | A-198 | B-9 |
| n3-3807 | A-199 | B-9 |
| n3-3808 | A-200 | B-9 |
| n3-3809 | A-201 | B-9 |
| n3-3810 | A-202 | B-9 |
| n3-3811 | A-203 | B-9 |
| n3-3812 | A-204 | B-9 |
| n3-3813 | A-205 | B-9 |
| n3-3814 | A-206 | B-9 |
| n3-3815 | A-207 | B-9 |
| n3-3816 | A-208 | B-9 |
| n3-3817 | A-209 | B-9 |
| n3-3818 | A-210 | B-9 |
| n3-3819 | A-211 | B-9 |
| n3-3820 | A-212 | B-9 |
| n3-3821 | A-213 | B-9 |
| n3-3822 | A-214 | B-9 |
| n3-3823 | A-215 | B-9 |
| n3-3824 | A-216 | B-9 |
| n3-3825 | A-217 | B-9 |
| n3-3826 | A-218 | B-9 |
| n3-3827 | A-219 | B-9 |
| n3-3828 | A-220 | B-9 |
| n3-3829 | A-221 | B-9 |
| n3-3830 | A-222 | B-9 |
| n3-3831 | A-223 | B-9 |
| n3-3832 | A-224 | B-9 |
| n3-3833 | A-225 | B-9 |
| n3-3834 | A-226 | B-9 |
| n3-3835 | A-227 | B-9 |
| n3-3836 | A-228 | B-9 |
| n3-3837 | A-229 | B-9 |
| n3-3838 | A-230 | B-9 |
| n3-3839 | A-231 | B-9 |
| n3-3840 | A-232 | B-9 |
| n3-3841 | A-233 | B-9 |
| n3-3842 | A-234 | B-9 |
| n3-3843 | A-235 | B-9 |
| n3-3844 | A-236 | B-9 |
| n3-3845 | A-237 | B-9 |
| n3-3846 | A-238 | B-9 |
| n3-3847 | A-239 | B-9 |
| n3-3848 | A-240 | B-9 |
| n3-3849 | A-241 | B-9 |
| n3-3850 | A-242 | B-9 |
| n3-3851 | A-243 | B-9 |
| n3-3852 | A-244 | B-9 |
| n3-3853 | A-245 | B-9 |
| n3-3854 | A-246 | B-9 |
| n3-3855 | A-247 | B-9 |
| n3-3856 | A-248 | B-9 |
| n3-3857 | A-249 | B-9 |
| n3-3858 | A-250 | B-9 |
| n3-3859 | A-251 | B-9 |
| n3-3860 | A-252 | B-9 |
| n3-3861 | A-253 | B-9 |
| n3-3862 | A-254 | B-9 |
| n3-3863 | A-255 | B-9 |
| n3-3864 | A-256 | B-9 |
| n3-3865 | A-257 | B-9 |
| n3-3866 | A-258 | B-9 |
| n3-3867 | A-259 | B-9 |
| n3-3868 | A-260 | B-9 |
| n3-3869 | A-261 | B-9 |
| n3-3870 | A-262 | B-9 |
| n3-3871 | A-263 | B-9 |
| n3-3872 | A-264 | B-9 |
| n3-3873 | A-265 | B-9 |
| n3-3874 | A-266 | B-9 |
| n3-3875 | A-267 | B-9 |
| n3-3876 | A-268 | B-9 |
| n3-3877 | A-269 | B-9 |
| n3-3878 | A-270 | B-9 |
| n3-3879 | A-271 | B-9 |
| n3-3880 | A-272 | B-9 |
| n3-3881 | A-273 | B-9 |
| n3-3882 | A-274 | B-9 |
| n3-3883 | A-275 | B-9 |
| n3-3884 | A-276 | B-9 |
| n3-3885 | A-277 | B-9 |
| n3-3886 | A-278 | B-9 |
| n3-3887 | A-279 | B-9 |

TABLE 1-continued

| epn | n = 3 A | B |
|---|---|---|
| n3-3888 | A-280 | B-9 |
| n3-3889 | A-281 | B-9 |
| n3-3890 | A-282 | B-9 |
| n3-3891 | A-283 | B-9 |
| n3-3892 | A-284 | B-9 |
| n3-3893 | A-285 | B-9 |
| n3-3894 | A-286 | B-9 |
| n3-3895 | A-287 | B-9 |
| n3-3896 | A-288 | B-9 |
| n3-3897 | A-289 | B-9 |
| n3-3898 | A-290 | B-9 |
| n3-3899 | A-291 | B-9 |
| n3-3900 | A-292 | B-9 |
| n3-3901 | A-293 | B-9 |
| n3-3902 | A-294 | B-9 |
| n3-3903 | A-295 | B-9 |
| n3-3904 | A-296 | B-9 |
| n3-3905 | A-297 | B-9 |
| n3-3906 | A-298 | B-9 |
| n3-3907 | A-299 | B-9 |
| n3-3908 | A-300 | B-9 |
| n3-3909 | A-301 | B-9 |
| n3-3910 | A-302 | B-9 |
| n3-3911 | A-303 | B-9 |
| n3-3912 | A-304 | B-9 |
| n3-3913 | A-305 | B-9 |
| n3-3914 | A-306 | B-9 |
| n3-3915 | A-307 | B-9 |
| n3-3916 | A-308 | B-9 |
| n3-3917 | A-309 | B-9 |
| n3-3918 | A-310 | B-9 |
| n3-3919 | A-311 | B-9 |
| n3-3920 | A-312 | B-9 |
| n3-3921 | A-313 | B-9 |
| n3-3922 | A-314 | B-9 |
| n3-3923 | A-315 | B-9 |
| n3-3924 | A-316 | B-9 |
| n3-3925 | A-317 | B-9 |
| n3-3926 | A-318 | B-9 |
| n3-3927 | A-319 | B-9 |
| n3-3928 | A-320 | B-9 |
| n3-3929 | A-321 | B-9 |
| n3-3930 | A-322 | B-9 |
| n3-3931 | A-323 | B-9 |
| n3-3932 | A-324 | B-9 |
| n3-3933 | A-325 | B-9 |
| n3-3934 | A-326 | B-9 |
| n3-3935 | A-327 | B-9 |
| n3-3936 | A-328 | B-9 |
| n3-3937 | A-329 | B-9 |
| n3-3938 | A-330 | B-9 |
| n3-3939 | A-331 | B-9 |
| n3-3940 | A-332 | B-9 |
| n3-3941 | A-333 | B-9 |
| n3-3942 | A-334 | B-9 |
| n3-3943 | A-335 | B-9 |
| n3-3944 | A-336 | B-9 |
| n3-3945 | A-337 | B-9 |
| n3-3946 | A-338 | B-9 |
| n3-3947 | A-339 | B-9 |
| n3-3948 | A-340 | B-9 |
| n3-3949 | A-341 | B-9 |
| n3-3950 | A-342 | B-9 |
| n3-3951 | A-343 | B-9 |
| n3-3952 | A-344 | B-9 |
| n3-3953 | A-345 | B-9 |
| n3-3954 | A-346 | B-9 |
| n3-3955 | A-347 | B-9 |
| n3-3956 | A-348 | B-9 |
| n3-3957 | A-349 | B-9 |
| n3-3958 | A-350 | B-9 |
| n3-3959 | A-351 | B-9 |
| n3-3960 | A-352 | B-9 |
| n3-3961 | A-353 | B-9 |
| n3-3962 | A-354 | B-9 |
| n3-3963 | A-355 | B-9 |
| n3-3964 | A-356 | B-9 |
| n3-3965 | A-357 | B-9 |
| n3-3966 | A-358 | B-9 |
| n3-3967 | A-359 | B-9 |
| n3-3968 | A-360 | B-9 |
| n3-3969 | A-361 | B-9 |
| n3-3970 | A-362 | B-9 |
| n3-3971 | A-363 | B-9 |
| n3-3972 | A-364 | B-9 |
| n3-3973 | A-365 | B-9 |
| n3-3974 | A-366 | B-9 |
| n3-3975 | A-367 | B-9 |
| n3-3976 | A-368 | B-9 |
| n3-3977 | A-369 | B-9 |
| n3-3978 | A-370 | B-9 |
| n3-3979 | A-371 | B-9 |
| n3-3980 | A-372 | B-9 |
| n3-3981 | A-373 | B-9 |
| n3-3982 | A-374 | B-9 |
| n3-3983 | A-375 | B-9 |
| n3-3984 | A-376 | B-9 |
| n3-3985 | A-377 | B-9 |
| n3-3986 | A-378 | B-9 |
| n3-3987 | A-379 | B-9 |
| n3-3988 | A-380 | B-9 |
| n3-3989 | A-381 | B-9 |
| n3-3990 | A-382 | B-9 |
| n3-3991 | A-383 | B-9 |
| n3-3992 | A-384 | B-9 |
| n3-3993 | A-385 | B-9 |
| n3-3994 | A-386 | B-9 |
| n3-3995 | A-387 | B-9 |
| n3-3996 | A-388 | B-9 |
| n3-3997 | A-389 | B-9 |
| n3-3998 | A-390 | B-9 |
| n3-3999 | A-391 | B-9 |
| n3-4000 | A-392 | B-9 |
| n3-4001 | A-393 | B-9 |
| n3-4002 | A-394 | B-9 |
| n3-4003 | A-395 | B-9 |
| n3-4004 | A-396 | B-9 |
| n3-4005 | A-397 | B-9 |
| n3-4006 | A-398 | B-9 |
| n3-4007 | A-399 | B-9 |
| n3-4008 | A-400 | B-9 |
| n3-4009 | A-401 | B-9 |
| n3-4010 | A-402 | B-9 |
| n3-4011 | A-403 | B-9 |
| n3-4012 | A-404 | B-9 |
| n3-4013 | A-405 | B-9 |
| n3-4014 | A-406 | B-9 |
| n3-4015 | A-407 | B-9 |
| n3-4016 | A-408 | B-9 |
| n3-4017 | A-409 | B-9 |
| n3-4018 | A-410 | B-9 |
| n3-4019 | A-411 | B-9 |
| n3-4020 | A-412 | B-9 |
| n3-4021 | A-413 | B-9 |
| n3-4022 | A-414 | B-9 |
| n3-4023 | A-415 | B-9 |
| n3-4024 | A-416 | B-9 |
| n3-4025 | A-417 | B-9 |
| n3-4026 | A-418 | B-9 |
| n3-4027 | A-419 | B-9 |
| n3-4028 | A-420 | B-9 |
| n3-4029 | A-421 | B-9 |
| n3-4030 | A-422 | B-9 |
| n3-4031 | A-423 | B-9 |
| n3-4032 | A-424 | B-9 |
| n3-4033 | A-425 | B-9 |
| n3-4034 | A-426 | B-9 |
| n3-4035 | A-427 | B-9 |
| n3-4036 | A-428 | B-9 |
| n3-4037 | A-429 | B-9 |

TABLE 1-continued

| | n = 3 | |
|---|---|---|
| epn | A | B |
| n3-4038 | A-430 | B-9 |
| n3-4039 | A-431 | B-9 |
| n3-4040 | A-432 | B-9 |
| n3-4041 | A-433 | B-9 |
| n3-4042 | A-434 | B-9 |
| n3-4043 | A-435 | B-9 |
| n3-4044 | A-436 | B-9 |
| n3-4045 | A-437 | B-9 |
| n3-4046 | A-438 | B-9 |
| n3-4047 | A-439 | B-9 |
| n3-4048 | A-440 | B-9 |
| n3-4049 | A-441 | B-9 |
| n3-4050 | A-442 | B-9 |
| n3-4051 | A-443 | B-9 |
| n3-4052 | A-444 | B-9 |
| n3-4053 | A-445 | B-9 |
| n3-4054 | A-446 | B-9 |
| n3-4055 | A-447 | B-9 |
| n3-4056 | A-448 | B-9 |
| n3-4057 | A-449 | B-9 |
| n3-4058 | A-450 | B-9 |
| n3-4059 | A-451 | B-9 |
| n3-4060 | A-1 | B-10 |
| n3-4061 | A-2 | B-10 |
| n3-4062 | A-3 | B-10 |
| n3-4063 | A-4 | B-10 |
| n3-4064 | A-5 | B-10 |
| n3-4065 | A-6 | B-10 |
| n3-4066 | A-7 | B-10 |
| n3-4067 | A-8 | B-10 |
| n3-4068 | A-9 | B-10 |
| n3-4069 | A-10 | B-10 |
| n3-4070 | A-11 | B-10 |
| n3-4071 | A-12 | B-10 |
| n3-4072 | A-13 | B-10 |
| n3-4073 | A-14 | B-10 |
| n3-4074 | A-15 | B-10 |
| n3-4075 | A-16 | B-10 |
| n3-4076 | A-17 | B-10 |
| n3-4077 | A-18 | B-10 |
| n3-4078 | A-19 | B-10 |
| n3-4079 | A-20 | B-10 |
| n3-4080 | A-21 | B-10 |
| n3-4081 | A-22 | B-10 |
| n3-4082 | A-23 | B-10 |
| n3-4083 | A-24 | B-10 |
| n3-4084 | A-25 | B-10 |
| n3-4085 | A-26 | B-10 |
| n3-4086 | A-27 | B-10 |
| n3-4087 | A-28 | B-10 |
| n3-4088 | A-29 | B-10 |
| n3-4089 | A-30 | B-10 |
| n3-4090 | A-31 | B-10 |
| n3-4091 | A-32 | B-10 |
| n3-4092 | A-33 | B-10 |
| n3-4093 | A-34 | B-10 |
| n3-4094 | A-35 | B-10 |
| n3-4095 | A-36 | B-10 |
| n3-4096 | A-37 | B-10 |
| n3-4097 | A-38 | B-10 |
| n3-4098 | A-39 | B-10 |
| n3-4099 | A-40 | B-10 |
| n3-4100 | A-41 | B-10 |
| n3-4101 | A-42 | B-10 |
| n3-4102 | A-43 | B-10 |
| n3-4103 | A-44 | B-10 |
| n3-4104 | A-45 | B-10 |
| n3-4105 | A-46 | B-10 |
| n3-4106 | A-47 | B-10 |
| n3-4107 | A-48 | B-10 |
| n3-4108 | A-49 | B-10 |
| n3-4109 | A-50 | B-10 |
| n3-4110 | A-51 | B-10 |
| n3-4111 | A-52 | B-10 |
| n3-4112 | A-53 | B-10 |
| n3-4113 | A-54 | B-10 |
| n3-4114 | A-55 | B-10 |
| n3-4115 | A-56 | B-10 |
| n3-4116 | A-57 | B-10 |
| n3-4117 | A-58 | B-10 |
| n3-4118 | A-59 | B-10 |
| n3-4119 | A-60 | B-10 |
| n3-4120 | A-61 | B-10 |
| n3-4121 | A-62 | B-10 |
| n3-4122 | A-63 | B-10 |
| n3-4123 | A-64 | B-10 |
| n3-4124 | A-65 | B-10 |
| n3-4125 | A-66 | B-10 |
| n3-4126 | A-67 | B-10 |
| n3-4127 | A-68 | B-10 |
| n3-4128 | A-69 | B-10 |
| n3-4129 | A-70 | B-10 |
| n3-4130 | A-71 | B-10 |
| n3-4131 | A-72 | B-10 |
| n3-4132 | A-73 | B-10 |
| n3-4133 | A-74 | B-10 |
| n3-4134 | A-75 | B-10 |
| n3-4135 | A-76 | B-10 |
| n3-4136 | A-77 | B-10 |
| n3-4137 | A-78 | B-10 |
| n3-4138 | A-79 | B-10 |
| n3-4139 | A-80 | B-10 |
| n3-4140 | A-81 | B-10 |
| n3-4141 | A-82 | B-10 |
| n3-4142 | A-83 | B-10 |
| n3-4143 | A-84 | B-10 |
| n3-4144 | A-85 | B-10 |
| n3-4145 | A-86 | B-10 |
| n3-4146 | A-87 | B-10 |
| n3-4147 | A-88 | B-10 |
| n3-4148 | A-89 | B-10 |
| n3-4149 | A-90 | B-10 |
| n3-4150 | A-91 | B-10 |
| n3-4151 | A-92 | B-10 |
| n3-4152 | A-93 | B-10 |
| n3-4153 | A-94 | B-10 |
| n3-4154 | A-95 | B-10 |
| n3-4155 | A-96 | B-10 |
| n3-4156 | A-97 | B-10 |
| n3-4157 | A-98 | B-10 |
| n3-4158 | A-99 | B-10 |
| n3-4159 | A-100 | B-10 |
| n3-4160 | A-101 | B-10 |
| n3-4161 | A-102 | B-10 |
| n3-4162 | A-103 | B-10 |
| n3-4163 | A-104 | B-10 |
| n3-4164 | A-105 | B-10 |
| n3-4165 | A-106 | B-10 |
| n3-4166 | A-107 | B-10 |
| n3-4167 | A-108 | B-10 |
| n3-4168 | A-109 | B-10 |
| n3-4169 | A-110 | B-10 |
| n3-4170 | A-111 | B-10 |
| n3-4171 | A-112 | B-10 |
| n3-4172 | A-113 | B-10 |
| n3-4173 | A-114 | B-10 |
| n3-4174 | A-115 | B-10 |
| n3-4175 | A-116 | B-10 |
| n3-4176 | A-117 | B-10 |
| n3-4177 | A-118 | B-10 |
| n3-4178 | A-119 | B-10 |
| n3-4179 | A-120 | B-10 |
| n3-4180 | A-121 | B-10 |
| n3-4181 | A-122 | B-10 |
| n3-4182 | A-123 | B-10 |
| n3-4183 | A-124 | B-10 |
| n3-4184 | A-125 | B-10 |
| n3-4185 | A-126 | B-10 |
| n3-4186 | A-127 | B-10 |
| n3-4187 | A-128 | B-10 |

TABLE 1-continued

| | n = 3 | |
|---|---|---|
| epn | A | B |
| n3-4188 | A-129 | B-10 |
| n3-4189 | A-130 | B-10 |
| n3-4190 | A-131 | B-10 |
| n3-4191 | A-132 | B-10 |
| n3-4192 | A-133 | B-10 |
| n3-4193 | A-134 | B-10 |
| n3-4194 | A-135 | B-10 |
| n3-4195 | A-136 | B-10 |
| n3-4196 | A-137 | B-10 |
| n3-4197 | A-138 | B-10 |
| n3-4198 | A-139 | B-10 |
| n3-4199 | A-140 | B-10 |
| n3-4200 | A-141 | B-10 |
| n3-4201 | A-142 | B-10 |
| n3-4202 | A-143 | B-10 |
| n3-4203 | A-144 | B-10 |
| n3-4204 | A-145 | B-10 |
| n3-4205 | A-146 | B-10 |
| n3-4206 | A-147 | B-10 |
| n3-4207 | A-148 | B-10 |
| n3-4208 | A-149 | B-10 |
| n3-4209 | A-150 | B-10 |
| n3-4210 | A-151 | B-10 |
| n3-4211 | A-152 | B-10 |
| n3-4212 | A-153 | B-10 |
| n3-4213 | A-154 | B-10 |
| n3-4214 | A-155 | B-10 |
| n3-4215 | A-156 | B-10 |
| n3-4216 | A-157 | B-10 |
| n3-4217 | A-158 | B-10 |
| n3-4218 | A-159 | B-10 |
| n3-4219 | A-160 | B-10 |
| n3-4220 | A-161 | B-10 |
| n3-4221 | A-162 | B-10 |
| n3-4222 | A-163 | B-10 |
| n3-4223 | A-164 | B-10 |
| n3-4224 | A-165 | B-10 |
| n3-4225 | A-166 | B-10 |
| n3-4226 | A-167 | B-10 |
| n3-4227 | A-168 | B-10 |
| n3-4228 | A-169 | B-10 |
| n3-4229 | A-170 | B-10 |
| n3-4230 | A-171 | B-10 |
| n3-4231 | A-172 | B-10 |
| n3-4232 | A-173 | B-10 |
| n3-4233 | A-174 | B-10 |
| n3-4234 | A-175 | B-10 |
| n3-4235 | A-176 | B-10 |
| n3-4236 | A-177 | B-10 |
| n3-4237 | A-178 | B-10 |
| n3-4238 | A-179 | B-10 |
| n3-4239 | A-180 | B-10 |
| n3-4240 | A-181 | B-10 |
| n3-4241 | A-182 | B-10 |
| n3-4242 | A-183 | B-10 |
| n3-4243 | A-184 | B-10 |
| n3-4244 | A-185 | B-10 |
| n3-4245 | A-186 | B-10 |
| n3-4246 | A-187 | B-10 |
| n3-4247 | A-188 | B-10 |
| n3-4248 | A-189 | B-10 |
| n3-4249 | A-190 | B-10 |
| n3-4250 | A-191 | B-10 |
| n3-4251 | A-192 | B-10 |
| n3-4252 | A-193 | B-10 |
| n3-4253 | A-194 | B-10 |
| n3-4254 | A-195 | B-10 |
| n3-4255 | A-196 | B-10 |
| n3-4256 | A-197 | B-10 |
| n3-4257 | A-198 | B-10 |
| n3-4258 | A-199 | B-10 |
| n3-4259 | A-200 | B-10 |
| n3-4260 | A-201 | B-10 |
| n3-4261 | A-202 | B-10 |
| n3-4262 | A-203 | B-10 |
| n3-4263 | A-204 | B-10 |
| n3-4264 | A-205 | B-10 |
| n3-4265 | A-206 | B-10 |
| n3-4266 | A-207 | B-10 |
| n3-4267 | A-208 | B-10 |
| n3-4268 | A-209 | B-10 |
| n3-4269 | A-210 | B-10 |
| n3-4270 | A-211 | B-10 |
| n3-4271 | A-212 | B-10 |
| n3-4272 | A-213 | B-10 |
| n3-4273 | A-214 | B-10 |
| n3-4274 | A-215 | B-10 |
| n3-4275 | A-216 | B-10 |
| n3-4276 | A-217 | B-10 |
| n3-4277 | A-218 | B-10 |
| n3-4278 | A-219 | B-10 |
| n3-4279 | A-220 | B-10 |
| n3-4280 | A-221 | B-10 |
| n3-4281 | A-222 | B-10 |
| n3-4282 | A-223 | B-10 |
| n3-4283 | A-224 | B-10 |
| n3-4284 | A-225 | B-10 |
| n3-4285 | A-226 | B-10 |
| n3-4286 | A-227 | B-10 |
| n3-4287 | A-228 | B-10 |
| n3-4288 | A-229 | B-10 |
| n3-4289 | A-230 | B-10 |
| n3-4290 | A-231 | B-10 |
| n3-4291 | A-232 | B-10 |
| n3-4292 | A-233 | B-10 |
| n3-4293 | A-234 | B-10 |
| n3-4294 | A-235 | B-10 |
| n3-4295 | A-236 | B-10 |
| n3-4296 | A-237 | B-10 |
| n3-4297 | A-238 | B-10 |
| n3-4298 | A-239 | B-10 |
| n3-4299 | A-240 | B-10 |
| n3-4300 | A-241 | B-10 |
| n3-4301 | A-242 | B-10 |
| n3-4302 | A-243 | B-10 |
| n3-4303 | A-244 | B-10 |
| n3-4304 | A-245 | B-10 |
| n3-4305 | A-246 | B-10 |
| n3-4306 | A-247 | B-10 |
| n3-4307 | A-248 | B-10 |
| n3-4308 | A-249 | B-10 |
| n3-4309 | A-250 | B-10 |
| n3-4310 | A-251 | B-10 |
| n3-4311 | A-252 | B-10 |
| n3-4312 | A-253 | B-10 |
| n3-4313 | A-254 | B-10 |
| n3-4314 | A-255 | B-10 |
| n3-4315 | A-256 | B-10 |
| n3-4316 | A-257 | B-10 |
| n3-4317 | A-258 | B-10 |
| n3-4318 | A-259 | B-10 |
| n3-4319 | A-260 | B-10 |
| n3-4320 | A-261 | B-10 |
| n3-4321 | A-262 | B-10 |
| n3-4322 | A-263 | B-10 |
| n3-4323 | A-264 | B-10 |
| n3-4324 | A-265 | B-10 |
| n3-4325 | A-266 | B-10 |
| n3-4326 | A-267 | B-10 |
| n3-4327 | A-268 | B-10 |
| n3-4328 | A-269 | B-10 |
| n3-4329 | A-270 | B-10 |
| n3-4330 | A-271 | B-10 |
| n3-4331 | A-272 | B-10 |
| n3-4332 | A-273 | B-10 |
| n3-4333 | A-274 | B-10 |
| n3-4334 | A-275 | B-10 |
| n3-4335 | A-276 | B-10 |
| n3-4336 | A-277 | B-10 |
| n3-4337 | A-278 | B-10 |

TABLE 1-continued

| | n = 3 | |
|---|---|---|
| epn | A | B |
| n3-4338 | A-279 | B-10 |
| n3-4339 | A-280 | B-10 |
| n3-4340 | A-281 | B-10 |
| n3-4341 | A-282 | B-10 |
| n3-4342 | A-283 | B-10 |
| n3-4343 | A-284 | B-10 |
| n3-4344 | A-285 | B-10 |
| n3-4345 | A-286 | B-10 |
| n3-4346 | A-287 | B-10 |
| n3-4347 | A-288 | B-10 |
| n3-4348 | A-289 | B-10 |
| n3-4349 | A-290 | B-10 |
| n3-4350 | A-291 | B-10 |
| n3-4351 | A-292 | B-10 |
| n3-4352 | A-293 | B-10 |
| n3-4353 | A-294 | B-10 |
| n3-4354 | A-295 | B-10 |
| n3-4355 | A-296 | B-10 |
| n3-4356 | A-297 | B-10 |
| n3-4357 | A-298 | B-10 |
| n3-4358 | A-299 | B-10 |
| n3-4359 | A-300 | B-10 |
| n3-4360 | A-301 | B-10 |
| n3-4361 | A-302 | B-10 |
| n3-4362 | A-303 | B-10 |
| n3-4363 | A-304 | B-10 |
| n3-4364 | A-305 | B-10 |
| n3-4365 | A-306 | B-10 |
| n3-4366 | A-307 | B-10 |
| n3-4367 | A-308 | B-10 |
| n3-4368 | A-309 | B-10 |
| n3-4369 | A-310 | B-10 |
| n3-4370 | A-311 | B-10 |
| n3-4371 | A-312 | B-10 |
| n3-4372 | A-313 | B-10 |
| n3-4373 | A-314 | B-10 |
| n3-4374 | A-315 | B-10 |
| n3-4375 | A-316 | B-10 |
| n3-4376 | A-317 | B-10 |
| n3-4377 | A-318 | B-10 |
| n3-4378 | A-319 | B-10 |
| n3-4379 | A-320 | B-10 |
| n3-4380 | A-321 | B-10 |
| n3-4381 | A-322 | B-10 |
| n3-4382 | A-323 | B-10 |
| n3-4383 | A-324 | B-10 |
| n3-4384 | A-325 | B-10 |
| n3-4385 | A-326 | B-10 |
| n3-4386 | A-327 | B-10 |
| n3-4387 | A-328 | B-10 |
| n3-4388 | A-329 | B-10 |
| n3-4389 | A-330 | B-10 |
| n3-4390 | A-331 | B-10 |
| n3-4391 | A-332 | B-10 |
| n3-4392 | A-333 | B-10 |
| n3-4393 | A-334 | B-10 |
| n3-4394 | A-335 | B-10 |
| n3-4395 | A-336 | B-10 |
| n3-4396 | A-337 | B-10 |
| n3-4397 | A-338 | B-10 |
| n3-4398 | A-339 | B-10 |
| n3-4399 | A-340 | B-10 |
| n3-4400 | A-341 | B-10 |
| n3-4401 | A-342 | B-10 |
| n3-4402 | A-343 | B-10 |
| n3-4403 | A-344 | B-10 |
| n3-4404 | A-345 | B-10 |
| n3-4405 | A-346 | B-10 |
| n3-4406 | A-347 | B-10 |
| n3-4407 | A-348 | B-10 |
| n3-4408 | A-349 | B-10 |
| n3-4409 | A-350 | B-10 |
| n3-4410 | A-351 | B-10 |
| n3-4411 | A-352 | B-10 |
| n3-4412 | A-353 | B-10 |
| n3-4413 | A-354 | B-10 |
| n3-4414 | A-355 | B-10 |
| n3-4415 | A-356 | B-10 |
| n3-4416 | A-357 | B-10 |
| n3-4417 | A-358 | B-10 |
| n3-4418 | A-359 | B-10 |
| n3-4419 | A-360 | B-10 |
| n3-4420 | A-361 | B-10 |
| n3-4421 | A-362 | B-10 |
| n3-4422 | A-363 | B-10 |
| n3-4423 | A-364 | B-10 |
| n3-4424 | A-365 | B-10 |
| n3-4425 | A-366 | B-10 |
| n3-4426 | A-367 | B-10 |
| n3-4427 | A-368 | B-10 |
| n3-4428 | A-369 | B-10 |
| n3-4429 | A-370 | B-10 |
| n3-4430 | A-371 | B-10 |
| n3-4431 | A-372 | B-10 |
| n3-4432 | A-373 | B-10 |
| n3-4433 | A-374 | B-10 |
| n3-4434 | A-375 | B-10 |
| n3-4435 | A-376 | B-10 |
| n3-4436 | A-377 | B-10 |
| n3-4437 | A-378 | B-10 |
| n3-4438 | A-379 | B-10 |
| n3-4439 | A-380 | B-10 |
| n3-4440 | A-381 | B-10 |
| n3-4441 | A-382 | B-10 |
| n3-4442 | A-383 | B-10 |
| n3-4443 | A-384 | B-10 |
| n3-4444 | A-385 | B-10 |
| n3-4445 | A-386 | B-10 |
| n3-4446 | A-387 | B-10 |
| n3-4447 | A-388 | B-10 |
| n3-4448 | A-389 | B-10 |
| n3-4449 | A-390 | B-10 |
| n3-4450 | A-391 | B-10 |
| n3-4451 | A-392 | B-10 |
| n3-4452 | A-393 | B-10 |
| n3-4453 | A-394 | B-10 |
| n3-4454 | A-395 | B-10 |
| n3-4455 | A-396 | B-10 |
| n3-4456 | A-397 | B-10 |
| n3-4457 | A-398 | B-10 |
| n3-4458 | A-399 | B-10 |
| n3-4459 | A-400 | B-10 |
| n3-4460 | A-401 | B-10 |
| n3-4461 | A-402 | B-10 |
| n3-4462 | A-403 | B-10 |
| n3-4463 | A-404 | B-10 |
| n3-4464 | A-405 | B-10 |
| n3-4465 | A-406 | B-10 |
| n3-4466 | A-407 | B-10 |
| n3-4467 | A-408 | B-10 |
| n3-4468 | A-409 | B-10 |
| n3-4469 | A-410 | B-10 |
| n3-4470 | A-411 | B-10 |
| n3-4471 | A-412 | B-10 |
| n3-4472 | A-413 | B-10 |
| n3-4473 | A-414 | B-10 |
| n3-4474 | A-415 | B-10 |
| n3-4475 | A-416 | B-10 |
| n3-4476 | A-417 | B-10 |
| n3-4477 | A-418 | B-10 |
| n3-4478 | A-419 | B-10 |
| n3-4479 | A-420 | B-10 |
| n3-4480 | A-421 | B-10 |
| n3-4481 | A-422 | B-10 |
| n3-4482 | A-423 | B-10 |
| n3-4483 | A-424 | B-10 |
| n3-4484 | A-425 | B-10 |
| n3-4485 | A-426 | B-10 |
| n3-4486 | A-427 | B-10 |
| n3-4487 | A-428 | B-10 |

TABLE 1-continued

| epn | n = 3 A | B |
|---|---|---|
| n3-4488 | A-429 | B-10 |
| n3-4489 | A-430 | B-10 |
| n3-4490 | A-431 | B-10 |
| n3-4491 | A-432 | B-10 |
| n3-4492 | A-433 | B-10 |
| n3-4493 | A-434 | B-10 |
| n3-4494 | A-435 | B-10 |
| n3-4495 | A-436 | B-10 |
| n3-4496 | A-437 | B-10 |
| n3-4497 | A-438 | B-10 |
| n3-4498 | A-439 | B-10 |
| n3-4499 | A-440 | B-10 |
| n3-4500 | A-441 | B-10 |
| n3-4501 | A-442 | B-10 |
| n3-4502 | A-443 | B-10 |
| n3-4503 | A-444 | B-10 |
| n3-4504 | A-445 | B-10 |
| n3-4505 | A-446 | B-10 |
| n3-4506 | A-447 | B-10 |
| n3-4507 | A-448 | B-10 |
| n3-4508 | A-449 | B-10 |
| n3-4509 | A-450 | B-10 |
| n3-4510 | A-451 | B-10 |
| n3-4511 | A-1 | B-11 |
| n3-4512 | A-2 | B-11 |
| n3-4513 | A-3 | B-11 |
| n3-4514 | A-4 | B-11 |
| n3-4515 | A-5 | B-11 |
| n3-4516 | A-6 | B-11 |
| n3-4517 | A-7 | B-11 |
| n3-4518 | A-8 | B-11 |
| n3-4519 | A-9 | B-11 |
| n3-4520 | A-10 | B-11 |
| n3-4521 | A-11 | B-11 |
| n3-4522 | A-12 | B-11 |
| n3-4523 | A-13 | B-11 |
| n3-4524 | A-14 | B-11 |
| n3-4525 | A-15 | B-11 |
| n3-4526 | A-16 | B-11 |
| n3-4527 | A-17 | B-11 |
| n3-4528 | A-18 | B-11 |
| n3-4529 | A-19 | B-11 |
| n3-4530 | A-20 | B-11 |
| n3-4531 | A-21 | B-11 |
| n3-4532 | A-22 | B-11 |
| n3-4533 | A-23 | B-11 |
| n3-4534 | A-24 | B-11 |
| n3-4535 | A-25 | B-11 |
| n3-4536 | A-26 | B-11 |
| n3-4537 | A-27 | B-11 |
| n3-4538 | A-28 | B-11 |
| n3-4539 | A-29 | B-11 |
| n3-4540 | A-30 | B-11 |
| n3-4541 | A-31 | B-11 |
| n3-4542 | A-32 | B-11 |
| n3-4543 | A-33 | B-11 |
| n3-4544 | A-34 | B-11 |
| n3-4545 | A-35 | B-11 |
| n3-4546 | A-36 | B-11 |
| n3-4547 | A-37 | B-11 |
| n3-4548 | A-38 | B-11 |
| n3-4549 | A-39 | B-11 |
| n3-4550 | A-40 | B-11 |
| n3-4551 | A-41 | B-11 |
| n3-4552 | A-42 | B-11 |
| n3-4553 | A-43 | B-11 |
| n3-4554 | A-44 | B-11 |
| n3-4555 | A-45 | B-11 |
| n3-4556 | A-46 | B-11 |
| n3-4557 | A-47 | B-11 |
| n3-4558 | A-48 | B-11 |
| n3-4559 | A-49 | B-11 |
| n3-4560 | A-50 | B-11 |
| n3-4561 | A-51 | B-11 |
| n3-4562 | A-52 | B-11 |
| n3-4563 | A-53 | B-11 |
| n3-4564 | A-54 | B-11 |
| n3-4565 | A-55 | B-11 |
| n3-4566 | A-56 | B-11 |
| n3-4567 | A-57 | B-11 |
| n3-4568 | A-58 | B-11 |
| n3-4569 | A-59 | B-11 |
| n3-4570 | A-60 | B-11 |
| n3-4571 | A-61 | B-11 |
| n3-4572 | A-62 | B-11 |
| n3-4573 | A-63 | B-11 |
| n3-4574 | A-64 | B-11 |
| n3-4575 | A-65 | B-11 |
| n3-4576 | A-66 | B-11 |
| n3-4577 | A-67 | B-11 |
| n3-4578 | A-68 | B-11 |
| n3-4579 | A-69 | B-11 |
| n3-4580 | A-70 | B-11 |
| n3-4581 | A-71 | B-11 |
| n3-4582 | A-72 | B-11 |
| n3-4583 | A-73 | B-11 |
| n3-4584 | A-74 | B-11 |
| n3-4585 | A-75 | B-11 |
| n3-4586 | A-76 | B-11 |
| n3-4587 | A-77 | B-11 |
| n3-4588 | A-78 | B-11 |
| n3-4589 | A-79 | B-11 |
| n3-4590 | A-80 | B-11 |
| n3-4591 | A-81 | B-11 |
| n3-4592 | A-82 | B-11 |
| n3-4593 | A-83 | B-11 |
| n3-4594 | A-84 | B-11 |
| n3-4595 | A-85 | B-11 |
| n3-4596 | A-86 | B-11 |
| n3-4597 | A-87 | B-11 |
| n3-4598 | A-88 | B-11 |
| n3-4599 | A-89 | B-11 |
| n3-4600 | A-90 | B-11 |
| n3-4601 | A-91 | B-11 |
| n3-4602 | A-92 | B-11 |
| n3-4603 | A-93 | B-11 |
| n3-4604 | A-94 | B-11 |
| n3-4605 | A-95 | B-11 |
| n3-4606 | A-96 | B-11 |
| n3-4607 | A-97 | B-11 |
| n3-4608 | A-98 | B-11 |
| n3-4609 | A-99 | B-11 |
| n3-4610 | A-100 | B-11 |
| n3-4611 | A-101 | B-11 |
| n3-4612 | A-102 | B-11 |
| n3-4613 | A-103 | B-11 |
| n3-4614 | A-104 | B-11 |
| n3-4615 | A-105 | B-11 |
| n3-4616 | A-106 | B-11 |
| n3-4617 | A-107 | B-11 |
| n3-4618 | A-108 | B-11 |
| n3-4619 | A-109 | B-11 |
| n3-4620 | A-110 | B-11 |
| n3-4621 | A-111 | B-11 |
| n3-4622 | A-112 | B-11 |
| n3-4623 | A-113 | B-11 |
| n3-4624 | A-114 | B-11 |
| n3-4625 | A-115 | B-11 |
| n3-4626 | A-116 | B-11 |
| n3-4627 | A-117 | B-11 |
| n3-4628 | A-118 | B-11 |
| n3-4629 | A-119 | B-11 |
| n3-4630 | A-120 | B-11 |
| n3-4631 | A-121 | B-11 |
| n3-4632 | A-122 | B-11 |
| n3-4633 | A-123 | B-11 |
| n3-4634 | A-124 | B-11 |
| n3-4635 | A-125 | B-11 |
| n3-4636 | A-126 | B-11 |
| n3-4637 | A-127 | B-11 |

TABLE 1-continued

| epn | n = 3 A | B |
|---|---|---|
| n3-4638 | A-128 | B-11 |
| n3-4639 | A-129 | B-11 |
| n3-4640 | A-130 | B-11 |
| n3-4641 | A-131 | B-11 |
| n3-4642 | A-132 | B-11 |
| n3-4643 | A-133 | B-11 |
| n3-4644 | A-134 | B-11 |
| n3-4645 | A-135 | B-11 |
| n3-4646 | A-136 | B-11 |
| n3-4647 | A-137 | B-11 |
| n3-4648 | A-138 | B-11 |
| n3-4649 | A-139 | B-11 |
| n3-4650 | A-140 | B-11 |
| n3-4651 | A-141 | B-11 |
| n3-4652 | A-142 | B-11 |
| n3-4653 | A-143 | B-11 |
| n3-4654 | A-144 | B-11 |
| n3-4655 | A-145 | B-11 |
| n3-4656 | A-146 | B-11 |
| n3-4657 | A-147 | B-11 |
| n3-4658 | A-148 | B-11 |
| n3-4659 | A-149 | B-11 |
| n3-4660 | A-150 | B-11 |
| n3-4661 | A-151 | B-11 |
| n3-4662 | A-152 | B-11 |
| n3-4663 | A-153 | B-11 |
| n3-4664 | A-154 | B-11 |
| n3-4665 | A-155 | B-11 |
| n3-4666 | A-156 | B-11 |
| n3-4667 | A-157 | B-11 |
| n3-4668 | A-158 | B-11 |
| n3-4669 | A-159 | B-11 |
| n3-4670 | A-160 | B-11 |
| n3-4671 | A-161 | B-11 |
| n3-4672 | A-162 | B-11 |
| n3-4673 | A-163 | B-11 |
| n3-4674 | A-164 | B-11 |
| n3-4675 | A-165 | B-11 |
| n3-4676 | A-166 | B-11 |
| n3-4677 | A-167 | B-11 |
| n3-4678 | A-168 | B-11 |
| n3-4679 | A-169 | B-11 |
| n3-4680 | A-170 | B-11 |
| n3-4681 | A-171 | B-11 |
| n3-4682 | A-172 | B-11 |
| n3-4683 | A-173 | B-11 |
| n3-4684 | A-174 | B-11 |
| n3-4685 | A-175 | B-11 |
| n3-4686 | A-176 | B-11 |
| n3-4687 | A-177 | B-11 |
| n3-4688 | A-178 | B-11 |
| n3-4689 | A-179 | B-11 |
| n3-4690 | A-180 | B-11 |
| n3-4691 | A-181 | B-11 |
| n3-4692 | A-182 | B-11 |
| n3-4693 | A-183 | B-11 |
| n3-4694 | A-184 | B-11 |
| n3-4695 | A-185 | B-11 |
| n3-4696 | A-186 | B-11 |
| n3-4697 | A-187 | B-11 |
| n3-4698 | A-188 | B-11 |
| n3-4699 | A-189 | B-11 |
| n3-4700 | A-190 | B-11 |
| n3-4701 | A-191 | B-11 |
| n3-4702 | A-192 | B-11 |
| n3-4703 | A-193 | B-11 |
| n3-4704 | A-194 | B-11 |
| n3-4705 | A-195 | B-11 |
| n3-4706 | A-196 | B-11 |
| n3-4707 | A-197 | B-11 |
| n3-4708 | A-198 | B-11 |
| n3-4709 | A-199 | B-11 |
| n3-4710 | A-200 | B-11 |
| n3-4711 | A-201 | B-11 |
| n3-4712 | A-202 | B-11 |
| n3-4713 | A-203 | B-11 |
| n3-4714 | A-204 | B-11 |
| n3-4715 | A-205 | B-11 |
| n3-4716 | A-206 | B-11 |
| n3-4717 | A-207 | B-11 |
| n3-4718 | A-208 | B-11 |
| n3-4719 | A-209 | B-11 |
| n3-4720 | A-210 | B-11 |
| n3-4721 | A-211 | B-11 |
| n3-4722 | A-212 | B-11 |
| n3-4723 | A-213 | B-11 |
| n3-4724 | A-214 | B-11 |
| n3-4725 | A-215 | B-11 |
| n3-4726 | A-216 | B-11 |
| n3-4727 | A-217 | B-11 |
| n3-4728 | A-218 | B-11 |
| n3-4729 | A-219 | B-11 |
| n3-4730 | A-220 | B-11 |
| n3-4731 | A-221 | B-11 |
| n3-4732 | A-222 | B-11 |
| n3-4733 | A-223 | B-11 |
| n3-4734 | A-224 | B-11 |
| n3-4735 | A-225 | B-11 |
| n3-4736 | A-226 | B-11 |
| n3-4737 | A-227 | B-11 |
| n3-4738 | A-228 | B-11 |
| n3-4739 | A-229 | B-11 |
| n3-4740 | A-230 | B-11 |
| n3-4741 | A-231 | B-11 |
| n3-4742 | A-232 | B-11 |
| n3-4743 | A-233 | B-11 |
| n3-4744 | A-234 | B-11 |
| n3-4745 | A-235 | B-11 |
| n3-4746 | A-236 | B-11 |
| n3-4747 | A-237 | B-11 |
| n3-4748 | A-238 | B-11 |
| n3-4749 | A-239 | B-11 |
| n3-4750 | A-240 | B-11 |
| n3-4751 | A-241 | B-11 |
| n3-4752 | A-242 | B-11 |
| n3-4753 | A-243 | B-11 |
| n3-4754 | A-244 | B-11 |
| n3-4755 | A-245 | B-11 |
| n3-4756 | A-246 | B-11 |
| n3-4757 | A-247 | B-11 |
| n3-4758 | A-248 | B-11 |
| n3-4759 | A-249 | B-11 |
| n3-4760 | A-250 | B-11 |
| n3-4761 | A-251 | B-11 |
| n3-4762 | A-252 | B-11 |
| n3-4763 | A-253 | B-11 |
| n3-4764 | A-254 | B-11 |
| n3-4765 | A-255 | B-11 |
| n3-4766 | A-256 | B-11 |
| n3-4767 | A-257 | B-11 |
| n3-4768 | A-258 | B-11 |
| n3-4769 | A-259 | B-11 |
| n3-4770 | A-260 | B-11 |
| n3-4771 | A-261 | B-11 |
| n3-4772 | A-262 | B-11 |
| n3-4773 | A-263 | B-11 |
| n3-4774 | A-264 | B-11 |
| n3-4775 | A-265 | B-11 |
| n3-4776 | A-266 | B-11 |
| n3-4777 | A-267 | B-11 |
| n3-4778 | A-268 | B-11 |
| n3-4779 | A-269 | B-11 |
| n3-4780 | A-270 | B-11 |
| n3-4781 | A-271 | B-11 |
| n3-4782 | A-272 | B-11 |
| n3-4783 | A-273 | B-11 |
| n3-4784 | A-274 | B-11 |
| n3-4785 | A-275 | B-11 |
| n3-4786 | A-276 | B-11 |
| n3-4787 | A-277 | B-11 |

TABLE 1-continued

| epn | n = 3 A | B |
|---|---|---|
| n3-4788 | A-278 | B-11 |
| n3-4789 | A-279 | B-11 |
| n3-4790 | A-280 | B-11 |
| n3-4791 | A-281 | B-11 |
| n3-4792 | A-282 | B-11 |
| n3-4793 | A-283 | B-11 |
| n3-4794 | A-284 | B-11 |
| n3-4795 | A-285 | B-11 |
| n3-4796 | A-286 | B-11 |
| n3-4797 | A-287 | B-11 |
| n3-4798 | A-288 | B-11 |
| n3-4799 | A-289 | B-11 |
| n3-4800 | A-290 | B-11 |
| n3-4801 | A-291 | B-11 |
| n3-4802 | A-292 | B-11 |
| n3-4803 | A-293 | B-11 |
| n3-4804 | A-294 | B-11 |
| n3-4805 | A-295 | B-11 |
| n3-4806 | A-296 | B-11 |
| n3-4807 | A-297 | B-11 |
| n3-4808 | A-298 | B-11 |
| n3-4809 | A-299 | B-11 |
| n3-4810 | A-300 | B-11 |
| n3-4811 | A-301 | B-11 |
| n3-4812 | A-302 | B-11 |
| n3-4813 | A-303 | B-11 |
| n3-4814 | A-304 | B-11 |
| n3-4815 | A-305 | B-11 |
| n3-4816 | A-306 | B-11 |
| n3-4817 | A-307 | B-11 |
| n3-4818 | A-308 | B-11 |
| n3-4819 | A-309 | B-11 |
| n3-4820 | A-310 | B-11 |
| n3-4821 | A-311 | B-11 |
| n3-4822 | A-312 | B-11 |
| n3-4823 | A-313 | B-11 |
| n3-4824 | A-314 | B-11 |
| n3-4825 | A-315 | B-11 |
| n3-4826 | A-316 | B-11 |
| n3-4827 | A-317 | B-11 |
| n3-4828 | A-318 | B-11 |
| n3-4829 | A-319 | B-11 |
| n3-4830 | A-320 | B-11 |
| n3-4831 | A-321 | B-11 |
| n3-4832 | A-322 | B-11 |
| n3-4833 | A-323 | B-11 |
| n3-4834 | A-324 | B-11 |
| n3-4835 | A-325 | B-11 |
| n3-4836 | A-326 | B-11 |
| n3-4837 | A-327 | B-11 |
| n3-4838 | A-328 | B-11 |
| n3-4839 | A-329 | B-11 |
| n3-4840 | A-330 | B-11 |
| n3-4841 | A-331 | B-11 |
| n3-4842 | A-332 | B-11 |
| n3-4843 | A-333 | B-11 |
| n3-4844 | A-334 | B-11 |
| n3-4845 | A-335 | B-11 |
| n3-4846 | A-336 | B-11 |
| n3-4847 | A-337 | B-11 |
| n3-4848 | A-338 | B-11 |
| n3-4849 | A-339 | B-11 |
| n3-4850 | A-340 | B-11 |
| n3-4851 | A-341 | B-11 |
| n3-4852 | A-342 | B-11 |
| n3-4853 | A-343 | B-11 |
| n3-4854 | A-344 | B-11 |
| n3-4855 | A-345 | B-11 |
| n3-4856 | A-346 | B-11 |
| n3-4857 | A-347 | B-11 |
| n3-4858 | A-348 | B-11 |
| n3-4859 | A-349 | B-11 |
| n3-4860 | A-350 | B-11 |
| n3-4861 | A-351 | B-11 |
| n3-4862 | A-352 | B-11 |
| n3-4863 | A-353 | B-11 |
| n3-4864 | A-354 | B-11 |
| n3-4865 | A-355 | B-11 |
| n3-4866 | A-356 | B-11 |
| n3-4867 | A-357 | B-11 |
| n3-4868 | A-358 | B-11 |
| n3-4869 | A-359 | B-11 |
| n3-4870 | A-360 | B-11 |
| n3-4871 | A-361 | B-11 |
| n3-4872 | A-362 | B-11 |
| n3-4873 | A-363 | B-11 |
| n3-4874 | A-364 | B-11 |
| n3-4875 | A-365 | B-11 |
| n3-4876 | A-366 | B-11 |
| n3-4877 | A-367 | B-11 |
| n3-4878 | A-368 | B-11 |
| n3-4879 | A-369 | B-11 |
| n3-4880 | A-370 | B-11 |
| n3-4881 | A-371 | B-11 |
| n3-4882 | A-372 | B-11 |
| n3-4883 | A-373 | B-11 |
| n3-4884 | A-374 | B-11 |
| n3-4885 | A-375 | B-11 |
| n3-4886 | A-376 | B-11 |
| n3-4887 | A-377 | B-11 |
| n3-4888 | A-378 | B-11 |
| n3-4889 | A-379 | B-11 |
| n3-4890 | A-380 | B-11 |
| n3-4891 | A-381 | B-11 |
| n3-4892 | A-382 | B-11 |
| n3-4893 | A-383 | B-11 |
| n3-4894 | A-384 | B-11 |
| n3-4895 | A-385 | B-11 |
| n3-4896 | A-386 | B-11 |
| n3-4897 | A-387 | B-11 |
| n3-4898 | A-388 | B-11 |
| n3-4899 | A-389 | B-11 |
| n3-4900 | A-390 | B-11 |
| n3-4901 | A-391 | B-11 |
| n3-4902 | A-392 | B-11 |
| n3-4903 | A-393 | B-11 |
| n3-4904 | A-394 | B-11 |
| n3-4905 | A-395 | B-11 |
| n3-4906 | A-396 | B-11 |
| n3-4907 | A-397 | B-11 |
| n3-4908 | A-398 | B-11 |
| n3-4909 | A-399 | B-11 |
| n3-4910 | A-400 | B-11 |
| n3-4911 | A-401 | B-11 |
| n3-4912 | A-402 | B-11 |
| n3-4913 | A-403 | B-11 |
| n3-4914 | A-404 | B-11 |
| n3-4915 | A-405 | B-11 |
| n3-4916 | A-406 | B-11 |
| n3-4917 | A-407 | B-11 |
| n3-4918 | A-408 | B-11 |
| n3-4919 | A-409 | B-11 |
| n3-4920 | A-410 | B-11 |
| n3-4921 | A-411 | B-11 |
| n3-4922 | A-412 | B-11 |
| n3-4923 | A-413 | B-11 |
| n3-4924 | A-414 | B-11 |
| n3-4925 | A-415 | B-11 |
| n3-4926 | A-416 | B-11 |
| n3-4927 | A-417 | B-11 |
| n3-4928 | A-418 | B-11 |
| n3-4929 | A-419 | B-11 |
| n3-4930 | A-420 | B-11 |
| n3-4931 | A-421 | B-11 |
| n3-4932 | A-422 | B-11 |
| n3-4933 | A-423 | B-11 |
| n3-4934 | A-424 | B-11 |
| n3-4935 | A-425 | B-11 |
| n3-4936 | A-426 | B-11 |
| n3-4937 | A-427 | B-11 |

TABLE 1-continued

| epn | n = 3 A | B |
|---|---|---|
| n3-4938 | A-428 | B-11 |
| n3-4939 | A-429 | B-11 |
| n3-4940 | A-430 | B-11 |
| n3-4941 | A-431 | B-11 |
| n3-4942 | A-432 | B-11 |
| n3-4943 | A-433 | B-11 |
| n3-4944 | A-434 | B-11 |
| n3-4945 | A-435 | B-11 |
| n3-4946 | A-436 | B-11 |
| n3-4947 | A-437 | B-11 |
| n3-4948 | A-438 | B-11 |
| n3-4949 | A-439 | B-11 |
| n3-4950 | A-440 | B-11 |
| n3-4951 | A-441 | B-11 |
| n3-4952 | A-442 | B-11 |
| n3-4953 | A-443 | B-11 |
| n3-4954 | A-444 | B-11 |
| n3-4955 | A-445 | B-11 |
| n3-4956 | A-446 | B-11 |
| n3-4957 | A-447 | B-11 |
| n3-4958 | A-448 | B-11 |
| n3-4959 | A-449 | B-11 |
| n3-4960 | A-450 | B-11 |
| n3-4961 | A-451 | B-11 |
| n3-4962 | A-1 | B-12 |
| n3-4963 | A-2 | B-12 |
| n3-4964 | A-3 | B-12 |
| n3-4965 | A-4 | B-12 |
| n3-4966 | A-5 | B-12 |
| n3-4967 | A-6 | B-12 |
| n3-4968 | A-7 | B-12 |
| n3-4969 | A-8 | B-12 |
| n3-4970 | A-9 | B-12 |
| n3-4971 | A-10 | B-12 |
| n3-4972 | A-11 | B-12 |
| n3-4973 | A-12 | B-12 |
| n3-4974 | A-13 | B-12 |
| n3-4975 | A-14 | B-12 |
| n3-4976 | A-15 | B-12 |
| n3-4977 | A-16 | B-12 |
| n3-4978 | A-17 | B-12 |
| n3-4979 | A-18 | B-12 |
| n3-4980 | A-19 | B-12 |
| n3-4981 | A-20 | B-12 |
| n3-4982 | A-21 | B-12 |
| n3-4983 | A-22 | B-12 |
| n3-4984 | A-23 | B-12 |
| n3-4985 | A-24 | B-12 |
| n3-4986 | A-25 | B-12 |
| n3-4987 | A-26 | B-12 |
| n3-4988 | A-27 | B-12 |
| n3-4989 | A-28 | B-12 |
| n3-4990 | A-29 | B-12 |
| n3-4991 | A-30 | B-12 |
| n3-4992 | A-31 | B-12 |
| n3-4993 | A-32 | B-12 |
| n3-4994 | A-33 | B-12 |
| n3-4995 | A-34 | B-12 |
| n3-4996 | A-35 | B-12 |
| n3-4997 | A-36 | B-12 |
| n3-4998 | A-37 | B-12 |
| n3-4999 | A-38 | B-12 |
| n3-5000 | A-39 | B-12 |
| n3-5001 | A-40 | B-12 |
| n3-5002 | A-41 | B-12 |
| n3-5003 | A-42 | B-12 |
| n3-5004 | A-43 | B-12 |
| n3-5005 | A-44 | B-12 |
| n3-5006 | A-45 | B-12 |
| n3-5007 | A-46 | B-12 |
| n3-5008 | A-47 | B-12 |
| n3-5009 | A-48 | B-12 |
| n3-5010 | A-49 | B-12 |
| n3-5011 | A-50 | B-12 |
| n3-5012 | A-51 | B-12 |
| n3-5013 | A-52 | B-12 |
| n3-5014 | A-53 | B-12 |
| n3-5015 | A-54 | B-12 |
| n3-5016 | A-55 | B-12 |
| n3-5017 | A-56 | B-12 |
| n3-5018 | A-57 | B-12 |
| n3-5019 | A-58 | B-12 |
| n3-5020 | A-59 | B-12 |
| n3-5021 | A-60 | B-12 |
| n3-5022 | A-61 | B-12 |
| n3-5023 | A-62 | B-12 |
| n3-5024 | A-63 | B-12 |
| n3-5025 | A-64 | B-12 |
| n3-5026 | A-65 | B-12 |
| n3-5027 | A-66 | B-12 |
| n3-5028 | A-67 | B-12 |
| n3-5029 | A-68 | B-12 |
| n3-5030 | A-69 | B-12 |
| n3-5031 | A-70 | B-12 |
| n3-5032 | A-71 | B-12 |
| n3-5033 | A-72 | B-12 |
| n3-5034 | A-73 | B-12 |
| n3-5035 | A-74 | B-12 |
| n3-5036 | A-75 | B-12 |
| n3-5037 | A-76 | B-12 |
| n3-5038 | A-77 | B-12 |
| n3-5039 | A-78 | B-12 |
| n3-5040 | A-79 | B-12 |
| n3-5041 | A-80 | B-12 |
| n3-5042 | A-81 | B-12 |
| n3-5043 | A-82 | B-12 |
| n3-5044 | A-83 | B-12 |
| n3-5045 | A-84 | B-12 |
| n3-5046 | A-85 | B-12 |
| n3-5047 | A-86 | B-12 |
| n3-5048 | A-87 | B-12 |
| n3-5049 | A-88 | B-12 |
| n3-5050 | A-89 | B-12 |
| n3-5051 | A-90 | B-12 |
| n3-5052 | A-91 | B-12 |
| n3-5053 | A-92 | B-12 |
| n3-5054 | A-93 | B-12 |
| n3-5055 | A-94 | B-12 |
| n3-5056 | A-95 | B-12 |
| n3-5057 | A-96 | B-12 |
| n3-5058 | A-97 | B-12 |
| n3-5059 | A-98 | B-12 |
| n3-5060 | A-99 | B-12 |
| n3-5061 | A-100 | B-12 |
| n3-5062 | A-101 | B-12 |
| n3-5063 | A-102 | B-12 |
| n3-5064 | A-103 | B-12 |
| n3-5065 | A-104 | B-12 |
| n3-5066 | A-105 | B-12 |
| n3-5067 | A-106 | B-12 |
| n3-5068 | A-107 | B-12 |
| n3-5069 | A-108 | B-12 |
| n3-5070 | A-109 | B-12 |
| n3-5071 | A-110 | B-12 |
| n3-5072 | A-111 | B-12 |
| n3-5073 | A-112 | B-12 |
| n3-5074 | A-113 | B-12 |
| n3-5075 | A-114 | B-12 |
| n3-5076 | A-115 | B-12 |
| n3-5077 | A-116 | B-12 |
| n3-5078 | A-117 | B-12 |
| n3-5079 | A-118 | B-12 |
| n3-5080 | A-119 | B-12 |
| n3-5081 | A-120 | B-12 |
| n3-5082 | A-121 | B-12 |
| n3-5083 | A-122 | B-12 |
| n3-5084 | A-123 | B-12 |
| n3-5085 | A-124 | B-12 |
| n3-5086 | A-125 | B-12 |
| n3-5087 | A-126 | B-12 |

TABLE 1-continued

| | n = 3 | |
|---|---|---|
| epn | A | B |
| n3-5088 | A-127 | B-12 |
| n3-5089 | A-128 | B-12 |
| n3-5090 | A-129 | B-12 |
| n3-5091 | A-130 | B-12 |
| n3-5092 | A-131 | B-12 |
| n3-5093 | A-132 | B-12 |
| n3-5094 | A-133 | B-12 |
| n3-5095 | A-134 | B-12 |
| n3-5096 | A-135 | B-12 |
| n3-5097 | A-136 | B-12 |
| n3-5098 | A-137 | B-12 |
| n3-5099 | A-138 | B-12 |
| n3-5100 | A-139 | B-12 |
| n3-5101 | A-140 | B-12 |
| n3-5102 | A-141 | B-12 |
| n3-5103 | A-142 | B-12 |
| n3-5104 | A-143 | B-12 |
| n3-5105 | A-144 | B-12 |
| n3-5106 | A-145 | B-12 |
| n3-5107 | A-146 | B-12 |
| n3-5108 | A-147 | B-12 |
| n3-5109 | A-148 | B-12 |
| n3-5110 | A-149 | B-12 |
| n3-5111 | A-150 | B-12 |
| n3-5112 | A-151 | B-12 |
| n3-5113 | A-152 | B-12 |
| n3-5114 | A-153 | B-12 |
| n3-5115 | A-154 | B-12 |
| n3-5116 | A-155 | B-12 |
| n3-5117 | A-156 | B-12 |
| n3-5118 | A-157 | B-12 |
| n3-5119 | A-158 | B-12 |
| n3-5120 | A-159 | B-12 |
| n3-5121 | A-160 | B-12 |
| n3-5122 | A-161 | B-12 |
| n3-5123 | A-162 | B-12 |
| n3-5124 | A-163 | B-12 |
| n3-5125 | A-164 | B-12 |
| n3-5126 | A-165 | B-12 |
| n3-5127 | A-166 | B-12 |
| n3-5128 | A-167 | B-12 |
| n3-5129 | A-168 | B-12 |
| n3-5130 | A-169 | B-12 |
| n3-5131 | A-170 | B-12 |
| n3-5132 | A-171 | B-12 |
| n3-5133 | A-172 | B-12 |
| n3-5134 | A-173 | B-12 |
| n3-5135 | A-174 | B-12 |
| n3-5136 | A-175 | B-12 |
| n3-5137 | A-176 | B-12 |
| n3-5138 | A-177 | B-12 |
| n3-5139 | A-178 | B-12 |
| n3-5140 | A-179 | B-12 |
| n3-5141 | A-180 | B-12 |
| n3-5142 | A-181 | B-12 |
| n3-5143 | A-182 | B-12 |
| n3-5144 | A-183 | B-12 |
| n3-5145 | A-184 | B-12 |
| n3-5146 | A-185 | B-12 |
| n3-5147 | A-186 | B-12 |
| n3-5148 | A-187 | B-12 |
| n3-5149 | A-188 | B-12 |
| n3-5150 | A-189 | B-12 |
| n3-5151 | A-190 | B-12 |
| n3-5152 | A-191 | B-12 |
| n3-5153 | A-192 | B-12 |
| n3-5154 | A-193 | B-12 |
| n3-5155 | A-194 | B-12 |
| n3-5156 | A-195 | B-12 |
| n3-5157 | A-196 | B-12 |
| n3-5158 | A-197 | B-12 |
| n3-5159 | A-198 | B-12 |
| n3-5160 | A-199 | B-12 |
| n3-5161 | A-200 | B-12 |
| n3-5162 | A-201 | B-12 |
| n3-5163 | A-202 | B-12 |
| n3-5164 | A-203 | B-12 |
| n3-5165 | A-204 | B-12 |
| n3-5166 | A-205 | B-12 |
| n3-5167 | A-206 | B-12 |
| n3-5168 | A-207 | B-12 |
| n3-5169 | A-208 | B-12 |
| n3-5170 | A-209 | B-12 |
| n3-5171 | A-210 | B-12 |
| n3-5172 | A-211 | B-12 |
| n3-5173 | A-212 | B-12 |
| n3-5174 | A-213 | B-12 |
| n3-5175 | A-214 | B-12 |
| n3-5176 | A-215 | B-12 |
| n3-5177 | A-216 | B-12 |
| n3-5178 | A-217 | B-12 |
| n3-5179 | A-218 | B-12 |
| n3-5180 | A-219 | B-12 |
| n3-5181 | A-220 | B-12 |
| n3-5182 | A-221 | B-12 |
| n3-5183 | A-222 | B-12 |
| n3-5184 | A-223 | B-12 |
| n3-5185 | A-224 | B-12 |
| n3-5186 | A-225 | B-12 |
| n3-5187 | A-226 | B-12 |
| n3-5188 | A-227 | B-12 |
| n3-5189 | A-228 | B-12 |
| n3-5190 | A-229 | B-12 |
| n3-5191 | A-230 | B-12 |
| n3-5192 | A-231 | B-12 |
| n3-5193 | A-232 | B-12 |
| n3-5194 | A-233 | B-12 |
| n3-5195 | A-234 | B-12 |
| n3-5196 | A-235 | B-12 |
| n3-5197 | A-236 | B-12 |
| n3-5198 | A-237 | B-12 |
| n3-5199 | A-238 | B-12 |
| n3-5200 | A-239 | B-12 |
| n3-5201 | A-240 | B-12 |
| n3-5202 | A-241 | B-12 |
| n3-5203 | A-242 | B-12 |
| n3-5204 | A-243 | B-12 |
| n3-5205 | A-244 | B-12 |
| n3-5206 | A-245 | B-12 |
| n3-5207 | A-246 | B-12 |
| n3-5208 | A-247 | B-12 |
| n3-5209 | A-248 | B-12 |
| n3-5210 | A-249 | B-12 |
| n3-5211 | A-250 | B-12 |
| n3-5212 | A-251 | B-12 |
| n3-5213 | A-252 | B-12 |
| n3-5214 | A-253 | B-12 |
| n3-5215 | A-254 | B-12 |
| n3-5216 | A-255 | B-12 |
| n3-5217 | A-256 | B-12 |
| n3-5218 | A-257 | B-12 |
| n3-5219 | A-258 | B-12 |
| n3-5220 | A-259 | B-12 |
| n3-5221 | A-260 | B-12 |
| n3-5222 | A-261 | B-12 |
| n3-5223 | A-262 | B-12 |
| n3-5224 | A-263 | B-12 |
| n3-5225 | A-264 | B-12 |
| n3-5226 | A-265 | B-12 |
| n3-5227 | A-266 | B-12 |
| n3-5228 | A-267 | B-12 |
| n3-5229 | A-268 | B-12 |
| n3-5230 | A-269 | B-12 |
| n3-5231 | A-270 | B-12 |
| n3-5232 | A-271 | B-12 |
| n3-5233 | A-272 | B-12 |
| n3-5234 | A-273 | B-12 |
| n3-5235 | A-274 | B-12 |
| n3-5236 | A-275 | B-12 |
| n3-5237 | A-276 | B-12 |

TABLE 1-continued

| epn | n = 3 A | B |
|---|---|---|
| n3-5238 | A-277 | B-12 |
| n3-5239 | A-278 | B-12 |
| n3-5240 | A-279 | B-12 |
| n3-5241 | A-280 | B-12 |
| n3-5242 | A-281 | B-12 |
| n3-5243 | A-282 | B-12 |
| n3-5244 | A-283 | B-12 |
| n3-5245 | A-284 | B-12 |
| n3-5246 | A-285 | B-12 |
| n3-5247 | A-286 | B-12 |
| n3-5248 | A-287 | B-12 |
| n3-5249 | A-288 | B-12 |
| n3-5250 | A-289 | B-12 |
| n3-5251 | A-290 | B-12 |
| n3-5252 | A-291 | B-12 |
| n3-5253 | A-292 | B-12 |
| n3-5254 | A-293 | B-12 |
| n3-5255 | A-294 | B-12 |
| n3-5256 | A-295 | B-12 |
| n3-5257 | A-296 | B-12 |
| n3-5258 | A-297 | B-12 |
| n3-5259 | A-298 | B-12 |
| n3-5260 | A-299 | B-12 |
| n3-5261 | A-300 | B-12 |
| n3-5262 | A-301 | B-12 |
| n3-5263 | A-302 | B-12 |
| n3-5264 | A-303 | B-12 |
| n3-5265 | A-304 | B-12 |
| n3-5266 | A-305 | B-12 |
| n3-5267 | A-306 | B-12 |
| n3-5268 | A-307 | B-12 |
| n3-5269 | A-308 | B-12 |
| n3-5270 | A-309 | B-12 |
| n3-5271 | A-310 | B-12 |
| n3-5272 | A-311 | B-12 |
| n3-5273 | A-312 | B-12 |
| n3-5274 | A-313 | B-12 |
| n3-5275 | A-314 | B-12 |
| n3-5276 | A-315 | B-12 |
| n3-5277 | A-316 | B-12 |
| n3-5278 | A-317 | B-12 |
| n3-5279 | A-318 | B-12 |
| n3-5280 | A-319 | B-12 |
| n3-5281 | A-320 | B-12 |
| n3-5282 | A-321 | B-12 |
| n3-5283 | A-322 | B-12 |
| n3-5284 | A-323 | B-12 |
| n3-5285 | A-324 | B-12 |
| n3-5286 | A-325 | B-12 |
| n3-5287 | A-326 | B-12 |
| n3-5288 | A-327 | B-12 |
| n3-5289 | A-328 | B-12 |
| n3-5290 | A-329 | B-12 |
| n3-5291 | A-330 | B-12 |
| n3-5292 | A-331 | B-12 |
| n3-5293 | A-332 | B-12 |
| n3-5294 | A-333 | B-12 |
| n3-5295 | A-334 | B-12 |
| n3-5296 | A-335 | B-12 |
| n3-5297 | A-336 | B-12 |
| n3-5298 | A-337 | B-12 |
| n3-5299 | A-338 | B-12 |
| n3-5300 | A-339 | B-12 |
| n3-5301 | A-340 | B-12 |
| n3-5302 | A-341 | B-12 |
| n3-5303 | A-342 | B-12 |
| n3-5304 | A-343 | B-12 |
| n3-5305 | A-344 | B-12 |
| n3-5306 | A-345 | B-12 |
| n3-5307 | A-346 | B-12 |
| n3-5308 | A-347 | B-12 |
| n3-5309 | A-348 | B-12 |
| n3-5310 | A-349 | B-12 |
| n3-5311 | A-350 | B-12 |
| n3-5312 | A-351 | B-12 |
| n3-5313 | A-352 | B-12 |
| n3-5314 | A-353 | B-12 |
| n3-5315 | A-354 | B-12 |
| n3-5316 | A-355 | B-12 |
| n3-5317 | A-356 | B-12 |
| n3-5318 | A-357 | B-12 |
| n3-5319 | A-358 | B-12 |
| n3-5320 | A-359 | B-12 |
| n3-5321 | A-360 | B-12 |
| n3-5322 | A-361 | B-12 |
| n3-5323 | A-362 | B-12 |
| n3-5324 | A-363 | B-12 |
| n3-5325 | A-364 | B-12 |
| n3-5326 | A-365 | B-12 |
| n3-5327 | A-366 | B-12 |
| n3-5328 | A-367 | B-12 |
| n3-5329 | A-368 | B-12 |
| n3-5330 | A-369 | B-12 |
| n3-5331 | A-370 | B-12 |
| n3-5332 | A-371 | B-12 |
| n3-5333 | A-372 | B-12 |
| n3-5334 | A-373 | B-12 |
| n3-5335 | A-374 | B-12 |
| n3-5336 | A-375 | B-12 |
| n3-5337 | A-376 | B-12 |
| n3-5338 | A-377 | B-12 |
| n3-5339 | A-378 | B-12 |
| n3-5340 | A-379 | B-12 |
| n3-5341 | A-380 | B-12 |
| n3-5342 | A-381 | B-12 |
| n3-5343 | A-382 | B-12 |
| n3-5344 | A-383 | B-12 |
| n3-5345 | A-384 | B-12 |
| n3-5346 | A-385 | B-12 |
| n3-5347 | A-386 | B-12 |
| n3-5348 | A-387 | B-12 |
| n3-5349 | A-388 | B-12 |
| n3-5350 | A-389 | B-12 |
| n3-5351 | A-390 | B-12 |
| n3-5352 | A-391 | B-12 |
| n3-5353 | A-392 | B-12 |
| n3-5354 | A-393 | B-12 |
| n3-5355 | A-394 | B-12 |
| n3-5356 | A-395 | B-12 |
| n3-5357 | A-396 | B-12 |
| n3-5358 | A-397 | B-12 |
| n3-5359 | A-398 | B-12 |
| n3-5360 | A-399 | B-12 |
| n3-5361 | A-400 | B-12 |
| n3-5362 | A-401 | B-12 |
| n3-5363 | A-402 | B-12 |
| n3-5364 | A-403 | B-12 |
| n3-5365 | A-404 | B-12 |
| n3-5366 | A-405 | B-12 |
| n3-5367 | A-406 | B-12 |
| n3-5368 | A-407 | B-12 |
| n3-5369 | A-408 | B-12 |
| n3-5370 | A-409 | B-12 |
| n3-5371 | A-410 | B-12 |
| n3-5372 | A-411 | B-12 |
| n3-5373 | A-412 | B-12 |
| n3-5374 | A-413 | B-12 |
| n3-5375 | A-414 | B-12 |
| n3-5376 | A-415 | B-12 |
| n3-5377 | A-416 | B-12 |
| n3-5378 | A-417 | B-12 |
| n3-5379 | A-418 | B-12 |
| n3-5380 | A-419 | B-12 |
| n3-5381 | A-420 | B-12 |
| n3-5382 | A-421 | B-12 |
| n3-5383 | A-422 | B-12 |
| n3-5384 | A-423 | B-12 |
| n3-5385 | A-424 | B-12 |
| n3-5386 | A-425 | B-12 |
| n3-5387 | A-426 | B-12 |

TABLE 1-continued

| epn | n = 3 A | B |
|---|---|---|
| n3-5388 | A-427 | B-12 |
| n3-5389 | A-428 | B-12 |
| n3-5390 | A-429 | B-12 |
| n3-5391 | A-430 | B-12 |
| n3-5392 | A-431 | B-12 |
| n3-5393 | A-432 | B-12 |
| n3-5394 | A-433 | B-12 |
| n3-5395 | A-434 | B-12 |
| n3-5396 | A-435 | B-12 |
| n3-5397 | A-436 | B-12 |
| n3-5398 | A-437 | B-12 |
| n3-5399 | A-438 | B-12 |
| n3-5400 | A-439 | B-12 |
| n3-5401 | A-440 | B-12 |
| n3-5402 | A-441 | B-12 |
| n3-5403 | A-442 | B-12 |
| n3-5404 | A-443 | B-12 |
| n3-5405 | A-444 | B-12 |
| n3-5406 | A-445 | B-12 |
| n3-5407 | A-446 | B-12 |
| n3-5408 | A-447 | B-12 |
| n3-5409 | A-448 | B-12 |
| n3-5410 | A-449 | B-12 |
| n3-5411 | A-450 | B-12 |
| n3-5412 | A-451 | B-12 |
| n3-5413 | A-1 | B-13 |
| n3-5414 | A-2 | B-13 |
| n3-5415 | A-3 | B-13 |
| n3-5416 | A-4 | B-13 |
| n3-5417 | A-5 | B-13 |
| n3-5418 | A-6 | B-13 |
| n3-5419 | A-7 | B-13 |
| n3-5420 | A-8 | B-13 |
| n3-5421 | A-9 | B-13 |
| n3-5422 | A-10 | B-13 |
| n3-5423 | A-11 | B-13 |
| n3-5424 | A-12 | B-13 |
| n3-5425 | A-13 | B-13 |
| n3-5426 | A-14 | B-13 |
| n3-5427 | A-15 | B-13 |
| n3-5428 | A-16 | B-13 |
| n3-5429 | A-17 | B-13 |
| n3-5430 | A-18 | B-13 |
| n3-5431 | A-19 | B-13 |
| n3-5432 | A-20 | B-13 |
| n3-5433 | A-21 | B-13 |
| n3-5434 | A-22 | B-13 |
| n3-5435 | A-23 | B-13 |
| n3-5436 | A-24 | B-13 |
| n3-5437 | A-25 | B-13 |
| n3-5438 | A-26 | B-13 |
| n3-5439 | A-27 | B-13 |
| n3-5440 | A-28 | B-13 |
| n3-5441 | A-29 | B-13 |
| n3-5442 | A-30 | B-13 |
| n3-5443 | A-31 | B-13 |
| n3-5444 | A-32 | B-13 |
| n3-5445 | A-33 | B-13 |
| n3-5446 | A-34 | B-13 |
| n3-5447 | A-35 | B-13 |
| n3-5448 | A-36 | B-13 |
| n3-5449 | A-37 | B-13 |
| n3-5450 | A-38 | B-13 |
| n3-5451 | A-39 | B-13 |
| n3-5452 | A-40 | B-13 |
| n3-5453 | A-41 | B-13 |
| n3-5454 | A-42 | B-13 |
| n3-5455 | A-43 | B-13 |
| n3-5456 | A-44 | B-13 |
| n3-5457 | A-45 | B-13 |
| n3-5458 | A-46 | B-13 |
| n3-5459 | A-47 | B-13 |
| n3-5460 | A-48 | B-13 |
| n3-5461 | A-49 | B-13 |
| n3-5462 | A-50 | B-13 |
| n3-5463 | A-51 | B-13 |
| n3-5464 | A-52 | B-13 |
| n3-5465 | A-53 | B-13 |
| n3-5466 | A-54 | B-13 |
| n3-5467 | A-55 | B-13 |
| n3-5468 | A-56 | B-13 |
| n3-5469 | A-57 | B-13 |
| n3-5470 | A-58 | B-13 |
| n3-5471 | A-59 | B-13 |
| n3-5472 | A-60 | B-13 |
| n3-5473 | A-61 | B-13 |
| n3-5474 | A-62 | B-13 |
| n3-5475 | A-63 | B-13 |
| n3-5476 | A-64 | B-13 |
| n3-5477 | A-65 | B-13 |
| n3-5478 | A-66 | B-13 |
| n3-5479 | A-67 | B-13 |
| n3-5480 | A-68 | B-13 |
| n3-5481 | A-69 | B-13 |
| n3-5482 | A-70 | B-13 |
| n3-5483 | A-71 | B-13 |
| n3-5484 | A-72 | B-13 |
| n3-5485 | A-73 | B-13 |
| n3-5486 | A-74 | B-13 |
| n3-5487 | A-75 | B-13 |
| n3-5488 | A-76 | B-13 |
| n3-5489 | A-77 | B-13 |
| n3-5490 | A-78 | B-13 |
| n3-5491 | A-79 | B-13 |
| n3-5492 | A-80 | B-13 |
| n3-5493 | A-81 | B-13 |
| n3-5494 | A-82 | B-13 |
| n3-5495 | A-83 | B-13 |
| n3-5496 | A-84 | B-13 |
| n3-5497 | A-85 | B-13 |
| n3-5498 | A-86 | B-13 |
| n3-5499 | A-87 | B-13 |
| n3-5500 | A-88 | B-13 |
| n3-5501 | A-89 | B-13 |
| n3-5502 | A-90 | B-13 |
| n3-5503 | A-91 | B-13 |
| n3-5504 | A-92 | B-13 |
| n3-5505 | A-93 | B-13 |
| n3-5506 | A-94 | B-13 |
| n3-5507 | A-95 | B-13 |
| n3-5508 | A-96 | B-13 |
| n3-5509 | A-97 | B-13 |
| n3-5510 | A-98 | B-13 |
| n3-5511 | A-99 | B-13 |
| n3-5512 | A-100 | B-13 |
| n3-5513 | A-101 | B-13 |
| n3-5514 | A-102 | B-13 |
| n3-5515 | A-103 | B-13 |
| n3-5516 | A-104 | B-13 |
| n3-5517 | A-105 | B-13 |
| n3-5518 | A-106 | B-13 |
| n3-5519 | A-107 | B-13 |
| n3-5520 | A-108 | B-13 |
| n3-5521 | A-109 | B-13 |
| n3-5522 | A-110 | B-13 |
| n3-5523 | A-111 | B-13 |
| n3-5524 | A-112 | B-13 |
| n3-5525 | A-113 | B-13 |
| n3-5526 | A-114 | B-13 |
| n3-5527 | A-115 | B-13 |
| n3-5528 | A-116 | B-13 |
| n3-5529 | A-117 | B-13 |
| n3-5530 | A-118 | B-13 |
| n3-5531 | A-119 | B-13 |
| n3-5532 | A-120 | B-13 |
| n3-5533 | A-121 | B-13 |
| n3-5534 | A-122 | B-13 |
| n3-5535 | A-123 | B-13 |
| n3-5536 | A-124 | B-13 |
| n3-5537 | A-125 | B-13 |

TABLE 1-continued

| epn | n = 3 A | B |
|---|---|---|
| n3-5538 | A-126 | B-13 |
| n3-5539 | A-127 | B-13 |
| n3-5540 | A-128 | B-13 |
| n3-5541 | A-129 | B-13 |
| n3-5542 | A-130 | B-13 |
| n3-5543 | A-131 | B-13 |
| n3-5544 | A-132 | B-13 |
| n3-5545 | A-133 | B-13 |
| n3-5546 | A-134 | B-13 |
| n3-5547 | A-135 | B-13 |
| n3-5548 | A-136 | B-13 |
| n3-5549 | A-137 | B-13 |
| n3-5550 | A-138 | B-13 |
| n3-5551 | A-139 | B-13 |
| n3-5552 | A-140 | B-13 |
| n3-5553 | A-141 | B-13 |
| n3-5554 | A-142 | B-13 |
| n3-5555 | A-143 | B-13 |
| n3-5556 | A-144 | B-13 |
| n3-5557 | A-145 | B-13 |
| n3-5558 | A-146 | B-13 |
| n3-5559 | A-147 | B-13 |
| n3-5560 | A-148 | B-13 |
| n3-5561 | A-149 | B-13 |
| n3-5562 | A-150 | B-13 |
| n3-5563 | A-151 | B-13 |
| n3-5564 | A-152 | B-13 |
| n3-5565 | A-153 | B-13 |
| n3-5566 | A-154 | B-13 |
| n3-5567 | A-155 | B-13 |
| n3-5568 | A-156 | B-13 |
| n3-5569 | A-157 | B-13 |
| n3-5570 | A-158 | B-13 |
| n3-5571 | A-159 | B-13 |
| n3-5572 | A-160 | B-13 |
| n3-5573 | A-161 | B-13 |
| n3-5574 | A-162 | B-13 |
| n3-5575 | A-163 | B-13 |
| n3-5576 | A-164 | B-13 |
| n3-5577 | A-165 | B-13 |
| n3-5578 | A-166 | B-13 |
| n3-5579 | A-167 | B-13 |
| n3-5580 | A-168 | B-13 |
| n3-5581 | A-169 | B-13 |
| n3-5582 | A-170 | B-13 |
| n3-5583 | A-171 | B-13 |
| n3-5584 | A-172 | B-13 |
| n3-5585 | A-173 | B-13 |
| n3-5586 | A-174 | B-13 |
| n3-5587 | A-175 | B-13 |
| n3-5588 | A-176 | B-13 |
| n3-5589 | A-177 | B-13 |
| n3-5590 | A-178 | B-13 |
| n3-5591 | A-179 | B-13 |
| n3-5592 | A-180 | B-13 |
| n3-5593 | A-181 | B-13 |
| n3-5594 | A-182 | B-13 |
| n3-5595 | A-183 | B-13 |
| n3-5596 | A-184 | B-13 |
| n3-5597 | A-185 | B-13 |
| n3-5598 | A-186 | B-13 |
| n3-5599 | A-187 | B-13 |
| n3-5600 | A-188 | B-13 |
| n3-5601 | A-189 | B-13 |
| n3-5602 | A-190 | B-13 |
| n3-5603 | A-191 | B-13 |
| n3-5604 | A-192 | B-13 |
| n3-5605 | A-193 | B-13 |
| n3-5606 | A-194 | B-13 |
| n3-5607 | A-195 | B-13 |
| n3-5608 | A-196 | B-13 |
| n3-5609 | A-197 | B-13 |
| n3-5610 | A-198 | B-13 |
| n3-5611 | A-199 | B-13 |
| n3-5612 | A-200 | B-13 |
| n3-5613 | A-201 | B-13 |
| n3-5614 | A-202 | B-13 |
| n3-5615 | A-203 | B-13 |
| n3-5616 | A-204 | B-13 |
| n3-5617 | A-205 | B-13 |
| n3-5618 | A-206 | B-13 |
| n3-5619 | A-207 | B-13 |
| n3-5620 | A-208 | B-13 |
| n3-5621 | A-209 | B-13 |
| n3-5622 | A-210 | B-13 |
| n3-5623 | A-211 | B-13 |
| n3-5624 | A-212 | B-13 |
| n3-5625 | A-213 | B-13 |
| n3-5626 | A-214 | B-13 |
| n3-5627 | A-215 | B-13 |
| n3-5628 | A-216 | B-13 |
| n3-5629 | A-217 | B-13 |
| n3-5630 | A-218 | B-13 |
| n3-5631 | A-219 | B-13 |
| n3-5632 | A-220 | B-13 |
| n3-5633 | A-221 | B-13 |
| n3-5634 | A-222 | B-13 |
| n3-5635 | A-223 | B-13 |
| n3-5636 | A-224 | B-13 |
| n3-5637 | A-225 | B-13 |
| n3-5638 | A-226 | B-13 |
| n3-5639 | A-227 | B-13 |
| n3-5640 | A-228 | B-13 |
| n3-5641 | A-229 | B-13 |
| n3-5642 | A-230 | B-13 |
| n3-5643 | A-231 | B-13 |
| n3-5644 | A-232 | B-13 |
| n3-5645 | A-233 | B-13 |
| n3-5646 | A-234 | B-13 |
| n3-5647 | A-235 | B-13 |
| n3-5648 | A-236 | B-13 |
| n3-5649 | A-237 | B-13 |
| n3-5650 | A-238 | B-13 |
| n3-5651 | A-239 | B-13 |
| n3-5652 | A-240 | B-13 |
| n3-5653 | A-241 | B-13 |
| n3-5654 | A-242 | B-13 |
| n3-5655 | A-243 | B-13 |
| n3-5656 | A-244 | B-13 |
| n3-5657 | A-245 | B-13 |
| n3-5658 | A-246 | B-13 |
| n3-5659 | A-247 | B-13 |
| n3-5660 | A-248 | B-13 |
| n3-5661 | A-249 | B-13 |
| n3-5662 | A-250 | B-13 |
| n3-5663 | A-251 | B-13 |
| n3-5664 | A-252 | B-13 |
| n3-5665 | A-253 | B-13 |
| n3-5666 | A-254 | B-13 |
| n3-5667 | A-255 | B-13 |
| n3-5668 | A-256 | B-13 |
| n3-5669 | A-257 | B-13 |
| n3-5670 | A-258 | B-13 |
| n3-5671 | A-259 | B-13 |
| n3-5672 | A-260 | B-13 |
| n3-5673 | A-261 | B-13 |
| n3-5674 | A-262 | B-13 |
| n3-5675 | A-263 | B-13 |
| n3-5676 | A-264 | B-13 |
| n3-5677 | A-265 | B-13 |
| n3-5678 | A-266 | B-13 |
| n3-5679 | A-267 | B-13 |
| n3-5680 | A-268 | B-13 |
| n3-5681 | A-269 | B-13 |
| n3-5682 | A-270 | B-13 |
| n3-5683 | A-271 | B-13 |
| n3-5684 | A-272 | B-13 |
| n3-5685 | A-273 | B-13 |
| n3-5686 | A-274 | B-13 |
| n3-5687 | A-275 | B-13 |

TABLE 1-continued

| epn | n = 3 A | B |
|---|---|---|
| n3-5688 | A-276 | B-13 |
| n3-5689 | A-277 | B-13 |
| n3-5690 | A-278 | B-13 |
| n3-5691 | A-279 | B-13 |
| n3-5692 | A-280 | B-13 |
| n3-5693 | A-281 | B-13 |
| n3-5694 | A-282 | B-13 |
| n3-5695 | A-283 | B-13 |
| n3-5696 | A-284 | B-13 |
| n3-5697 | A-285 | B-13 |
| n3-5698 | A-286 | B-13 |
| n3-5699 | A-287 | B-13 |
| n3-5700 | A-288 | B-13 |
| n3-5701 | A-289 | B-13 |
| n3-5702 | A-290 | B-13 |
| n3-5703 | A-291 | B-13 |
| n3-5704 | A-292 | B-13 |
| n3-5705 | A-293 | B-13 |
| n3-5706 | A-294 | B-13 |
| n3-5707 | A-295 | B-13 |
| n3-5708 | A-296 | B-13 |
| n3-5709 | A-297 | B-13 |
| n3-5710 | A-298 | B-13 |
| n3-5711 | A-299 | B-13 |
| n3-5712 | A-300 | B-13 |
| n3-5713 | A-301 | B-13 |
| n3-5714 | A-302 | B-13 |
| n3-5715 | A-303 | B-13 |
| n3-5716 | A-304 | B-13 |
| n3-5717 | A-305 | B-13 |
| n3-5718 | A-306 | B-13 |
| n3-5719 | A-307 | B-13 |
| n3-5720 | A-308 | B-13 |
| n3-5721 | A-309 | B-13 |
| n3-5722 | A-310 | B-13 |
| n3-5723 | A-311 | B-13 |
| n3-5724 | A-312 | B-13 |
| n3-5725 | A-313 | B-13 |
| n3-5726 | A-314 | B-13 |
| n3-5727 | A-315 | B-13 |
| n3-5728 | A-316 | B-13 |
| n3-5729 | A-317 | B-13 |
| n3-5730 | A-318 | B-13 |
| n3-5731 | A-319 | B-13 |
| n3-5732 | A-320 | B-13 |
| n3-5733 | A-321 | B-13 |
| n3-5734 | A-322 | B-13 |
| n3-5735 | A-323 | B-13 |
| n3-5736 | A-324 | B-13 |
| n3-5737 | A-325 | B-13 |
| n3-5738 | A-326 | B-13 |
| n3-5739 | A-327 | B-13 |
| n3-5740 | A-328 | B-13 |
| n3-5741 | A-329 | B-13 |
| n3-5742 | A-330 | B-13 |
| n3-5743 | A-331 | B-13 |
| n3-5744 | A-332 | B-13 |
| n3-5745 | A-333 | B-13 |
| n3-5746 | A-334 | B-13 |
| n3-5747 | A-335 | B-13 |
| n3-5748 | A-336 | B-13 |
| n3-5749 | A-337 | B-13 |
| n3-5750 | A-338 | B-13 |
| n3-5751 | A-339 | B-13 |
| n3-5752 | A-340 | B-13 |
| n3-5753 | A-341 | B-13 |
| n3-5754 | A-342 | B-13 |
| n3-5755 | A-343 | B-13 |
| n3-5756 | A-344 | B-13 |
| n3-5757 | A-345 | B-13 |
| n3-5758 | A-346 | B-13 |
| n3-5759 | A-347 | B-13 |
| n3-5760 | A-348 | B-13 |
| n3-5761 | A-349 | B-13 |
| n3-5762 | A-350 | B-13 |
| n3-5763 | A-351 | B-13 |
| n3-5764 | A-352 | B-13 |
| n3-5765 | A-353 | B-13 |
| n3-5766 | A-354 | B-13 |
| n3-5767 | A-355 | B-13 |
| n3-5768 | A-356 | B-13 |
| n3-5769 | A-357 | B-13 |
| n3-5770 | A-358 | B-13 |
| n3-5771 | A-359 | B-13 |
| n3-5772 | A-360 | B-13 |
| n3-5773 | A-361 | B-13 |
| n3-5774 | A-362 | B-13 |
| n3-5775 | A-363 | B-13 |
| n3-5776 | A-364 | B-13 |
| n3-5777 | A-365 | B-13 |
| n3-5778 | A-366 | B-13 |
| n3-5779 | A-367 | B-13 |
| n3-5780 | A-368 | B-13 |
| n3-5781 | A-369 | B-13 |
| n3-5782 | A-370 | B-13 |
| n3-5783 | A-371 | B-13 |
| n3-5784 | A-372 | B-13 |
| n3-5785 | A-373 | B-13 |
| n3-5786 | A-374 | B-13 |
| n3-5787 | A-375 | B-13 |
| n3-5788 | A-376 | B-13 |
| n3-5789 | A-377 | B-13 |
| n3-5790 | A-378 | B-13 |
| n3-5791 | A-379 | B-13 |
| n3-5792 | A-380 | B-13 |
| n3-5793 | A-381 | B-13 |
| n3-5794 | A-382 | B-13 |
| n3-5795 | A-383 | B-13 |
| n3-5796 | A-384 | B-13 |
| n3-5797 | A-385 | B-13 |
| n3-5798 | A-386 | B-13 |
| n3-5799 | A-387 | B-13 |
| n3-5800 | A-388 | B-13 |
| n3-5801 | A-389 | B-13 |
| n3-5802 | A-390 | B-13 |
| n3-5803 | A-391 | B-13 |
| n3-5804 | A-392 | B-13 |
| n3-5805 | A-393 | B-13 |
| n3-5806 | A-394 | B-13 |
| n3-5807 | A-395 | B-13 |
| n3-5808 | A-396 | B-13 |
| n3-5809 | A-397 | B-13 |
| n3-5810 | A-398 | B-13 |
| n3-5811 | A-399 | B-13 |
| n3-5812 | A-400 | B-13 |
| n3-5813 | A-401 | B-13 |
| n3-5814 | A-402 | B-13 |
| n3-5815 | A-403 | B-13 |
| n3-5816 | A-404 | B-13 |
| n3-5817 | A-405 | B-13 |
| n3-5818 | A-406 | B-13 |
| n3-5819 | A-407 | B-13 |
| n3-5820 | A-408 | B-13 |
| n3-5821 | A-409 | B-13 |
| n3-5822 | A-410 | B-13 |
| n3-5823 | A-411 | B-13 |
| n3-5824 | A-412 | B-13 |
| n3-5825 | A-413 | B-13 |
| n3-5826 | A-414 | B-13 |
| n3-5827 | A-415 | B-13 |
| n3-5828 | A-416 | B-13 |
| n3-5829 | A-417 | B-13 |
| n3-5830 | A-418 | B-13 |
| n3-5831 | A-419 | B-13 |
| n3-5832 | A-420 | B-13 |
| n3-5833 | A-421 | B-13 |
| n3-5834 | A-422 | B-13 |
| n3-5835 | A-423 | B-13 |
| n3-5836 | A-424 | B-13 |
| n3-5837 | A-425 | B-13 |

TABLE 1-continued

| epn | n = 3 A | B |
|---|---|---|
| n3-5838 | A-426 | B-13 |
| n3-5839 | A-427 | B-13 |
| n3-5840 | A-428 | B-13 |
| n3-5841 | A-429 | B-13 |
| n3-5842 | A-430 | B-13 |
| n3-5843 | A-431 | B-13 |
| n3-5844 | A-432 | B-13 |
| n3-5845 | A-433 | B-13 |
| n3-5846 | A-434 | B-13 |
| n3-5847 | A-435 | B-13 |
| n3-5848 | A-436 | B-13 |
| n3-5849 | A-437 | B-13 |
| n3-5850 | A-438 | B-13 |
| n3-5851 | A-439 | B-13 |
| n3-5852 | A-440 | B-13 |
| n3-5853 | A-441 | B-13 |
| n3-5854 | A-442 | B-13 |
| n3-5855 | A-443 | B-13 |
| n3-5856 | A-444 | B-13 |
| n3-5857 | A-445 | B-13 |
| n3-5858 | A-446 | B-13 |
| n3-5859 | A-447 | B-13 |
| n3-5860 | A-448 | B-13 |
| n3-5861 | A-449 | B-13 |
| n3-5862 | A-450 | B-13 |
| n3-5863 | A-451 | B-13 |
| n3-5864 | A-1 | B-14 |
| n3-5865 | A-2 | B-14 |
| n3-5866 | A-3 | B-14 |
| n3-5867 | A-4 | B-14 |
| n3-5868 | A-5 | B-14 |
| n3-5869 | A-6 | B-14 |
| n3-5870 | A-7 | B-14 |
| n3-5871 | A-8 | B-14 |
| n3-5872 | A-9 | B-14 |
| n3-5873 | A-10 | B-14 |
| n3-5874 | A-11 | B-14 |
| n3-5875 | A-12 | B-14 |
| n3-5876 | A-13 | B-14 |
| n3-5877 | A-14 | B-14 |
| n3-5878 | A-15 | B-14 |
| n3-5879 | A-16 | B-14 |
| n3-5880 | A-17 | B-14 |
| n3-5881 | A-18 | B-14 |
| n3-5882 | A-19 | B-14 |
| n3-5883 | A-20 | B-14 |
| n3-5884 | A-21 | B-14 |
| n3-5885 | A-22 | B-14 |
| n3-5886 | A-23 | B-14 |
| n3-5887 | A-24 | B-14 |
| n3-5888 | A-25 | B-14 |
| n3-5889 | A-26 | B-14 |
| n3-5890 | A-27 | B-14 |
| n3-5891 | A-28 | B-14 |
| n3-5892 | A-29 | B-14 |
| n3-5893 | A-30 | B-14 |
| n3-5894 | A-31 | B-14 |
| n3-5895 | A-32 | B-14 |
| n3-5896 | A-33 | B-14 |
| n3-5897 | A-34 | B-14 |
| n3-5898 | A-35 | B-14 |
| n3-5899 | A-36 | B-14 |
| n3-5900 | A-37 | B-14 |
| n3-5901 | A-38 | B-14 |
| n3-5902 | A-39 | B-14 |
| n3-5903 | A-40 | B-14 |
| n3-5904 | A-41 | B-14 |
| n3-5905 | A-42 | B-14 |
| n3-5906 | A-43 | B-14 |
| n3-5907 | A-44 | B-14 |
| n3-5908 | A-45 | B-14 |
| n3-5909 | A-46 | B-14 |
| n3-5910 | A-47 | B-14 |
| n3-5911 | A-48 | B-14 |
| n3-5912 | A-49 | B-14 |
| n3-5913 | A-50 | B-14 |
| n3-5914 | A-51 | B-14 |
| n3-5915 | A-52 | B-14 |
| n3-5916 | A-53 | B-14 |
| n3-5917 | A-54 | B-14 |
| n3-5918 | A-55 | B-14 |
| n3-5919 | A-56 | B-14 |
| n3-5920 | A-57 | B-14 |
| n3-5921 | A-58 | B-14 |
| n3-5922 | A-59 | B-14 |
| n3-5923 | A-60 | B-14 |
| n3-5924 | A-61 | B-14 |
| n3-5925 | A-62 | B-14 |
| n3-5926 | A-63 | B-14 |
| n3-5927 | A-64 | B-14 |
| n3-5928 | A-65 | B-14 |
| n3-5929 | A-66 | B-14 |
| n3-5930 | A-67 | B-14 |
| n3-5931 | A-68 | B-14 |
| n3-5932 | A-69 | B-14 |
| n3-5933 | A-70 | B-14 |
| n3-5934 | A-71 | B-14 |
| n3-5935 | A-72 | B-14 |
| n3-5936 | A-73 | B-14 |
| n3-5937 | A-74 | B-14 |
| n3-5938 | A-75 | B-14 |
| n3-5939 | A-76 | B-14 |
| n3-5940 | A-77 | B-14 |
| n3-5941 | A-78 | B-14 |
| n3-5942 | A-79 | B-14 |
| n3-5943 | A-80 | B-14 |
| n3-5944 | A-81 | B-14 |
| n3-5945 | A-82 | B-14 |
| n3-5946 | A-83 | B-14 |
| n3-5947 | A-84 | B-14 |
| n3-5948 | A-85 | B-14 |
| n3-5949 | A-86 | B-14 |
| n3-5950 | A-87 | B-14 |
| n3-5951 | A-88 | B-14 |
| n3-5952 | A-89 | B-14 |
| n3-5953 | A-90 | B-14 |
| n3-5954 | A-91 | B-14 |
| n3-5955 | A-92 | B-14 |
| n3-5956 | A-93 | B-14 |
| n3-5957 | A-94 | B-14 |
| n3-5958 | A-95 | B-14 |
| n3-5959 | A-96 | B-14 |
| n3-5960 | A-97 | B-14 |
| n3-5961 | A-98 | B-14 |
| n3-5962 | A-99 | B-14 |
| n3-5963 | A-100 | B-14 |
| n3-5964 | A-101 | B-14 |
| n3-5965 | A-102 | B-14 |
| n3-5966 | A-103 | B-14 |
| n3-5967 | A-104 | B-14 |
| n3-5968 | A-105 | B-14 |
| n3-5969 | A-106 | B-14 |
| n3-5970 | A-107 | B-14 |
| n3-5971 | A-108 | B-14 |
| n3-5972 | A-109 | B-14 |
| n3-5973 | A-110 | B-14 |
| n3-5974 | A-111 | B-14 |
| n3-5975 | A-112 | B-14 |
| n3-5976 | A-113 | B-14 |
| n3-5977 | A-114 | B-14 |
| n3-5978 | A-115 | B-14 |
| n3-5979 | A-116 | B-14 |
| n3-5980 | A-117 | B-14 |
| n3-5981 | A-118 | B-14 |
| n3-5982 | A-119 | B-14 |
| n3-5983 | A-120 | B-14 |
| n3-5984 | A-121 | B-14 |
| n3-5985 | A-122 | B-14 |
| n3-5986 | A-123 | B-14 |
| n3-5987 | A-124 | B-14 |

TABLE 1-continued

| | n = 3 | |
|---|---|---|
| epn | A | B |
| n3-5988 | A-125 | B-14 |
| n3-5989 | A-126 | B-14 |
| n3-5990 | A-127 | B-14 |
| n3-5991 | A-128 | B-14 |
| n3-5992 | A-129 | B-14 |
| n3-5993 | A-130 | B-14 |
| n3-5994 | A-131 | B-14 |
| n3-5995 | A-132 | B-14 |
| n3-5996 | A-133 | B-14 |
| n3-5997 | A-134 | B-14 |
| n3-5998 | A-135 | B-14 |
| n3-5999 | A-136 | B-14 |
| n3-6000 | A-137 | B-14 |
| n3-6001 | A-138 | B-14 |
| n3-6002 | A-139 | B-14 |
| n3-6003 | A-140 | B-14 |
| n3-6004 | A-141 | B-14 |
| n3-6005 | A-142 | B-14 |
| n3-6006 | A-143 | B-14 |
| n3-6007 | A-144 | B-14 |
| n3-6008 | A-145 | B-14 |
| n3-6009 | A-146 | B-14 |
| n3-6010 | A-147 | B-14 |
| n3-6011 | A-148 | B-14 |
| n3-6012 | A-149 | B-14 |
| n3-6013 | A-150 | B-14 |
| n3-6014 | A-151 | B-14 |
| n3-6015 | A-152 | B-14 |
| n3-6016 | A-153 | B-14 |
| n3-6017 | A-154 | B-14 |
| n3-6018 | A-155 | B-14 |
| n3-6019 | A-156 | B-14 |
| n3-6020 | A-157 | B-14 |
| n3-6021 | A-158 | B-14 |
| n3-6022 | A-159 | B-14 |
| n3-6023 | A-160 | B-14 |
| n3-6024 | A-161 | B-14 |
| n3-6025 | A-162 | B-14 |
| n3-6026 | A-163 | B-14 |
| n3-6027 | A-164 | B-14 |
| n3-6028 | A-165 | B-14 |
| n3-6029 | A-166 | B-14 |
| n3-6030 | A-167 | B-14 |
| n3-6031 | A-168 | B-14 |
| n3-6032 | A-169 | B-14 |
| n3-6033 | A-170 | B-14 |
| n3-6034 | A-171 | B-14 |
| n3-6035 | A-172 | B-14 |
| n3-6036 | A-173 | B-14 |
| n3-6037 | A-174 | B-14 |
| n3-6038 | A-175 | B-14 |
| n3-6039 | A-176 | B-14 |
| n3-6040 | A-177 | B-14 |
| n3-6041 | A-178 | B-14 |
| n3-6042 | A-179 | B-14 |
| n3-6043 | A-180 | B-14 |
| n3-6044 | A-181 | B-14 |
| n3-6045 | A-182 | B-14 |
| n3-6046 | A-183 | B-14 |
| n3-6047 | A-184 | B-14 |
| n3-6048 | A-185 | B-14 |
| n3-6049 | A-186 | B-14 |
| n3-6050 | A-187 | B-14 |
| n3-6051 | A-188 | B-14 |
| n3-6052 | A-189 | B-14 |
| n3-6053 | A-190 | B-14 |
| n3-6054 | A-191 | B-14 |
| n3-6055 | A-192 | B-14 |
| n3-6056 | A-193 | B-14 |
| n3-6057 | A-194 | B-14 |
| n3-6058 | A-195 | B-14 |
| n3-6059 | A-196 | B-14 |
| n3-6060 | A-197 | B-14 |
| n3-6061 | A-198 | B-14 |
| n3-6062 | A-199 | B-14 |
| n3-6063 | A-200 | B-14 |
| n3-6064 | A-201 | B-14 |
| n3-6065 | A-202 | B-14 |
| n3-6066 | A-203 | B-14 |
| n3-6067 | A-204 | B-14 |
| n3-6068 | A-205 | B-14 |
| n3-6069 | A-206 | B-14 |
| n3-6070 | A-207 | B-14 |
| n3-6071 | A-208 | B-14 |
| n3-6072 | A-209 | B-14 |
| n3-6073 | A-210 | B-14 |
| n3-6074 | A-211 | B-14 |
| n3-6075 | A-212 | B-14 |
| n3-6076 | A-213 | B-14 |
| n3-6077 | A-214 | B-14 |
| n3-6078 | A-215 | B-14 |
| n3-6079 | A-216 | B-14 |
| n3-6080 | A-217 | B-14 |
| n3-6081 | A-218 | B-14 |
| n3-6082 | A-219 | B-14 |
| n3-6083 | A-220 | B-14 |
| n3-6084 | A-221 | B-14 |
| n3-6085 | A-222 | B-14 |
| n3-6086 | A-223 | B-14 |
| n3-6087 | A-224 | B-14 |
| n3-6088 | A-225 | B-14 |
| n3-6089 | A-226 | B-14 |
| n3-6090 | A-227 | B-14 |
| n3-6091 | A-228 | B-14 |
| n3-6092 | A-229 | B-14 |
| n3-6093 | A-230 | B-14 |
| n3-6094 | A-231 | B-14 |
| n3-6095 | A-232 | B-14 |
| n3-6096 | A-233 | B-14 |
| n3-6097 | A-234 | B-14 |
| n3-6098 | A-235 | B-14 |
| n3-6099 | A-236 | B-14 |
| n3-6100 | A-237 | B-14 |
| n3-6101 | A-238 | B-14 |
| n3-6102 | A-239 | B-14 |
| n3-6103 | A-240 | B-14 |
| n3-6104 | A-241 | B-14 |
| n3-6105 | A-242 | B-14 |
| n3-6106 | A-243 | B-14 |
| n3-6107 | A-244 | B-14 |
| n3-6108 | A-245 | B-14 |
| n3-6109 | A-246 | B-14 |
| n3-6110 | A-247 | B-14 |
| n3-6111 | A-248 | B-14 |
| n3-6112 | A-249 | B-14 |
| n3-6113 | A-250 | B-14 |
| n3-6114 | A-251 | B-14 |
| n3-6115 | A-252 | B-14 |
| n3-6116 | A-253 | B-14 |
| n3-6117 | A-254 | B-14 |
| n3-6118 | A-255 | B-14 |
| n3-6119 | A-256 | B-14 |
| n3-6120 | A-257 | B-14 |
| n3-6121 | A-258 | B-14 |
| n3-6122 | A-259 | B-14 |
| n3-6123 | A-260 | B-14 |
| n3-6124 | A-261 | B-14 |
| n3-6125 | A-262 | B-14 |
| n3-6126 | A-263 | B-14 |
| n3-6127 | A-264 | B-14 |
| n3-6128 | A-265 | B-14 |
| n3-6129 | A-266 | B-14 |
| n3-6130 | A-267 | B-14 |
| n3-6131 | A-268 | B-14 |
| n3-6132 | A-269 | B-14 |
| n3-6133 | A-270 | B-14 |
| n3-6134 | A-271 | B-14 |
| n3-6135 | A-272 | B-14 |
| n3-6136 | A-273 | B-14 |
| n3-6137 | A-274 | B-14 |

TABLE 1-continued

| epn | n = 3 A | B |
|---|---|---|
| n3-6138 | A-275 | B-14 |
| n3-6139 | A-276 | B-14 |
| n3-6140 | A-277 | B-14 |
| n3-6141 | A-278 | B-14 |
| n3-6142 | A-279 | B-14 |
| n3-6143 | A-280 | B-14 |
| n3-6144 | A-281 | B-14 |
| n3-6145 | A-282 | B-14 |
| n3-6146 | A-283 | B-14 |
| n3-6147 | A-284 | B-14 |
| n3-6148 | A-285 | B-14 |
| n3-6149 | A-286 | B-14 |
| n3-6150 | A-287 | B-14 |
| n3-6151 | A-288 | B-14 |
| n3-6152 | A-289 | B-14 |
| n3-6153 | A-290 | B-14 |
| n3-6154 | A-291 | B-14 |
| n3-6155 | A-292 | B-14 |
| n3-6156 | A-293 | B-14 |
| n3-6157 | A-294 | B-14 |
| n3-6158 | A-295 | B-14 |
| n3-6159 | A-296 | B-14 |
| n3-6160 | A-297 | B-14 |
| n3-6161 | A-298 | B-14 |
| n3-6162 | A-299 | B-14 |
| n3-6163 | A-300 | B-14 |
| n3-6164 | A-301 | B-14 |
| n3-6165 | A-302 | B-14 |
| n3-6166 | A-303 | B-14 |
| n3-6167 | A-304 | B-14 |
| n3-6168 | A-305 | B-14 |
| n3-6169 | A-306 | B-14 |
| n3-6170 | A-307 | B-14 |
| n3-6171 | A-308 | B-14 |
| n3-6172 | A-309 | B-14 |
| n3-6173 | A-310 | B-14 |
| n3-6174 | A-311 | B-14 |
| n3-6175 | A-312 | B-14 |
| n3-6176 | A-313 | B-14 |
| n3-6177 | A-314 | B-14 |
| n3-6178 | A-315 | B-14 |
| n3-6179 | A-316 | B-14 |
| n3-6180 | A-317 | B-14 |
| n3-6181 | A-318 | B-14 |
| n3-6182 | A-319 | B-14 |
| n3-6183 | A-320 | B-14 |
| n3-6184 | A-321 | B-14 |
| n3-6185 | A-322 | B-14 |
| n3-6186 | A-323 | B-14 |
| n3-6187 | A-324 | B-14 |
| n3-6188 | A-325 | B-14 |
| n3-6189 | A-326 | B-14 |
| n3-6190 | A-327 | B-14 |
| n3-6191 | A-328 | B-14 |
| n3-6192 | A-329 | B-14 |
| n3-6193 | A-330 | B-14 |
| n3-6194 | A-331 | B-14 |
| n3-6195 | A-332 | B-14 |
| n3-6196 | A-333 | B-14 |
| n3-6197 | A-334 | B-14 |
| n3-6198 | A-335 | B-14 |
| n3-6199 | A-336 | B-14 |
| n3-6200 | A-337 | B-14 |
| n3-6201 | A-338 | B-14 |
| n3-6202 | A-339 | B-14 |
| n3-6203 | A-340 | B-14 |
| n3-6204 | A-341 | B-14 |
| n3-6205 | A-342 | B-14 |
| n3-6206 | A-343 | B-14 |
| n3-6207 | A-344 | B-14 |
| n3-6208 | A-345 | B-14 |
| n3-6209 | A-346 | B-14 |
| n3-6210 | A-347 | B-14 |
| n3-6211 | A-348 | B-14 |
| n3-6212 | A-349 | B-14 |
| n3-6213 | A-350 | B-14 |
| n3-6214 | A-351 | B-14 |
| n3-6215 | A-352 | B-14 |
| n3-6216 | A-353 | B-14 |
| n3-6217 | A-354 | B-14 |
| n3-6218 | A-355 | B-14 |
| n3-6219 | A-356 | B-14 |
| n3-6220 | A-357 | B-14 |
| n3-6221 | A-358 | B-14 |
| n3-6222 | A-359 | B-14 |
| n3-6223 | A-360 | B-14 |
| n3-6224 | A-361 | B-14 |
| n3-6225 | A-362 | B-14 |
| n3-6226 | A-363 | B-14 |
| n3-6227 | A-364 | B-14 |
| n3-6228 | A-365 | B-14 |
| n3-6229 | A-366 | B-14 |
| n3-6230 | A-367 | B-14 |
| n3-6231 | A-368 | B-14 |
| n3-6232 | A-369 | B-14 |
| n3-6233 | A-370 | B-14 |
| n3-6234 | A-371 | B-14 |
| n3-6235 | A-372 | B-14 |
| n3-6236 | A-373 | B-14 |
| n3-6237 | A-374 | B-14 |
| n3-6238 | A-375 | B-14 |
| n3-6239 | A-376 | B-14 |
| n3-6240 | A-377 | B-14 |
| n3-6241 | A-378 | B-14 |
| n3-6242 | A-379 | B-14 |
| n3-6243 | A-380 | B-14 |
| n3-6244 | A-381 | B-14 |
| n3-6245 | A-382 | B-14 |
| n3-6246 | A-383 | B-14 |
| n3-6247 | A-384 | B-14 |
| n3-6248 | A-385 | B-14 |
| n3-6249 | A-386 | B-14 |
| n3-6250 | A-387 | B-14 |
| n3-6251 | A-388 | B-14 |
| n3-6252 | A-389 | B-14 |
| n3-6253 | A-390 | B-14 |
| n3-6254 | A-391 | B-14 |
| n3-6255 | A-392 | B-14 |
| n3-6256 | A-393 | B-14 |
| n3-6257 | A-394 | B-14 |
| n3-6258 | A-395 | B-14 |
| n3-6259 | A-396 | B-14 |
| n3-6260 | A-397 | B-14 |
| n3-6261 | A-398 | B-14 |
| n3-6262 | A-399 | B-14 |
| n3-6263 | A-400 | B-14 |
| n3-6264 | A-401 | B-14 |
| n3-6265 | A-402 | B-14 |
| n3-6266 | A-403 | B-14 |
| n3-6267 | A-404 | B-14 |
| n3-6268 | A-405 | B-14 |
| n3-6269 | A-406 | B-14 |
| n3-6270 | A-407 | B-14 |
| n3-6271 | A-408 | B-14 |
| n3-6272 | A-409 | B-14 |
| n3-6273 | A-410 | B-14 |
| n3-6274 | A-411 | B-14 |
| n3-6275 | A-412 | B-14 |
| n3-6276 | A-413 | B-14 |
| n3-6277 | A-414 | B-14 |
| n3-6278 | A-415 | B-14 |
| n3-6279 | A-416 | B-14 |
| n3-6280 | A-417 | B-14 |
| n3-6281 | A-418 | B-14 |
| n3-6282 | A-419 | B-14 |
| n3-6283 | A-420 | B-14 |
| n3-6284 | A-421 | B-14 |
| n3-6285 | A-422 | B-14 |
| n3-6286 | A-423 | B-14 |
| n3-6287 | A-424 | B-14 |

TABLE 1-continued

| epn | n = 3 A | B |
|---|---|---|
| n3-6288 | A-425 | B-14 |
| n3-6289 | A-426 | B-14 |
| n3-6290 | A-427 | B-14 |
| n3-6291 | A-428 | B-14 |
| n3-6292 | A-429 | B-14 |
| n3-6293 | A-430 | B-14 |
| n3-6294 | A-431 | B-14 |
| n3-6295 | A-432 | B-14 |
| n3-6296 | A-433 | B-14 |
| n3-6297 | A-434 | B-14 |
| n3-6298 | A-435 | B-14 |
| n3-6299 | A-436 | B-14 |
| n3-6300 | A-437 | B-14 |
| n3-6301 | A-438 | B-14 |
| n3-6302 | A-439 | B-14 |
| n3-6303 | A-440 | B-14 |
| n3-6304 | A-441 | B-14 |
| n3-6305 | A-442 | B-14 |
| n3-6306 | A-443 | B-14 |
| n3-6307 | A-444 | B-14 |
| n3-6308 | A-445 | B-14 |
| n3-6309 | A-446 | B-14 |
| n3-6310 | A-447 | B-14 |
| n3-6311 | A-448 | B-14 |
| n3-6312 | A-449 | B-14 |
| n3-6313 | A-450 | B-14 |
| n3-6314 | A-451 | B-14 |
| n3-6315 | A-1 | B-15 |
| n3-6316 | A-2 | B-15 |
| n3-6317 | A-3 | B-15 |
| n3-6318 | A-4 | B-15 |
| n3-6319 | A-5 | B-15 |
| n3-6320 | A-6 | B-15 |
| n3-6321 | A-7 | B-15 |
| n3-6322 | A-8 | B-15 |
| n3-6323 | A-9 | B-15 |
| n3-6324 | A-10 | B-15 |
| n3-6325 | A-11 | B-15 |
| n3-6326 | A-12 | B-15 |
| n3-6327 | A-13 | B-15 |
| n3-6328 | A-14 | B-15 |
| n3-6329 | A-15 | B-15 |
| n3-6330 | A-16 | B-15 |
| n3-6331 | A-17 | B-15 |
| n3-6332 | A-18 | B-15 |
| n3-6333 | A-19 | B-15 |
| n3-6334 | A-20 | B-15 |
| n3-6335 | A-21 | B-15 |
| n3-6336 | A-22 | B-15 |
| n3-6337 | A-23 | B-15 |
| n3-6338 | A-24 | B-15 |
| n3-6339 | A-25 | B-15 |
| n3-6340 | A-26 | B-15 |
| n3-6341 | A-27 | B-15 |
| n3-6342 | A-28 | B-15 |
| n3-6343 | A-29 | B-15 |
| n3-6344 | A-30 | B-15 |
| n3-6345 | A-31 | B-15 |
| n3-6346 | A-32 | B-15 |
| n3-6347 | A-33 | B-15 |
| n3-6348 | A-34 | B-15 |
| n3-6349 | A-35 | B-15 |
| n3-6350 | A-36 | B-15 |
| n3-6351 | A-37 | B-15 |
| n3-6352 | A-38 | B-15 |
| n3-6353 | A-39 | B-15 |
| n3-6354 | A-40 | B-15 |
| n3-6355 | A-41 | B-15 |
| n3-6356 | A-42 | B-15 |
| n3-6357 | A-43 | B-15 |
| n3-6358 | A-44 | B-15 |
| n3-6359 | A-45 | B-15 |
| n3-6360 | A-46 | B-15 |
| n3-6361 | A-47 | B-15 |
| n3-6362 | A-48 | B-15 |
| n3-6363 | A-49 | B-15 |
| n3-6364 | A-50 | B-15 |
| n3-6365 | A-51 | B-15 |
| n3-6366 | A-52 | B-15 |
| n3-6367 | A-53 | B-15 |
| n3-6368 | A-54 | B-15 |
| n3-6369 | A-55 | B-15 |
| n3-6370 | A-56 | B-15 |
| n3-6371 | A-57 | B-15 |
| n3-6372 | A-58 | B-15 |
| n3-6373 | A-59 | B-15 |
| n3-6374 | A-60 | B-15 |
| n3-6375 | A-61 | B-15 |
| n3-6376 | A-62 | B-15 |
| n3-6377 | A-63 | B-15 |
| n3-6378 | A-64 | B-15 |
| n3-6379 | A-65 | B-15 |
| n3-6380 | A-66 | B-15 |
| n3-6381 | A-67 | B-15 |
| n3-6382 | A-68 | B-15 |
| n3-6383 | A-69 | B-15 |
| n3-6384 | A-70 | B-15 |
| n3-6385 | A-71 | B-15 |
| n3-6386 | A-72 | B-15 |
| n3-6387 | A-73 | B-15 |
| n3-6388 | A-74 | B-15 |
| n3-6389 | A-75 | B-15 |
| n3-6390 | A-76 | B-15 |
| n3-6391 | A-77 | B-15 |
| n3-6392 | A-78 | B-15 |
| n3-6393 | A-79 | B-15 |
| n3-6394 | A-80 | B-15 |
| n3-6395 | A-81 | B-15 |
| n3-6396 | A-82 | B-15 |
| n3-6397 | A-83 | B-15 |
| n3-6398 | A-84 | B-15 |
| n3-6399 | A-85 | B-15 |
| n3-6400 | A-86 | B-15 |
| n3-6401 | A-87 | B-15 |
| n3-6402 | A-88 | B-15 |
| n3-6403 | A-89 | B-15 |
| n3-6404 | A-90 | B-15 |
| n3-6405 | A-91 | B-15 |
| n3-6406 | A-92 | B-15 |
| n3-6407 | A-93 | B-15 |
| n3-6408 | A-94 | B-15 |
| n3-6409 | A-95 | B-15 |
| n3-6410 | A-96 | B-15 |
| n3-6411 | A-97 | B-15 |
| n3-6412 | A-98 | B-15 |
| n3-6413 | A-99 | B-15 |
| n3-6414 | A-100 | B-15 |
| n3-6415 | A-101 | B-15 |
| n3-6416 | A-102 | B-15 |
| n3-6417 | A-103 | B-15 |
| n3-6418 | A-104 | B-15 |
| n3-6419 | A-105 | B-15 |
| n3-6420 | A-106 | B-15 |
| n3-6421 | A-107 | B-15 |
| n3-6422 | A-108 | B-15 |
| n3-6423 | A-109 | B-15 |
| n3-6424 | A-110 | B-15 |
| n3-6425 | A-111 | B-15 |
| n3-6426 | A-112 | B-15 |
| n3-6427 | A-113 | B-15 |
| n3-6428 | A-114 | B-15 |
| n3-6429 | A-115 | B-15 |
| n3-6430 | A-116 | B-15 |
| n3-6431 | A-117 | B-15 |
| n3-6432 | A-118 | B-15 |
| n3-6433 | A-119 | B-15 |
| n3-6434 | A-120 | B-15 |
| n3-6435 | A-121 | B-15 |
| n3-6436 | A-122 | B-15 |
| n3-6437 | A-123 | B-15 |

TABLE 1-continued

| | n = 3 | |
|---|---|---|
| epn | A | B |
| n3-6438 | A-124 | B-15 |
| n3-6439 | A-125 | B-15 |
| n3-6440 | A-126 | B-15 |
| n3-6441 | A-127 | B-15 |
| n3-6442 | A-128 | B-15 |
| n3-6443 | A-129 | B-15 |
| n3-6444 | A-130 | B-15 |
| n3-6445 | A-131 | B-15 |
| n3-6446 | A-132 | B-15 |
| n3-6447 | A-133 | B-15 |
| n3-6448 | A-134 | B-15 |
| n3-6449 | A-135 | B-15 |
| n3-6450 | A-136 | B-15 |
| n3-6451 | A-137 | B-15 |
| n3-6452 | A-138 | B-15 |
| n3-6453 | A-139 | B-15 |
| n3-6454 | A-140 | B-15 |
| n3-6455 | A-141 | B-15 |
| n3-6456 | A-142 | B-15 |
| n3-6457 | A-143 | B-15 |
| n3-6458 | A-144 | B-15 |
| n3-6459 | A-145 | B-15 |
| n3-6460 | A-146 | B-15 |
| n3-6461 | A-147 | B-15 |
| n3-6462 | A-148 | B-15 |
| n3-6463 | A-149 | B-15 |
| n3-6464 | A-150 | B-15 |
| n3-6465 | A-151 | B-15 |
| n3-6466 | A-152 | B-15 |
| n3-6467 | A-153 | B-15 |
| n3-6468 | A-154 | B-15 |
| n3-6469 | A-155 | B-15 |
| n3-6470 | A-156 | B-15 |
| n3-6471 | A-157 | B-15 |
| n3-6472 | A-158 | B-15 |
| n3-6473 | A-159 | B-15 |
| n3-6474 | A-160 | B-15 |
| n3-6475 | A-161 | B-15 |
| n3-6476 | A-162 | B-15 |
| n3-6477 | A-163 | B-15 |
| n3-6478 | A-164 | B-15 |
| n3-6479 | A-165 | B-15 |
| n3-6480 | A-166 | B-15 |
| n3-6481 | A-167 | B-15 |
| n3-6482 | A-168 | B-15 |
| n3-6483 | A-169 | B-15 |
| n3-6484 | A-170 | B-15 |
| n3-6485 | A-171 | B-15 |
| n3-6486 | A-172 | B-15 |
| n3-6487 | A-173 | B-15 |
| n3-6488 | A-174 | B-15 |
| n3-6489 | A-175 | B-15 |
| n3-6490 | A-176 | B-15 |
| n3-6491 | A-177 | B-15 |
| n3-6492 | A-178 | B-15 |
| n3-6493 | A-179 | B-15 |
| n3-6494 | A-180 | B-15 |
| n3-6495 | A-181 | B-15 |
| n3-6496 | A-182 | B-15 |
| n3-6497 | A-183 | B-15 |
| n3-6498 | A-184 | B-15 |
| n3-6499 | A-185 | B-15 |
| n3-6500 | A-186 | B-15 |
| n3-6501 | A-187 | B-15 |
| n3-6502 | A-188 | B-15 |
| n3-6503 | A-189 | B-15 |
| n3-6504 | A-190 | B-15 |
| n3-6505 | A-191 | B-15 |
| n3-6506 | A-192 | B-15 |
| n3-6507 | A-193 | B-15 |
| n3-6508 | A-194 | B-15 |
| n3-6509 | A-195 | B-15 |
| n3-6510 | A-196 | B-15 |
| n3-6511 | A-197 | B-15 |
| n3-6512 | A-198 | B-15 |
| n3-6513 | A-199 | B-15 |
| n3-6514 | A-200 | B-15 |
| n3-6515 | A-201 | B-15 |
| n3-6516 | A-202 | B-15 |
| n3-6517 | A-203 | B-15 |
| n3-6518 | A-204 | B-15 |
| n3-6519 | A-205 | B-15 |
| n3-6520 | A-206 | B-15 |
| n3-6521 | A-207 | B-15 |
| n3-6522 | A-208 | B-15 |
| n3-6523 | A-209 | B-15 |
| n3-6524 | A-210 | B-15 |
| n3-6525 | A-211 | B-15 |
| n3-6526 | A-212 | B-15 |
| n3-6527 | A-213 | B-15 |
| n3-6528 | A-214 | B-15 |
| n3-6529 | A-215 | B-15 |
| n3-6530 | A-216 | B-15 |
| n3-6531 | A-217 | B-15 |
| n3-6532 | A-218 | B-15 |
| n3-6533 | A-219 | B-15 |
| n3-6534 | A-220 | B-15 |
| n3-6535 | A-221 | B-15 |
| n3-6536 | A-222 | B-15 |
| n3-6537 | A-223 | B-15 |
| n3-6538 | A-224 | B-15 |
| n3-6539 | A-225 | B-15 |
| n3-6540 | A-226 | B-15 |
| n3-6541 | A-227 | B-15 |
| n3-6542 | A-228 | B-15 |
| n3-6543 | A-229 | B-15 |
| n3-6544 | A-230 | B-15 |
| n3-6545 | A-231 | B-15 |
| n3-6546 | A-232 | B-15 |
| n3-6547 | A-233 | B-15 |
| n3-6548 | A-234 | B-15 |
| n3-6549 | A-235 | B-15 |
| n3-6550 | A-236 | B-15 |
| n3-6551 | A-237 | B-15 |
| n3-6552 | A-238 | B-15 |
| n3-6553 | A-239 | B-15 |
| n3-6554 | A-240 | B-15 |
| n3-6555 | A-241 | B-15 |
| n3-6556 | A-242 | B-15 |
| n3-6557 | A-243 | B-15 |
| n3-6558 | A-244 | B-15 |
| n3-6559 | A-245 | B-15 |
| n3-6560 | A-246 | B-15 |
| n3-6561 | A-247 | B-15 |
| n3-6562 | A-248 | B-15 |
| n3-6563 | A-249 | B-15 |
| n3-6564 | A-250 | B-15 |
| n3-6565 | A-251 | B-15 |
| n3-6566 | A-252 | B-15 |
| n3-6567 | A-253 | B-15 |
| n3-6568 | A-254 | B-15 |
| n3-6569 | A-255 | B-15 |
| n3-6570 | A-256 | B-15 |
| n3-6571 | A-257 | B-15 |
| n3-6572 | A-258 | B-15 |
| n3-6573 | A-259 | B-15 |
| n3-6574 | A-260 | B-15 |
| n3-6575 | A-261 | B-15 |
| n3-6576 | A-262 | B-15 |
| n3-6577 | A-263 | B-15 |
| n3-6578 | A-264 | B-15 |
| n3-6579 | A-265 | B-15 |
| n3-6580 | A-266 | B-15 |
| n3-6581 | A-267 | B-15 |
| n3-6582 | A-268 | B-15 |
| n3-6583 | A-269 | B-15 |
| n3-6584 | A-270 | B-15 |
| n3-6585 | A-271 | B-15 |
| n3-6586 | A-272 | B-15 |
| n3-6587 | A-273 | B-15 |

TABLE 1-continued

| epn | n = 3 A | B |
|---|---|---|
| n3-6588 | A-274 | B-15 |
| n3-6589 | A-275 | B-15 |
| n3-6590 | A-276 | B-15 |
| n3-6591 | A-277 | B-15 |
| n3-6592 | A-278 | B-15 |
| n3-6593 | A-279 | B-15 |
| n3-6594 | A-280 | B-15 |
| n3-6595 | A-281 | B-15 |
| n3-6596 | A-282 | B-15 |
| n3-6597 | A-283 | B-15 |
| n3-6598 | A-284 | B-15 |
| n3-6599 | A-285 | B-15 |
| n3-6600 | A-286 | B-15 |
| n3-6601 | A-287 | B-15 |
| n3-6602 | A-288 | B-15 |
| n3-6603 | A-289 | B-15 |
| n3-6604 | A-290 | B-15 |
| n3-6605 | A-291 | B-15 |
| n3-6606 | A-292 | B-15 |
| n3-6607 | A-293 | B-15 |
| n3-6608 | A-294 | B-15 |
| n3-6609 | A-295 | B-15 |
| n3-6610 | A-296 | B-15 |
| n3-6611 | A-297 | B-15 |
| n3-6612 | A-298 | B-15 |
| n3-6613 | A-299 | B-15 |
| n3-6614 | A-300 | B-15 |
| n3-6615 | A-301 | B-15 |
| n3-6616 | A-302 | B-15 |
| n3-6617 | A-303 | B-15 |
| n3-6618 | A-304 | B-15 |
| n3-6619 | A-305 | B-15 |
| n3-6620 | A-306 | B-15 |
| n3-6621 | A-307 | B-15 |
| n3-6622 | A-308 | B-15 |
| n3-6623 | A-309 | B-15 |
| n3-6624 | A-310 | B-15 |
| n3-6625 | A-311 | B-15 |
| n3-6626 | A-312 | B-15 |
| n3-6627 | A-313 | B-15 |
| n3-6628 | A-314 | B-15 |
| n3-6629 | A-315 | B-15 |
| n3-6630 | A-316 | B-15 |
| n3-6631 | A-317 | B-15 |
| n3-6632 | A-318 | B-15 |
| n3-6633 | A-319 | B-15 |
| n3-6634 | A-320 | B-15 |
| n3-6635 | A-321 | B-15 |
| n3-6636 | A-322 | B-15 |
| n3-6637 | A-323 | B-15 |
| n3-6638 | A-324 | B-15 |
| n3-6639 | A-325 | B-15 |
| n3-6640 | A-326 | B-15 |
| n3-6641 | A-327 | B-15 |
| n3-6642 | A-328 | B-15 |
| n3-6643 | A-329 | B-15 |
| n3-6644 | A-330 | B-15 |
| n3-6645 | A-331 | B-15 |
| n3-6646 | A-332 | B-15 |
| n3-6647 | A-333 | B-15 |
| n3-6648 | A-334 | B-15 |
| n3-6649 | A-335 | B-15 |
| n3-6650 | A-336 | B-15 |
| n3-6651 | A-337 | B-15 |
| n3-6652 | A-338 | B-15 |
| n3-6653 | A-339 | B-15 |
| n3-6654 | A-340 | B-15 |
| n3-6655 | A-341 | B-15 |
| n3-6656 | A-342 | B-15 |
| n3-6657 | A-343 | B-15 |
| n3-6658 | A-344 | B-15 |
| n3-6659 | A-345 | B-15 |
| n3-6660 | A-346 | B-15 |
| n3-6661 | A-347 | B-15 |
| n3-6662 | A-348 | B-15 |
| n3-6663 | A-349 | B-15 |
| n3-6664 | A-350 | B-15 |
| n3-6665 | A-351 | B-15 |
| n3-6666 | A-352 | B-15 |
| n3-6667 | A-353 | B-15 |
| n3-6668 | A-354 | B-15 |
| n3-6669 | A-355 | B-15 |
| n3-6670 | A-356 | B-15 |
| n3-6671 | A-357 | B-15 |
| n3-6672 | A-358 | B-15 |
| n3-6673 | A-359 | B-15 |
| n3-6674 | A-360 | B-15 |
| n3-6675 | A-361 | B-15 |
| n3-6676 | A-362 | B-15 |
| n3-6677 | A-363 | B-15 |
| n3-6678 | A-364 | B-15 |
| n3-6679 | A-365 | B-15 |
| n3-6680 | A-366 | B-15 |
| n3-6681 | A-367 | B-15 |
| n3-6682 | A-368 | B-15 |
| n3-6683 | A-369 | B-15 |
| n3-6684 | A-370 | B-15 |
| n3-6685 | A-371 | B-15 |
| n3-6686 | A-372 | B-15 |
| n3-6687 | A-373 | B-15 |
| n3-6688 | A-374 | B-15 |
| n3-6689 | A-375 | B-15 |
| n3-6690 | A-376 | B-15 |
| n3-6691 | A-377 | B-15 |
| n3-6692 | A-378 | B-15 |
| n3-6693 | A-379 | B-15 |
| n3-6694 | A-380 | B-15 |
| n3-6695 | A-381 | B-15 |
| n3-6696 | A-382 | B-15 |
| n3-6697 | A-383 | B-15 |
| n3-6698 | A-384 | B-15 |
| n3-6699 | A-385 | B-15 |
| n3-6700 | A-386 | B-15 |
| n3-6701 | A-387 | B-15 |
| n3-6702 | A-388 | B-15 |
| n3-6703 | A-389 | B-15 |
| n3-6704 | A-390 | B-15 |
| n3-6705 | A-391 | B-15 |
| n3-6706 | A-392 | B-15 |
| n3-6707 | A-393 | B-15 |
| n3-6708 | A-394 | B-15 |
| n3-6709 | A-395 | B-15 |
| n3-6710 | A-396 | B-15 |
| n3-6711 | A-397 | B-15 |
| n3-6712 | A-398 | B-15 |
| n3-6713 | A-399 | B-15 |
| n3-6714 | A-400 | B-15 |
| n3-6715 | A-401 | B-15 |
| n3-6716 | A-402 | B-15 |
| n3-6717 | A-403 | B-15 |
| n3-6718 | A-404 | B-15 |
| n3-6719 | A-405 | B-15 |
| n3-6720 | A-406 | B-15 |
| n3-6721 | A-407 | B-15 |
| n3-6722 | A-408 | B-15 |
| n3-6723 | A-409 | B-15 |
| n3-6724 | A-410 | B-15 |
| n3-6725 | A-411 | B-15 |
| n3-6726 | A-412 | B-15 |
| n3-6727 | A-413 | B-15 |
| n3-6728 | A-414 | B-15 |
| n3-6729 | A-415 | B-15 |
| n3-6730 | A-416 | B-15 |
| n3-6731 | A-417 | B-15 |
| n3-6732 | A-418 | B-15 |
| n3-6733 | A-419 | B-15 |
| n3-6734 | A-420 | B-15 |
| n3-6735 | A-421 | B-15 |
| n3-6736 | A-422 | B-15 |
| n3-6737 | A-423 | B-15 |

TABLE 1-continued

| epn | n = 3 A | B |
|---|---|---|
| n3-6738 | A-424 | B-15 |
| n3-6739 | A-425 | B-15 |
| n3-6740 | A-426 | B-15 |
| n3-6741 | A-427 | B-15 |
| n3-6742 | A-428 | B-15 |
| n3-6743 | A-429 | B-15 |
| n3-6744 | A-430 | B-15 |
| n3-6745 | A-431 | B-15 |
| n3-6746 | A-432 | B-15 |
| n3-6747 | A-433 | B-15 |
| n3-6748 | A-434 | B-15 |
| n3-6749 | A-435 | B-15 |
| n3-6750 | A-436 | B-15 |
| n3-6751 | A-437 | B-15 |
| n3-6752 | A-438 | B-15 |
| n3-6753 | A-439 | B-15 |
| n3-6754 | A-440 | B-15 |
| n3-6755 | A-441 | B-15 |
| n3-6756 | A-442 | B-15 |
| n3-6757 | A-443 | B-15 |
| n3-6758 | A-444 | B-15 |
| n3-6759 | A-445 | B-15 |
| n3-6760 | A-446 | B-15 |
| n3-6761 | A-447 | B-15 |
| n3-6762 | A-448 | B-15 |
| n3-6763 | A-449 | B-15 |
| n3-6764 | A-450 | B-15 |
| n3-6765 | A-451 | B-15 |
| n3-6766 | A-1 | B-16 |
| n3-6767 | A-2 | B-16 |
| n3-6768 | A-3 | B-16 |
| n3-6769 | A-4 | B-16 |
| n3-6770 | A-5 | B-16 |
| n3-6771 | A-6 | B-16 |
| n3-6772 | A-7 | B-16 |
| n3-6773 | A-8 | B-16 |
| n3-6774 | A-9 | B-16 |
| n3-6775 | A-10 | B-16 |
| n3-6776 | A-11 | B-16 |
| n3-6777 | A-12 | B-16 |
| n3-6778 | A-13 | B-16 |
| n3-6779 | A-14 | B-16 |
| n3-6780 | A-15 | B-16 |
| n3-6781 | A-16 | B-16 |
| n3-6782 | A-17 | B-16 |
| n3-6783 | A-18 | B-16 |
| n3-6784 | A-19 | B-16 |
| n3-6785 | A-20 | B-16 |
| n3-6786 | A-21 | B-16 |
| n3-6787 | A-22 | B-16 |
| n3-6788 | A-23 | B-16 |
| n3-6789 | A-24 | B-16 |
| n3-6790 | A-25 | B-16 |
| n3-6791 | A-26 | B-16 |
| n3-6792 | A-27 | B-16 |
| n3-6793 | A-28 | B-16 |
| n3-6794 | A-29 | B-16 |
| n3-6795 | A-30 | B-16 |
| n3-6796 | A-31 | B-16 |
| n3-6797 | A-32 | B-16 |
| n3-6798 | A-33 | B-16 |
| n3-6799 | A-34 | B-16 |
| n3-6800 | A-35 | B-16 |
| n3-6801 | A-36 | B-16 |
| n3-6802 | A-37 | B-16 |
| n3-6803 | A-38 | B-16 |
| n3-6804 | A-39 | B-16 |
| n3-6805 | A-40 | B-16 |
| n3-6806 | A-41 | B-16 |
| n3-6807 | A-42 | B-16 |
| n3-6808 | A-43 | B-16 |
| n3-6809 | A-44 | B-16 |
| n3-6810 | A-45 | B-16 |
| n3-6811 | A-46 | B-16 |
| n3-6812 | A-47 | B-16 |
| n3-6813 | A-48 | B-16 |
| n3-6814 | A-49 | B-16 |
| n3-6815 | A-50 | B-16 |
| n3-6816 | A-51 | B-16 |
| n3-6817 | A-52 | B-16 |
| n3-6818 | A-53 | B-16 |
| n3-6819 | A-54 | B-16 |
| n3-6820 | A-55 | B-16 |
| n3-6821 | A-56 | B-16 |
| n3-6822 | A-57 | B-16 |
| n3-6823 | A-58 | B-16 |
| n3-6824 | A-59 | B-16 |
| n3-6825 | A-60 | B-16 |
| n3-6826 | A-61 | B-16 |
| n3-6827 | A-62 | B-16 |
| n3-6828 | A-63 | B-16 |
| n3-6829 | A-64 | B-16 |
| n3-6830 | A-65 | B-16 |
| n3-6831 | A-66 | B-16 |
| n3-6832 | A-67 | B-16 |
| n3-6833 | A-68 | B-16 |
| n3-6834 | A-69 | B-16 |
| n3-6835 | A-70 | B-16 |
| n3-6836 | A-71 | B-16 |
| n3-6837 | A-72 | B-16 |
| n3-6838 | A-73 | B-16 |
| n3-6839 | A-74 | B-16 |
| n3-6840 | A-75 | B-16 |
| n3-6841 | A-76 | B-16 |
| n3-6842 | A-77 | B-16 |
| n3-6843 | A-78 | B-16 |
| n3-6844 | A-79 | B-16 |
| n3-6845 | A-80 | B-16 |
| n3-6846 | A-81 | B-16 |
| n3-6847 | A-82 | B-16 |
| n3-6848 | A-83 | B-16 |
| n3-6849 | A-84 | B-16 |
| n3-6850 | A-85 | B-16 |
| n3-6851 | A-86 | B-16 |
| n3-6852 | A-87 | B-16 |
| n3-6853 | A-88 | B-16 |
| n3-6854 | A-89 | B-16 |
| n3-6855 | A-90 | B-16 |
| n3-6856 | A-91 | B-16 |
| n3-6857 | A-92 | B-16 |
| n3-6858 | A-93 | B-16 |
| n3-6859 | A-94 | B-16 |
| n3-6860 | A-95 | B-16 |
| n3-6861 | A-96 | B-16 |
| n3-6862 | A-97 | B-16 |
| n3-6863 | A-98 | B-16 |
| n3-6864 | A-99 | B-16 |
| n3-6865 | A-100 | B-16 |
| n3-6866 | A-101 | B-16 |
| n3-6867 | A-102 | B-16 |
| n3-6868 | A-103 | B-16 |
| n3-6869 | A-104 | B-16 |
| n3-6870 | A-105 | B-16 |
| n3-6871 | A-106 | B-16 |
| n3-6872 | A-107 | B-16 |
| n3-6873 | A-108 | B-16 |
| n3-6874 | A-109 | B-16 |
| n3-6875 | A-110 | B-16 |
| n3-6876 | A-111 | B-16 |
| n3-6877 | A-112 | B-16 |
| n3-6878 | A-113 | B-16 |
| n3-6879 | A-114 | B-16 |
| n3-6880 | A-115 | B-16 |
| n3-6881 | A-116 | B-16 |
| n3-6882 | A-117 | B-16 |
| n3-6883 | A-118 | B-16 |
| n3-6884 | A-119 | B-16 |
| n3-6885 | A-120 | B-16 |
| n3-6886 | A-121 | B-16 |
| n3-6887 | A-122 | B-16 |

TABLE 1-continued

| epn | n = 3 A | B |
|---|---|---|
| n3-6888 | A-123 | B-16 |
| n3-6889 | A-124 | B-16 |
| n3-6890 | A-125 | B-16 |
| n3-6891 | A-126 | B-16 |
| n3-6892 | A-127 | B-16 |
| n3-6893 | A-128 | B-16 |
| n3-6894 | A-129 | B-16 |
| n3-6895 | A-130 | B-16 |
| n3-6896 | A-131 | B-16 |
| n3-6897 | A-132 | B-16 |
| n3-6898 | A-133 | B-16 |
| n3-6899 | A-134 | B-16 |
| n3-6900 | A-135 | B-16 |
| n3-6901 | A-136 | B-16 |
| n3-6902 | A-137 | B-16 |
| n3-6903 | A-138 | B-16 |
| n3-6904 | A-139 | B-16 |
| n3-6905 | A-140 | B-16 |
| n3-6906 | A-141 | B-16 |
| n3-6907 | A-142 | B-16 |
| n3-6908 | A-143 | B-16 |
| n3-6909 | A-144 | B-16 |
| n3-6910 | A-145 | B-16 |
| n3-6911 | A-146 | B-16 |
| n3-6912 | A-147 | B-16 |
| n3-6913 | A-148 | B-16 |
| n3-6914 | A-149 | B-16 |
| n3-6915 | A-150 | B-16 |
| n3-6916 | A-151 | B-16 |
| n3-6917 | A-152 | B-16 |
| n3-6918 | A-153 | B-16 |
| n3-6919 | A-154 | B-16 |
| n3-6920 | A-155 | B-16 |
| n3-6921 | A-156 | B-16 |
| n3-6922 | A-157 | B-16 |
| n3-6923 | A-158 | B-16 |
| n3-6924 | A-159 | B-16 |
| n3-6925 | A-160 | B-16 |
| n3-6926 | A-161 | B-16 |
| n3-6927 | A-162 | B-16 |
| n3-6928 | A-163 | B-16 |
| n3-6929 | A-164 | B-16 |
| n3-6930 | A-165 | B-16 |
| n3-6931 | A-166 | B-16 |
| n3-6932 | A-167 | B-16 |
| n3-6933 | A-168 | B-16 |
| n3-6934 | A-169 | B-16 |
| n3-6935 | A-170 | B-16 |
| n3-6936 | A-171 | B-16 |
| n3-6937 | A-172 | B-16 |
| n3-6938 | A-173 | B-16 |
| n3-6939 | A-174 | B-16 |
| n3-6940 | A-175 | B-16 |
| n3-6941 | A-176 | B-16 |
| n3-6942 | A-177 | B-16 |
| n3-6943 | A-178 | B-16 |
| n3-6944 | A-179 | B-16 |
| n3-6945 | A-180 | B-16 |
| n3-6946 | A-181 | B-16 |
| n3-6947 | A-182 | B-16 |
| n3-6948 | A-183 | B-16 |
| n3-6949 | A-184 | B-16 |
| n3-6950 | A-185 | B-16 |
| n3-6951 | A-186 | B-16 |
| n3-6952 | A-187 | B-16 |
| n3-6953 | A-188 | B-16 |
| n3-6954 | A-189 | B-16 |
| n3-6955 | A-190 | B-16 |
| n3-6956 | A-191 | B-16 |
| n3-6957 | A-192 | B-16 |
| n3-6958 | A-193 | B-16 |
| n3-6959 | A-194 | B-16 |
| n3-6960 | A-195 | B-16 |
| n3-6961 | A-196 | B-16 |
| n3-6962 | A-197 | B-16 |
| n3-6963 | A-198 | B-16 |
| n3-6964 | A-199 | B-16 |
| n3-6965 | A-200 | B-16 |
| n3-6966 | A-201 | B-16 |
| n3-6967 | A-202 | B-16 |
| n3-6968 | A-203 | B-16 |
| n3-6969 | A-204 | B-16 |
| n3-6970 | A-205 | B-16 |
| n3-6971 | A-206 | B-16 |
| n3-6972 | A-207 | B-16 |
| n3-6973 | A-208 | B-16 |
| n3-6974 | A-209 | B-16 |
| n3-6975 | A-210 | B-16 |
| n3-6976 | A-211 | B-16 |
| n3-6977 | A-212 | B-16 |
| n3-6978 | A-213 | B-16 |
| n3-6979 | A-214 | B-16 |
| n3-6980 | A-215 | B-16 |
| n3-6981 | A-216 | B-16 |
| n3-6982 | A-217 | B-16 |
| n3-6983 | A-218 | B-16 |
| n3-6984 | A-219 | B-16 |
| n3-6985 | A-220 | B-16 |
| n3-6986 | A-221 | B-16 |
| n3-6987 | A-222 | B-16 |
| n3-6988 | A-223 | B-16 |
| n3-6989 | A-224 | B-16 |
| n3-6990 | A-225 | B-16 |
| n3-6991 | A-226 | B-16 |
| n3-6992 | A-227 | B-16 |
| n3-6993 | A-228 | B-16 |
| n3-6994 | A-229 | B-16 |
| n3-6995 | A-230 | B-16 |
| n3-6996 | A-231 | B-16 |
| n3-6997 | A-232 | B-16 |
| n3-6998 | A-233 | B-16 |
| n3-6999 | A-234 | B-16 |
| n3-7000 | A-235 | B-16 |
| n3-7001 | A-236 | B-16 |
| n3-7002 | A-237 | B-16 |
| n3-7003 | A-238 | B-16 |
| n3-7004 | A-239 | B-16 |
| n3-7005 | A-240 | B-16 |
| n3-7006 | A-241 | B-16 |
| n3-7007 | A-242 | B-16 |
| n3-7008 | A-243 | B-16 |
| n3-7009 | A-244 | B-16 |
| n3-7010 | A-245 | B-16 |
| n3-7011 | A-246 | B-16 |
| n3-7012 | A-247 | B-16 |
| n3-7013 | A-248 | B-16 |
| n3-7014 | A-249 | B-16 |
| n3-7015 | A-250 | B-16 |
| n3-7016 | A-251 | B-16 |
| n3-7017 | A-252 | B-16 |
| n3-7018 | A-253 | B-16 |
| n3-7019 | A-254 | B-16 |
| n3-7020 | A-255 | B-16 |
| n3-7021 | A-256 | B-16 |
| n3-7022 | A-257 | B-16 |
| n3-7023 | A-258 | B-16 |
| n3-7024 | A-259 | B-16 |
| n3-7025 | A-260 | B-16 |
| n3-7026 | A-261 | B-16 |
| n3-7027 | A-262 | B-16 |
| n3-7028 | A-263 | B-16 |
| n3-7029 | A-264 | B-16 |
| n3-7030 | A-265 | B-16 |
| n3-7031 | A-266 | B-16 |
| n3-7032 | A-267 | B-16 |
| n3-7033 | A-268 | B-16 |
| n3-7034 | A-269 | B-16 |
| n3-7035 | A-270 | B-16 |
| n3-7036 | A-271 | B-16 |
| n3-7037 | A-272 | B-16 |

TABLE 1-continued

| epn | n = 3 A | B |
|---|---|---|
| n3-7038 | A-273 | B-16 |
| n3-7039 | A-274 | B-16 |
| n3-7040 | A-275 | B-16 |
| n3-7041 | A-276 | B-16 |
| n3-7042 | A-277 | B-16 |
| n3-7043 | A-278 | B-16 |
| n3-7044 | A-279 | B-16 |
| n3-7045 | A-280 | B-16 |
| n3-7046 | A-281 | B-16 |
| n3-7047 | A-282 | B-16 |
| n3-7048 | A-283 | B-16 |
| n3-7049 | A-284 | B-16 |
| n3-7050 | A-285 | B-16 |
| n3-7051 | A-286 | B-16 |
| n3-7052 | A-287 | B-16 |
| n3-7053 | A-288 | B-16 |
| n3-7054 | A-289 | B-16 |
| n3-7055 | A-290 | B-16 |
| n3-7056 | A-291 | B-16 |
| n3-7057 | A-292 | B-16 |
| n3-7058 | A-293 | B-16 |
| n3-7059 | A-294 | B-16 |
| n3-7060 | A-295 | B-16 |
| n3-7061 | A-296 | B-16 |
| n3-7062 | A-297 | B-16 |
| n3-7063 | A-298 | B-16 |
| n3-7064 | A-299 | B-16 |
| n3-7065 | A-300 | B-16 |
| n3-7066 | A-301 | B-16 |
| n3-7067 | A-302 | B-16 |
| n3-7068 | A-303 | B-16 |
| n3-7069 | A-304 | B-16 |
| n3-7070 | A-305 | B-16 |
| n3-7071 | A-306 | B-16 |
| n3-7072 | A-307 | B-16 |
| n3-7073 | A-308 | B-16 |
| n3-7074 | A-309 | B-16 |
| n3-7075 | A-310 | B-16 |
| n3-7076 | A-311 | B-16 |
| n3-7077 | A-312 | B-16 |
| n3-7078 | A-313 | B-16 |
| n3-7079 | A-314 | B-16 |
| n3-7080 | A-315 | B-16 |
| n3-7081 | A-316 | B-16 |
| n3-7082 | A-317 | B-16 |
| n3-7083 | A-318 | B-16 |
| n3-7084 | A-319 | B-16 |
| n3-7085 | A-320 | B-16 |
| n3-7086 | A-321 | B-16 |
| n3-7087 | A-322 | B-16 |
| n3-7088 | A-323 | B-16 |
| n3-7089 | A-324 | B-16 |
| n3-7090 | A-325 | B-16 |
| n3-7091 | A-326 | B-16 |
| n3-7092 | A-327 | B-16 |
| n3-7093 | A-328 | B-16 |
| n3-7094 | A-329 | B-16 |
| n3-7095 | A-330 | B-16 |
| n3-7096 | A-331 | B-16 |
| n3-7097 | A-332 | B-16 |
| n3-7098 | A-333 | B-16 |
| n3-7099 | A-334 | B-16 |
| n3-7100 | A-335 | B-16 |
| n3-7101 | A-336 | B-16 |
| n3-7102 | A-337 | B-16 |
| n3-7103 | A-338 | B-16 |
| n3-7104 | A-339 | B-16 |
| n3-7105 | A-340 | B-16 |
| n3-7106 | A-341 | B-16 |
| n3-7107 | A-342 | B-16 |
| n3-7108 | A-343 | B-16 |
| n3-7109 | A-344 | B-16 |
| n3-7110 | A-345 | B-16 |
| n3-7111 | A-346 | B-16 |
| n3-7112 | A-347 | B-16 |
| n3-7113 | A-348 | B-16 |
| n3-7114 | A-349 | B-16 |
| n3-7115 | A-350 | B-16 |
| n3-7116 | A-351 | B-16 |
| n3-7117 | A-352 | B-16 |
| n3-7118 | A-353 | B-16 |
| n3-7119 | A-354 | B-16 |
| n3-7120 | A-355 | B-16 |
| n3-7121 | A-356 | B-16 |
| n3-7122 | A-357 | B-16 |
| n3-7123 | A-358 | B-16 |
| n3-7124 | A-359 | B-16 |
| n3-7125 | A-360 | B-16 |
| n3-7126 | A-361 | B-16 |
| n3-7127 | A-362 | B-16 |
| n3-7128 | A-363 | B-16 |
| n3-7129 | A-364 | B-16 |
| n3-7130 | A-365 | B-16 |
| n3-7131 | A-366 | B-16 |
| n3-7132 | A-367 | B-16 |
| n3-7133 | A-368 | B-16 |
| n3-7134 | A-369 | B-16 |
| n3-7135 | A-370 | B-16 |
| n3-7136 | A-371 | B-16 |
| n3-7137 | A-372 | B-16 |
| n3-7138 | A-373 | B-16 |
| n3-7139 | A-374 | B-16 |
| n3-7140 | A-375 | B-16 |
| n3-7141 | A-376 | B-16 |
| n3-7142 | A-377 | B-16 |
| n3-7143 | A-378 | B-16 |
| n3-7144 | A-379 | B-16 |
| n3-7145 | A-380 | B-16 |
| n3-7146 | A-381 | B-16 |
| n3-7147 | A-382 | B-16 |
| n3-7148 | A-383 | B-16 |
| n3-7149 | A-384 | B-16 |
| n3-7150 | A-385 | B-16 |
| n3-7151 | A-386 | B-16 |
| n3-7152 | A-387 | B-16 |
| n3-7153 | A-388 | B-16 |
| n3-7154 | A-389 | B-16 |
| n3-7155 | A-390 | B-16 |
| n3-7156 | A-391 | B-16 |
| n3-7157 | A-392 | B-16 |
| n3-7158 | A-393 | B-16 |
| n3-7159 | A-394 | B-16 |
| n3-7160 | A-395 | B-16 |
| n3-7161 | A-396 | B-16 |
| n3-7162 | A-397 | B-16 |
| n3-7163 | A-398 | B-16 |
| n3-7164 | A-399 | B-16 |
| n3-7165 | A-400 | B-16 |
| n3-7166 | A-401 | B-16 |
| n3-7167 | A-402 | B-16 |
| n3-7168 | A-403 | B-16 |
| n3-7169 | A-404 | B-16 |
| n3-7170 | A-405 | B-16 |
| n3-7171 | A-406 | B-16 |
| n3-7172 | A-407 | B-16 |
| n3-7173 | A-408 | B-16 |
| n3-7174 | A-409 | B-16 |
| n3-7175 | A-410 | B-16 |
| n3-7176 | A-411 | B-16 |
| n3-7177 | A-412 | B-16 |
| n3-7178 | A-413 | B-16 |
| n3-7179 | A-414 | B-16 |
| n3-7180 | A-415 | B-16 |
| n3-7181 | A-416 | B-16 |
| n3-7182 | A-417 | B-16 |
| n3-7183 | A-418 | B-16 |
| n3-7184 | A-419 | B-16 |
| n3-7185 | A-420 | B-16 |
| n3-7186 | A-421 | B-16 |
| n3-7187 | A-422 | B-16 |

TABLE 1-continued

| epn | n = 3 A | B |
|---|---|---|
| n3-7188 | A-423 | B-16 |
| n3-7189 | A-424 | B-16 |
| n3-7190 | A-425 | B-16 |
| n3-7191 | A-426 | B-16 |
| n3-7192 | A-427 | B-16 |
| n3-7193 | A-428 | B-16 |
| n3-7194 | A-429 | B-16 |
| n3-7195 | A-430 | B-16 |
| n3-7196 | A-431 | B-16 |
| n3-7197 | A-432 | B-16 |
| n3-7198 | A-433 | B-16 |
| n3-7199 | A-434 | B-16 |
| n3-7200 | A-435 | B-16 |
| n3-7201 | A-436 | B-16 |
| n3-7202 | A-437 | B-16 |
| n3-7203 | A-438 | B-16 |
| n3-7204 | A-439 | B-16 |
| n3-7205 | A-440 | B-16 |
| n3-7206 | A-441 | B-16 |
| n3-7207 | A-442 | B-16 |
| n3-7208 | A-443 | B-16 |
| n3-7209 | A-444 | B-16 |
| n3-7210 | A-445 | B-16 |
| n3-7211 | A-446 | B-16 |
| n3-7212 | A-447 | B-16 |
| n3-7213 | A-448 | B-16 |
| n3-7214 | A-449 | B-16 |
| n3-7215 | A-450 | B-16 |
| n3-7216 | A-451 | B-16 |
| n3-7217 | A-1 | B-17 |
| n3-7218 | A-2 | B-17 |
| n3-7219 | A-3 | B-17 |
| n3-7220 | A-4 | B-17 |
| n3-7221 | A-5 | B-17 |
| n3-7222 | A-6 | B-17 |
| n3-7223 | A-7 | B-17 |
| n3-7224 | A-8 | B-17 |
| n3-7225 | A-9 | B-17 |
| n3-7226 | A-10 | B-17 |
| n3-7227 | A-11 | B-17 |
| n3-7228 | A-12 | B-17 |
| n3-7229 | A-13 | B-17 |
| n3-7230 | A-14 | B-17 |
| n3-7231 | A-15 | B-17 |
| n3-7232 | A-16 | B-17 |
| n3-7233 | A-17 | B-17 |
| n3-7234 | A-18 | B-17 |
| n3-7235 | A-19 | B-17 |
| n3-7236 | A-20 | B-17 |
| n3-7237 | A-21 | B-17 |
| n3-7238 | A-22 | B-17 |
| n3-7239 | A-23 | B-17 |
| n3-7240 | A-24 | B-17 |
| n3-7241 | A-25 | B-17 |
| n3-7242 | A-26 | B-17 |
| n3-7243 | A-27 | B-17 |
| n3-7244 | A-28 | B-17 |
| n3-7245 | A-29 | B-17 |
| n3-7246 | A-30 | B-17 |
| n3-7247 | A-31 | B-17 |
| n3-7248 | A-32 | B-17 |
| n3-7249 | A-33 | B-17 |
| n3-7250 | A-34 | B-17 |
| n3-7251 | A-35 | B-17 |
| n3-7252 | A-36 | B-17 |
| n3-7253 | A-37 | B-17 |
| n3-7254 | A-38 | B-17 |
| n3-7255 | A-39 | B-17 |
| n3-7256 | A-40 | B-17 |
| n3-7257 | A-41 | B-17 |
| n3-7258 | A-42 | B-17 |
| n3-7259 | A-43 | B-17 |
| n3-7260 | A-44 | B-17 |
| n3-7261 | A-45 | B-17 |
| n3-7262 | A-46 | B-17 |
| n3-7263 | A-47 | B-17 |
| n3-7264 | A-48 | B-17 |
| n3-7265 | A-49 | B-17 |
| n3-7266 | A-50 | B-17 |
| n3-7267 | A-51 | B-17 |
| n3-7268 | A-52 | B-17 |
| n3-7269 | A-53 | B-17 |
| n3-7270 | A-54 | B-17 |
| n3-7271 | A-55 | B-17 |
| n3-7272 | A-56 | B-17 |
| n3-7273 | A-57 | B-17 |
| n3-7274 | A-58 | B-17 |
| n3-7275 | A-59 | B-17 |
| n3-7276 | A-60 | B-17 |
| n3-7277 | A-61 | B-17 |
| n3-7278 | A-62 | B-17 |
| n3-7279 | A-63 | B-17 |
| n3-7280 | A-64 | B-17 |
| n3-7281 | A-65 | B-17 |
| n3-7282 | A-66 | B-17 |
| n3-7283 | A-67 | B-17 |
| n3-7284 | A-68 | B-17 |
| n3-7285 | A-69 | B-17 |
| n3-7286 | A-70 | B-17 |
| n3-7287 | A-71 | B-17 |
| n3-7288 | A-72 | B-17 |
| n3-7289 | A-73 | B-17 |
| n3-7290 | A-74 | B-17 |
| n3-7291 | A-75 | B-17 |
| n3-7292 | A-76 | B-17 |
| n3-7293 | A-77 | B-17 |
| n3-7294 | A-78 | B-17 |
| n3-7295 | A-79 | B-17 |
| n3-7296 | A-80 | B-17 |
| n3-7297 | A-81 | B-17 |
| n3-7298 | A-82 | B-17 |
| n3-7299 | A-83 | B-17 |
| n3-7300 | A-84 | B-17 |
| n3-7301 | A-85 | B-17 |
| n3-7302 | A-86 | B-17 |
| n3-7303 | A-87 | B-17 |
| n3-7304 | A-88 | B-17 |
| n3-7305 | A-89 | B-17 |
| n3-7306 | A-90 | B-17 |
| n3-7307 | A-91 | B-17 |
| n3-7308 | A-92 | B-17 |
| n3-7309 | A-93 | B-17 |
| n3-7310 | A-94 | B-17 |
| n3-7311 | A-95 | B-17 |
| n3-7312 | A-96 | B-17 |
| n3-7313 | A-97 | B-17 |
| n3-7314 | A-98 | B-17 |
| n3-7315 | A-99 | B-17 |
| n3-7316 | A-100 | B-17 |
| n3-7317 | A-101 | B-17 |
| n3-7318 | A-102 | B-17 |
| n3-7319 | A-103 | B-17 |
| n3-7320 | A-104 | B-17 |
| n3-7321 | A-105 | B-17 |
| n3-7322 | A-106 | B-17 |
| n3-7323 | A-107 | B-17 |
| n3-7324 | A-108 | B-17 |
| n3-7325 | A-109 | B-17 |
| n3-7326 | A-110 | B-17 |
| n3-7327 | A-111 | B-17 |
| n3-7328 | A-112 | B-17 |
| n3-7329 | A-113 | B-17 |
| n3-7330 | A-114 | B-17 |
| n3-7331 | A-115 | B-17 |
| n3-7332 | A-116 | B-17 |
| n3-7333 | A-117 | B-17 |
| n3-7334 | A-118 | B-17 |
| n3-7335 | A-119 | B-17 |
| n3-7336 | A-120 | B-17 |
| n3-7337 | A-121 | B-17 |

TABLE 1-continued

| epn | n = 3 A | B |
|---|---|---|
| n3-7338 | A-122 | B-17 |
| n3-7339 | A-123 | B-17 |
| n3-7340 | A-124 | B-17 |
| n3-7341 | A-125 | B-17 |
| n3-7342 | A-126 | B-17 |
| n3-7343 | A-127 | B-17 |
| n3-7344 | A-128 | B-17 |
| n3-7345 | A-129 | B-17 |
| n3-7346 | A-130 | B-17 |
| n3-7347 | A-131 | B-17 |
| n3-7348 | A-132 | B-17 |
| n3-7349 | A-133 | B-17 |
| n3-7350 | A-134 | B-17 |
| n3-7351 | A-135 | B-17 |
| n3-7352 | A-136 | B-17 |
| n3-7353 | A-137 | B-17 |
| n3-7354 | A-138 | B-17 |
| n3-7355 | A-139 | B-17 |
| n3-7356 | A-140 | B-17 |
| n3-7357 | A-141 | B-17 |
| n3-7358 | A-142 | B-17 |
| n3-7359 | A-143 | B-17 |
| n3-7360 | A-144 | B-17 |
| n3-7361 | A-145 | B-17 |
| n3-7362 | A-146 | B-17 |
| n3-7363 | A-147 | B-17 |
| n3-7364 | A-148 | B-17 |
| n3-7365 | A-149 | B-17 |
| n3-7366 | A-150 | B-17 |
| n3-7367 | A-151 | B-17 |
| n3-7368 | A-152 | B-17 |
| n3-7369 | A-153 | B-17 |
| n3-7370 | A-154 | B-17 |
| n3-7371 | A-155 | B-17 |
| n3-7372 | A-156 | B-17 |
| n3-7373 | A-157 | B-17 |
| n3-7374 | A-158 | B-17 |
| n3-7375 | A-159 | B-17 |
| n3-7376 | A-160 | B-17 |
| n3-7377 | A-161 | B-17 |
| n3-7378 | A-162 | B-17 |
| n3-7379 | A-163 | B-17 |
| n3-7380 | A-164 | B-17 |
| n3-7381 | A-165 | B-17 |
| n3-7382 | A-166 | B-17 |
| n3-7383 | A-167 | B-17 |
| n3-7384 | A-168 | B-17 |
| n3-7385 | A-169 | B-17 |
| n3-7386 | A-170 | B-17 |
| n3-7387 | A-171 | B-17 |
| n3-7388 | A-172 | B-17 |
| n3-7389 | A-173 | B-17 |
| n3-7390 | A-174 | B-17 |
| n3-7391 | A-175 | B-17 |
| n3-7392 | A-176 | B-17 |
| n3-7393 | A-177 | B-17 |
| n3-7394 | A-178 | B-17 |
| n3-7395 | A-179 | B-17 |
| n3-7396 | A-180 | B-17 |
| n3-7397 | A-181 | B-17 |
| n3-7398 | A-182 | B-17 |
| n3-7399 | A-183 | B-17 |
| n3-7400 | A-184 | B-17 |
| n3-7401 | A-185 | B-17 |
| n3-7402 | A-186 | B-17 |
| n3-7403 | A-187 | B-17 |
| n3-7404 | A-188 | B-17 |
| n3-7405 | A-189 | B-17 |
| n3-7406 | A-190 | B-17 |
| n3-7407 | A-191 | B-17 |
| n3-7408 | A-192 | B-17 |
| n3-7409 | A-193 | B-17 |
| n3-7410 | A-194 | B-17 |
| n3-7411 | A-195 | B-17 |
| n3-7412 | A-196 | B-17 |
| n3-7413 | A-197 | B-17 |
| n3-7414 | A-198 | B-17 |
| n3-7415 | A-199 | B-17 |
| n3-7416 | A-200 | B-17 |
| n3-7417 | A-201 | B-17 |
| n3-7418 | A-202 | B-17 |
| n3-7419 | A-203 | B-17 |
| n3-7420 | A-204 | B-17 |
| n3-7421 | A-205 | B-17 |
| n3-7422 | A-206 | B-17 |
| n3-7423 | A-207 | B-17 |
| n3-7424 | A-208 | B-17 |
| n3-7425 | A-209 | B-17 |
| n3-7426 | A-210 | B-17 |
| n3-7427 | A-211 | B-17 |
| n3-7428 | A-212 | B-17 |
| n3-7429 | A-213 | B-17 |
| n3-7430 | A-214 | B-17 |
| n3-7431 | A-215 | B-17 |
| n3-7432 | A-216 | B-17 |
| n3-7433 | A-217 | B-17 |
| n3-7434 | A-218 | B-17 |
| n3-7435 | A-219 | B-17 |
| n3-7436 | A-220 | B-17 |
| n3-7437 | A-221 | B-17 |
| n3-7438 | A-222 | B-17 |
| n3-7439 | A-223 | B-17 |
| n3-7440 | A-224 | B-17 |
| n3-7441 | A-225 | B-17 |
| n3-7442 | A-226 | B-17 |
| n3-7443 | A-227 | B-17 |
| n3-7444 | A-228 | B-17 |
| n3-7445 | A-229 | B-17 |
| n3-7446 | A-230 | B-17 |
| n3-7447 | A-231 | B-17 |
| n3-7448 | A-232 | B-17 |
| n3-7449 | A-233 | B-17 |
| n3-7450 | A-234 | B-17 |
| n3-7451 | A-235 | B-17 |
| n3-7452 | A-236 | B-17 |
| n3-7453 | A-237 | B-17 |
| n3-7454 | A-238 | B-17 |
| n3-7455 | A-239 | B-17 |
| n3-7456 | A-240 | B-17 |
| n3-7457 | A-241 | B-17 |
| n3-7458 | A-242 | B-17 |
| n3-7459 | A-243 | B-17 |
| n3-7460 | A-244 | B-17 |
| n3-7461 | A-245 | B-17 |
| n3-7462 | A-246 | B-17 |
| n3-7463 | A-247 | B-17 |
| n3-7464 | A-248 | B-17 |
| n3-7465 | A-249 | B-17 |
| n3-7466 | A-250 | B-17 |
| n3-7467 | A-251 | B-17 |
| n3-7468 | A-252 | B-17 |
| n3-7469 | A-253 | B-17 |
| n3-7470 | A-254 | B-17 |
| n3-7471 | A-255 | B-17 |
| n3-7472 | A-256 | B-17 |
| n3-7473 | A-257 | B-17 |
| n3-7474 | A-258 | B-17 |
| n3-7475 | A-259 | B-17 |
| n3-7476 | A-260 | B-17 |
| n3-7477 | A-261 | B-17 |
| n3-7478 | A-262 | B-17 |
| n3-7479 | A-263 | B-17 |
| n3-7480 | A-264 | B-17 |
| n3-7481 | A-265 | B-17 |
| n3-7482 | A-266 | B-17 |
| n3-7483 | A-267 | B-17 |
| n3-7484 | A-268 | B-17 |
| n3-7485 | A-269 | B-17 |
| n3-7486 | A-270 | B-17 |
| n3-7487 | A-271 | B-17 |

TABLE 1-continued

| epn | n = 3 A | B |
|---|---|---|
| n3-7488 | A-272 | B-17 |
| n3-7489 | A-273 | B-17 |
| n3-7490 | A-274 | B-17 |
| n3-7491 | A-275 | B-17 |
| n3-7492 | A-276 | B-17 |
| n3-7493 | A-277 | B-17 |
| n3-7494 | A-278 | B-17 |
| n3-7495 | A-279 | B-17 |
| n3-7496 | A-280 | B-17 |
| n3-7497 | A-281 | B-17 |
| n3-7498 | A-282 | B-17 |
| n3-7499 | A-283 | B-17 |
| n3-7500 | A-284 | B-17 |
| n3-7501 | A-285 | B-17 |
| n3-7502 | A-286 | B-17 |
| n3-7503 | A-287 | B-17 |
| n3-7504 | A-288 | B-17 |
| n3-7505 | A-289 | B-17 |
| n3-7506 | A-290 | B-17 |
| n3-7507 | A-291 | B-17 |
| n3-7508 | A-292 | B-17 |
| n3-7509 | A-293 | B-17 |
| n3-7510 | A-294 | B-17 |
| n3-7511 | A-295 | B-17 |
| n3-7512 | A-296 | B-17 |
| n3-7513 | A-297 | B-17 |
| n3-7514 | A-298 | B-17 |
| n3-7515 | A-299 | B-17 |
| n3-7516 | A-300 | B-17 |
| n3-7517 | A-301 | B-17 |
| n3-7518 | A-302 | B-17 |
| n3-7519 | A-303 | B-17 |
| n3-7520 | A-304 | B-17 |
| n3-7521 | A-305 | B-17 |
| n3-7522 | A-306 | B-17 |
| n3-7523 | A-307 | B-17 |
| n3-7524 | A-308 | B-17 |
| n3-7525 | A-309 | B-17 |
| n3-7526 | A-310 | B-17 |
| n3-7527 | A-311 | B-17 |
| n3-7528 | A-312 | B-17 |
| n3-7529 | A-313 | B-17 |
| n3-7530 | A-314 | B-17 |
| n3-7531 | A-315 | B-17 |
| n3-7532 | A-316 | B-17 |
| n3-7533 | A-317 | B-17 |
| n3-7534 | A-318 | B-17 |
| n3-7535 | A-319 | B-17 |
| n3-7536 | A-320 | B-17 |
| n3-7537 | A-321 | B-17 |
| n3-7538 | A-322 | B-17 |
| n3-7539 | A-323 | B-17 |
| n3-7540 | A-324 | B-17 |
| n3-7541 | A-325 | B-17 |
| n3-7542 | A-326 | B-17 |
| n3-7543 | A-327 | B-17 |
| n3-7544 | A-328 | B-17 |
| n3-7545 | A-329 | B-17 |
| n3-7546 | A-330 | B-17 |
| n3-7547 | A-331 | B-17 |
| n3-7548 | A-332 | B-17 |
| n3-7549 | A-333 | B-17 |
| n3-7550 | A-334 | B-17 |
| n3-7551 | A-335 | B-17 |
| n3-7552 | A-336 | B-17 |
| n3-7553 | A-337 | B-17 |
| n3-7554 | A-338 | B-17 |
| n3-7555 | A-339 | B-17 |
| n3-7556 | A-340 | B-17 |
| n3-7557 | A-341 | B-17 |
| n3-7558 | A-342 | B-17 |
| n3-7559 | A-343 | B-17 |
| n3-7560 | A-344 | B-17 |
| n3-7561 | A-345 | B-17 |
| n3-7562 | A-346 | B-17 |
| n3-7563 | A-347 | B-17 |
| n3-7564 | A-348 | B-17 |
| n3-7565 | A-349 | B-17 |
| n3-7566 | A-350 | B-17 |
| n3-7567 | A-351 | B-17 |
| n3-7568 | A-352 | B-17 |
| n3-7569 | A-353 | B-17 |
| n3-7570 | A-354 | B-17 |
| n3-7571 | A-355 | B-17 |
| n3-7572 | A-356 | B-17 |
| n3-7573 | A-357 | B-17 |
| n3-7574 | A-358 | B-17 |
| n3-7575 | A-359 | B-17 |
| n3-7576 | A-360 | B-17 |
| n3-7577 | A-361 | B-17 |
| n3-7578 | A-362 | B-17 |
| n3-7579 | A-363 | B-17 |
| n3-7580 | A-364 | B-17 |
| n3-7581 | A-365 | B-17 |
| n3-7582 | A-366 | B-17 |
| n3-7583 | A-367 | B-17 |
| n3-7584 | A-368 | B-17 |
| n3-7585 | A-369 | B-17 |
| n3-7586 | A-370 | B-17 |
| n3-7587 | A-371 | B-17 |
| n3-7588 | A-372 | B-17 |
| n3-7589 | A-373 | B-17 |
| n3-7590 | A-374 | B-17 |
| n3-7591 | A-375 | B-17 |
| n3-7592 | A-376 | B-17 |
| n3-7593 | A-377 | B-17 |
| n3-7594 | A-378 | B-17 |
| n3-7595 | A-379 | B-17 |
| n3-7596 | A-380 | B-17 |
| n3-7597 | A-381 | B-17 |
| n3-7598 | A-382 | B-17 |
| n3-7599 | A-383 | B-17 |
| n3-7600 | A-384 | B-17 |
| n3-7601 | A-385 | B-17 |
| n3-7602 | A-386 | B-17 |
| n3-7603 | A-387 | B-17 |
| n3-7604 | A-388 | B-17 |
| n3-7605 | A-389 | B-17 |
| n3-7606 | A-390 | B-17 |
| n3-7607 | A-391 | B-17 |
| n3-7608 | A-392 | B-17 |
| n3-7609 | A-393 | B-17 |
| n3-7610 | A-394 | B-17 |
| n3-7611 | A-395 | B-17 |
| n3-7612 | A-396 | B-17 |
| n3-7613 | A-397 | B-17 |
| n3-7614 | A-398 | B-17 |
| n3-7615 | A-399 | B-17 |
| n3-7616 | A-400 | B-17 |
| n3-7617 | A-401 | B-17 |
| n3-7618 | A-402 | B-17 |
| n3-7619 | A-403 | B-17 |
| n3-7620 | A-404 | B-17 |
| n3-7621 | A-405 | B-17 |
| n3-7622 | A-406 | B-17 |
| n3-7623 | A-407 | B-17 |
| n3-7624 | A-408 | B-17 |
| n3-7625 | A-409 | B-17 |
| n3-7626 | A-410 | B-17 |
| n3-7627 | A-411 | B-17 |
| n3-7628 | A-412 | B-17 |
| n3-7629 | A-413 | B-17 |
| n3-7630 | A-414 | B-17 |
| n3-7631 | A-415 | B-17 |
| n3-7632 | A-416 | B-17 |
| n3-7633 | A-417 | B-17 |
| n3-7634 | A-418 | B-17 |
| n3-7635 | A-419 | B-17 |
| n3-7636 | A-420 | B-17 |
| n3-7637 | A-421 | B-17 |

TABLE 1-continued

| epn | n = 3 | |
|---|---|---|
| | A | B |
| n3-7638 | A-422 | B-17 |
| n3-7639 | A-423 | B-17 |
| n3-7640 | A-424 | B-17 |
| n3-7641 | A-425 | B-17 |
| n3-7642 | A-426 | B-17 |
| n3-7643 | A-427 | B-17 |
| n3-7644 | A-428 | B-17 |
| n3-7645 | A-429 | B-17 |
| n3-7646 | A-430 | B-17 |
| n3-7647 | A-431 | B-17 |
| n3-7648 | A-432 | B-17 |
| n3-7649 | A-433 | B-17 |
| n3-7650 | A-434 | B-17 |
| n3-7651 | A-435 | B-17 |
| n3-7652 | A-436 | B-17 |
| n3-7653 | A-437 | B-17 |
| n3-7654 | A-438 | B-17 |
| n3-7655 | A-439 | B-17 |
| n3-7656 | A-440 | B-17 |
| n3-7657 | A-441 | B-17 |
| n3-7658 | A-442 | B-17 |
| n3-7659 | A-443 | B-17 |
| n3-7660 | A-444 | B-17 |
| n3-7661 | A-445 | B-17 |
| n3-7662 | A-446 | B-17 |
| n3-7663 | A-447 | B-17 |
| n3-7664 | A-448 | B-17 |
| n3-7665 | A-449 | B-17 |
| n3-7666 | A-450 | B-17 |
| n3-7667 | A-451 | B-17 |
| n3-7668 | A-1 | B-18 |
| n3-7669 | A-2 | B-18 |
| n3-7670 | A-3 | B-18 |
| n3-7671 | A-4 | B-18 |
| n3-7672 | A-5 | B-18 |
| n3-7673 | A-6 | B-18 |
| n3-7674 | A-7 | B-18 |
| n3-7675 | A-8 | B-18 |
| n3-7676 | A-9 | B-18 |
| n3-7677 | A-10 | B-18 |
| n3-7678 | A-11 | B-18 |
| n3-7679 | A-12 | B-18 |
| n3-7680 | A-13 | B-18 |
| n3-7681 | A-14 | B-18 |
| n3-7682 | A-15 | B-18 |
| n3-7683 | A-16 | B-18 |
| n3-7684 | A-17 | B-18 |
| n3-7685 | A-18 | B-18 |
| n3-7686 | A-19 | B-18 |
| n3-7687 | A-20 | B-18 |
| n3-7688 | A-21 | B-18 |
| n3-7689 | A-22 | B-18 |
| n3-7690 | A-23 | B-18 |
| n3-7691 | A-24 | B-18 |
| n3-7692 | A-25 | B-18 |
| n3-7693 | A-26 | B-18 |
| n3-7694 | A-27 | B-18 |
| n3-7695 | A-28 | B-18 |
| n3-7696 | A-29 | B-18 |
| n3-7697 | A-30 | B-18 |
| n3-7698 | A-31 | B-18 |
| n3-7699 | A-32 | B-18 |
| n3-7700 | A-33 | B-18 |
| n3-7701 | A-34 | B-18 |
| n3-7702 | A-35 | B-18 |
| n3-7703 | A-36 | B-18 |
| n3-7704 | A-37 | B-18 |
| n3-7705 | A-38 | B-18 |
| n3-7706 | A-39 | B-18 |
| n3-7707 | A-40 | B-18 |
| n3-7708 | A-41 | B-18 |
| n3-7709 | A-42 | B-18 |
| n3-7710 | A-43 | B-18 |
| n3-7711 | A-44 | B-18 |
| n3-7712 | A-45 | B-18 |
| n3-7713 | A-46 | B-18 |
| n3-7714 | A-47 | B-18 |
| n3-7715 | A-48 | B-18 |
| n3-7716 | A-49 | B-18 |
| n3-7717 | A-50 | B-18 |
| n3-7718 | A-51 | B-18 |
| n3-7719 | A-52 | B-18 |
| n3-7720 | A-53 | B-18 |
| n3-7721 | A-54 | B-18 |
| n3-7722 | A-55 | B-18 |
| n3-7723 | A-56 | B-18 |
| n3-7724 | A-57 | B-18 |
| n3-7725 | A-58 | B-18 |
| n3-7726 | A-59 | B-18 |
| n3-7727 | A-60 | B-18 |
| n3-7728 | A-61 | B-18 |
| n3-7729 | A-62 | B-18 |
| n3-7730 | A-63 | B-18 |
| n3-7731 | A-64 | B-18 |
| n3-7732 | A-65 | B-18 |
| n3-7733 | A-66 | B-18 |
| n3-7734 | A-67 | B-18 |
| n3-7735 | A-68 | B-18 |
| n3-7736 | A-69 | B-18 |
| n3-7737 | A-70 | B-18 |
| n3-7738 | A-71 | B-18 |
| n3-7739 | A-72 | B-18 |
| n3-7740 | A-73 | B-18 |
| n3-7741 | A-74 | B-18 |
| n3-7742 | A-75 | B-18 |
| n3-7743 | A-76 | B-18 |
| n3-7744 | A-77 | B-18 |
| n3-7745 | A-78 | B-18 |
| n3-7746 | A-79 | B-18 |
| n3-7747 | A-80 | B-18 |
| n3-7748 | A-81 | B-18 |
| n3-7749 | A-82 | B-18 |
| n3-7750 | A-83 | B-18 |
| n3-7751 | A-84 | B-18 |
| n3-7752 | A-85 | B-18 |
| n3-7753 | A-86 | B-18 |
| n3-7754 | A-87 | B-18 |
| n3-7755 | A-88 | B-18 |
| n3-7756 | A-89 | B-18 |
| n3-7757 | A-90 | B-18 |
| n3-7758 | A-91 | B-18 |
| n3-7759 | A-92 | B-18 |
| n3-7760 | A-93 | B-18 |
| n3-7761 | A-94 | B-18 |
| n3-7762 | A-95 | B-18 |
| n3-7763 | A-96 | B-18 |
| n3-7764 | A-97 | B-18 |
| n3-7765 | A-98 | B-18 |
| n3-7766 | A-99 | B-18 |
| n3-7767 | A-100 | B-18 |
| n3-7768 | A-101 | B-18 |
| n3-7769 | A-102 | B-18 |
| n3-7770 | A-103 | B-18 |
| n3-7771 | A-104 | B-18 |
| n3-7772 | A-105 | B-18 |
| n3-7773 | A-106 | B-18 |
| n3-7774 | A-107 | B-18 |
| n3-7775 | A-108 | B-18 |
| n3-7776 | A-109 | B-18 |
| n3-7777 | A-110 | B-18 |
| n3-7778 | A-111 | B-18 |
| n3-7779 | A-112 | B-18 |
| n3-7780 | A-113 | B-18 |
| n3-7781 | A-114 | B-18 |
| n3-7782 | A-115 | B-18 |
| n3-7783 | A-116 | B-18 |
| n3-7784 | A-117 | B-18 |
| n3-7785 | A-118 | B-18 |
| n3-7786 | A-119 | B-18 |
| n3-7787 | A-120 | B-18 |

TABLE 1-continued

| epn | n = 3 A | B |
|---|---|---|
| n3-7788 | A-121 | B-18 |
| n3-7789 | A-122 | B-18 |
| n3-7790 | A-123 | B-18 |
| n3-7791 | A-124 | B-18 |
| n3-7792 | A-125 | B-18 |
| n3-7793 | A-126 | B-18 |
| n3-7794 | A-127 | B-18 |
| n3-7795 | A-128 | B-18 |
| n3-7796 | A-129 | B-18 |
| n3-7797 | A-130 | B-18 |
| n3-7798 | A-131 | B-18 |
| n3-7799 | A-132 | B-18 |
| n3-7800 | A-133 | B-18 |
| n3-7801 | A-134 | B-18 |
| n3-7802 | A-135 | B-18 |
| n3-7803 | A-136 | B-18 |
| n3-7804 | A-137 | B-18 |
| n3-7805 | A-138 | B-18 |
| n3-7806 | A-139 | B-18 |
| n3-7807 | A-140 | B-18 |
| n3-7808 | A-141 | B-18 |
| n3-7809 | A-142 | B-18 |
| n3-7810 | A-143 | B-18 |
| n3-7811 | A-144 | B-18 |
| n3-7812 | A-145 | B-18 |
| n3-7813 | A-146 | B-18 |
| n3-7814 | A-147 | B-18 |
| n3-7815 | A-148 | B-18 |
| n3-7816 | A-149 | B-18 |
| n3-7817 | A-150 | B-18 |
| n3-7818 | A-151 | B-18 |
| n3-7819 | A-152 | B-18 |
| n3-7820 | A-153 | B-18 |
| n3-7821 | A-154 | B-18 |
| n3-7822 | A-155 | B-18 |
| n3-7823 | A-156 | B-18 |
| n3-7824 | A-157 | B-18 |
| n3-7825 | A-158 | B-18 |
| n3-7826 | A-159 | B-18 |
| n3-7827 | A-160 | B-18 |
| n3-7828 | A-161 | B-18 |
| n3-7829 | A-162 | B-18 |
| n3-7830 | A-163 | B-18 |
| n3-7831 | A-164 | B-18 |
| n3-7832 | A-165 | B-18 |
| n3-7833 | A-166 | B-18 |
| n3-7834 | A-167 | B-18 |
| n3-7835 | A-168 | B-18 |
| n3-7836 | A-169 | B-18 |
| n3-7837 | A-170 | B-18 |
| n3-7838 | A-171 | B-18 |
| n3-7839 | A-172 | B-18 |
| n3-7840 | A-173 | B-18 |
| n3-7841 | A-174 | B-18 |
| n3-7842 | A-175 | B-18 |
| n3-7843 | A-176 | B-18 |
| n3-7844 | A-177 | B-18 |
| n3-7845 | A-178 | B-18 |
| n3-7846 | A-179 | B-18 |
| n3-7847 | A-180 | B-18 |
| n3-7848 | A-181 | B-18 |
| n3-7849 | A-182 | B-18 |
| n3-7850 | A-183 | B-18 |
| n3-7851 | A-184 | B-18 |
| n3-7852 | A-185 | B-18 |
| n3-7853 | A-186 | B-18 |
| n3-7854 | A-187 | B-18 |
| n3-7855 | A-188 | B-18 |
| n3-7856 | A-189 | B-18 |
| n3-7857 | A-190 | B-18 |
| n3-7858 | A-191 | B-18 |
| n3-7859 | A-192 | B-18 |
| n3-7860 | A-193 | B-18 |
| n3-7861 | A-194 | B-18 |
| n3-7862 | A-195 | B-18 |
| n3-7863 | A-196 | B-18 |
| n3-7864 | A-197 | B-18 |
| n3-7865 | A-198 | B-18 |
| n3-7866 | A-199 | B-18 |
| n3-7867 | A-200 | B-18 |
| n3-7868 | A-201 | B-18 |
| n3-7869 | A-202 | B-18 |
| n3-7870 | A-203 | B-18 |
| n3-7871 | A-204 | B-18 |
| n3-7872 | A-205 | B-18 |
| n3-7873 | A-206 | B-18 |
| n3-7874 | A-207 | B-18 |
| n3-7875 | A-208 | B-18 |
| n3-7876 | A-209 | B-18 |
| n3-7877 | A-210 | B-18 |
| n3-7878 | A-211 | B-18 |
| n3-7879 | A-212 | B-18 |
| n3-7880 | A-213 | B-18 |
| n3-7881 | A-214 | B-18 |
| n3-7882 | A-215 | B-18 |
| n3-7883 | A-216 | B-18 |
| n3-7884 | A-217 | B-18 |
| n3-7885 | A-218 | B-18 |
| n3-7886 | A-219 | B-18 |
| n3-7887 | A-220 | B-18 |
| n3-7888 | A-221 | B-18 |
| n3-7889 | A-222 | B-18 |
| n3-7890 | A-223 | B-18 |
| n3-7891 | A-224 | B-18 |
| n3-7892 | A-225 | B-18 |
| n3-7893 | A-226 | B-18 |
| n3-7894 | A-227 | B-18 |
| n3-7895 | A-228 | B-18 |
| n3-7896 | A-229 | B-18 |
| n3-7897 | A-230 | B-18 |
| n3-7898 | A-231 | B-18 |
| n3-7899 | A-232 | B-18 |
| n3-7900 | A-233 | B-18 |
| n3-7901 | A-234 | B-18 |
| n3-7902 | A-235 | B-18 |
| n3-7903 | A-236 | B-18 |
| n3-7904 | A-237 | B-18 |
| n3-7905 | A-238 | B-18 |
| n3-7906 | A-239 | B-18 |
| n3-7907 | A-240 | B-18 |
| n3-7908 | A-241 | B-18 |
| n3-7909 | A-242 | B-18 |
| n3-7910 | A-243 | B-18 |
| n3-7911 | A-244 | B-18 |
| n3-7912 | A-245 | B-18 |
| n3-7913 | A-246 | B-18 |
| n3-7914 | A-247 | B-18 |
| n3-7915 | A-248 | B-18 |
| n3-7916 | A-249 | B-18 |
| n3-7917 | A-250 | B-18 |
| n3-7918 | A-251 | B-18 |
| n3-7919 | A-252 | B-18 |
| n3-7920 | A-253 | B-18 |
| n3-7921 | A-254 | B-18 |
| n3-7922 | A-255 | B-18 |
| n3-7923 | A-256 | B-18 |
| n3-7924 | A-257 | B-18 |
| n3-7925 | A-258 | B-18 |
| n3-7926 | A-259 | B-18 |
| n3-7927 | A-260 | B-18 |
| n3-7928 | A-261 | B-18 |
| n3-7929 | A-262 | B-18 |
| n3-7930 | A-263 | B-18 |
| n3-7931 | A-264 | B-18 |
| n3-7932 | A-265 | B-18 |
| n3-7933 | A-266 | B-18 |
| n3-7934 | A-267 | B-18 |
| n3-7935 | A-268 | B-18 |
| n3-7936 | A-269 | B-18 |
| n3-7937 | A-270 | B-18 |

TABLE 1-continued

| | n = 3 | |
|---|---|---|
| epn | A | B |
| n3-7938 | A-271 | B-18 |
| n3-7939 | A-272 | B-18 |
| n3-7940 | A-273 | B-18 |
| n3-7941 | A-274 | B-18 |
| n3-7942 | A-275 | B-18 |
| n3-7943 | A-276 | B-18 |
| n3-7944 | A-277 | B-18 |
| n3-7945 | A-278 | B-18 |
| n3-7946 | A-279 | B-18 |
| n3-7947 | A-280 | B-18 |
| n3-7948 | A-281 | B-18 |
| n3-7949 | A-282 | B-18 |
| n3-7950 | A-283 | B-18 |
| n3-7951 | A-284 | B-18 |
| n3-7952 | A-285 | B-18 |
| n3-7953 | A-286 | B-18 |
| n3-7954 | A-287 | B-18 |
| n3-7955 | A-288 | B-18 |
| n3-7956 | A-289 | B-18 |
| n3-7957 | A-290 | B-18 |
| n3-7958 | A-291 | B-18 |
| n3-7959 | A-292 | B-18 |
| n3-7960 | A-293 | B-18 |
| n3-7961 | A-294 | B-18 |
| n3-7962 | A-295 | B-18 |
| n3-7963 | A-296 | B-18 |
| n3-7964 | A-297 | B-18 |
| n3-7965 | A-298 | B-18 |
| n3-7966 | A-299 | B-18 |
| n3-7967 | A-300 | B-18 |
| n3-7968 | A-301 | B-18 |
| n3-7969 | A-302 | B-18 |
| n3-7970 | A-303 | B-18 |
| n3-7971 | A-304 | B-18 |
| n3-7972 | A-305 | B-18 |
| n3-7973 | A-306 | B-18 |
| n3-7974 | A-307 | B-18 |
| n3-7975 | A-308 | B-18 |
| n3-7976 | A-309 | B-18 |
| n3-7977 | A-310 | B-18 |
| n3-7978 | A-311 | B-18 |
| n3-7979 | A-312 | B-18 |
| n3-7980 | A-313 | B-18 |
| n3-7981 | A-314 | B-18 |
| n3-7982 | A-315 | B-18 |
| n3-7983 | A-316 | B-18 |
| n3-7984 | A-317 | B-18 |
| n3-7985 | A-318 | B-18 |
| n3-7986 | A-319 | B-18 |
| n3-7987 | A-320 | B-18 |
| n3-7988 | A-321 | B-18 |
| n3-7989 | A-322 | B-18 |
| n3-7990 | A-323 | B-18 |
| n3-7991 | A-324 | B-18 |
| n3-7992 | A-325 | B-18 |
| n3-7993 | A-326 | B-18 |
| n3-7994 | A-327 | B-18 |
| n3-7995 | A-328 | B-18 |
| n3-7996 | A-329 | B-18 |
| n3-7997 | A-330 | B-18 |
| n3-7998 | A-331 | B-18 |
| n3-7999 | A-332 | B-18 |
| n3-8000 | A-333 | B-18 |
| n3-8001 | A-334 | B-18 |
| n3-8002 | A-335 | B-18 |
| n3-8003 | A-336 | B-18 |
| n3-8004 | A-337 | B-18 |
| n3-8005 | A-338 | B-18 |
| n3-8006 | A-339 | B-18 |
| n3-8007 | A-340 | B-18 |
| n3-8008 | A-341 | B-18 |
| n3-8009 | A-342 | B-18 |
| n3-8010 | A-343 | B-18 |
| n3-8011 | A-344 | B-18 |
| n3-8012 | A-345 | B-18 |
| n3-8013 | A-346 | B-18 |
| n3-8014 | A-347 | B-18 |
| n3-8015 | A-348 | B-18 |
| n3-8016 | A-349 | B-18 |
| n3-8017 | A-350 | B-18 |
| n3-8018 | A-351 | B-18 |
| n3-8019 | A-352 | B-18 |
| n3-8020 | A-353 | B-18 |
| n3-8021 | A-354 | B-18 |
| n3-8022 | A-355 | B-18 |
| n3-8023 | A-356 | B-18 |
| n3-8024 | A-357 | B-18 |
| n3-8025 | A-358 | B-18 |
| n3-8026 | A-359 | B-18 |
| n3-8027 | A-360 | B-18 |
| n3-8028 | A-361 | B-18 |
| n3-8029 | A-362 | B-18 |
| n3-8030 | A-363 | B-18 |
| n3-8031 | A-364 | B-18 |
| n3-8032 | A-365 | B-18 |
| n3-8033 | A-366 | B-18 |
| n3-8034 | A-367 | B-18 |
| n3-8035 | A-368 | B-18 |
| n3-8036 | A-369 | B-18 |
| n3-8037 | A-370 | B-18 |
| n3-8038 | A-371 | B-18 |
| n3-8039 | A-372 | B-18 |
| n3-8040 | A-373 | B-18 |
| n3-8041 | A-374 | B-18 |
| n3-8042 | A-375 | B-18 |
| n3-8043 | A-376 | B-18 |
| n3-8044 | A-377 | B-18 |
| n3-8045 | A-378 | B-18 |
| n3-8046 | A-379 | B-18 |
| n3-8047 | A-380 | B-18 |
| n3-8048 | A-381 | B-18 |
| n3-8049 | A-382 | B-18 |
| n3-8050 | A-383 | B-18 |
| n3-8051 | A-384 | B-18 |
| n3-8052 | A-385 | B-18 |
| n3-8053 | A-386 | B-18 |
| n3-8054 | A-387 | B-18 |
| n3-8055 | A-388 | B-18 |
| n3-8056 | A-389 | B-18 |
| n3-8057 | A-390 | B-18 |
| n3-8058 | A-391 | B-18 |
| n3-8059 | A-392 | B-18 |
| n3-8060 | A-393 | B-18 |
| n3-8061 | A-394 | B-18 |
| n3-8062 | A-395 | B-18 |
| n3-8063 | A-396 | B-18 |
| n3-8064 | A-397 | B-18 |
| n3-8065 | A-398 | B-18 |
| n3-8066 | A-399 | B-18 |
| n3-8067 | A-400 | B-18 |
| n3-8068 | A-401 | B-18 |
| n3-8069 | A-402 | B-18 |
| n3-8070 | A-403 | B-18 |
| n3-8071 | A-404 | B-18 |
| n3-8072 | A-405 | B-18 |
| n3-8073 | A-406 | B-18 |
| n3-8074 | A-407 | B-18 |
| n3-8075 | A-408 | B-18 |
| n3-8076 | A-409 | B-18 |
| n3-8077 | A-410 | B-18 |
| n3-8078 | A-411 | B-18 |
| n3-8079 | A-412 | B-18 |
| n3-8080 | A-413 | B-18 |
| n3-8081 | A-414 | B-18 |
| n3-8082 | A-415 | B-18 |
| n3-8083 | A-416 | B-18 |
| n3-8084 | A-417 | B-18 |
| n3-8085 | A-418 | B-18 |
| n3-8086 | A-419 | B-18 |
| n3-8087 | A-420 | B-18 |

TABLE 1-continued

| epn | n = 3 A | B |
|---|---|---|
| n3-8088 | A-421 | B-18 |
| n3-8089 | A-422 | B-18 |
| n3-8090 | A-423 | B-18 |
| n3-8091 | A-424 | B-18 |
| n3-8092 | A-425 | B-18 |
| n3-8093 | A-426 | B-18 |
| n3-8094 | A-427 | B-18 |
| n3-8095 | A-428 | B-18 |
| n3-8096 | A-429 | B-18 |
| n3-8097 | A-430 | B-18 |
| n3-8098 | A-431 | B-18 |
| n3-8099 | A-432 | B-18 |
| n3-8100 | A-433 | B-18 |
| n3-8101 | A-434 | B-18 |
| n3-8102 | A-435 | B-18 |
| n3-8103 | A-436 | B-18 |
| n3-8104 | A-437 | B-18 |
| n3-8105 | A-438 | B-18 |
| n3-8106 | A-439 | B-18 |
| n3-8107 | A-440 | B-18 |
| n3-8108 | A-441 | B-18 |
| n3-8109 | A-442 | B-18 |
| n3-8110 | A-443 | B-18 |
| n3-8111 | A-444 | B-18 |
| n3-8112 | A-445 | B-18 |
| n3-8113 | A-446 | B-18 |
| n3-8114 | A-447 | B-18 |
| n3-8115 | A-448 | B-18 |
| n3-8116 | A-449 | B-18 |
| n3-8117 | A-450 | B-18 |
| n3-8118 | A-451 | B-18 |
| n3-8119 | A-1 | B-19 |
| n3-8120 | A-2 | B-19 |
| n3-8121 | A-3 | B-19 |
| n3-8122 | A-4 | B-19 |
| n3-8123 | A-5 | B-19 |
| n3-8124 | A-6 | B-19 |
| n3-8125 | A-7 | B-19 |
| n3-8126 | A-8 | B-19 |
| n3-8127 | A-9 | B-19 |
| n3-8128 | A-10 | B-19 |
| n3-8129 | A-11 | B-19 |
| n3-8130 | A-12 | B-19 |
| n3-8131 | A-13 | B-19 |
| n3-8132 | A-14 | B-19 |
| n3-8133 | A-15 | B-19 |
| n3-8134 | A-16 | B-19 |
| n3-8135 | A-17 | B-19 |
| n3-8136 | A-18 | B-19 |
| n3-8137 | A-19 | B-19 |
| n3-8138 | A-20 | B-19 |
| n3-8139 | A-21 | B-19 |
| n3-8140 | A-22 | B-19 |
| n3-8141 | A-23 | B-19 |
| n3-8142 | A-24 | B-19 |
| n3-8143 | A-25 | B-19 |
| n3-8144 | A-26 | B-19 |
| n3-8145 | A-27 | B-19 |
| n3-8146 | A-28 | B-19 |
| n3-8147 | A-29 | B-19 |
| n3-8148 | A-30 | B-19 |
| n3-8149 | A-31 | B-19 |
| n3-8150 | A-32 | B-19 |
| n3-8151 | A-33 | B-19 |
| n3-8152 | A-34 | B-19 |
| n3-8153 | A-35 | B-19 |
| n3-8154 | A-36 | B-19 |
| n3-8155 | A-37 | B-19 |
| n3-8156 | A-38 | B-19 |
| n3-8157 | A-39 | B-19 |
| n3-8158 | A-40 | B-19 |
| n3-8159 | A-41 | B-19 |
| n3-8160 | A-42 | B-19 |
| n3-8161 | A-43 | B-19 |
| n3-8162 | A-44 | B-19 |
| n3-8163 | A-45 | B-19 |
| n3-8164 | A-46 | B-19 |
| n3-8165 | A-47 | B-19 |
| n3-8166 | A-48 | B-19 |
| n3-8167 | A-49 | B-19 |
| n3-8168 | A-50 | B-19 |
| n3-8169 | A-51 | B-19 |
| n3-8170 | A-52 | B-19 |
| n3-8171 | A-53 | B-19 |
| n3-8172 | A-54 | B-19 |
| n3-8173 | A-55 | B-19 |
| n3-8174 | A-56 | B-19 |
| n3-8175 | A-57 | B-19 |
| n3-8176 | A-58 | B-19 |
| n3-8177 | A-59 | B-19 |
| n3-8178 | A-60 | B-19 |
| n3-8179 | A-61 | B-19 |
| n3-8180 | A-62 | B-19 |
| n3-8181 | A-63 | B-19 |
| n3-8182 | A-64 | B-19 |
| n3-8183 | A-65 | B-19 |
| n3-8184 | A-66 | B-19 |
| n3-8185 | A-67 | B-19 |
| n3-8186 | A-68 | B-19 |
| n3-8187 | A-69 | B-19 |
| n3-8188 | A-70 | B-19 |
| n3-8189 | A-71 | B-19 |
| n3-8190 | A-72 | B-19 |
| n3-8191 | A-73 | B-19 |
| n3-8192 | A-74 | B-19 |
| n3-8193 | A-75 | B-19 |
| n3-8194 | A-76 | B-19 |
| n3-8195 | A-77 | B-19 |
| n3-8196 | A-78 | B-19 |
| n3-8197 | A-79 | B-19 |
| n3-8198 | A-80 | B-19 |
| n3-8199 | A-81 | B-19 |
| n3-8200 | A-82 | B-19 |
| n3-8201 | A-83 | B-19 |
| n3-8202 | A-84 | B-19 |
| n3-8203 | A-85 | B-19 |
| n3-8204 | A-86 | B-19 |
| n3-8205 | A-87 | B-19 |
| n3-8206 | A-88 | B-19 |
| n3-8207 | A-89 | B-19 |
| n3-8208 | A-90 | B-19 |
| n3-8209 | A-91 | B-19 |
| n3-8210 | A-92 | B-19 |
| n3-8211 | A-93 | B-19 |
| n3-8212 | A-94 | B-19 |
| n3-8213 | A-95 | B-19 |
| n3-8214 | A-96 | B-19 |
| n3-8215 | A-97 | B-19 |
| n3-8216 | A-98 | B-19 |
| n3-8217 | A-99 | B-19 |
| n3-8218 | A-100 | B-19 |
| n3-8219 | A-101 | B-19 |
| n3-8220 | A-102 | B-19 |
| n3-8221 | A-103 | B-19 |
| n3-8222 | A-104 | B-19 |
| n3-8223 | A-105 | B-19 |
| n3-8224 | A-106 | B-19 |
| n3-8225 | A-107 | B-19 |
| n3-8226 | A-108 | B-19 |
| n3-8227 | A-109 | B-19 |
| n3-8228 | A-110 | B-19 |
| n3-8229 | A-111 | B-19 |
| n3-8230 | A-112 | B-19 |
| n3-8231 | A-113 | B-19 |
| n3-8232 | A-114 | B-19 |
| n3-8233 | A-115 | B-19 |
| n3-8234 | A-116 | B-19 |
| n3-8235 | A-117 | B-19 |
| n3-8236 | A-118 | B-19 |
| n3-8237 | A-119 | B-19 |

TABLE 1-continued

| epn | n = 3 A | B |
|---|---|---|
| n3-8238 | A-120 | B-19 |
| n3-8239 | A-121 | B-19 |
| n3-8240 | A-122 | B-19 |
| n3-8241 | A-123 | B-19 |
| n3-8242 | A-124 | B-19 |
| n3-8243 | A-125 | B-19 |
| n3-8244 | A-126 | B-19 |
| n3-8245 | A-127 | B-19 |
| n3-8246 | A-128 | B-19 |
| n3-8247 | A-129 | B-19 |
| n3-8248 | A-130 | B-19 |
| n3-8249 | A-131 | B-19 |
| n3-8250 | A-132 | B-19 |
| n3-8251 | A-133 | B-19 |
| n3-8252 | A-134 | B-19 |
| n3-8253 | A-135 | B-19 |
| n3-8254 | A-136 | B-19 |
| n3-8255 | A-137 | B-19 |
| n3-8256 | A-138 | B-19 |
| n3-8257 | A-139 | B-19 |
| n3-8258 | A-140 | B-19 |
| n3-8259 | A-141 | B-19 |
| n3-8260 | A-142 | B-19 |
| n3-8261 | A-143 | B-19 |
| n3-8262 | A-144 | B-19 |
| n3-8263 | A-145 | B-19 |
| n3-8264 | A-146 | B-19 |
| n3-8265 | A-147 | B-19 |
| n3-8266 | A-148 | B-19 |
| n3-8267 | A-149 | B-19 |
| n3-8268 | A-150 | B-19 |
| n3-8269 | A-151 | B-19 |
| n3-8270 | A-152 | B-19 |
| n3-8271 | A-153 | B-19 |
| n3-8272 | A-154 | B-19 |
| n3-8273 | A-155 | B-19 |
| n3-8274 | A-156 | B-19 |
| n3-8275 | A-157 | B-19 |
| n3-8276 | A-158 | B-19 |
| n3-8277 | A-159 | B-19 |
| n3-8278 | A-160 | B-19 |
| n3-8279 | A-161 | B-19 |
| n3-8280 | A-162 | B-19 |
| n3-8281 | A-163 | B-19 |
| n3-8282 | A-164 | B-19 |
| n3-8283 | A-165 | B-19 |
| n3-8284 | A-166 | B-19 |
| n3-8285 | A-167 | B-19 |
| n3-8286 | A-168 | B-19 |
| n3-8287 | A-169 | B-19 |
| n3-8288 | A-170 | B-19 |
| n3-8289 | A-171 | B-19 |
| n3-8290 | A-172 | B-19 |
| n3-8291 | A-173 | B-19 |
| n3-8292 | A-174 | B-19 |
| n3-8293 | A-175 | B-19 |
| n3-8294 | A-176 | B-19 |
| n3-8295 | A-177 | B-19 |
| n3-8296 | A-178 | B-19 |
| n3-8297 | A-179 | B-19 |
| n3-8298 | A-180 | B-19 |
| n3-8299 | A-181 | B-19 |
| n3-8300 | A-182 | B-19 |
| n3-8301 | A-183 | B-19 |
| n3-8302 | A-184 | B-19 |
| n3-8303 | A-185 | B-19 |
| n3-8304 | A-186 | B-19 |
| n3-8305 | A-187 | B-19 |
| n3-8306 | A-188 | B-19 |
| n3-8307 | A-189 | B-19 |
| n3-8308 | A-190 | B-19 |
| n3-8309 | A-191 | B-19 |
| n3-8310 | A-192 | B-19 |
| n3-8311 | A-193 | B-19 |
| n3-8312 | A-194 | B-19 |
| n3-8313 | A-195 | B-19 |
| n3-8314 | A-196 | B-19 |
| n3-8315 | A-197 | B-19 |
| n3-8316 | A-198 | B-19 |
| n3-8317 | A-199 | B-19 |
| n3-8318 | A-200 | B-19 |
| n3-8319 | A-201 | B-19 |
| n3-8320 | A-202 | B-19 |
| n3-8321 | A-203 | B-19 |
| n3-8322 | A-204 | B-19 |
| n3-8323 | A-205 | B-19 |
| n3-8324 | A-206 | B-19 |
| n3-8325 | A-207 | B-19 |
| n3-8326 | A-208 | B-19 |
| n3-8327 | A-209 | B-19 |
| n3-8328 | A-210 | B-19 |
| n3-8329 | A-211 | B-19 |
| n3-8330 | A-212 | B-19 |
| n3-8331 | A-213 | B-19 |
| n3-8332 | A-214 | B-19 |
| n3-8333 | A-215 | B-19 |
| n3-8334 | A-216 | B-19 |
| n3-8335 | A-217 | B-19 |
| n3-8336 | A-218 | B-19 |
| n3-8337 | A-219 | B-19 |
| n3-8338 | A-220 | B-19 |
| n3-8339 | A-221 | B-19 |
| n3-8340 | A-222 | B-19 |
| n3-8341 | A-223 | B-19 |
| n3-8342 | A-224 | B-19 |
| n3-8343 | A-225 | B-19 |
| n3-8344 | A-226 | B-19 |
| n3-8345 | A-227 | B-19 |
| n3-8346 | A-228 | B-19 |
| n3-8347 | A-229 | B-19 |
| n3-8348 | A-230 | B-19 |
| n3-8349 | A-231 | B-19 |
| n3-8350 | A-232 | B-19 |
| n3-8351 | A-233 | B-19 |
| n3-8352 | A-234 | B-19 |
| n3-8353 | A-235 | B-19 |
| n3-8354 | A-236 | B-19 |
| n3-8355 | A-237 | B-19 |
| n3-8356 | A-238 | B-19 |
| n3-8357 | A-239 | B-19 |
| n3-8358 | A-240 | B-19 |
| n3-8359 | A-241 | B-19 |
| n3-8360 | A-242 | B-19 |
| n3-8361 | A-243 | B-19 |
| n3-8362 | A-244 | B-19 |
| n3-8363 | A-245 | B-19 |
| n3-8364 | A-246 | B-19 |
| n3-8365 | A-247 | B-19 |
| n3-8366 | A-248 | B-19 |
| n3-8367 | A-249 | B-19 |
| n3-8368 | A-250 | B-19 |
| n3-8369 | A-251 | B-19 |
| n3-8370 | A-252 | B-19 |
| n3-8371 | A-253 | B-19 |
| n3-8372 | A-254 | B-19 |
| n3-8373 | A-255 | B-19 |
| n3-8374 | A-256 | B-19 |
| n3-8375 | A-257 | B-19 |
| n3-8376 | A-258 | B-19 |
| n3-8377 | A-259 | B-19 |
| n3-8378 | A-260 | B-19 |
| n3-8379 | A-261 | B-19 |
| n3-8380 | A-262 | B-19 |
| n3-8381 | A-263 | B-19 |
| n3-8382 | A-264 | B-19 |
| n3-8383 | A-265 | B-19 |
| n3-8384 | A-266 | B-19 |
| n3-8385 | A-267 | B-19 |
| n3-8386 | A-268 | B-19 |
| n3-8387 | A-269 | B-19 |

TABLE 1-continued

| epn | n = 3 A | B |
|---|---|---|
| n3-8388 | A-270 | B-19 |
| n3-8389 | A-271 | B-19 |
| n3-8390 | A-272 | B-19 |
| n3-8391 | A-273 | B-19 |
| n3-8392 | A-274 | B-19 |
| n3-8393 | A-275 | B-19 |
| n3-8394 | A-276 | B-19 |
| n3-8395 | A-277 | B-19 |
| n3-8396 | A-278 | B-19 |
| n3-8397 | A-279 | B-19 |
| n3-8398 | A-280 | B-19 |
| n3-8399 | A-281 | B-19 |
| n3-8400 | A-282 | B-19 |
| n3-8401 | A-283 | B-19 |
| n3-8402 | A-284 | B-19 |
| n3-8403 | A-285 | B-19 |
| n3-8404 | A-286 | B-19 |
| n3-8405 | A-287 | B-19 |
| n3-8406 | A-288 | B-19 |
| n3-8407 | A-289 | B-19 |
| n3-8408 | A-290 | B-19 |
| n3-8409 | A-291 | B-19 |
| n3-8410 | A-292 | B-19 |
| n3-8411 | A-293 | B-19 |
| n3-8412 | A-294 | B-19 |
| n3-8413 | A-295 | B-19 |
| n3-8414 | A-296 | B-19 |
| n3-8415 | A-297 | B-19 |
| n3-8416 | A-298 | B-19 |
| n3-8417 | A-299 | B-19 |
| n3-8418 | A-300 | B-19 |
| n3-8419 | A-301 | B-19 |
| n3-8420 | A-302 | B-19 |
| n3-8421 | A-303 | B-19 |
| n3-8422 | A-304 | B-19 |
| n3-8423 | A-305 | B-19 |
| n3-8424 | A-306 | B-19 |
| n3-8425 | A-307 | B-19 |
| n3-8426 | A-308 | B-19 |
| n3-8427 | A-309 | B-19 |
| n3-8428 | A-310 | B-19 |
| n3-8429 | A-311 | B-19 |
| n3-8430 | A-312 | B-19 |
| n3-8431 | A-313 | B-19 |
| n3-8432 | A-314 | B-19 |
| n3-8433 | A-315 | B-19 |
| n3-8434 | A-316 | B-19 |
| n3-8435 | A-317 | B-19 |
| n3-8436 | A-318 | B-19 |
| n3-8437 | A-319 | B-19 |
| n3-8438 | A-320 | B-19 |
| n3-8439 | A-321 | B-19 |
| n3-8440 | A-322 | B-19 |
| n3-8441 | A-323 | B-19 |
| n3-8442 | A-324 | B-19 |
| n3-8443 | A-325 | B-19 |
| n3-8444 | A-326 | B-19 |
| n3-8445 | A-327 | B-19 |
| n3-8446 | A-328 | B-19 |
| n3-8447 | A-329 | B-19 |
| n3-8448 | A-330 | B-19 |
| n3-8449 | A-331 | B-19 |
| n3-8450 | A-332 | B-19 |
| n3-8451 | A-333 | B-19 |
| n3-8452 | A-334 | B-19 |
| n3-8453 | A-335 | B-19 |
| n3-8454 | A-336 | B-19 |
| n3-8455 | A-337 | B-19 |
| n3-8456 | A-338 | B-19 |
| n3-8457 | A-339 | B-19 |
| n3-8458 | A-340 | B-19 |
| n3-8459 | A-341 | B-19 |
| n3-8460 | A-342 | B-19 |
| n3-8461 | A-343 | B-19 |
| n3-8462 | A-344 | B-19 |
| n3-8463 | A-345 | B-19 |
| n3-8464 | A-346 | B-19 |
| n3-8465 | A-347 | B-19 |
| n3-8466 | A-348 | B-19 |
| n3-8467 | A-349 | B-19 |
| n3-8468 | A-350 | B-19 |
| n3-8469 | A-351 | B-19 |
| n3-8470 | A-352 | B-19 |
| n3-8471 | A-353 | B-19 |
| n3-8472 | A-354 | B-19 |
| n3-8473 | A-355 | B-19 |
| n3-8474 | A-356 | B-19 |
| n3-8475 | A-357 | B-19 |
| n3-8476 | A-358 | B-19 |
| n3-8477 | A-359 | B-19 |
| n3-8478 | A-360 | B-19 |
| n3-8479 | A-361 | B-19 |
| n3-8480 | A-362 | B-19 |
| n3-8481 | A-363 | B-19 |
| n3-8482 | A-364 | B-19 |
| n3-8483 | A-365 | B-19 |
| n3-8484 | A-366 | B-19 |
| n3-8485 | A-367 | B-19 |
| n3-8486 | A-368 | B-19 |
| n3-8487 | A-369 | B-19 |
| n3-8488 | A-370 | B-19 |
| n3-8489 | A-371 | B-19 |
| n3-8490 | A-372 | B-19 |
| n3-8491 | A-373 | B-19 |
| n3-8492 | A-374 | B-19 |
| n3-8493 | A-375 | B-19 |
| n3-8494 | A-376 | B-19 |
| n3-8495 | A-377 | B-19 |
| n3-8496 | A-378 | B-19 |
| n3-8497 | A-379 | B-19 |
| n3-8498 | A-380 | B-19 |
| n3-8499 | A-381 | B-19 |
| n3-8500 | A-382 | B-19 |
| n3-8501 | A-383 | B-19 |
| n3-8502 | A-384 | B-19 |
| n3-8503 | A-385 | B-19 |
| n3-8504 | A-386 | B-19 |
| n3-8505 | A-387 | B-19 |
| n3-8506 | A-388 | B-19 |
| n3-8507 | A-389 | B-19 |
| n3-8508 | A-390 | B-19 |
| n3-8509 | A-391 | B-19 |
| n3-8510 | A-392 | B-19 |
| n3-8511 | A-393 | B-19 |
| n3-8512 | A-394 | B-19 |
| n3-8513 | A-395 | B-19 |
| n3-8514 | A-396 | B-19 |
| n3-8515 | A-397 | B-19 |
| n3-8516 | A-398 | B-19 |
| n3-8517 | A-399 | B-19 |
| n3-8518 | A-400 | B-19 |
| n3-8519 | A-401 | B-19 |
| n3-8520 | A-402 | B-19 |
| n3-8521 | A-403 | B-19 |
| n3-8522 | A-404 | B-19 |
| n3-8523 | A-405 | B-19 |
| n3-8524 | A-406 | B-19 |
| n3-8525 | A-407 | B-19 |
| n3-8526 | A-408 | B-19 |
| n3-8527 | A-409 | B-19 |
| n3-8528 | A-410 | B-19 |
| n3-8529 | A-411 | B-19 |
| n3-8530 | A-412 | B-19 |
| n3-8531 | A-413 | B-19 |
| n3-8532 | A-414 | B-19 |
| n3-8533 | A-415 | B-19 |
| n3-8534 | A-416 | B-19 |
| n3-8535 | A-417 | B-19 |
| n3-8536 | A-418 | B-19 |
| n3-8537 | A-419 | B-19 |

TABLE 1-continued

| epn | n = 3 A | B |
|---|---|---|
| n3-8538 | A-420 | B-19 |
| n3-8539 | A-421 | B-19 |
| n3-8540 | A-422 | B-19 |
| n3-8541 | A-423 | B-19 |
| n3-8542 | A-424 | B-19 |
| n3-8543 | A-425 | B-19 |
| n3-8544 | A-426 | B-19 |
| n3-8545 | A-427 | B-19 |
| n3-8546 | A-428 | B-19 |
| n3-8547 | A-429 | B-19 |
| n3-8548 | A-430 | B-19 |
| n3-8549 | A-431 | B-19 |
| n3-8550 | A-432 | B-19 |
| n3-8551 | A-433 | B-19 |
| n3-8552 | A-434 | B-19 |
| n3-8553 | A-435 | B-19 |
| n3-8554 | A-436 | B-19 |
| n3-8555 | A-437 | B-19 |
| n3-8556 | A-438 | B-19 |
| n3-8557 | A-439 | B-19 |
| n3-8558 | A-440 | B-19 |
| n3-8559 | A-441 | B-19 |
| n3-8560 | A-442 | B-19 |
| n3-8561 | A-443 | B-19 |
| n3-8562 | A-444 | B-19 |
| n3-8563 | A-445 | B-19 |
| n3-8564 | A-446 | B-19 |
| n3-8565 | A-447 | B-19 |
| n3-8566 | A-448 | B-19 |
| n3-8567 | A-449 | B-19 |
| n3-8568 | A-450 | B-19 |
| n3-8569 | A-451 | B-19 |
| n3-8570 | A-1 | B-20 |
| n3-8571 | A-2 | B-20 |
| n3-8572 | A-3 | B-20 |
| n3-8573 | A-4 | B-20 |
| n3-8574 | A-5 | B-20 |
| n3-8575 | A-6 | B-20 |
| n3-8576 | A-7 | B-20 |
| n3-8577 | A-8 | B-20 |
| n3-8578 | A-9 | B-20 |
| n3-8579 | A-10 | B-20 |
| n3-8580 | A-11 | B-20 |
| n3-8581 | A-12 | B-20 |
| n3-8582 | A-13 | B-20 |
| n3-8583 | A-14 | B-20 |
| n3-8584 | A-15 | B-20 |
| n3-8585 | A-16 | B-20 |
| n3-8586 | A-17 | B-20 |
| n3-8587 | A-18 | B-20 |
| n3-8588 | A-19 | B-20 |
| n3-8589 | A-20 | B-20 |
| n3-8590 | A-21 | B-20 |
| n3-8591 | A-22 | B-20 |
| n3-8592 | A-23 | B-20 |
| n3-8593 | A-24 | B-20 |
| n3-8594 | A-25 | B-20 |
| n3-8595 | A-26 | B-20 |
| n3-8596 | A-27 | B-20 |
| n3-8597 | A-28 | B-20 |
| n3-8598 | A-29 | B-20 |
| n3-8599 | A-30 | B-20 |
| n3-8600 | A-31 | B-20 |
| n3-8601 | A-32 | B-20 |
| n3-8602 | A-33 | B-20 |
| n3-8603 | A-34 | B-20 |
| n3-8604 | A-35 | B-20 |
| n3-8605 | A-36 | B-20 |
| n3-8606 | A-37 | B-20 |
| n3-8607 | A-38 | B-20 |
| n3-8608 | A-39 | B-20 |
| n3-8609 | A-40 | B-20 |
| n3-8610 | A-41 | B-20 |
| n3-8611 | A-42 | B-20 |
| n3-8612 | A-43 | B-20 |
| n3-8613 | A-44 | B-20 |
| n3-8614 | A-45 | B-20 |
| n3-8615 | A-46 | B-20 |
| n3-8616 | A-47 | B-20 |
| n3-8617 | A-48 | B-20 |
| n3-8618 | A-49 | B-20 |
| n3-8619 | A-50 | B-20 |
| n3-8620 | A-51 | B-20 |
| n3-8621 | A-52 | B-20 |
| n3-8622 | A-53 | B-20 |
| n3-8623 | A-54 | B-20 |
| n3-8624 | A-55 | B-20 |
| n3-8625 | A-56 | B-20 |
| n3-8626 | A-57 | B-20 |
| n3-8627 | A-58 | B-20 |
| n3-8628 | A-59 | B-20 |
| n3-8629 | A-60 | B-20 |
| n3-8630 | A-61 | B-20 |
| n3-8631 | A-62 | B-20 |
| n3-8632 | A-63 | B-20 |
| n3-8633 | A-64 | B-20 |
| n3-8634 | A-65 | B-20 |
| n3-8635 | A-66 | B-20 |
| n3-8636 | A-67 | B-20 |
| n3-8637 | A-68 | B-20 |
| n3-8638 | A-69 | B-20 |
| n3-8639 | A-70 | B-20 |
| n3-8640 | A-71 | B-20 |
| n3-8641 | A-72 | B-20 |
| n3-8642 | A-73 | B-20 |
| n3-8643 | A-74 | B-20 |
| n3-8644 | A-75 | B-20 |
| n3-8645 | A-76 | B-20 |
| n3-8646 | A-77 | B-20 |
| n3-8647 | A-78 | B-20 |
| n3-8648 | A-79 | B-20 |
| n3-8649 | A-80 | B-20 |
| n3-8650 | A-81 | B-20 |
| n3-8651 | A-82 | B-20 |
| n3-8652 | A-83 | B-20 |
| n3-8653 | A-84 | B-20 |
| n3-8654 | A-85 | B-20 |
| n3-8655 | A-86 | B-20 |
| n3-8656 | A-87 | B-20 |
| n3-8657 | A-88 | B-20 |
| n3-8658 | A-89 | B-20 |
| n3-8659 | A-90 | B-20 |
| n3-8660 | A-91 | B-20 |
| n3-8661 | A-92 | B-20 |
| n3-8662 | A-93 | B-20 |
| n3-8663 | A-94 | B-20 |
| n3-8664 | A-95 | B-20 |
| n3-8665 | A-96 | B-20 |
| n3-8666 | A-97 | B-20 |
| n3-8667 | A-98 | B-20 |
| n3-8668 | A-99 | B-20 |
| n3-8669 | A-100 | B-20 |
| n3-8670 | A-101 | B-20 |
| n3-8671 | A-102 | B-20 |
| n3-8672 | A-103 | B-20 |
| n3-8673 | A-104 | B-20 |
| n3-8674 | A-105 | B-20 |
| n3-8675 | A-106 | B-20 |
| n3-8676 | A-107 | B-20 |
| n3-8677 | A-108 | B-20 |
| n3-8678 | A-109 | B-20 |
| n3-8679 | A-110 | B-20 |
| n3-8680 | A-111 | B-20 |
| n3-8681 | A-112 | B-20 |
| n3-8682 | A-113 | B-20 |
| n3-8683 | A-114 | B-20 |
| n3-8684 | A-115 | B-20 |
| n3-8685 | A-116 | B-20 |
| n3-8686 | A-117 | B-20 |
| n3-8687 | A-118 | B-20 |

TABLE 1-continued

| epn | n = 3 A | B |
|---|---|---|
| n3-8688 | A-119 | B-20 |
| n3-8689 | A-120 | B-20 |
| n3-8690 | A-121 | B-20 |
| n3-8691 | A-122 | B-20 |
| n3-8692 | A-123 | B-20 |
| n3-8693 | A-124 | B-20 |
| n3-8694 | A-125 | B-20 |
| n3-8695 | A-126 | B-20 |
| n3-8696 | A-127 | B-20 |
| n3-8697 | A-128 | B-20 |
| n3-8698 | A-129 | B-20 |
| n3-8699 | A-130 | B-20 |
| n3-8700 | A-131 | B-20 |
| n3-8701 | A-132 | B-20 |
| n3-8702 | A-133 | B-20 |
| n3-8703 | A-134 | B-20 |
| n3-8704 | A-135 | B-20 |
| n3-8705 | A-136 | B-20 |
| n3-8706 | A-137 | B-20 |
| n3-8707 | A-138 | B-20 |
| n3-8708 | A-139 | B-20 |
| n3-8709 | A-140 | B-20 |
| n3-8710 | A-141 | B-20 |
| n3-8711 | A-142 | B-20 |
| n3-8712 | A-143 | B-20 |
| n3-8713 | A-144 | B-20 |
| n3-8714 | A-145 | B-20 |
| n3-8715 | A-146 | B-20 |
| n3-8716 | A-147 | B-20 |
| n3-8717 | A-148 | B-20 |
| n3-8718 | A-149 | B-20 |
| n3-8719 | A-150 | B-20 |
| n3-8720 | A-151 | B-20 |
| n3-8721 | A-152 | B-20 |
| n3-8722 | A-153 | B-20 |
| n3-8723 | A-154 | B-20 |
| n3-8724 | A-155 | B-20 |
| n3-8725 | A-156 | B-20 |
| n3-8726 | A-157 | B-20 |
| n3-8727 | A-158 | B-20 |
| n3-8728 | A-159 | B-20 |
| n3-8729 | A-160 | B-20 |
| n3-8730 | A-161 | B-20 |
| n3-8731 | A-162 | B-20 |
| n3-8732 | A-163 | B-20 |
| n3-8733 | A-164 | B-20 |
| n3-8734 | A-165 | B-20 |
| n3-8735 | A-166 | B-20 |
| n3-8736 | A-167 | B-20 |
| n3-8737 | A-168 | B-20 |
| n3-8738 | A-169 | B-20 |
| n3-8739 | A-170 | B-20 |
| n3-8740 | A-171 | B-20 |
| n3-8741 | A-172 | B-20 |
| n3-8742 | A-173 | B-20 |
| n3-8743 | A-174 | B-20 |
| n3-8744 | A-175 | B-20 |
| n3-8745 | A-176 | B-20 |
| n3-8746 | A-177 | B-20 |
| n3-8747 | A-178 | B-20 |
| n3-8748 | A-179 | B-20 |
| n3-8749 | A-180 | B-20 |
| n3-8750 | A-181 | B-20 |
| n3-8751 | A-182 | B-20 |
| n3-8752 | A-183 | B-20 |
| n3-8753 | A-184 | B-20 |
| n3-8754 | A-185 | B-20 |
| n3-8755 | A-186 | B-20 |
| n3-8756 | A-187 | B-20 |
| n3-8757 | A-188 | B-20 |
| n3-8758 | A-189 | B-20 |
| n3-8759 | A-190 | B-20 |
| n3-8760 | A-191 | B-20 |
| n3-8761 | A-192 | B-20 |
| n3-8762 | A-193 | B-20 |
| n3-8763 | A-194 | B-20 |
| n3-8764 | A-195 | B-20 |
| n3-8765 | A-196 | B-20 |
| n3-8766 | A-197 | B-20 |
| n3-8767 | A-198 | B-20 |
| n3-8768 | A-199 | B-20 |
| n3-8769 | A-200 | B-20 |
| n3-8770 | A-201 | B-20 |
| n3-8771 | A-202 | B-20 |
| n3-8772 | A-203 | B-20 |
| n3-8773 | A-204 | B-20 |
| n3-8774 | A-205 | B-20 |
| n3-8775 | A-206 | B-20 |
| n3-8776 | A-207 | B-20 |
| n3-8777 | A-208 | B-20 |
| n3-8778 | A-209 | B-20 |
| n3-8779 | A-210 | B-20 |
| n3-8780 | A-211 | B-20 |
| n3-8781 | A-212 | B-20 |
| n3-8782 | A-213 | B-20 |
| n3-8783 | A-214 | B-20 |
| n3-8784 | A-215 | B-20 |
| n3-8785 | A-216 | B-20 |
| n3-8786 | A-217 | B-20 |
| n3-8787 | A-218 | B-20 |
| n3-8788 | A-219 | B-20 |
| n3-8789 | A-220 | B-20 |
| n3-8790 | A-221 | B-20 |
| n3-8791 | A-222 | B-20 |
| n3-8792 | A-223 | B-20 |
| n3-8793 | A-224 | B-20 |
| n3-8794 | A-225 | B-20 |
| n3-8795 | A-226 | B-20 |
| n3-8796 | A-227 | B-20 |
| n3-8797 | A-228 | B-20 |
| n3-8798 | A-229 | B-20 |
| n3-8799 | A-230 | B-20 |
| n3-8800 | A-231 | B-20 |
| n3-8801 | A-232 | B-20 |
| n3-8802 | A-233 | B-20 |
| n3-8803 | A-234 | B-20 |
| n3-8804 | A-235 | B-20 |
| n3-8805 | A-236 | B-20 |
| n3-8806 | A-237 | B-20 |
| n3-8807 | A-238 | B-20 |
| n3-8808 | A-239 | B-20 |
| n3-8809 | A-240 | B-20 |
| n3-8810 | A-241 | B-20 |
| n3-8811 | A-242 | B-20 |
| n3-8812 | A-243 | B-20 |
| n3-8813 | A-244 | B-20 |
| n3-8814 | A-245 | B-20 |
| n3-8815 | A-246 | B-20 |
| n3-8816 | A-247 | B-20 |
| n3-8817 | A-248 | B-20 |
| n3-8818 | A-249 | B-20 |
| n3-8819 | A-250 | B-20 |
| n3-8820 | A-251 | B-20 |
| n3-8821 | A-252 | B-20 |
| n3-8822 | A-253 | B-20 |
| n3-8823 | A-254 | B-20 |
| n3-8824 | A-255 | B-20 |
| n3-8825 | A-256 | B-20 |
| n3-8826 | A-257 | B-20 |
| n3-8827 | A-258 | B-20 |
| n3-8828 | A-259 | B-20 |
| n3-8829 | A-260 | B-20 |
| n3-8830 | A-261 | B-20 |
| n3-8831 | A-262 | B-20 |
| n3-8832 | A-263 | B-20 |
| n3-8833 | A-264 | B-20 |
| n3-8834 | A-265 | B-20 |
| n3-8835 | A-266 | B-20 |
| n3-8836 | A-267 | B-20 |
| n3-8837 | A-268 | B-20 |

TABLE 1-continued

| epn | n = 3 A | B |
|---|---|---|
| n3-8838 | A-269 | B-20 |
| n3-8839 | A-270 | B-20 |
| n3-8840 | A-271 | B-20 |
| n3-8841 | A-272 | B-20 |
| n3-8842 | A-273 | B-20 |
| n3-8843 | A-274 | B-20 |
| n3-8844 | A-275 | B-20 |
| n3-8845 | A-276 | B-20 |
| n3-8846 | A-277 | B-20 |
| n3-8847 | A-278 | B-20 |
| n3-8848 | A-279 | B-20 |
| n3-8849 | A-280 | B-20 |
| n3-8850 | A-281 | B-20 |
| n3-8851 | A-282 | B-20 |
| n3-8852 | A-283 | B-20 |
| n3-8853 | A-284 | B-20 |
| n3-8854 | A-285 | B-20 |
| n3-8855 | A-286 | B-20 |
| n3-8856 | A-287 | B-20 |
| n3-8857 | A-288 | B-20 |
| n3-8858 | A-289 | B-20 |
| n3-8859 | A-290 | B-20 |
| n3-8860 | A-291 | B-20 |
| n3-8861 | A-292 | B-20 |
| n3-8862 | A-293 | B-20 |
| n3-8863 | A-294 | B-20 |
| n3-8864 | A-295 | B-20 |
| n3-8865 | A-296 | B-20 |
| n3-8866 | A-297 | B-20 |
| n3-8867 | A-298 | B-20 |
| n3-8868 | A-299 | B-20 |
| n3-8869 | A-300 | B-20 |
| n3-8870 | A-301 | B-20 |
| n3-8871 | A-302 | B-20 |
| n3-8872 | A-303 | B-20 |
| n3-8873 | A-304 | B-20 |
| n3-8874 | A-305 | B-20 |
| n3-8875 | A-306 | B-20 |
| n3-8876 | A-307 | B-20 |
| n3-8877 | A-308 | B-20 |
| n3-8878 | A-309 | B-20 |
| n3-8879 | A-310 | B-20 |
| n3-8880 | A-311 | B-20 |
| n3-8881 | A-312 | B-20 |
| n3-8882 | A-313 | B-20 |
| n3-8883 | A-314 | B-20 |
| n3-8884 | A-315 | B-20 |
| n3-8885 | A-316 | B-20 |
| n3-8886 | A-317 | B-20 |
| n3-8887 | A-318 | B-20 |
| n3-8888 | A-319 | B-20 |
| n3-8889 | A-320 | B-20 |
| n3-8890 | A-321 | B-20 |
| n3-8891 | A-322 | B-20 |
| n3-8892 | A-323 | B-20 |
| n3-8893 | A-324 | B-20 |
| n3-8894 | A-325 | B-20 |
| n3-8895 | A-326 | B-20 |
| n3-8896 | A-327 | B-20 |
| n3-8897 | A-328 | B-20 |
| n3-8898 | A-329 | B-20 |
| n3-8899 | A-330 | B-20 |
| n3-8900 | A-331 | B-20 |
| n3-8901 | A-332 | B-20 |
| n3-8902 | A-333 | B-20 |
| n3-8903 | A-334 | B-20 |
| n3-8904 | A-335 | B-20 |
| n3-8905 | A-336 | B-20 |
| n3-8906 | A-337 | B-20 |
| n3-8907 | A-338 | B-20 |
| n3-8908 | A-339 | B-20 |
| n3-8909 | A-340 | B-20 |
| n3-8910 | A-341 | B-20 |
| n3-8911 | A-342 | B-20 |
| n3-8912 | A-343 | B-20 |
| n3-8913 | A-344 | B-20 |
| n3-8914 | A-345 | B-20 |
| n3-8915 | A-346 | B-20 |
| n3-8916 | A-347 | B-20 |
| n3-8917 | A-348 | B-20 |
| n3-8918 | A-349 | B-20 |
| n3-8919 | A-350 | B-20 |
| n3-8920 | A-351 | B-20 |
| n3-8921 | A-352 | B-20 |
| n3-8922 | A-353 | B-20 |
| n3-8923 | A-354 | B-20 |
| n3-8924 | A-355 | B-20 |
| n3-8925 | A-356 | B-20 |
| n3-8926 | A-357 | B-20 |
| n3-8927 | A-358 | B-20 |
| n3-8928 | A-359 | B-20 |
| n3-8929 | A-360 | B-20 |
| n3-8930 | A-361 | B-20 |
| n3-8931 | A-362 | B-20 |
| n3-8932 | A-363 | B-20 |
| n3-8933 | A-364 | B-20 |
| n3-8934 | A-365 | B-20 |
| n3-8935 | A-366 | B-20 |
| n3-8936 | A-367 | B-20 |
| n3-8937 | A-368 | B-20 |
| n3-8938 | A-369 | B-20 |
| n3-8939 | A-370 | B-20 |
| n3-8940 | A-371 | B-20 |
| n3-8941 | A-372 | B-20 |
| n3-8942 | A-373 | B-20 |
| n3-8943 | A-374 | B-20 |
| n3-8944 | A-375 | B-20 |
| n3-8945 | A-376 | B-20 |
| n3-8946 | A-377 | B-20 |
| n3-8947 | A-378 | B-20 |
| n3-8948 | A-379 | B-20 |
| n3-8949 | A-380 | B-20 |
| n3-8950 | A-381 | B-20 |
| n3-8951 | A-382 | B-20 |
| n3-8952 | A-383 | B-20 |
| n3-8953 | A-384 | B-20 |
| n3-8954 | A-385 | B-20 |
| n3-8955 | A-386 | B-20 |
| n3-8956 | A-387 | B-20 |
| n3-8957 | A-388 | B-20 |
| n3-8958 | A-389 | B-20 |
| n3-8959 | A-390 | B-20 |
| n3-8960 | A-391 | B-20 |
| n3-8961 | A-392 | B-20 |
| n3-8962 | A-393 | B-20 |
| n3-8963 | A-394 | B-20 |
| n3-8964 | A-395 | B-20 |
| n3-8965 | A-396 | B-20 |
| n3-8966 | A-397 | B-20 |
| n3-8967 | A-398 | B-20 |
| n3-8968 | A-399 | B-20 |
| n3-8969 | A-400 | B-20 |
| n3-8970 | A-401 | B-20 |
| n3-8971 | A-402 | B-20 |
| n3-8972 | A-403 | B-20 |
| n3-8973 | A-404 | B-20 |
| n3-8974 | A-405 | B-20 |
| n3-8975 | A-406 | B-20 |
| n3-8976 | A-407 | B-20 |
| n3-8977 | A-408 | B-20 |
| n3-8978 | A-409 | B-20 |
| n3-8979 | A-410 | B-20 |
| n3-8980 | A-411 | B-20 |
| n3-8981 | A-412 | B-20 |
| n3-8982 | A-413 | B-20 |
| n3-8983 | A-414 | B-20 |
| n3-8984 | A-415 | B-20 |
| n3-8985 | A-416 | B-20 |
| n3-8986 | A-417 | B-20 |
| n3-8987 | A-418 | B-20 |

TABLE 1-continued

| epn | n = 3 A | B |
|---|---|---|
| n3-8988 | A-419 | B-20 |
| n3-8989 | A-420 | B-20 |
| n3-8990 | A-421 | B-20 |
| n3-8991 | A-422 | B-20 |
| n3-8992 | A-423 | B-20 |
| n3-8993 | A-424 | B-20 |
| n3-8994 | A-425 | B-20 |
| n3-8995 | A-426 | B-20 |
| n3-8996 | A-427 | B-20 |
| n3-8997 | A-428 | B-20 |
| n3-8998 | A-429 | B-20 |
| n3-8999 | A-430 | B-20 |
| n3-9000 | A-431 | B-20 |
| n3-9001 | A-432 | B-20 |
| n3-9002 | A-433 | B-20 |
| n3-9003 | A-434 | B-20 |
| n3-9004 | A-435 | B-20 |
| n3-9005 | A-436 | B-20 |
| n3-9006 | A-437 | B-20 |
| n3-9007 | A-438 | B-20 |
| n3-9008 | A-439 | B-20 |
| n3-9009 | A-440 | B-20 |
| n3-9010 | A-441 | B-20 |
| n3-9011 | A-442 | B-20 |
| n3-9012 | A-443 | B-20 |
| n3-9013 | A-444 | B-20 |
| n3-9014 | A-445 | B-20 |
| n3-9015 | A-446 | B-20 |
| n3-9016 | A-447 | B-20 |
| n3-9017 | A-448 | B-20 |
| n3-9018 | A-449 | B-20 |
| n3-9019 | A-450 | B-20 |
| n3-9020 | A-451 | B-20 |
| n3-9021 | A-1 | B-21 |
| n3-9022 | A-2 | B-21 |
| n3-9023 | A-3 | B-21 |
| n3-9024 | A-4 | B-21 |
| n3-9025 | A-5 | B-21 |
| n3-9026 | A-6 | B-21 |
| n3-9027 | A-7 | B-21 |
| n3-9028 | A-8 | B-21 |
| n3-9029 | A-9 | B-21 |
| n3-9030 | A-10 | B-21 |
| n3-9031 | A-11 | B-21 |
| n3-9032 | A-12 | B-21 |
| n3-9033 | A-13 | B-21 |
| n3-9034 | A-14 | B-21 |
| n3-9035 | A-15 | B-21 |
| n3-9036 | A-16 | B-21 |
| n3-9037 | A-17 | B-21 |
| n3-9038 | A-18 | B-21 |
| n3-9039 | A-19 | B-21 |
| n3-9040 | A-20 | B-21 |
| n3-9041 | A-21 | B-21 |
| n3-9042 | A-22 | B-21 |
| n3-9043 | A-23 | B-21 |
| n3-9044 | A-24 | B-21 |
| n3-9045 | A-25 | B-21 |
| n3-9046 | A-26 | B-21 |
| n3-9047 | A-27 | B-21 |
| n3-9048 | A-28 | B-21 |
| n3-9049 | A-29 | B-21 |
| n3-9050 | A-30 | B-21 |
| n3-9051 | A-31 | B-21 |
| n3-9052 | A-32 | B-21 |
| n3-9053 | A-33 | B-21 |
| n3-9054 | A-34 | B-21 |
| n3-9055 | A-35 | B-21 |
| n3-9056 | A-36 | B-21 |
| n3-9057 | A-37 | B-21 |
| n3-9058 | A-38 | B-21 |
| n3-9059 | A-39 | B-21 |
| n3-9060 | A-40 | B-21 |
| n3-9061 | A-41 | B-21 |
| n3-9062 | A-42 | B-21 |
| n3-9063 | A-43 | B-21 |
| n3-9064 | A-44 | B-21 |
| n3-9065 | A-45 | B-21 |
| n3-9066 | A-46 | B-21 |
| n3-9067 | A-47 | B-21 |
| n3-9068 | A-48 | B-21 |
| n3-9069 | A-49 | B-21 |
| n3-9070 | A-50 | B-21 |
| n3-9071 | A-51 | B-21 |
| n3-9072 | A-52 | B-21 |
| n3-9073 | A-53 | B-21 |
| n3-9074 | A-54 | B-21 |
| n3-9075 | A-55 | B-21 |
| n3-9076 | A-56 | B-21 |
| n3-9077 | A-57 | B-21 |
| n3-9078 | A-58 | B-21 |
| n3-9079 | A-59 | B-21 |
| n3-9080 | A-60 | B-21 |
| n3-9081 | A-61 | B-21 |
| n3-9082 | A-62 | B-21 |
| n3-9083 | A-63 | B-21 |
| n3-9084 | A-64 | B-21 |
| n3-9085 | A-65 | B-21 |
| n3-9086 | A-66 | B-21 |
| n3-9087 | A-67 | B-21 |
| n3-9088 | A-68 | B-21 |
| n3-9089 | A-69 | B-21 |
| n3-9090 | A-70 | B-21 |
| n3-9091 | A-71 | B-21 |
| n3-9092 | A-72 | B-21 |
| n3-9093 | A-73 | B-21 |
| n3-9094 | A-74 | B-21 |
| n3-9095 | A-75 | B-21 |
| n3-9096 | A-76 | B-21 |
| n3-9097 | A-77 | B-21 |
| n3-9098 | A-78 | B-21 |
| n3-9099 | A-79 | B-21 |
| n3-9100 | A-80 | B-21 |
| n3-9101 | A-81 | B-21 |
| n3-9102 | A-82 | B-21 |
| n3-9103 | A-83 | B-21 |
| n3-9104 | A-84 | B-21 |
| n3-9105 | A-85 | B-21 |
| n3-9106 | A-86 | B-21 |
| n3-9107 | A-87 | B-21 |
| n3-9108 | A-88 | B-21 |
| n3-9109 | A-89 | B-21 |
| n3-9110 | A-90 | B-21 |
| n3-9111 | A-91 | B-21 |
| n3-9112 | A-92 | B-21 |
| n3-9113 | A-93 | B-21 |
| n3-9114 | A-94 | B-21 |
| n3-9115 | A-95 | B-21 |
| n3-9116 | A-96 | B-21 |
| n3-9117 | A-97 | B-21 |
| n3-9118 | A-98 | B-21 |
| n3-9119 | A-99 | B-21 |
| n3-9120 | A-100 | B-21 |
| n3-9121 | A-101 | B-21 |
| n3-9122 | A-102 | B-21 |
| n3-9123 | A-103 | B-21 |
| n3-9124 | A-104 | B-21 |
| n3-9125 | A-105 | B-21 |
| n3-9126 | A-106 | B-21 |
| n3-9127 | A-107 | B-21 |
| n3-9128 | A-108 | B-21 |
| n3-9129 | A-109 | B-21 |
| n3-9130 | A-110 | B-21 |
| n3-9131 | A-111 | B-21 |
| n3-9132 | A-112 | B-21 |
| n3-9133 | A-113 | B-21 |
| n3-9134 | A-114 | B-21 |
| n3-9135 | A-115 | B-21 |
| n3-9136 | A-116 | B-21 |
| n3-9137 | A-117 | B-21 |

TABLE 1-continued

| epn | n = 3 A | B |
|---|---|---|
| n3-9138 | A-118 | B-21 |
| n3-9139 | A-119 | B-21 |
| n3-9140 | A-120 | B-21 |
| n3-9141 | A-121 | B-21 |
| n3-9142 | A-122 | B-21 |
| n3-9143 | A-123 | B-21 |
| n3-9144 | A-124 | B-21 |
| n3-9145 | A-125 | B-21 |
| n3-9146 | A-126 | B-21 |
| n3-9147 | A-127 | B-21 |
| n3-9148 | A-128 | B-21 |
| n3-9149 | A-129 | B-21 |
| n3-9150 | A-130 | B-21 |
| n3-9151 | A-131 | B-21 |
| n3-9152 | A-132 | B-21 |
| n3-9153 | A-133 | B-21 |
| n3-9154 | A-134 | B-21 |
| n3-9155 | A-135 | B-21 |
| n3-9156 | A-136 | B-21 |
| n3-9157 | A-137 | B-21 |
| n3-9158 | A-138 | B-21 |
| n3-9159 | A-139 | B-21 |
| n3-9160 | A-140 | B-21 |
| n3-9161 | A-141 | B-21 |
| n3-9162 | A-142 | B-21 |
| n3-9163 | A-143 | B-21 |
| n3-9164 | A-144 | B-21 |
| n3-9165 | A-145 | B-21 |
| n3-9166 | A-146 | B-21 |
| n3-9167 | A-147 | B-21 |
| n3-9168 | A-148 | B-21 |
| n3-9169 | A-149 | B-21 |
| n3-9170 | A-150 | B-21 |
| n3-9171 | A-151 | B-21 |
| n3-9172 | A-152 | B-21 |
| n3-9173 | A-153 | B-21 |
| n3-9174 | A-154 | B-21 |
| n3-9175 | A-155 | B-21 |
| n3-9176 | A-156 | B-21 |
| n3-9177 | A-157 | B-21 |
| n3-9178 | A-158 | B-21 |
| n3-9179 | A-159 | B-21 |
| n3-9180 | A-160 | B-21 |
| n3-9181 | A-161 | B-21 |
| n3-9182 | A-162 | B-21 |
| n3-9183 | A-163 | B-21 |
| n3-9184 | A-164 | B-21 |
| n3-9185 | A-165 | B-21 |
| n3-9186 | A-166 | B-21 |
| n3-9187 | A-167 | B-21 |
| n3-9188 | A-168 | B-21 |
| n3-9189 | A-169 | B-21 |
| n3-9190 | A-170 | B-21 |
| n3-9191 | A-171 | B-21 |
| n3-9192 | A-172 | B-21 |
| n3-9193 | A-173 | B-21 |
| n3-9194 | A-174 | B-21 |
| n3-9195 | A-175 | B-21 |
| n3-9196 | A-176 | B-21 |
| n3-9197 | A-177 | B-21 |
| n3-9198 | A-178 | B-21 |
| n3-9199 | A-179 | B-21 |
| n3-9200 | A-180 | B-21 |
| n3-9201 | A-181 | B-21 |
| n3-9202 | A-182 | B-21 |
| n3-9203 | A-183 | B-21 |
| n3-9204 | A-184 | B-21 |
| n3-9205 | A-185 | B-21 |
| n3-9206 | A-186 | B-21 |
| n3-9207 | A-187 | B-21 |
| n3-9208 | A-188 | B-21 |
| n3-9209 | A-189 | B-21 |
| n3-9210 | A-190 | B-21 |
| n3-9211 | A-191 | B-21 |
| n3-9212 | A-192 | B-21 |
| n3-9213 | A-193 | B-21 |
| n3-9214 | A-194 | B-21 |
| n3-9215 | A-195 | B-21 |
| n3-9216 | A-196 | B-21 |
| n3-9217 | A-197 | B-21 |
| n3-9218 | A-198 | B-21 |
| n3-9219 | A-199 | B-21 |
| n3-9220 | A-200 | B-21 |
| n3-9221 | A-201 | B-21 |
| n3-9222 | A-202 | B-21 |
| n3-9223 | A-203 | B-21 |
| n3-9224 | A-204 | B-21 |
| n3-9225 | A-205 | B-21 |
| n3-9226 | A-206 | B-21 |
| n3-9227 | A-207 | B-21 |
| n3-9228 | A-208 | B-21 |
| n3-9229 | A-209 | B-21 |
| n3-9230 | A-210 | B-21 |
| n3-9231 | A-211 | B-21 |
| n3-9232 | A-212 | B-21 |
| n3-9233 | A-213 | B-21 |
| n3-9234 | A-214 | B-21 |
| n3-9235 | A-215 | B-21 |
| n3-9236 | A-216 | B-21 |
| n3-9237 | A-217 | B-21 |
| n3-9238 | A-218 | B-21 |
| n3-9239 | A-219 | B-21 |
| n3-9240 | A-220 | B-21 |
| n3-9241 | A-221 | B-21 |
| n3-9242 | A-222 | B-21 |
| n3-9243 | A-223 | B-21 |
| n3-9244 | A-224 | B-21 |
| n3-9245 | A-225 | B-21 |
| n3-9246 | A-226 | B-21 |
| n3-9247 | A-227 | B-21 |
| n3-9248 | A-228 | B-21 |
| n3-9249 | A-229 | B-21 |
| n3-9250 | A-230 | B-21 |
| n3-9251 | A-231 | B-21 |
| n3-9252 | A-232 | B-21 |
| n3-9253 | A-233 | B-21 |
| n3-9254 | A-234 | B-21 |
| n3-9255 | A-235 | B-21 |
| n3-9256 | A-236 | B-21 |
| n3-9257 | A-237 | B-21 |
| n3-9258 | A-238 | B-21 |
| n3-9259 | A-239 | B-21 |
| n3-9260 | A-240 | B-21 |
| n3-9261 | A-241 | B-21 |
| n3-9262 | A-242 | B-21 |
| n3-9263 | A-243 | B-21 |
| n3-9264 | A-244 | B-21 |
| n3-9265 | A-245 | B-21 |
| n3-9266 | A-246 | B-21 |
| n3-9267 | A-247 | B-21 |
| n3-9268 | A-248 | B-21 |
| n3-9269 | A-249 | B-21 |
| n3-9270 | A-250 | B-21 |
| n3-9271 | A-251 | B-21 |
| n3-9272 | A-252 | B-21 |
| n3-9273 | A-253 | B-21 |
| n3-9274 | A-254 | B-21 |
| n3-9275 | A-255 | B-21 |
| n3-9276 | A-256 | B-21 |
| n3-9277 | A-257 | B-21 |
| n3-9278 | A-258 | B-21 |
| n3-9279 | A-259 | B-21 |
| n3-9280 | A-260 | B-21 |
| n3-9281 | A-261 | B-21 |
| n3-9282 | A-262 | B-21 |
| n3-9283 | A-263 | B-21 |
| n3-9284 | A-264 | B-21 |
| n3-9285 | A-265 | B-21 |
| n3-9286 | A-266 | B-21 |
| n3-9287 | A-267 | B-21 |

TABLE 1-continued

| epn | n = 3 A | B |
|---|---|---|
| n3-9288 | A-268 | B-21 |
| n3-9289 | A-269 | B-21 |
| n3-9290 | A-270 | B-21 |
| n3-9291 | A-271 | B-21 |
| n3-9292 | A-272 | B-21 |
| n3-9293 | A-273 | B-21 |
| n3-9294 | A-274 | B-21 |
| n3-9295 | A-275 | B-21 |
| n3-9296 | A-276 | B-21 |
| n3-9297 | A-277 | B-21 |
| n3-9298 | A-278 | B-21 |
| n3-9299 | A-279 | B-21 |
| n3-9300 | A-280 | B-21 |
| n3-9301 | A-281 | B-21 |
| n3-9302 | A-282 | B-21 |
| n3-9303 | A-283 | B-21 |
| n3-9304 | A-284 | B-21 |
| n3-9305 | A-285 | B-21 |
| n3-9306 | A-286 | B-21 |
| n3-9307 | A-287 | B-21 |
| n3-9308 | A-288 | B-21 |
| n3-9309 | A-289 | B-21 |
| n3-9310 | A-290 | B-21 |
| n3-9311 | A-291 | B-21 |
| n3-9312 | A-292 | B-21 |
| n3-9313 | A-293 | B-21 |
| n3-9314 | A-294 | B-21 |
| n3-9315 | A-295 | B-21 |
| n3-9316 | A-296 | B-21 |
| n3-9317 | A-297 | B-21 |
| n3-9318 | A-298 | B-21 |
| n3-9319 | A-299 | B-21 |
| n3-9320 | A-300 | B-21 |
| n3-9321 | A-301 | B-21 |
| n3-9322 | A-302 | B-21 |
| n3-9323 | A-303 | B-21 |
| n3-9324 | A-304 | B-21 |
| n3-9325 | A-305 | B-21 |
| n3-9326 | A-306 | B-21 |
| n3-9327 | A-307 | B-21 |
| n3-9328 | A-308 | B-21 |
| n3-9329 | A-309 | B-21 |
| n3-9330 | A-310 | B-21 |
| n3-9331 | A-311 | B-21 |
| n3-9332 | A-312 | B-21 |
| n3-9333 | A-313 | B-21 |
| n3-9334 | A-314 | B-21 |
| n3-9335 | A-315 | B-21 |
| n3-9336 | A-316 | B-21 |
| n3-9337 | A-317 | B-21 |
| n3-9338 | A-318 | B-21 |
| n3-9339 | A-319 | B-21 |
| n3-9340 | A-320 | B-21 |
| n3-9341 | A-321 | B-21 |
| n3-9342 | A-322 | B-21 |
| n3-9343 | A-323 | B-21 |
| n3-9344 | A-324 | B-21 |
| n3-9345 | A-325 | B-21 |
| n3-9346 | A-326 | B-21 |
| n3-9347 | A-327 | B-21 |
| n3-9348 | A-328 | B-21 |
| n3-9349 | A-329 | B-21 |
| n3-9350 | A-330 | B-21 |
| n3-9351 | A-331 | B-21 |
| n3-9352 | A-332 | B-21 |
| n3-9353 | A-333 | B-21 |
| n3-9354 | A-334 | B-21 |
| n3-9355 | A-335 | B-21 |
| n3-9356 | A-336 | B-21 |
| n3-9357 | A-337 | B-21 |
| n3-9358 | A-338 | B-21 |
| n3-9359 | A-339 | B-21 |
| n3-9360 | A-340 | B-21 |
| n3-9361 | A-341 | B-21 |
| n3-9362 | A-342 | B-21 |
| n3-9363 | A-343 | B-21 |
| n3-9364 | A-344 | B-21 |
| n3-9365 | A-345 | B-21 |
| n3-9366 | A-346 | B-21 |
| n3-9367 | A-347 | B-21 |
| n3-9368 | A-348 | B-21 |
| n3-9369 | A-349 | B-21 |
| n3-9370 | A-350 | B-21 |
| n3-9371 | A-351 | B-21 |
| n3-9372 | A-352 | B-21 |
| n3-9373 | A-353 | B-21 |
| n3-9374 | A-354 | B-21 |
| n3-9375 | A-355 | B-21 |
| n3-9376 | A-356 | B-21 |
| n3-9377 | A-357 | B-21 |
| n3-9378 | A-358 | B-21 |
| n3-9379 | A-359 | B-21 |
| n3-9380 | A-360 | B-21 |
| n3-9381 | A-361 | B-21 |
| n3-9382 | A-362 | B-21 |
| n3-9383 | A-363 | B-21 |
| n3-9384 | A-364 | B-21 |
| n3-9385 | A-365 | B-21 |
| n3-9386 | A-366 | B-21 |
| n3-9387 | A-367 | B-21 |
| n3-9388 | A-368 | B-21 |
| n3-9389 | A-369 | B-21 |
| n3-9390 | A-370 | B-21 |
| n3-9391 | A-371 | B-21 |
| n3-9392 | A-372 | B-21 |
| n3-9393 | A-373 | B-21 |
| n3-9394 | A-374 | B-21 |
| n3-9395 | A-375 | B-21 |
| n3-9396 | A-376 | B-21 |
| n3-9397 | A-377 | B-21 |
| n3-9398 | A-378 | B-21 |
| n3-9399 | A-379 | B-21 |
| n3-9400 | A-380 | B-21 |
| n3-9401 | A-381 | B-21 |
| n3-9402 | A-382 | B-21 |
| n3-9403 | A-383 | B-21 |
| n3-9404 | A-384 | B-21 |
| n3-9405 | A-385 | B-21 |
| n3-9406 | A-386 | B-21 |
| n3-9407 | A-387 | B-21 |
| n3-9408 | A-388 | B-21 |
| n3-9409 | A-389 | B-21 |
| n3-9410 | A-390 | B-21 |
| n3-9411 | A-391 | B-21 |
| n3-9412 | A-392 | B-21 |
| n3-9413 | A-393 | B-21 |
| n3-9414 | A-394 | B-21 |
| n3-9415 | A-395 | B-21 |
| n3-9416 | A-396 | B-21 |
| n3-9417 | A-397 | B-21 |
| n3-9418 | A-398 | B-21 |
| n3-9419 | A-399 | B-21 |
| n3-9420 | A-400 | B-21 |
| n3-9421 | A-401 | B-21 |
| n3-9422 | A-402 | B-21 |
| n3-9423 | A-403 | B-21 |
| n3-9424 | A-404 | B-21 |
| n3-9425 | A-405 | B-21 |
| n3-9426 | A-406 | B-21 |
| n3-9427 | A-407 | B-21 |
| n3-9428 | A-408 | B-21 |
| n3-9429 | A-409 | B-21 |
| n3-9430 | A-410 | B-21 |
| n3-9431 | A-411 | B-21 |
| n3-9432 | A-412 | B-21 |
| n3-9433 | A-413 | B-21 |
| n3-9434 | A-414 | B-21 |
| n3-9435 | A-415 | B-21 |
| n3-9436 | A-416 | B-21 |
| n3-9437 | A-417 | B-21 |

TABLE 1-continued

| epn | n = 3 A | B |
|---|---|---|
| n3-9438 | A-418 | B-21 |
| n3-9439 | A-419 | B-21 |
| n3-9440 | A-420 | B-21 |
| n3-9441 | A-421 | B-21 |
| n3-9442 | A-422 | B-21 |
| n3-9443 | A-423 | B-21 |
| n3-9444 | A-424 | B-21 |
| n3-9445 | A-425 | B-21 |
| n3-9446 | A-426 | B-21 |
| n3-9447 | A-427 | B-21 |
| n3-9448 | A-428 | B-21 |
| n3-9449 | A-429 | B-21 |
| n3-9450 | A-430 | B-21 |
| n3-9451 | A-431 | B-21 |
| n3-9452 | A-432 | B-21 |
| n3-9453 | A-433 | B-21 |
| n3-9454 | A-434 | B-21 |
| n3-9455 | A-435 | B-21 |
| n3-9456 | A-436 | B-21 |
| n3-9457 | A-437 | B-21 |
| n3-9458 | A-438 | B-21 |
| n3-9459 | A-439 | B-21 |
| n3-9460 | A-440 | B-21 |
| n3-9461 | A-441 | B-21 |
| n3-9462 | A-442 | B-21 |
| n3-9463 | A-443 | B-21 |
| n3-9464 | A-444 | B-21 |
| n3-9465 | A-445 | B-21 |
| n3-9466 | A-446 | B-21 |
| n3-9467 | A-447 | B-21 |
| n3-9468 | A-448 | B-21 |
| n3-9469 | A-449 | B-21 |
| n3-9470 | A-450 | B-21 |
| n3-9471 | A-451 | B-21 |

TABLE 2

| epn | n = 3 A | B |
|---|---|---|
| n3-9472 | A-452 | B-1 |
| n3-9473 | A-453 | B-1 |
| n3-9474 | A-454 | B-1 |
| n3-9475 | A-455 | B-1 |
| n3-9476 | A-456 | B-1 |
| n3-9477 | A-457 | B-1 |
| n3-9478 | A-458 | B-1 |
| n3-9479 | A-459 | B-1 |
| n3-9480 | A-460 | B-1 |
| n3-9481 | A-461 | B-1 |
| n3-9482 | A-462 | B-1 |
| n3-9483 | A-463 | B-1 |
| n3-9484 | A-464 | B-1 |
| n3-9485 | A-465 | B-1 |
| n3-9486 | A-466 | B-1 |
| n3-9487 | A-467 | B-1 |
| n3-9488 | A-468 | B-1 |
| n3-9489 | A-469 | B-1 |
| n3-9490 | A-470 | B-1 |
| n3-9491 | A-471 | B-1 |
| n3-9492 | A-472 | B-1 |
| n3-9493 | A-473 | B-1 |
| n3-9494 | A-474 | B-1 |
| n3-9495 | A-475 | B-1 |
| n3-9496 | A-476 | B-1 |
| n3-9497 | A-477 | B-1 |
| n3-9498 | A-478 | B-1 |
| n3-9499 | A-479 | B-1 |
| n3-9500 | A-480 | B-1 |
| n3-9501 | A-481 | B-1 |
| n3-9502 | A-482 | B-1 |

TABLE 2-continued

| epn | n = 3 A | B |
|---|---|---|
| n3-9503 | A-483 | B-1 |
| n3-9504 | A-484 | B-1 |
| n3-9505 | A-485 | B-1 |
| n3-9506 | A-486 | B-1 |
| n3-9507 | A-487 | B-1 |
| n3-9508 | A-488 | B-1 |
| n3-9509 | A-489 | B-1 |
| n3-9510 | A-490 | B-1 |
| n3-9511 | A-491 | B-1 |
| n3-9512 | A-492 | B-1 |
| n3-9513 | A-493 | B-1 |
| n3-9514 | A-494 | B-1 |
| n3-9515 | A-495 | B-1 |
| n3-9516 | A-496 | B-1 |
| n3-9517 | A-497 | B-1 |
| n3-9518 | A-498 | B-1 |
| n3-9519 | A-499 | B-1 |
| n3-9520 | A-500 | B-1 |
| n3-9521 | A-501 | B-1 |
| n3-9522 | A-502 | B-1 |
| n3-9523 | A-503 | B-1 |
| n3-9524 | A-504 | B-1 |
| n3-9525 | A-505 | B-1 |
| n3-9526 | A-506 | B-1 |
| n3-9527 | A-507 | B-1 |
| n3-9528 | A-508 | B-1 |
| n3-9529 | A-509 | B-1 |
| n3-9530 | A-510 | B-1 |
| n3-9531 | A-511 | B-1 |
| n3-9532 | A-512 | B-1 |
| n3-9533 | A-513 | B-1 |
| n3-9534 | A-514 | B-1 |
| n3-9535 | A-515 | B-1 |
| n3-9536 | A-516 | B-1 |
| n3-9537 | A-517 | B-1 |
| n3-9538 | A-518 | B-1 |
| n3-9539 | A-519 | B-1 |
| n3-9540 | A-520 | B-1 |
| n3-9541 | A-521 | B-1 |
| n3-9542 | A-522 | B-1 |
| n3-9543 | A-523 | B-1 |
| n3-9544 | A-524 | B-1 |
| n3-9545 | A-525 | B-1 |
| n3-9546 | A-526 | B-1 |
| n3-9547 | A-527 | B-1 |
| n3-9548 | A-528 | B-1 |
| n3-9549 | A-529 | B-1 |
| n3-9550 | A-530 | B-1 |
| n3-9551 | A-531 | B-1 |
| n3-9552 | A-532 | B-1 |
| n3-9553 | A-533 | B-1 |
| n3-9554 | A-534 | B-1 |
| n3-9555 | A-535 | B-1 |
| n3-9556 | A-536 | B-1 |
| n3-9557 | A-537 | B-1 |
| n3-9558 | A-538 | B-1 |
| n3-9559 | A-539 | B-1 |
| n3-9560 | A-540 | B-1 |
| n3-9561 | A-541 | B-1 |
| n3-9562 | A-542 | B-1 |
| n3-9563 | A-543 | B-1 |
| n3-9564 | A-544 | B-1 |
| n3-9565 | A-545 | B-1 |
| n3-9566 | A-546 | B-1 |
| n3-9567 | A-547 | B-1 |
| n3-9568 | A-548 | B-1 |
| n3-9569 | A-549 | B-1 |
| n3-9570 | A-550 | B-1 |
| n3-9571 | A-551 | B-1 |
| n3-9572 | A-552 | B-1 |
| n3-9573 | A-553 | B-1 |
| n3-9574 | A-554 | B-1 |
| n3-9575 | A-555 | B-1 |
| n3-9576 | A-556 | B-1 |
| n3-9577 | A-557 | B-1 |

TABLE 2-continued

| epn | n = 3 A | B |
|---|---|---|
| n3-9578 | A-558 | B-1 |
| n3-9579 | A-559 | B-1 |
| n3-9580 | A-560 | B-1 |
| n3-9581 | A-561 | B-1 |
| n3-9582 | A-562 | B-1 |
| n3-9583 | A-563 | B-1 |
| n3-9584 | A-564 | B-1 |
| n3-9585 | A-565 | B-1 |
| n3-9586 | A-566 | B-1 |
| n3-9587 | A-567 | B-1 |
| n3-9588 | A-568 | B-1 |
| n3-9589 | A-569 | B-1 |
| n3-9590 | A-570 | B-1 |
| n3-9591 | A-571 | B-1 |
| n3-9592 | A-572 | B-1 |
| n3-9593 | A-573 | B-1 |
| n3-9594 | A-574 | B-1 |
| n3-9595 | A-575 | B-1 |
| n3-9596 | A-576 | B-1 |
| n3-9597 | A-577 | B-1 |
| n3-9598 | A-578 | B-1 |
| n3-9599 | A-579 | B-1 |
| n3-9600 | A-580 | B-1 |
| n3-9601 | A-581 | B-1 |
| n3-9602 | A-582 | B-1 |
| n3-9603 | A-583 | B-1 |
| n3-9604 | A-584 | B-1 |
| n3-9605 | A-585 | B-1 |
| n3-9606 | A-586 | B-1 |
| n3-9607 | A-587 | B-1 |
| n3-9608 | A-588 | B-1 |
| n3-9609 | A-589 | B-1 |
| n3-9610 | A-590 | B-1 |
| n3-9611 | A-452 | B-2 |
| n3-9612 | A-453 | B-2 |
| n3-9613 | A-454 | B-2 |
| n3-9614 | A-455 | B-2 |
| n3-9615 | A-456 | B-2 |
| n3-9616 | A-457 | B-2 |
| n3-9617 | A-458 | B-2 |
| n3-9618 | A-459 | B-2 |
| n3-9619 | A-460 | B-2 |
| n3-9620 | A-461 | B-2 |
| n3-9621 | A-462 | B-2 |
| n3-9622 | A-463 | B-2 |
| n3-9623 | A-464 | B-2 |
| n3-9624 | A-465 | B-2 |
| n3-9625 | A-466 | B-2 |
| n3-9626 | A-467 | B-2 |
| n3-9627 | A-468 | B-2 |
| n3-9628 | A-469 | B-2 |
| n3-9629 | A-470 | B-2 |
| n3-9630 | A-471 | B-2 |
| n3-9631 | A-472 | B-2 |
| n3-9632 | A-473 | B-2 |
| n3-9633 | A-474 | B-2 |
| n3-9634 | A-475 | B-2 |
| n3-9635 | A-476 | B-2 |
| n3-9636 | A-477 | B-2 |
| n3-9637 | A-478 | B-2 |
| n3-9638 | A-479 | B-2 |
| n3-9639 | A-480 | B-2 |
| n3-9640 | A-481 | B-2 |
| n3-9641 | A-482 | B-2 |
| n3-9642 | A-483 | B-2 |
| n3-9643 | A-484 | B-2 |
| n3-9644 | A-485 | B-2 |
| n3-9645 | A-486 | B-2 |
| n3-9646 | A-487 | B-2 |
| n3-9647 | A-488 | B-2 |
| n3-9648 | A-489 | B-2 |
| n3-9649 | A-490 | B-2 |
| n3-9650 | A-491 | B-2 |
| n3-9651 | A-492 | B-2 |
| n3-9652 | A-493 | B-2 |
| n3-9653 | A-494 | B-2 |
| n3-9654 | A-495 | B-2 |
| n3-9655 | A-496 | B-2 |
| n3-9656 | A-497 | B-2 |
| n3-9657 | A-498 | B-2 |
| n3-9658 | A-499 | B-2 |
| n3-9659 | A-500 | B-2 |
| n3-9660 | A-501 | B-2 |
| n3-9661 | A-502 | B-2 |
| n3-9662 | A-503 | B-2 |
| n3-9663 | A-504 | B-2 |
| n3-9664 | A-505 | B-2 |
| n3-9665 | A-506 | B-2 |
| n3-9666 | A-507 | B-2 |
| n3-9667 | A-508 | B-2 |
| n3-9668 | A-509 | B-2 |
| n3-9669 | A-510 | B-2 |
| n3-9670 | A-511 | B-2 |
| n3-9671 | A-512 | B-2 |
| n3-9672 | A-513 | B-2 |
| n3-9673 | A-514 | B-2 |
| n3-9674 | A-515 | B-2 |
| n3-9675 | A-516 | B-2 |
| n3-9676 | A-517 | B-2 |
| n3-9677 | A-518 | B-2 |
| n3-9678 | A-519 | B-2 |
| n3-9679 | A-520 | B-2 |
| n3-9680 | A-521 | B-2 |
| n3-9681 | A-522 | B-2 |
| n3-9682 | A-523 | B-2 |
| n3-9683 | A-524 | B-2 |
| n3-9684 | A-525 | B-2 |
| n3-9685 | A-526 | B-2 |
| n3-9686 | A-527 | B-2 |
| n3-9687 | A-528 | B-2 |
| n3-9688 | A-529 | B-2 |
| n3-9689 | A-530 | B-2 |
| n3-9690 | A-531 | B-2 |
| n3-9691 | A-532 | B-2 |
| n3-9692 | A-533 | B-2 |
| n3-9693 | A-534 | B-2 |
| n3-9694 | A-535 | B-2 |
| n3-9695 | A-536 | B-2 |
| n3-9696 | A-537 | B-2 |
| n3-9697 | A-538 | B-2 |
| n3-9698 | A-539 | B-2 |
| n3-9699 | A-540 | B-2 |
| n3-9700 | A-541 | B-2 |
| n3-9701 | A-542 | B-2 |
| n3-9702 | A-543 | B-2 |
| n3-9703 | A-544 | B-2 |
| n3-9704 | A-545 | B-2 |
| n3-9705 | A-546 | B-2 |
| n3-9706 | A-547 | B-2 |
| n3-9707 | A-548 | B-2 |
| n3-9708 | A-549 | B-2 |
| n3-9709 | A-550 | B-2 |
| n3-9710 | A-551 | B-2 |
| n3-9711 | A-552 | B-2 |
| n3-9712 | A-553 | B-2 |
| n3-9713 | A-554 | B-2 |
| n3-9714 | A-555 | B-2 |
| n3-9715 | A-556 | B-2 |
| n3-9716 | A-557 | B-2 |
| n3-9717 | A-558 | B-2 |
| n3-9718 | A-559 | B-2 |
| n3-9719 | A-560 | B-2 |
| n3-9720 | A-561 | B-2 |
| n3-9721 | A-562 | B-2 |
| n3-9722 | A-563 | B-2 |
| n3-9723 | A-564 | B-2 |
| n3-9724 | A-565 | B-2 |
| n3-9725 | A-566 | B-2 |
| n3-9726 | A-567 | B-2 |
| n3-9727 | A-568 | B-2 |

TABLE 2-continued

| epn | n = 3 A | B |
|---|---|---|
| n3-9728 | A-569 | B-2 |
| n3-9729 | A-570 | B-2 |
| n3-9730 | A-571 | B-2 |
| n3-9731 | A-572 | B-2 |
| n3-9732 | A-573 | B-2 |
| n3-9733 | A-574 | B-2 |
| n3-9734 | A-575 | B-2 |
| n3-9735 | A-576 | B-2 |
| n3-9736 | A-577 | B-2 |
| n3-9737 | A-578 | B-2 |
| n3-9738 | A-579 | B-2 |
| n3-9739 | A-580 | B-2 |
| n3-9740 | A-581 | B-2 |
| n3-9741 | A-582 | B-2 |
| n3-9742 | A-583 | B-2 |
| n3-9743 | A-584 | B-2 |
| n3-9744 | A-585 | B-2 |
| n3-9745 | A-586 | B-2 |
| n3-9746 | A-587 | B-2 |
| n3-9747 | A-588 | B-2 |
| n3-9748 | A-589 | B-2 |
| n3-9749 | A-590 | B-2 |
| n3-9750 | A-452 | B-3 |
| n3-9751 | A-453 | B-3 |
| n3-9752 | A-454 | B-3 |
| n3-9753 | A-455 | B-3 |
| n3-9754 | A-456 | B-3 |
| n3-9755 | A-457 | B-3 |
| n3-9756 | A-458 | B-3 |
| n3-9757 | A-459 | B-3 |
| n3-9758 | A-460 | B-3 |
| n3-9759 | A-461 | B-3 |
| n3-9760 | A-462 | B-3 |
| n3-9761 | A-463 | B-3 |
| n3-9762 | A-464 | B-3 |
| n3-9763 | A-465 | B-3 |
| n3-9764 | A-466 | B-3 |
| n3-9765 | A-467 | B-3 |
| n3-9766 | A-468 | B-3 |
| n3-9767 | A-469 | B-3 |
| n3-9768 | A-470 | B-3 |
| n3-9769 | A-471 | B-3 |
| n3-9770 | A-472 | B-3 |
| n3-9771 | A-473 | B-3 |
| n3-9772 | A-474 | B-3 |
| n3-9773 | A-475 | B-3 |
| n3-9774 | A-476 | B-3 |
| n3-9775 | A-477 | B-3 |
| n3-9776 | A-478 | B-3 |
| n3-9777 | A-479 | B-3 |
| n3-9778 | A-480 | B-3 |
| n3-9779 | A-481 | B-3 |
| n3-9780 | A-482 | B-3 |
| n3-9781 | A-483 | B-3 |
| n3-9782 | A-484 | B-3 |
| n3-9783 | A-485 | B-3 |
| n3-9784 | A-486 | B-3 |
| n3-9785 | A-487 | B-3 |
| n3-9786 | A-488 | B-3 |
| n3-9787 | A-489 | B-3 |
| n3-9788 | A-490 | B-3 |
| n3-9789 | A-491 | B-3 |
| n3-9790 | A-492 | B-3 |
| n3-9791 | A-493 | B-3 |
| n3-9792 | A-494 | B-3 |
| n3-9793 | A-495 | B-3 |
| n3-9794 | A-496 | B-3 |
| n3-9795 | A-497 | B-3 |
| n3-9796 | A-498 | B-3 |
| n3-9797 | A-499 | B-3 |
| n3-9798 | A-500 | B-3 |
| n3-9799 | A-501 | B-3 |
| n3-9800 | A-502 | B-3 |
| n3-9801 | A-503 | B-3 |
| n3-9802 | A-504 | B-3 |
| n3-9803 | A-505 | B-3 |
| n3-9804 | A-506 | B-3 |
| n3-9805 | A-507 | B-3 |
| n3-9806 | A-508 | B-3 |
| n3-9807 | A-509 | B-3 |
| n3-9808 | A-510 | B-3 |
| n3-9809 | A-511 | B-3 |
| n3-9810 | A-512 | B-3 |
| n3-9811 | A-513 | B-3 |
| n3-9812 | A-514 | B-3 |
| n3-9813 | A-515 | B-3 |
| n3-9814 | A-516 | B-3 |
| n3-9815 | A-517 | B-3 |
| n3-9816 | A-518 | B-3 |
| n3-9817 | A-519 | B-3 |
| n3-9818 | A-520 | B-3 |
| n3-9819 | A-521 | B-3 |
| n3-9820 | A-522 | B-3 |
| n3-9821 | A-523 | B-3 |
| n3-9822 | A-524 | B-3 |
| n3-9823 | A-525 | B-3 |
| n3-9824 | A-526 | B-3 |
| n3-9825 | A-527 | B-3 |
| n3-9826 | A-528 | B-3 |
| n3-9827 | A-529 | B-3 |
| n3-9828 | A-530 | B-3 |
| n3-9829 | A-531 | B-3 |
| n3-9830 | A-532 | B-3 |
| n3-9831 | A-533 | B-3 |
| n3-9832 | A-534 | B-3 |
| n3-9833 | A-535 | B-3 |
| n3-9834 | A-536 | B-3 |
| n3-9835 | A-537 | B-3 |
| n3-9836 | A-538 | B-3 |
| n3-9837 | A-539 | B-3 |
| n3-9838 | A-540 | B-3 |
| n3-9839 | A-541 | B-3 |
| n3-9840 | A-542 | B-3 |
| n3-9841 | A-543 | B-3 |
| n3-9842 | A-544 | B-3 |
| n3-9843 | A-545 | B-3 |
| n3-9844 | A-546 | B-3 |
| n3-9845 | A-547 | B-3 |
| n3-9846 | A-548 | B-3 |
| n3-9847 | A-549 | B-3 |
| n3-9848 | A-550 | B-3 |
| n3-9849 | A-551 | B-3 |
| n3-9850 | A-552 | B-3 |
| n3-9851 | A-553 | B-3 |
| n3-9852 | A-554 | B-3 |
| n3-9853 | A-555 | B-3 |
| n3-9854 | A-556 | B-3 |
| n3-9855 | A-557 | B-3 |
| n3-9856 | A-558 | B-3 |
| n3-9857 | A-559 | B-3 |
| n3-9858 | A-560 | B-3 |
| n3-9859 | A-561 | B-3 |
| n3-9860 | A-562 | B-3 |
| n3-9861 | A-563 | B-3 |
| n3-9862 | A-564 | B-3 |
| n3-9863 | A-565 | B-3 |
| n3-9864 | A-566 | B-3 |
| n3-9865 | A-567 | B-3 |
| n3-9866 | A-568 | B-3 |
| n3-9867 | A-569 | B-3 |
| n3-9868 | A-570 | B-3 |
| n3-9869 | A-571 | B-3 |
| n3-9870 | A-572 | B-3 |
| n3-9871 | A-573 | B-3 |
| n3-9872 | A-574 | B-3 |
| n3-9873 | A-575 | B-3 |
| n3-9874 | A-576 | B-3 |
| n3-9875 | A-577 | B-3 |
| n3-9876 | A-578 | B-3 |
| n3-9877 | A-579 | B-3 |

TABLE 2-continued

| epn | n = 3 A | B |
|---|---|---|
| n3-9878 | A-580 | B-3 |
| n3-9879 | A-581 | B-3 |
| n3-9880 | A-582 | B-3 |
| n3-9881 | A-583 | B-3 |
| n3-9882 | A-584 | B-3 |
| n3-9883 | A-585 | B-3 |
| n3-9884 | A-586 | B-3 |
| n3-9885 | A-587 | B-3 |
| n3-9886 | A-588 | B-3 |
| n3-9887 | A-589 | B-3 |
| n3-9888 | A-590 | B-3 |
| n3-9889 | A-452 | B-4 |
| n3-9890 | A-453 | B-4 |
| n3-9891 | A-454 | B-4 |
| n3-9892 | A-455 | B-4 |
| n3-9893 | A-456 | B-4 |
| n3-9894 | A-457 | B-4 |
| n3-9895 | A-458 | B-4 |
| n3-9896 | A-459 | B-4 |
| n3-9897 | A-460 | B-4 |
| n3-9898 | A-461 | B-4 |
| n3-9899 | A-462 | B-4 |
| n3-9900 | A-463 | B-4 |
| n3-9901 | A-464 | B-4 |
| n3-9902 | A-465 | B-4 |
| n3-9903 | A-466 | B-4 |
| n3-9904 | A-467 | B-4 |
| n3-9905 | A-468 | B-4 |
| n3-9906 | A-469 | B-4 |
| n3-9907 | A-470 | B-4 |
| n3-9908 | A-471 | B-4 |
| n3-9909 | A-472 | B-4 |
| n3-9910 | A-473 | B-4 |
| n3-9911 | A-474 | B-4 |
| n3-9912 | A-475 | B-4 |
| n3-9913 | A-476 | B-4 |
| n3-9914 | A-477 | B-4 |
| n3-9915 | A-478 | B-4 |
| n3-9916 | A-479 | B-4 |
| n3-9917 | A-480 | B-4 |
| n3-9918 | A-481 | B-4 |
| n3-9919 | A-482 | B-4 |
| n3-9920 | A-483 | B-4 |
| n3-9921 | A-484 | B-4 |
| n3-9922 | A-485 | B-4 |
| n3-9923 | A-486 | B-4 |
| n3-9924 | A-487 | B-4 |
| n3-9925 | A-488 | B-4 |
| n3-9926 | A-489 | B-4 |
| n3-9927 | A-490 | B-4 |
| n3-9928 | A-491 | B-4 |
| n3-9929 | A-492 | B-4 |
| n3-9930 | A-493 | B-4 |
| n3-9931 | A-494 | B-4 |
| n3-9932 | A-495 | B-4 |
| n3-9933 | A-496 | B-4 |
| n3-9934 | A-497 | B-4 |
| n3-9935 | A-498 | B-4 |
| n3-9936 | A-499 | B-4 |
| n3-9937 | A-500 | B-4 |
| n3-9938 | A-501 | B-4 |
| n3-9939 | A-502 | B-4 |
| n3-9940 | A-503 | B-4 |
| n3-9941 | A-504 | B-4 |
| n3-9942 | A-505 | B-4 |
| n3-9943 | A-506 | B-4 |
| n3-9944 | A-507 | B-4 |
| n3-9945 | A-508 | B-4 |
| n3-9946 | A-509 | B-4 |
| n3-9947 | A-510 | B-4 |
| n3-9948 | A-511 | B-4 |
| n3-9949 | A-512 | B-4 |
| n3-9950 | A-513 | B-4 |
| n3-9951 | A-514 | B-4 |
| n3-9952 | A-515 | B-4 |
| n3-9953 | A-516 | B-4 |
| n3-9954 | A-517 | B-4 |
| n3-9955 | A-518 | B-4 |
| n3-9956 | A-519 | B-4 |
| n3-9957 | A-520 | B-4 |
| n3-9958 | A-521 | B-4 |
| n3-9959 | A-522 | B-4 |
| n3-9960 | A-523 | B-4 |
| n3-9961 | A-524 | B-4 |
| n3-9962 | A-525 | B-4 |
| n3-9963 | A-526 | B-4 |
| n3-9964 | A-527 | B-4 |
| n3-9965 | A-528 | B-4 |
| n3-9966 | A-529 | B-4 |
| n3-9967 | A-530 | B-4 |
| n3-9968 | A-531 | B-4 |
| n3-9969 | A-532 | B-4 |
| n3-9970 | A-533 | B-4 |
| n3-9971 | A-534 | B-4 |
| n3-9972 | A-535 | B-4 |
| n3-9973 | A-536 | B-4 |
| n3-9974 | A-537 | B-4 |
| n3-9975 | A-538 | B-4 |
| n3-9976 | A-539 | B-4 |
| n3-9977 | A-540 | B-4 |
| n3-9978 | A-541 | B-4 |
| n3-9979 | A-542 | B-4 |
| n3-9980 | A-543 | B-4 |
| n3-9981 | A-544 | B-4 |
| n3-9982 | A-545 | B-4 |
| n3-9983 | A-546 | B-4 |
| n3-9984 | A-547 | B-4 |
| n3-9985 | A-548 | B-4 |
| n3-9986 | A-549 | B-4 |
| n3-9987 | A-550 | B-4 |
| n3-9988 | A-551 | B-4 |
| n3-9989 | A-552 | B-4 |
| n3-9990 | A-553 | B-4 |
| n3-9991 | A-554 | B-4 |
| n3-9992 | A-555 | B-4 |
| n3-9993 | A-556 | B-4 |
| n3-9994 | A-557 | B-4 |
| n3-9995 | A-558 | B-4 |
| n3-9996 | A-559 | B-4 |
| n3-9997 | A-560 | B-4 |
| n3-9998 | A-561 | B-4 |
| n3-9999 | A-562 | B-4 |
| n3-10000 | A-563 | B-4 |
| n3-10001 | A-564 | B-4 |
| n3-10002 | A-565 | B-4 |
| n3-10003 | A-566 | B-4 |
| n3-10004 | A-567 | B-4 |
| n3-10005 | A-568 | B-4 |
| n3-10006 | A-569 | B-4 |
| n3-10007 | A-570 | B-4 |
| n3-10008 | A-571 | B-4 |
| n3-10009 | A-572 | B-4 |
| n3-10010 | A-573 | B-4 |
| n3-10011 | A-574 | B-4 |
| n3-10012 | A-575 | B-4 |
| n3-10013 | A-576 | B-4 |
| n3-10014 | A-577 | B-4 |
| n3-10015 | A-578 | B-4 |
| n3-10016 | A-579 | B-4 |
| n3-10017 | A-580 | B-4 |
| n3-10018 | A-581 | B-4 |
| n3-10019 | A-582 | B-4 |
| n3-10020 | A-583 | B-4 |
| n3-10021 | A-584 | B-4 |
| n3-10022 | A-585 | B-4 |
| n3-10023 | A-586 | B-4 |
| n3-10024 | A-587 | B-4 |
| n3-10025 | A-588 | B-4 |
| n3-10026 | A-589 | B-4 |
| n3-10027 | A-590 | B-4 |

TABLE 2-continued

| epn | n = 3 A | B |
|---|---|---|
| n3-10028 | A-452 | B-5 |
| n3-10029 | A-453 | B-5 |
| n3-10030 | A-454 | B-5 |
| n3-10031 | A-455 | B-5 |
| n3-10032 | A-456 | B-5 |
| n3-10033 | A-457 | B-5 |
| n3-10034 | A-458 | B-5 |
| n3-10035 | A-459 | B-5 |
| n3-10036 | A-460 | B-5 |
| n3-10037 | A-461 | B-5 |
| n3-10038 | A-462 | B-5 |
| n3-10039 | A-463 | B-5 |
| n3-10040 | A-464 | B-5 |
| n3-10041 | A-465 | B-5 |
| n3-10042 | A-466 | B-5 |
| n3-10043 | A-467 | B-5 |
| n3-10044 | A-468 | B-5 |
| n3-10045 | A-469 | B-5 |
| n3-10046 | A-470 | B-5 |
| n3-10047 | A-471 | B-5 |
| n3-10048 | A-472 | B-5 |
| n3-10049 | A-473 | B-5 |
| n3-10050 | A-474 | B-5 |
| n3-10051 | A-475 | B-5 |
| n3-10052 | A-476 | B-5 |
| n3-10053 | A-477 | B-5 |
| n3-10054 | A-478 | B-5 |
| n3-10055 | A-479 | B-5 |
| n3-10056 | A-480 | B-5 |
| n3-10057 | A-481 | B-5 |
| n3-10058 | A-482 | B-5 |
| n3-10059 | A-483 | B-5 |
| n3-10060 | A-484 | B-5 |
| n3-10061 | A-485 | B-5 |
| n3-10062 | A-486 | B-5 |
| n3-10063 | A-487 | B-5 |
| n3-10064 | A-488 | B-5 |
| n3-10065 | A-489 | B-5 |
| n3-10066 | A-490 | B-5 |
| n3-10067 | A-491 | B-5 |
| n3-10068 | A-492 | B-5 |
| n3-10069 | A-493 | B-5 |
| n3-10070 | A-494 | B-5 |
| n3-10071 | A-495 | B-5 |
| n3-10072 | A-496 | B-5 |
| n3-10073 | A-497 | B-5 |
| n3-10074 | A-498 | B-5 |
| n3-10075 | A-499 | B-5 |
| n3-10076 | A-500 | B-5 |
| n3-10077 | A-501 | B-5 |
| n3-10078 | A-502 | B-5 |
| n3-10079 | A-503 | B-5 |
| n3-10080 | A-504 | B-5 |
| n3-10081 | A-505 | B-5 |
| n3-10082 | A-506 | B-5 |
| n3-10083 | A-507 | B-5 |
| n3-10084 | A-508 | B-5 |
| n3-10085 | A-509 | B-5 |
| n3-10086 | A-510 | B-5 |
| n3-10087 | A-511 | B-5 |
| n3-10088 | A-512 | B-5 |
| n3-10089 | A-513 | B-5 |
| n3-10090 | A-514 | B-5 |
| n3-10091 | A-515 | B-5 |
| n3-10092 | A-516 | B-5 |
| n3-10093 | A-517 | B-5 |
| n3-10094 | A-518 | B-5 |
| n3-10095 | A-519 | B-5 |
| n3-10096 | A-520 | B-5 |
| n3-10097 | A-521 | B-5 |
| n3-10098 | A-522 | B-5 |
| n3-10099 | A-523 | B-5 |
| n3-10100 | A-524 | B-5 |
| n3-10101 | A-525 | B-5 |
| n3-10102 | A-526 | B-5 |
| n3-10103 | A-527 | B-5 |
| n3-10104 | A-528 | B-5 |
| n3-10105 | A-529 | B-5 |
| n3-10106 | A-530 | B-5 |
| n3-10107 | A-531 | B-5 |
| n3-10108 | A-532 | B-5 |
| n3-10109 | A-533 | B-5 |
| n3-10110 | A-534 | B-5 |
| n3-10111 | A-535 | B-5 |
| n3-10112 | A-536 | B-5 |
| n3-10113 | A-537 | B-5 |
| n3-10114 | A-538 | B-5 |
| n3-10115 | A-539 | B-5 |
| n3-10116 | A-540 | B-5 |
| n3-10117 | A-541 | B-5 |
| n3-10118 | A-542 | B-5 |
| n3-10119 | A-543 | B-5 |
| n3-10120 | A-544 | B-5 |
| n3-10121 | A-545 | B-5 |
| n3-10122 | A-546 | B-5 |
| n3-10123 | A-547 | B-5 |
| n3-10124 | A-548 | B-5 |
| n3-10125 | A-549 | B-5 |
| n3-10126 | A-550 | B-5 |
| n3-10127 | A-551 | B-5 |
| n3-10128 | A-552 | B-5 |
| n3-10129 | A-553 | B-5 |
| n3-10130 | A-554 | B-5 |
| n3-10131 | A-555 | B-5 |
| n3-10132 | A-556 | B-5 |
| n3-10133 | A-557 | B-5 |
| n3-10134 | A-558 | B-5 |
| n3-10135 | A-559 | B-5 |
| n3-10136 | A-560 | B-5 |
| n3-10137 | A-561 | B-5 |
| n3-10138 | A-562 | B-5 |
| n3-10139 | A-563 | B-5 |
| n3-10140 | A-564 | B-5 |
| n3-10141 | A-565 | B-5 |
| n3-10142 | A-566 | B-5 |
| n3-10143 | A-567 | B-5 |
| n3-10144 | A-568 | B-5 |
| n3-10145 | A-569 | B-5 |
| n3-10146 | A-570 | B-5 |
| n3-10147 | A-571 | B-5 |
| n3-10148 | A-572 | B-5 |
| n3-10149 | A-573 | B-5 |
| n3-10150 | A-574 | B-5 |
| n3-10151 | A-575 | B-5 |
| n3-10152 | A-576 | B-5 |
| n3-10153 | A-577 | B-5 |
| n3-10154 | A-578 | B-5 |
| n3-10155 | A-579 | B-5 |
| n3-10156 | A-580 | B-5 |
| n3-10157 | A-581 | B-5 |
| n3-10158 | A-582 | B-5 |
| n3-10159 | A-583 | B-5 |
| n3-10160 | A-584 | B-5 |
| n3-10161 | A-585 | B-5 |
| n3-10162 | A-586 | B-5 |
| n3-10163 | A-587 | B-5 |
| n3-10164 | A-588 | B-5 |
| n3-10165 | A-589 | B-5 |
| n3-10166 | A-590 | B-5 |
| n3-10167 | A-452 | B-6 |
| n3-10168 | A-453 | B-6 |
| n3-10169 | A-454 | B-6 |
| n3-10170 | A-455 | B-6 |
| n3-10171 | A-456 | B-6 |
| n3-10172 | A-457 | B-6 |
| n3-10173 | A-458 | B-6 |
| n3-10174 | A-459 | B-6 |
| n3-10175 | A-460 | B-6 |
| n3-10176 | A-461 | B-6 |
| n3-10177 | A-462 | B-6 |

TABLE 2-continued

| | n = 3 | |
|---|---|---|
| epn | A | B |
| n3-10178 | A-463 | B-6 |
| n3-10179 | A-464 | B-6 |
| n3-10180 | A-465 | B-6 |
| n3-10181 | A-466 | B-6 |
| n3-10182 | A-467 | B-6 |
| n3-10183 | A-468 | B-6 |
| n3-10184 | A-469 | B-6 |
| n3-10185 | A-470 | B-6 |
| n3-10186 | A-471 | B-6 |
| n3-10187 | A-472 | B-6 |
| n3-10188 | A-473 | B-6 |
| n3-10189 | A-474 | B-6 |
| n3-10190 | A-475 | B-6 |
| n3-10191 | A-476 | B-6 |
| n3-10192 | A-477 | B-6 |
| n3-10193 | A-478 | B-6 |
| n3-10194 | A-479 | B-6 |
| n3-10195 | A-480 | B-6 |
| n3-10196 | A-481 | B-6 |
| n3-10197 | A-482 | B-6 |
| n3-10198 | A-483 | B-6 |
| n3-10199 | A-484 | B-6 |
| n3-10200 | A-485 | B-6 |
| n3-10201 | A-486 | B-6 |
| n3-10202 | A-487 | B-6 |
| n3-10203 | A-488 | B-6 |
| n3-10204 | A-489 | B-6 |
| n3-10205 | A-490 | B-6 |
| n3-10206 | A-491 | B-6 |
| n3-10207 | A-492 | B-6 |
| n3-10208 | A-493 | B-6 |
| n3-10209 | A-494 | B-6 |
| n3-10210 | A-495 | B-6 |
| n3-10211 | A-496 | B-6 |
| n3-10212 | A-497 | B-6 |
| n3-10213 | A-498 | B-6 |
| n3-10214 | A-499 | B-6 |
| n3-10215 | A-500 | B-6 |
| n3-10216 | A-501 | B-6 |
| n3-10217 | A-502 | B-6 |
| n3-10218 | A-503 | B-6 |
| n3-10219 | A-504 | B-6 |
| n3-10220 | A-505 | B-6 |
| n3-10221 | A-506 | B-6 |
| n3-10222 | A-507 | B-6 |
| n3-10223 | A-508 | B-6 |
| n3-10224 | A-509 | B-6 |
| n3-10225 | A-510 | B-6 |
| n3-10226 | A-511 | B-6 |
| n3-10227 | A-512 | B-6 |
| n3-10228 | A-513 | B-6 |
| n3-10229 | A-514 | B-6 |
| n3-10230 | A-515 | B-6 |
| n3-10231 | A-516 | B-6 |
| n3-10232 | A-517 | B-6 |
| n3-10233 | A-518 | B-6 |
| n3-10234 | A-519 | B-6 |
| n3-10235 | A-520 | B-6 |
| n3-10236 | A-521 | B-6 |
| n3-10237 | A-522 | B-6 |
| n3-10238 | A-523 | B-6 |
| n3-10239 | A-524 | B-6 |
| n3-10240 | A-525 | B-6 |
| n3-10241 | A-526 | B-6 |
| n3-10242 | A-527 | B-6 |
| n3-10243 | A-528 | B-6 |
| n3-10244 | A-529 | B-6 |
| n3-10245 | A-530 | B-6 |
| n3-10246 | A-531 | B-6 |
| n3-10247 | A-532 | B-6 |
| n3-10248 | A-533 | B-6 |
| n3-10249 | A-534 | B-6 |
| n3-10250 | A-535 | B-6 |
| n3-10251 | A-536 | B-6 |
| n3-10252 | A-537 | B-6 |
| n3-10253 | A-538 | B-6 |
| n3-10254 | A-539 | B-6 |
| n3-10255 | A-540 | B-6 |
| n3-10256 | A-541 | B-6 |
| n3-10257 | A-542 | B-6 |
| n3-10258 | A-543 | B-6 |
| n3-10259 | A-544 | B-6 |
| n3-10260 | A-545 | B-6 |
| n3-10261 | A-546 | B-6 |
| n3-10262 | A-547 | B-6 |
| n3-10263 | A-548 | B-6 |
| n3-10264 | A-549 | B-6 |
| n3-10265 | A-550 | B-6 |
| n3-10266 | A-551 | B-6 |
| n3-10267 | A-552 | B-6 |
| n3-10268 | A-553 | B-6 |
| n3-10269 | A-554 | B-6 |
| n3-10270 | A-555 | B-6 |
| n3-10271 | A-556 | B-6 |
| n3-10272 | A-557 | B-6 |
| n3-10273 | A-558 | B-6 |
| n3-10274 | A-559 | B-6 |
| n3-10275 | A-560 | B-6 |
| n3-10276 | A-561 | B-6 |
| n3-10277 | A-562 | B-6 |
| n3-10278 | A-563 | B-6 |
| n3-10279 | A-564 | B-6 |
| n3-10280 | A-565 | B-6 |
| n3-10281 | A-566 | B-6 |
| n3-10282 | A-567 | B-6 |
| n3-10283 | A-568 | B-6 |
| n3-10284 | A-569 | B-6 |
| n3-10285 | A-570 | B-6 |
| n3-10286 | A-571 | B-6 |
| n3-10287 | A-572 | B-6 |
| n3-10288 | A-573 | B-6 |
| n3-10289 | A-574 | B-6 |
| n3-10290 | A-575 | B-6 |
| n3-10291 | A-576 | B-6 |
| n3-10292 | A-577 | B-6 |
| n3-10293 | A-578 | B-6 |
| n3-10294 | A-579 | B-6 |
| n3-10295 | A-580 | B-6 |
| n3-10296 | A-581 | B-6 |
| n3-10297 | A-582 | B-6 |
| n3-10298 | A-583 | B-6 |
| n3-10299 | A-584 | B-6 |
| n3-10300 | A-585 | B-6 |
| n3-10301 | A-586 | B-6 |
| n3-10302 | A-587 | B-6 |
| n3-10303 | A-588 | B-6 |
| n3-10304 | A-589 | B-6 |
| n3-10305 | A-590 | B-6 |
| n3-10306 | A-452 | B-7 |
| n3-10307 | A-453 | B-7 |
| n3-10308 | A-454 | B-7 |
| n3-10309 | A-455 | B-7 |
| n3-10310 | A-456 | B-7 |
| n3-10311 | A-457 | B-7 |
| n3-10312 | A-458 | B-7 |
| n3-10313 | A-459 | B-7 |
| n3-10314 | A-460 | B-7 |
| n3-10315 | A-461 | B-7 |
| n3-10316 | A-462 | B-7 |
| n3-10317 | A-463 | B-7 |
| n3-10318 | A-464 | B-7 |
| n3-10319 | A-465 | B-7 |
| n3-10320 | A-466 | B-7 |
| n3-10321 | A-467 | B-7 |
| n3-10322 | A-468 | B-7 |
| n3-10323 | A-469 | B-7 |
| n3-10324 | A-470 | B-7 |
| n3-10325 | A-471 | B-7 |
| n3-10326 | A-472 | B-7 |
| n3-10327 | A-473 | B-7 |

TABLE 2-continued

| | n = 3 | |
|---|---|---|
| epn | A | B |
| n3-10328 | A-474 | B-7 |
| n3-10329 | A-475 | B-7 |
| n3-10330 | A-476 | B-7 |
| n3-10331 | A-477 | B-7 |
| n3-10332 | A-478 | B-7 |
| n3-10333 | A-479 | B-7 |
| n3-10334 | A-480 | B-7 |
| n3-10335 | A-481 | B-7 |
| n3-10336 | A-482 | B-7 |
| n3-10337 | A-483 | B-7 |
| n3-10338 | A-484 | B-7 |
| n3-10339 | A-485 | B-7 |
| n3-10340 | A-486 | B-7 |
| n3-10341 | A-487 | B-7 |
| n3-10342 | A-488 | B-7 |
| n3-10343 | A-489 | B-7 |
| n3-10344 | A-490 | B-7 |
| n3-10345 | A-491 | B-7 |
| n3-10346 | A-492 | B-7 |
| n3-10347 | A-493 | B-7 |
| n3-10348 | A-494 | B-7 |
| n3-10349 | A-495 | B-7 |
| n3-10350 | A-496 | B-7 |
| n3-10351 | A-497 | B-7 |
| n3-10352 | A-498 | B-7 |
| n3-10353 | A-499 | B-7 |
| n3-10354 | A-500 | B-7 |
| n3-10355 | A-501 | B-7 |
| n3-10356 | A-502 | B-7 |
| n3-10357 | A-503 | B-7 |
| n3-10358 | A-504 | B-7 |
| n3-10359 | A-505 | B-7 |
| n3-10360 | A-506 | B-7 |
| n3-10361 | A-507 | B-7 |
| n3-10362 | A-508 | B-7 |
| n3-10363 | A-509 | B-7 |
| n3-10364 | A-510 | B-7 |
| n3-10365 | A-511 | B-7 |
| n3-10366 | A-512 | B-7 |
| n3-10367 | A-513 | B-7 |
| n3-10368 | A-514 | B-7 |
| n3-10369 | A-515 | B-7 |
| n3-10370 | A-516 | B-7 |
| n3-10371 | A-517 | B-7 |
| n3-10372 | A-518 | B-7 |
| n3-10373 | A-519 | B-7 |
| n3-10374 | A-520 | B-7 |
| n3-10375 | A-521 | B-7 |
| n3-10376 | A-522 | B-7 |
| n3-10377 | A-523 | B-7 |
| n3-10378 | A-524 | B-7 |
| n3-10379 | A-525 | B-7 |
| n3-10380 | A-526 | B-7 |
| n3-10381 | A-527 | B-7 |
| n3-10382 | A-528 | B-7 |
| n3-10383 | A-529 | B-7 |
| n3-10384 | A-530 | B-7 |
| n3-10385 | A-531 | B-7 |
| n3-10386 | A-532 | B-7 |
| n3-10387 | A-533 | B-7 |
| n3-10388 | A-534 | B-7 |
| n3-10389 | A-535 | B-7 |
| n3-10390 | A-536 | B-7 |
| n3-10391 | A-537 | B-7 |
| n3-10392 | A-538 | B-7 |
| n3-10393 | A-539 | B-7 |
| n3-10394 | A-540 | B-7 |
| n3-10395 | A-541 | B-7 |
| n3-10396 | A-542 | B-7 |
| n3-10397 | A-543 | B-7 |
| n3-10398 | A-544 | B-7 |
| n3-10399 | A-545 | B-7 |
| n3-10400 | A-546 | B-7 |
| n3-10401 | A-547 | B-7 |
| n3-10402 | A-548 | B-7 |
| n3-10403 | A-549 | B-7 |
| n3-10404 | A-550 | B-7 |
| n3-10405 | A-551 | B-7 |
| n3-10406 | A-552 | B-7 |
| n3-10407 | A-553 | B-7 |
| n3-10408 | A-554 | B-7 |
| n3-10409 | A-555 | B-7 |
| n3-10410 | A-556 | B-7 |
| n3-10411 | A-557 | B-7 |
| n3-10412 | A-558 | B-7 |
| n3-10413 | A-559 | B-7 |
| n3-10414 | A-560 | B-7 |
| n3-10415 | A-561 | B-7 |
| n3-10416 | A-562 | B-7 |
| n3-10417 | A-563 | B-7 |
| n3-10418 | A-564 | B-7 |
| n3-10419 | A-565 | B-7 |
| n3-10420 | A-566 | B-7 |
| n3-10421 | A-567 | B-7 |
| n3-10422 | A-568 | B-7 |
| n3-10423 | A-569 | B-7 |
| n3-10424 | A-570 | B-7 |
| n3-10425 | A-571 | B-7 |
| n3-10426 | A-572 | B-7 |
| n3-10427 | A-573 | B-7 |
| n3-10428 | A-574 | B-7 |
| n3-10429 | A-575 | B-7 |
| n3-10430 | A-576 | B-7 |
| n3-10431 | A-577 | B-7 |
| n3-10432 | A-578 | B-7 |
| n3-10433 | A-579 | B-7 |
| n3-10434 | A-580 | B-7 |
| n3-10435 | A-581 | B-7 |
| n3-10436 | A-582 | B-7 |
| n3-10437 | A-583 | B-7 |
| n3-10438 | A-584 | B-7 |
| n3-10439 | A-585 | B-7 |
| n3-10440 | A-586 | B-7 |
| n3-10441 | A-587 | B-7 |
| n3-10442 | A-588 | B-7 |
| n3-10443 | A-589 | B-7 |
| n3-10444 | A-590 | B-7 |
| n3-10445 | A-452 | B-8 |
| n3-10446 | A-453 | B-8 |
| n3-10447 | A-454 | B-8 |
| n3-10448 | A-455 | B-8 |
| n3-10449 | A-456 | B-8 |
| n3-10450 | A-457 | B-8 |
| n3-10451 | A-458 | B-8 |
| n3-10452 | A-459 | B-8 |
| n3-10453 | A-460 | B-8 |
| n3-10454 | A-461 | B-8 |
| n3-10455 | A-462 | B-8 |
| n3-10456 | A-463 | B-8 |
| n3-10457 | A-464 | B-8 |
| n3-10458 | A-465 | B-8 |
| n3-10459 | A-466 | B-8 |
| n3-10460 | A-467 | B-8 |
| n3-10461 | A-468 | B-8 |
| n3-10462 | A-469 | B-8 |
| n3-10463 | A-470 | B-8 |
| n3-10464 | A-471 | B-8 |
| n3-10465 | A-472 | B-8 |
| n3-10466 | A-473 | B-8 |
| n3-10467 | A-474 | B-8 |
| n3-10468 | A-475 | B-8 |
| n3-10469 | A-476 | B-8 |
| n3-10470 | A-477 | B-8 |
| n3-10471 | A-478 | B-8 |
| n3-10472 | A-479 | B-8 |
| n3-10473 | A-480 | B-8 |
| n3-10474 | A-481 | B-8 |
| n3-10475 | A-482 | B-8 |
| n3-10476 | A-483 | B-8 |
| n3-10477 | A-484 | B-8 |

TABLE 2-continued

| | n = 3 | |
|---|---|---|
| epn | A | B |
| n3-10478 | A-485 | B-8 |
| n3-10479 | A-486 | B-8 |
| n3-10480 | A-487 | B-8 |
| n3-10481 | A-488 | B-8 |
| n3-10482 | A-489 | B-8 |
| n3-10483 | A-490 | B-8 |
| n3-10484 | A-491 | B-8 |
| n3-10485 | A-492 | B-8 |
| n3-10486 | A-493 | B-8 |
| n3-10487 | A-494 | B-8 |
| n3-10488 | A-495 | B-8 |
| n3-10489 | A-496 | B-8 |
| n3-10490 | A-497 | B-8 |
| n3-10491 | A-498 | B-8 |
| n3-10492 | A-499 | B-8 |
| n3-10493 | A-500 | B-8 |
| n3-10494 | A-501 | B-8 |
| n3-10495 | A-502 | B-8 |
| n3-10496 | A-503 | B-8 |
| n3-10497 | A-504 | B-8 |
| n3-10498 | A-505 | B-8 |
| n3-10499 | A-506 | B-8 |
| n3-10500 | A-507 | B-8 |
| n3-10501 | A-508 | B-8 |
| n3-10502 | A-509 | B-8 |
| n3-10503 | A-510 | B-8 |
| n3-10504 | A-511 | B-8 |
| n3-10505 | A-512 | B-8 |
| n3-10506 | A-513 | B-8 |
| n3-10507 | A-514 | B-8 |
| n3-10508 | A-515 | B-8 |
| n3-10509 | A-516 | B-8 |
| n3-10510 | A-517 | B-8 |
| n3-10511 | A-518 | B-8 |
| n3-10512 | A-519 | B-8 |
| n3-10513 | A-520 | B-8 |
| n3-10514 | A-521 | B-8 |
| n3-10515 | A-522 | B-8 |
| n3-10516 | A-523 | B-8 |
| n3-10517 | A-524 | B-8 |
| n3-10518 | A-525 | B-8 |
| n3-10519 | A-526 | B-8 |
| n3-10520 | A-527 | B-8 |
| n3-10521 | A-528 | B-8 |
| n3-10522 | A-529 | B-8 |
| n3-10523 | A-530 | B-8 |
| n3-10524 | A-531 | B-8 |
| n3-10525 | A-532 | B-8 |
| n3-10526 | A-533 | B-8 |
| n3-10527 | A-534 | B-8 |
| n3-10528 | A-535 | B-8 |
| n3-10529 | A-536 | B-8 |
| n3-10530 | A-537 | B-8 |
| n3-10531 | A-538 | B-8 |
| n3-10532 | A-539 | B-8 |
| n3-10533 | A-540 | B-8 |
| n3-10534 | A-541 | B-8 |
| n3-10535 | A-542 | B-8 |
| n3-10536 | A-543 | B-8 |
| n3-10537 | A-544 | B-8 |
| n3-10538 | A-545 | B-8 |
| n3-10539 | A-546 | B-8 |
| n3-10540 | A-547 | B-8 |
| n3-10541 | A-548 | B-8 |
| n3-10542 | A-549 | B-8 |
| n3-10543 | A-550 | B-8 |
| n3-10544 | A-551 | B-8 |
| n3-10545 | A-552 | B-8 |
| n3-10546 | A-553 | B-8 |
| n3-10547 | A-554 | B-8 |
| n3-10548 | A-555 | B-8 |
| n3-10549 | A-556 | B-8 |
| n3-10550 | A-557 | B-8 |
| n3-10551 | A-558 | B-8 |
| n3-10552 | A-559 | B-8 |
| n3-10553 | A-560 | B-8 |
| n3-10554 | A-561 | B-8 |
| n3-10555 | A-562 | B-8 |
| n3-10556 | A-563 | B-8 |
| n3-10557 | A-564 | B-8 |
| n3-10558 | A-565 | B-8 |
| n3-10559 | A-566 | B-8 |
| n3-10560 | A-567 | B-8 |
| n3-10561 | A-568 | B-8 |
| n3-10562 | A-569 | B-8 |
| n3-10563 | A-570 | B-8 |
| n3-10564 | A-571 | B-8 |
| n3-10565 | A-572 | B-8 |
| n3-10566 | A-573 | B-8 |
| n3-10567 | A-574 | B-8 |
| n3-10568 | A-575 | B-8 |
| n3-10569 | A-576 | B-8 |
| n3-10570 | A-577 | B-8 |
| n3-10571 | A-578 | B-8 |
| n3-10572 | A-579 | B-8 |
| n3-10573 | A-580 | B-8 |
| n3-10574 | A-581 | B-8 |
| n3-10575 | A-582 | B-8 |
| n3-10576 | A-583 | B-8 |
| n3-10577 | A-584 | B-8 |
| n3-10578 | A-585 | B-8 |
| n3-10579 | A-586 | B-8 |
| n3-10580 | A-587 | B-8 |
| n3-10581 | A-588 | B-8 |
| n3-10582 | A-589 | B-8 |
| n3-10583 | A-590 | B-8 |
| n3-10584 | A-452 | B-9 |
| n3-10585 | A-453 | B-9 |
| n3-10586 | A-454 | B-9 |
| n3-10587 | A-455 | B-9 |
| n3-10588 | A-456 | B-9 |
| n3-10589 | A-457 | B-9 |
| n3-10590 | A-458 | B-9 |
| n3-10591 | A-459 | B-9 |
| n3-10592 | A-460 | B-9 |
| n3-10593 | A-461 | B-9 |
| n3-10594 | A-462 | B-9 |
| n3-10595 | A-463 | B-9 |
| n3-10596 | A-464 | B-9 |
| n3-10597 | A-465 | B-9 |
| n3-10598 | A-466 | B-9 |
| n3-10599 | A-467 | B-9 |
| n3-10600 | A-468 | B-9 |
| n3-10601 | A-469 | B-9 |
| n3-10602 | A-470 | B-9 |
| n3-10603 | A-471 | B-9 |
| n3-10604 | A-472 | B-9 |
| n3-10605 | A-473 | B-9 |
| n3-10606 | A-474 | B-9 |
| n3-10607 | A-475 | B-9 |
| n3-10608 | A-476 | B-9 |
| n3-10609 | A-477 | B-9 |
| n3-10610 | A-478 | B-9 |
| n3-10611 | A-479 | B-9 |
| n3-10612 | A-480 | B-9 |
| n3-10613 | A-481 | B-9 |
| n3-10614 | A-482 | B-9 |
| n3-10615 | A-483 | B-9 |
| n3-10616 | A-484 | B-9 |
| n3-10617 | A-485 | B-9 |
| n3-10618 | A-486 | B-9 |
| n3-10619 | A-487 | B-9 |
| n3-10620 | A-488 | B-9 |
| n3-10621 | A-489 | B-9 |
| n3-10622 | A-490 | B-9 |
| n3-10623 | A-491 | B-9 |
| n3-10624 | A-492 | B-9 |
| n3-10625 | A-493 | B-9 |
| n3-10626 | A-494 | B-9 |
| n3-10627 | A-495 | B-9 |

TABLE 2-continued

| epn | n = 3 A | B |
|---|---|---|
| n3-10628 | A-496 | B-9 |
| n3-10629 | A-497 | B-9 |
| n3-10630 | A-498 | B-9 |
| n3-10631 | A-499 | B-9 |
| n3-10632 | A-500 | B-9 |
| n3-10633 | A-501 | B-9 |
| n3-10634 | A-502 | B-9 |
| n3-10635 | A-503 | B-9 |
| n3-10636 | A-504 | B-9 |
| n3-10637 | A-505 | B-9 |
| n3-10638 | A-506 | B-9 |
| n3-10639 | A-507 | B-9 |
| n3-10640 | A-508 | B-9 |
| n3-10641 | A-509 | B-9 |
| n3-10642 | A-510 | B-9 |
| n3-10643 | A-511 | B-9 |
| n3-10644 | A-512 | B-9 |
| n3-10645 | A-513 | B-9 |
| n3-10646 | A-514 | B-9 |
| n3-10647 | A-515 | B-9 |
| n3-10648 | A-516 | B-9 |
| n3-10649 | A-517 | B-9 |
| n3-10650 | A-518 | B-9 |
| n3-10651 | A-519 | B-9 |
| n3-10652 | A-520 | B-9 |
| n3-10653 | A-521 | B-9 |
| n3-10654 | A-522 | B-9 |
| n3-10655 | A-523 | B-9 |
| n3-10656 | A-524 | B-9 |
| n3-10657 | A-525 | B-9 |
| n3-10658 | A-526 | B-9 |
| n3-10659 | A-527 | B-9 |
| n3-10660 | A-528 | B-9 |
| n3-10661 | A-529 | B-9 |
| n3-10662 | A-530 | B-9 |
| n3-10663 | A-531 | B-9 |
| n3-10664 | A-532 | B-9 |
| n3-10665 | A-533 | B-9 |
| n3-10666 | A-534 | B-9 |
| n3-10667 | A-535 | B-9 |
| n3-10668 | A-536 | B-9 |
| n3-10669 | A-537 | B-9 |
| n3-10670 | A-538 | B-9 |
| n3-10671 | A-539 | B-9 |
| n3-10672 | A-540 | B-9 |
| n3-10673 | A-541 | B-9 |
| n3-10674 | A-542 | B-9 |
| n3-10675 | A-543 | B-9 |
| n3-10676 | A-544 | B-9 |
| n3-10677 | A-545 | B-9 |
| n3-10678 | A-546 | B-9 |
| n3-10679 | A-547 | B-9 |
| n3-10680 | A-548 | B-9 |
| n3-10681 | A-549 | B-9 |
| n3-10682 | A-550 | B-9 |
| n3-10683 | A-551 | B-9 |
| n3-10684 | A-552 | B-9 |
| n3-10685 | A-553 | B-9 |
| n3-10686 | A-554 | B-9 |
| n3-10687 | A-555 | B-9 |
| n3-10688 | A-556 | B-9 |
| n3-10689 | A-557 | B-9 |
| n3-10690 | A-558 | B-9 |
| n3-10691 | A-559 | B-9 |
| n3-10692 | A-560 | B-9 |
| n3-10693 | A-561 | B-9 |
| n3-10694 | A-562 | B-9 |
| n3-10695 | A-563 | B-9 |
| n3-10696 | A-564 | B-9 |
| n3-10697 | A-565 | B-9 |
| n3-10698 | A-566 | B-9 |
| n3-10699 | A-567 | B-9 |
| n3-10700 | A-568 | B-9 |
| n3-10701 | A-569 | B-9 |
| n3-10702 | A-570 | B-9 |
| n3-10703 | A-571 | B-9 |
| n3-10704 | A-572 | B-9 |
| n3-10705 | A-573 | B-9 |
| n3-10706 | A-574 | B-9 |
| n3-10707 | A-575 | B-9 |
| n3-10708 | A-576 | B-9 |
| n3-10709 | A-577 | B-9 |
| n3-10710 | A-578 | B-9 |
| n3-10711 | A-579 | B-9 |
| n3-10712 | A-580 | B-9 |
| n3-10713 | A-581 | B-9 |
| n3-10714 | A-582 | B-9 |
| n3-10715 | A-583 | B-9 |
| n3-10716 | A-584 | B-9 |
| n3-10717 | A-585 | B-9 |
| n3-10718 | A-586 | B-9 |
| n3-10719 | A-587 | B-9 |
| n3-10720 | A-588 | B-9 |
| n3-10721 | A-589 | B-9 |
| n3-10722 | A-590 | B-9 |
| n3-10723 | A-452 | B-10 |
| n3-10724 | A-453 | B-10 |
| n3-10725 | A-454 | B-10 |
| n3-10726 | A-455 | B-10 |
| n3-10727 | A-456 | B-10 |
| n3-10728 | A-457 | B-10 |
| n3-10729 | A-458 | B-10 |
| n3-10730 | A-459 | B-10 |
| n3-10731 | A-460 | B-10 |
| n3-10732 | A-461 | B-10 |
| n3-10733 | A-462 | B-10 |
| n3-10734 | A-463 | B-10 |
| n3-10735 | A-464 | B-10 |
| n3-10736 | A-465 | B-10 |
| n3-10737 | A-466 | B-10 |
| n3-10738 | A-467 | B-10 |
| n3-10739 | A-468 | B-10 |
| n3-10740 | A-469 | B-10 |
| n3-10741 | A-470 | B-10 |
| n3-10742 | A-471 | B-10 |
| n3-10743 | A-472 | B-10 |
| n3-10744 | A-473 | B-10 |
| n3-10745 | A-474 | B-10 |
| n3-10746 | A-475 | B-10 |
| n3-10747 | A-476 | B-10 |
| n3-10748 | A-477 | B-10 |
| n3-10749 | A-478 | B-10 |
| n3-10750 | A-479 | B-10 |
| n3-10751 | A-480 | B-10 |
| n3-10752 | A-481 | B-10 |
| n3-10753 | A-482 | B-10 |
| n3-10754 | A-483 | B-10 |
| n3-10755 | A-484 | B-10 |
| n3-10756 | A-485 | B-10 |
| n3-10757 | A-486 | B-10 |
| n3-10758 | A-487 | B-10 |
| n3-10759 | A-488 | B-10 |
| n3-10760 | A-489 | B-10 |
| n3-10761 | A-490 | B-10 |
| n3-10762 | A-491 | B-10 |
| n3-10763 | A-492 | B-10 |
| n3-10764 | A-493 | B-10 |
| n3-10765 | A-494 | B-10 |
| n3-10766 | A-495 | B-10 |
| n3-10767 | A-496 | B-10 |
| n3-10768 | A-497 | B-10 |
| n3-10769 | A-498 | B-10 |
| n3-10770 | A-499 | B-10 |
| n3-10771 | A-500 | B-10 |
| n3-10772 | A-501 | B-10 |
| n3-10773 | A-502 | B-10 |
| n3-10774 | A-503 | B-10 |
| n3-10775 | A-504 | B-10 |
| n3-10776 | A-505 | B-10 |
| n3-10777 | A-506 | B-10 |

TABLE 2-continued

| epn | n = 3 A | B |
|---|---|---|
| n3-10778 | A-507 | B-10 |
| n3-10779 | A-508 | B-10 |
| n3-10780 | A-509 | B-10 |
| n3-10781 | A-510 | B-10 |
| n3-10782 | A-511 | B-10 |
| n3-10783 | A-512 | B-10 |
| n3-10784 | A-513 | B-10 |
| n3-10785 | A-514 | B-10 |
| n3-10786 | A-515 | B-10 |
| n3-10787 | A-516 | B-10 |
| n3-10788 | A-517 | B-10 |
| n3-10789 | A-518 | B-10 |
| n3-10790 | A-519 | B-10 |
| n3-10791 | A-520 | B-10 |
| n3-10792 | A-521 | B-10 |
| n3-10793 | A-522 | B-10 |
| n3-10794 | A-523 | B-10 |
| n3-10795 | A-524 | B-10 |
| n3-10796 | A-525 | B-10 |
| n3-10797 | A-526 | B-10 |
| n3-10798 | A-527 | B-10 |
| n3-10799 | A-528 | B-10 |
| n3-10800 | A-529 | B-10 |
| n3-10801 | A-530 | B-10 |
| n3-10802 | A-531 | B-10 |
| n3-10803 | A-532 | B-10 |
| n3-10804 | A-533 | B-10 |
| n3-10805 | A-534 | B-10 |
| n3-10806 | A-535 | B-10 |
| n3-10807 | A-536 | B-10 |
| n3-10808 | A-537 | B-10 |
| n3-10809 | A-538 | B-10 |
| n3-10810 | A-539 | B-10 |
| n3-10811 | A-540 | B-10 |
| n3-10812 | A-541 | B-10 |
| n3-10813 | A-542 | B-10 |
| n3-10814 | A-543 | B-10 |
| n3-10815 | A-544 | B-10 |
| n3-10816 | A-545 | B-10 |
| n3-10817 | A-546 | B-10 |
| n3-10818 | A-547 | B-10 |
| n3-10819 | A-548 | B-10 |
| n3-10820 | A-549 | B-10 |
| n3-10821 | A-550 | B-10 |
| n3-10822 | A-551 | B-10 |
| n3-10823 | A-552 | B-10 |
| n3-10824 | A-553 | B-10 |
| n3-10825 | A-554 | B-10 |
| n3-10826 | A-555 | B-10 |
| n3-10827 | A-556 | B-10 |
| n3-10828 | A-557 | B-10 |
| n3-10829 | A-558 | B-10 |
| n3-10830 | A-559 | B-10 |
| n3-10831 | A-560 | B-10 |
| n3-10832 | A-561 | B-10 |
| n3-10833 | A-562 | B-10 |
| n3-10834 | A-563 | B-10 |
| n3-10835 | A-564 | B-10 |
| n3-10836 | A-565 | B-10 |
| n3-10837 | A-566 | B-10 |
| n3-10838 | A-567 | B-10 |
| n3-10839 | A-568 | B-10 |
| n3-10840 | A-569 | B-10 |
| n3-10841 | A-570 | B-10 |
| n3-10842 | A-571 | B-10 |
| n3-10843 | A-572 | B-10 |
| n3-10844 | A-573 | B-10 |
| n3-10845 | A-574 | B-10 |
| n3-10846 | A-575 | B-10 |
| n3-10847 | A-576 | B-10 |
| n3-10848 | A-577 | B-10 |
| n3-10849 | A-578 | B-10 |
| n3-10850 | A-579 | B-10 |
| n3-10851 | A-580 | B-10 |
| n3-10852 | A-581 | B-10 |
| n3-10853 | A-582 | B-10 |
| n3-10854 | A-583 | B-10 |
| n3-10855 | A-584 | B-10 |
| n3-10856 | A-585 | B-10 |
| n3-10857 | A-586 | B-10 |
| n3-10858 | A-587 | B-10 |
| n3-10859 | A-588 | B-10 |
| n3-10860 | A-589 | B-10 |
| n3-10861 | A-590 | B-10 |
| n3-10862 | A-452 | B-11 |
| n3-10863 | A-453 | B-11 |
| n3-10864 | A-454 | B-11 |
| n3-10865 | A-455 | B-11 |
| n3-10866 | A-456 | B-11 |
| n3-10867 | A-457 | B-11 |
| n3-10868 | A-458 | B-11 |
| n3-10869 | A-459 | B-11 |
| n3-10870 | A-460 | B-11 |
| n3-10871 | A-461 | B-11 |
| n3-10872 | A-462 | B-11 |
| n3-10873 | A-463 | B-11 |
| n3-10874 | A-464 | B-11 |
| n3-10875 | A-465 | B-11 |
| n3-10876 | A-466 | B-11 |
| n3-10877 | A-467 | B-11 |
| n3-10878 | A-468 | B-11 |
| n3-10879 | A-469 | B-11 |
| n3-10880 | A-470 | B-11 |
| n3-10881 | A-471 | B-11 |
| n3-10882 | A-472 | B-11 |
| n3-10883 | A-473 | B-11 |
| n3-10884 | A-474 | B-11 |
| n3-10885 | A-475 | B-11 |
| n3-10886 | A-476 | B-11 |
| n3-10887 | A-477 | B-11 |
| n3-10888 | A-478 | B-11 |
| n3-10889 | A-479 | B-11 |
| n3-10890 | A-480 | B-11 |
| n3-10891 | A-481 | B-11 |
| n3-10892 | A-482 | B-11 |
| n3-10893 | A-483 | B-11 |
| n3-10894 | A-484 | B-11 |
| n3-10895 | A-485 | B-11 |
| n3-10896 | A-486 | B-11 |
| n3-10897 | A-487 | B-11 |
| n3-10898 | A-488 | B-11 |
| n3-10899 | A-489 | B-11 |
| n3-10900 | A-490 | B-11 |
| n3-10901 | A-491 | B-11 |
| n3-10902 | A-492 | B-11 |
| n3-10903 | A-493 | B-11 |
| n3-10904 | A-494 | B-11 |
| n3-10905 | A-495 | B-11 |
| n3-10906 | A-496 | B-11 |
| n3-10907 | A-497 | B-11 |
| n3-10908 | A-498 | B-11 |
| n3-10909 | A-499 | B-11 |
| n3-10910 | A-500 | B-11 |
| n3-10911 | A-501 | B-11 |
| n3-10912 | A-502 | B-11 |
| n3-10913 | A-503 | B-11 |
| n3-10914 | A-504 | B-11 |
| n3-10915 | A-505 | B-11 |
| n3-10916 | A-506 | B-11 |
| n3-10917 | A-507 | B-11 |
| n3-10918 | A-508 | B-11 |
| n3-10919 | A-509 | B-11 |
| n3-10920 | A-510 | B-11 |
| n3-10921 | A-511 | B-11 |
| n3-10922 | A-512 | B-11 |
| n3-10923 | A-513 | B-11 |
| n3-10924 | A-514 | B-11 |
| n3-10925 | A-515 | B-11 |
| n3-10926 | A-516 | B-11 |
| n3-10927 | A-517 | B-11 |

TABLE 2-continued

| | n = 3 | |
|---|---|---|
| epn | A | B |
| n3-10928 | A-518 | B-11 |
| n3-10929 | A-519 | B-11 |
| n3-10930 | A-520 | B-11 |
| n3-10931 | A-521 | B-11 |
| n3-10932 | A-522 | B-11 |
| n3-10933 | A-523 | B-11 |
| n3-10934 | A-524 | B-11 |
| n3-10935 | A-525 | B-11 |
| n3-10936 | A-526 | B-11 |
| n3-10937 | A-527 | B-11 |
| n3-10938 | A-528 | B-11 |
| n3-10939 | A-529 | B-11 |
| n3-10940 | A-530 | B-11 |
| n3-10941 | A-531 | B-11 |
| n3-10942 | A-532 | B-11 |
| n3-10943 | A-533 | B-11 |
| n3-10944 | A-534 | B-11 |
| n3-10945 | A-535 | B-11 |
| n3-10946 | A-536 | B-11 |
| n3-10947 | A-537 | B-11 |
| n3-10948 | A-538 | B-11 |
| n3-10949 | A-539 | B-11 |
| n3-10950 | A-540 | B-11 |
| n3-10951 | A-541 | B-11 |
| n3-10952 | A-542 | B-11 |
| n3-10953 | A-543 | B-11 |
| n3-10954 | A-544 | B-11 |
| n3-10955 | A-545 | B-11 |
| n3-10956 | A-546 | B-11 |
| n3-10957 | A-547 | B-11 |
| n3-10958 | A-548 | B-11 |
| n3-10959 | A-549 | B-11 |
| n3-10960 | A-550 | B-11 |
| n3-10961 | A-551 | B-11 |
| n3-10962 | A-552 | B-11 |
| n3-10963 | A-553 | B-11 |
| n3-10964 | A-554 | B-11 |
| n3-10965 | A-555 | B-11 |
| n3-10966 | A-556 | B-11 |
| n3-10967 | A-557 | B-11 |
| n3-10968 | A-558 | B-11 |
| n3-10969 | A-559 | B-11 |
| n3-10970 | A-560 | B-11 |
| n3-10971 | A-561 | B-11 |
| n3-10972 | A-562 | B-11 |
| n3-10973 | A-563 | B-11 |
| n3-10974 | A-564 | B-11 |
| n3-10975 | A-565 | B-11 |
| n3-10976 | A-566 | B-11 |
| n3-10977 | A-567 | B-11 |
| n3-10978 | A-568 | B-11 |
| n3-10979 | A-569 | B-11 |
| n3-10980 | A-570 | B-11 |
| n3-10981 | A-571 | B-11 |
| n3-10982 | A-572 | B-11 |
| n3-10983 | A-573 | B-11 |
| n3-10984 | A-574 | B-11 |
| n3-10985 | A-575 | B-11 |
| n3-10986 | A-576 | B-11 |
| n3-10987 | A-577 | B-11 |
| n3-10988 | A-578 | B-11 |
| n3-10989 | A-579 | B-11 |
| n3-10990 | A-580 | B-11 |
| n3-10991 | A-581 | B-11 |
| n3-10992 | A-582 | B-11 |
| n3-10993 | A-583 | B-11 |
| n3-10994 | A-584 | B-11 |
| n3-10995 | A-585 | B-11 |
| n3-10996 | A-586 | B-11 |
| n3-10997 | A-587 | B-11 |
| n3-10998 | A-588 | B-11 |
| n3-10999 | A-589 | B-11 |
| n3-11000 | A-590 | B-11 |
| n3-11001 | A-452 | B-12 |
| n3-11002 | A-453 | B-12 |
| n3-11003 | A-454 | B-12 |
| n3-11004 | A-455 | B-12 |
| n3-11005 | A-456 | B-12 |
| n3-11006 | A-457 | B-12 |
| n3-11007 | A-458 | B-12 |
| n3-11008 | A-459 | B-12 |
| n3-11009 | A-460 | B-12 |
| n3-11010 | A-461 | B-12 |
| n3-11011 | A-462 | B-12 |
| n3-11012 | A-463 | B-12 |
| n3-11013 | A-464 | B-12 |
| n3-11014 | A-465 | B-12 |
| n3-11015 | A-466 | B-12 |
| n3-11016 | A-467 | B-12 |
| n3-11017 | A-468 | B-12 |
| n3-11018 | A-469 | B-12 |
| n3-11019 | A-470 | B-12 |
| n3-11020 | A-471 | B-12 |
| n3-11021 | A-472 | B-12 |
| n3-11022 | A-473 | B-12 |
| n3-11023 | A-474 | B-12 |
| n3-11024 | A-475 | B-12 |
| n3-11025 | A-476 | B-12 |
| n3-11026 | A-477 | B-12 |
| n3-11027 | A-478 | B-12 |
| n3-11028 | A-479 | B-12 |
| n3-11029 | A-480 | B-12 |
| n3-11030 | A-481 | B-12 |
| n3-11031 | A-482 | B-12 |
| n3-11032 | A-483 | B-12 |
| n3-11033 | A-484 | B-12 |
| n3-11034 | A-485 | B-12 |
| n3-11035 | A-486 | B-12 |
| n3-11036 | A-487 | B-12 |
| n3-11037 | A-488 | B-12 |
| n3-11038 | A-489 | B-12 |
| n3-11039 | A-490 | B-12 |
| n3-11040 | A-491 | B-12 |
| n3-11041 | A-492 | B-12 |
| n3-11042 | A-493 | B-12 |
| n3-11043 | A-494 | B-12 |
| n3-11044 | A-495 | B-12 |
| n3-11045 | A-496 | B-12 |
| n3-11046 | A-497 | B-12 |
| n3-11047 | A-498 | B-12 |
| n3-11048 | A-499 | B-12 |
| n3-11049 | A-500 | B-12 |
| n3-11050 | A-501 | B-12 |
| n3-11051 | A-502 | B-12 |
| n3-11052 | A-503 | B-12 |
| n3-11053 | A-504 | B-12 |
| n3-11054 | A-505 | B-12 |
| n3-11055 | A-506 | B-12 |
| n3-11056 | A-507 | B-12 |
| n3-11057 | A-508 | B-12 |
| n3-11058 | A-509 | B-12 |
| n3-11059 | A-510 | B-12 |
| n3-11060 | A-511 | B-12 |
| n3-11061 | A-512 | B-12 |
| n3-11062 | A-513 | B-12 |
| n3-11063 | A-514 | B-12 |
| n3-11064 | A-515 | B-12 |
| n3-11065 | A-516 | B-12 |
| n3-11066 | A-517 | B-12 |
| n3-11067 | A-518 | B-12 |
| n3-11068 | A-519 | B-12 |
| n3-11069 | A-520 | B-12 |
| n3-11070 | A-521 | B-12 |
| n3-11071 | A-522 | B-12 |
| n3-11072 | A-523 | B-12 |
| n3-11073 | A-524 | B-12 |
| n3-11074 | A-525 | B-12 |
| n3-11075 | A-526 | B-12 |
| n3-11076 | A-527 | B-12 |
| n3-11077 | A-528 | B-12 |

TABLE 2-continued

| epn | n = 3 A | B |
|---|---|---|
| n3-11078 | A-529 | B-12 |
| n3-11079 | A-530 | B-12 |
| n3-11080 | A-531 | B-12 |
| n3-11081 | A-532 | B-12 |
| n3-11082 | A-533 | B-12 |
| n3-11083 | A-534 | B-12 |
| n3-11084 | A-535 | B-12 |
| n3-11085 | A-536 | B-12 |
| n3-11086 | A-537 | B-12 |
| n3-11087 | A-538 | B-12 |
| n3-11088 | A-539 | B-12 |
| n3-11089 | A-540 | B-12 |
| n3-11090 | A-541 | B-12 |
| n3-11091 | A-542 | B-12 |
| n3-11092 | A-543 | B-12 |
| n3-11093 | A-544 | B-12 |
| n3-11094 | A-545 | B-12 |
| n3-11095 | A-546 | B-12 |
| n3-11096 | A-547 | B-12 |
| n3-11097 | A-548 | B-12 |
| n3-11098 | A-549 | B-12 |
| n3-11099 | A-550 | B-12 |
| n3-11100 | A-551 | B-12 |
| n3-11101 | A-552 | B-12 |
| n3-11102 | A-553 | B-12 |
| n3-11103 | A-554 | B-12 |
| n3-11104 | A-555 | B-12 |
| n3-11105 | A-556 | B-12 |
| n3-11106 | A-557 | B-12 |
| n3-11107 | A-558 | B-12 |
| n3-11108 | A-559 | B-12 |
| n3-11109 | A-560 | B-12 |
| n3-11110 | A-561 | B-12 |
| n3-11111 | A-562 | B-12 |
| n3-11112 | A-563 | B-12 |
| n3-11113 | A-564 | B-12 |
| n3-11114 | A-565 | B-12 |
| n3-11115 | A-566 | B-12 |
| n3-11116 | A-567 | B-12 |
| n3-11117 | A-568 | B-12 |
| n3-11118 | A-569 | B-12 |
| n3-11119 | A-570 | B-12 |
| n3-11120 | A-571 | B-12 |
| n3-11121 | A-572 | B-12 |
| n3-11122 | A-573 | B-12 |
| n3-11123 | A-574 | B-12 |
| n3-11124 | A-575 | B-12 |
| n3-11125 | A-576 | B-12 |
| n3-11126 | A-577 | B-12 |
| n3-11127 | A-578 | B-12 |
| n3-11128 | A-579 | B-12 |
| n3-11129 | A-580 | B-12 |
| n3-11130 | A-581 | B-12 |
| n3-11131 | A-582 | B-12 |
| n3-11132 | A-583 | B-12 |
| n3-11133 | A-584 | B-12 |
| n3-11134 | A-585 | B-12 |
| n3-11135 | A-586 | B-12 |
| n3-11136 | A-587 | B-12 |
| n3-11137 | A-588 | B-12 |
| n3-11138 | A-589 | B-12 |
| n3-11139 | A-590 | B-12 |
| n3-11140 | A-452 | B-13 |
| n3-11141 | A-453 | B-13 |
| n3-11142 | A-454 | B-13 |
| n3-11143 | A-455 | B-13 |
| n3-11144 | A-456 | B-13 |
| n3-11145 | A-457 | B-13 |
| n3-11146 | A-458 | B-13 |
| n3-11147 | A-459 | B-13 |
| n3-11148 | A-460 | B-13 |
| n3-11149 | A-461 | B-13 |
| n3-11150 | A-462 | B-13 |
| n3-11151 | A-463 | B-13 |
| n3-11152 | A-464 | B-13 |
| n3-11153 | A-465 | B-13 |
| n3-11154 | A-466 | B-13 |
| n3-11155 | A-467 | B-13 |
| n3-11156 | A-468 | B-13 |
| n3-11157 | A-469 | B-13 |
| n3-11158 | A-470 | B-13 |
| n3-11159 | A-471 | B-13 |
| n3-11160 | A-472 | B-13 |
| n3-11161 | A-473 | B-13 |
| n3-11162 | A-474 | B-13 |
| n3-11163 | A-475 | B-13 |
| n3-11164 | A-476 | B-13 |
| n3-11165 | A-477 | B-13 |
| n3-11166 | A-478 | B-13 |
| n3-11167 | A-479 | B-13 |
| n3-11168 | A-480 | B-13 |
| n3-11169 | A-481 | B-13 |
| n3-11170 | A-482 | B-13 |
| n3-11171 | A-483 | B-13 |
| n3-11172 | A-484 | B-13 |
| n3-11173 | A-485 | B-13 |
| n3-11174 | A-486 | B-13 |
| n3-11175 | A-487 | B-13 |
| n3-11176 | A-488 | B-13 |
| n3-11177 | A-489 | B-13 |
| n3-11178 | A-490 | B-13 |
| n3-11179 | A-491 | B-13 |
| n3-11180 | A-492 | B-13 |
| n3-11181 | A-493 | B-13 |
| n3-11182 | A-494 | B-13 |
| n3-11183 | A-495 | B-13 |
| n3-11184 | A-496 | B-13 |
| n3-11185 | A-497 | B-13 |
| n3-11186 | A-498 | B-13 |
| n3-11187 | A-499 | B-13 |
| n3-11188 | A-500 | B-13 |
| n3-11189 | A-501 | B-13 |
| n3-11190 | A-502 | B-13 |
| n3-11191 | A-503 | B-13 |
| n3-11192 | A-504 | B-13 |
| n3-11193 | A-505 | B-13 |
| n3-11194 | A-506 | B-13 |
| n3-11195 | A-507 | B-13 |
| n3-11196 | A-508 | B-13 |
| n3-11197 | A-509 | B-13 |
| n3-11198 | A-510 | B-13 |
| n3-11199 | A-511 | B-13 |
| n3-11200 | A-512 | B-13 |
| n3-11201 | A-513 | B-13 |
| n3-11202 | A-514 | B-13 |
| n3-11203 | A-515 | B-13 |
| n3-11204 | A-516 | B-13 |
| n3-11205 | A-517 | B-13 |
| n3-11206 | A-518 | B-13 |
| n3-11207 | A-519 | B-13 |
| n3-11208 | A-520 | B-13 |
| n3-11209 | A-521 | B-13 |
| n3-11210 | A-522 | B-13 |
| n3-11211 | A-523 | B-13 |
| n3-11212 | A-524 | B-13 |
| n3-11213 | A-525 | B-13 |
| n3-11214 | A-526 | B-13 |
| n3-11215 | A-527 | B-13 |
| n3-11216 | A-528 | B-13 |
| n3-11217 | A-529 | B-13 |
| n3-11218 | A-530 | B-13 |
| n3-11219 | A-531 | B-13 |
| n3-11220 | A-532 | B-13 |
| n3-11221 | A-533 | B-13 |
| n3-11222 | A-534 | B-13 |
| n3-11223 | A-535 | B-13 |
| n3-11224 | A-536 | B-13 |
| n3-11225 | A-537 | B-13 |
| n3-11226 | A-538 | B-13 |
| n3-11227 | A-539 | B-13 |

TABLE 2-continued

| epn | n = 3 A | B |
|---|---|---|
| n3-11228 | A-540 | B-13 |
| n3-11229 | A-541 | B-13 |
| n3-11230 | A-542 | B-13 |
| n3-11231 | A-543 | B-13 |
| n3-11232 | A-544 | B-13 |
| n3-11233 | A-545 | B-13 |
| n3-11234 | A-546 | B-13 |
| n3-11235 | A-547 | B-13 |
| n3-11236 | A-548 | B-13 |
| n3-11237 | A-549 | B-13 |
| n3-11238 | A-550 | B-13 |
| n3-11239 | A-551 | B-13 |
| n3-11240 | A-552 | B-13 |
| n3-11241 | A-553 | B-13 |
| n3-11242 | A-554 | B-13 |
| n3-11243 | A-555 | B-13 |
| n3-11244 | A-556 | B-13 |
| n3-11245 | A-557 | B-13 |
| n3-11246 | A-558 | B-13 |
| n3-11247 | A-559 | B-13 |
| n3-11248 | A-560 | B-13 |
| n3-11249 | A-561 | B-13 |
| n3-11250 | A-562 | B-13 |
| n3-11251 | A-563 | B-13 |
| n3-11252 | A-564 | B-13 |
| n3-11253 | A-565 | B-13 |
| n3-11254 | A-566 | B-13 |
| n3-11255 | A-567 | B-13 |
| n3-11256 | A-568 | B-13 |
| n3-11257 | A-569 | B-13 |
| n3-11258 | A-570 | B-13 |
| n3-11259 | A-571 | B-13 |
| n3-11260 | A-572 | B-13 |
| n3-11261 | A-573 | B-13 |
| n3-11262 | A-574 | B-13 |
| n3-11263 | A-575 | B-13 |
| n3-11264 | A-576 | B-13 |
| n3-11265 | A-577 | B-13 |
| n3-11266 | A-578 | B-13 |
| n3-11267 | A-579 | B-13 |
| n3-11268 | A-580 | B-13 |
| n3-11269 | A-581 | B-13 |
| n3-11270 | A-582 | B-13 |
| n3-11271 | A-583 | B-13 |
| n3-11272 | A-584 | B-13 |
| n3-11273 | A-585 | B-13 |
| n3-11274 | A-586 | B-13 |
| n3-11275 | A-587 | B-13 |
| n3-11276 | A-588 | B-13 |
| n3-11277 | A-589 | B-13 |
| n3-11278 | A-590 | B-13 |
| n3-11279 | A-452 | B-14 |
| n3-11280 | A-453 | B-14 |
| n3-11281 | A-454 | B-14 |
| n3-11282 | A-455 | B-14 |
| n3-11283 | A-456 | B-14 |
| n3-11284 | A-457 | B-14 |
| n3-11285 | A-458 | B-14 |
| n3-11286 | A-459 | B-14 |
| n3-11287 | A-460 | B-14 |
| n3-11288 | A-461 | B-14 |
| n3-11289 | A-462 | B-14 |
| n3-11290 | A-463 | B-14 |
| n3-11291 | A-464 | B-14 |
| n3-11292 | A-465 | B-14 |
| n3-11293 | A-466 | B-14 |
| n3-11294 | A-467 | B-14 |
| n3-11295 | A-468 | B-14 |
| n3-11296 | A-469 | B-14 |
| n3-11297 | A-470 | B-14 |
| n3-11298 | A-471 | B-14 |
| n3-11299 | A-472 | B-14 |
| n3-11300 | A-473 | B-14 |
| n3-11301 | A-474 | B-14 |
| n3-11302 | A-475 | B-14 |
| n3-11303 | A-476 | B-14 |
| n3-11304 | A-477 | B-14 |
| n3-11305 | A-478 | B-14 |
| n3-11306 | A-479 | B-14 |
| n3-11307 | A-480 | B-14 |
| n3-11308 | A-481 | B-14 |
| n3-11309 | A-482 | B-14 |
| n3-11310 | A-483 | B-14 |
| n3-11311 | A-484 | B-14 |
| n3-11312 | A-485 | B-14 |
| n3-11313 | A-486 | B-14 |
| n3-11314 | A-487 | B-14 |
| n3-11315 | A-488 | B-14 |
| n3-11316 | A-489 | B-14 |
| n3-11317 | A-490 | B-14 |
| n3-11318 | A-491 | B-14 |
| n3-11319 | A-492 | B-14 |
| n3-11320 | A-493 | B-14 |
| n3-11321 | A-494 | B-14 |
| n3-11322 | A-495 | B-14 |
| n3-11323 | A-496 | B-14 |
| n3-11324 | A-497 | B-14 |
| n3-11325 | A-498 | B-14 |
| n3-11326 | A-499 | B-14 |
| n3-11327 | A-500 | B-14 |
| n3-11328 | A-501 | B-14 |
| n3-11329 | A-502 | B-14 |
| n3-11330 | A-503 | B-14 |
| n3-11331 | A-504 | B-14 |
| n3-11332 | A-505 | B-14 |
| n3-11333 | A-506 | B-14 |
| n3-11334 | A-507 | B-14 |
| n3-11335 | A-508 | B-14 |
| n3-11336 | A-509 | B-14 |
| n3-11337 | A-510 | B-14 |
| n3-11338 | A-511 | B-14 |
| n3-11339 | A-512 | B-14 |
| n3-11340 | A-513 | B-14 |
| n3-11341 | A-514 | B-14 |
| n3-11342 | A-515 | B-14 |
| n3-11343 | A-516 | B-14 |
| n3-11344 | A-517 | B-14 |
| n3-11345 | A-518 | B-14 |
| n3-11346 | A-519 | B-14 |
| n3-11347 | A-520 | B-14 |
| n3-11348 | A-521 | B-14 |
| n3-11349 | A-522 | B-14 |
| n3-11350 | A-523 | B-14 |
| n3-11351 | A-524 | B-14 |
| n3-11352 | A-525 | B-14 |
| n3-11353 | A-526 | B-14 |
| n3-11354 | A-527 | B-14 |
| n3-11355 | A-528 | B-14 |
| n3-11356 | A-529 | B-14 |
| n3-11357 | A-530 | B-14 |
| n3-11358 | A-531 | B-14 |
| n3-11359 | A-532 | B-14 |
| n3-11360 | A-533 | B-14 |
| n3-11361 | A-534 | B-14 |
| n3-11362 | A-535 | B-14 |
| n3-11363 | A-536 | B-14 |
| n3-11364 | A-537 | B-14 |
| n3-11365 | A-538 | B-14 |
| n3-11366 | A-539 | B-14 |
| n3-11367 | A-540 | B-14 |
| n3-11368 | A-541 | B-14 |
| n3-11369 | A-542 | B-14 |
| n3-11370 | A-543 | B-14 |
| n3-11371 | A-544 | B-14 |
| n3-11372 | A-545 | B-14 |
| n3-11373 | A-546 | B-14 |
| n3-11374 | A-547 | B-14 |
| n3-11375 | A-548 | B-14 |
| n3-11376 | A-549 | B-14 |
| n3-11377 | A-550 | B-14 |

TABLE 2-continued

| | n = 3 | |
|---|---|---|
| epn | A | B |
| n3-11378 | A-551 | B-14 |
| n3-11379 | A-552 | B-14 |
| n3-11380 | A-553 | B-14 |
| n3-11381 | A-554 | B-14 |
| n3-11382 | A-555 | B-14 |
| n3-11383 | A-556 | B-14 |
| n3-11384 | A-557 | B-14 |
| n3-11385 | A-558 | B-14 |
| n3-11386 | A-559 | B-14 |
| n3-11387 | A-560 | B-14 |
| n3-11388 | A-561 | B-14 |
| n3-11389 | A-562 | B-14 |
| n3-11390 | A-563 | B-14 |
| n3-11391 | A-564 | B-14 |
| n3-11392 | A-565 | B-14 |
| n3-11393 | A-566 | B-14 |
| n3-11394 | A-567 | B-14 |
| n3-11395 | A-568 | B-14 |
| n3-11396 | A-569 | B-14 |
| n3-11397 | A-570 | B-14 |
| n3-11398 | A-571 | B-14 |
| n3-11399 | A-572 | B-14 |
| n3-11400 | A-573 | B-14 |
| n3-11401 | A-574 | B-14 |
| n3-11402 | A-575 | B-14 |
| n3-11403 | A-576 | B-14 |
| n3-11404 | A-577 | B-14 |
| n3-11405 | A-578 | B-14 |
| n3-11406 | A-579 | B-14 |
| n3-11407 | A-580 | B-14 |
| n3-11408 | A-581 | B-14 |
| n3-11409 | A-582 | B-14 |
| n3-11410 | A-583 | B-14 |
| n3-11411 | A-584 | B-14 |
| n3-11412 | A-585 | B-14 |
| n3-11413 | A-586 | B-14 |
| n3-11414 | A-587 | B-14 |
| n3-11415 | A-588 | B-14 |
| n3-11416 | A-589 | B-14 |
| n3-11417 | A-590 | B-14 |
| n3-11418 | A-452 | B-15 |
| n3-11419 | A-453 | B-15 |
| n3-11420 | A-454 | B-15 |
| n3-11421 | A-455 | B-15 |
| n3-11422 | A-456 | B-15 |
| n3-11423 | A-457 | B-15 |
| n3-11424 | A-458 | B-15 |
| n3-11425 | A-459 | B-15 |
| n3-11426 | A-460 | B-15 |
| n3-11427 | A-461 | B-15 |
| n3-11428 | A-462 | B-15 |
| n3-11429 | A-463 | B-15 |
| n3-11430 | A-464 | B-15 |
| n3-11431 | A-465 | B-15 |
| n3-11432 | A-466 | B-15 |
| n3-11433 | A-467 | B-15 |
| n3-11434 | A-468 | B-15 |
| n3-11435 | A-469 | B-15 |
| n3-11436 | A-470 | B-15 |
| n3-11437 | A-471 | B-15 |
| n3-11438 | A-472 | B-15 |
| n3-11439 | A-473 | B-15 |
| n3-11440 | A-474 | B-15 |
| n3-11441 | A-475 | B-15 |
| n3-11442 | A-476 | B-15 |
| n3-11443 | A-477 | B-15 |
| n3-11444 | A-478 | B-15 |
| n3-11445 | A-479 | B-15 |
| n3-11446 | A-480 | B-15 |
| n3-11447 | A-481 | B-15 |
| n3-11448 | A-482 | B-15 |
| n3-11449 | A-483 | B-15 |
| n3-11450 | A-484 | B-15 |
| n3-11451 | A-485 | B-15 |
| n3-11452 | A-486 | B-15 |
| n3-11453 | A-487 | B-15 |
| n3-11454 | A-488 | B-15 |
| n3-11455 | A-489 | B-15 |
| n3-11456 | A-490 | B-15 |
| n3-11457 | A-491 | B-15 |
| n3-11458 | A-492 | B-15 |
| n3-11459 | A-493 | B-15 |
| n3-11460 | A-494 | B-15 |
| n3-11461 | A-495 | B-15 |
| n3-11462 | A-496 | B-15 |
| n3-11463 | A-497 | B-15 |
| n3-11464 | A-498 | B-15 |
| n3-11465 | A-499 | B-15 |
| n3-11466 | A-500 | B-15 |
| n3-11467 | A-501 | B-15 |
| n3-11468 | A-502 | B-15 |
| n3-11469 | A-503 | B-15 |
| n3-11470 | A-504 | B-15 |
| n3-11471 | A-505 | B-15 |
| n3-11472 | A-506 | B-15 |
| n3-11473 | A-507 | B-15 |
| n3-11474 | A-508 | B-15 |
| n3-11475 | A-509 | B-15 |
| n3-11476 | A-510 | B-15 |
| n3-11477 | A-511 | B-15 |
| n3-11478 | A-512 | B-15 |
| n3-11479 | A-513 | B-15 |
| n3-11480 | A-514 | B-15 |
| n3-11481 | A-515 | B-15 |
| n3-11482 | A-516 | B-15 |
| n3-11483 | A-517 | B-15 |
| n3-11484 | A-518 | B-15 |
| n3-11485 | A-519 | B-15 |
| n3-11486 | A-520 | B-15 |
| n3-11487 | A-521 | B-15 |
| n3-11488 | A-522 | B-15 |
| n3-11489 | A-523 | B-15 |
| n3-11490 | A-524 | B-15 |
| n3-11491 | A-525 | B-15 |
| n3-11492 | A-526 | B-15 |
| n3-11493 | A-527 | B-15 |
| n3-11494 | A-528 | B-15 |
| n3-11495 | A-529 | B-15 |
| n3-11496 | A-530 | B-15 |
| n3-11497 | A-531 | B-15 |
| n3-11498 | A-532 | B-15 |
| n3-11499 | A-533 | B-15 |
| n3-11500 | A-534 | B-15 |
| n3-11501 | A-535 | B-15 |
| n3-11502 | A-536 | B-15 |
| n3-11503 | A-537 | B-15 |
| n3-11504 | A-538 | B-15 |
| n3-11505 | A-539 | B-15 |
| n3-11506 | A-540 | B-15 |
| n3-11507 | A-541 | B-15 |
| n3-11508 | A-542 | B-15 |
| n3-11509 | A-543 | B-15 |
| n3-11510 | A-544 | B-15 |
| n3-11511 | A-545 | B-15 |
| n3-11512 | A-546 | B-15 |
| n3-11513 | A-547 | B-15 |
| n3-11514 | A-548 | B-15 |
| n3-11515 | A-549 | B-15 |
| n3-11516 | A-550 | B-15 |
| n3-11517 | A-551 | B-15 |
| n3-11518 | A-552 | B-15 |
| n3-11519 | A-553 | B-15 |
| n3-11520 | A-554 | B-15 |
| n3-11521 | A-555 | B-15 |
| n3-11522 | A-556 | B-15 |
| n3-11523 | A-557 | B-15 |
| n3-11524 | A-558 | B-15 |
| n3-11525 | A-559 | B-15 |
| n3-11526 | A-560 | B-15 |
| n3-11527 | A-561 | B-15 |

TABLE 2-continued

| epn | n = 3 A | B |
|---|---|---|
| n3-11528 | A-562 | B-15 |
| n3-11529 | A-563 | B-15 |
| n3-11530 | A-564 | B-15 |
| n3-11531 | A-565 | B-15 |
| n3-11532 | A-566 | B-15 |
| n3-11533 | A-567 | B-15 |
| n3-11534 | A-568 | B-15 |
| n3-11535 | A-569 | B-15 |
| n3-11536 | A-570 | B-15 |
| n3-11537 | A-571 | B-15 |
| n3-11538 | A-572 | B-15 |
| n3-11539 | A-573 | B-15 |
| n3-11540 | A-574 | B-15 |
| n3-11541 | A-575 | B-15 |
| n3-11542 | A-576 | B-15 |
| n3-11543 | A-577 | B-15 |
| n3-11544 | A-578 | B-15 |
| n3-11545 | A-579 | B-15 |
| n3-11546 | A-580 | B-15 |
| n3-11547 | A-581 | B-15 |
| n3-11548 | A-582 | B-15 |
| n3-11549 | A-583 | B-15 |
| n3-11550 | A-584 | B-15 |
| n3-11551 | A-585 | B-15 |
| n3-11552 | A-586 | B-15 |
| n3-11553 | A-587 | B-15 |
| n3-11554 | A-588 | B-15 |
| n3-11555 | A-589 | B-15 |
| n3-11556 | A-590 | B-15 |
| n3-11557 | A-452 | B-16 |
| n3-11558 | A-453 | B-16 |
| n3-11559 | A-454 | B-16 |
| n3-11560 | A-455 | B-16 |
| n3-11561 | A-456 | B-16 |
| n3-11562 | A-457 | B-16 |
| n3-11563 | A-458 | B-16 |
| n3-11564 | A-459 | B-16 |
| n3-11565 | A-460 | B-16 |
| n3-11566 | A-461 | B-16 |
| n3-11567 | A-462 | B-16 |
| n3-11568 | A-463 | B-16 |
| n3-11569 | A-464 | B-16 |
| n3-11570 | A-465 | B-16 |
| n3-11571 | A-466 | B-16 |
| n3-11572 | A-467 | B-16 |
| n3-11573 | A-468 | B-16 |
| n3-11574 | A-469 | B-16 |
| n3-11575 | A-470 | B-16 |
| n3-11576 | A-471 | B-16 |
| n3-11577 | A-472 | B-16 |
| n3-11578 | A-473 | B-16 |
| n3-11579 | A-474 | B-16 |
| n3-11580 | A-475 | B-16 |
| n3-11581 | A-476 | B-16 |
| n3-11582 | A-477 | B-16 |
| n3-11583 | A-478 | B-16 |
| n3-11584 | A-479 | B-16 |
| n3-11585 | A-480 | B-16 |
| n3-11586 | A-481 | B-16 |
| n3-11587 | A-482 | B-16 |
| n3-11588 | A-483 | B-16 |
| n3-11589 | A-484 | B-16 |
| n3-11590 | A-485 | B-16 |
| n3-11591 | A-486 | B-16 |
| n3-11592 | A-487 | B-16 |
| n3-11593 | A-488 | B-16 |
| n3-11594 | A-489 | B-16 |
| n3-11595 | A-490 | B-16 |
| n3-11596 | A-491 | B-16 |
| n3-11597 | A-492 | B-16 |
| n3-11598 | A-493 | B-16 |
| n3-11599 | A-494 | B-16 |
| n3-11600 | A-495 | B-16 |
| n3-11601 | A-496 | B-16 |
| n3-11602 | A-497 | B-16 |
| n3-11603 | A-498 | B-16 |
| n3-11604 | A-499 | B-16 |
| n3-11605 | A-500 | B-16 |
| n3-11606 | A-501 | B-16 |
| n3-11607 | A-502 | B-16 |
| n3-11608 | A-503 | B-16 |
| n3-11609 | A-504 | B-16 |
| n3-11610 | A-505 | B-16 |
| n3-11611 | A-506 | B-16 |
| n3-11612 | A-507 | B-16 |
| n3-11613 | A-508 | B-16 |
| n3-11614 | A-509 | B-16 |
| n3-11615 | A-510 | B-16 |
| n3-11616 | A-511 | B-16 |
| n3-11617 | A-512 | B-16 |
| n3-11618 | A-513 | B-16 |
| n3-11619 | A-514 | B-16 |
| n3-11620 | A-515 | B-16 |
| n3-11621 | A-516 | B-16 |
| n3-11622 | A-517 | B-16 |
| n3-11623 | A-518 | B-16 |
| n3-11624 | A-519 | B-16 |
| n3-11625 | A-520 | B-16 |
| n3-11626 | A-521 | B-16 |
| n3-11627 | A-522 | B-16 |
| n3-11628 | A-523 | B-16 |
| n3-11629 | A-524 | B-16 |
| n3-11630 | A-525 | B-16 |
| n3-11631 | A-526 | B-16 |
| n3-11632 | A-527 | B-16 |
| n3-11633 | A-528 | B-16 |
| n3-11634 | A-529 | B-16 |
| n3-11635 | A-530 | B-16 |
| n3-11636 | A-531 | B-16 |
| n3-11637 | A-532 | B-16 |
| n3-11638 | A-533 | B-16 |
| n3-11639 | A-534 | B-16 |
| n3-11640 | A-535 | B-16 |
| n3-11641 | A-536 | B-16 |
| n3-11642 | A-537 | B-16 |
| n3-11643 | A-538 | B-16 |
| n3-11644 | A-539 | B-16 |
| n3-11645 | A-540 | B-16 |
| n3-11646 | A-541 | B-16 |
| n3-11647 | A-542 | B-16 |
| n3-11648 | A-543 | B-16 |
| n3-11649 | A-544 | B-16 |
| n3-11650 | A-545 | B-16 |
| n3-11651 | A-546 | B-16 |
| n3-11652 | A-547 | B-16 |
| n3-11653 | A-548 | B-16 |
| n3-11654 | A-549 | B-16 |
| n3-11655 | A-550 | B-16 |
| n3-11656 | A-551 | B-16 |
| n3-11657 | A-552 | B-16 |
| n3-11658 | A-553 | B-16 |
| n3-11659 | A-554 | B-16 |
| n3-11660 | A-555 | B-16 |
| n3-11661 | A-556 | B-16 |
| n3-11662 | A-557 | B-16 |
| n3-11663 | A-558 | B-16 |
| n3-11664 | A-559 | B-16 |
| n3-11665 | A-560 | B-16 |
| n3-11666 | A-561 | B-16 |
| n3-11667 | A-562 | B-16 |
| n3-11668 | A-563 | B-16 |
| n3-11669 | A-564 | B-16 |
| n3-11670 | A-565 | B-16 |
| n3-11671 | A-566 | B-16 |
| n3-11672 | A-567 | B-16 |
| n3-11673 | A-568 | B-16 |
| n3-11674 | A-569 | B-16 |
| n3-11675 | A-570 | B-16 |
| n3-11676 | A-571 | B-16 |
| n3-11677 | A-572 | B-16 |

TABLE 2-continued

| epn | n = 3 A | B |
|---|---|---|
| n3-11678 | A-573 | B-16 |
| n3-11679 | A-574 | B-16 |
| n3-11680 | A-575 | B-16 |
| n3-11681 | A-576 | B-16 |
| n3-11682 | A-577 | B-16 |
| n3-11683 | A-578 | B-16 |
| n3-11684 | A-579 | B-16 |
| n3-11685 | A-580 | B-16 |
| n3-11686 | A-581 | B-16 |
| n3-11687 | A-582 | B-16 |
| n3-11688 | A-583 | B-16 |
| n3-11689 | A-584 | B-16 |
| n3-11690 | A-585 | B-16 |
| n3-11691 | A-586 | B-16 |
| n3-11692 | A-587 | B-16 |
| n3-11693 | A-588 | B-16 |
| n3-11694 | A-589 | B-16 |
| n3-11695 | A-590 | B-16 |
| n3-11696 | A-452 | B-17 |
| n3-11697 | A-453 | B-17 |
| n3-11698 | A-454 | B-17 |
| n3-11699 | A-455 | B-17 |
| n3-11700 | A-456 | B-17 |
| n3-11701 | A-457 | B-17 |
| n3-11702 | A-458 | B-17 |
| n3-11703 | A-459 | B-17 |
| n3-11704 | A-460 | B-17 |
| n3-11705 | A-461 | B-17 |
| n3-11706 | A-462 | B-17 |
| n3-11707 | A-463 | B-17 |
| n3-11708 | A-464 | B-17 |
| n3-11709 | A-465 | B-17 |
| n3-11710 | A-466 | B-17 |
| n3-11711 | A-467 | B-17 |
| n3-11712 | A-468 | B-17 |
| n3-11713 | A-469 | B-17 |
| n3-11714 | A-470 | B-17 |
| n3-11715 | A-471 | B-17 |
| n3-11716 | A-472 | B-17 |
| n3-11717 | A-473 | B-17 |
| n3-11718 | A-474 | B-17 |
| n3-11719 | A-475 | B-17 |
| n3-11720 | A-476 | B-17 |
| n3-11721 | A-477 | B-17 |
| n3-11722 | A-478 | B-17 |
| n3-11723 | A-479 | B-17 |
| n3-11724 | A-480 | B-17 |
| n3-11725 | A-481 | B-17 |
| n3-11726 | A-482 | B-17 |
| n3-11727 | A-483 | B-17 |
| n3-11728 | A-484 | B-17 |
| n3-11729 | A-485 | B-17 |
| n3-11730 | A-486 | B-17 |
| n3-11731 | A-487 | B-17 |
| n3-11732 | A-488 | B-17 |
| n3-11733 | A-489 | B-17 |
| n3-11734 | A-490 | B-17 |
| n3-11735 | A-491 | B-17 |
| n3-11736 | A-492 | B-17 |
| n3-11737 | A-493 | B-17 |
| n3-11738 | A-494 | B-17 |
| n3-11739 | A-495 | B-17 |
| n3-11740 | A-496 | B-17 |
| n3-11741 | A-497 | B-17 |
| n3-11742 | A-498 | B-17 |
| n3-11743 | A-499 | B-17 |
| n3-11744 | A-500 | B-17 |
| n3-11745 | A-501 | B-17 |
| n3-11746 | A-502 | B-17 |
| n3-11747 | A-503 | B-17 |
| n3-11748 | A-504 | B-17 |
| n3-11749 | A-505 | B-17 |
| n3-11750 | A-506 | B-17 |
| n3-11751 | A-507 | B-17 |
| n3-11752 | A-508 | B-17 |
| n3-11753 | A-509 | B-17 |
| n3-11754 | A-510 | B-17 |
| n3-11755 | A-511 | B-17 |
| n3-11756 | A-512 | B-17 |
| n3-11757 | A-513 | B-17 |
| n3-11758 | A-514 | B-17 |
| n3-11759 | A-515 | B-17 |
| n3-11760 | A-516 | B-17 |
| n3-11761 | A-517 | B-17 |
| n3-11762 | A-518 | B-17 |
| n3-11763 | A-519 | B-17 |
| n3-11764 | A-520 | B-17 |
| n3-11765 | A-521 | B-17 |
| n3-11766 | A-522 | B-17 |
| n3-11767 | A-523 | B-17 |
| n3-11768 | A-524 | B-17 |
| n3-11769 | A-525 | B-17 |
| n3-11770 | A-526 | B-17 |
| n3-11771 | A-527 | B-17 |
| n3-11772 | A-528 | B-17 |
| n3-11773 | A-529 | B-17 |
| n3-11774 | A-530 | B-17 |
| n3-11775 | A-531 | B-17 |
| n3-11776 | A-532 | B-17 |
| n3-11777 | A-533 | B-17 |
| n3-11778 | A-534 | B-17 |
| n3-11779 | A-535 | B-17 |
| n3-11780 | A-536 | B-17 |
| n3-11781 | A-537 | B-17 |
| n3-11782 | A-538 | B-17 |
| n3-11783 | A-539 | B-17 |
| n3-11784 | A-540 | B-17 |
| n3-11785 | A-541 | B-17 |
| n3-11786 | A-542 | B-17 |
| n3-11787 | A-543 | B-17 |
| n3-11788 | A-544 | B-17 |
| n3-11789 | A-545 | B-17 |
| n3-11790 | A-546 | B-17 |
| n3-11791 | A-547 | B-17 |
| n3-11792 | A-548 | B-17 |
| n3-11793 | A-549 | B-17 |
| n3-11794 | A-550 | B-17 |
| n3-11795 | A-551 | B-17 |
| n3-11796 | A-552 | B-17 |
| n3-11797 | A-553 | B-17 |
| n3-11798 | A-554 | B-17 |
| n3-11799 | A-555 | B-17 |
| n3-11800 | A-556 | B-17 |
| n3-11801 | A-557 | B-17 |
| n3-11802 | A-558 | B-17 |
| n3-11803 | A-559 | B-17 |
| n3-11804 | A-560 | B-17 |
| n3-11805 | A-561 | B-17 |
| n3-11806 | A-562 | B-17 |
| n3-11807 | A-563 | B-17 |
| n3-11808 | A-564 | B-17 |
| n3-11809 | A-565 | B-17 |
| n3-11810 | A-566 | B-17 |
| n3-11811 | A-567 | B-17 |
| n3-11812 | A-568 | B-17 |
| n3-11813 | A-569 | B-17 |
| n3-11814 | A-570 | B-17 |
| n3-11815 | A-571 | B-17 |
| n3-11816 | A-572 | B-17 |
| n3-11817 | A-573 | B-17 |
| n3-11818 | A-574 | B-17 |
| n3-11819 | A-575 | B-17 |
| n3-11820 | A-576 | B-17 |
| n3-11821 | A-577 | B-17 |
| n3-11822 | A-578 | B-17 |
| n3-11823 | A-579 | B-17 |
| n3-11824 | A-580 | B-17 |
| n3-11825 | A-581 | B-17 |
| n3-11826 | A-582 | B-17 |
| n3-11827 | A-583 | B-17 |

TABLE 2-continued

| epn | n = 3 A | B |
|---|---|---|
| n3-11828 | A-584 | B-17 |
| n3-11829 | A-585 | B-17 |
| n3-11830 | A-586 | B-17 |
| n3-11831 | A-587 | B-17 |
| n3-11832 | A-588 | B-17 |
| n3-11833 | A-589 | B-17 |
| n3-11834 | A-590 | B-17 |
| n3-11835 | A-452 | B-18 |
| n3-11836 | A-453 | B-18 |
| n3-11837 | A-454 | B-18 |
| n3-11838 | A-455 | B-18 |
| n3-11839 | A-456 | B-18 |
| n3-11840 | A-457 | B-18 |
| n3-11841 | A-458 | B-18 |
| n3-11842 | A-459 | B-18 |
| n3-11843 | A-460 | B-18 |
| n3-11844 | A-461 | B-18 |
| n3-11845 | A-462 | B-18 |
| n3-11846 | A-463 | B-18 |
| n3-11847 | A-464 | B-18 |
| n3-11848 | A-465 | B-18 |
| n3-11849 | A-466 | B-18 |
| n3-11850 | A-467 | B-18 |
| n3-11851 | A-468 | B-18 |
| n3-11852 | A-469 | B-18 |
| n3-11853 | A-470 | B-18 |
| n3-11854 | A-471 | B-18 |
| n3-11855 | A-472 | B-18 |
| n3-11856 | A-473 | B-18 |
| n3-11857 | A-474 | B-18 |
| n3-11858 | A-475 | B-18 |
| n3-11859 | A-476 | B-18 |
| n3-11860 | A-477 | B-18 |
| n3-11861 | A-478 | B-18 |
| n3-11862 | A-479 | B-18 |
| n3-11863 | A-480 | B-18 |
| n3-11864 | A-481 | B-18 |
| n3-11865 | A-482 | B-18 |
| n3-11866 | A-483 | B-18 |
| n3-11867 | A-484 | B-18 |
| n3-11868 | A-485 | B-18 |
| n3-11869 | A-486 | B-18 |
| n3-11870 | A-487 | B-18 |
| n3-11871 | A-488 | B-18 |
| n3-11872 | A-489 | B-18 |
| n3-11873 | A-490 | B-18 |
| n3-11874 | A-491 | B-18 |
| n3-11875 | A-492 | B-18 |
| n3-11876 | A-493 | B-18 |
| n3-11877 | A-494 | B-18 |
| n3-11878 | A-495 | B-18 |
| n3-11879 | A-496 | B-18 |
| n3-11880 | A-497 | B-18 |
| n3-11881 | A-498 | B-18 |
| n3-11882 | A-499 | B-18 |
| n3-11883 | A-500 | B-18 |
| n3-11884 | A-501 | B-18 |
| n3-11885 | A-502 | B-18 |
| n3-11886 | A-503 | B-18 |
| n3-11887 | A-504 | B-18 |
| n3-11888 | A-505 | B-18 |
| n3-11889 | A-506 | B-18 |
| n3-11890 | A-507 | B-18 |
| n3-11891 | A-508 | B-18 |
| n3-11892 | A-509 | B-18 |
| n3-11893 | A-510 | B-18 |
| n3-11894 | A-511 | B-18 |
| n3-11895 | A-512 | B-18 |
| n3-11896 | A-513 | B-18 |
| n3-11897 | A-514 | B-18 |
| n3-11898 | A-515 | B-18 |
| n3-11899 | A-516 | B-18 |
| n3-11900 | A-517 | B-18 |
| n3-11901 | A-518 | B-18 |
| n3-11902 | A-519 | B-18 |
| n3-11903 | A-520 | B-18 |
| n3-11904 | A-521 | B-18 |
| n3-11905 | A-522 | B-18 |
| n3-11906 | A-523 | B-18 |
| n3-11907 | A-524 | B-18 |
| n3-11908 | A-525 | B-18 |
| n3-11909 | A-526 | B-18 |
| n3-11910 | A-527 | B-18 |
| n3-11911 | A-528 | B-18 |
| n3-11912 | A-529 | B-18 |
| n3-11913 | A-530 | B-18 |
| n3-11914 | A-531 | B-18 |
| n3-11915 | A-532 | B-18 |
| n3-11916 | A-533 | B-18 |
| n3-11917 | A-534 | B-18 |
| n3-11918 | A-535 | B-18 |
| n3-11919 | A-536 | B-18 |
| n3-11920 | A-537 | B-18 |
| n3-11921 | A-538 | B-18 |
| n3-11922 | A-539 | B-18 |
| n3-11923 | A-540 | B-18 |
| n3-11924 | A-541 | B-18 |
| n3-11925 | A-542 | B-18 |
| n3-11926 | A-543 | B-18 |
| n3-11927 | A-544 | B-18 |
| n3-11928 | A-545 | B-18 |
| n3-11929 | A-546 | B-18 |
| n3-11930 | A-547 | B-18 |
| n3-11931 | A-548 | B-18 |
| n3-11932 | A-549 | B-18 |
| n3-11933 | A-550 | B-18 |
| n3-11934 | A-551 | B-18 |
| n3-11935 | A-552 | B-18 |
| n3-11936 | A-553 | B-18 |
| n3-11937 | A-554 | B-18 |
| n3-11938 | A-555 | B-18 |
| n3-11939 | A-556 | B-18 |
| n3-11940 | A-557 | B-18 |
| n3-11941 | A-558 | B-18 |
| n3-11942 | A-559 | B-18 |
| n3-11943 | A-560 | B-18 |
| n3-11944 | A-561 | B-18 |
| n3-11945 | A-562 | B-18 |
| n3-11946 | A-563 | B-18 |
| n3-11947 | A-564 | B-18 |
| n3-11948 | A-565 | B-18 |
| n3-11949 | A-566 | B-18 |
| n3-11950 | A-567 | B-18 |
| n3-11951 | A-568 | B-18 |
| n3-11952 | A-569 | B-18 |
| n3-11953 | A-570 | B-18 |
| n3-11954 | A-571 | B-18 |
| n3-11955 | A-572 | B-18 |
| n3-11956 | A-573 | B-18 |
| n3-11957 | A-574 | B-18 |
| n3-11958 | A-575 | B-18 |
| n3-11959 | A-576 | B-18 |
| n3-11960 | A-577 | B-18 |
| n3-11961 | A-578 | B-18 |
| n3-11962 | A-579 | B-18 |
| n3-11963 | A-580 | B-18 |
| n3-11964 | A-581 | B-18 |
| n3-11965 | A-582 | B-18 |
| n3-11966 | A-583 | B-18 |
| n3-11967 | A-584 | B-18 |
| n3-11968 | A-585 | B-18 |
| n3-11969 | A-586 | B-18 |
| n3-11970 | A-587 | B-18 |
| n3-11971 | A-588 | B-18 |
| n3-11972 | A-589 | B-18 |
| n3-11973 | A-590 | B-18 |
| n3-11974 | A-452 | B-19 |
| n3-11975 | A-453 | B-19 |
| n3-11976 | A-454 | B-19 |
| n3-11977 | A-455 | B-19 |

TABLE 2-continued

| | n = 3 | |
|---|---|---|
| epn | A | B |
| n3-11978 | A-456 | B-19 |
| n3-11979 | A-457 | B-19 |
| n3-11980 | A-458 | B-19 |
| n3-11981 | A-459 | B-19 |
| n3-11982 | A-460 | B-19 |
| n3-11983 | A-461 | B-19 |
| n3-11984 | A-462 | B-19 |
| n3-11985 | A-463 | B-19 |
| n3-11986 | A-464 | B-19 |
| n3-11987 | A-465 | B-19 |
| n3-11988 | A-466 | B-19 |
| n3-11989 | A-467 | B-19 |
| n3-11990 | A-468 | B-19 |
| n3-11991 | A-469 | B-19 |
| n3-11992 | A-470 | B-19 |
| n3-11993 | A-471 | B-19 |
| n3-11994 | A-472 | B-19 |
| n3-11995 | A-473 | B-19 |
| n3-11996 | A-474 | B-19 |
| n3-11997 | A-475 | B-19 |
| n3-11998 | A-476 | B-19 |
| n3-11999 | A-477 | B-19 |
| n3-12000 | A-478 | B-19 |
| n3-12001 | A-479 | B-19 |
| n3-12002 | A-480 | B-19 |
| n3-12003 | A-481 | B-19 |
| n3-12004 | A-482 | B-19 |
| n3-12005 | A-483 | B-19 |
| n3-12006 | A-484 | B-19 |
| n3-12007 | A-485 | B-19 |
| n3-12008 | A-486 | B-19 |
| n3-12009 | A-487 | B-19 |
| n3-12010 | A-488 | B-19 |
| n3-12011 | A-489 | B-19 |
| n3-12012 | A-490 | B-19 |
| n3-12013 | A-491 | B-19 |
| n3-12014 | A-492 | B-19 |
| n3-12015 | A-493 | B-19 |
| n3-12016 | A-494 | B-19 |
| n3-12017 | A-495 | B-19 |
| n3-12018 | A-496 | B-19 |
| n3-12019 | A-497 | B-19 |
| n3-12020 | A-498 | B-19 |
| n3-12021 | A-499 | B-19 |
| n3-12022 | A-500 | B-19 |
| n3-12023 | A-501 | B-19 |
| n3-12024 | A-502 | B-19 |
| n3-12025 | A-503 | B-19 |
| n3-12026 | A-504 | B-19 |
| n3-12027 | A-505 | B-19 |
| n3-12028 | A-506 | B-19 |
| n3-12029 | A-507 | B-19 |
| n3-12030 | A-508 | B-19 |
| n3-12031 | A-509 | B-19 |
| n3-12032 | A-510 | B-19 |
| n3-12033 | A-511 | B-19 |
| n3-12034 | A-512 | B-19 |
| n3-12035 | A-513 | B-19 |
| n3-12036 | A-514 | B-19 |
| n3-12037 | A-515 | B-19 |
| n3-12038 | A-516 | B-19 |
| n3-12039 | A-517 | B-19 |
| n3-12040 | A-518 | B-19 |
| n3-12041 | A-519 | B-19 |
| n3-12042 | A-520 | B-19 |
| n3-12043 | A-521 | B-19 |
| n3-12044 | A-522 | B-19 |
| n3-12045 | A-523 | B-19 |
| n3-12046 | A-524 | B-19 |
| n3-12047 | A-525 | B-19 |
| n3-12048 | A-526 | B-19 |
| n3-12049 | A-527 | B-19 |
| n3-12050 | A-528 | B-19 |
| n3-12051 | A-529 | B-19 |
| n3-12052 | A-530 | B-19 |
| n3-12053 | A-531 | B-19 |
| n3-12054 | A-532 | B-19 |
| n3-12055 | A-533 | B-19 |
| n3-12056 | A-534 | B-19 |
| n3-12057 | A-535 | B-19 |
| n3-12058 | A-536 | B-19 |
| n3-12059 | A-537 | B-19 |
| n3-12060 | A-538 | B-19 |
| n3-12061 | A-539 | B-19 |
| n3-12062 | A-540 | B-19 |
| n3-12063 | A-541 | B-19 |
| n3-12064 | A-542 | B-19 |
| n3-12065 | A-543 | B-19 |
| n3-12066 | A-544 | B-19 |
| n3-12067 | A-545 | B-19 |
| n3-12068 | A-546 | B-19 |
| n3-12069 | A-547 | B-19 |
| n3-12070 | A-548 | B-19 |
| n3-12071 | A-549 | B-19 |
| n3-12072 | A-550 | B-19 |
| n3-12073 | A-551 | B-19 |
| n3-12074 | A-552 | B-19 |
| n3-12075 | A-553 | B-19 |
| n3-12076 | A-554 | B-19 |
| n3-12077 | A-555 | B-19 |
| n3-12078 | A-556 | B-19 |
| n3-12079 | A-557 | B-19 |
| n3-12080 | A-558 | B-19 |
| n3-12081 | A-559 | B-19 |
| n3-12082 | A-560 | B-19 |
| n3-12083 | A-561 | B-19 |
| n3-12084 | A-562 | B-19 |
| n3-12085 | A-563 | B-19 |
| n3-12086 | A-564 | B-19 |
| n3-12087 | A-565 | B-19 |
| n3-12088 | A-566 | B-19 |
| n3-12089 | A-567 | B-19 |
| n3-12090 | A-568 | B-19 |
| n3-12091 | A-569 | B-19 |
| n3-12092 | A-570 | B-19 |
| n3-12093 | A-571 | B-19 |
| n3-12094 | A-572 | B-19 |
| n3-12095 | A-573 | B-19 |
| n3-12096 | A-574 | B-19 |
| n3-12097 | A-575 | B-19 |
| n3-12098 | A-576 | B-19 |
| n3-12099 | A-577 | B-19 |
| n3-12100 | A-578 | B-19 |
| n3-12101 | A-579 | B-19 |
| n3-12102 | A-580 | B-19 |
| n3-12103 | A-581 | B-19 |
| n3-12104 | A-582 | B-19 |
| n3-12105 | A-583 | B-19 |
| n3-12106 | A-584 | B-19 |
| n3-12107 | A-585 | B-19 |
| n3-12108 | A-586 | B-19 |
| n3-12109 | A-587 | B-19 |
| n3-12110 | A-588 | B-19 |
| n3-12111 | A-589 | B-19 |
| n3-12112 | A-590 | B-19 |
| n3-12113 | A-452 | B-20 |
| n3-12114 | A-453 | B-20 |
| n3-12115 | A-454 | B-20 |
| n3-12116 | A-455 | B-20 |
| n3-12117 | A-456 | B-20 |
| n3-12118 | A-457 | B-20 |
| n3-12119 | A-458 | B-20 |
| n3-12120 | A-459 | B-20 |
| n3-12121 | A-460 | B-20 |
| n3-12122 | A-461 | B-20 |
| n3-12123 | A-462 | B-20 |
| n3-12124 | A-463 | B-20 |
| n3-12125 | A-464 | B-20 |
| n3-12126 | A-465 | B-20 |
| n3-12127 | A-466 | B-20 |

TABLE 2-continued

| | n = 3 | |
|---|---|---|
| epn | A | B |
| n3-12128 | A-467 | B-20 |
| n3-12129 | A-468 | B-20 |
| n3-12130 | A-469 | B-20 |
| n3-12131 | A-470 | B-20 |
| n3-12132 | A-471 | B-20 |
| n3-12133 | A-472 | B-20 |
| n3-12134 | A-473 | B-20 |
| n3-12135 | A-474 | B-20 |
| n3-12136 | A-475 | B-20 |
| n3-12137 | A-476 | B-20 |
| n3-12138 | A-477 | B-20 |
| n3-12139 | A-478 | B-20 |
| n3-12140 | A-479 | B-20 |
| n3-12141 | A-480 | B-20 |
| n3-12142 | A-481 | B-20 |
| n3-12143 | A-482 | B-20 |
| n3-12144 | A-483 | B-20 |
| n3-12145 | A-484 | B-20 |
| n3-12146 | A-485 | B-20 |
| n3-12147 | A-486 | B-20 |
| n3-12148 | A-487 | B-20 |
| n3-12149 | A-488 | B-20 |
| n3-12150 | A-489 | B-20 |
| n3-12151 | A-490 | B-20 |
| n3-12152 | A-491 | B-20 |
| n3-12153 | A-492 | B-20 |
| n3-12154 | A-493 | B-20 |
| n3-12155 | A-494 | B-20 |
| n3-12156 | A-495 | B-20 |
| n3-12157 | A-496 | B-20 |
| n3-12158 | A-497 | B-20 |
| n3-12159 | A-498 | B-20 |
| n3-12160 | A-499 | B-20 |
| n3-12161 | A-500 | B-20 |
| n3-12162 | A-501 | B-20 |
| n3-12163 | A-502 | B-20 |
| n3-12164 | A-503 | B-20 |
| n3-12165 | A-504 | B-20 |
| n3-12166 | A-505 | B-20 |
| n3-12167 | A-506 | B-20 |
| n3-12168 | A-507 | B-20 |
| n3-12169 | A-508 | B-20 |
| n3-12170 | A-509 | B-20 |
| n3-12171 | A-510 | B-20 |
| n3-12172 | A-511 | B-20 |
| n3-12173 | A-512 | B-20 |
| n3-12174 | A-513 | B-20 |
| n3-12175 | A-514 | B-20 |
| n3-12176 | A-515 | B-20 |
| n3-12177 | A-516 | B-20 |
| n3-12178 | A-517 | B-20 |
| n3-12179 | A-518 | B-20 |
| n3-12180 | A-519 | B-20 |
| n3-12181 | A-520 | B-20 |
| n3-12182 | A-521 | B-20 |
| n3-12183 | A-522 | B-20 |
| n3-12184 | A-523 | B-20 |
| n3-12185 | A-524 | B-20 |
| n3-12186 | A-525 | B-20 |
| n3-12187 | A-526 | B-20 |
| n3-12188 | A-527 | B-20 |
| n3-12189 | A-528 | B-20 |
| n3-12190 | A-529 | B-20 |
| n3-12191 | A-530 | B-20 |
| n3-12192 | A-531 | B-20 |
| n3-12193 | A-532 | B-20 |
| n3-12194 | A-533 | B-20 |
| n3-12195 | A-534 | B-20 |
| n3-12196 | A-535 | B-20 |
| n3-12197 | A-536 | B-20 |
| n3-12198 | A-537 | B-20 |
| n3-12199 | A-538 | B-20 |
| n3-12200 | A-539 | B-20 |
| n3-12201 | A-540 | B-20 |
| n3-12202 | A-541 | B-20 |
| n3-12203 | A-542 | B-20 |
| n3-12204 | A-543 | B-20 |
| n3-12205 | A-544 | B-20 |
| n3-12206 | A-545 | B-20 |
| n3-12207 | A-546 | B-20 |
| n3-12208 | A-547 | B-20 |
| n3-12209 | A-548 | B-20 |
| n3-12210 | A-549 | B-20 |
| n3-12211 | A-550 | B-20 |
| n3-12212 | A-551 | B-20 |
| n3-12213 | A-552 | B-20 |
| n3-12214 | A-553 | B-20 |
| n3-12215 | A-554 | B-20 |
| n3-12216 | A-555 | B-20 |
| n3-12217 | A-556 | B-20 |
| n3-12218 | A-557 | B-20 |
| n3-12219 | A-558 | B-20 |
| n3-12220 | A-559 | B-20 |
| n3-12221 | A-560 | B-20 |
| n3-12222 | A-561 | B-20 |
| n3-12223 | A-562 | B-20 |
| n3-12224 | A-563 | B-20 |
| n3-12225 | A-564 | B-20 |
| n3-12226 | A-565 | B-20 |
| n3-12227 | A-566 | B-20 |
| n3-12228 | A-567 | B-20 |
| n3-12229 | A-568 | B-20 |
| n3-12230 | A-569 | B-20 |
| n3-12231 | A-570 | B-20 |
| n3-12232 | A-571 | B-20 |
| n3-12233 | A-572 | B-20 |
| n3-12234 | A-573 | B-20 |
| n3-12235 | A-574 | B-20 |
| n3-12236 | A-575 | B-20 |
| n3-12237 | A-576 | B-20 |
| n3-12238 | A-577 | B-20 |
| n3-12239 | A-578 | B-20 |
| n3-12240 | A-579 | B-20 |
| n3-12241 | A-580 | B-20 |
| n3-12242 | A-581 | B-20 |
| n3-12243 | A-582 | B-20 |
| n3-12244 | A-583 | B-20 |
| n3-12245 | A-584 | B-20 |
| n3-12246 | A-585 | B-20 |
| n3-12247 | A-586 | B-20 |
| n3-12248 | A-587 | B-20 |
| n3-12249 | A-588 | B-20 |
| n3-12250 | A-589 | B-20 |
| n3-12251 | A-590 | B-20 |
| n3-12252 | A-452 | B-21 |
| n3-12253 | A-453 | B-21 |
| n3-12254 | A-454 | B-21 |
| n3-12255 | A-455 | B-21 |
| n3-12256 | A-456 | B-21 |
| n3-12257 | A-457 | B-21 |
| n3-12258 | A-458 | B-21 |
| n3-12259 | A-459 | B-21 |
| n3-12260 | A-460 | B-21 |
| n3-12261 | A-461 | B-21 |
| n3-12262 | A-462 | B-21 |
| n3-12263 | A-463 | B-21 |
| n3-12264 | A-464 | B-21 |
| n3-12265 | A-465 | B-21 |
| n3-12266 | A-466 | B-21 |
| n3-12267 | A-467 | B-21 |
| n3-12268 | A-468 | B-21 |
| n3-12269 | A-469 | B-21 |
| n3-12270 | A-470 | B-21 |
| n3-12271 | A-471 | B-21 |
| n3-12272 | A-472 | B-21 |
| n3-12273 | A-473 | B-21 |
| n3-12274 | A-474 | B-21 |
| n3-12275 | A-475 | B-21 |
| n3-12276 | A-476 | B-21 |
| n3-12277 | A-477 | B-21 |

TABLE 2-continued

| | n = 3 | |
|---|---|---|
| epn | A | B |
| n3-12278 | A-478 | B-21 |
| n3-12279 | A-479 | B-21 |
| n3-12280 | A-480 | B-21 |
| n3-12281 | A-481 | B-21 |
| n3-12282 | A-482 | B-21 |
| n3-12283 | A-483 | B-21 |
| n3-12284 | A-484 | B-21 |
| n3-12285 | A-485 | B-21 |
| n3-12286 | A-486 | B-21 |
| n3-12287 | A-487 | B-21 |
| n3-12288 | A-488 | B-21 |
| n3-12289 | A-489 | B-21 |
| n3-12290 | A-490 | B-21 |
| n3-12291 | A-491 | B-21 |
| n3-12292 | A-492 | B-21 |
| n3-12293 | A-493 | B-21 |
| n3-12294 | A-494 | B-21 |
| n3-12295 | A-495 | B-21 |
| n3-12296 | A-496 | B-21 |
| n3-12297 | A-497 | B-21 |
| n3-12298 | A-498 | B-21 |
| n3-12299 | A-499 | B-21 |
| n3-12300 | A-500 | B-21 |
| n3-12301 | A-501 | B-21 |
| n3-12302 | A-502 | B-21 |
| n3-12303 | A-503 | B-21 |
| n3-12304 | A-504 | B-21 |
| n3-12305 | A-505 | B-21 |
| n3-12306 | A-506 | B-21 |
| n3-12307 | A-507 | B-21 |
| n3-12308 | A-508 | B-21 |
| n3-12309 | A-509 | B-21 |
| n3-12310 | A-510 | B-21 |
| n3-12311 | A-511 | B-21 |
| n3-12312 | A-512 | B-21 |
| n3-12313 | A-513 | B-21 |
| n3-12314 | A-514 | B-21 |
| n3-12315 | A-515 | B-21 |
| n3-12316 | A-516 | B-21 |
| n3-12317 | A-517 | B-21 |
| n3-12318 | A-518 | B-21 |
| n3-12319 | A-519 | B-21 |
| n3-12320 | A-520 | B-21 |
| n3-12321 | A-521 | B-21 |
| n3-12322 | A-522 | B-21 |
| n3-12323 | A-523 | B-21 |
| n3-12324 | A-524 | B-21 |
| n3-12325 | A-525 | B-21 |
| n3-12326 | A-526 | B-21 |
| n3-12327 | A-527 | B-21 |
| n3-12328 | A-528 | B-21 |
| n3-12329 | A-529 | B-21 |
| n3-12330 | A-530 | B-21 |
| n3-12331 | A-531 | B-21 |
| n3-12332 | A-532 | B-21 |
| n3-12333 | A-533 | B-21 |
| n3-12334 | A-534 | B-21 |
| n3-12335 | A-535 | B-21 |
| n3-12336 | A-536 | B-21 |
| n3-12337 | A-537 | B-21 |
| n3-12338 | A-538 | B-21 |
| n3-12339 | A-539 | B-21 |
| n3-12340 | A-540 | B-21 |
| n3-12341 | A-541 | B-21 |
| n3-12342 | A-542 | B-21 |
| n3-12343 | A-543 | B-21 |
| n3-12344 | A-544 | B-21 |
| n3-12345 | A-545 | B-21 |
| n3-12346 | A-546 | B-21 |
| n3-12347 | A-547 | B-21 |
| n3-12348 | A-548 | B-21 |
| n3-12349 | A-549 | B-21 |
| n3-12350 | A-550 | B-21 |
| n3-12351 | A-551 | B-21 |
| n3-12352 | A-552 | B-21 |
| n3-12353 | A-553 | B-21 |
| n3-12354 | A-554 | B-21 |
| n3-12355 | A-555 | B-21 |
| n3-12356 | A-556 | B-21 |
| n3-12357 | A-557 | B-21 |
| n3-12358 | A-558 | B-21 |
| n3-12359 | A-559 | B-21 |
| n3-12360 | A-560 | B-21 |
| n3-12361 | A-561 | B-21 |
| n3-12362 | A-562 | B-21 |
| n3-12363 | A-563 | B-21 |
| n3-12364 | A-564 | B-21 |
| n3-12365 | A-565 | B-21 |
| n3-12366 | A-566 | B-21 |
| n3-12367 | A-567 | B-21 |
| n3-12368 | A-568 | B-21 |
| n3-12369 | A-569 | B-21 |
| n3-12370 | A-570 | B-21 |
| n3-12371 | A-571 | B-21 |
| n3-12372 | A-572 | B-21 |
| n3-12373 | A-573 | B-21 |
| n3-12374 | A-574 | B-21 |
| n3-12375 | A-575 | B-21 |
| n3-12376 | A-576 | B-21 |
| n3-12377 | A-577 | B-21 |
| n3-12378 | A-578 | B-21 |
| n3-12379 | A-579 | B-21 |
| n3-12380 | A-580 | B-21 |
| n3-12381 | A-581 | B-21 |
| n3-12382 | A-582 | B-21 |
| n3-12383 | A-583 | B-21 |
| n3-12384 | A-584 | B-21 |
| n3-12385 | A-585 | B-21 |
| n3-12386 | A-586 | B-21 |
| n3-12387 | A-587 | B-21 |
| n3-12388 | A-588 | B-21 |
| n3-12389 | A-589 | B-21 |
| n3-12390 | A-590 | B-21 |

The compounds of the present invention represented by the formula (1) can be prepared by, for example, the following methods. However, the synthetic methods are not limited to the following methods.

Synthetic Method A

For example, by reducing a compound represented by the formula (3):

[Formula 12]

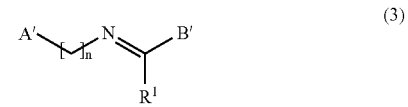

(3)

wherein A' represents a group selected from the group consisting of (1) a saturated heterocyclic group, (2) a 5-membered heteroaromatic group having two heteroatoms in the ring which may be substituted, (3) a group represented by the following formula A1', (4) a group represented by the following formula A2', (5) a group represented by the following formula A3', and (6) a group represented by the following formula A4':

[Formula 13]

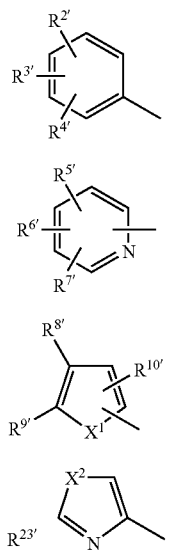

wherein $R^{2'}$, $R^{3'}$, and $R^{4'}$ may be the same or different, and independently represent hydrogen atom, a hydroxyl group which may have a protective group, a halogen atom, an alkyl group, phenyl group, a substituted phenyl group which may have a protective group in a substituent, benzyl group, a substituted benzyl group which may have a protective group in a substituent, a monocyclic heteroaromatic group which may be substituted with a substituent which may have a protective group, a bicyclic heteroaromatic group which may be substituted with a substituent which may have a protective group, an alkoxyl group, an alkyl group arbitrarily substituted with one or more halogen atoms, an alkoxyl group arbitrarily substituted with one or more halogen atoms, nitro group or $N(R^{16'})(R^{17'})$ wherein $R^{16'}$ and $R^{17'}$ may be the same or different, and independently represent hydrogen atom, an alkyl group, an acyl group, $SO_2R^{18}$, or a protective group for the nitrogen atom, wherein $R^{18}$ represents a lower alkyl group, or $R^{16'}$ and $R^{17'}$ together form a 3- to 7-membered ring to represent a cyclic amine as $N(R^{16'})(R^{17'})$; $R^{5'}$, $R^{6'}$, and $R^{7'}$ may be the same or different, and independently represent hydrogen atom, hydroxyl group which may have a protective group, a halogen atom, an alkyl group, phenyl group, a substituted phenyl group which may have a protective group in a substituent, benzyl group, a substituted benzyl group which may have a protective group in a substituent, a monocyclic heteroaromatic group, a monocyclic heteroaromatic group which may be substituted with a substituent which may have a protective group, a bicyclic heteroaromatic group which may be substituted with a substituent which may have a protective group, an alkoxyl group, an alkyl group arbitrarily substituted with one or more halogen atoms, an alkoxyl group arbitrarily substituted with one or more halogen atoms, nitro group, or $N(R^{16'})(R^{17'})$ wherein $R^{16'}$ and $R^{17'}$ may be the same or different, and independently represent hydrogen atom, an alkyl group, an acyl group, $SO_2R^{18}$, or a protective group of the nitrogen atom, wherein $R^{18}$ represents a lower alkyl group, or $R^{16'}$ and $R^{17'}$ together form a 3- to 7-membered ring to represent a cyclic amine as $N(R^{16'})(R^{17'})$; $R^{8'}$, $R^{9'}$, and $R^{10'}$ may be the same or different, and independently represent hydrogen atom, hydroxyl group which may have a protective group, a halogen atom, an alkyl group, a phenyl group, a substituted phenyl group which may have a protective group in a substituent, benzyl group, a substituted benzyl group which may have a protective group in a substituent, a monocyclic heteroaromatic group which may be substituted with a substituent which may have a protective group, a bicyclic heteroaromatic group which may be substituted with a substituent which may have a protective group, an alkoxyl group, an alkyl group arbitrarily substituted with one or more halogen atoms, an alkoxyl group arbitrarily substituted with one or more halogen atoms, nitro group, or $N(R^{16'})(R^{17'})$ wherein $R^{16'}$ and $R^{17'}$ may be the same or different, and independently represent hydrogen atom, an alkyl group, an acyl group, $SO_2R^{18}$, or a protective group of the nitrogen atom, wherein $R^{18}$ represents a lower alkyl group, or $R^{16'}$ and $R^{17'}$ together form a 3- to 7-membered ring to represent a cyclic amine as $N(R^{16'})(R^{17'})$, or $R^8$ and $R^9$ may together form a benzene ring and thus form a bicyclic heteroaromatic group as a group represented by the formula A3'; and $X^1$ represent oxygen atom, sulfur atom, or $N-R^{19}$ wherein $R^{19}$ represents hydrogen atom, an alkyl group, phenyl group, or a substituted phenyl group; $X^2$ represents oxygen atom, or sulfur atom, and $R^{23'}$ represents a substituted phenyl group which may have a protective group in a substituent, a monocyclic heteroaromatic group which may be substituted with a substituent which may have a protective group, or a bicyclic heteroaromatic group which may be substituted with a substituent which may have a protective group, B' represents a group selected from the group consisting of a group represented by the following formula B1', B2', B3', B4', or B5':

[Formula 14]

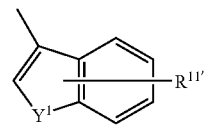

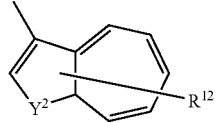

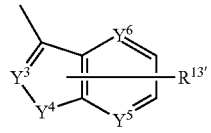

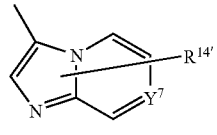

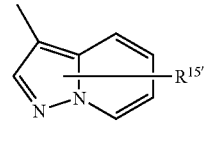

wherein $R^{11'}$ represents hydrogen atom, hydroxyl group which may have a protective group, a halogen atom, an alkyl group, an alkoxyl group, a thioalkoxyl group, hydroxymethyl group, an alkyl group arbitrarily substituted with one or more halogen atoms, an alkoxyl group arbitrarily substituted with one or more halogen atoms, nitro group, or $N(R^{20'})(R^{21'})$ wherein $R^{20'}$ and $R^{21'}$ may be the same or different, and independently represent hydrogen atom, an alkyl group, an acyl group, $SO_2R^{22}$, or a protective group of the nitrogen atom, wherein $R^{22}$ represents a lower alkyl group, or $R^{20'''}$ and $R^{21'''}$ together form a 3- to 7-membered ring to represent a cyclic amine as $N(R^{20'})(R^{21'})$, $Y^{1'}$ represents sulfur atom or oxygen atom; $R^{12}$ represent hydrogen atom or an alkyl group, $Y^2$ represents CH or nitrogen atom; $R^{13'}$ represents hydrogen atom, hydroxyl group which may have a protective group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20'})(R^{21'})$ wherein $R^{20'}$ and $R^{21'}$ may be the same or different, and independently represent hydrogen atom, an alkyl group, an acyl group, $SO_2R^{22}$, or a protective group of the nitrogen atom, wherein $R^{22}$ represents a lower alkyl group, or $R^{20'''}$ and $R^{21'''}$ together form a 3- to 7-membered ring to represent a cyclic amine as $N(R^{20'})(R^{21'})$, $Y^4$ represents sulfur atom or oxygen atom, and one of $Y^3$, $Y^5$, and $Y^6$ represents nitrogen atom, and the remaining groups represent CH; $R^{14'}$ represents hydrogen atom, hydroxyl group which may have a protective group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20'})(R^{21'})$ wherein $R^{20'}$ and $R^{21'}$ may be the same or different, and independently represent hydrogen atom, an alkyl group, an acyl group, $SO_2R^{22}$, or a protective group of the nitrogen atom, wherein $R^{22}$ represents a lower alkyl group, or $R^{20'''}$ and $R^{21'''}$ together form a 3- to 7-membered ring to represent a cyclic amine as $N(R^{20'})(R^{21'})$, $Y^7$ represent CH or nitrogen atom; and $R^{15'}$ represents hydrogen atom, hydroxyl group which may have a protective group, a halogen atom, an alkyl group, an alkoxyl group, an alkyl group arbitrarily substituted with one or more halogen atoms, an alkoxyl group arbitrarily substituted with one or more halogen atoms, nitro group, or $N(R^{20'})(R^{21'})$ wherein $R^{20'}$ and $R^{21'}$ may be the same or different, and independently represent hydrogen atom, an alkyl group, an acyl group, $SO_2R^{22}$, or a protective group of the nitrogen atom, wherein $R^{22}$ represents a lower alkyl group, or $R^{20'''}$ and $R^{21'''}$ together form a 3- to 7-membered ring to represent a cyclic amine as $N(R^{20'})(R^{21'})$;

$R^1$ represents an alkyl group, and symbol "n" represents an integer of 2 to 6, compounds represented by the following formula (2):

[Formula 15]

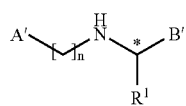

(2)

wherein A', B', $R^1$, and n have the same meanings as those defined above, and * represents a carbon atom in S-configuration, R-configuration, or the both configurations, can be obtained, and when A' or B' has a protective group, by deprotecting such a compound, compounds represented by the formula (1) can be prepared.

The method of reducing a compound represented by the formula (3) to obtain a compound represented by the formula (2) can be performed, for example, according to known reduction amination reaction methods described in a publication (Jikken Kagaku Koza (Lecture of Experiment Chemistry), 4th-edition, Vol. 20, Chapter 6, Maruzen), literature (Robert M. B. et al., Tetrahedron Letters, Vol. 39, 1998, pp. 3451-3454), and the like.

Type of the reducing agent used for the reduction reaction is not particularly limited, and examples include, for example, hydrogen, lithium aluminum hydride, sodium borohydride, sodium cyanoborohydride, sodium triacetoxyborohydride, borane, formic acid-triethyl amine complex, and the like, and preferred example include hydrogen, sodium borohydride, sodium cyanoborohydride, sodium triacetoxyborohydride, borane, and formic acid-triethyl amine complex. Type of the solvent used for the reaction is not particularly limited so long as a solvent inert to the reduction reaction is chosen. Examples include an alcohol type solvent, a saturated hydrocarbon type solvent, a chlorinated hydrocarbon type solvent, an ether type solvent, an aromatic hydrocarbon type solvent, dimethylformamide, dimethyl sulfoxide, and the like, and individuals and mixed solvents at arbitrary ratios of these solvents are included. Examples of the alcohol type solvent include methanol, ethanol, and 2-propanol, examples of the saturated hydrocarbon type solvent include pentane, hexane, heptane, and cyclohexane, and examples of chlorinated hydrocarbon type solvent include methylene chloride, chloroform, and 1,2-dichloroethane. Examples of the ether type solvent include tetrahydrofuran, diethyl ether, and 1,4-dioxane, and examples of aromatic hydrocarbon type solvent include toluene, xylene, and the like. Preferred examples include 2-propanol, methylene chloride, tetrahydrofuran, toluene, dimethylformamide, and the like.

The reducing agent is preferably used in an amount of 0.1 mole or more, more preferably in an equimolar amount or more, based on the compound represented by the formula (3). Further, the agent is preferably used in an amount of 100 moles or less, more preferably 10 moles or less. Although the reaction temperature is not particularly limited, the reaction is preferably performed at a temperature of −20° C. or higher, more preferably 20° C. or higher. The reaction time is not particularly limited. Progress of the reaction can be easily monitored by an analysis method such as thin layer chromatography (TLC), high performance liquid chromatography (HPLC), and gas chromatography (GC), and therefore the reaction can be terminated when the maximum yield of objective substance is obtained.

The compounds represented by the formula (2) have asymmetric carbons indicated with *, and according to the aforementioned method, the objective substance is obtained as a racemate. In order to obtain an optically active substance, for example, asymmetric reduction can be performed as the reduction reaction with a hydrogen supplying compound in the presence of an asymmetric reduction catalyst. Examples of the asymmetric reduction catalyst include combinations of an optically active aminosulfonamide and arene chloride-ruthenium complex, optically active ruthenium complex and optically active titanium complex prepared from these complexes, and the like.

Examples of the optically active aminosulfonamide include, for example, (1R,2R)-N-(p-toluenesulfonyl)-1,2-diphenyl-1,2-ethanediamine, (1S,2S)-N-(p-toluenesulfonyl)-1,2-diphenyl-1,2-ethanediamine, (1R,2R)-N-methanesulfonyl-1,2-diphenyl-1,2-ethanediamine, (1S,2S)-N-methanesulfonyl-1,2-diphenyl-1,2-ethanediamine, (1R,2R)-N-benzenesulfonyl-1,2-diphenyl-1,2-ethanediamine, (1S,2S)-N-benzenesulfonyl-1,2-diphenyl-1,2-ethanediamine, (1R,2R)-N-mesitylenesulfonyl-1,2-diphenyl-1,2-ethanediamine, (1S,2S)-N-mesitylenesulfonyl-1,2-diphenyl-1,2- ethanediamine, (1R,2R)-N-(p-toluenesulfonyl)-1,2-cyclohexyldiamine, (1S,2S)-N-(p-toluenesulfonyl)-1,2-cyclohexyldiamine, and the like. Examples of the arene chloride-ruthenium complex include, for example, dichlorobenzene ruthenium dimer, dichloro(p-cymene)ruthenium dimer, dichloromesitylene ruthenium dimer, and the like.

Examples of the optically active ruthenium catalyst include, for example, [(1R,2R)-N-(p-toluenesulfonyl)-1,2-diphenyl-1,2-ethanediamine](p-cymene)ruthenium, [(1S,2S)-N-(p-toluenesulfonyl)-1,2-diphenyl-1,2-ethanediamine](p-cymene)ruthenium, [(1R,2R)-N-methanesulfonyl-1,2-diphenyl-1,2-ethanediamine](p-cymene)ruthenium, [(1S,2S)-N-methanesulfonyl-1,2-diphenyl-1,2-ethanediamine](p-cymene)ruthenium, [(1R,2R)-N-(p-toluenesulfonyl)-1,2-diphenyl-1,2-ethanediamine](benzene)ruthenium, [(1S,2S)-N-(p-toluenesulfonyl)-1,2-diphenyl-1,2-ethanediamine](benzene)ruthenium, and the like. Examples of the optically active titanium complex include, for example, (R,R)-ethylene-1,2-bis($\eta^5$-4,5,6,7-tetrahydro-1-indenyl)titanium difluoride, (S,S)-ethylene-1,2-bis($\eta^5$-4,5,6,7-tetrahydro-1-indenyl)titanium difluoride, (R,R)-ethylene-1,2-bis($\eta^5$-4,5,6,7-tetrahydro-1-indenyl)titanium dichloride, (S,S)-ethylene-1,2-bis($\eta^5$-4,5,6,7-tetrahydro-1-indenyl)titanium dichloride, (R,R)-ethylene-1,2-bis($\eta^5$-4,5,6,7-tetrahydro-1-indenyl)titanium (R)-1,1'-binaphth-2,2'-diolate, and (S,S)-ethylene-1,2-bis($\eta^5$-4,5,6,7-tetrahydro-1-indenyl)titanium (S)-1,1'-binaphth-2,2'-diolate.

Examples of the hydrogen supplying compound include, for example, a formic acid-tertiary amine mixture, 2-propanol, and an alkylsilane, examples of the formic acid-tertiary amine mixture include a formic acid-triethylamine mixture, and examples of the alkylsilane include phenylsilane. Examples of the solvent for carrying out the asymmetric reduction include, for example, an alcohol type solvent, an ether type solvent, a chlorinated hydrocarbon type solvent, acetonitrile, dimethyl sulfoxide, dimethylformamide, acetone, and the like, and a single solvent and mixtures at arbitrary ratios of these solvents are included. Examples of the alcohol type solvent include methanol, ethanol, and 2-propanol, examples of the ether type solvent include diethyl ether, tetrahydrofuran, and 1,4-dioxane, and examples of the chlorinated hydrocarbon type solvent include dichloromethane, and 1,2-dichloroethane. Further, the asymmetric reduction reaction can also be performed without solvent.

The asymmetric reduction can be performed according to methods described in the literature, for example, Noyori et al., J. Am. Chem. Soc., Vol. 118, pp. 4916-4917, 1996; Johansson A., Contemp. Org. Synth., Vol. 2, pp. 393-407, 1995; Buchwald S. L. et al., Angew. Chem. Int. Ed., Vol. 37, pp. 1103-1107, 1998; Buchwald S. L. et al., Tetrahedron Letters, Vol. 3740, pp. 2033-2034, 1999 and the like. It is preferable to appropriately choose a method from those described in the aforementioned literature to prepare a compound of the formula (1) as the ultimate objective compound in which the carbon atom corresponding to the asymmetric carbon indicated with * in the aforementioned formula (2) is in the R-configuration. As the reduction reaction, asymmetric reduction is preferably performed.

Further, when a compound represented by the formula (2) is obtained as a racemate, the racemate can be converted into an addition salt with an optically active acid such as camphorsulfonic acid, mandelic acid, and tartaric acid, and then subjected to fractional recrystallization to separate an optically active substance. Further, the separation can also be performed by using a commercially available optically active column.

After a compound represented by the formula (2) is obtained, when a protective group exists in A' or B', the compound can be deprotected to obtain a compound represented by the formula (1). In addition, a compound represented by the formula (2) in which a protective group does not exist in A' and B' corresponds to the compound of the formula (1). Also for the aforementioned compound, an optically active substance can be obtained by the aforementioned method.

When the protective group contained in A' or B' is a protective group of hydroxyl group, the protective group of hydroxyl group is not limited so long as a protective group ordinarily used in the organic synthesis is chosen, and preferred examples include a trialkylsilyl group, a benzyl group which may be substituted, an n-alkyl group, an acyl group, and the like. Examples of the trialkylsilyl group include, for example, a trialkylsilyl group such as t-butyldimethylsilyl group, trimethylsilyl group, and triethylsilyl group, t-butyldiphenylsilyl group, and the like. Examples of the benzyl group which may be substituted include, for example, benzyl group, 4-methoxybenzyl group, 4-nitrobenzyl group, and the like. Examples of the n-alkyl group include, for example, methyl group. Examples of the acyl group include, for example, acetyl group, benzoyl group, and the like.

When the protective group contained in A' or B' is a protective group of amino group, the protective group of amino group is not limited so long as a protective group ordinarily used in the organic synthesis is chosen, and preferred examples include, for example, benzyl group which may be substituted, an alkyloxycarbonyl group, and an acyl group. Examples of the benzyl group which may be substituted include, for example, benzyl group, 4-methoxybenzyl group, and 4-nitrobenzyl group. Examples of the alkyloxycarbonyl group include, for example, t-butyloxycarbonyl group, benzyloxycarbonyl group, and the like. Examples of the acyl group include, for example, acetyl group, benzoyl group, and the like.

As for the deprotection, when two or more kinds of protective groups are removed, they may be removed sequentially or simultaneously. For example, it is preferable to first remove the protective group of hydroxyl group in A' or B', and then subsequently remove the protective group of amino group in A' or B'. Further, it is also preferable to perform sequential deprotection under different deprotection conditions.

For example, when the protective group of hydroxyl group in A' or B' contains a benzyl group which may be substituted, or when the protective group of amino group contains a benzyl group which may be substituted or benzyloxycarbonyl group, a method of performing hydrogenolysis in an inert solvent in the presence of a metal catalyst may be used. Examples of the inert solvent include, an alcohol type solvent, an ester type solvent, and an ether type solvent. Examples of the alcohol type solvent include methanol, ethanol, and 2-propanol, examples of the ester type solvent include ethyl acetate and the like, and examples of the ether type solvent include tetrahydrofuran, 1,4-dioxane, and the like. The hydrogenolysis may be performed in a simple solvent or a mixed solvent at an arbitrary ratio of these solvents. Examples of the metal catalyst include, for example, a simple catalyst and a catalyst carried on carbon powder of palladium, nickel, and the like. Examples of the method of the hydrogenolysis include a method of using hydrogen gas, and a method of carrying out the reaction by generating active type hydrogen in a reaction system using formic acid, ammonium formate, or the like as in methods described in the literature (B. ElAmin et al., J. Org. Chem., Vol. 44, p. 3442, 1979; T. Bieg et al., Synthesis, p 76, 1978).

When the protective group of hydroxyl group in A' or B' contains benzyl group which may be substituted or n-alkyl group, the deprotection method may be, for example, a method of treating the compound with a dealkylation agent in a chlorinated hydrocarbon solvent. Examples of the chlorinated hydrocarbon include, for example, simple solvents and mixed solvents at an arbitrary ratio of 1,2-dichloroethane, methylene chloride, and the like. Examples of the dealkylation agent include a Lewis acid such as boron tribromide, hydrogen iodide, and the like.

When the hydroxyl group of A' or B' contains a hydroxyl group protected with an acyl group, or when the amino group of A' and B' contains an amino group protected with an acyl group, known conditions for hydrolysis of esters using an alkali or acid can be used. Examples of the solvent include a single solvent of an alcohol type solvent such as methanol and ethanol or water, and a mixed solvent thereof at an arbitrary ratio with a water-soluble ether type solvent such as tetrahydrofuran, and 1,4-dioxane. Examples of the alkali include sodium hydroxide, potassium hydroxide, and the like, and examples of the acid include a mineral acid such as hydrochloric acid, nitric acid, and sulfuric acid.

When the protective group of hydroxyl group of A' or B' contains a trialkylsilyl group, known conditions for removing a silyl group can be used. The method may be, for example, a reaction using acetic acid, and tetrabutylammonium fluoride in a water-soluble ether type solvent such as tetrahydrofuran. The amount of tetrabutylammonium fluoride is preferably 1 mole or more and 5 moles or less based on the protective group contained in the compound represented by the formula (2). The reaction time is not particularly limited. Progress of the reaction can be easily monitored by the aforementioned analysis methods, and therefore the reaction can be terminated when the maximum yield of the objective substance is obtained.

When the protective group of amine in A' or B' contains t-butyloxycarbonyl group, deprotection can be performed by a method of treating the compound with an acid in an inert solvent. Examples of the inert solvent include an ether type solvent, an ester type solvent, and an alcohol type solvent. Examples of the ether type solvent include diethyl ether and 1,4-dioxane, examples of the ester type solvent include ethyl acetate, examples of the alcohol type solvent include methanol, ethanol, and the like, and a single solvent and a mixed solvent at an arbitrary ratio of these solvents are included. Examples of the acid include hydrochloric acid, trifluoroacetic acid, and the like. Although the reaction temperature is not particularly limited, the reaction is preferably carried out at a temperature of 0° C. or higher, more preferably 20° C. or higher. It is also preferable to carry out the reaction with heating, and the upper limit of the temperature is, for example, the reflux temperature of the solvent.

The compounds represented by the formula (3) can be prepared by reacting an amine represented by the formula (4):

[Formula 16]

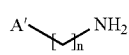

(4)

wherein A' and n have the same meanings as those defined above, with a carbonyl compound represented by the formula (5):

[Formula 17]

(5)

wherein $R^1$ and B' have the same meanings as those defined above, in an inert solvent, or without solvent.

The amount of the compound represented by the formula (4) is preferably 0.8 mole or more, more preferably an equimolar amount or more, based on the compound represented by the formula (5). The amount is preferably 5 moles or less, more preferably 2 moles or less. Further, a dehydration agent may be added as a reagent for promoting generation of an imine. Examples of the dehydration agent include, for example, titanium tetraisopropoxide, potassium hydroxide, titanium tetrachloride, molecular sieves, and the like. The amount of the dehydration agent is preferably 0.8 mole or more, more preferably an equimolar amount or more, based on the compound represented by the formula (4). The amount is preferably 5 moles or less, more preferably 2 moles or less.

Examples of the inert solvent include, for example, an alcohol type solvent, a chlorinated hydrocarbon type solvent, an ether type solvent, a hydrocarbon type solvent, an aromatic hydrocarbon type solvent, dimethyl formamide, dimethyl sulfoxide, and the like. Examples of the alcohol type solvent include methanol, ethanol, 2-propanol, and the like, examples of the chlorinated hydrocarbon type solvent include methylene chloride, chloroform, 1,2-dichloroethane, and the like, and examples of the ether type solvent include tetrahydrofuran, diethyl ether, and the like. Examples of the hydrocarbon type solvent include pentane, hexane, and the like. Examples of the aromatic hydrocarbon type solvent include toluene, xylene, and the like. Preferred examples of the solvent include methanol, ethanol, 2-propanol, diethyl ether, and toluene. Further, this reaction can also be performed without solvent, and the reaction without solvent is also preferred. Although the reaction temperature is not particularly limited, the reaction is performed at a temperature of −20° C. or higher, preferably 0° C. or higher. Although the upper limit of the reaction temperature is not particularly limited so long as the compound is not decomposed, the reaction can be preferably performed at a temperature up to the boiling point of the solvent, and when the reaction is performed without solvent, the upper limit is, for example, 100° C. Although the reaction time is not particularly limited, the reaction is usually performed for 10 minutes to 48 hours. Further, progress of the reaction can be easily monitored by the aforementioned methods, and therefore the reaction can be terminated when the maximum yield of the objective substance is obtained.

Further, although the obtained compound of the formula (3) can be used for the subsequent reduction reaction without being isolated from a reaction mixture, the compound may be extracted, or purified as required, and then used for the reduction reaction. The reaction of the compound of the formula (4) and the compound of the formula (5) can be performed according to, for example, a known imine synthesis method described in a publication (Jikken Kagaku Koza (Lecture of Experiment Chemistry), 4th-edition, Vol. 20, Chapter 6, Maruzen, or WO93/04373), and the like.

The compounds represented by the formula (4) are known compounds, and can be obtained as commercial products, or easily synthesized by introducing a suitable protective group into commercially available or known corresponding various amidated compounds or nitrile compounds as required and then reducing the amide group or nitrile group into an amine according to a method described in the literature (Toson et al., Bioorg. Med. Chem., Vol. 5, pp. 1675-1684, 1997), or a publication (Jikken Kagaku Koza (Lecture of Experiment Chemistry), 4th-edition, Vol. 20, Chapter 6, Maruzen).

The compounds providing the groups represented by the formulas A1', A2', A3', and A4' can be obtained as commercial products, or can be synthesized from a corresponding alcohol according to methods described in the literature (Campi, E. M. et al., Tetrahedron; Vol. 50, pp. 2533-2542, 1994; Reddy, G. V. S. et al., Synth. Commun., Vol. 30, pp. 2233-2237, 2000), or by converting a corresponding carboxylic acid synthesized according to methods described in the literature (Toth, G. et al., Synth. Commun., Vol. 25, pp. 3067-3074, 1995; Uenishi, J. et al., J. Org. Chem., Vol. 62, pp. 1692-1701, 1997 and the like) into an amide and then reducing the amide into an amine.

The compounds represented by the formula (5) are also known compounds, and can be obtained as commercial products. Further, the compounds wherein B' is a group represented by the formula B1' can be synthesized by, for example, synthesizing a corresponding $R^{11'}$-substituted benzoxazole or $R^{11'}$-substituted benzothiazole according to methods described in the literature and publications (Robertson et al., Eur. J. Med. Chem. Chim. Ther., Vol. 21, pp 223-230, 1986; Yamanaka et al., Chemistry of Heterocyclic Compounds, Chapter 2, Kodansha, 1988 and the like) and then acylating the resultant according to the Friedel-Crafts reaction, Vilsmeier reaction, or the like described in the literature and publications (Shirley et al., J. Org. Chem., Vol. 23, 1024p, 1958; Jackson, J. Chem. Soc. Perkin Trans., 1, pp 681-687, 1990; Yamanaka et al., Chemistry of Heterocyclic Compounds, Chapter 6, Kodansha, 1988 and the like). The compounds of the formula (5) wherein B' is a group represented by the formula B2', and $Y^2$ is CH can be synthesized, for example, according to methods described in the literature (Anderson et al., J. Am. Chem. Soc., Vol. 77, pp. 6321-6323, 1955; Gerdil et al., Helv. Chim. Acta, Vol. 40, pp. 141-155, 1957; Hafner et al., Justus Liebigs Ann. Chem., Vol. 625, pp. 108-122, 1959; Nozoe et al., Heterocycles, Vol. 31, pp. 17-22, 1990). The compounds of the formula (5) wherein B' is a group represented by the formula B2', and $Y^2$ is nitrogen atom can be synthesized, for example, according to a method described in the literature (Nitta et al., Heterocycles, Vol. 32, pp. 23-28, 1991). The compounds of the formula (5) wherein B' is a group represented by the formula B3', $Y^2$ is sulfur atom, and $Y^5$ or $Y^6$ is nitrogen atom can be synthesized, for example, according to methods described in the literature (Klemm, L. H. et al., J. Heterocycl. Chem., Vol. 11, pp. 205-209, 1974; Klemm, L. H. et al., J. Heterocycl. Chem., Vol. 11, pp. 355-361, 1974). The compounds of the formula (5) wherein B' is a group represented by the formula B4', and $Y^2$ is CH can be synthesized, for example, according to a method described in the literature (Kawamoto T. et al., Tetrahedron. Lett., Vol. 41, pp. 3447-3451, 2000). The compounds of the formula (5) wherein B' is a group represented by the formula B4', and $Y^7$ is nitrogen atom can be synthesized, for example, according to a method described in the literature (Lumma, W. C. Jr. et al., J. Org. Chem., Vol. 46, pp. 3735-3736, 1981). The compounds of the formula (5) wherein B' is a group represented by the formula B5' can be synthesized, for example, according to a method described in the literature (Tanji K. et al., Heterocycles, Vol. 35, pp. 915-924, 1993). Protective groups in the groups represented by the formulas B1', B2', B3', B4', and B5' may be introduced at an appropriate stage as required.

Synthetic Method B

The compounds of the present invention represented by the formula (1) can also be produced by the following method, that is, a method of synthesizing a compound represented by the formula (6):

[Formula 18]

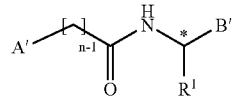

(6)

wherein A', B', $R^1$, n, and * have the same meanings as those defined above, reducing the compound represented by the formula (6) to obtain a compound represented by the formula (2), and then obtaining a compound represented by the formula (1) from the compound represented by the formula (2) according to Synthetic method A.

The method of reducing a compound represented by the formula (6) to the compound of the formula (2) can be performed, for example, according to a known method for reducing to an amide into an amine described in a publication (Jikken Kagaku Koza (Lecture of Experiment Chemistry), 4th-edition, Vol. 20, Chapter 6, Maruzen) and the like.

A type of the reducing agent used for the reduction reaction is not particularly limited. Examples include lithium aluminum hydride, sodium borohydride, sodium cyanoborohydride, sodium triacetoxyborohydride, borane, and the like, and preferred examples include lithium aluminum hydride, sodium borohydride, sodium cyanoborohydride, sodium triacetoxyborohydride, and borane. Further, in order to enhance reactivity, a Lewis acid may be added. Examples include aluminum chloride, titanium tetrachloride, tin tetrachloride, triethyloxonium tetrafluoroborate, and the like, and preferred examples include titanium tetrachloride and triethyloxonium tetrafluoroborate. Type of the solvent used for the reaction is not particularly limited so long as a solvent inert to the reduction reaction is chosen. Examples include a saturated hydrocarbon type solvent, a chlorinated hydrocarbon type solvent, an ether type solvent, an aromatic hydrocarbon type solvent, dimethylformamide, dimethyl sulfoxide, and the like, and a single solvent and a mixed solvent at an arbitrary ratio of these solvents are included. Examples of the saturated hydrocarbon type solvent include pentane, hexane, heptane, and cyclohexane, and examples of chlorinated hydrocarbon type solvent include methylene chloride, chloroform, and 1,2-dichloroethane. Examples of the ether type solvent include tetrahydrofuran, diethyl ether, and 1,4-dioxane, and examples of the aromatic hydrocarbon type solvent include toluene, xylene, dimethylformamide, and the like. Preferred examples include methylene chloride, tetrahydrofuran, toluene, dimethylformamide, and the like. The reducing agent is preferably used in an amount of 0.1 mole or more, more preferably in an equimolar amount or more, based on the compound represented by the formula (6). Further, the agent is preferably used in an amount of 100 moles or less, more preferably 10 moles or less. When a Lewis acid is added, the acid is preferably used in an amount of 0.01 mole or more, more preferably in an equimolar amount or more, based on the reducing agent. Further, the acid is preferably used in an amount of 10 moles or less, more preferably 2 moles or less. Although the reaction temperature is not particularly limited, the reaction is preferably performed at a temperature of −20° C. or higher, more preferably 20° C. or higher. The reaction time is not particularly limited. Progress of the reaction can be easily monitored by an analysis method such as thin layer chromatography (TLC), high performance liquid chromatography (HPLC), and gas chromatography (GC), and therefore the reaction can be terminated when the maximum yield of objective substance is obtained.

The compounds represented by the formula (2) have an asymmetric carbon indicated with *, and according to the aforementioned method, the compound is usually obtained as a compound retaining the three-dimensional structure of the compound represented by the formula (6).

Further, when the compound represented by the formula (2) is obtained as a racemate, the racemate can be converted into an addition salt with an optically active acid such as camphorsulfonic acid, mandelic acid, and tartaric acid, and then subjected to fractional recrystallization to separate an optically active substance. Further, the separation can also be performed by using a commercially available optically active column as already described above.

After a compound represented by the formula (2) is obtained, when a protective group exists in A' or B', the compound can be deprotected to obtain a compound represented by the formula (1). In addition, a compound represented by the formula (2) in which a protective group does not exist in A' and B' corresponds to the compound of the formula (1). As described above, an optically active substance can be obtained by the aforementioned method also for this compound.

The compounds represented by the formula (6) can be synthesized by reacting a carboxylic acid represented by the formula (7):

[Formula 19]

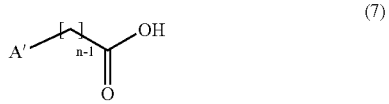

(7)

wherein A' and n are have the same meanings as those defined above, with an amine represented by the formula (8):

[Formula 20]

(8)

wherein B', $R^1$, and * have the same meanings as those defined above. Further, the compounds of the formula (6) can also be obtained by reacting an alkaline metal salt, active ester derivative, acid anhydride, or acid halide corresponding to a compound of the formula (7), which can be readily synthesized from the compound of the formula (7) by a known method, with an amine of the formula (8).

As for the method for obtaining the compounds of the formula (6) from compounds represented by the formulas (7) and (8), the compounds of the formula (6) can be readily synthesized by a known amidation reaction described in a publication (Jikken Kagaku Koza (Lecture of Experiment Chemistry), 4th-edition, Vol. 22, Chapters 1 and 2, Maruzen).

Examples of the condensing agent used for the amidation include dicyclohexylcarbodiimide, diisopropylcarbodiimide, N-ethyl-N'-3-dimethylaminopropylcarbodiimide, N-ethyl-N'-3-dimethylaminopropylcarbodiimide hydrochloride, benzotriazol-1-yl-tris (dimethylamino)phosphonium hexafluorophosphide salt, diphenylphosphorylazide, and the like. These agents may be used as a single agent, or used in combination with N-hydroxysuccinimide, 1-hydroxybenzotriazole, or 3-hydroxy-4-oxo-3,4-dihydro-1,2,3-benzotriazine as an additive. Further, a base may be added to neutralize the acid generated in the reaction system, and examples include a tertiary amine such as triethylamine, trimethylamine, and pyridine, carbonic acid salt such as potassium carbonate, sodium carbonate, potassium carbonate, and cesium carbonate, lithium hydroxide, sodium hydroxide, potassium hydroxide, magnesium hydroxide, calcium hydroxide, and the like.

Type of the solvent used for the reaction is not particularly limited so long as a solvent inert to the reduction reaction is chosen. Examples include a saturated hydrocarbon type solvent, a chlorinated hydrocarbon type solvent, an ether type solvent, an aromatic hydrocarbon type solvent, acetonitrile, dimethylformamide, dimethylacetamide, dimethyl sulfoxide, and the like, and a single solvent and a mixed solvent at an arbitrary ratio of these solvents are included. Examples of the saturated hydrocarbon type solvent include pentane, hexane, heptane, and cyclohexane, and examples of chlorinated hydrocarbon type solvents include methylene chloride, chloroform, and 1,2-dichloroethane. Examples of the ether type solvent include tetrahydrofuran, diethyl ether, and 1,4-dioxane, and examples of the aromatic hydrocarbon type solvent include toluene, xylene, and the like. Preferred examples include methylene chloride, tetrahydrofuran, toluene, dimethylformamide, acetonitrile, and the like. The condensing agent is preferably used in an amount of 0.8 mole or more, more preferably in an equimolar amount or more, based on the compound represented by the formula (7). Further, the agent is preferably used in an amount of 5 moles or less, more preferably 2 moles or less. The additive is preferably used in an amount of 0.8 mole or more, more preferably in an equimolar amount or more, based on the compound represented by the formula (7). Further, the additive is preferably used in an amount of 5 moles or less, more preferably 2 moles or less. When a base is added, the base is preferably added in an amount of 0.8 mole or more, more preferably in an equimolar amount or more, based on the acid generated in the reaction system. Further, the base is preferably added in an amount of 5 moles or less, more preferably 2 moles or less. Although the reaction temperature is not particularly limited, the reaction is preferably performed at a temperature of 0° C. or higher, more preferably 20° C. or higher. The reaction time is not particularly limited. Progress of the reaction can be easily monitored by an analysis method such as thin layer chromatography (TLC), high performance liquid chromatography (HPLC), and gas chromatography (GC), and therefore the reaction can be terminated when the maximum yield of objective substance is obtained.

When an alkaline metal salt or active ester of a compound represented by the formula (7) is used instead of the compound represented by the formula (7), the reaction can also be performed in a manner similar to that of the aforementioned amidation.

Further, when an acid anhydride or acid halide of a compound represented by the formula (7) is used instead of the compound represented by the formula (7), the agent can be reacted with a compound represented by the formula (8) in an inert solvent or without solvent in the presence of a base to synthesize the desired compound. Examples of the base include a tertiary amine such as triethylamine, and pyridine, carbonic acid salt such as potassium carbonate, sodium carbonate, and potassium carbonate, lithium hydroxide, sodium hydroxide, potassium hydroxide, and the like. Type of the solvent used for the reaction is not particularly limited so long as a solvent inert to the reduction reaction is chosen. Examples include a saturated hydrocarbon type solvent, a chlorinated hydrocarbon type solvent, an ether type solvent, an aromatic hydrocarbon type solvent, acetonitrile, dimethylformamide, dimethylacetamide, dimethyl sulfoxide, and the like, and simple solvents and mixed solvents at an arbitrary ratio of these solvents are included. Examples of the saturated hydrocarbon type solvent include pentane, hexane, heptane, and cyclohexane, and examples of the chlorinated hydrocarbon type solvent include methylene chloride, chloroform, and 1,2-dichloroethane. Examples of the ether type solvent include tetrahydrofuran, diethyl ether, and 1,4-dioxane, and examples of the aromatic hydrocarbon type solvent include toluene, xylene, and the like. Preferred examples include methylene chloride, tetrahydrofuran, toluene, dimethylformamide, and the like. Further, it is also preferable to directly use a tertiary amine such as pyridine and triethylamine as the solvent, and pyridine is preferred for such a purpose. The base is preferably used in an amount of 0.8 mole or more, more preferably in an equimolar amount or more, based on the compound represented by the formula (7).

The compounds represented by the formula (7) can be obtained as commercial products, or can be synthesized according to known methods described in the literature (Toth, G. et al., Synth. Commun., Vol. 25, pp. 3067-3074, 1995; Uenishi, J. et al., J. Org. Chem.; Vol. 62, pp. 1692-1701, 1997 and the like). Alkali metal salts of the compounds represented by the formula (7) can be easily obtained by neutralizing a compound represented by the formula (7) with an equivalent amount of an alkali metal hydroxide compound such as lithium hydroxide, sodium hydroxide, and potassium hydroxide in an alcohol solvent such as methanol and ethanol, or water. Further, acid anhydrides or acid halides of the compounds of the formula (7) can also be easily synthesized by known methods described in publications (Jikken Kagaku Koza (Lecture of Experiment Chemistry), 4th-edition, Vol. 22, Chapter 1, Maruzen and the like).

The compounds represented by the formula (8) can be obtained as commercial products, or can be synthesized from a compound represented by the formula (5) according to known methods described in the literature (B. Sukanta et al., Syn. Lett., Vol. 11, pp. 1781-1783, 1999 and the like). Examples of the compounds represented by the formula (8) include the followings compounds.

[Formula 21]

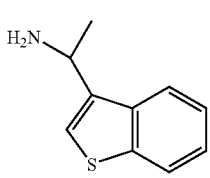
(ami-1)

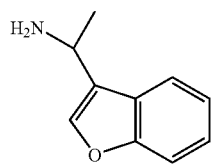
(ami-2)

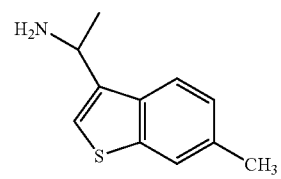
(ami-3)

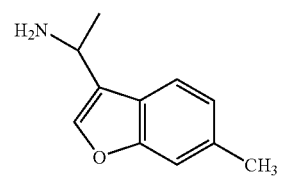
(ami-4)

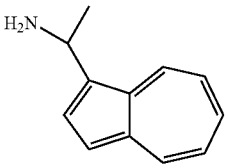
(ami-5)

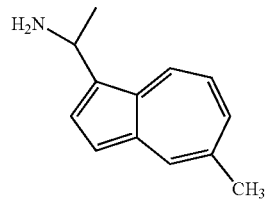
(ami-6)

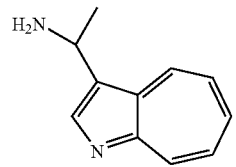
(ami-7)

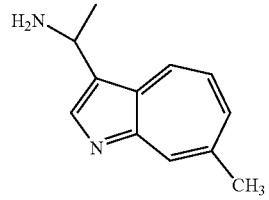
(ami-8)

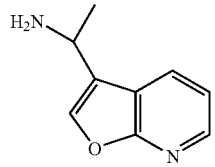
(ami-9)

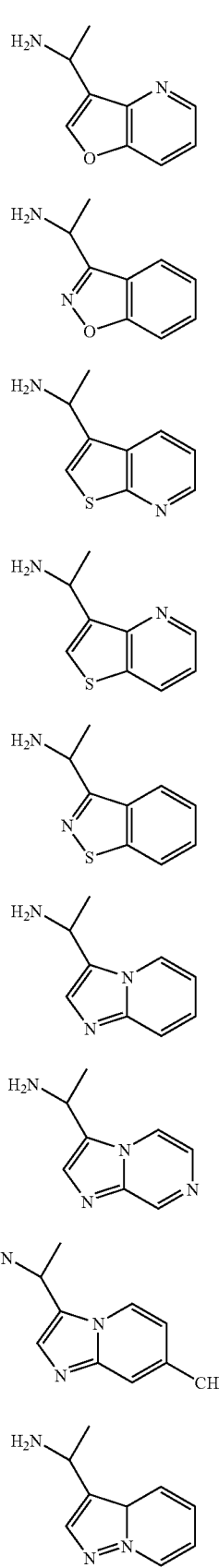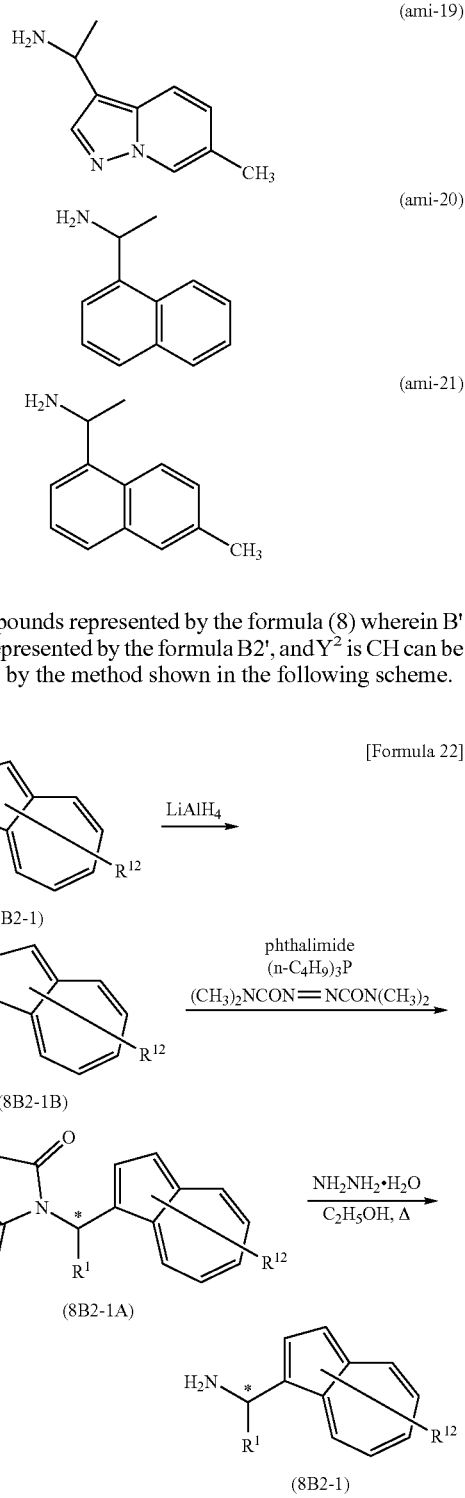

The compounds represented by the formula (8) wherein B' is a group represented by the formula B2', and Y² is CH can be synthesized by the method shown in the following scheme.

More specifically, a ketone represented by the formula (5B2-1) in the scheme is converted into an alcohol represented by the formula (8B2-1B) in the scheme by reduction with lithium aluminum hydride, and then the alcohol is reacted with phthalimide in the presence of tri-n-butylphosphine and 1,1'-azobis(N,N'-dimethylformamide) and thereby converted into a compound represented by the formula (8B2-

1A) in the scheme. Finally, the resulting product can be deprotected with hydrazine to obtain a compound represented by the formula (8B2-1) in the scheme. The compounds represented by the formula (8B2-1) and (8B2-1A) in the scheme are novel substances, and are extremely useful compounds for carrying out the present invention. The reducing agent used for obtaining a compound represented by the formula (8B2-1B) in the scheme from a compound represented by the formula (5B2-1) in the scheme is not limited to lithium aluminum hydride, and various reducing agents can be used. Further, as the phosphine and azo regent used for obtaining a compound represented by the formula (8B2-1A) in the scheme from a compound represented by the formula (8B2-1B) in the scheme, those other than the substances mentioned in the scheme may be used, and instead of the phthalimide used in the scheme, other imides such as maleimide and succinimide may be used. Further, the deprotection agent used for obtaining a compound represented by the formula (8B2-1) in the scheme from a compound represented by the formula (8B2-1A) in the scheme is not limited to hydrazine, and various deprotection agents can be used. The compounds represented by the formulas (8B2-1B), (8B2-1A), and (8B2-1) in the scheme have asymmetric carbons indicated with *, and racemate of each can be separated by using a commercially available optically active column to obtain an optically active substance. Further, by performing the aforementioned asymmetric reduction reaction in the reaction for obtaining a compound represented by the formula (8B2-1B), an optically active substance can be obtained. Furthermore, the compounds represented by the formula (8B2-1) can also be obtained by carrying out fractionation recrystallization after formation of an addition salt with the aforementioned optically active acid.

Synthetic Method C

The compounds of the present invention represented by the formula (1) can also be produced by the following method, i.e., a method for synthesizing a compound represented by the formula (9):

[Formula 23]

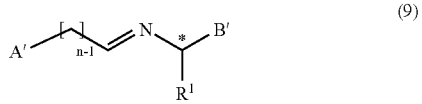
(9)

wherein A', B', $R^1$, n, and * have the same meanings as those defined above, then reducing the compound represented by the formula (9) to synthesize a compound represented by the formula (2), and further obtaining a compound represented by the formula (1) from the compound represented by the formula (2) according to the method described in Synthetic method A.

The method of reducing a compound represented by the formula (9) to obtain a compound of the formula (2) can be performed according to the method for obtaining a compound of the formula (2) from a compound of the formula (3) described in Synthetic method A.

The compounds represented by the formula (9) can be synthesized by reacting an amine represented by the formula (8):

[Formula 24]

(8)

with an aldehyde represented by the formula (10):

[Formula 25]

(10)

wherein A' and n have the same meanings as those defined above.

The method for obtaining a compound of the formula (9) from a compound of the formula (8) and a compound of the formula (10) can be performed according to the method for obtaining a compound of the formula (3) from a compound of the formula (4) and a compound of the formula (5) described in Synthetic method A.

The compounds represented by the formula (10) can be obtained as commercial products, or can be synthesized according to known methods described in the literature (Roger et al., Bioorg. J. Med. Chem. Lett., Vol. 36, pp. 5461-5464, 1995; Williams J. M. et al., Tetrahedron Letters, Vol. 6, pp. 1691-1696, 1996). The compounds represented by the formula (10) can also be obtained by oxidizing a corresponding alcohol by the method described in publications (Jikken Kagaku Koza (Lecture of Experiment Chemistry), 4th-edition, Vol. 23, Maruzen). Carboxylic acids, esters, and alcohols corresponding to the compounds represented by the formula (10) can be obtained as commercial products, or can be easily synthesized by known methods.

Examples of the compounds represented by the formula (10) include the followings compounds.

[Formula 26]

(AL-1)

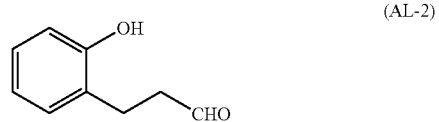
(AL-2)

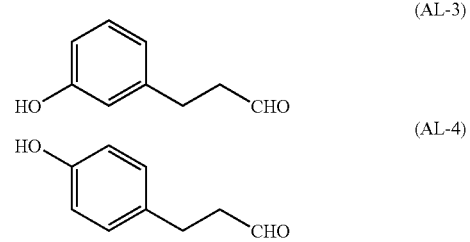
(AL-3)

(AL-4)

-continued
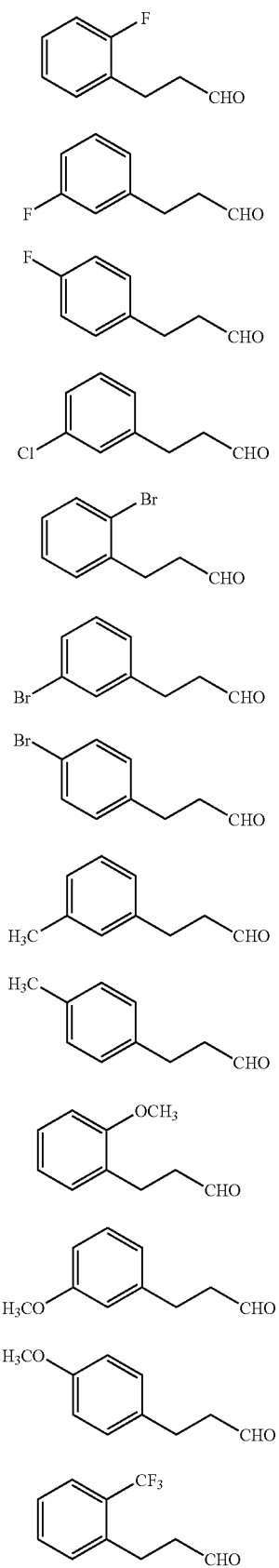
(AL-5)
(AL-6)
(AL-7)
(AL-8)
(AL-9)
(AL-10)
(AL-11)
(AL-12)
(AL-13)
(AL-14)
(AL-15)
(AL-16)
(AL-17)
-continued
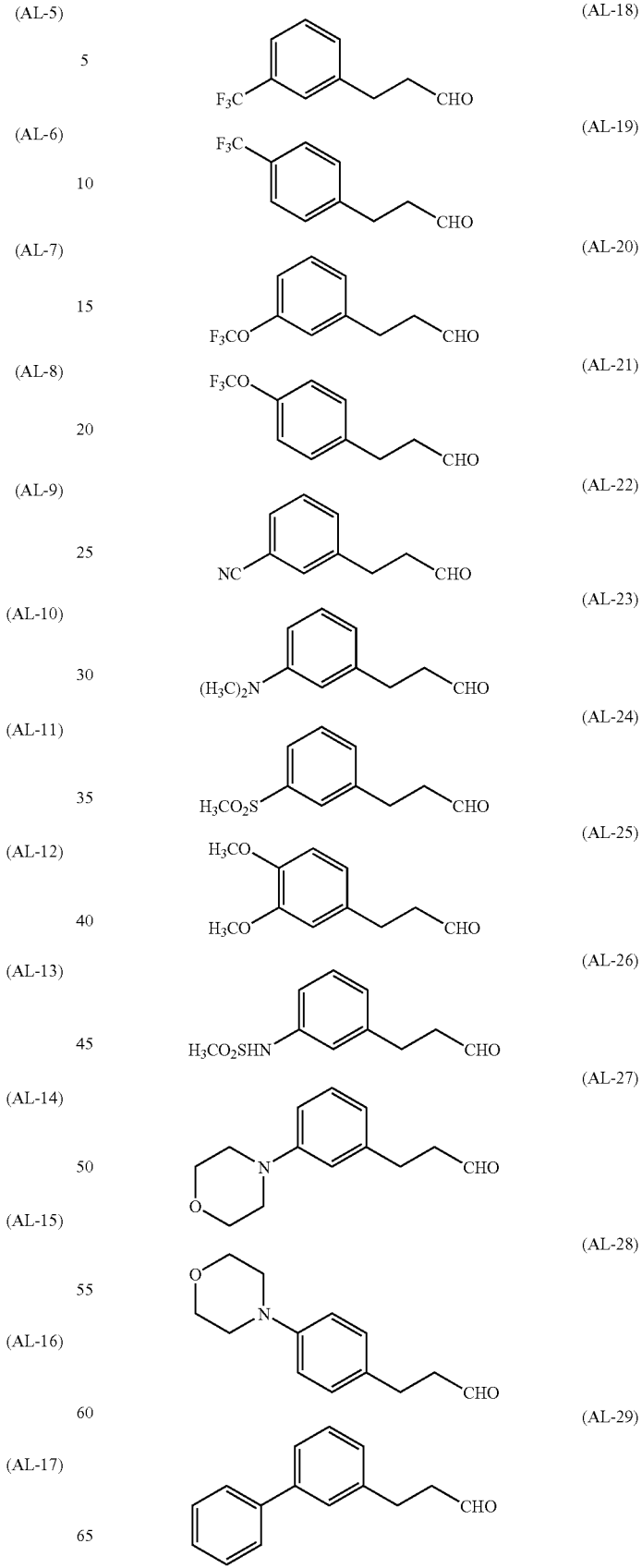
(AL-18)
(AL-19)
(AL-20)
(AL-21)
(AL-22)
(AL-23)
(AL-24)
(AL-25)
(AL-26)
(AL-27)
(AL-28)
(AL-29)

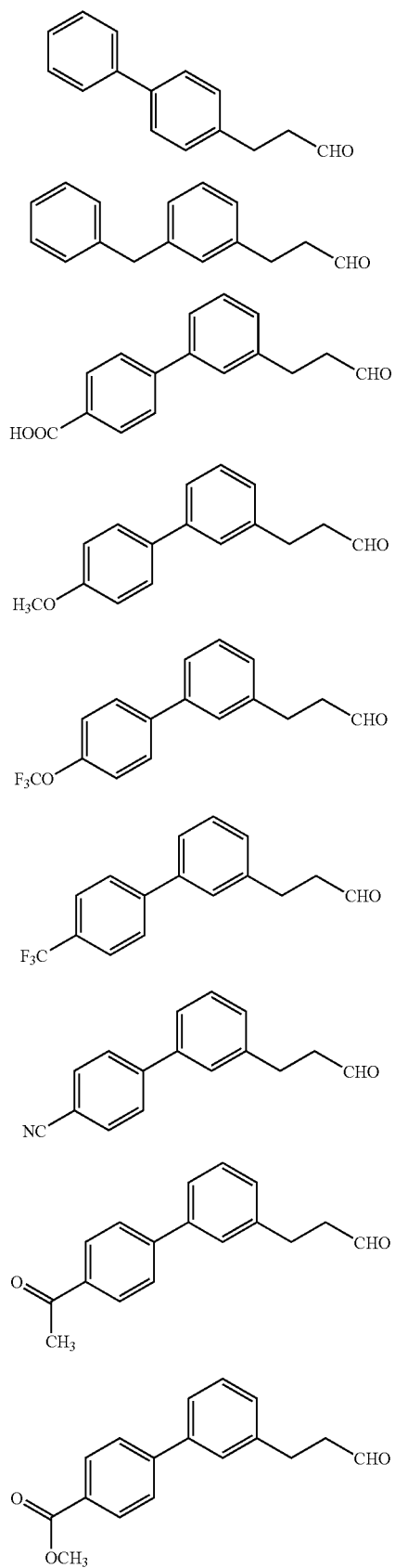

(AL-46)
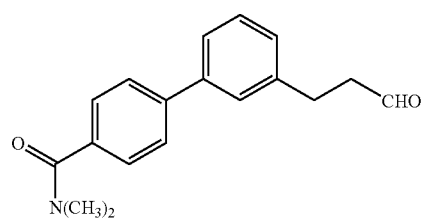
(AL-47)
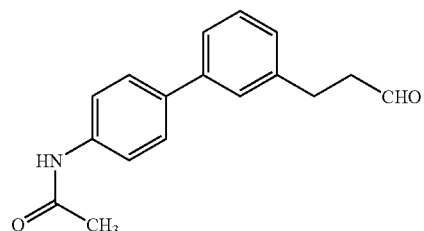
(AL-48)
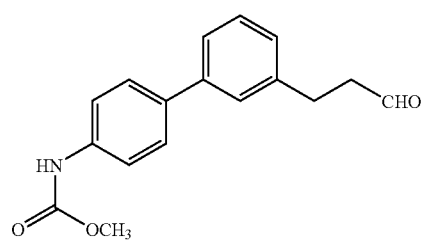
(AL-49)
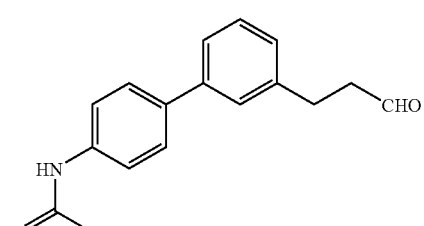
(AL-50)
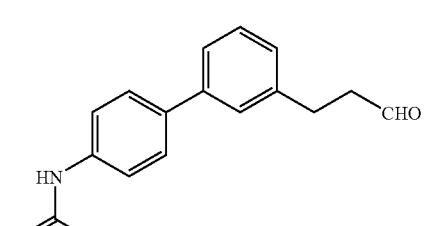
(AL-51)
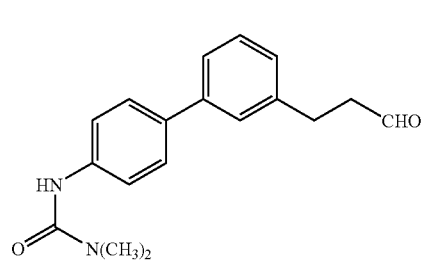
(AL-52)
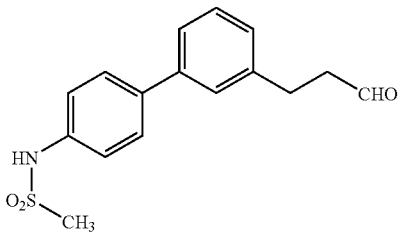
(AL-53)
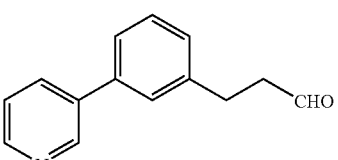
(AL-54)
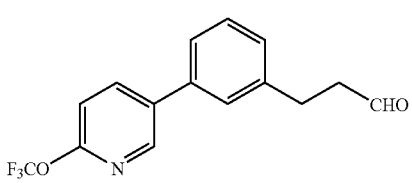
(AL-55)
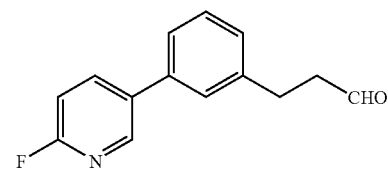
(AL-56)
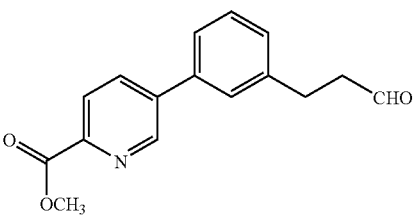
(AL-57)
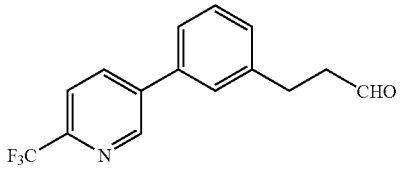
(AL-58)
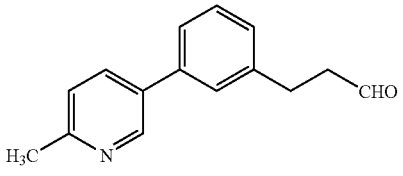
(AL-59)
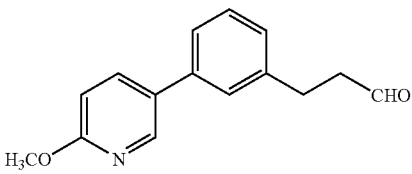

-continued (AL-60) (AL-73) (AL-61) (AL-74) (AL-62) (AL-75) (AL-63) (AL-76) (AL-64) (AL-77) (AL-65) (AL-78) (AL-66) (AL-79) (AL-67) (AL-80) (AL-68) (AL-81) (AL-69) (AL-82) (AL-70) (AL-71) (AL-83) (AL-72)

-continued
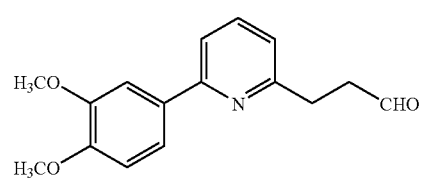 (AL-84)
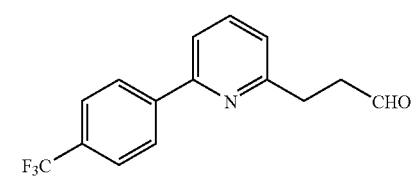 (AL-85)
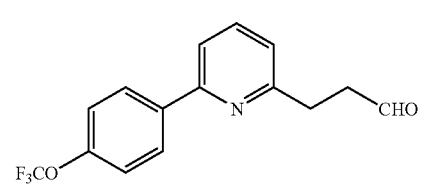 (AL-86)
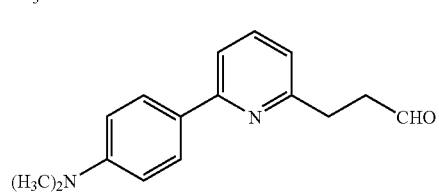 (AL-87)
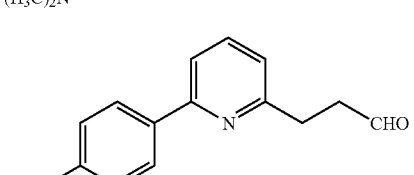 (AL-88)
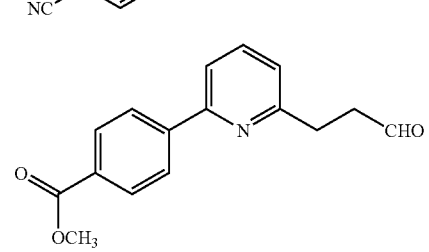 (AL-89)
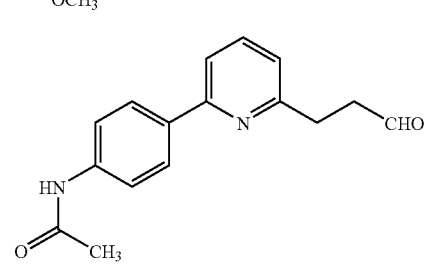 (AL-90)
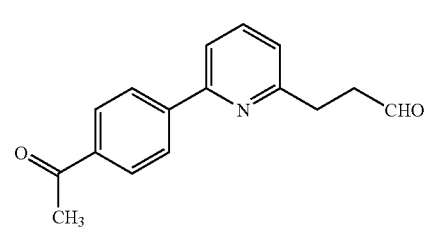 (AL-91)
-continued
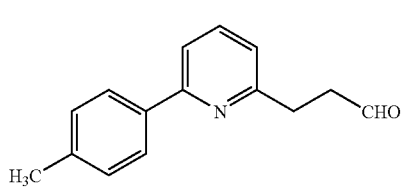 (AL-92)
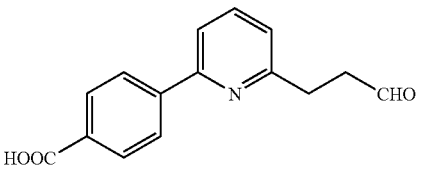 (AL-93)
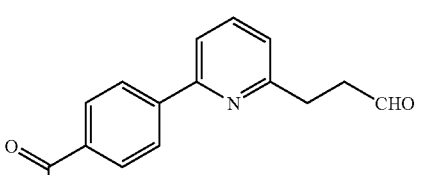 (AL-94)
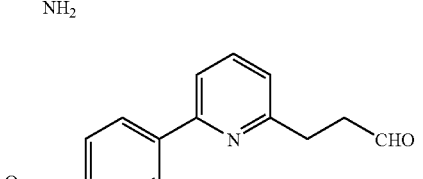 (AL-95)
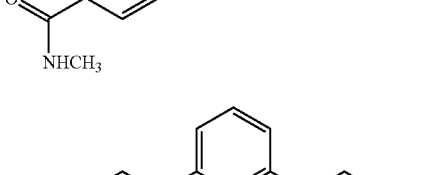 (AL-96)
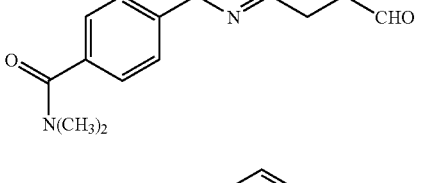 (AL-97)
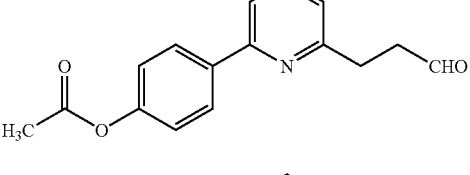 (AL-98)
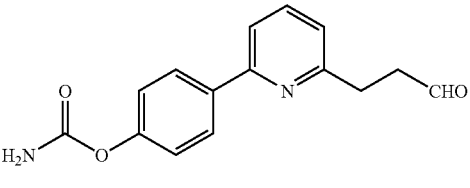 (AL-99)

-continued
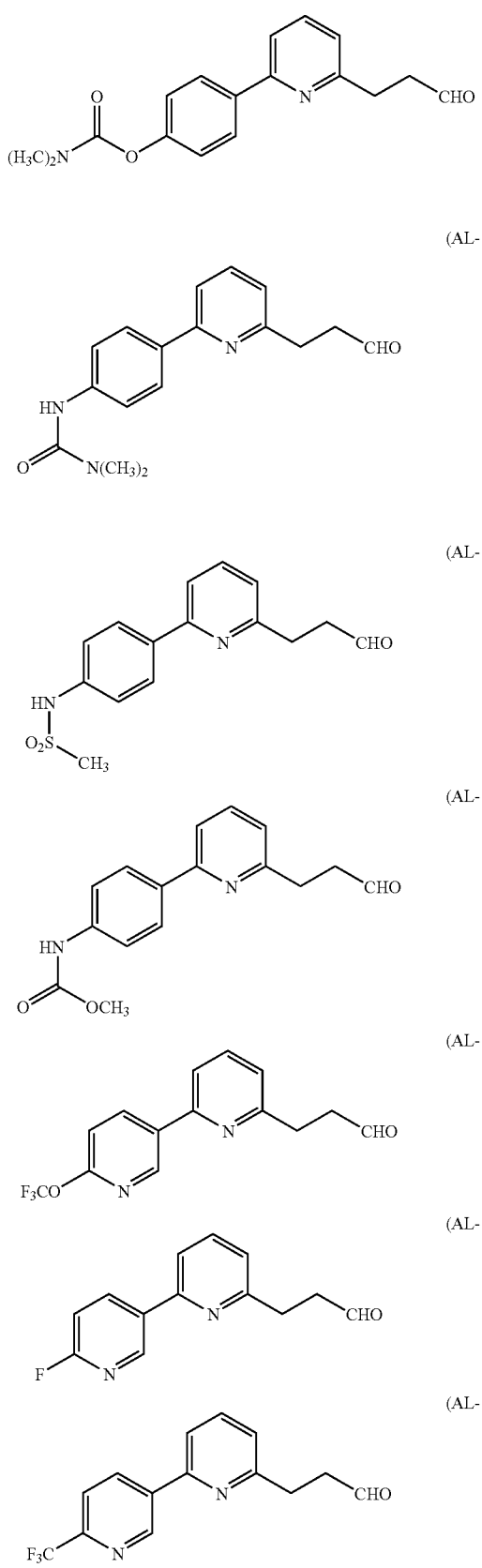
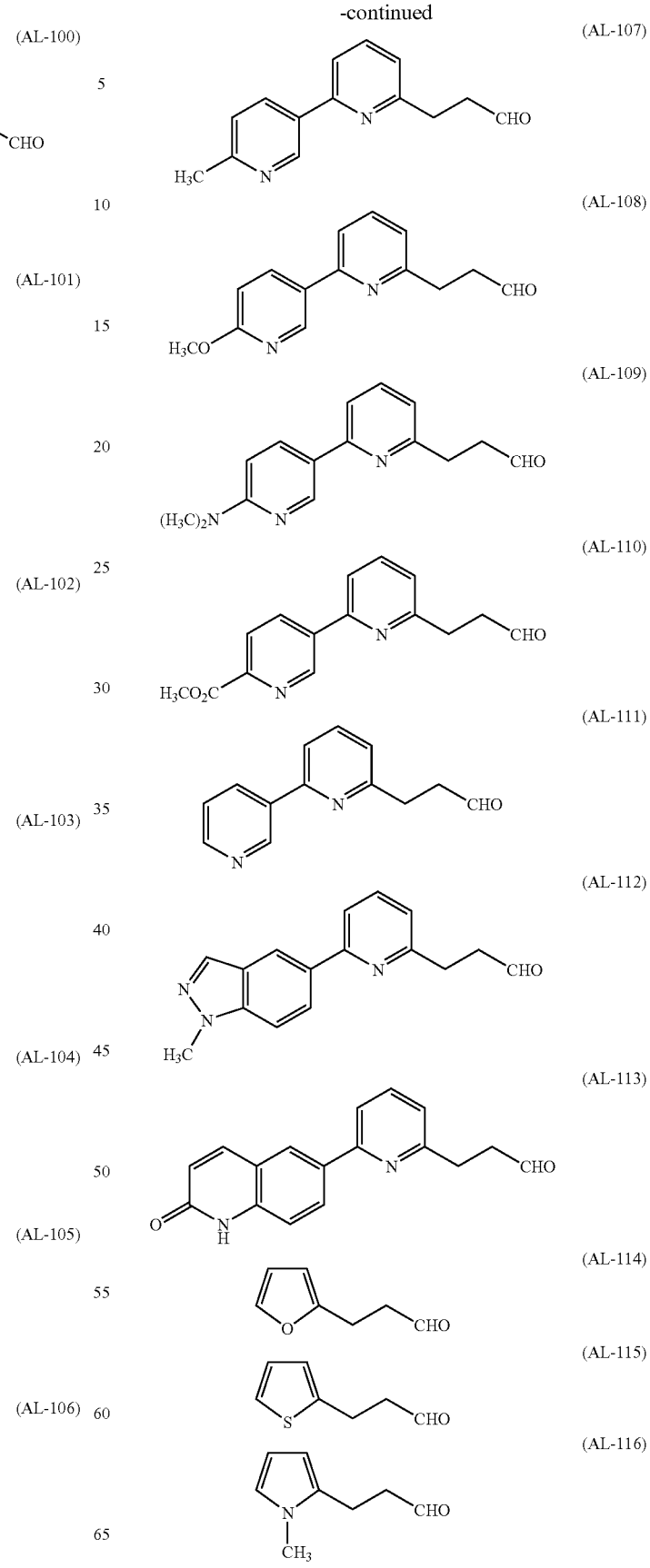

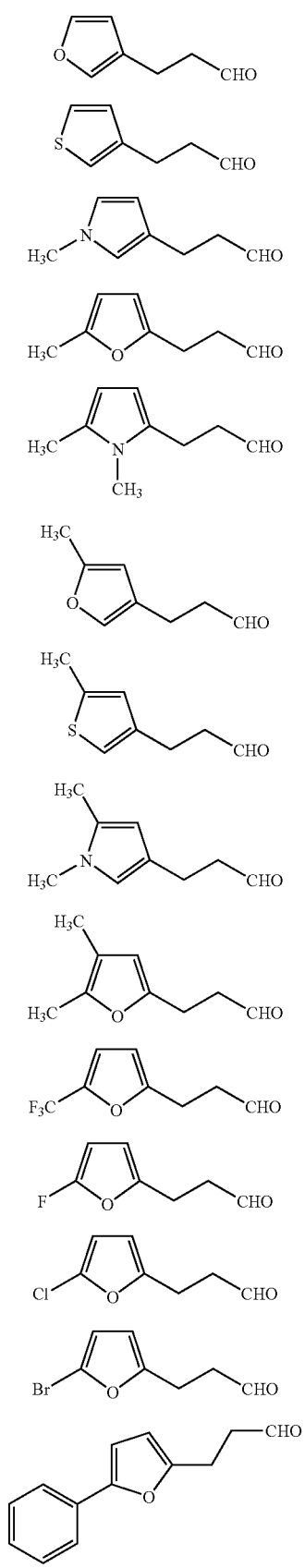
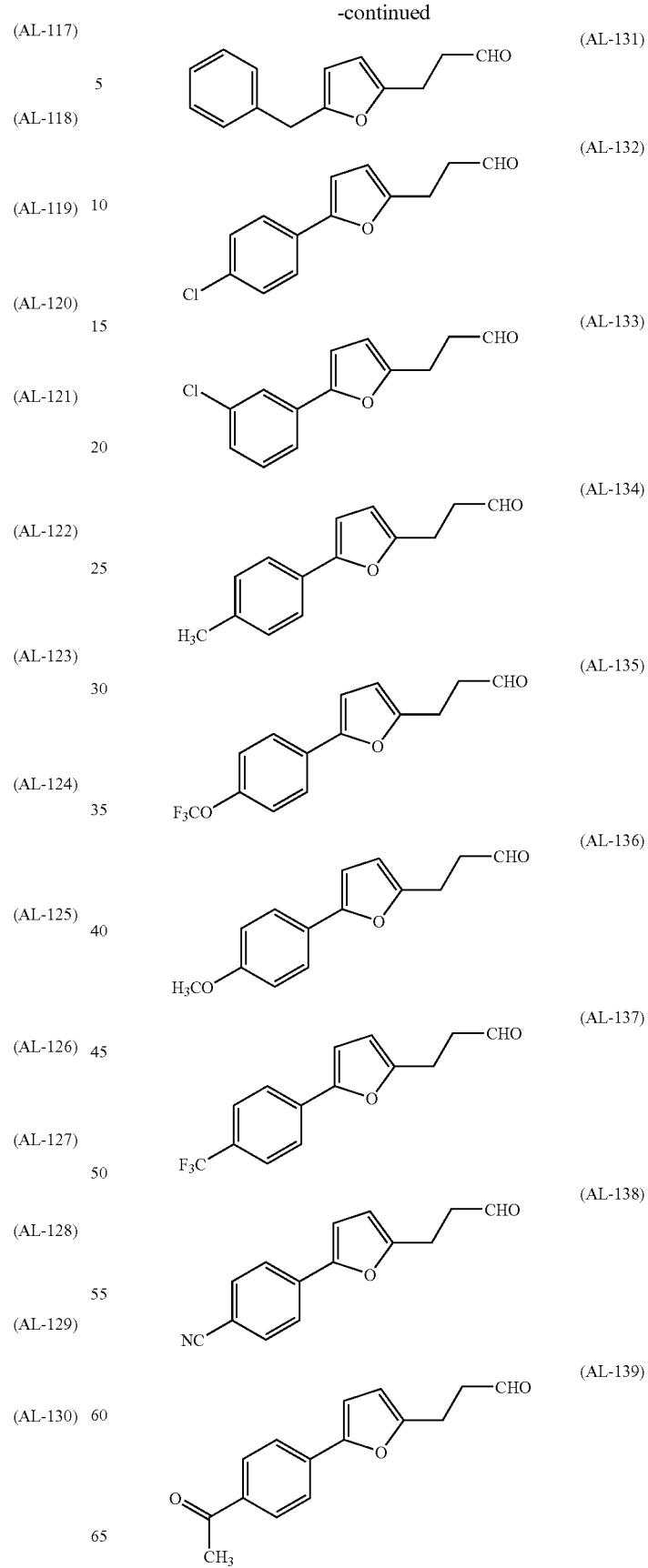

-continued
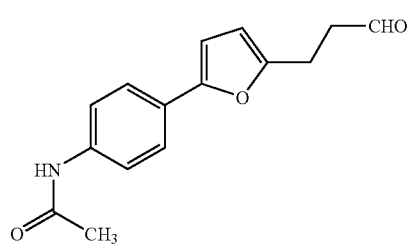
(AL-140)
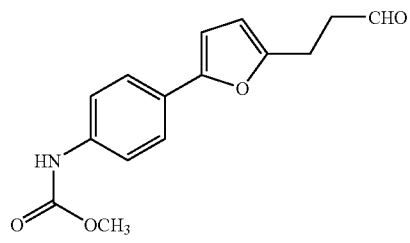
(AL-141)
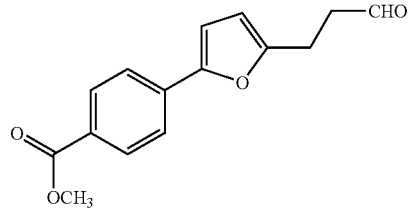
(AL-142)
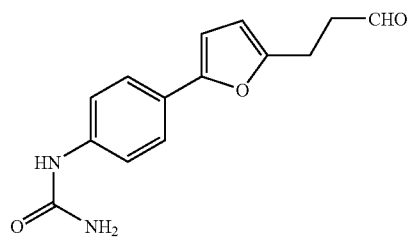
(AL-143)
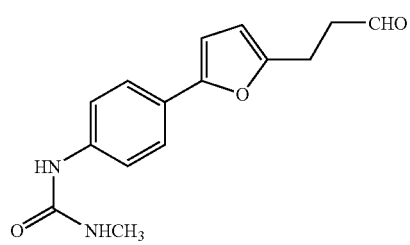
(AL-144)
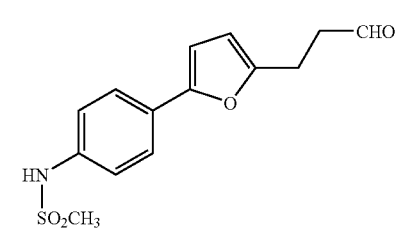
(AL-145)
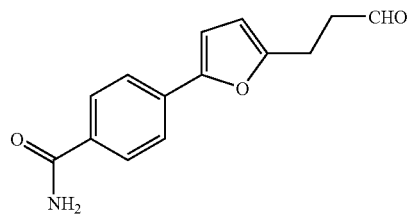
(AL-146)
-continued
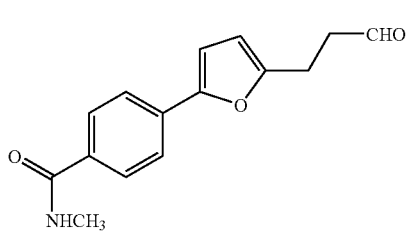
(AL-147)
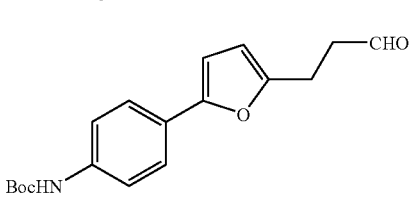
(AL-148)
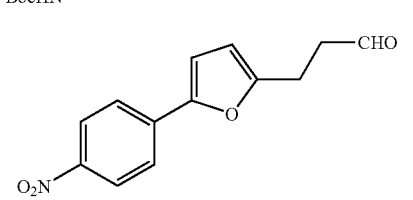
(AL-149)
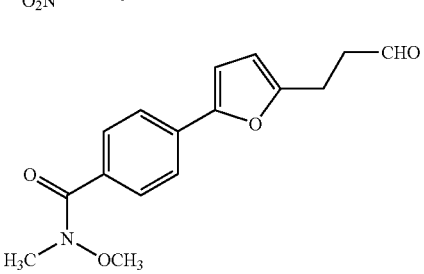
(AL-150)
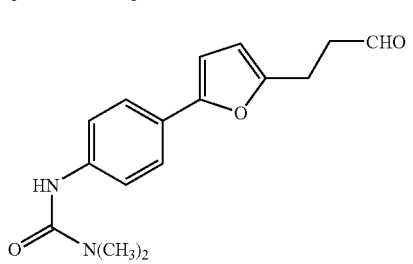
(AL-151)
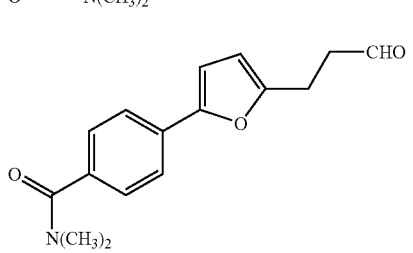
(AL-152)
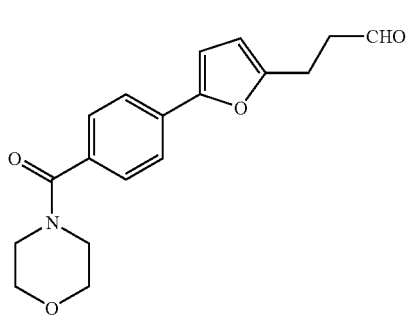
(AL-153)

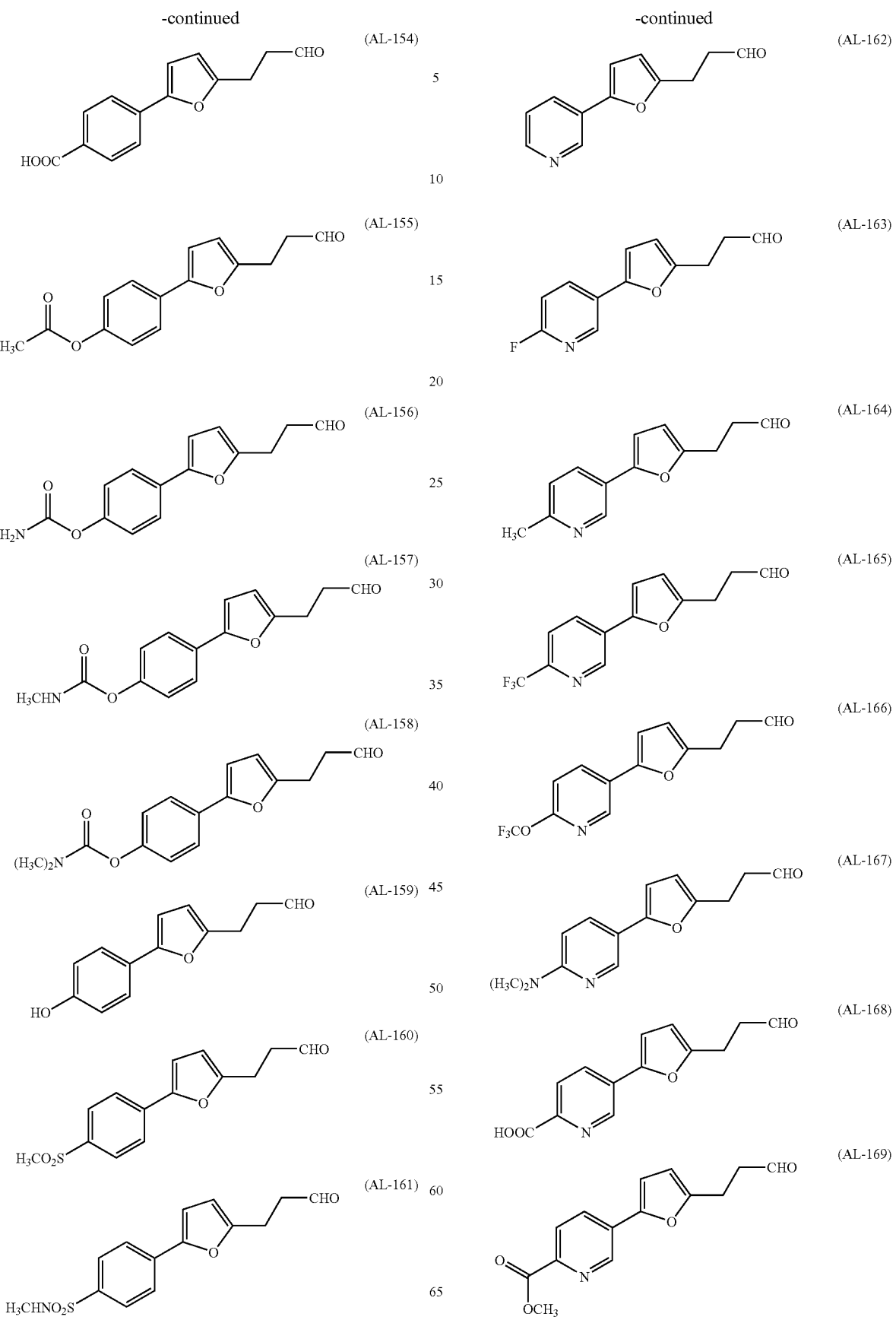

-continued (AL-170) (AL-171) (AL-172) (AL-173) (AL-174) (AL-175) (AL-176) (AL-177) (AL-178) (AL-179) (AL-180) (AL-181) (AL-182) (AL-183) (AL-184) (AL-185) (AL-186) (AL-187) (AL-188) (AL-189)

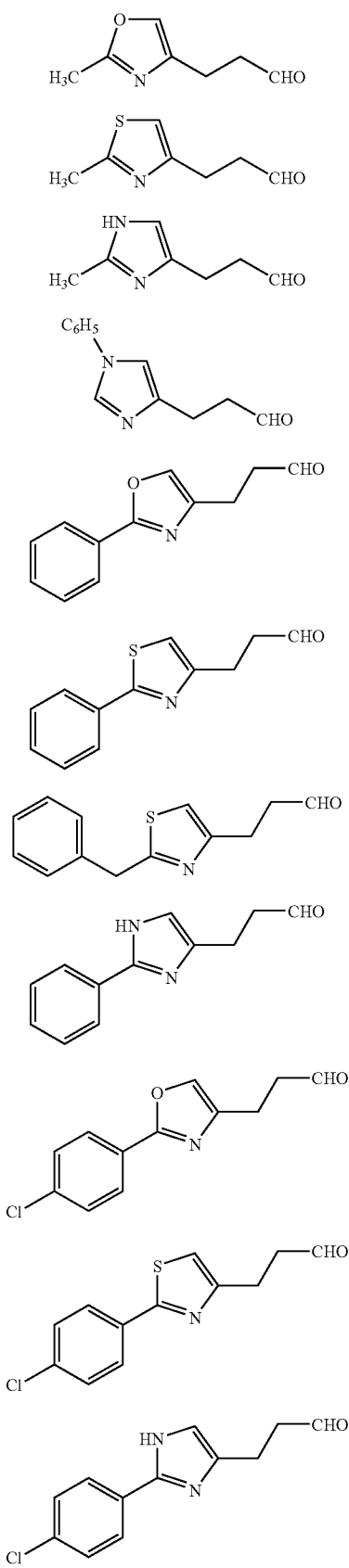
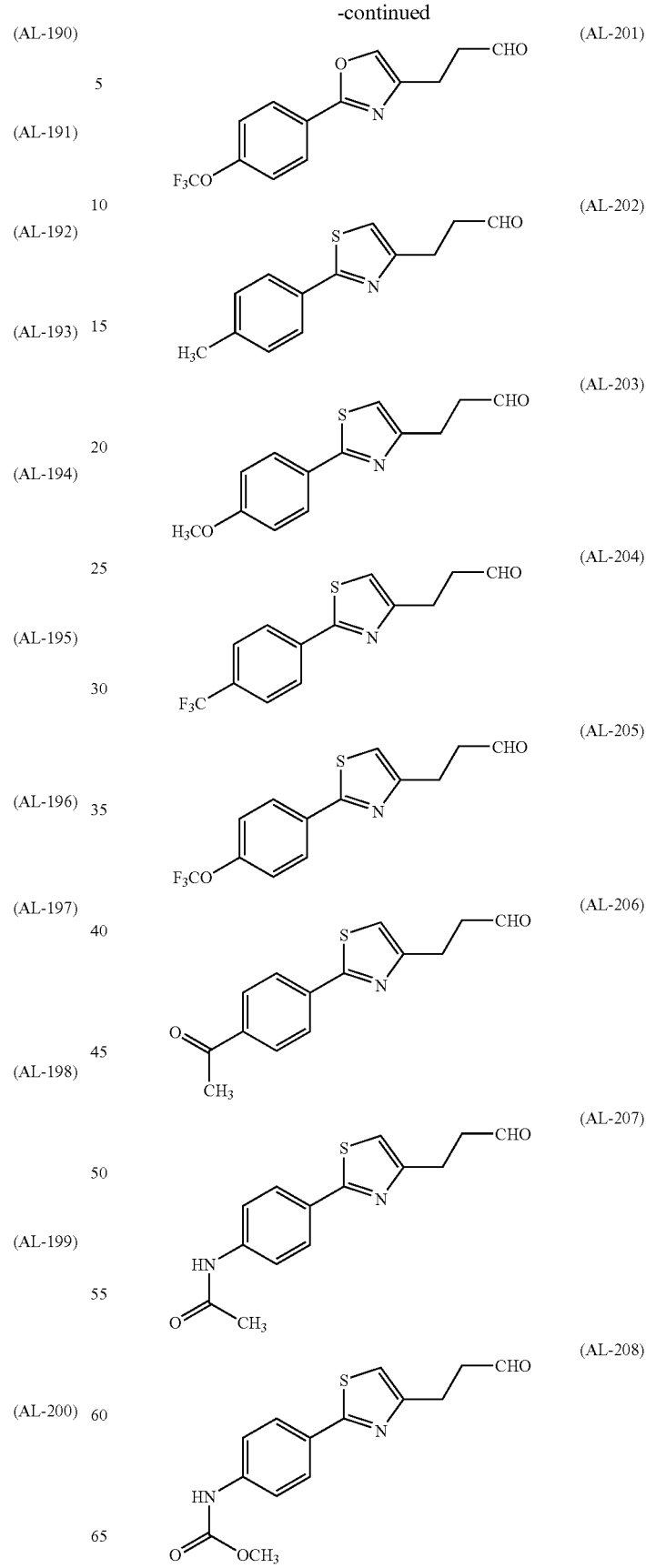

-continued
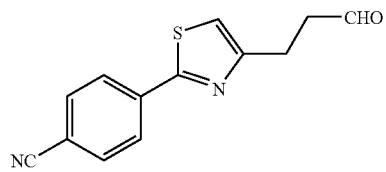 (AL-209)
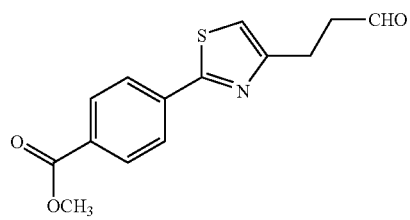 (AL-210)
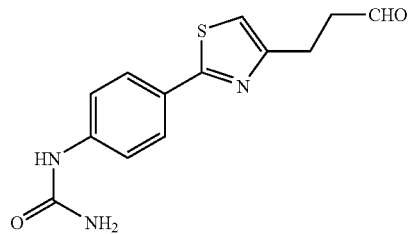 (AL-211)
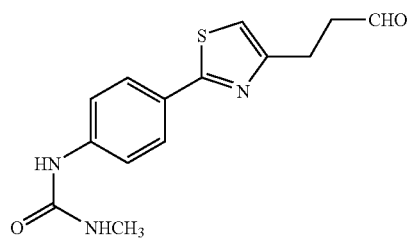 (AL-212)
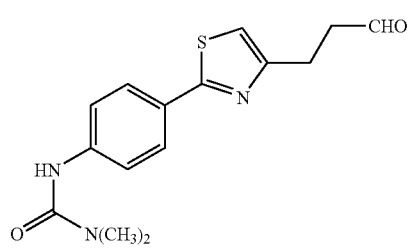 (AL-213)
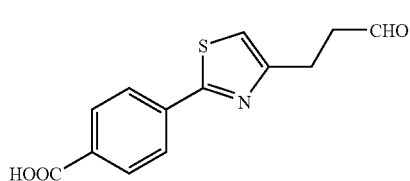 (AL-214)
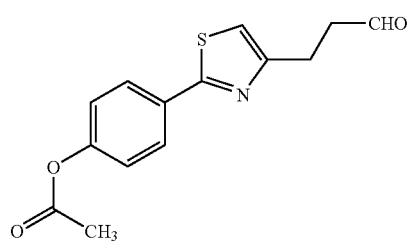 (AL-215)
-continued
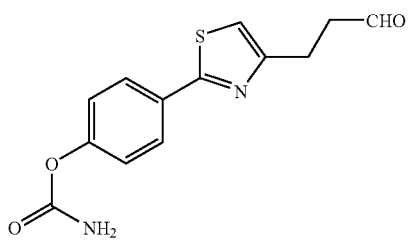 (AL-216)
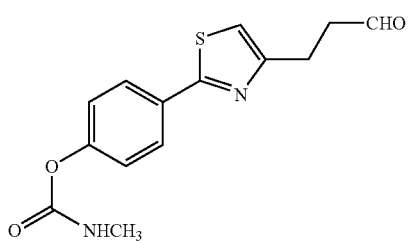 (AL-217)
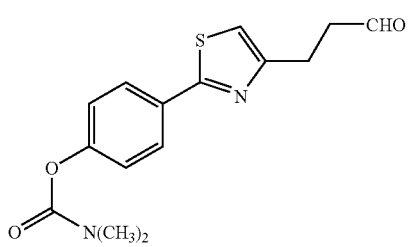 (AL-218)
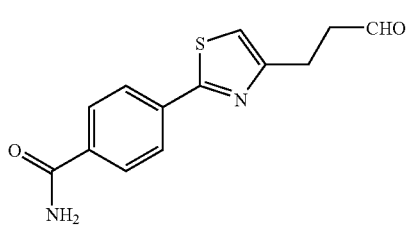 (AL-219)
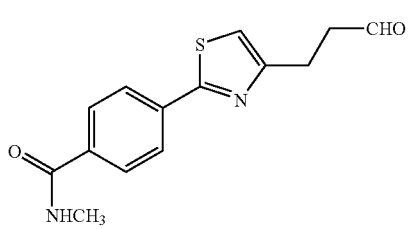 (AL-220)
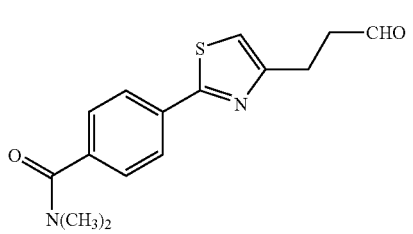 (AL-221)
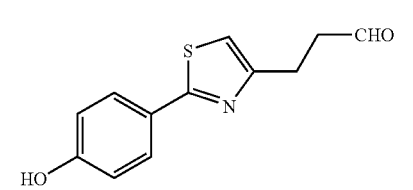 (AL-222)

-continued
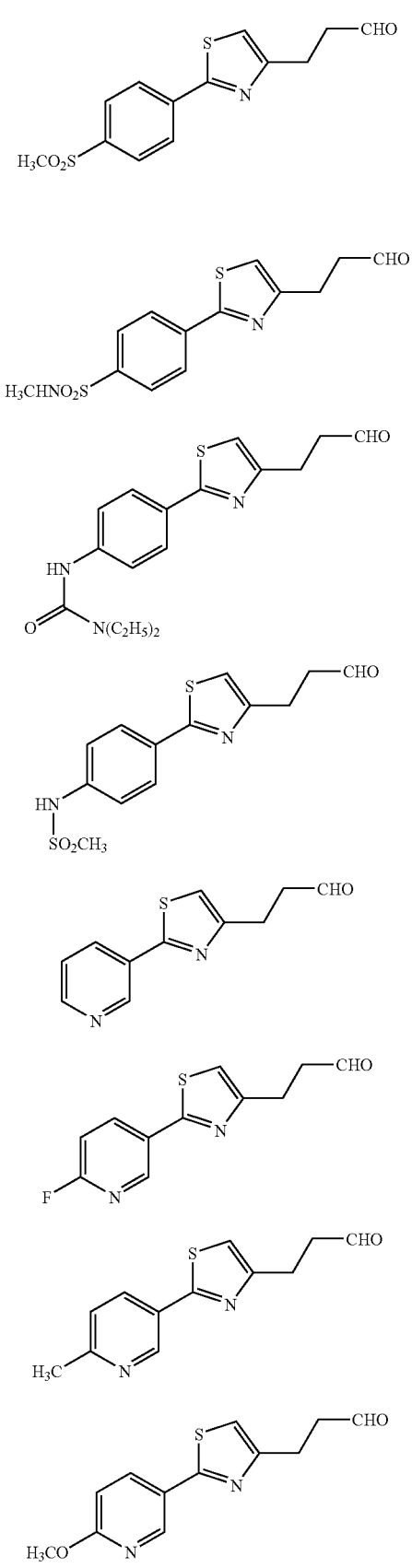
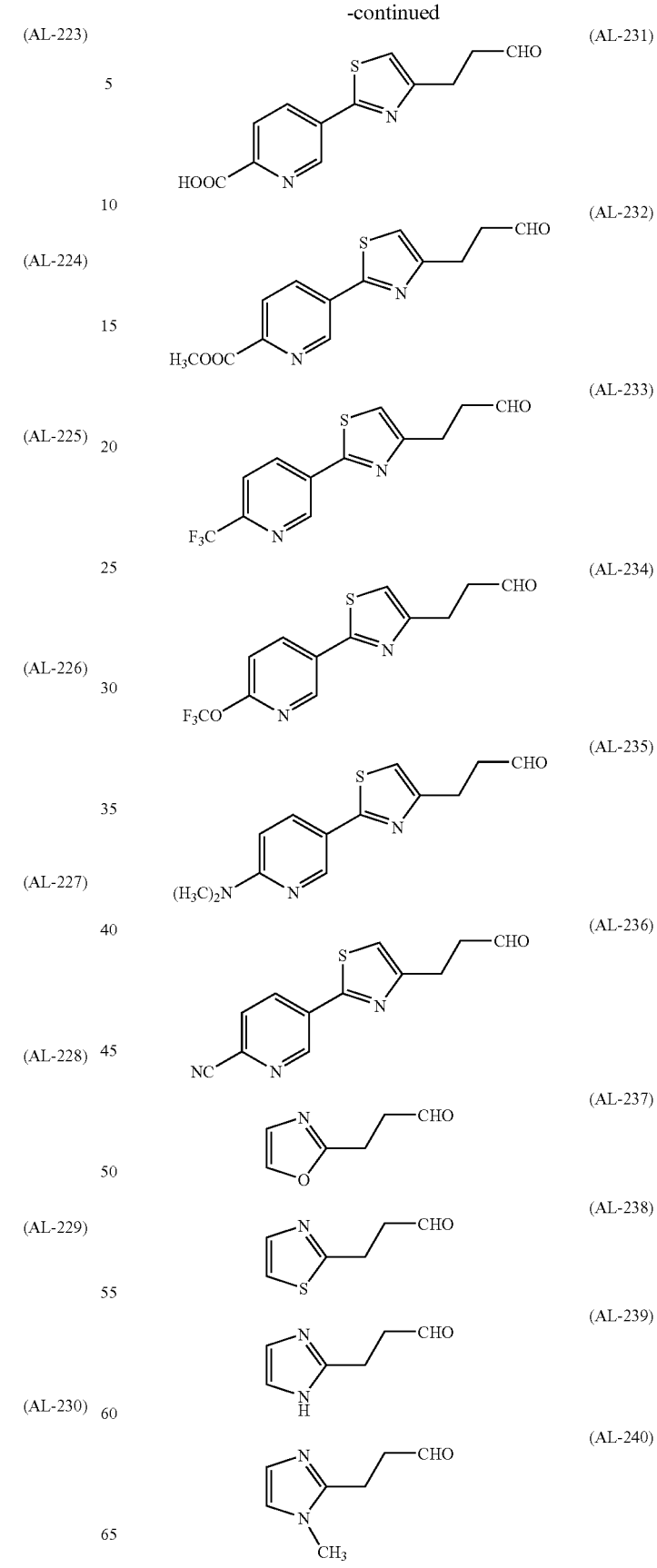

-continued
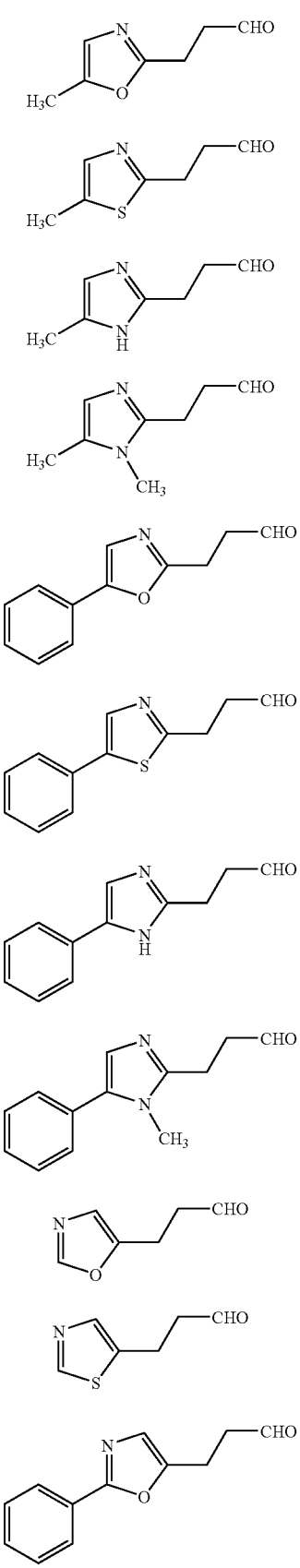
(AL-241)
(AL-242)
(AL-243)
(AL-244)
(AL-245)
(AL-246)
(AL-247)
(AL-248)
(AL-249)
(AL-250)
(AL-251)
-continued
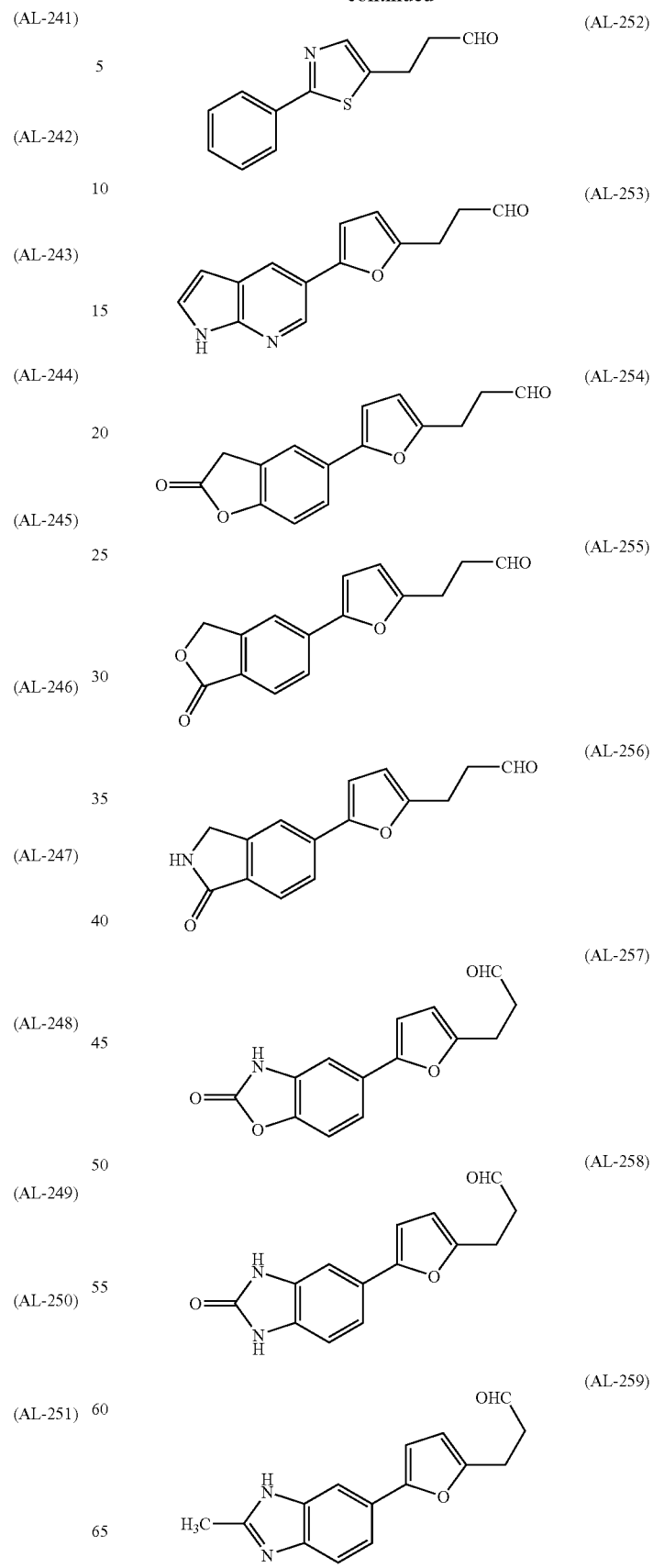
(AL-252)
(AL-253)
(AL-254)
(AL-255)
(AL-256)
(AL-257)
(AL-258)
(AL-259)

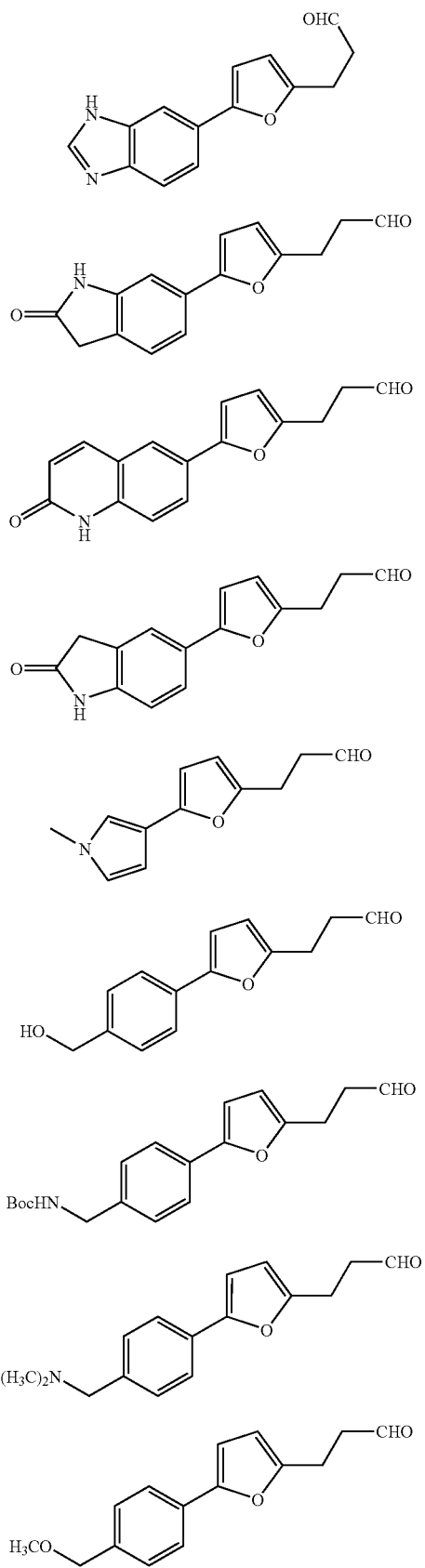
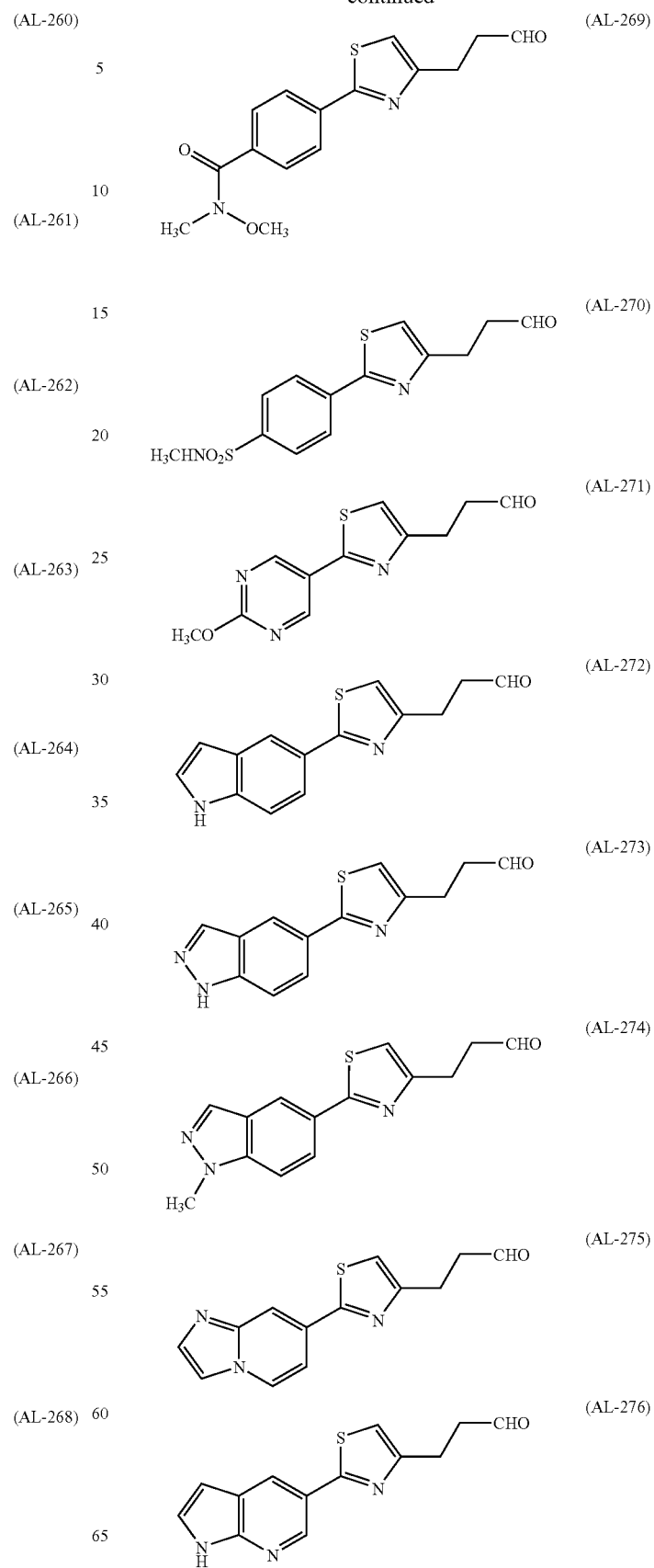

-continued
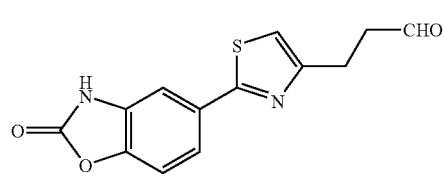 (AL-277)
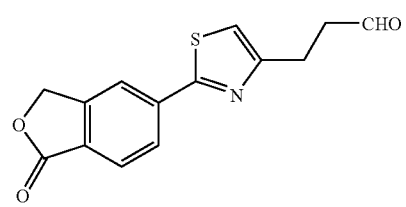 (AL-278)
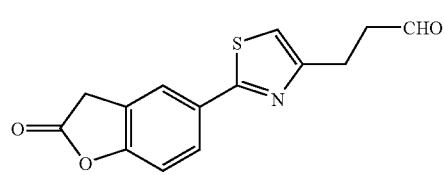 (AL-279)
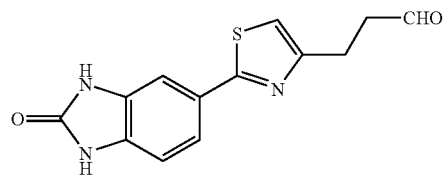 (AL-280)
 (AL-281)
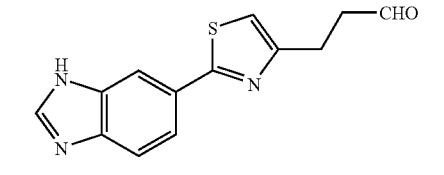 (AL-282)
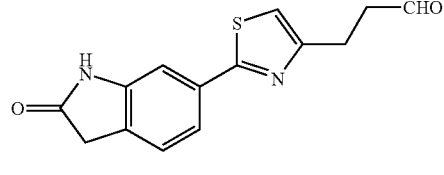 (AL-283)
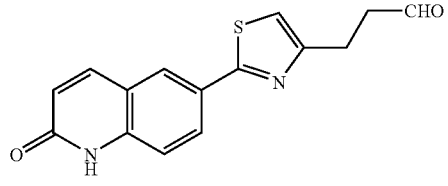 (AL-284)
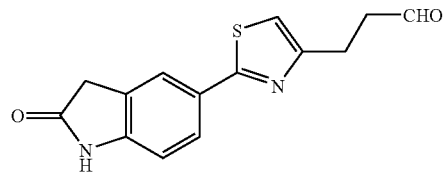 (AL-285)
-continued
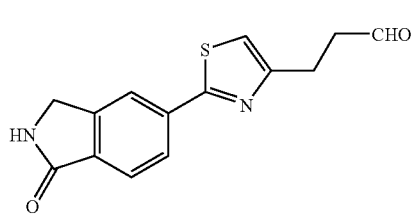 (AL-286)
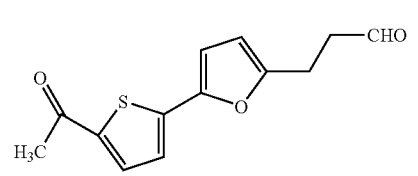 (AL-287)
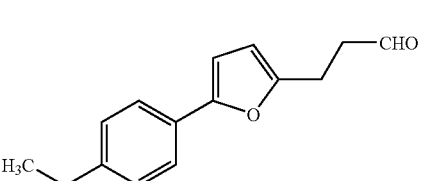 (AL-288)
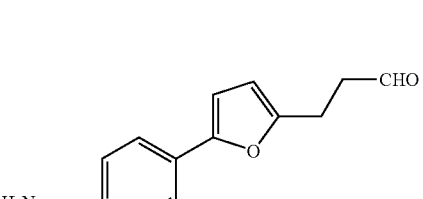 (AL-289)
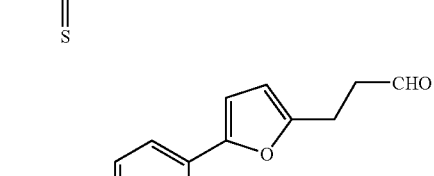 (AL-290)
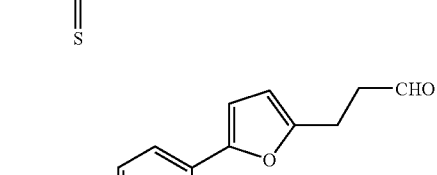 (AL-291)
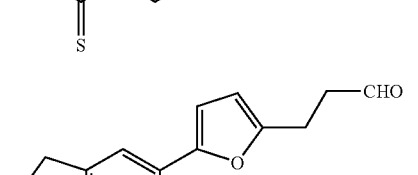 (AL-292)

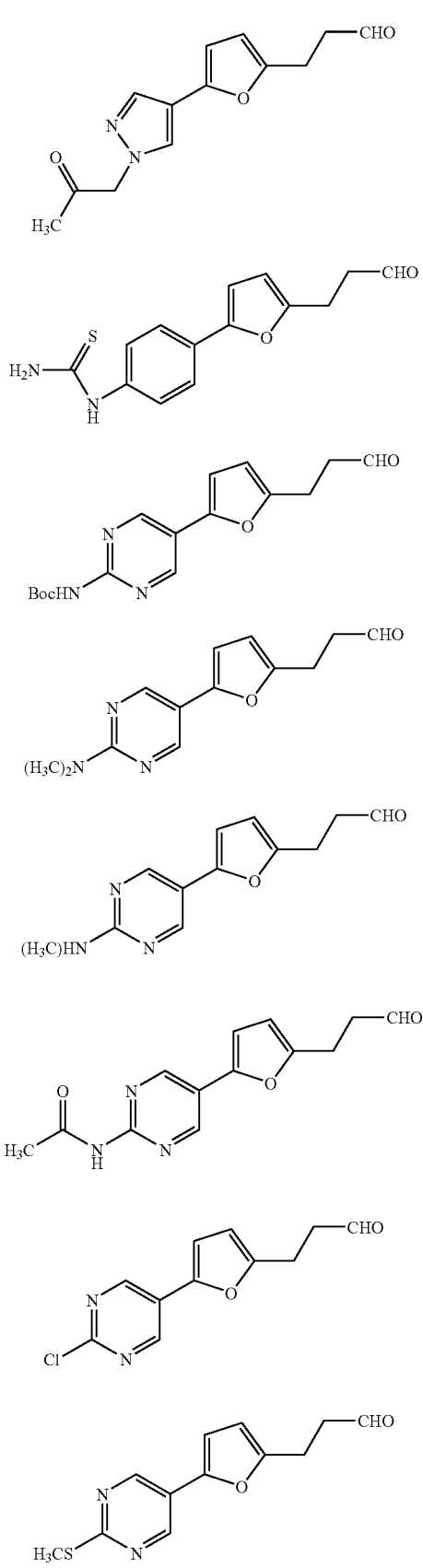
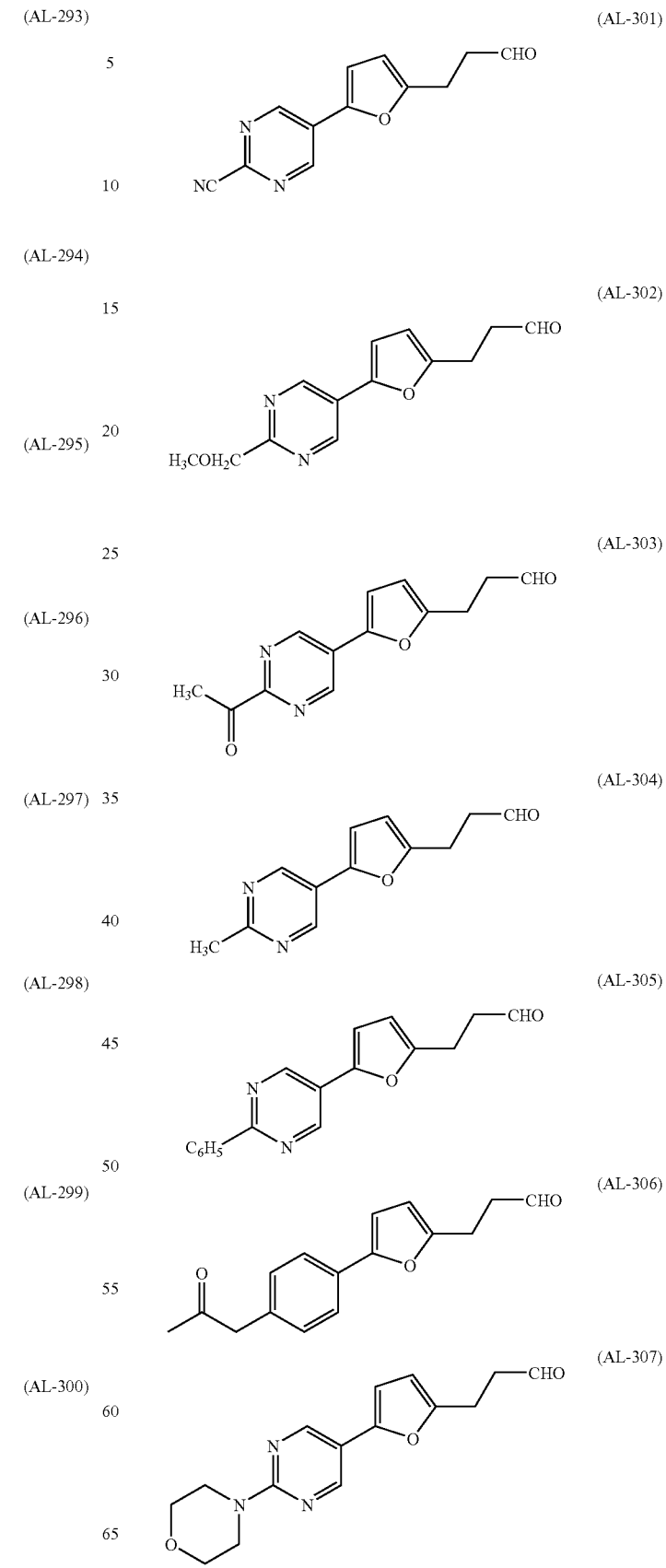

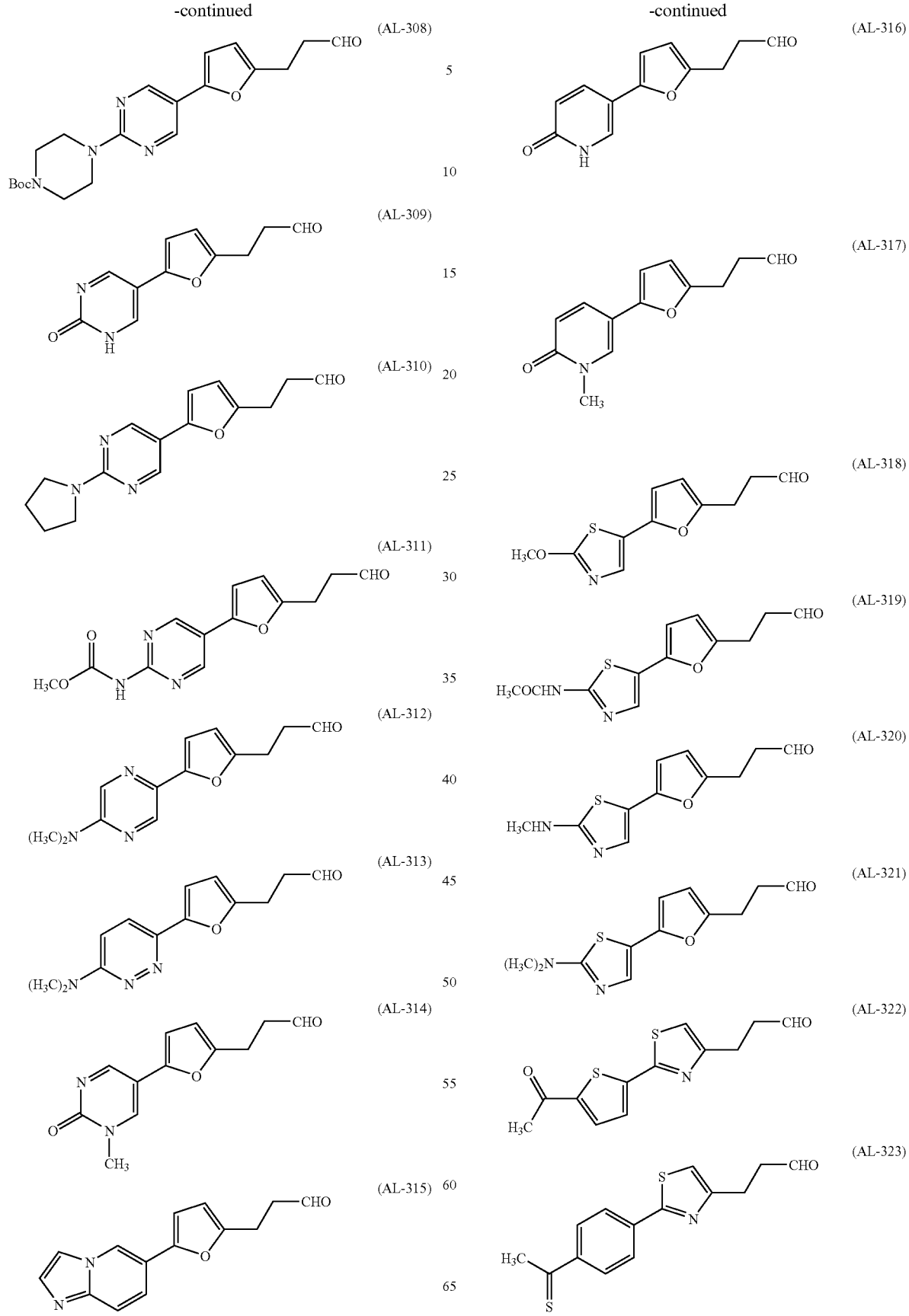

315

-continued (AL-324)

(AL-325)

(AL-326)

(AL-327)

(AL-328)

(AL-329)

(AL-330)

316

-continued (AL-331)

(AL-332)

(AL-333)

(AL-334)

(AL-335)

(AL-336)

(AL-337)

(AL-338)

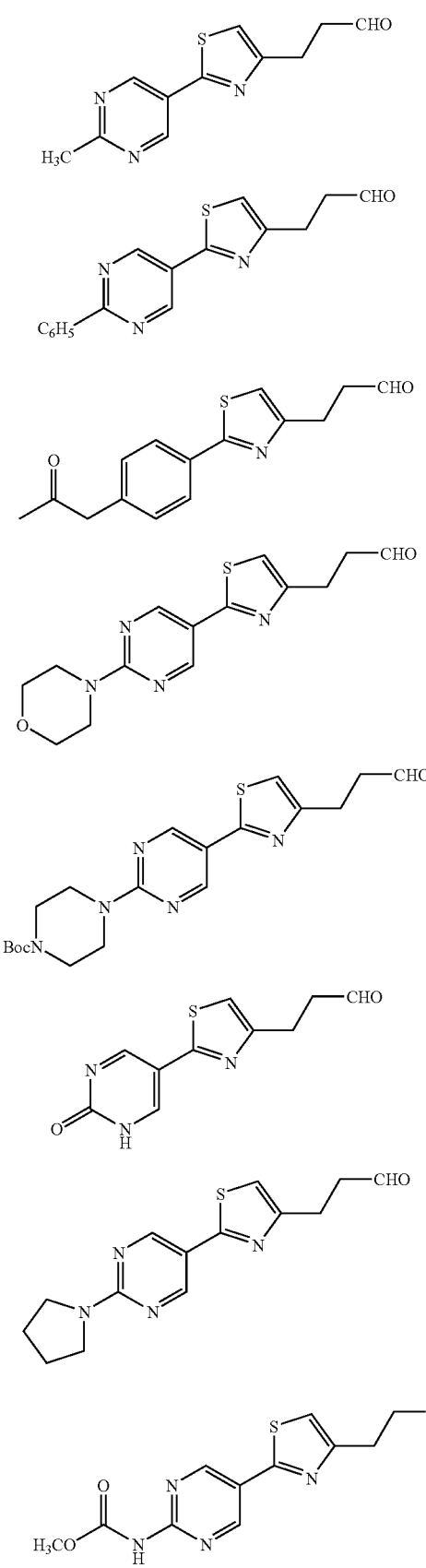
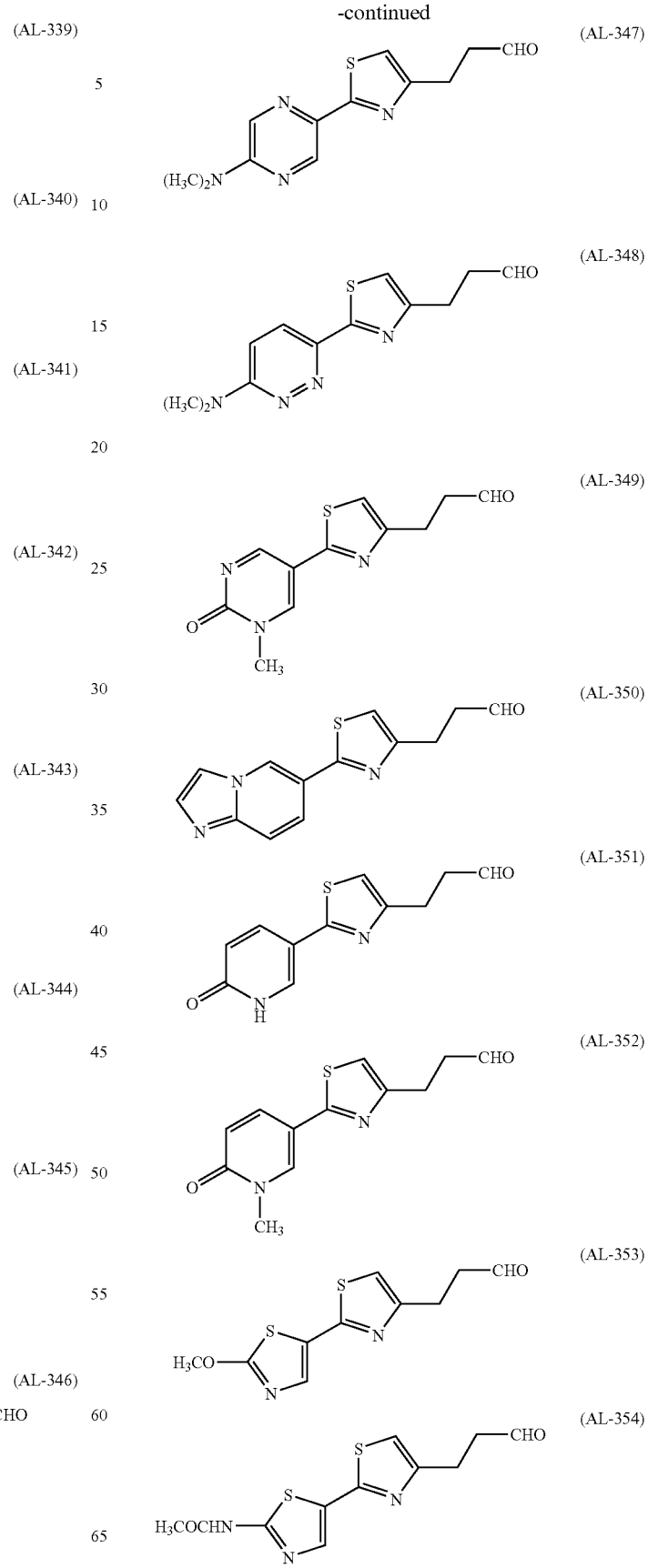

-continued

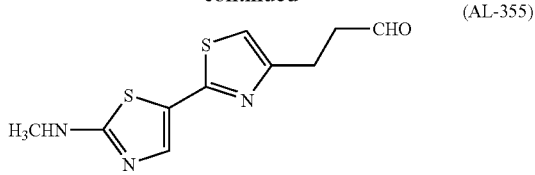

(AL-355)

The compounds of the formula (1) wherein the group represented by B is naphthalene group or a substituted naphthalene group also fall within the scope of the compounds of the present invention. As for the production of these compounds, they can be produced by according to Synthetic method A or Synthetic method B described above as the synthetic methods of the compounds represented by the formula (1). Namely, a compound represented by the formula (5) or (8) wherein the group represented by B' is naphthalene group, or a substituted naphthalene group of which substituent may have a protective group may be used as a starting material.

The compounds represented by the formula (5) wherein the group represented by B' is naphthalene group can be obtained as commercial products.

The compounds represented by the formula (5) wherein the group represented by B' is a substituted naphthalene group of which substituent may have a protective group can be synthesized by acylating a commercially available substituted naphthalene using a Friedel-Craft reaction with a commercially available compound represented by $R^1COCl$ or $(R^1CO)_2O$ in the presence of a Lewis acid such as aluminum chloride or titanium tetrachloride according to methods described in the literature (Brown et at., J. Org. Chem., Vol. 11, p. 163, 1946; Snatzke G. et al., Chem. Ber., Vol. 106, pp. 1341-1362, 1973 and the like). Further, they can also be synthesized according to another method described in the literature (Amin S. et at., J. Org. Chem., Vol. 46, pp. 2394-2398, 1981). The protective group in a substituent may be introduced at appropriate time before or after the acylation depending on the conditions.

The compounds represented by the formula (8) wherein the group represented by B' is naphthalene group can be obtained as commercial products.

The compounds represented by the formula (8) wherein the group represented by B' is a substituted naphthalene group of which substituent may have a protective group can be synthesized from a corresponding compound represented by the formula (5) according to methods described in the literature (B. Sukanta et at., Syn. Lett., Vol. 11, pp. 1781-1783, 1999; Roberts et al., J. Med. Chem., Vol. 15, pp. 1270-1273, 1972; Nagashima et at., Chem. Pharm. Bull., Vol. 15, pp. 251-257, 1984 and the like).

The compounds of the present invention obtained as described above as well as starting compounds and synthetic intermediates for said compounds can be isolated and purified by performing conventional operations such as extraction, distillation, and chromatography, as required. When a salt of a compound of the formula (1) is prepared, the compound of the formula (1) can be dissolved in an alcohol type solvent such as methanol and ethanol and converted into an acid addition salt by addition of an equivalent amount or an amount of several times of equivalents of an acid component. Examples of the acid component used include, for example, hydrochloric acid, hydrobromic acid, sulfuric acid, hydrogensulfate, dihydrogenphosphate, citric acid, maleic acid, tartaric acid, fumaric acid, gluconic acid, methanesulfonic acid, and the like, and it is preferable to use a physiologically acceptable mineral acid or organic acid.

The compounds of the present invention and physiologically acceptable salts thereof have no toxicity as demonstrated in the examples described later, and have a PTH depressing action, and therefore they are useful as active ingredients of medicaments. The PTH depressing agent of the present invention can be expected to exhibit a blood PTH concentration depressing action, or in addition, a PTH concentration depressing action in various organs and the like. The PTH depressing action of the compounds of the present invention or physiologically acceptable salts thereof can be evaluated by using the blood PTH concentration depressing action or the like observed, for example, when they are administered to laboratory animals such as rats, as a marker. Further, the PTH concentration depressing action can also be evaluated on the basis of the blood PTH concentration depressing action or bone metabolism improving action as a marker by using disease model animals such as rats with experimentally induced chronic renal failure.

The medicament of the present invention comprising a compound represented by the aforementioned formula (1) or a physiologically acceptable salt thereof as an active ingredient can depress PTH in vertebrates including human, preferably mammals, and is useful as a medicament for prophylactic and/or therapeutic treatment of, for example, hyperPTHemia. Furthermore, the medicament of the present invention is useful for prophylactic and/or therapeutic treatment of various bone diseases (e.g., osteoporosis and the like) associated with increase in blood PTH, or can depress blood PTH in patients of hypercalcemia to depress blood calcium concentration, and thereby prevent and/or cure hypercalcemia. Although the blood PTH concentration may not be so high as that in hyperPTHemia in these diseases, the medicament of the present invention can also be suitably used for these diseases.

The hyperPTHemia is defined as a disease exhibiting a high blood PTH concentration beyond the range of normal value. As for a human, a disease exhibiting a high blood PTH concentration beyond the range of normal value can be diagnosed by measuring the intact blood PTH concentration by applying an immunoradiometric assay (IRMA) method (Nihon Medi-Physics Co., Ltd, Allegro intact PTH kit) using a radiolabeled anti-human N-terminus (1-34) antibody and anti-human C-terminus (39-84) antibody, and comparing the measured value with the normal value of human measured by the same method (13 to 53 pg/ml) (Takuwa, A "V. Endocrinological Inspection, B. Thyroid and Parathyroid-Related Inspection, Parathyroid Hormone", Nippon Rinsho (The Japanese Journal of Clinical Medicine), Vol. 53 (Special number), pp. 393-396, 1995). A normal value of the blood PTH concentration varies depending on a measurement system, an animal species and the like. Therefore, a normal value given by each of measurement systems, literature, or medical research facilities may be referred to.

Examples of the causative disease of hyperPTHemia include hyperparathyroidism and the like, and the hyperparathyroidism is basically classified into primary hyperparathyroidism and secondary hyperparathyroidism depending on critical pathological mechanism.

The primary hyperparathyroidism is a generic name of diseases in which abnormalities are observed in the PTH secretion regulation mechanism in the parathyroid, and PTH is secreted at an inappropriately high concentration compared with an extracellular calcium concentration. Specific examples thereof include parathyroid adenoma, parathyroid hyperplasia, parathyroid carcinoma, multiple endocrine neoplasia type 1, multiple endocrine neoplasia type 2A, familial isolated hyperparathyroidism (FIHP) hyperparathyroidism-lower jaw tumor syndrome (HPT-JT), familial hypocalciuric hypercalcaemia (FHH), and the like (Ohara, T., "4. Abnormality of Calcium Metabolism, (1) Primary Hyperparathyroidism", Hormone to Rinsho (Clinical Endocrinology), 49, Suppl., pp. 74-76, 2001).

The secondary hyperparathyroidism is a generic term of diseases in which PTH secretion is promoted as a reaction to hypocalcemia, hyperphosphoremia, activated vitamin D resistance and the like induced by various causes other than those originated in the parathyroid. Specific examples thereof include hyperparathyroidism resulting from chronic renal failure, hyperparathyroidism resulting from osteomalacia (or rachitis), hyperparathyroidism resulting from renal tubule dysfunction, hyperparathyroidism resulting from malabsorption syndromes originating in stomach extraction, intestinal diseases, and the like, hyperparathyroidism resulting from vitamin D deficiency or vitamin D activation disorder, hyperparathyroidism resulting from osteoporosis, hyperparathyroidism resulting from pseudohypoparathyroidism, hyperparathyroidism resulting from pregnancy and breast-feeding, hyperparathyroidism resulting from Cushing syndrome, hyperparathyroidism resulting from hypercalcitonism, hyperparathyroidism resulting from administration of drug such as anticonvulsant, hyperparathyroidism resulting from shortage of calcium ingestion or excessive loss of calcium in urine, hyperparathyroidism resulting from excessive ingestion of phosphorus, and the like (Tabata, T. and Nishizawa, Y., "Secondary Hyperparathyroidism", Igaku no Ayumi, Separate volume of October (Endocrinological and Metabolic Diseases), pp. 374-376, 1997; Tomita, A., "Secondary Hyperparathyroidism", Saisin Naikagaku Taikei (Newest Internal Medicine Study System) 14, Endocrinological Diseases 3 (edited by Inoue, H. et al.), pp. 72-79, Nakayama Shoten, Tokyo, 1993; Nakanishi, S. and Fukagawa, M., "Pathological Mechanism of Renal Hyperparathyroidism", CLINICAL CALCIUM, pp. 1625-1630, 2002).

Furthermore, hyperparathyroidism that originates in chronic renal failure is highly frequently complicated with various bone metabolic disorders. Such bone metabolic disorders generically called renal osteodystrophia (or renal osteopathy or dialysis osteopathy), and examples thereof include fibrous ostitis, osteomalacia (or rachitis), mixed ostitis, and the like (Tabata, T. and Nishizawa, Y., "Renal Osteodystrophia", Newest Osteoporosis (edited by Orishige, H.), pp. 87-91, Life Science Publishing, Tokyo, 1999; Tsukamoto, Y., "Renal Osteodystrophia", Hormone to Rinsho (Clinical Endocrinology), 49, Suppl., pp. 77-80, 2001). The fibrous ostitis is characterized by increase in intramedullary fibrous tissues, and osteomalacia (or rachitis) is characterized by excessive deposition of osteoid due to calcification disorder. Further, the mixed ostitis is characterized by intermingled pathological change of fibrous ostitis and osteomalacia in the same tissue. These fibrous ostitis, osteomalacia (or rachitis), and mixed ostitis are also included in the pathological conditions of hyperparathyroidism resulting from chronic renal failure, and they can be therapeutically or prophylactically treated by using the medicament of the present invention. Furthermore, chronic renal failure may be complicated with osteopenia or osteoporosis (osteoporosis is a generic term of systemic bone diseases characterized by decrease in bone mass, collapse of the microstructure of bone tissues, resulting increase in bone brittleness, bone fracture susceptibility, and the like), which is diagnosed by using the bone mineral amount as a marker (Taal et al. "Risk factors for reduced bone density in haemodialysis patients, "Nephrol. Dial. Transplant., 14. pp. 1922-1928, 1999). These conditions are also included in the pathological conditions of hyperparathyroidism, and can be therapeutically or prophylactically treated by using the medicament of the present invention.

Further, chronic renal failure may present various clinical symptoms besides the bone metabolic disorders. For example, influences on the cranial nerve system, cardiovascular system, skeletal muscles, hemopoietic and immune systems, endocrine and metabolic systems, and respiratory system are observed as peripheral influences, and systemic influences are also often observed. Specifically, for example, there are electroencephalographic dysrhythmia, behavior disorder, peripheral nerve disease and the like for the cranial nerve system, ventricular hypofunction, cardiac myopathy and the like for the cardiovascular system, hypodynamia, adynamic attack, tendon rupture and the like for skeletal muscles, anemia, leukocytic and lymphatic hypofunction and the like for the hemopoietic and immune systems, glucose tolerance abnormality, lipid metabolic disorders such as hyperlipidemia, hypogonadism and the like for the endocrine and metabolic system, diffusion disturbance, increased right ventricular pressure and the like for the respiratory system, ectopic calcification in arterial walls, eyes, visceral organs and circumferences of joints, itch, abnormal blood pressure and the like as systemic symptoms (Kurihara R., "Whether Optimum PTH Exists for Dialysis Patient?", CLINICAL CALCIUM, 9, pp. 734-740, 1999; Tahara H. et al., "4. Pathological Conditions of Secondary Hyperparathyroidism, 1) Clinical Features", Iyaku Journal, 37, pp. 148-152, 2001), and these conditions are also included in the pathological conditions of hyperparathyroidism, and can be therapeutically or prophylactically treated by using the medicament of the present invention.

Further, controlling progression of renal disorder on the basis of the effect of improving hyperPTHemia has been reported (Shigematsu et al. "Parathyroid removal prevents the progression of chronic renal failure induced by high protein diet", Kidney Int., 44, pp. 173-181, 1993). The medicament of the present invention has an action of improving hyperPTHemia, and thus the medicament of the present invention is effective for pre-dialysis chronic renal failure (not yet in a stage of dialysis treatment) presenting hyperparathyroidism for improving renal disorder to prolong a period before dialysis theatment becomes necessary. Therefore, the use of the medicament of the present invention for the disease as a therapeutic or prophylactic agent is also included in the applications of the present invention.

Besides these diseases, any diseases exhibiting a high blood PTH concentration beyond a range of normal value are included in the category of hyperPTHemia, and can be therapeutically or prophylactically treated by using the medicament of the present invention.

The medicament of the present invention can be used for the prophylactic and/or therapeutic treatment of various bone diseases associated with relative increase in blood PTH, even if a blood PTH concentration before the administration of the medicament is within a range of normal value. Examples of such bone diseases include osteoporosis and the like, and examples of osteoporosis according to such classification include postmenopausal osteoporosis, senile osteoporosis, osteoporosis induced by a drug such as adrenal cortex hormone, and the like (Morii, H., "Definition and Concept of Osteoporosis", Newest Osteoporosis (edited by Orishige H.), pp. 39-42, Life Science Publishing, Tokyo, 1999). It is pointed out that, in these types of osteoporosis, when a degree of bone mass reduction is higher or pathological condition is severer, a blood PTH concentration is relatively increased (most of the increase is observed within the range of the normal value), and as a result, bone resorption is being promoted to advance the bone mass reduction (Tomita, A. and Negoro, Y., "Biochemical Diagnosis Method of Osteoporosis", Osteoporosis/Diagnosis and Treatment (edited by Fujita., T), pp. 285-293, Life Science Publishing, Tokyo, 1992). The medicament of the present invention achieves suppression of the increase of bone resorption by depressing PTH, and as a result, the medicament is useful for prophylactic and/or therapeutic treatment of osteoporosis.

Further, the medicament of the present invention exhibits an action of depressing the blood calcium concentration on the bases of the blood PTH concentration depressing action, and therefore the medicament can be used for prophylactic and/or therapeutic treatment of hypercalcemia and the like. Examples of hypercalcemia include hypercalcemia originating in a malignant tumor. Examples of hypercalcemia originating in a malignant tumor include humoral hypercalcemia of malignancy (HHM) in which bone resorption promotion factors, produced by tumor cells of epidermoid carcinoma, urologic cancer or the like, causes systemic bone resorption to induce hypercalcemia, and local osteolytic hypercalcemia (LOH) in which bone resorption promotion factor secreted from blood tumors such as multiple myeloma cause local osteolysis to induce hypercalcemia (Okano, K., "Concept and Pathology of Hypercalcemia", Hormone to Rinsho (Clinical Endocrinology), 41, 1-6, 1993). Besides these diseases, any diseases for which prophylactic and/or therapeutic effect may be achieved by depressing the blood PTH concentration may be applicable by the medicament of the present invention.

The medicament of the present invention is preferably used for prophylactic and/or therapeutic treatment of hyper-PTHemia, osteoporosis, and hypercalcemia, more preferably used for prophylactic and/or therapeutic treatment of hyper-PTHemia, and still more preferably used for prophylactic and/or therapeutic treatment of hyperparathyroidism.

The medicament of the present invention can be prepared as a medicament comprising a compound represented by the formula (1) or a physiologically acceptable salt thereof as an active ingredient. For example, a compound or a salt thereof, which is administered as a prodrug and produces the compound represented by the formula (1) or a physiologically acceptable salt thereof after in vivo metabolism, also falls within the scope of the medicament of the present invention. A compound represented by the formula (1) or a physiologically acceptable salt thereof, per se, may be used as the medicament of the present invention. It is preferable to add one or more kinds of pharmaceutically acceptable carriers to the compound represented by the formula (1) or a physiologically acceptable salt thereof to prepare a pharmaceutical composition and administer the composition. Types of pharmacologically acceptable carriers are not particularly limited, and examples include, for example, excipients, binders such as carboxymethylcellulose, disintegrating agents, lubricants, additives, and the like. A hydrate or solvate of a compound represented by the formula (1) or a physiologically acceptable salt thereof may also be used as an active ingredient of the medicament of the present invention. When the medicament of the present invention is administered to a human, the medicament can be orally administered in a form of, for example, a tablet, a powder, a granule, a capsule, a sugar-coated pill, a solution, a syrup or the like, or the medicament can also be parenterally administered in a form of an injection, a drip infusion, a suppository, a transdermal preparation or the like.

An administration period of the medicament of the present invention is not particularly limited. In principle, the medicament is administered during a period where it is judged that clinical symptoms of a disease are expressed, and it is common to continue the administration for several weeks to one year. However, it is also possible to extend the administration period depending on pathological conditions, or continue the administration even after recovery of the clinical symptoms. The medicament may also be prophylactically administered by a decision of a medical doctor even if a clinical symptom is not expressed. A dose of the medicament of the present invention is not particularly limited. The medicament may generally be administered in an amount of 0.01 to 2000 mg per day as the active ingredient once or several times as divided portions. As for administration frequency, the medicament may be administered once a month to every day, and the medicament may preferably be administered once to three times per week or five times per week, or every day. The daily dose, administration period, and administration frequency may be suitably increased or decreased depending on various factors such as the age, weight, degree of physical healthiness of a patient, a type and severity of a disease to be treated.

For example, when hyperparathyroidism is prevented and/or treated with the medicament of the present invention, the medicament of the present invention can be used together with one or more kinds of medicaments selected from the group consisting of vitamin D agents including vitamin D derivatives and/or phosphorus depressing agents simultaneously or at different time. Further, the medicament of the present invention can also be prepared as a so-called combined medicament together with the medicament exemplified above and then administered. Examples of the vitamin D agents including vitamin D derivatives include, for example, calcitriol, alfacalcidol, farecalcitriol, paricalcitol, doxercalciferol, maxacalcitol, secalciferol, and the like, and examples of the phosphorus depressing agents include, for example, calcium carbonate, calcium lactate, calcium gluconate, calcium acetate, calcium chloride, calcium citrate, magnesium carbonate, calcium hydrogenphosphate, calcium L-aspartate, polynuclear ferric hydroxide, sevelamer hydrochloride, lanthanum carbonate, resin ion-exchange resins, colestimide, and the like. Further, agents having an inhibitory action on the phosphorus absorption mechanism from an alimentary canal such as niceritrol are also included in the phosphorus depressing agents. The vitamin D agents including vitamin D derivatives and/or phosphorus depressing agents, which are used together with the medicament of the present invention or used for preparing so-called combined drug to treat or prevent hyperparathyroidism, are not limited to these examples.

Further, when osteoporosis is prevented and/or treated with the medicament of the present invention, for example, the medicament of the present invention can be used together with one or more kinds of medicaments selected from the group consisting of bone activating agents, osteogenesis promoting agents, bone resorption suppressing agents, bone metabolism improving agents, sexual hormone preparations, and calcium preparations, simultaneously or at different time. Further, the medicament of the present invention can also be prepared as a so-called combined drug together with the medicament exemplified above and then administered. Examples of the bone activating agents include, for example, calcitriol, alfacalcidol, OCT, ED-71, and the like, examples of the osteogenesis promoting agents include, for example, menatetrenone, teriparatide, somatropin, insulin-like growth factor, EP4 agonist, EP2 agonist, growth hormone secretagogues, and the like, examples of the bone resorption suppressing agents include, for example, elcatonin, calcitonin salmon, etidronate, pamidronate, clodronate, alendronate, incadronate, risedronate, minodronate, ibandronate, cathepsin K inhibitors, osteoprotegerin, anti-RANKL antibodies, and the like, examples of the bone metabolism improving agents include, for example, fluoride, ipriflavone, and the like, examples of the sexual hormone preparations, include, for example, estriol, estradiol, conjugated estrogen, progesterone, medroxyprogesterone, testosterone, metyltestosterone, mestanolone, stanozolol, metenolone, nandrolone, selective estrogen receptor modulators (SERM: raloxifen, lasofoxifene, bazedoxifene, ospemifene, arzoxifene, CHF4227, PSK-3471, and the like), selective androgen receptor modulators (SARM), and the like, and examples of the calcium preparations include calcium carbonate, calcium lactate, calcium gluconate, calcium acetate, calcium chloride, calcium citrate, calcium hydrogenphosphate, calcium L-aspartate, and the like. The bone activating agents, osteogenesis promoting agents, bone resorption suppressing agents, bone metabolism improvement agents, sexual hormone preparations, and calcium preparations used together with the medicament of the present invention, or used for preparing the so-called combined drug together with the medicament of the present invention to treat or prevent osteoporosis are not limited to these examples.

Further, the medicament of the present invention can also be administered together with one or more kinds of medicaments suitably selected from prophylactic agents and curative agents for various abnormalities and diseases complicating with hyperPTHemia including hyperparathyroidism, osteoporosis, and hypercalcemia [e.g., antibacterial agents, antiviral agents, antifungal agents, antiparasitic (antihelminth, antiprotozoan) agents, vaccination agents, antiseptics, anticancer agents, immunosuppressive agents, adrenal-cortex steroids, nonsteroidal anti-inflammatory agents, antirheumatic agents, antarthritics, anti-inflammatory enzymes, antihistaminic agents, antiallergic agents, antidiabetic agents, female hormone preparations, male hormone preparations, other hormone preparations, thyroid disease curative agents, bone and calcium metabolic agents, vitamin preparations, fluid-therapy preparations (electrolyte fluid, dialysis and peritoneal dialysis solutions, and the like), blood preparations, hematopoietic agents, hypoleukocytemia curative agents, hemostatic agents, antithrombotic agents, antihyperlipidemic agents, cardiac stimulants (heart failure curative agents), antiarrhythmic agents, antianginal agents, vasodilators, antihypertensive agents, vasopressors, diuretic agents, bronchodilators, bronchial asthma curative agents, respiratory stimulants, antitussive agents, expectorants, stomachic digestants and gastrointestinal promotility agents, digestive ulcer curative agents (antacids, antispasmodic agents, antiulcer agents), intestinal disease curative agents, purgatives (cathartics), biliary disease curative agents, liver disease curative agents, pancreatic disease curative agents, hypnotic and sedative agents, analgetic and antipyretic agents and comprehensive cold remedies, antiepileptic agents, psychotropic agents (antipsychotics, antidepressants, antimanics, psychostimulants, antialcoholic agents, and the like), antianxiety agents (mild tranquilizers), cerebral circulation and metabolism improvers, autonomic agents, antiemetic agents and antidizziness agents, Parkinson's disease curative agents, muscle relaxants, local analgesics, general anesthetics, ophthalmologic agents (anticataract agents, and the like), otolaryngologic agents, dermatologic agents, agents for urinary and generative organs (calculus excretion promoting agents, and the like), antihemorrhoidal agents, agents for uterus, agents for dentistry and oral cavity, detoxification agents, anorectic agents, weight gaining agents, metabolic antagonists, carnitine deficiency improvers, phenylalaninemia curative agents, urea cycle abnormality curative agents, non-smoking auxiliary agents, patent ductus arteriosus curative agents, cardiac muscle protecting agents, anti-ALS agents, immune enhancement agents, Chinese medicines, contrast media, and the like]. Further, the medicament of the present invention can also be prepared as a so-called combined drug with one or more kinds of medicaments suitably selected from the medicaments exemplified above and then administered.

Examples of the antibacterial agents include, for example, penicillin agents such as ampicillin, cephem agents such as cefazolin and cephalexin, macrolide agents such as erythromycin, tetracycline agents such as minocycline, aminoglycoside agents such as gentamycin, quinolone agents such as ciprofloxacin, monobactam agents such as azthreonam, carbapenem agents such as meropenem, glycopeptide agents such as vancomycin, antituberculosis agents such as rifampicin, and ethambutol, and the like, examples of the antiviral agents include, for example, aciclovir, nevirapine, ritonavir, and the like, examples of the antifungal agents include, for example, amphotericin B, itraconazole, and the like, examples of the antiparasitic (antihelminth, antiprotozoan) agents include, for example, pyrantel pamoate, praziquantel, quinine, metronidazole, and the like, examples of the vaccination agents include, for example, adsorbed tetanus toxoid, influenza vaccine, and the like, examples of the anticancer agents include, for example, antimetabolites such as fluorouracil, anticancer antibiotics such as bleomycin and mitomycin-C, alkylating agents such as busulfan, alkaloids such as vincristine and paclitaxel, platinum preparations such as cisplatin, hormone therapy agents such as tamoxifen, immunostimulants such as interferon-α, interferon-β, interleukin-2, and OK-432, other substances such as octreotide, pentostatin, and the like, examples of the immunosuppressive agents include, for example, azathioprine, mizoribine, cyclosporin, cyclophosphamide, and the like, examples of the adrenal-cortex steroids include, for example, prednisolone, methylprednisolone, and the like, examples of the nonsteroidal anti-inflammatory agents include, for example, salicylic acid agents such as sodium salicylate, fenam agents such as mefenamic acid, arylacetic acid agents such as indometacin, propionate agents such as ibuprofen, oxicam agents such as piroxicam, basic nonsteroidal agents such as tiaramide, cartilage protecting agents such as hyaluronate sodium, and the like, examples of the antirheumatic agents include, for example, auranofin, lobenzarit, methotrexate, and the like, examples of the antarthritics include, for example, colchicine, allopurinol, benzbromarone, and the like, examples of the antiinflammatory enzymes include, for example, bromelain, serrapeptase, lysozyme, and the like, examples of the antihistaminic agents include, for example, ethanolamine agents such as diphenhydramine, propylamine agents such as triprolidine, phenothiazine agents such as promethazine, piperazine agents such as and hydroxyzine, piperidine agents such as cyproheptadine, antirheumatic agents of the second or subsequent generation such as terfenadine, and loratadine, examples of the antiallergic agents include, for example, mediator release suppressing agents, such as tranilast, TXA2 inhibitors such as ozagrel, leucotriene inhibitors such as pranlukast, Th2 cytokine inhibitors such as suplatast, antihistaminic agents, and the like, examples of the antidiabetic agents include, for example, insulin preparations such as insulin, sulfonylurea agents such as tolbutamide, and glibenclamide, fast-acting insulin secretion promoting agents such as nateglinide, sulfonamide agents such as glybuzole, biguanide agents such as metformin, insulin resistance improving agents such as pioglitazone and rosiglitazone, α-glucosidase inhibitors such as voglibose, somatomedin C preparations such as mecasermin, GLP-1, DPP-IV inhibitors, and the like, examples of the female hormone preparations include, for example, estrogen agents such as estriol, estradiol, and conjugated estrogen, gestagen preparations such as progesterone, medroxyprogesterone, and norethisterone, as well as pregnanediol, matharmon-F, danazol, selective estrogen receptor modulators (SERM: raloxifen, lasofoxifene, bazedoxifene, ospemifene, arzoxifene, CHF4227, PSK-3471, and the like), and the like, examples of the male hormone preparations include, for example, male hormone preparations such as testosterone and metyltestosterone, protein assimilation steroids such as mestanolone, stanozolol, metenolone, and nandrolone, selective androgen receptor modulators (SARM), and the like, examples of other hormone preparations include, for example, hypothalamic hormones such as LH-RH, protirelin, somatorelin, and corticorelin, adenohypophysial hormones such as somatropin, gonadotrophic hormones such as ACTH (adrenocorticotropic hormone), HCG, and HMG, ovulation inducing agents such as cyclofenil, neurohypophyseal hormones such as oxytocin, vasopressin, and desmopressin, parotid gland hormones, ergot alkaloids such as glucagon, and terguride, anti-mammary gland tumor agents such as epitiostanol, adrenal cortex hormone synthesis inhibitors such as mitotane, somatostatin analogues such as octreotide, iodine preparations, and the like, examples of the thyroid disease curative agents include, for example, thyroid hormones such as levothyroxine, antithyroid agents such as propylthiouracil, and the like, examples of the bone and calcium metabolic agents include, for example, examples of the bone activating agents include, for example, calcitriol, alfacalcidol, OCT, ED-71, and the like, examples of the osteogenesis promoting agents include, for example, menatetrenone, teriparatide, somatropin, insulin-like growth factor, EP4 agonist, EP2 agonist, growth hormone secretagogues, and the like, examples of the bone resorption suppressing agents include, for example, elcatonin, calcitonin salmon, etidronate, pamidronate, clodronate, alendronate, incadronate, risedronate, minodronate, ibandronate, cathepsin K inhibitors, osteoprotegerin, anti-RANKL antibodies, and the like, examples of the bone metabolism improving agents include, for example, fluoride, ipriflavone, and the like, examples of the sexual hormone preparations include, for example, estriol, estradiol, conjugated estrogen, progesterone, medroxyprogesterone, testosterone, metyltestosterone, mestanolone, stanozolol, metenolone, nandrolone, selective estrogen receptor modulators (SERM: raloxifen, lasofoxifene, bazedoxifene, ospemifene, arzoxifene, CHF4227, PSK-3471, and the like), selective androgen receptor modulators (SARM), and the like, examples of the calcium preparations include, for example, calcium carbonate, calcium lactate, calcium gluconate, calcium acetate, calcium chloride, calcium citrate, calcium hydrogenphosphate, calcium L-aspartate, and the like, examples of the vitamin preparations include, for example, vitamin A and retinoids, vitamin B1 and vitamin B1 derivatives, vitamin B2, nicotinic acid, pantothenic acid, vitamin B6, vitamin B12, folic acid, mixed vitamin B, vitamin C, vitamin K, vitamin E, vitamin H, multiple vitamin agents, and the like, examples of the fluid therapy preparations include, for example, electrolyte fluids, potassium preparations, preparations for correction, carbohydrate fluids, comprehensive amino acid preparations, amino acid preparations for renal failure, amino acid preparations for hepatic failure, other amino acid preparations, fat emulsion preparations, basic solutions for high calorie fluid therapy, enteral hyperalimentation preparations, nutrient preparations of ingredients for hepatic insufficiency, plasma volume increasing agents, trace element preparations, dialysis and peritoneal dialysis solutions such as AK-solita-D, and kindaly AF-3, and the like, examples of the blood preparations include, for example, albumin preparations, globulin preparations, blood coagulation factor preparations, fibrinogen preparations, antilymphocyte globulin preparations, antithrombin III preparations, C1-inactivator preparations, haptoglobin preparations, arginine and vasopressin derivatives, and the like, examples of the hematopoietic agents include, for example, examples of the antianemic agents include, for example, iron agents such as sodium ferrous citrate, erythropoietin preparations such as epoetin alfa, G-CSF preparations such as filgrastim, M-CSF preparations such as mirimostim, immunoglobulin preparations, tubercle bacillus preparations, romurtide, imiglucerase, and the like, examples of the hypoleukocytemia curative agents include, for example, adenine, L-cystein, cepharanthin, glutathion, cytochrome C, and the like, examples of the hemostatic agents include, for example, adrenochromes such as carbazochrome, antiplasmin agents such as tranexamic acid, blood coagulation factor-like effect agents such as hemocoaglase, cellulose preparations, gelatin preparations, agents for esophageal varices sclerosing therapy such as poridocanol, and the like, examples of the antithrombotic agents include, for example, anticoagulants (heparin and heparinoids such as danaparoid, oral anticoagulants such as warfarin, antithrombin agents such as argatroban, FXa inhibitors, FVIIa inhibitors, thrombolytic agents (urokinase preparations, t-PA preparations, and the like), protease inhibitors such as nafamostat, and the like), antiplatelet agents (aspirin, ethyl icosapentate, beraprost, sarpogrelate, dilazep, dipyridamole, ticlopidine, cilostazol, P2Y12 inhibitors, and the like), dried and concentrated L active protein C, thrombomodulin preparations, and the like, examples of the antihyperlipidemic agents include, for example, fibrate agents such as clinofibrate, nicotinic acid agents such as niceritorol, HMG-CoA reductase inhibitors such as pravastatin, simvastatin, fluvastatin, cerivastatin, atorvastatin, and lovastatin, anion exchange resins such as cholestyramine, probucol, melinamide, pantethine, ethyl icosapentate, elastase, dextran sulfate sodium sulfur, polyenephosphatidylcholine, ezetimib, bile acid re-absorption inhibitors (IBAT inhibitors), ACAT inhibitors, MTP inhibitors, CETP inhibitors, LXR regulating agents, and the like, examples of the cardiac stimulants (heart failure curative agents) include, for example, examples of the cardiac stimulants include, for example, digitalis preparations such as digoxin, β-metildigoxin, and digitoxin, xanthine agents such as aminophylline, catecholamine agents such as docarpamine, PDEIII inhibitors such as amrinone, denopamine, ubidecarenone, vesnarinone, aminoethylsulfonic acid, pimobendan, carperitide, corforsin daropate, and the like, examples of the antiarrhythmic agents include, for example, class Ia agents such as procainamide and cibenzoline, class Ib agents such as lidocaine, aprindine, and mexiletine, class Ic agents such as flecainide, propafenone, and pilsicainide, class III agents such as nifekalant, and verapamil, β-blockers (class II agents), Ca antagonist (class IV agents), and the like, examples of the antianginal agents include, for example, nitric acid agents such as nitroglycerin and isosorbide dinitrate, β-blockers such as propranolol, Ca antagonists such as nifedipine, dipyridamole, etafenone, dilazep, trapidil, nicorandil, and the like, examples of the vasodilators include, for example, prostaglandin preparations such as limaprost alfadex, nicotinic acid agents such as tocopherol nicotinate, β-receptor stimulants such as isoxsuprine, β-receptor suppressants such as tolazoline, circulatory hormone preparations such as kallidinogenase, and the like, examples of the antihypertensive agents include, for example, Ca antagonists such as diltiazem, nicardipine, nisoldipine, barnidipine, nifedipine, aranidipine, cilnidipine, nitrendipine, nilvadipine, felodipine, benidipine, and amlodipine, β-blokers such as atenolol, alprenolol, bisoprolol, betaxolol, bevantolol, acebutolol, celiprolol, nipradilol, tilisolol, nadolol, indenolol, bunitrolol, penbutolol, bopindolol, propranolol, metoprolol, pindolol, carteolol, and timolol, diuretic agents such as furosemide, ACE inhibitors such as enalapril, lisinopril, captopril, alacepril, delapril, cilazapril, benazepril, imidapril, temocapril, quinapril, trandolapril, and perindopril, angiotensin II receptor antagonists such as losartan, candesartan, and valsartan, α-blockers such urapidil, terazosin, doxazosin, bunazosin, prazosin and phentolamine, α,β-blokers such as carvedilol, amosulalol, arotinolol, and labetalol, central sympathetic nerve suppressants such as methyldopa, clonidine, guanabenz, and guanfacine, peripheral sympathetic nerve blocking agents such as betanidine, autonomic nerve blocking agents such as trimetaphan, rauwolfia preparations such as reserpine, and rescinnamine, vasodilative antihypertensive agents such as hydralazine, todralazine, budralazine, and cadralazine, nitric acid agents such as nitroglycerin, circulatory system acting enzyme agents such as kallidinogenase, dihydroergotoxine, alprostadil alfadex, and the like, examples of the vasopressors include, for example, catecholamine agents such as norepinephrine, dopamine, and dobutamine, non-catecholamine agents such as metaraminol and amezinium metilsulfate, and the like, examples of the diuretic agents include, for example, thiazide diuretic agents such as hydrochlorothiazide, non-thiazide diuretic agents such as chlortalidone, loop diuretics such as furosemide, K sparing diuretic agents such as spironolactone, carbonic anhydrase inhibitors such as acetazolamide, and osmotic diuretic agents such as D-mannitol, examples of the bronchodilators include, for example, xanthine derivatives such as theophylline, β-stimulants such as epinephrine, ephedrine, dl-methylephedrine, isoprenaline, orciprenaline, clorprenaline, trimetoquinol, salbutamol, terbutaline, tulobuterol, procaterol, fenoterol, formoterol, and clenbuterol, parasympathetic blocking agents such as ipratropium, flutropium, and oxitropium, and the like, examples of the bronchial asthma curative agents include, for example, steroid agents for inhalation such as beclomethasone, and fluticasone, vaccine therapy agents, histamine-added human immunoglobulin, and the like, examples of the respiratory stimulants include, for example, central respiratory stimulants such as dimorpholamine, peripheral respiratory stimulants such as doxapram, xanthine derivatives such as theophylline, narcotic antagonists such as levallorphan, lung-surfactants, and the like, examples of the antitussive agents include, for example, centeral narcotic antitussive agents such as codein, dihydrocodeine, and oxymetebanol, central non-narcotic antitussive agents such as dextromethorphan, pentoxyverine, dimemorfan, cloperastine, benproperine, fominoben, and eprazinone, and the like, examples of the expectorants include, for example, respiratory tract mucus dissolving agents such as acetylcysteine, respiratory tract mucus healing agents such as bromhexine, respiratory tract lubricants such as ambroxol, surface active agents such as tyloxapol, salt expectorants, stimulant expectorants, herbal agent expectorants, and the like, examples of the stomachic digestants and gastrointestinal promotility agents include, for example, stomachic combination agents such as S-M, digestive enzyme agents such as diastase, and Takadiastase, parasympathomimetic agents such as carnitine and carpronium, serotonin agonists such as cisapride, and mosapride, antidopamine agents such as metoclopramide, domperidone, and itopride, opiate agonists such as trimebutine, and the like, examples of the digestive ulcer curative agents (antacids, antispasmodic agents, antiulcer agents) include, for example, antacids such as sodium hydrogencarbonate, dried aluminum hydroxide gel, and hydrotalcite, belladonna alkaloids such as atropine sulfate, cholinergic agents such as acetylcholine chloride, tertiary amine synthetic anticholinergic agents such as piperidolate, quarternary ammonium salt synthetic anticholinergic agents such as propantheline, methylbenactyzium, and methyloctatropine, selective antimuscarine agents such as tiquizium and pirenzepine, antigastrin agents such as secretin, proglumide, and urogastrone, histamine H2 receptor antagonists such as cimetidine, ranitidine, famotidine, roxatidine, nizatidine, and lafutidine, proton pump inhibitors such as omeprazole, lansoprazole, and rabeprazole, prostaglandin preparations such as ornoprostil, misoprostol, and enprostil, defensive factor enhancers such as methylmethionine sulfonium chloride, sucralfate, L-glutamine, sodium azulenesulfonate, gefarnate, aldioxa, aceglutamide aluminum, cetraxate, sofalcone, teprenone, sodium alginate, plaunotol, troxipide, benexate hydrochloride betadex, rebamipide, polaprezinc, irsogladine, ecabet, and egualen, antidopamine agents such as sulpiride, and clebopride, organ extracts such as Solcoseryl, combination agents such as aluminum hydroxide gel and magnesium hydroxide combination agents, and the like, examples of the intestinal disease curative agents include, for example, astringent agents such as albumin tannate, microbicides such as berberine, lactic acid bacterium preparations such as lactomin, lactose decomposition enzyme agents such as tilactase, adsorbents for alimentary canals such as natural aluminum silicate, antidiarrheal agents such as loperamide, alimentary canal gas elimination agents such as dimethicone, irritable colon syndrome curative agents such as mesalazine, betamethasone, mepenzolate, and polycarbophil calcium, and the like, examples of the purgatives (cathartics) include, for example, salt purgatives such as magnesium sulfate, bulk cathartics such as carmelose, infiltrative purgatives such as DSS, sugar purgatives such as lactulose, small intestine stimulating purgatives such as castor oil, large intestine stimulating purgatives such as senna, and rheum, glycerin, and the like, examples of the biliary disease curative agents include, for example, choleretics such as ursodeoxycholic acid, and chenodeoxycholic acid, cholekinetics such as papaverine, flopropione, hymecromone, and trepibutone, bile acid deposition agents such as colestyramine, and colestimide, and the like, examples of the liver disease curative agents include, for example, liver function improving agents such as glutathione, glucuronate, glycyrrhizin, tiopronin, and vitamin U, liver protein metabolism improving agents such as malotilate, hepatic insufficiency curative agents such as liver hydrolysates, liver extract preparations, sodium glutaminate, amino acid combination agents, lactulose, and lactitol hydrate, interferon-α, interferon-β, immunoglobulins, hepatitis vaccines, shosaikoto, and the like, examples of the pancreatic disease curative agents include, for example, protease inhibitors such as camostat, nafamostat, gabexate, and ulinastatin, pancreatitis curative agents such as citicolin, pancreatic exocrine stimulants such as fenipentol, and the like, examples of the hypnotic and sedative agents include, for example, barbituric acid agents such as barbital, amobarbital, and phenobarbital, non-barbituric acid agents such as triclofos and chloral hydrate, benzodiazepine agents such as triazolam, midazolam, lormetazepam, rilmazafone, estazolam, nimetazepam, flunitrazepam, haloxazolam, quazepam, brotizolam, nitrazepam, and flurazepam, cyclopyrrolone agents such as zopiclone, and zolpidem, belladonna alkaloids such as scopolamine, and the like, examples of the analgetic and antipyretic agents and comprehensive cold remedies include, for example, narcotic analgesics such as opium, morphine, pethidine, droperidol, and fentanyl citrate, non-narcotic analgesics such as pentazocine, tramadol, buprenorphine, eptazocine, and butorphanol, nonsteroidal antiinflammatory agents such as flurbiprofen, loxoprofen, indometacin, diclofenac, and sulindac, pyrazolone antipyretic analgesics such as sulpyrine, and migrenin, and combination agents containing these, non-pyrazolone antipyretic analgesics such as acetaminophen, phenacetin, and dimetotiazine, and cold remedies as combination agents containing these, xanthine preparations such as caffeine, ergotamine preparations such as dihydroergotamine, Ca antagonists such as lomerizine, triptane anti-migraine agents such as sumatriptan, and the like, examples of the antiepileptic agents include, for example, hydantoin agents such as phenyloin, barbituric acid agents such as primidone, acetyl ureas such as acetylpheneturide, benzisoxazole agents such as zonisamide, benzodiazepine agents such as clonazepam, diazepam, clobazam, and trimethadione, ethosuximide, carbamazepine, sultiame, sodium valproate, and the like, examples of the psychotropic agents (antipsychotics, antidepressants, psychostimulants, antialcoholic agents, and the like) include, for example, phenothiazine agents such as chlorpromazine, levomepromazine, fluphenazine, thioridazine, propericiazine, perphenazine, and prochlorperazine, butyrophenone agents such as haloperidol, bromperidol, pipamperone, spiperone, moperone, and timiperone, benzamide agents such as sultopride, nemonapride, sulpiride, and tiapride, serotonin and dopamine antagonists such as olanzapine, and risperidone, anti-schizophrenia agents such as pimozide, clocapramine, carpipramine, mosapramine, oxypertine, zotepine, and carbamazepin, tricyclic antidepressants such as imipramine, clomipramine, amitriptyline, lofepramine, amoxapine, dosuleptin, and nortriptyline, tetracyclic antidepressants such as maprotiline, and mianserin, selective serotonin reuptake inhibitors (SSRI) such as fluvoxamine, and paroxetine, serotonin and noradrenalin reuptake inhibitors (SNRI) such as milnacipran, antidepressants such as trazodone, psychostimulants such as methamphetamine, methylphenidate, and pemoline, and the like, examples of the antianxiety agents (mild tranquilizers) include, for example, benzodiazepine agents such as chlordiazepoxide, diazepam, cloxazolam, oxazolam, medazepam, bromazepam, lorazepam, prazepam, fludiazepam, clorazepate, mexazolam, alprazolam, flutazolam, flutoprazepam, ethyl loflazepate, clotiazepam, and etizolam, tandospirone, hydroxyzine, and the like, examples of the cerebral circulation and metabolism improvers include, for example, ifenprodil, vinpocetine, ibudilast, nicergoline, nilvadipine, amantadine, cytochrome C, ATP, meclofenoxate, citicolin, γ-aminobutyric acid, calcium hopantenate, dihydroergotoxine, fasudil, nizofenone, sodium ozagrel, donepezil, and the like, examples of the autonomic agents include, for example, choline analogue agents such as acetylcholine chloride, and bethanechol, anti-cholinesterase agents such as neostigmine, ambenonium, distigmine, pyridostigmine, and edrophonium, autonomic nerve regulating agents such as tofisopam and γ-oryzanol, β-blockers such as atenolol, alprenolol, bisoprolol, betaxolol, bevantolol, acebutolol, celiprolol, nipradilol, tilisolol, nadolol, indenolol, bunitrolol, penbutolol, bopindolol, propranolol, metoprolol, pindolol, carteolol, and timolol, α-blockers such as urapidil, terazosin, doxazosin, bunazosin, prazosin, and phentolamine, α,β-blockers such as carvedilol, amosulalol, arotinolol, and labetalol, β-stimulants such as epinephrine, ephedrine, dl-methylephedrine, isoprenaline, orciprenaline, clorprenaline, trimetoquinol, salbutamol, terbutaline, tulobuterol, procaterol, fenoterol, formoterol, and clenbuterol, parasympatholytic agents (anticholinergic agents) such as ipratropium, flutropium, and oxitropium, autonomic nerve blocking agents such as trimetaphan, and the like, examples of the antiemetic agents and antidizziness agents include, for example, phenothiazine agents such as perphenazine, and prochlorperazine, antihistaminic agents such as dimenhydrinate, and similar agents, 5-HT3 receptor antagonist type antiemetic agents such as granisetron, ondansetron, azasetron, ramosetron, and tropisetron, sympathetic nerve stimulants such as isoprenaline, antacidus neutralizers such as sodium hydrogencarbonate, antidizziness agents such as betahistine, and difenidol, cerebral circulation and metabolism improvers such as disodium adenosine triphosphate, phenothiazine agents such as prochlorperazine, benzodiazepine agents such as diazepam, gastroenteric promotility agents such as metoclopramide, domperidone, mosapride, cisapride, and trimebutine, gastric mucous membrane local analgesics such as oxethazaine, abirritants such as scopolamine, diphenhydramine, diprophylline, and the like, examples of the Parkinson's disease curative agents include, for example, L-DOPA containing preparations such as levodopa, dopamine release promoting agents such as amantadine, dopamine receptor agonists such as bromocriptine, pergolide, cabergoline, talipexole, and ropinirol, norepinephrine precursors such as droxidopa, monoamine oxidase (MAO) inhibitors such as selegiline, muscle relaxants such as tizanidine, dantrolene, and vecuronium, parasympatholytic agents such as profenamine, mazaticol, trihexyphenidyl, biperiden, piroheptine, and metixene, and the like, examples of the muscle relaxants include, for example, central muscle relaxants such as tolperisone, methocarbamol, pridinol, chlorphenesin, baclofen, and tizanidine, peripheral muscle relaxants such as suxamethonium, dantrolene, pancuronium, and vecuronium, and the like, examples of the local analgesics include, for example, procaine, ethyl aminobenzoate, cocaine, lidocaine, dibucaine, bupivacaine, and the like, examples of the general anesthetics include, for example, halogenated hydrocarbon preparations such as halothane, barbituric acid preparations such as thiamylal, thiopental, and pentobarbiturate, benzodiazepine preparations such as midazolam, halogenated ether preparations such as isoflurane, ketamine, droperidol, propofol, anesthetic ether, nitrous suboxide, and the like, examples of the ophthalmologic agents (anticataract agents, and the like) include, for example, miotic agents such as pilocarpine, mydriatic agents such as cyclopentolate, and epinephrine, anticataract agents such as pirenoxine, glutathione, tiopronin, and salivary gland hormone, cornea curative agents such as sodium chondroitinsulfate, vasoconstrictors such as naphazoline, tetrahydrozoline, and oxymetazoline, adrenal cortex hormones such as dexamethasone, and prednisolone, β-blockers such as timolol, befunolol, carteolol, betaxolol, nipradilol, and levobunolol, carbonate dehydratase inhibitors such as dorzolamide, antibiotic preparations such as sulfisoxazole, antiviral agents such as aciclovir, and idoxuridine, antiallergic agents such as sodium cromoglicate, amlexanox, ketotifen, tranilast, and levocabastine, prostaglandin preparations such as isopropyl unoprostoe, and latanoprost, antiinflammatory agents such as azulene, indometacin, and pranoprofen, cyanocobalamin, lysozyme chloride, and the like, examples of the otolaryngologic agents include, for example, vasoconstrictors such as naphazoline, tetrahydrozoline, oxymetazoline, and tramazoline, adrenal cortex hormones such as flunisolide, beclometasone, fluticasone, and dexamethasone, antibacterial agents such as cefmenoxime, antiallergic agents such as sodium cromoglicate, amlexanox, ketotifen, emedastine, epinastine, and suplatast, antihistaminic agents such as levocarbastine, anticholinergic agents such as flutropium, and ipratropium, respiratory tract mucus restoration agents such as carbocisteine, and the like, examples of the dermatologic agents include, for example, leukoderma curative agents such as methoxsalen, inflammatory anthema curative agents such as pregnanediol, keratosis curative agents such as etretinate, calcipotriol, urea, and tacalcitol, clavus curative agents such as salicyclic acid, psoriasis curative agents such as ciclosporin, depilation and leukoderma curative agents such as carpronium, Hansen's disease curative agents such as diaphenylsulfone, atopic dermatitis curative agents such as tacrolimus, antiallergic agents such as cromoglicate, tranilast, emedastine, epinastine, and suplatast, antipruritic agents such as crotamiton, and diphenhydramine, skin ulcer curative agents such as azulene, sulfadiazine, tretinoin tocoferil and bucladesine, and the like, examples of the agents for urinary and generative organs (calculus excretion promoting agents, and the like) include, for example, tertiary amine synthetic anticholinergic agents, quarternary ammonium salt synthetic anticholinergic agents, calculus excretion promoting agents such as flopropione, Quercus salicina extract, and α,β-pinene and d-camphene preparations, aciduria improving agents such as potassium citrate and sodium citrate preparations, thamuria curative agents such as flavoxate, oxybutynin, propiverine, clenbuterol, and mesna, urinary disturbance curative agents such as paraprost, neostigmine, oxendolone, prazosin, terazosin, urapidil, tamsulosin, and naftopidil, agents for generative organs (PDE-5 inhibitors and the like) such as sildenafil, and the like, examples of the antihemorrhoidal agents include, for example, tribenoside, Lithospermi radix extract, ethyl aminobenzoate and dibucaine hydrochloride preparations, and the like, examples of the agents for uterus include, for example, uterotonic agents such as ergometrine, dinoprost, dinoprostone, and gemeprost, uterine motility suppressing agents such as ritodrine, isoxsuprine, and piperidolate, hormone therapy agents such as danazol, buserelin, nafarelin, leuprorelin, goserelin, cetrorelix, teverelix, abarelix, and sodium prasterone sulfate, autonomic nerve controlling agents such as tofisopam, and the like, examples of the agents for dentistry and oral cavity include, for example, collutories such as azulene, and povidone-iodine, troches such as chlorhexidine, troches containing an antibiotic such as tetracycline, stomatitis curative agents such as azulene, triamcinolone, dexamethasone, and beclometasone, artificial saliva such as saliveht, and the like, examples of the detoxification agents include, for example, metal detoxification agents such as dimercaprol, anti-barbituric acid agents such as bemegride, narcotic antagonists such as naloxone, folic acid antagonists such as calcium folinate, iphosphamide-indeced bladder dyscrasia curative agents such as mesna, heparin antagonists such as protemin, antiallergic agents such as glycyrrhizin, antialcoholic agents such as cyanamide, and disulfiram, glutathione, ipecac, carbon (Kremezin), and the like, examples of the anorectic agents include, for example, mazindol, MCH antagonists, MC4 antagonists, and the like, examples of the weight gaining agents include, for example, somatropin and the like, examples of the metabolic antagonists include, for example, sodium chondroitinsulfate and the like, examples of the carnitine deficiency improving agents include, for example, levocarnitine and the like, examples of the phenylalaninemia curative agents include, for example, sapropterin, and the like, examples of the urea cycle abnormality curative agents include, for example, arginine hydrochloride, and the like, examples of the non-smoking auxiliary agents include, for example, nicotin, and the like, examples of the patent ductus arteriosus curative agents include, for example, indometacin, and the like, examples of the cardiac muscle protecting agents include, for example, miotecter, and the like, examples of the anti-ALS agents include, for example, riluzole, and the like, examples of the immune enhancement agents include, for example, interferon-β 1b, and the like, and examples of the Chinese drugs and contrast media include, for example, contrast media for urography such as iopamidol, iohexol, ioversol, iopromide, iomeprol, ioxilan, and ioxaglic acid, contrast media for retrograde urography such as amidotrizoic acid, and iothalamic acid, alimentary canal contrast media such as amidotrizoic acid, salivary gland contrast media such as amidotrizoic acid, contrast media for cisternography and myelography such as iotrolan, contrast media for spermatocystography such as iothalamic acid, contrast media for uterosalpingography such as iotrolan, contrast media for MRI such as gadodiamide hydrate, contrast media for echography such as galactose-palmitic acid, contrast media such as iodixanol, and the like (Jinzobyo Chiryoyaku Manual (Manual of Renal Disease Curative Agents), Ed. by Nihei H., Tokyo Igaku Sha, Tokyo, 2002; Konnichi no Tiryoyaku (Today's Curative Agents) 2001, Ed. by Mizushima H, Nankodo, Tokyo, 2001). However, examples of the prophylactic or therapeutic agents for the various abnormalities and diseases complicating with hyperPTHemia including hyperparathyroidism, osteoporosis, and hypercalcemia used in combination or prepared into a so-called combined drug with the medicament of the present invention are not limited to the aforementioned specific agents.

When a medicament used in combination or prepared into a so-called combined drug with the medicament of the present invention is selected, a type, dose, administration time and the like of the medicament may be appropriately selected and adjusted so that the interactions between the medicaments are minimized by referring to information of package inserts, product summaries, interview forms and the like of the medicaments. For example, it has been reported that the antihyperlipidemic drug, atorvastatin, is metabolized by the drug metabolism enzyme CYP3A4 in the liver after administration, and therefore if a medicament having a CYP3A4 enzyme inhibitory action (e.g., azole antifungal agents) is used in combination, blood level of atorvastatin rises, and risk of side effects such as rhabdomyolysis increases (Bernini et al., "Saftey of HMG-CoA reductase inhibitors: focus on atorvastatin", Cardiovasc. Drugs Ther., 15, pp. 211-218, 2001). Further, it has been reported that the antidepressant, imipramine, is metabolized by the drug metabolism enzyme CYP2D6 in the liver after administration, and therefore, if a medicament having a CYP2D6 enzyme inhibitory action (e.g., paroxetine) is used in combination, blood level of the antidepressant rises, and undesirable excessive anticholinergic action is expressed (Albers et al., "Paroxetine shifts imipramine metabolism", Psychiatry Res., 59, pp. 189-196, 1996). Therefore, for example, when the medicament of the present invention is administered to a patient of hyper-PTHemia including hyperparathyroidism, osteoporosis, or hypercalcemia taking atorvastatin or imipramine, it is very desirable to choose a medicament having negligible CYP3A4 or CYP2D6 inhibitory action.

EXAMPLES

The present invention will be more specifically explained by referring to examples. However, the scope of the present invention is not limited by the following examples.

In the following examples, various analyses were performed as follows.

(1) Fast Atomic Bombardment Mass Spectrum (FAB-MS)

Spectra were measured by using a mass spectrometer Model JMS-AX500 or JMS-SX102 produced by JEOL Ltd. As the matrix, 3-nitrobenzyl alcohol was used.

(2) Liquid Chromatography-mass Spectrometry Spectrum (LC-MS)

As the mass spectrometer, Platform-LC type mass spectrometer produced by Micromass, England (electrospray ionization (ESI) method was used for ionization).

As the liquid chromatography apparatus, an apparatus produced by GILSON, France, was used. As the separation column, Mightysil RP-18 GP 50-4.6 produced by Kanto Kagaku, Japan (product number: 25468-96) was used. The elution conditions are mentioned below.

Flow rate: 2 ml/minute
Solvent:
Solution A=water containing 0.1% (v/v) acetic acid
Solution B=acetonitrile containing 0.1% (v/v) acetic acid
Elution was performed with a linear gradient of 5 to 100% (v/v) of Solution B from 0 minute to 5 minutes.

(3) Proton Nuclear Magnetic Resonance ($^1$H-NMR) Spectrum

Spectra were measured by using Gemini-300 nuclear magnetic resonance apparatus produced by Varian, U.S. As the internal standard, tetramethylsilane was used. Chemical shifts are indicated in terms of δ values (ppm). Splitting patterns are indicated with the following abbreviations: s: singlet, d: doublet, t: triplet, q: quadruplet, quintet: quintet, m: multiplet, dd: double doublet, dt: double triplet, and brs: broad singlet (4) Thin Layer Chromatography (TLC)

A TLC plate produced by Merck, Germany (Silica Gel 60 $F_{254}$, product number: 1,05715) was used. Compounds were detected by irradiating the TLC plate after deployment with an ultraviolet ray having a wavelength of 254 nm.

(5) Purification Chromatography

Silica gel column purification was performed by using Silica Gel 60 produced by Merck, Germany or a full automatic preparative chromatography apparatus Parallel Prep produced by YAMAZEN CORP. with a packed column for medium pressure preparation, Hi-Flash column (trade name), and objective substances were eluted with a mixed solvent (n-hexane/ethyl acetate, or chloroform/methanol).

For purification with a reverse phase column, a column produced by YMC, Japan (YMC CombiPrep ODS-A CCAAS05-0520WT) was used, and target substances were eluted with a water/acetonitrile (containing 0.1% (v/v) acetic acid) gradient.

Detailed elution conditions are mentioned below.

Flow rate: 20 ml/minute
Solvent:
Solution A=water containing 0.1% (v/v) trifluoroacetic acid
Solution B=acetonitrile containing 0.1% (v/v) trifluoroacetic acid
Elution was performed with:
5% of Solution B from 0 minute to 1 minute,
linear gradient of 5 to 50% (v/v) of Solution B from 1 minute to 11 minutes
linear gradient of 50 to 100% (v/v) of Solution B from 11 minutes to 16 minutes Example 1

Synthesis of [1-(benzothiophen-3-yl)ethyl][3-(3-trifluoromethylphenyl)propyl]amine hydrochloride

[3-(3-Trifluoromethylphenyl)propyl]amine (101.6 mg) synthesized according to a method described in the literature (Fujimura et al., Bioorg. Med. Chem., Vol. 5, pp. 1675-1684, 1997) and 3-acetylbenzothiophene (90 mg) were added to an argon substituted recovery flask, added with titanium tetraisopropoxide (190 μL), and stirred at room temperature for 17 minutes. The reaction mixture was added with dehydrated 2-propanol (0.5 mL), and stirred at room temperature for 14 hours and then at 100° C. for 6 hours. The reaction mixture was cooled to room temperature, added with sodium cyanoborohydride (34 mg) and dehydrated ethanol (0.75 mL), and stirred at room temperature for 38.5 hours. The reaction mixture was further added with sodium cyanoborohydride (35 mg), stirred at room temperature for 3 hours, then further added with sodium cyanoborohydride (100 mg), and stirred for 45 hours. The reaction mixture was added with saturated aqueous sodium hydrogencarbonate, and extracted with ethyl acetate. The organic layer was washed with saturated brine, and dried over anhydrous sodium sulfate, and the solvent was evaporated under reduced pressure. The residue was purified twice by silica gel column chromatography (chloroform:methanol=100:0→90:10) to obtain 156 mg of the title compound in the free form. This product was dissolved in chloroform, and added with a 0.1 N solution of hydrochloric acid in ethanol (4.8 mL), and the solvent was evaporated under reduced pressure to obtain 174 mg of the title compound.

¹H-NMR (DMSO-d₆); δ (ppm) 1.67 (3H, d, J=6.6), 1.96 (2H, m), 2.72 (2H, t, J=7.7), 2.70-2.84 (1H, m), 2.90-3.04 (1H, m), 4.92 (1H, m), 7.42-7.56 (6H, m), 8.02-8.12 (3H, m), 9.26 (1H, brs), 9.60 (1H, brs)

Reference Example

Synthesis of N-[1-(benzothiophen-3-yl)ethyl]-3-(2-furyl)propionamide 3-(2-Furyl)propionic acid (368 mg), 1-(benzothiophen-3-yl)ethylamine (443 mg), N-ethyl-N'-dimethylaminopropyl-carbodiimide hydrochloride (575 mg), 1-hydroxybenzotriazole (405 mg), and triethylamine (304 mg) were added to dehydrated dimethylformamide (DMF, 15 mL), and stirred at room temperature for 12 hours. The reaction mixture was added with water, and extracted with ethyl acetate. The organic layer was dried, and the solvent was evaporated under reduced pressure. The residue was purified by silica gel column chromatography (hexane:ethyl acetate=2:1) to obtain 628 mg of the title compound.

¹H-NMR (CDCl₃); δ (ppm) 1.67 (3H, d, J=6.6), 2.49 (2H, t, J=7.5), 3.00 (2H, t, J=7.5), 5.57 (1H, q, J=7.5), 5.62 (1H, brs), 5.98 (1H, d, J=0.9), 6.22 (1H, dd, J=1.20, 3.00), 7.23 (1H, d, 1.20), 7.35-7.39 (2H, m), 7.75-7.79 (1H, m), 7.80-7.88 (1H, m), 8.00 (1H, s)

Example 2

Synthesis of [1-(benzothiophen-3-yl)ethyl][3-(2-furyl)propyl]amine

The compound of Reference Example (600 mg) was dissolved in dehydrated THF, added with lithium aluminum hydride (379 mg), and refluxed under nitrogen atmosphere for 12 hours. The reaction mixture was cooled on ice, and carefully added with water with stirring. The solids were removed by filtration, and the filtrate was concentrated under reduced pressure. The residue was purified by silica gel column chromatography (hexane:ethyl acetate=2:1) to obtain 393 mg of the title compound.

¹H-NMR (CDCl₃); δ (ppm) 1.48 (3H, d, J=6.6), 1.85 (2H, quintet, J=7.2), 2.59-2.74 (4H, m), 4.24 (1H, q, J=6.6), 5.92 (1H, d, J=0.9), 6.25 (1H, dd, J=1.8, 2.7), 7.23-7.39 (4H, m), 7.84-7.91 (2H, m)

The compounds of Examples 3 to 8 were synthesized in the same manner as in Example 1, Reference Example, or Example 2.

Example 3

[1-(Benzothiophen-3-yl)ethyl][3-[5-(3-chlorophenyl)furan-2-yl]propyl]amine

¹H-NMR (CDCl₃); δ (ppm) 1.49 (3H, d, J=6.6), 1.89 (2H, m), 2.64-2.78 (4H, m), 4.26 (1H, q, J=6.6), 6.01 (1H, d, J=3.3), 6.51 (1H, d, J=3.3), 7.18-7.39 (5H, m), 7.60 (2H, d, J=8.4), 7.84-7.91 (2H, m)

Example 4

[1-(Benzothiophen-3-yl)ethyl][3-(3-furyl)propyl]amine

¹H-NMR (CDCl₃); δ (ppm) 1.49 (3H, d, J=6.6), 1.70-1.79 (2H, m), 2.36-2.52 (2H, m), 2.58-2.72 (2H, m), 4.23 (1H, q, J=6.6), 6.22 (1H, s), 7.14 (1H, s), 7.30-7.39 (4H, m), 7.84-7.90 (2H, m)

Example 5

[1-(Benzothiophen-3-yl)ethyl][3-(thiophen-3-yl)propyl]amine

¹H-NMR (CDCl₃); δ (ppm) 1.48 (3H, d, J=6.6), 1.77-1.87 (2H, m), 2.58-2.73 (4H, m), 4.23 (1H, q, J=6.6), 6.87-6.90 (2H, m), 7.20-7.22 (1H, m), 7.29 (1H, s), 7.31-7.40 (2H, m), 7.84-7.90 (2H, m)

Example 6

[1-(Azulen-1-yl)ethyl][3-(thiophen-3-yl)propyl]amine

¹H-NMR (CDCl₃); δ (ppm) 1.58 (3H, d, J=6.6), 1.75-1.88 (2H, m), 2.45-2.68 (5H, m), 4.57 (1H, q, J=6.6), 6.82-6.85 (2H, m), 7.09-7.19 (3H, m), 7.38 (1H, d, J=3.9), 7.57 (1H, t, J=9.9), 8.00 (1H, d, J=3.9), 8.29 (1H, d, J=9.9), 8.41 (1H, d, J=9.9)

Example 7

[1-(Azulen-1-yl)ethyl][3-(2-furyl)propyl]amine

¹H-NMR (CDCl₃); δ (ppm) 1.60 (3H, d, J=6.9), 1.82-1.88 (2H, m), 2.29 (1H, brs), 2.46-2.69 (4H, m), 4.59 (1H, q, J=6.9), 5.89-5.90 (1H, m), 6.20-6.22 (1H, m), 7.10-7.38 (3H, m), 7.37 (1H, d, J=3.9), 7.57 (1H, t, J=9.6), 8.01 (1H, d, J=3.9), 8.29 (1H, d, J=9.6), 8.42 (1H, d, J=9.6)

Example 8

[1-(Thieno[2,3-b]pyridin-3-yl)ethyl][3-(3-trifluoromethylphenyl)propyl]amine

¹H-NMR (CDCl₃); δ (ppm) 1.50 (3H, d, J=6.6), 1.80 (2H, quintet, J=7.2), 2.04 (1H, brs), 2.53-2.79 (4H, m), 4.20 (1H, q, J=6.6), 7.25-7.53 (6H, m), 8.23-8.27 (1H, m), 8.55-8.57 (1H, m)

The compounds mentioned in Tables 3, 4, 5, and 6 (Examples 9 to 71) were synthesized in the same manner as in Example 1, Reference Example, or Example 2. As a result of measurement of liquid chromatography mass spectrometry spectra (LC-MS) of the compounds mentioned in Tables 3, 4, 5, and 6, it was confirmed that the objective compounds were produced.

TABLE 3

[Structure: A-(CH)n-NH-CH(R¹)-[heteroaryl with Y¹ and R¹¹]]

| Example | A | n | R¹ | Y¹ | R¹¹ |
|---|---|---|---|---|---|
| Example 9 | 3-(trifluoromethyl)phenyl | 3 | CH₃ | S | 5-CH₃ |
| Example 10 | 3-(trifluoromethyl)phenyl | 2 | CH₃ | S | H |
| Example 11 | phenyl | 3 | CH₃ | S | H |
| Example 12 | 2-(trifluoromethyl)phenyl | 3 | CH₃ | S | H |
| Example 13 | 4-(trifluoromethyl)phenyl | 3 | CH₃ | S | H |
| Example 14 | 4-fluorophenyl | 3 | CH₃ | S | H |
| Example 15 | 2-methoxyphenyl | 3 | CH₃ | S | H |
| Example 16 | 3-methoxyphenyl | 3 | CH₃ | S | H |
| Example 17 | 4-methoxyphenyl | 3 | CH₃ | S | H |
| Example 18 | 3-fluorophenyl | 3 | CH₃ | S | H |
| Example 19 | 3-aminophenyl | 3 | CH₃ | S | H |
| Example 20 | 2-fluorophenyl | 3 | CH₃ | S | H |

TABLE 3-continued

| Example | A | n | R¹ | Y¹ | R¹¹ |
|---|---|---|---|---|---|
| Example 21 | phenyl | 2 | $CH_3$ | S | H |
| Example 22 | pyridin-2-yl | 3 | $CH_3$ | S | H |
| Example 23 | 3-fluorophenyl | 2 | $CH_3$ | S | H |
| Example 24 | pyridin-3-yl | 3 | $CH_3$ | S | H |
| Example 25 | pyridin-4-yl | 3 | $CH_3$ | S | H |
| Example 26 | phenyl | 5 | $CH_3$ | S | H |
| Example 27 | 3-(trifluoromethyl)phenyl | 3 | $CH_3$ | S | 5-Br |
| Example 28 | 3-(trifluoromethyl)phenyl | 3 | $CH_3$ | S | $5-NH_2$ |
| Example 29 | 3-(trifluoromethyl)phenyl | 3 | $CH_3$ | S | $5-NHSO_2CH_3$ |
| Example 30 | 2-hydroxyphenyl | 3 | $CH_3$ | S | H |
| Example 31 | 3-hydroxyphenyl | 3 | $CH_3$ | S | H |
| Example 32 | 4-hydroxyphenyl | 3 | $CH_3$ | S | H |

TABLE 3-continued

| Example | A | n | R¹ | Y¹ | R¹¹ |
|---|---|---|---|---|---|
| Example 33 | 3-CF₃-phenyl | 3 | $CH_3$ | S | 5-$OCH_3$ |
| Example 34 | 3-CF₃-phenyl | 3 | $CH_3$ | S | 5-OH |
| Example 35 | 3-CF₃-phenyl | 3 | $CH_3$ | S | 5-$CH_2OH$ |
| Example 36 | 3-CF₃-phenyl | 3 | $CH_3$ | S | 5-$SCH_3$ |
| Example 37 | 4-$H_2N$-phenyl | 3 | $CH_3$ | S | H |
| Example 38 | 1-methyl-pyrrol-2-yl | 3 | $CH_3$ | S | H |
| Example 39 | 1-methyl-pyrrol-2-yl | 2 | $CH_3$ | S | H |
| Example 40 | tetrahydrofuran-3-yl | 3 | $CH_3$ | S | H |
| Example 41 | tetrahydrofuran-2-yl | 3 | $CH_3$ | S | H |
| Example 42 | 1-methyl-pyrrolidin-2-yl | 3 | $CH_3$ | S | H |
| Example 43 | 1-methyl-piperidin-2-yl | 3 | $CH_3$ | S | H |
| Example 44 | morpholin-4-yl | 3 | $CH_3$ | S | H |

TABLE 3-continued
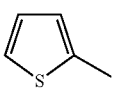
| Example | A | n | R¹ | Y¹ | R¹¹ |
|---|---|---|---|---|---|
| Example 45 | 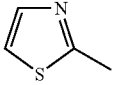 | 3 | $CH_3$ | S | H |
| Example 46 | 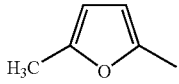 | 3 | $CH_3$ | S | H |
| Example 47 | 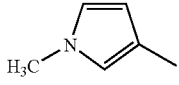 | 3 | $CH_3$ | S | H |
| Example 48 | 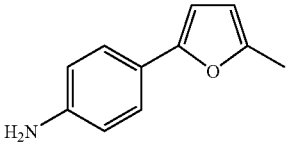 | 3 | $CH_3$ | S | H |
| Example 49 | 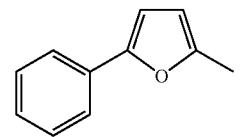 | 3 | $CH_3$ | S | H |
| Example 50 | 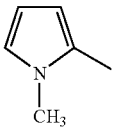 | 3 | $CH_3$ | S | H |
| Example 51 | 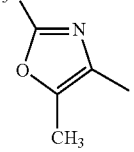 | 4 | $CH_3$ | S | H |
| Example 52 | 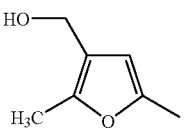 | 3 | $CH_3$ | S | H |
| Example 53 | 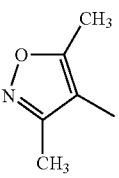 | 3 | $CH_3$ | S | H |
| Example 54 |  | 3 | $CH_3$ | S | H |

TABLE 3-continued

| Example | A | n | R¹ | Y¹ | R¹¹ |
|---|---|---|---|---|---|
| Example 55 | 1,3-dimethylpyrazol-5-yl (H₃C, N-CH₃) | 3 | CH₃ | S | H |
| Example 56 | 3-(5-methylfuran-2-yl)aniline (H₂N-phenyl-furan-CH₃) | 3 | CH₃ | S | H |
| Example 57 | 2-(5-methylfuran-2-yl)aniline (phenyl-NH₂, furan-CH₃) | 3 | CH₃ | S | H |

TABLE 4

| Example | A | n | R¹ | Y¹ | R¹² |
|---|---|---|---|---|---|
| Example 58 | 3-(trifluoromethyl)phenyl (F₃C-phenyl) | 3 | CH₃ | CH | H |
| Example 59 | 3-(trifluoromethyl)phenyl (F₃C-phenyl) | 3 | CH₃ | CH | 6-iPr |
| Example 60 | 1-methylpyrrol-2-yl | 3 | CH₃ | CH | H |

TABLE 5

| Example | A | n | R¹ | B |
|---|---|---|---|---|
| Example 61 | 3-(trifluoromethyl)phenyl | 3 | CH₃ | 3-methylpyrazolo[1,5-a]pyridin-2-yl |
| Example 62 | 3-methoxyphenyl | 3 | CH₃ | 3-methylpyrazolo[1,5-a]pyridin-2-yl |
| Example 63 | 1H-indol-3-yl | 3 | CH₃ | 3-methylbenzothiophen-2-yl |
| Example 64 | 3-methylbenzothiophen-2-yl | 3 | CH₃ | 3-methylbenzothiophen-2-yl |

TABLE 5-continued

A—[CH₂]n—NH—CHR¹—B

| Example | A | n | R¹ | B |
|---|---|---|---|---|
| Example 65 | 2-methylbenzofuran-yl | 3 | CH₃ | 3-methylbenzothiophen-yl |

TABLE 6

A—[CH₂]n—NH—CH(CH₃)—(1-naphthyl)

| Example | A | n |
|---|---|---|
| Example 66 | 2-methylfuran-yl | 3 |
| Example 67 | 1,2-dimethylpyrrol-yl (N-CH₃) | 3 |
| Example 68 | 3-methylthiophen-yl | 3 |
| Example 69 | 2-methylthiophen-yl | 3 |
| Example 70 | 3-methylfuran-yl | 3 |
| Example 71 | 2-amino-4-methylthiophen-yl | 3 |

Example 72

Synthesis of 1-(azulen-1-yl)ethylamine

A. Synthesis of 1-(azulen-1-yl)ethanol 1-(Azulen-1-yl)ethanone (13.0 g) prepared according to a method described in the literature (Mori et al., J. Heterocycl. Chem., Vol. 33, 1996, pp. 841-846) was dissolved in dehydrated THF (380 mL), and stirried with cooling on ice under nitrogen atmosphere. This reaction mixture was carefully added with lithium aluminum hydride (1.45 g, Wako Pure Chemical Industries), and stirried with cooling on ice for 1 hour. The reaction mixture was carefully added with 2 N aqueous sodium hydroxide with cooling on ice and stirring. The reaction mixture was added with anhydrous magnesium sulfate, and stirred, then the solid was removed by filtration, and the filtrate was concentrated under reduced pressure. The residue was used for the subsequent reaction as it was.

¹H-NMR (CDCl₃); δ (ppm) 1.74 (3H, d, J=6.6), 5.61 (1H, q, J=6.6), 7.17 (2H, q, J=9.3), 7.35 (1H, d, J=4.2), 7.99 (1H, d, J=4.2), 8.32 (1H, d, J=9.9), 8.54 (1H, d, J=9.9)

B. Synthesis of 2-[1-(azulen-1-yl)ethyl]-isoindole-1,3-dione

The crude 1-(azulen-1-yl)ethanol prepared in Example 72, Step A was dissolved in dehydrated THF (380 mL), and stirred with cooling on ice under nitrogen atmosphere. This reaction mixture was added with phthalimide (45.0 g, Kanto Kagaku), tri-n-butylphosphine (37.7 mL, Kanto Kagaku), and 1,1'-azobis(N,N'-dimethylformamide) (26.3 g, Midori Kagaku), and stirred at room temperature for 16 hours under nitrogen atmosphere. The solid was removed by filtration, and the filtrate was concentrated under reduced pressure. The residue was added with saturated aqueous sodium hydrogencarbonate, and extracted with ethyl acetate. The organic layer was washed with saturated brine, and dried over anhydrous sodium sulfate, and the solvent was evaporated under reduced pressure. The residue was purified by silica gel chromatography (hexane:ethyl acetate=6:1), to obtain 16.8 g of the title compound.

¹H-NMR (CDCl₃); δ (ppm) 2.11 (3H, d, J=7.2), 6.30 (1H, q, J=7.2), 7.11-7.29 (2H, m), 7.39 (1H, d, J=4.2), 7.74-7.77 (2H, m), 7.83-7.86 (2H, m), 8.31 (1H, d, J=9.7), 8.39 (1H, d, J=4.2), 8.43 (1H, d, J=9.7)

C. Synthesis of 1-azulen-1-yl-ethylamine

2-[1-(Azulen-1-yl)ethyl]-isoindole-1,3-dione (16.8 g) prepared in Example 72, Step B was dissolved in ethanol (400 mL), added with hydrazine monohydrate (3.1 g, Wako Pure Chemical Industries), and stirred at 30° C. for 72 hours. The solid was removed by filtration, and the filtrate was concentrated under reduced pressure. The residue was added with saturated aqueous sodium hydrogencarbonate, and extracted with chloroform. The organic layer was dried over anhydrous sodium sulfate, and the solvent was evaporated under reduced pressure. The residue was purified by NH silica gel chromatography (NH-DM1020, Fuji Silysia, hexane:ethyl acetate=3:1-1:1) to obtain 9.26 g of the title compound.

¹H-NMR (CDCl₃); δ (ppm) 1.60 (3H, d, J=6.6), 4.85 (1H, q, J=6.6), 7.12 (2H, q, J=9.3), 7.36 (1H, d, J=3.6), 7.56 (1H, t, J=9.9), 7.98 (1H, d, J=3.6), 8.29 (1H, d, J=9.6), 8.43 (1H, d, J=9.6)

HPLC

Retention time: 8.82 minutes for S-isomer and 10.09 minutes for R-isomer

Column: CHIRALCEL OJ (trade name of Daicel Chemical Industries, 4.6 mm ID×250 mm)

Solvent: hexane/ethanol=50/50

Flow rate: 0.5 ml/min

Detection wavelength: 254 nm, 25° C.

Example 73

[1-(Azulen-1-yl)ethyl]-[3-(6-phenylpyridin-2-yl)propyl]amine hydrochloride

Dehydrated methylene chloride (2 mL) was added with 3-(6-phenylpyridin-2-yl)propane aldehyde (52.5 mg), [1-(azulen-1-yl)ethyl]amine (63.3 mg), and sodium triacetoxyborohydride (158.9 mg, Aldrich), and stirred at room temperature for 72 hours. The reaction mixture was added with 2 N sodium hydroxide, and extracted with chloroform. The organic layer was dried over sodium sulfate, and the solvent was evaporated under reduced pressure. The residue was purified by silica gel chromatography (chloroform:methanol=15:1) to obtain 63.2 mg of the title compound in the free form. This compound was dissolved in chloroform, and added with 0.1 N solution of hydrochloric acid in methanol (1.7 mL), and the solvent was evaporated under reduced pressure to obtain 69.3 mg of the title compound.

$^1$H-NMR (DMSO-$d_6$); δ (ppm) 1.70 (3H, d, J=6.6), 2.03-2.56 (2H, m), 2.51-2.92 (4H, m), 4.53 (1H, brs), 5.15 (1H, s), 7.29-7.46 (2H, m), 7.47-7.48 (4H, m), 7.43-7.82 (4H, m), 8.30-8.34 (1H, m), 8.48 (1H, d, J=9.3), 8.75 (1H, d, J=9.9), 9.26 (1H, brs), 9.72 (1H, brs)

Example 74

Synthesis of [1-(azulen-1-yl)ethyl]-{3-[5-(4-trifluoromethoxyphenyl)furan-2-yl]propyl}amine hydrochloride 3-[5-(4-Trifluoromethoxyphenyl)furan-2-yl]propane aldehyde (44.3 mg), and [1-(azulen-1-yl)ethyl]amine (27.4 mg) were dissolved in dehydrated ethanol (1 mL), and this solution was added with titanium tetraisopropoxide (70.8 μL, Kanto Kagaku), and stirred at 40° C. for 2 hours. The reaction mixture was further added with sodium borohydride (10 mg, Wako Pure Chemical Industries), and stirred at room temperature for 1 hour. The reaction mixture was added with saturated aqueous sodium hydrogencarbonate, and extracted with chloroform. The organic layer was dried over anhydrous sodium sulfate, and the solvent was evaporated under reduced pressure. The residue was purified by silica gel column chromatography (chloroform:methanol=30:1-20:1) to obtain 43.2 mg of the title compound in the free form. This compound was dissolved in chloroform, and added with 0.1 N solution of hydrochloric acid in ethanol (980 μL), and the solvent was evaporated under reduced pressure to obtain 46.0 mg of the title compound.

$^1$H-NMR (compound in the free form, CDCl$_3$); δ (ppm) 2.06 (3H, d, J=6.9), 2.26-2.31 (2H, m), 2.56-2.76 (4H, m), 5.00 (1H, brs), 5.56 (1H, d, J=3.3), 6.31 (1H, d, J=3.3), 7.09 (2H, d, J=8.4), 7.21-7.27 (1H, m), 7.39-7.44 (4H, m), 7.64 (1H, t, J=9.9), 8.32 (2H, t, J=9.6), 8.49 (1H, d, J=3.9), 9.91 (1H, brs), 10.3 (1H, brs)

Example 75

Synthesis of [1-(azulen-1-yl)ethyl]-[3-(2-phenylthiazol-4-yl)propyl]amine hydrochloride 3-(2-Phenylthiazol-4-yl)propane aldehyde (60.9 mg), and [1-(azulen-1-yl)ethyl]amine (43.4 mg) were dissolved in dehydrated ethanol (3 mL), and stirred at room temperature for 2 hours under nitrogen atmosphere. The reaction mixture was cooled on ice, added with sodium borohydride (33.0 mg, Wako Pure Chemical Industries), and stirred at room temperature for 30 minutes. The reaction mixture was poured with saturated aqueous sodium hydrogencarbonate, and extracted with chloroform. The organic layer was dried over anhydrous sodium sulfate, and the solvent was evaporated under reduced pressure. The residue was purified by silica gel chromatography (chloroform:methanol=15:1) to obtain 82.5 mg of the title compound in the free form. This compound was dissolved in chloroform, and added with 0.1 N solution of hydrochloric acid in ethanol, and the solvent was evaporated under reduced pressure to obtain 90.5 mg of the title compounds.

$^1$H-NMR (CDCl$_3$); δ (ppm) 1.83 (3H, d, J=6.9), 2.26-2.36 (2H, m), 3.05-3.12 (3H, m), 3.19-3.28 (1H, m), 4.95 (1H, brs), 7.22 (1H, dt, J=4.5, 9.8), 7.27-7.32 (1H, m), 7.49-7.67 (7H, m), 7.86 (1H, t, J=8.1), 7.95 (2H, dd, J=1.5, 8.4), 8.14 (1H, d, J=4.2), 8.27 (1H, d, J=9.9), 8.31 (1H, d, J=9.3), 10.1 (1H, brs), 10.7 (1H, brs)

The compounds of Examples 76 to 785 shown in Tables 7 and 8 (in the table, example numbers are shown in the columns of "Exp-No", reaction regents are shown in the columns of "regent", and compounds of examples are shown in the columns of "ex-comp") were obtained by using any of the various aldehydes (al-1) to (al-355) represented by the aforementioned formula (10) and any of the various amines (ami-1) to (ami-21) represented by the aforementioned formula (8) in the same manner as in Example 73 as shown in the following equation with carrying out deprotection, if deprotection was necessary. A in the formula represents any of (A-1) to (A-590) mentioned above, and B in the formula represents any of (B-1) to (B-21) mentioned above. Liquid chromatography mass spectrometry (LC-MS) spectra of the compounds mentioned in Tables 7 and 8 were measured to confirm that the objective compounds were produced.

TABLE 7

$$(al\text{-}1)\sim(al\text{-}355) \xrightarrow{(ami\text{-}1)\sim(ami\text{-}21)} A\underset{\underset{CH_3}{|}}{\overset{H}{\underset{|}{N}}}B$$

(1A)

| exp-No | regent | | ex-comp | |
|---|---|---|---|---|
| | al | ami | A | B |
| 76 | al-1 | ami-1 | A-1 | B-1 |
| 77 | al-2 | ami-1 | A-2 | B-1 |
| 78 | al-3 | ami-1 | A-3 | B-1 |
| 79 | al-4 | ami-1 | A-4 | B-1 |
| 80 | al-5 | ami-1 | A-5 | B-1 |
| 81 | al-6 | ami-1 | A-6 | B-1 |
| 82 | al-7 | ami-1 | A-7 | B-1 |
| 83 | al-8 | ami-1 | A-8 | B-1 |
| 84 | al-9 | ami-1 | A-9 | B-1 |
| 85 | al-10 | ami-1 | A-10 | B-1 |
| 86 | al-11 | ami-1 | A-11 | B-1 |
| 87 | al-12 | ami-1 | A-12 | B-1 |
| 88 | al-13 | ami-1 | A-13 | B-1 |
| 89 | al-14 | ami-1 | A-14 | B-1 |
| 90 | al-15 | ami-1 | A-15 | B-1 |
| 91 | al-16 | ami-1 | A-16 | B-1 |
| 92 | al-17 | ami-1 | A-17 | B-1 |
| 93 | al-18 | ami-1 | A-18 | B-1 |
| 94 | al-19 | ami-1 | A-19 | B-1 |
| 95 | al-20 | ami-1 | A-20 | B-1 |
| 96 | al-21 | ami-1 | A-21 | B-1 |
| 97 | al-22 | ami-1 | A-22 | B-1 |
| 98 | al-23 | ami-1 | A-23 | B-1 |
| 99 | al-24 | ami-1 | A-24 | B-1 |
| 100 | al-25 | ami-1 | A-25 | B-1 |
| 101 | al-26 | ami-1 | A-26 | B-1 |

TABLE 7-continued $$(al\text{-}1)\sim(al\text{-}355) \xrightarrow{(ami\text{-}1)\sim(ami\text{-}21)} A\underset{(\text{CH}_3)}{\overset{H}{\underset{|}{\text{N}}}}B$$

(1A)

| exp-No | regent al | regent ami | ex-comp A | ex-comp B |
|---|---|---|---|---|
| 102 | al-27 | ami-1 | A-27 | B-1 |
| 103 | al-28 | ami-1 | A-28 | B-1 |
| 104 | al-29 | ami-1 | A-29 | B-1 |
| 105 | al-30 | ami-1 | A-30 | B-1 |
| 106 | al-31 | ami-1 | A-31 | B-1 |
| 107 | al-32 | ami-1 | A-32 | B-1 |
| 108 | al-33 | ami-1 | A-33 | B-1 |
| 109 | al-34 | ami-1 | A-34 | B-1 |
| 110 | al-35 | ami-1 | A-35 | B-1 |
| 111 | al-36 | ami-1 | A-36 | B-1 |
| 112 | al-37 | ami-1 | A-37 | B-1 |
| 113 | al-38 | ami-1 | A-38 | B-1 |
| 114 | al-39 | ami-1 | A-39 | B-1 |
| 115 | al-40 | ami-1 | A-40 | B-1 |
| 116 | al-41 | ami-1 | A-41 | B-1 |
| 117 | al-42 | ami-1 | A-42 | B-1 |
| 118 | al-43 | ami-1 | A-43 | B-1 |
| 119 | al-44 | ami-1 | A-44 | B-1 |
| 120 | al-45 | ami-1 | A-A5 | B-1 |
| 121 | al-46 | ami-1 | A-46 | B-1 |
| 122 | al-47 | ami-1 | A-47 | B-1 |
| 123 | al-48 | ami-1 | A-48 | B-1 |
| 124 | al-49 | ami-1 | A-49 | B-1 |
| 125 | al-50 | ami-1 | A-50 | B-1 |
| 126 | al-51 | ami-1 | A-51 | B-1 |
| 127 | al-52 | ami-1 | A-52 | B-1 |
| 128 | al-53 | ami-1 | A-53 | B-1 |
| 129 | al-54 | ami-1 | A-54 | B-1 |
| 130 | al-55 | ami-1 | A-55 | B-1 |
| 131 | al-56 | ami-1 | A-56 | B-1 |
| 132 | al-57 | ami-1 | A-57 | B-1 |
| 133 | al-58 | ami-1 | A-58 | B-1 |
| 134 | al-59 | ami-1 | A-59 | B-1 |
| 135 | al-60 | ami-1 | A-60 | B-1 |
| 136 | al-61 | ami-1 | A-61 | B-1 |
| 137 | al-62 | ami-1 | A-62 | B-1 |
| 138 | al-63 | ami-1 | A-63 | B-1 |
| 139 | al-64 | ami-1 | A-64 | B-1 |
| 140 | al-65 | ami-1 | A-65 | B-1 |
| 141 | al-66 | ami-1 | A-66 | B-1 |
| 142 | al-67 | ami-1 | A-67 | B-1 |
| 143 | al-68 | ami-1 | A-68 | B-1 |
| 144 | al-69 | ami-1 | A-69 | B-1 |
| 145 | al-70 | ami-1 | A-70 | B-1 |
| 146 | al-71 | ami-1 | A-71 | B-1 |
| 147 | al-72 | ami-1 | A-72 | B-1 |
| 148 | al-73 | ami-1 | A-73 | B-1 |
| 149 | al-74 | ami-1 | A-74 | B-1 |
| 150 | al-75 | ami-1 | A-75 | B-1 |
| 151 | al-76 | ami-1 | A-76 | B-1 |
| 152 | al-77 | ami-1 | A-77 | B-1 |
| 153 | al-78 | ami-1 | A-78 | B-1 |
| 154 | al-79 | ami-1 | A-79 | B-1 |
| 155 | al-80 | ami-1 | A-80 | B-1 |
| 156 | al-81 | ami-1 | A-81 | B-1 |
| 157 | al-82 | ami-1 | A-82 | B-1 |
| 158 | al-83 | ami-1 | A-83 | B-1 |
| 159 | al-84 | ami-1 | A-84 | B-1 |
| 160 | al-85 | ami-1 | A-85 | B-1 |
| 161 | al-86 | ami-1 | A-86 | B-1 |
| 162 | al-87 | ami-1 | A-87 | B-1 |
| 163 | al-88 | ami-1 | A-88 | B-1 |
| 164 | al-89 | ami-1 | A-89 | B-1 |
| 165 | al-90 | ami-1 | A-90 | B-1 |
| 166 | al-91 | ami-1 | A-91 | B-1 |
| 167 | al-92 | ami-1 | A-92 | B-1 |
| 168 | al-93 | ami-1 | A-93 | B-1 |
| 169 | al-94 | ami-1 | A-94 | B-1 |
| 170 | al-95 | ami-1 | A-95 | B-1 |
| 171 | al-96 | ami-1 | A-96 | B-1 |
| 172 | al-97 | ami-1 | A-97 | B-1 |
| 173 | al-98 | ami-1 | A-98 | B-1 |
| 174 | al-99 | ami-1 | A-99 | B-1 |
| 175 | al-100 | ami-1 | A-100 | B-1 |
| 176 | al-101 | ami-1 | A-101 | B-1 |
| 177 | al-102 | ami-1 | A-102 | B-1 |
| 178 | al-103 | ami-1 | A-103 | B-1 |
| 179 | al-104 | ami-1 | A-104 | B-1 |
| 180 | al-105 | ami-1 | A-105 | B-1 |
| 181 | al-106 | ami-1 | A-106 | B-1 |
| 182 | al-107 | ami-1 | A-107 | B-1 |
| 183 | al-108 | ami-1 | A-108 | B-1 |
| 184 | al-109 | ami-1 | A-109 | B-1 |
| 185 | al-110 | ami-1 | A-110 | B-1 |
| 186 | al-111 | ami-1 | A-111 | B-1 |
| 187 | al-112 | ami-1 | A-112 | B-1 |
| 188 | al-113 | ami-1 | A-113 | B-1 |
| 189 | al-114 | ami-1 | A-114 | B-1 |
| 190 | al-115 | ami-1 | A-115 | B-1 |
| 191 | al-116 | ami-1 | A-116 | B-1 |
| 192 | al-117 | ami-1 | A-117 | B-1 |
| 193 | al-118 | ami-1 | A-118 | B-1 |
| 194 | al-119 | ami-1 | A-119 | B-1 |
| 195 | al-120 | ami-1 | A-120 | B-1 |
| 196 | al-121 | ami-1 | A-121 | B-1 |
| 197 | al-122 | ami-1 | A-122 | B-1 |
| 198 | al-123 | ami-1 | A-123 | B-1 |
| 199 | al-124 | ami-1 | A-124 | B-1 |
| 200 | al-125 | ami-1 | A-125 | B-1 |
| 201 | al-126 | ami-1 | A-126 | B-1 |
| 202 | al-127 | ami-1 | A-127 | B-1 |
| 203 | al-128 | ami-1 | A-128 | B-1 |
| 204 | al-129 | ami-1 | A-129 | B-1 |
| 205 | al-130 | ami-1 | A-130 | B-1 |
| 206 | al-131 | ami-1 | A-131 | B-1 |
| 207 | al-132 | ami-1 | A-132 | B-1 |
| 208 | al-133 | ami-1 | A-133 | B-1 |
| 209 | al-134 | ami-1 | A-134 | B-1 |
| 210 | al-135 | ami-1 | A-135 | B-1 |
| 211 | al-136 | ami-1 | A-136 | B-1 |
| 212 | al-137 | ami-1 | A-137 | B-1 |
| 213 | al-138 | ami-1 | A-138 | B-1 |
| 214 | al-139 | ami-1 | A-139 | B-1 |
| 215 | al-140 | ami-1 | A-140 | B-1 |
| 216 | al-141 | ami-1 | A-141 | B-1 |
| 217 | al-142 | ami-1 | A-142 | B-1 |
| 218 | al-143 | ami-1 | A-143 | B-1 |
| 219 | al-144 | ami-1 | A-144 | B-1 |
| 220 | al-145 | ami-1 | A-145 | B-1 |
| 221 | al-146 | ami-1 | A-146 | B-1 |
| 222 | al-147 | ami-1 | A-147 | B-1 |
| 223 | al-148 | ami-1 | A-148 | B-1 |
| 224 | al-149 | ami-1 | A-149 | B-1 |
| 225 | al-150 | ami-1 | A-150 | B-1 |
| 226 | al-151 | ami-1 | A-151 | B-1 |
| 227 | al-152 | ami-1 | A-152 | B-1 |
| 228 | al-153 | ami-1 | A-153 | B-1 |
| 229 | al-154 | ami-1 | A-154 | B-1 |
| 230 | al-155 | ami-1 | A-155 | B-1 |
| 231 | al-156 | ami-1 | A-156 | B-1 |
| 232 | al-157 | ami-1 | A-157 | B-1 |
| 233 | al-158 | ami-1 | A-158 | B-1 |
| 234 | al-159 | ami-1 | A-159 | B-1 |
| 235 | al-160 | ami-1 | A-160 | B-1 |

TABLE 7-continued

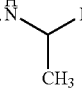

(1A)

| exp-No | regent | | ex-comp | |
|---|---|---|---|---|
| | al | ami | A | B |
| 236 | al-161 | ami-1 | A-161 | B-1 |
| 237 | al-162 | ami-1 | A-162 | B-1 |
| 238 | al-163 | ami-1 | A-163 | B-1 |
| 239 | al-164 | ami-1 | A-164 | B-1 |
| 240 | al-165 | ami-1 | A-165 | B-1 |
| 241 | al-166 | ami-1 | A-166 | B-1 |
| 242 | al-167 | ami-1 | A-167 | B-1 |
| 243 | al-168 | ami-1 | A-168 | B-1 |
| 244 | al-169 | ami-1 | A-169 | B-1 |
| 245 | al-170 | ami-1 | A-170 | B-1 |
| 246 | al-171 | ami-1 | A-171 | B-1 |
| 247 | al-172 | ami-1 | A-172 | B-1 |
| 248 | al-173 | ami-1 | A-173 | B-1 |
| 249 | al-174 | ami-1 | A-174 | B-1 |
| 250 | al-175 | ami-1 | A-175 | B-1 |
| 251 | al-176 | ami-1 | A-176 | B-1 |
| 252 | al-177 | ami-1 | A-177 | B-1 |
| 253 | al-178 | ami-1 | A-178 | B-1 |
| 254 | al-179 | ami-1 | A-179 | B-1 |
| 255 | al-180 | ami-1 | A-180 | B-1 |
| 256 | al-181 | ami-1 | A-181 | B-1 |
| 257 | al-182 | ami-1 | A-182 | B-1 |
| 258 | al-183 | ami-1 | A-183 | B-1 |
| 259 | al-184 | ami-1 | A-184 | B-1 |
| 260 | al-185 | ami-1 | A-185 | B-1 |
| 261 | al-186 | ami-1 | A-186 | B-1 |
| 262 | al-187 | ami-1 | A-187 | B-1 |
| 263 | al-188 | ami-1 | A-188 | B-1 |
| 264 | al-189 | ami-1 | A-189 | B-1 |
| 265 | al-190 | ami-1 | A-190 | B-1 |
| 266 | al-191 | ami-1 | A-191 | B-1 |
| 267 | al-192 | ami-1 | A-192 | B-1 |
| 268 | al-193 | ami-1 | A-193 | B-1 |
| 269 | al-194 | ami-1 | A-194 | B-1 |
| 270 | al-195 | ami-1 | A-195 | B-1 |
| 271 | al-196 | ami-1 | A-196 | B-1 |
| 272 | al-197 | ami-1 | A-197 | B-1 |
| 273 | al-198 | ami-1 | A-198 | B-1 |
| 274 | al-199 | ami-1 | A-199 | B-1 |
| 275 | al-200 | ami-1 | A-200 | B-1 |
| 276 | al-201 | ami-1 | A-201 | B-1 |
| 277 | al-202 | ami-1 | A-202 | B-1 |
| 278 | al-203 | ami-1 | A-203 | B-1 |
| 279 | al-204 | ami-1 | A-204 | B-1 |
| 280 | al-205 | ami-1 | A-205 | B-1 |
| 281 | al-206 | ami-1 | A-206 | B-1 |
| 282 | al-207 | ami-1 | A-207 | B-1 |
| 283 | al-208 | ami-1 | A-208 | B-1 |
| 284 | al-209 | ami-1 | A-209 | B-1 |
| 285 | al-210 | ami-1 | A-210 | B-1 |
| 286 | al-211 | ami-1 | A-211 | B-1 |
| 287 | al-212 | ami-1 | A-212 | B-1 |
| 288 | al-213 | ami-1 | A-213 | B-1 |
| 289 | al-214 | ami-1 | A-214 | B-1 |
| 290 | al-215 | ami-1 | A-215 | B-1 |
| 291 | al-216 | ami-1 | A-216 | B-1 |
| 292 | al-217 | ami-1 | A-217 | B-1 |
| 293 | al-218 | ami-1 | A-218 | B-1 |
| 294 | al-219 | ami-1 | A-219 | B-1 |
| 295 | al-220 | ami-1 | A-220 | B-1 |
| 296 | al-221 | ami-1 | A-221 | B-1 |
| 297 | al-222 | ami-1 | A-222 | B-1 |
| 298 | al-223 | ami-1 | A-223 | B-1 |
| 299 | al-224 | ami-1 | A-224 | B-1 |
| 300 | al-225 | ami-1 | A-225 | B-1 |
| 301 | al-226 | ami-1 | A-226 | B-1 |
| 302 | al-227 | ami-1 | A-227 | B-1 |
| 303 | al-228 | ami-1 | A-228 | B-1 |
| 304 | al-229 | ami-1 | A-229 | B-1 |
| 305 | al-230 | ami-1 | A-230 | B-1 |
| 306 | al-231 | ami-1 | A-231 | B-1 |
| 307 | al-232 | ami-1 | A-232 | B-1 |
| 308 | al-233 | ami-1 | A-233 | B-1 |
| 309 | al-234 | ami-1 | A-234 | B-1 |
| 310 | al-235 | ami-1 | A-235 | B-1 |
| 311 | al-236 | ami-1 | A-236 | B-1 |
| 312 | al-237 | ami-1 | A-237 | B-1 |
| 313 | al-238 | ami-1 | A-238 | B-1 |
| 314 | al-239 | ami-1 | A-239 | B-1 |
| 315 | al-240 | ami-1 | A-240 | B-1 |
| 316 | al-241 | ami-1 | A-241 | B-1 |
| 317 | al-242 | ami-1 | A-242 | B-1 |
| 318 | al-243 | ami-1 | A-243 | B-1 |
| 319 | al-244 | ami-1 | A-244 | B-1 |
| 320 | al-245 | ami-1 | A-245 | B-1 |
| 321 | al-246 | ami-1 | A-246 | B-1 |
| 322 | al-247 | ami-1 | A-247 | B-1 |
| 323 | al-248 | ami-1 | A-248 | B-1 |
| 324 | al-249 | ami-1 | A-249 | B-1 |
| 325 | al-250 | ami-1 | A-250 | B-1 |
| 326 | al-251 | ami-1 | A-251 | B-1 |
| 327 | al-252 | ami-1 | A-252 | B-1 |
| 328 | al-1 | ami-5 | A-1 | B-5 |
| 329 | al-2 | ami-5 | A-2 | B-5 |
| 330 | al-3 | ami-5 | A-3 | B-5 |
| 331 | al-4 | ami-5 | A-4 | B-5 |
| 332 | al-5 | ami-5 | A-5 | B-5 |
| 333 | al-6 | ami-5 | A-6 | B-5 |
| 334 | al-7 | ami-5 | A-7 | B-5 |
| 335 | al-8 | ami-5 | A-8 | B-5 |
| 336 | al-9 | ami-5 | A-9 | B-5 |
| 337 | al-10 | ami-5 | A-10 | B-5 |
| 338 | al-11 | ami-5 | A-11 | B-5 |
| 339 | al-12 | ami-5 | A-12 | B-5 |
| 340 | al-13 | ami-5 | A-13 | B-5 |
| 341 | al-14 | ami-5 | A-14 | B-5 |
| 342 | al-15 | ami-5 | A-15 | B-5 |
| 343 | al-16 | ami-5 | A-16 | B-5 |
| 344 | al-17 | ami-5 | A-17 | B-5 |
| 345 | al-18 | ami-5 | A-18 | B-5 |
| 346 | al-19 | ami-5 | A-19 | B-5 |
| 347 | al-20 | ami-5 | A-20 | B-5 |
| 348 | al-21 | ami-5 | A-21 | B-5 |
| 349 | al-22 | ami-5 | A-22 | B-5 |
| 350 | al-23 | ami-5 | A-23 | B-5 |
| 351 | al-24 | ami-5 | A-24 | B-5 |
| 352 | al-25 | ami-5 | A-25 | B-5 |
| 353 | al-26 | ami-5 | A-26 | B-5 |
| 354 | al-27 | ami-5 | A-27 | B-5 |
| 355 | al-28 | ami-5 | A-28 | B-5 |
| 356 | al-29 | ami-5 | A-29 | B-5 |
| 357 | al-30 | ami-5 | A-30 | B-5 |
| 358 | al-31 | ami-5 | A-31 | B-5 |
| 359 | al-32 | ami-5 | A-32 | B-5 |
| 360 | al-33 | ami-5 | A-33 | B-5 |
| 361 | al-34 | ami-5 | A-34 | B-5 |
| 362 | al-35 | ami-5 | A-35 | B-5 |
| 363 | al-36 | ami-5 | A-36 | B-5 |
| 364 | al-37 | ami-5 | A-37 | B-5 |
| 365 | al-38 | ami-5 | A-38 | B-5 |
| 366 | al-39 | ami-5 | A-39 | B-5 |
| 367 | al-40 | ami-5 | A-40 | B-5 |
| 368 | al-4i | ami-5 | A-41 | B-5 |
| 369 | al-42 | ami-5 | A-42 | B-5 |

TABLE 7-continued (al-1)~(al-355) —(ami-1)~(ami-21)→ (1A)

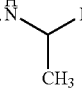

| exp-No | al | ami | A | B |
|---|---|---|---|---|
| 370 | al-43 | ami-5 | A-43 | B-5 |
| 371 | al-44 | ami-5 | A-44 | B-5 |
| 372 | al-45 | ami-5 | A-45 | B-5 |
| 373 | al-46 | ami-5 | A-46 | B-5 |
| 374 | al-47 | ami-5 | A-47 | B-5 |
| 375 | al-48 | ami-5 | A-48 | B-5 |
| 376 | al-49 | ami-5 | A-49 | B-5 |
| 377 | al-50 | ami-5 | A-50 | B-5 |
| 378 | al-51 | ami-5 | A-51 | B-5 |
| 379 | al-52 | ami-5 | A-52 | B-5 |
| 380 | al-53 | ami-5 | A-53 | B-5 |
| 381 | al-54 | ami-5 | A-54 | B-5 |
| 382 | al-55 | ami-5 | A-55 | B-5 |
| 383 | al-56 | ami-5 | A-56 | B-5 |
| 384 | al-57 | ami-5 | A-57 | B-5 |
| 385 | al-58 | ami-5 | A-58 | B-5 |
| 386 | al-59 | ami-5 | A-59 | B-5 |
| 387 | al-60 | ami-5 | A-60 | B-5 |
| 388 | al-61 | ami-5 | A-61 | B-5 |
| 389 | al-62 | ami-5 | A-62 | B-5 |
| 390 | al-63 | ami-5 | A-63 | B-5 |
| 391 | al-64 | ami-5 | A-64 | B-5 |
| 392 | al-65 | ami-5 | A-65 | B-5 |
| 393 | al-66 | ami-5 | A-66 | B-5 |
| 394 | al-67 | ami-5 | A-67 | B-5 |
| 395 | al-68 | ami-5 | A-68 | B-5 |
| 396 | al-69 | ami-5 | A-69 | B-5 |
| 397 | al-70 | ami-5 | A-70 | B-5 |
| 398 | al-71 | ami-5 | A-71 | B-5 |
| 399 | al-72 | ami-5 | A-72 | B-5 |
| 400 | al-73 | ami-5 | A-73 | B-5 |
| 401 | al-74 | ami-5 | A-74 | B-5 |
| 402 | al-75 | ami-5 | A-75 | B-5 |
| 403 | al-76 | ami-5 | A-76 | B-5 |
| 404 | al-77 | ami-5 | A-77 | B-5 |
| 405 | al-78 | ami-5 | A-78 | B-5 |
| 406 | al-79 | ami-5 | A-79 | B-5 |
| 407 | al-80 | ami-5 | A-80 | B-5 |
| 408 | al-81 | ami-5 | A-81 | B-5 |
| 409 | al-82 | ami-5 | A-82 | B-5 |
| 410 | al-83 | ami-5 | A-83 | B-5 |
| 411 | al-84 | ami-5 | A-84 | B-5 |
| 412 | al-85 | ami-5 | A-85 | B-5 |
| 413 | al-86 | ami-5 | A-86 | B-5 |
| 414 | al-87 | ami-5 | A-87 | B-5 |
| 415 | al-88 | ami-5 | A-88 | B-5 |
| 416 | al-89 | ami-5 | A-89 | B-5 |
| 417 | al-90 | ami-5 | A-90 | B-5 |
| 418 | al-91 | ami-5 | A-91 | B-5 |
| 419 | al-92 | ami-5 | A-92 | B-5 |
| 420 | al-93 | ami-5 | A-93 | B-5 |
| 421 | al-94 | ami-5 | A-94 | B-5 |
| 422 | al-95 | ami-5 | A-95 | B-5 |
| 423 | al-96 | ami-5 | A-96 | B-5 |
| 424 | al-97 | ami-5 | A-97 | B-5 |
| 425 | al-98 | ami-5 | A-98 | B-5 |
| 426 | al-99 | ami-5 | A-99 | B-5 |
| 427 | al-100 | ami-5 | A-100 | B-5 |
| 428 | al-101 | ami-5 | A-101 | B-5 |
| 429 | al-102 | ami-5 | A-102 | B-5 |
| 430 | al-103 | ami-5 | A-103 | B-5 |
| 431 | al-104 | ami-5 | A-104 | B-5 |
| 432 | al-105 | ami-5 | A-105 | B-5 |
| 433 | al-106 | ami-5 | A-106 | B-5 |
| 434 | al-107 | ami-5 | A-107 | B-5 |
| 435 | al-108 | ami-5 | A-108 | B-5 |
| 436 | al-109 | ami-5 | A-109 | B-5 |
| 437 | al-110 | ami-5 | A-110 | B-5 |
| 438 | al-111 | ami-5 | A-111 | B-5 |
| 439 | al-112 | ami-5 | A-112 | B-5 |
| 440 | al-113 | ami-5 | A-113 | B-5 |
| 441 | al-114 | ami-5 | A-114 | B-5 |
| 442 | al-115 | ami-5 | A-115 | B-5 |
| 443 | al-1h6 | ami-5 | A-116 | B-5 |
| 444 | al-117 | ami-5 | A-117 | B-5 |
| 445 | al-118 | ami-5 | A-118 | B-5 |
| 446 | al-119 | ami-5 | A-119 | B-5 |
| 447 | al-120 | ami-5 | A-120 | B-5 |
| 448 | al-121 | ami-5 | A-121 | B-5 |
| 449 | al-122 | ami-5 | A-122 | B-5 |
| 450 | al-123 | ami-5 | A-123 | B-5 |
| 451 | al-124 | ami-5 | A-124 | B-5 |
| 452 | al-125 | ami-5 | A-125 | B-5 |
| 453 | al-126 | ami-5 | A-126 | B-5 |
| 454 | al-127 | ami-5 | A-127 | B-5 |
| 455 | al-128 | ami-5 | A-128 | B-5 |
| 456 | al-129 | ami-5 | A-129 | B-5 |
| 457 | al-130 | ami-5 | A-130 | B-5 |
| 458 | al-131 | ami-5 | A-131 | B-5 |
| 459 | al-132 | ami-5 | A-132 | B-5 |
| 460 | al-133 | ami-5 | A-133 | B-5 |
| 461 | al-134 | ami-5 | A-134 | B-5 |
| 462 | al-135 | ami-5 | A-135 | B-5 |
| 463 | al-136 | ami-5 | A-136 | B-5 |
| 464 | al-137 | ami-5 | A-137 | B-5 |
| 465 | al-138 | ami-5 | A-138 | B-5 |
| 466 | al-139 | ami-5 | A-139 | B-5 |
| 467 | al-140 | ami-5 | A-140 | B-5 |
| 468 | al-141 | ami-5 | A-141 | B-5 |
| 469 | al-142 | ami-5 | A-142 | B-5 |
| 470 | al-143 | ami-5 | A-143 | B-5 |
| 471 | al-144 | ami-5 | A-144 | B-5 |
| 472 | al-145 | ami-5 | A-145 | B-5 |
| 473 | al-146 | ami-5 | A-146 | B-5 |
| 474 | al-147 | ami-5 | A-147 | B-5 |
| 475 | al-148 | ami-5 | A-148 | B-5 |
| 476 | al-149 | ami-5 | A-149 | B-5 |
| 477 | al-150 | ami-5 | A-150 | B-5 |
| 478 | al-151 | ami-5 | A-151 | B-5 |
| 479 | al-152 | ami-5 | A-152 | B-5 |
| 480 | al-153 | ami-5 | A-153 | B-5 |
| 481 | al-154 | ami-5 | A-154 | B-5 |
| 482 | al-155 | ami-5 | A-155 | B-5 |
| 483 | al-156 | ami-5 | A-156 | B-5 |
| 484 | al-157 | ami-5 | A-157 | B-5 |
| 485 | al-158 | ami-5 | A-158 | B-5 |
| 486 | al-159 | ami-5 | A-159 | B-5 |
| 487 | al-160 | ami-5 | A-160 | B-5 |
| 488 | al-161 | ami-5 | A-161 | B-5 |
| 489 | al-162 | ami-5 | A-162 | B-5 |
| 490 | al-163 | ami-5 | A-163 | B-5 |
| 491 | al-164 | ami-5 | A-164 | B-5 |
| 492 | al-165 | ami-5 | A-165 | B-5 |
| 493 | al-166 | ami-5 | A-166 | B-5 |
| 494 | al-167 | ami-5 | A-167 | B-5 |
| 495 | al-168 | ami-5 | A-168 | B-5 |
| 496 | al-169 | ami-5 | A-169 | B-5 |
| 497 | al-170 | ami-5 | A-170 | B-5 |
| 498 | al-171 | ami-5 | A-171 | B-5 |
| 499 | al-172 | ami-5 | A-172 | B-5 |
| 500 | al-173 | ami-5 | A-173 | B-5 |
| 501 | al-174 | ami-5 | A-174 | B-5 |
| 502 | al-175 | ami-5 | A-175 | B-5 |
| 503 | al-176 | ami-5 | A-176 | B-5 |

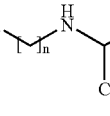

TABLE 7-continued (al-1)~(al-355) (ami-1)~(ami-21) → (1A)

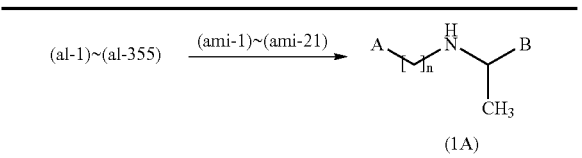

| exp-No | regent al | regent ami | ex-comp A | ex-comp B |
|---|---|---|---|---|
| 504 | al-177 | ami-5 | A-177 | B-5 |
| 5O5 | al-178 | ami-5 | A-178 | B-5 |
| 506 | al-179 | ami-5 | A-179 | B-5 |
| 507 | al-180 | ami-5 | A-180 | B-5 |
| 508 | al-181 | ami-5 | A-181 | B-5 |
| 509 | al-182 | ami-5 | A-182 | B-5 |
| 510 | al-183 | ami-5 | A-183 | B-5 |
| 511 | al-184 | ami-5 | A-184 | B-5 |
| 512 | al-185 | ami-5 | A-185 | B-5 |
| 513 | al-186 | ami-5 | A-186 | B-5 |
| 514 | al-187 | ami-5 | A-187 | B-5 |
| 515 | al-188 | ami-5 | A-188 | B-5 |
| 516 | al-189 | ami-5 | A-189 | B-5 |
| 517 | al-190 | ami-5 | A-190 | B-5 |
| 518 | al-19i | ami-5 | A-191 | B-5 |
| 519 | al-192 | ami-5 | A-192 | B-5 |
| 520 | al-193 | ami-5 | A-193 | B-5 |
| 521 | al-194 | ami-5 | A-194 | B-5 |
| 522 | al-195 | ami-5 | A-195 | B-5 |
| 523 | al-196 | ami-5 | A-196 | B-5 |
| 524 | al-197 | ami-5 | A-197 | B-5 |
| 525 | al-198 | ami-5 | A-198 | B-5 |
| 526 | al-199 | ami-5 | A-199 | B-5 |
| 527 | al-200 | ami-5 | A-200 | B-5 |
| 528 | al-201 | ami-5 | A-201 | B-5 |
| 529 | al-202 | ami-5 | A-202 | B-5 |
| 530 | al-203 | ami-5 | A-203 | B-5 |
| 531 | al-204 | ami-5 | A-204 | B-5 |
| 532 | al-205 | ami-5 | A-205 | B-5 |
| 533 | al-206 | ami-5 | A-206 | B-5 |
| 534 | al-207 | ami-5 | A-207 | B-5 |
| 535 | al-208 | ami-5 | A-208 | B-5 |
| 536 | al-209 | ami-5 | A-209 | B-5 |
| 537 | al-210 | ami-5 | A-210 | B-5 |
| 538 | al-211 | ami-5 | A-211 | B-5 |
| 539 | al-212 | ami-5 | A-212 | B-5 |
| 540 | al-213 | ami-5 | A-213 | B-5 |
| 541 | al-214 | ami-5 | A-214 | B-5 |
| 542 | al-215 | ami-5 | A-215 | B-5 |
| 543 | al-216 | ami-5 | A-216 | B-5 |
| 544 | al-217 | ami-5 | A-217 | B-5 |
| 545 | al-218 | ami-5 | A-218 | B-5 |
| 546 | al-219 | ami-5 | A-219 | B-5 |
| 547 | al-220 | ami-5 | A-220 | B-5 |
| 548 | al-221 | ami-5 | A-221 | B-5 |
| 549 | al-222 | ami-5 | A-222 | B-5 |
| 550 | al-223 | ami-5 | A-223 | B-5 |
| 551 | al-224 | ami-5 | A-224 | B-5 |
| 552 | al-225 | ami-5 | A-225 | B-5 |
| 553 | al-226 | ami-5 | A-226 | B-5 |
| 554 | al-227 | ami-5 | A-227 | B-5 |
| 555 | al-228 | ami-5 | A-228 | B-5 |
| 556 | al-229 | ami-5 | A-229 | B-5 |
| 557 | al-230 | ami-5 | A-230 | B-5 |
| 558 | al-231 | ami-5 | A-231 | B-5 |
| 559 | al-232 | ami-5 | A-232 | B-5 |
| 560 | al-233 | ami-5 | A-233 | B-5 |
| 561 | al-234 | ami-5 | A-234 | B-5 |
| 562 | al-235 | ami-5 | A-235 | B-5 |
| 563 | al-236 | ami-5 | A-236 | B-5 |
| 564 | al-237 | ami-5 | A-237 | B-5 |
| 565 | al-238 | ami-5 | A-238 | B-5 |
| 566 | al-239 | ami-5 | A-239 | B-5 |
| 567 | al-240 | ami-5 | A-240 | B-5 |
| 568 | al-241 | ami-5 | A-241 | B-5 |
| 569 | al-242 | ami-5 | A-242 | B-5 |
| 570 | al-243 | ami-5 | A-243 | B-5 |

TABLE 7-continued (al-1)~(al-355) (ami-1)~(ami-21) → (1A)

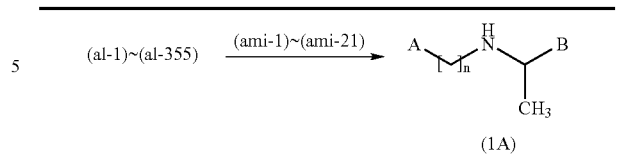

| exp-No | regent al | regent ami | ex-comp A | ex-comp B |
|---|---|---|---|---|
| 571 | al-244 | ami-5 | A-244 | B-5 |
| 572 | al-245 | ami-5 | A-245 | B-5 |
| 573 | al-246 | ami-5 | A-246 | B-5 |
| 574 | al-247 | ami-5 | A-247 | B-5 |
| 575 | al-248 | ami-5 | A-248 | B-5 |
| 576 | al-249 | ami-5 | A-249 | B-5 |
| 577 | al-250 | ami-5 | A-250 | B-5 |
| 578 | al-251 | ami-5 | A-251 | B-5 |
| 579 | al-252 | ami-5 | A-252 | B-5 |

TABLE 8

| exp-No | regent al | regent ami | ex-comp A | ex-comp B |
|---|---|---|---|---|
| 580 | al-253 | ami-1 | A-380 | B-1 |
| 581 | al-254 | ami-1 | A-381 | B-1 |
| 582 | al-255 | ami-1 | A-382 | B-1 |
| 583 | al-256 | ami-1 | A-383 | B-1 |
| 584 | al-257 | ami-1 | A-384 | B-1 |
| 585 | al-258 | ami-1 | A-385 | B-1 |
| 586 | al-259 | ami-1 | A-386 | B-1 |
| 587 | al-260 | ami-1 | A-387 | B-1 |
| 588 | al-261 | ami-1 | A-388 | B-1 |
| 589 | al-262 | ami-1 | A-389 | B-1 |
| 590 | al-263 | ami-1 | A-390 | B-1 |
| 591 | al-264 | ami-1 | A-391 | B-1 |
| 592 | al-265 | ami-1 | A-396 | B-1 |
| 593 | al-266 | ami-1 | A-397 | B-1 |
| 594 | al-267 | ami-1 | A-398 | B-1 |
| 595 | al-268 | ami-1 | A-399 | B-1 |
| 596 | al-269 | ami-1 | A-409 | B-1 |
| 597 | al-270 | ami-1 | A-410 | B-1 |
| 598 | al-271 | ami-1 | A-411 | B-1 |
| 599 | al-272 | ami-1 | A-412 | B-1 |
| 600 | al-273 | ami-1 | A-413 | B-1 |
| 601 | al-274 | ami-1 | A-414 | B-1 |
| 602 | al-275 | ami-1 | A-415 | B-1 |
| 603 | al-276 | ami-1 | A-416 | B-1 |
| 604 | al-277 | ami-1 | A-417 | B-1 |
| 605 | al-278 | ami-1 | A-418 | B-1 |
| 606 | al-279 | ami-1 | A-419 | B-1 |
| 607 | al-280 | ami-1 | A-420 | B-1 |
| 608 | al-281 | ami-1 | A-421 | B-1 |
| 609 | al-282 | ami-1 | A-422 | B-1 |
| 610 | al-283 | ami-1 | A-423 | B-1 |
| 611 | al-284 | ami-1 | A-424 | B-1 |
| 612 | al-285 | ami-1 | A-425 | B-1 |
| 613 | al-286 | ami-1 | A-426 | B-1 |
| 614 | al-287 | ami-1 | A-522 | B-1 |
| 615 | al-288 | ami-1 | A-523 | B-1 |
| 616 | al-289 | ami-1 | A-524 | B-1 |
| 617 | al-290 | ami-1 | A-525 | B-1 |
| 618 | al-291 | ami-1 | A-526 | B-1 |
| 619 | al-292 | ami-1 | A-527 | B-1 |
| 620 | al-293 | ami-1 | A-528 | B-1 |
| 621 | al-294 | ami-1 | A-529 | B-1 |
| 622 | al-295 | ami-1 | A-530 | B-1 |
| 623 | al-296 | ami-1 | A-531 | B-1 |
| 624 | al-297 | ami-1 | A-532 | B-1 |
| 625 | al-298 | ami-1 | A-533 | B-1 |
| 626 | al-299 | ami-1 | A-534 | B-1 |
| 627 | al-300 | ami-1 | A-535 | B-1 |
| 628 | al-301 | ami-1 | A-536 | B-1 |

TABLE 8-continued

| | regent | | ex-comp | |
|---|---|---|---|---|
| exp-No | al | ami | A | B |
| 629 | al-302 | ami-1 | A-537 | B-1 |
| 630 | al-303 | ami-1 | A-538 | B-1 |
| 631 | al-304 | ami-1 | A-539 | B-1 |
| 632 | al-305 | ami-1 | A-540 | B-1 |
| 633 | al-306 | ami-1 | A-541 | B-1 |
| 634 | al-307 | ami-1 | A-542 | B-1 |
| 635 | al-308 | ami-1 | A-543 | B-1 |
| 636 | al-309 | ami-1 | A-544 | B-1 |
| 637 | al-310 | ami-1 | A-545 | B-1 |
| 638 | al-311 | ami-1 | A-546 | B-1 |
| 639 | al-312 | ami-1 | A-547 | B-1 |
| 640 | al-313 | ami-1 | A-548 | B-1 |
| 641 | al-314 | ami-1 | A-549 | B-1 |
| 642 | al-315 | ami-1 | A-550 | B-1 |
| 643 | al-316 | ami-1 | A-551 | B-1 |
| 644 | al-317 | ami-1 | A-552 | B-1 |
| 645 | al-318 | ami-1 | A-553 | B-1 |
| 646 | al-319 | ami-1 | A-554 | B-1 |
| 647 | al-320 | ami-1 | A-555 | B-1 |
| 648 | al-321 | ami-1 | A-556 | B-1 |
| 649 | al-322 | ami-1 | A-557 | B-1 |
| 650 | al-323 | ami-1 | A-558 | B-1 |
| 651 | al-324 | ami-1 | A-559 | B-1 |
| 652 | al-325 | ami-1 | A-560 | B-1 |
| 653 | al-326 | ami-1 | A-561 | B-1 |
| 654 | al-327 | ami-1 | A-562 | B-1 |
| 655 | al-328 | ami-1 | A-563 | B-1 |
| 656 | al-329 | ami-1 | A-564 | B-1 |
| 657 | al-330 | ami-1 | A-565 | B-1 |
| 658 | al-331 | ami-1 | A-566 | B-1 |
| 659 | al-332 | ami-1 | A-567 | B-1 |
| 660 | al-333 | ami-1 | A-568 | B-1 |
| 661 | al-334 | ami-1 | A-569 | B-1 |
| 662 | al-335 | ami-1 | A-570 | B-1 |
| 663 | al-336 | ami-1 | A-571 | B-1 |
| 664 | al-337 | ami-1 | A-572 | B-1 |
| 665 | al-338 | ami-1 | A-573 | B-1 |
| 666 | al-339 | ami-1 | A-574 | B-1 |
| 667 | al-340 | ami-1 | A-575 | B-1 |
| 668 | al-341 | ami-1 | A-576 | B-1 |
| 669 | al-342 | ami-1 | A-577 | B-1 |
| 670 | al-343 | ami-1 | A-578 | B-1 |
| 671 | al-344 | ami-1 | A-579 | B-1 |
| 672 | al-345 | ami-1 | A-580 | B-1 |
| 673 | al-346 | ami-1 | A-581 | B-1 |
| 674 | al-347 | ami-i | A-582 | B-1 |
| 675 | al-348 | ami-1 | A-583 | B-1 |
| 676 | al-349 | ami-1 | A-584 | B-1 |
| 677 | al-350 | ami-1 | A-585 | B-1 |
| 678 | al-351 | ami-1 | A-586 | B-1 |
| 679 | al-352 | ami-1 | A-587 | B-1 |
| 680 | al-353 | ami-1 | A-588 | B-1 |
| 681 | al-354 | ami-1 | A-589 | B-1 |
| 682 | al-355 | ami-1 | A-590 | B-1 |
| 683 | al-253 | ami-5 | A-380 | B-5 |
| 684 | al-254 | ami-5 | A-381 | B-5 |
| 685 | al-255 | ami-5 | A-382 | B-5 |
| 686 | al-256 | ami-5 | A-383 | B-5 |
| 687 | al-257 | ami-5 | A-384 | B-5 |
| 688 | al-258 | ami-5 | A-385 | B-5 |
| 689 | al-259 | ami-5 | A-386 | B-5 |
| 690 | al-260 | ami-5 | A-387 | B-5 |
| 691 | al-261 | ami-5 | A-388 | B-5 |
| 692 | al-262 | ami-5 | A-389 | B-5 |
| 693 | al-263 | ami-5 | A-390 | B-5 |
| 694 | al-264 | ami-5 | A-391 | B-5 |
| 695 | al-265 | ami-5 | A-396 | B-5 |
| 696 | al-266 | ami-5 | A-397 | B-5 |
| 697 | al-267 | ami-5 | A-398 | B-5 |
| 698 | al-268 | ami-5 | A-399 | B-5 |
| 699 | al-269 | ami-5 | A-409 | B-5 |
| 700 | al-270 | ami-5 | A-410 | B-5 |
| 701 | al-271 | ami-5 | A-411 | B-5 |
| 702 | al-272 | ami-5 | A-412 | B-5 |
| 703 | al-273 | ami-5 | A-413 | B-5 |
| 704 | al-274 | ami-5 | A-414 | B-5 |
| 705 | al-275 | ami-5 | A-415 | B-5 |
| 706 | al-276 | ami-5 | A-416 | B-5 |
| 707 | al-277 | ami-5 | A-417 | B-5 |
| 708 | al-278 | ami-5 | A-418 | B-5 |
| 709 | al-279 | ami-5 | A-419 | B-5 |
| 710 | al-280 | ami-5 | A-420 | B-5 |
| 711 | al-281 | ami-5 | A-421 | B-5 |
| 712 | al-282 | ami-5 | A-422 | B-5 |
| 713 | al-283 | ami-5 | A-423 | B-5 |
| 714 | al-284 | ami-5 | A-424 | B-5 |
| 715 | al-285 | ami-5 | A-425 | B-5 |
| 716 | al-286 | ami-5 | A-426 | B-5 |
| 717 | al-287 | ami-5 | A-522 | B-5 |
| 718 | al-288 | ami-5 | A-523 | B-5 |
| 719 | al-289 | ami-5 | A-524 | B-5 |
| 720 | al-290 | ami-5 | A-525 | B-5 |
| 721 | al-291 | ami-5 | A-526 | B-5 |
| 722 | al-292 | ami-5 | A-527 | B-5 |
| 723 | al-293 | ami-5 | A-528 | B-5 |
| 724 | al-294 | ami-5 | A-529 | B-5 |
| 725 | al-295 | ami-5 | A-530 | B-5 |
| 726 | al-296 | ami-5 | A-531 | B-5 |
| 727 | al-297 | ami-5 | A-532 | B-5 |
| 728 | al-298 | ami-5 | A-533 | B-5 |
| 729 | al-299 | ami-5 | A-534 | B-5 |
| 730 | al-300 | ami-5 | A-535 | B-5 |
| 731 | al-301 | ami-5 | A-536 | B-5 |
| 732 | al-302 | ami-5 | A-537 | B-5 |
| 733 | al-303 | ami-5 | A-538 | B-5 |
| 734 | al-304 | ami-5 | A-539 | B-5 |
| 735 | al-305 | ami-5 | A-540 | B-5 |
| 736 | al-306 | ami-5 | A-541 | B-5 |
| 737 | al-307 | ami-5 | A-542 | B-5 |
| 738 | al-308 | ami-5 | A-543 | B-5 |
| 739 | al-309 | ami-5 | A-544 | B-5 |
| 740 | al-310 | ami-5 | A-545 | B-5 |
| 741 | al-311 | ami-5 | A-546 | B-5 |
| 742 | al-312 | ami-5 | A-547 | B-5 |
| 743 | al-313 | ami-5 | A-548 | B-5 |
| 744 | al-314 | ami-5 | A-549 | B-5 |
| 745 | al-315 | ami-5 | A-550 | B-5 |
| 746 | al-316 | ami-5 | A-551 | B-5 |
| 747 | al-317 | ami-5 | A-552 | B-5 |
| 748 | al-318 | ami-5 | A-553 | B-5 |
| 749 | al-319 | ami-5 | A-554 | B-5 |
| 750 | al-320 | ami-5 | A-555 | B-5 |
| 751 | al-321 | ami-5 | A-556 | B-5 |
| 752 | al-322 | ami-5 | A-557 | B-5 |
| 753 | al-323 | ami-5 | A-558 | B-5 |
| 754 | al-324 | ami-5 | A-559 | B-5 |
| 755 | al-325 | ami-5 | A-560 | B-5 |
| 756 | al-326 | ami-5 | A-561 | B-5 |
| 757 | al-327 | ami-5 | A-562 | B-5 |
| 758 | al-328 | ami-5 | A-563 | B-5 |
| 759 | al-329 | ami-5 | A-564 | B-5 |
| 760 | al-330 | ami-5 | A-565 | B-5 |
| 76i | al-331 | ami-5 | A-566 | B-5 |
| 762 | al-332 | ami-5 | A-567 | B-5 |
| 763 | al-333 | ami-5 | A-568 | B-5 |
| 764 | al-334 | ami-5 | A-569 | B-5 |
| 765 | al-335 | ami-5 | A-570 | B-5 |
| 766 | al-336 | ami-5 | A-571 | B-5 |
| 767 | al-337 | ami-5 | A-572 | B-5 |
| 768 | al-338 | ami-5 | A-573 | B-5 |
| 769 | al-339 | ami-5 | A-574 | B-5 |
| 770 | al-340 | ami-5 | A-575 | B-5 |
| 77i | al-341 | ami-5 | A-576 | B-5 |
| 772 | al-342 | ami-5 | A-577 | B-5 |
| 773 | al-343 | ami-5 | A-578 | B-5 |
| 774 | al-344 | ami-5 | A-579 | B-5 |
| 775 | al-345 | ami-5 | A-580 | B-5 |
| 776 | al-346 | ami-5 | A-581 | B-5 |
| 777 | al-347 | ami-5 | A-582 | B-5 |
| 778 | al-348 | ami-5 | A-583 | B-5 |

TABLE 8-continued

| | regent | | ex-comp | |
|---|---|---|---|---|
| exp-No | al | ami | A | B |
| 779 | al-349 | ami-5 | A-584 | B-5 |
| 780 | al-350 | ami-5 | A-585 | B-5 |
| 781 | al-351 | ami-5 | A-586 | B-5 |
| 782 | al-352 | ami-5 | A-587 | B-5 |
| 783 | al-353 | ami-5 | A-588 | B-5 |
| 784 | al-354 | ami-5 | A-589 | B-5 |
| 785 | al-355 | ami-5 | A-590 | B-5 |

Test Example 1

Blood PTH Concentration Depressing Action

Each of the compounds described in Examples 1 to 71 was dissolved in a suitable solvent (20 to 50% PEG400, 15% cyclodextrin, and the like), and intravenously administered to 8-week old SD rats (Charles River Japan, 250 to 300 g) at a dose of 1 mg/kg.

The rats were anesthetized with ether 20 minutes after the administration, and the whole blood was collected from the abdominal aortas into test tubes treated with heparin. Plasma was separated from the whole blood at 4° C. and 3000 rpm, and blood PTH concentration was measured by using Rat PTH IRMA Kit (Immutopics, 50-2000) to evaluate the blood PTH concentration depressing action.

All the compounds described in the example reduced the blood PTH concentration by 15 to 95% compared with the values observed before the administration. Further, no death was observed in the administration groups for any of the compounds, and thus it was demonstrated that the compounds of the present invention can be safely administered.

Test Example 2

Action on Blood PTH Concentration and Bone in HyperPTHemia Model (1)

Renal failure rats were prepared by referring to the literature (Jablonski G. et al., "Surgically induced uremia in rats 1: effect on bone strength and metabolism", Biosci. Rep., 13, 275-287, 1993). Specifically, ⅔ each of left kidneys of 7-week old SD male rats (Charles River Japan, 230 to 255 g) was excised, and one week after, whole right kidneys were extracted to prepare 5/6-nephrectomized rats. Then, the rats were fed for 90 days, and used as renal failure rats.

Each of the compounds described in Examples 1 to 71 was dissolved in a suitable solvent (20 to 50% PEG400, 15% cyclodextrin, and the like), and orally adminstered every day to the rats at a dose of 50 mg/kg for 30 days. Twenty-four hours after the final administration, the animals were sacrificed by exsanguination, and non-decalcificated sections of left tibias were prepared. According to bone morphological measurement techniques, bone volume (BV/TV) and fibrosis tissue volume (Fb.V/TV) of the proximal epiphyses were measured to evaluate degree of onset of fibrous ostitis. Further, 1 hour after the final administration, blood was partially collected from the cervical veins, and the blood PTH concentration was measured by using Rat PTH IRMA Kit (Immutopics, 50-2000) to evaluate the blood PTH concentration depressing action.

The blood PTH concentrations observed in the pathological group (group administered with no compound) significantly increased (p<0.05) compared with the normal group (false operation group), and significant reduction (p<0.05) of bone volume and significant increase (p<0.01) of fibrosis tissue volume were observed in the pathological group.

Whilst, effects of depressing the blood PTH concentration by 20 to 95% was observed in the groups administered with the compounds of the examples as compared to the pathological group, and suppressing reduction of bone volume by 10 to 90% in the pathological group was also observed. Further, suppression of the increase in fibrosis tissue volume by 10 to 90% in the pathological group was typically demonstrated. No death was observed in the groups administered with the compounds.

Test Example 3

Action on Blood PTH Concentration and Bone in HyperPTHemia Model (2)

Renal failure rats were prepared by referring to the literature (Ishii H. et al., "Daily intermittent decreases in serum levels of parathyroid hormone have an anabolic-like action on the bones of uremic rats with low-turnover bone and osteomalacia", Bone, 26, 175-182, 2000). Specifically, 5-week old SD male rats (Charles River Japan, 100 to 135 g) were intravenously administered with adriamycin (doxorubicin hydrochloride, Wako Pure Chemical Industries, 040-21521) at a dose of 3 mg/kg, and then, after 3 weeks, further administered with 2 mg/kg. After 14 weeks of the additional administration of adriamycin, each of the compounds described in Examples 1 to 71 dissolved in a suitable solvent (20 to 50% PEG400, 15% cyclodextrin, and the like) was orally administered every day to the rats at a dose of 50 mg/kg for 60 days.

Twenty-four hours after the final administration, the animals were sacrificed by exsanguination, and non-decalcificated sections of left tibias were prepared. According to bone morphological measurement techniques, bone volume (BV/TV) and osteoid volume (OV/TV) of the proximal metaphysis were measured to evaluate degree of onset of osteomalacia. Further, 1 hour after the final administration, blood was partially collected from the cervical veins, and the blood PTH concentration was measured by using Rat PTH IRMA Kit (Immutopics, 50-2000) to evaluate the blood PTH concentration depressing action.

The blood PTH concentrations observed in the pathological group (group administered with no compound) significantly increased (p<0.05) compared with the normal group (false operation group), and significant reduction (p<0.05) of bone volume and significant increase (p<0.01) of osteoid volume were observed in the pathological group.

Whilst, effects of depressing the blood PTH concentration by 20 to 95% in the groups administered with the compounds of the examples compared to the pathological group was observed, and suppressing reduction of bone volume by 10 to 90% in the pathological group was also observed. Further, suppression of the increase in osteoid volume by 10 to 90% in the pathological group were typically demonstrated. No death was observed in the groups administered with the compounds.

Test Example 4

Action on Blood PTH Concentration and Bone in HyperPTHemia Model (3)

Malabsorption rats were prepared by referring to the literature (Suzuki, H. "Experimental Analysis Concerning Osteopathia After Total Gastrectomy and Influence of Menopause", Journal of Jikei University School of Medicine, 114, 77-87, 1999). Specifically, stomachs of 40-week old Wister male rats (Charles River Japan, 275 to 310 g) were totally extracted, and ends of esophagi and duodenums were anastomosed to prepare totally gastrectomized (malabsorption) rats. Eight weeks after the operation, each of the compounds described in Examples 1 to 71 dissolved in a suitable solvent (20 to 50% PEG400, 15% cyclodextrin, and the like) was orally administered every day to the rats at a dose of 50 mg/kg for 30 days. Twenty-four hours after the final administration, the animals were sacrificed by exsanguination, and non-decalcificated sections of left tibias were prepared. According to bone morphological measurement techniques, bone volume (BV/TV) and osteoid volume (OV/TV) of the proximal metaphysis were measured to evaluate degree of onset of osteomalacia. Further, 15 minutes, 30 minutes or 1 hour after the final administration, blood was partially collected from the cervical veins, and the blood PTH concentration was measured by using Rat PTH IRMA Kit (Immutopics, 50-2000) to evaluate the blood PTH concentration depressing action.

The blood PTH concentrations observed in the pathological group (group administered with no compound) significantly increased (p<0.05) compared with the normal group (false operation group), and significant reduction (p<0.05) of bone volume and significant increase (p<0.01) of osteoid volume were observed in the pathological group. Whilst, effects of depressing the blood PTH concentration by 20 to 95% was observed in the groups administered with the compounds of the examples compared to the pathological group. Suppressing reduction of bone volume by 10 to 90% in the pathological group was also observed. Further, suppression of the increase in osteoid volume by 10 to 90% in the pathological group were typically demonstrated. No death was observed in the groups administered with the compounds.

Test Example 5

Inhibitory Action Against Drug Metabolism Enzyme CYP3A4

Inhibitory action of the compounds of the present invention against the drug metabolism enzyme CYP3A4, which is considered to seriously affect drug interactions with a combination drug, was examined. A test compound was dissolved and diluted in a buffer (200 mM potassium phosphate, 1.3 mM NADP+, 3.3 mM magnesium chloride, 3.3 mM glucose-6-phosphate, 0.4 units/mL of glucose-6-phosphate dehydrogenase, 0.048 mg/mL of Control Microsome (produced by GENTEST, 242311), pH7.4), added with 5 nM CYP3A4 (produced by GENTEST, 242328) and 0.1 mM BFC ((7-benzyloxy-4-trifluoromethyl)coumarin) as a substrate, and incubated at 37° C. After 30 minutes, the reaction was terminated by addition of 0.1 M Tris containing 80% acetonitrile, and fluorescence was measured at Ex 409 nm/Em 530 nm. The enzyme inhibitory activity was represented in terms of $IC_{50}$ value.

Typical $IC_{50}$ values of the compounds described in the examples were found to be in a range of 100 nM to higher than 30 µM, and accordingly, it is concluded that a risk of occurrence of an interaction with the combination drug, which might result in side effects, is low.

Test Example 6

Inhibitory Action Against Drug Metabolism Enzyme CYP2D6

Inhibitory action of the compounds of the present invention against the drug metabolism enzyme CYP2D6, which is considered to seriously affect drug interactions with a combination drug, was examined. A test compound was dissolved and diluted in a buffer (100 mM potassium phosphate, 0.008 mM NADP+, 0.4 mM magnesium chloride, 0.4 mM glucose-6-phosphate, 0.4 units/mL of glucose-6-phosphate dehydrogenase, 0.048 mg/mL of Control Microsome (produced by GENTEST, 242311), pH7.4), added with 7.5 nM CYP2D6 (produced by GENTEST, 242217) and 0.0015 mM AMMC (3-[2-(N,N-diethyl-N-methylamino)ethyl]-7-methoxy-4-methylcoumarin) as a substrate, and incubated at 37° C. After 30 minutes, the reaction was terminated by addition of 0.1 M Tris containing 80% acetonitrile, and fluorescence was measured at Ex 390 nm/Em 460 nm. The enzyme inhibitory activity was represented in terms of $IC_{50}$ value.

Typical $IC_{50}$ values of the compounds described in the examples were found to be in a range of 100 nM to higher than 30 µM, and accordingly, it is concluded that a risk of occurrence of an interaction with the combination drug, which might result in side effects, is low.

Preparation Example

A preparation example will be specifically explained below. However, the scope of the present invention is not limited by the following example.

Preparation Example 1

Tablets

The compound of Example 1 in an amount of 2.5 g was mixed with 4.9 g of lactose, 2.1 g of cornstarch, and 0.4 g of hydroxypropylcellulose, granulated by using distilled water, and dried. Then, the granules were added with 0.1 g of magnesium stearate, and compressed by using a pressurization-type compressing machine to prepare tablets having a weight of 200 mg per tablet and a diameter of 8 mm.

INDUSTRIAL APPLICABILITY

The compounds of the present invention show potent PTH depressiong activity when they are administered to a human or animal in the free forms or salt forms thereof, and they are useful as an active ingredient of medicaments for prophylactic and/or therapeutic treatment of, for example, hyper-PTHemia.

The invention claimed is:

1. A compound represented by the following formula (1) or a salt thereof:

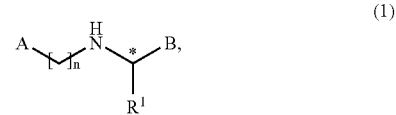

wherein:
A represents a group selected from the group consisting of (1) a saturated heterocyclic group, (2) a 5-membered heteroaromatic group having two heteroatoms in the ring which may be substituted, (3) a group represented by the following formula A1, (4) a group represented by the following formula A2, and (5) a group represented by the following formula A3:

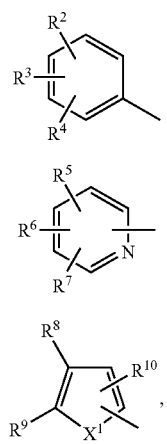

in which
R², R³, and R⁴ may be the same or different, and independently represent a hydrogen atom, a hydroxyl group, a halogen atom, an alkyl group, a phenyl group, a substituted phenyl group, a benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, a nitro group, or N (R¹⁶) (R¹⁷), wherein R¹⁶ and R¹⁷ may be the same or different, and independently represent a hydrogen atom, an alkyl group, an acyl group, or SO₂R¹⁸, wherein R¹⁸ represents a lower alkyl group, or R¹⁶ and R¹⁷ together form a 3- to 7-membered ring to represent a cyclic amine as N (R¹⁶) (R¹⁷);
R⁵, R⁶ and R⁷ may be the same or different, and independently represent a hydrogen atom, a hydroxyl group, a halogen atom, an alkyl group, a phenyl group, a substituted phenyl group, a benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, a nitro group, or N (R¹⁶) (R¹⁷), wherein R¹⁶ and R¹⁷ may be the same or different, and independently represent a hydrogen atom, an alkyl group, an acyl group, or SO₂R¹⁸, wherein R¹⁸ represents a lower alkyl group, or R¹⁶ and R¹⁷ together form a 3- to 7-membered ring to represent a cyclic amine as N (R¹⁶) (R¹⁷);
R⁸, R⁹ and R¹⁰ independently represent a hydrogen atom, a hydroxyl group, a halogen atom, an alkyl group, a phenyl group, a substituted phenyl group, a benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, an alkoxyl group arbitrarily substituted with one or more halogen atoms, a nitro group, or N (R¹⁶) (R¹⁷), wherein R¹⁶ and R¹⁷ may be the same or different, and independently represent a hydrogen atom, an alkyl group, an acyl group, or SO₂R¹⁸, wherein R¹⁸ represents a lower alkyl group, or R¹⁶ and R¹⁷ together form a 3- to 7-membered ring to represent a cyclic amine as N (R¹⁶) (R¹⁷), or R⁸ and R⁹ may together form a benzene ring to represent a bicyclic heteroaromatic group as the group represented by the formula A3;
X¹ represents oxygen atom, sulfur atom, or N—R¹⁹ wherein R¹⁹ represents a hydrogen atom, an alkyl group, phenyl group, or a substituted phenyl group;
B is a group represented by the formula B2:

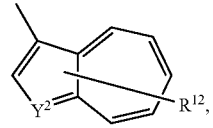

wherein R¹² represents a hydrogen atom or an alkyl group, Y² represents CH or a nitrogen atom;
R¹ represents an alkyl group; and
n represents an integer of 2 to 6.

2. The compound or salt thereof according to claim 1, wherein A is a group represented by the formula A2.

3. The compound or salt thereof according to claim 2, wherein A is a group represented by the formula A2, wherein R⁶ and R⁷ are hydrogen atoms, and R⁵ is a phenyl group, a substituted phenyl group, a benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, or an alkoxyl group arbitrarily substituted with one or more halogen atoms, and
B is a group represented by the formula B2, wherein R¹² is a hydrogen atom, and Y² is CH.

4. The compound or salt thereof according to claim 3, wherein R⁵ is a substituted phenyl group, a monocyclic heteroaromatic group which may be substituted, or a bicyclic heteroaromatic group which may be substituted.

5. The compound or salt thereof according to claim 1, wherein A is a group represented by the formula A3.

6. The compound or salt thereof according to claim 5, wherein A is a group represented by the formula A3, wherein R⁸ and R¹⁰ are hydrogen atoms, and R⁹ is a phenyl group, a substituted phenyl group, a benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, or an alkoxyl group arbitrarily substituted with one or more halogen atoms, and
B is a group represented by the formula B2, wherein R¹² is a hydrogen atom, and Y² is CH.

7. The compound or salt thereof according to claim 6, wherein R⁹ is a substituted phenyl group, a monocyclic heteroaromatic group which may be substituted, or a bicyclic heteroaromatic group which may be substituted.

8. A compound represented by the following formula (1) or a salt thereof:

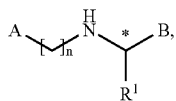
(1)

wherein:
A is a group represented by the following formula A4

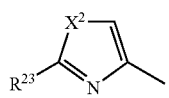
A4 in which
R$^{23}$ is a phenyl group, a substituted phenyl group, a benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, or an alkoxyl group arbitrarily substituted with one or more halogen atoms;
X$^2$ represents an oxygen atom, a sulfur atom, or N—R$^{19}$, wherein R$^{19}$ represents a hydrogen atom, an alkyl group, a phenyl group, or a substituted phenyl group, and
B is a group represented by the formula B2:

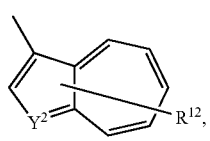
B2 wherein R$^{12}$ represents hydrogen atom or an alkyl group, Y$^2$ represents CH or nitrogen atom,
R$^1$ represents an alkyl group, and
n represents an integer of 2 to.
9. The compound or salt thereof according to claim 8, wherein A is a group represented by the formula A4, wherein R$^{23}$ is a phenyl group, a substituted phenyl group, a benzyl group, a substituted benzyl group, a monocyclic heteroaromatic group which may be substituted, a bicyclic heteroaromatic group which may be substituted, an alkoxyl group, an alkyl group arbitrarily substituted with one or more halogen atoms, or an alkoxyl group arbitrarily substituted with one or more halogen atoms, and
B is a group represented by the formula B2, wherein R$^{12}$ is a hydrogen atom, and Y$^2$ is CH.
10. The compound or salt thereof according to claim 9, wherein R$^{23}$ is a substituted phenyl group, a monocyclic heteroaromatic group which may be substituted, or a bicyclic heteroaromatic group which may be substituted.
11. The compound or salt thereof according to claim 1, wherein A is a group represented by the formula A2 or A3, or a 5-membered heteroaromatic group having two hetero atoms in the ring.
12. A medicament containing the compound according to claim 1 or a physiologically acceptable salt thereof as an active ingredient.
13. The medicament according to claim 12, which is used for therapeutic treatment of hyperparathormonemia.
14. The medicament according to claim 12, which is used for therapeutic treatment of hyperparathyroidism.
15. The medicament according to claim 12, which is used for therapeutic treatment of a bone disease associated with increase in blood parathyroid hormone level.
16. A method of treating condition selected from the group consisting of hyperparathormonemia, hyperparathyroidism, and bone disease associated with increase in blood parathyroid hormone level, said method comprising administering to a patient in need thereof a composition comprising an effective amount of the compound of claim 1.
17. A method of treating condition selected from the group consisting of hyperparathormonemia, hyperparathyroidism, and bone disease associated with increase in blood parathyroid hormone level, said method comprising administering to a patient in need thereof a composition comprising an effective amount of the compound of claim 2.
18. A method of treating condition selected from the group consisting of hyperparathormonemia, hyperparathyroidism, and bone disease associated with increase in blood parathyroid hormone level, said method comprising administering to a patient in need thereof a composition comprising an effective amount of the compound of claim 9.

* * * * *

UNITED STATES PATENT AND TRADEMARK OFFICE
CERTIFICATE OF CORRECTION

PATENT NO.         : 7,582,658 B2
APPLICATION NO. : 11/019632
DATED              : September 1, 2009
INVENTOR(S)        : Miyoshi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1029 days.

Signed and Sealed this

Fourteenth Day of September, 2010

David J. Kappos
*Director of the United States Patent and Trademark Office*